United States Patent
Buckman et al.

(10) Patent No.: US 10,590,084 B2
(45) Date of Patent: Mar. 17, 2020

(54) CYCLIC KETO-AMIDE COMPOUNDS AS CALPAIN MODULATORS AND METHODS OF PRODUCTION AND USE THEREOF

(71) Applicant: Blade Therapeutics, Inc., South San Francisco, CA (US)

(72) Inventors: Brad Owen Buckman, Oakland, CA (US); John Beamond Nicholas, Redwood City, CA (US); Shendong Yuan, San Ramon, CA (US); Marc Adler, Orinda, CA (US)

(73) Assignee: Blade Therapeutics, Inc., South San Francisco, CA (US)

( * ) Notice: Subject to any disclaimer, the term of this patent is extended or adjusted under 35 U.S.C. 154(b) by 0 days.

(21) Appl. No.: 16/083,189

(22) PCT Filed: Mar. 8, 2017

(86) PCT No.: PCT/US2017/021285
§ 371 (c)(1),
(2) Date: Sep. 7, 2018

(87) PCT Pub. No.: WO2017/156071
PCT Pub. Date: Sep. 14, 2017

(65) Prior Publication Data
US 2019/0194139 A1    Jun. 27, 2019

Related U.S. Application Data

(60) Provisional application No. 62/306,026, filed on Mar. 9, 2016.

(51) Int. Cl.
*C07D 223/12* (2006.01)
*C07D 225/02* (2006.01)
*C07D 211/58* (2006.01)
*C07K 5/062* (2006.01)
*A61P 19/04* (2006.01)
*A61K 38/00* (2006.01)

(52) U.S. Cl.
CPC ............ *C07D 223/12* (2013.01); *A61P 19/04* (2018.01); *C07D 211/58* (2013.01); *C07D 225/02* (2013.01); *C07K 5/06034* (2013.01); *A61K 38/00* (2013.01)

(58) Field of Classification Search
CPC .............................. C07D 223/12; A61P 19/04
See application file for complete search history.

(56) References Cited

U.S. PATENT DOCUMENTS

| | | |
|---|---|---|
| 5,145,684 A | 9/1992 | Liversidge et al. |
| 5,463,124 A | 10/1995 | Jacobi et al. |
| 5,852,007 A | 12/1998 | Chatterjee |
| 5,952,322 A | 9/1999 | Hoover et al. |
| 6,083,944 A | 7/2000 | Chatterjee et al. |
| 6,103,720 A | 8/2000 | Lubisch et al. |
| 6,172,072 B1 | 1/2001 | Lubisch et al. |
| 6,251,917 B1 | 6/2001 | Lubisch et al. |
| 6,358,978 B1 | 3/2002 | Ritzeler et al. |
| 6,380,220 B1 | 4/2002 | Lubisch et al. |
| 6,436,925 B1 | 8/2002 | Lubisch et al. |
| 6,448,254 B1 | 9/2002 | Lubisch et al. |
| 6,482,832 B1 | 11/2002 | Lubisch et al. |
| 6,582,827 B1 | 5/2003 | Lubisch et al. |
| 6,630,493 B1 | 10/2003 | Lubisch et al. |
| 7,956,093 B2 | 6/2011 | Lubisch et al. |
| 7,964,624 B1 | 6/2011 | Cottrell et al. |
| 8,283,363 B2 | 10/2012 | MacK et al. |
| 9,434,762 B2 | 9/2016 | Abell et al. |
| 2004/0097508 A1 | 5/2004 | Lubisch et al. |
| 2004/0242542 A1 | 12/2004 | Shea et al. |
| 2010/0216844 A1 | 8/2010 | Kling et al. |
| 2010/0298326 A1 | 11/2010 | Kling et al. |
| 2011/0021434 A1 | 1/2011 | Abell et al. |
| 2011/0059968 A1 | 3/2011 | Hornberger et al. |
| 2011/0086879 A1 | 4/2011 | MacK et al. |
| 2011/0152265 A1 | 6/2011 | Kling et al. |
| 2011/0152325 A1 | 6/2011 | Kling et al. |
| 2012/0010235 A1 | 1/2012 | Chu et al. |
| 2014/0005227 A1 | 1/2014 | Kling et al. |

(Continued)

FOREIGN PATENT DOCUMENTS

| | | |
|---|---|---|
| CA | 2328440 | 10/1999 |
| CA | 2328720 | 10/1999 |
| CA | 2943005 | 9/2015 |

(Continued)

OTHER PUBLICATIONS

Blum et al., 2003, Complementary use of ion trap / time-of-flight mass spectrometry in combination with capillary high-pressure liquid chromatography: Early characterization of in vivo metabolites of the cathepsin K inhibitor NVP-AAV490 in rat. J Chromatography B. 787:255-270.

(Continued)

*Primary Examiner* — Golam M Shameem

(74) *Attorney, Agent, or Firm* — Knobbe, Martens, Olson & Bear, LLP

(57) ABSTRACT

The present technology relates to cyclic keto-amide compounds of general formulae I to XXXII, compositions and kits thereof as calpain modulators and methods useful for the treatment of various diseases or disorders such as fibrotic disease or cancer which are associated or mediated, by calpains, such as CAPN1, CAPN2, and/or CAPN9. The present technology is also applicable to cyclic keto-amide compounds which inhibit myofibroblast differentiation.

19 Claims, No Drawings

(56) References Cited

U.S. PATENT DOCUMENTS

| | | | |
|---|---|---|---|
| 2015/0065477 A1 | 3/2015 | Kling et al. | |
| 2015/0133368 A1 | 5/2015 | Chang et al. | |

FOREIGN PATENT DOCUMENTS

| | | |
|---|---|---|
| CN | 105669520 | 6/2016 |
| EP | 0530167 | 3/1993 |
| EP | 1493739 | 1/2005 |
| GB | 2467561 | 8/2010 |
| WO | WO 1987/005297 | 9/1987 |
| WO | WO 1991/013889 A1 | 9/1991 |
| WO | WO 1992/13549 | 8/1992 |
| WO | WO 1994/00095 | 1/1994 |
| WO | WO 1995/09859 | 4/1995 |
| WO | WO 1996/12499 | 5/1996 |
| WO | WO 1998/016512 | 4/1998 |
| WO | WO 1998/21186 | 5/1998 |
| WO | WO 1998/041092 | 9/1998 |
| WO | WO 1998/041506 | 9/1998 |
| WO | WO 1999/17790 | 4/1999 |
| WO | WO 1999/50264 | 10/1999 |
| WO | WO 1999/054304 | 10/1999 |
| WO | WO 2000/055114 | 9/2000 |
| WO | WO 2000/055125 | 9/2000 |
| WO | WO 2001/089584 | 11/2001 |
| WO | WO 2003/064440 | 8/2003 |
| WO | WO 2003/080182 | 10/2003 |
| WO | WO 2004/014844 | 2/2004 |
| WO | WO 2004/062601 | 7/2004 |
| WO | WO 2005/000793 | 1/2005 |
| WO | WO 2005/014006 | 2/2005 |
| WO | WO 2005/014534 | 2/2005 |
| WO | WO 2003/091202 | 9/2005 |
| WO | WO 2006/052722 | 5/2006 |
| WO | WO 2007/016476 | 2/2007 |
| WO | WO 2007/025307 | 3/2007 |
| WO | WO 2007/076423 | 7/2007 |
| WO | WO 2007/081530 | 7/2007 |
| WO | WO 2007/089618 | 8/2007 |
| WO | WO 2007/097980 | 8/2007 |
| WO | WO 2007/109080 | 9/2007 |
| WO | WO 2007/141473 | 12/2007 |
| WO | WO 2005/102381 | 3/2008 |
| WO | WO 2008/048121 | 4/2008 |
| WO | WO 2008/080969 | 7/2008 |
| WO | WO 2008/106058 | 9/2008 |
| WO | WO 2008/152093 | 12/2008 |
| WO | WO 2008/154642 | 12/2008 |
| WO | WO 2010/023609 | 3/2010 |
| WO | WO 2010/077836 | 7/2010 |
| WO | WO 2010/094755 | 8/2010 |
| WO | WO 2011/082285 | 7/2011 |
| WO | WO 2011/133346 | 10/2011 |
| WO | WO 2011/133871 | 10/2011 |
| WO | WO 2011/159781 | 12/2011 |
| WO | WO 2012/021788 A2 | 2/2012 |
| WO | WO 2012/040242 | 3/2012 |
| WO | WO 2012/076639 | 6/2012 |
| WO | WO 2012/122420 | 9/2012 |
| WO | WO 2012/122422 | 9/2012 |
| WO | WO 2012/140500 A9 | 10/2012 |
| WO | WO 2013/033396 | 3/2013 |
| WO | WO 2013/076063 | 5/2013 |
| WO | WO 2013/104613 | 7/2013 |
| WO | WO 2013/149800 | 10/2013 |
| WO | WO 2014/075146 | 5/2014 |
| WO | WO 2015/002915 | 1/2015 |
| WO | WO 2015/073763 | 5/2015 |
| WO | WO 2015/124443 | 8/2015 |
| WO | WO 2015/179441 | 11/2015 |
| WO | WO 2016/027284 | 2/2016 |
| WO | WO 2016/036893 | 3/2016 |
| WO | WO 2016/089648 | 6/2016 |
| WO | WO 2017/100201 | 6/2017 |

OTHER PUBLICATIONS

CAS Registry No. 1309010-71-6; STN entry date: Jun. 13, 2011; D-Alanine, N-[(1-phenyl-1H-imidazol-5-yl)carbonyl] in 1 page.
CAS Registry No. 2094533-75-0; STN entry date: May 2, 2017; Benzamide, N-(2-amino-1,1-dimethyl-2-oxoethyl)-2-bromo-5-chloro-3-fluoro-, in 1 page.
CAS Registry No. 1629446-68-9; STN entry date: Oct. 21, 2014; Benzamide, 3-cyano-N-[(1S)-1-formyl-2-phenylethyl], in 1 page.
CAS Registry No. 2094410-58-7; STN entry date: May 2, 2017; Benzamide, 2-bromo-5-chloro-N-(1-cyano-2-methoxy-1-methylethyl)-3-fluoro-, in 1 page.
CAS Registry No. 2037707-18-7; STN entry date: Nov. 25, 2016; Alanine, 3-fluoro-N-(2-fluoro-6-methoxybenzoyl)-, in 1 page.
CAS Registry No. 1938924-09-4; STN entry date: Jun. 24, 2016; D-Leucine, N-(2-bromo-6-fluoro-3-methylbenzoyl)-, in 1 page.
CAS Registry No. 2048401-56-3; STN entry date: Dec. 14, 2016; 4-Hexenoic acid, 2-[(4,5-dichloro-2-methoxybenzoyl)amino]-, in 1 page,
CAS Registry No. 2026949-92-6; STN entry date: Nov. 8, 2016; D-Leucine, N-[(6-bromo-3,4-dihydro-3-oxo-2H-1,4-benzoxazin-7-yl)carbonyl]-, in 1 page.
CAS Registry No. 1031704-04-7; STN entry date: Jun. 30, 2008; L-Valine, N-[(5,7,8,10-tetrahydro-7,8-dioxo-6-undecyl-2-phenazinyl)carbonyl]-, in 1 page.
CAS Registry No. 566157-42-4; STN entry date: Aug. 14, 2003; Alanine, N-[(9,10-dihydro-9-oxo-3-acridinyl)carbonyl]-2-methyl-, in 1 page.
CAS Registry No. 289062-66-4; STN entry date: Sep. 14, 2000; Acetic acid, [(2,4-dichlorobenzoyl)amino](phenylthio)-, in 1 page.
CAS Registry No. 15643-65-9; STN entry date: Nov. 16, 1984; Acetic acid, [(3,4-dichlorobenzoyl)amino]phenoxy-, in 1 page.
CAS Registry No. 1347051-33-5, Entered STN: Dec. 1, 2011; 1 H-Imidazole-5-hexanoic acid, β-[[[(6S,8aS)-octahydro-4-oxo-2-(phenylmethyl)sulfonyl]pyrrolo[1,2-a]pyrazin-6-yl]carbonyl]amino]-a-oxo-, methyl ester, 1 p.
CAS Registry No. 1026166-23-3, Entered STN: Jun. 8, 2008 ; Hexanoic acid, 3-[[[(1R,2S,5S)-3-[(2S)-2-cyclohexyl-2-[(3,3-dimethyl-1-oxobutyl)amino]acetyl]-6,6-dimethyl-3-azabicyclo[3.1.0]hex-2-yl]carbonyl]amino]-6,6,6-trifluoro-2-oxo-, 1 page.
CAS Registry No. 2026817-08-1, Entered STN: Nov. 8, 2016; D-Leucine, N-[[3-(3-thienyl)-1H-pyrazol-4-yl]carbonyl]-, 1 page.
CAS Registry No. 2049278-49-9, Entered STN: Dec. 15, 2016; 4-Hexenoic acid, 2-[[[1-methyl-3-(2-thienyl)-1H-pyrazol-4-yl]carbonyl]amino]-, 1 page.
CAS Registry No. 2039960-52-4, Entered STN: Nov. 28, 2016; 5-Hexenoic acid, 2-[[[1-methyl-3-(2-thienyl)-1H-pyrazol-4-yl]carbonyl]amino]-, 1 page.
CAS Registry No. 2026895-95-2, Entered STN:Nov. 8, 2016; L-Norleucine, N-[[3-(5-chloro-2-thienyl)-1H-pyrazol-4-yl]carbonyl]-, 1 page.
CAS Registry No. 2026863-64-7, Entered STN: Nov. 8, 2016; L-Norleucine, N-[[4-(5-chloro-2-thienyl)-1H-pyrrol-3-yl]carbonyl]-, 1 page.
CAS Registry No. 1796920-43-8, Entered STN: Jul. 8, 2015; 1H-Pyrrole-3-carboxamide, N-(2-amino-1-methyl-2-oxoethyl)-4-(5-chloro-2-thienyl)-, 1 page.
Chatterjee et al., 1999, P2-achiral, P'-extended alpha-ketoamide inhibitors of calpain I. Bioorg Med Chem Lett. 9(16):2371-2374.
Cohrt A. Emil. 2014, Solid-phase synthesis of peptide thioureas and thiazole-containing macrocycles through Ru-catalyzed ring-closing metathesis, ACS Comb Sci. 16(2):71-77 and Supporting Information in 55 pages.
Gopalsamy et al., 2004, Identification of [(naphthalene-1-carbonyl)-amino]-acetic acid derivatives as nonnucleoside inhibitors of HCV NS5B RNA dependent RNA polymerase. Bioorg Med Chem Lett. 14(16):4221-4224.
Kling et al., 2018, Mitigating the Metabolic Liability of Carbonyl Reduction: Novel Calpain Inhibitors with P1' Extension, ACS Med Chem Lett. 9(3):221-226.
Li et al., 1996, Novel peptidyl alpha-keto amide inhibitors of calpains and other cysteine proteases, J Med Chem. 39(20):4089-4098.

(56) References Cited

OTHER PUBLICATIONS

Li et al., 2015, Synthesis and Cytotoxic Activities of Novel Amino Acid-Conjugates of Pyrrole Derivatives. Youji Huaxue. 35:167-174.
Lu et al., 2015, Mechanism of Action of Thalassospiramides, A New Class of Calpain Inhibitors, Sci Rep. 5:8783 in 8 pages.
Lubisch et al., 2003, Benzoylalanine-derived ketoamides carrying vinylbenzyl amino residues: discovery of potent water-soluble calpain inhibitors with oral bioavailability, J Med Chem. 46(12):2404-2412.
Muniappan et al., 2017, Calpain Inhibition Attenuates Adipose Tissue Inflammation and Fibrosis in Diet-induced Obese Mice, Sci Rep. 7:14398.
Nimmrich et al., 2008, Inhibition of Calpain Prevents N-Methyl-D-aspartate-Induced Degeneration of the Nucleus Basalis and Associated Behavioral Dysfunction, J Pharmacol Exp Ther. 327(2):343-352.
Oh et al., 2007, Thalassospiramides A and B, Immunosuppressive Peptides from the Marine *Bacterium thalassospira* sp., Org Ltts. 9(8):1525-1528.
Sasmal et al., 2011, Structure-activity relationship studies of novel pyrazole and imidazole carboxamides as cannabinoid-1 (CB1) antagonists. Bioorg Med Chem Lett. 21(16):4913-4918.
Singh et al., 2015, Identification of amino acid appended acridines as potential leads to anti-cancer drugs. Bioorg Med Chem Lett. 25(18):3854-3858.
Skogh et al., 2013, Aminocarbonylation of 4-Iodo-1H-imidazoles with an Amino Acid Amide Nucleophile: Synthesis of Constrained H-Phe-Phe-NH$_2$ Analogues. J Org Chem. 78:12251-12256.
Vengeliene et al., 2016, The Calpain Inhibitor A-705253 Attenuates Alcohol-Seeking and Relapse with Low Side-Effect Profile, Neuropsychopharmacology. 41(4):979-988 [online published Jul. 28, 2015].
Zhong et al., 2005, 3-(2-Chlorophenyl)-N-(2-cyano-4-methyl-2-pentyl)-5-methylisoxazole-4-carboxamide. Acta Cryst. Section E. E61:o2621-o2622 in 7 pages.
European Extended Search Report dated Jul. 12, 2019 for Application No. EP 17763962.2, filed Oct. 9, 2018.
Abell et al., 2009, Molecular Modeling, Synthesis, and Biological Evaluation of Macrocyclic Calpain Inhibitors, Angew Chem Int Ed Engl. 48(8):1455-1458.
Bihovsky et al., 2004, 1,2-Benzothiazine 1,1-dioxide α-ketoamide analogues as potent calpain I inhibitors, Bioorg Med Chem Lett. 14(4):1035-1038.
Brodney et al., 2015, Utilizing Structures of CYP2D6 and BACE1 Complexes To Reduce Risk of Drug-Drug Interactions with a Novel Series of Centrally Efficacious BACE1 Inhibitors, J Med Chem. 58:3223-3252.
Chen et al., 2012, New Tripeptide-Based Macrocyclic Calpain Inhibitors Formed by N-Alkylation of Histidine, Chem Biodiver. 9(11):2473-2484.
Damalanka et al., 2016, Oxadiazole-Based Cell Permeable Macrocyclic Transition State Inhibitors of Norovirus 3Cl Protease, J Med Chem. 59(5):1899-1913.
Dourdin et al., 2001, Reduced Cell Migration and Disruption of the Actin Cytoskeleton in Calpain-deficient embryonic Fibroblasts, J Biol Chem. 276(51):48382-48388.
Gardiner et al., 2006, Ring closing metathesis of α- and β-amino acid derived dienes, J Organomet Chem. 691:5487-5496.
Goll et al., 2003, The Calpain System, Physiol Rev. 83(3):731-801.
Halland et al., 2014, Small Macrocycles as Highly Active Integrin α2β1 Antagonists, ACS Med Chem Lett. 5(2):193-198.
Jánossy et al., 2004, Calpain as a multi-site regulator of cell cycle, Biochem Pharmacol. 67(8):1513-1521.
Jones et al., 2009, Efficient Large-Scale Synthesis of CAT811, a Potent Calpain Inhibitor of Interest in the Treatment of Cataracts, Aust J Chem. 62:671-675.
Jones et al., 2013, A Template-Based Approach to Inhibitors of Calpain 1, 20S Proteasome, and HIV-1 Protease, Chem Med Chem. 8(12):1918-1921.
Jones et al., 2014, The Preparation of Macrocyclic Calpain Inhibitors by Ring Closing Metathesis and Cross Metathesis, Aust J. Chem. 67:1257-1263.
Kim et al., 2011, Synthesis of chromone carboxamide derivatives with antioxidative and calpain inhibitory properties, Eur J Med Chem. 46(5):1721-1728.
Kim et al., 2015, Discovery and structure-activity relationships of pyrazolodiazepine derivatives as the first small molecule agonists of the *Drosophila* sex peptide receptor, Bioorg Med Chem. 23:1808-1816.
Kling et al., 2017, Discovery of Novel and Highly Selective Inhibitors of Calpain for the Treatment of Alzheimer's Disease: 2-(3-Phenyl-1H-pyrazol-1-yl)-nicotinamides, J Med Chem. 60:7123-7138.
Lamouille et al., 2014, Molecular mechanisms of epithelial-mesenchymal transition, Nat Rev Mol Cell Biol. 15(3):178-196 in 46 pages.
Lee et al., 2005, Synthesis and biological evaluation of chromone carboxamides as calpain inhibitors, Bioorg Med Chem Lett., 15(11):2857-2860.
Leloup et al., 2006, Involvement of calpains in growth factor-mediated migration, Int J Biochem Cell Biol. 38(12):2049-2063.
Low et al., 2016, Rational Design of Calpain Inhibitors Based on Calpastatin Peptidomimetics, J Med Chem. 59(11):5403-5415.
Lubisch et al., 2002, Discovery of phenyl alanine derived ketoamides carrying benzoyl residues as novel calpain inhibitors, Bioorg Med Chem Lett., 12(10):1335-1338.
Mandadapu et al., 2013, Macrocyclic Inhibitors of 3C and 3C-like Proteases of Picornavirus, Norovirus, and Coronavirus, Bioorg Med Chem Lett. 23(13):3709-3712.
Miettinen et al., 1994, TGF-β Induced Transdifferentiation of Mammary Epithelial Cells to Mesenchymal Cells: Involvement of Type I Receptors, J Cell Biol. 127(6 Pt 2):2021-2036.
Morton et al., 2013, A Macrocyclic Caplain Inhibitor Slows the Development of Inherited Cortical Cataracts in a Sheep Model, Invest Ophthal Visual Science. 54(1):389-395.
Nam et al., 2008, Design and synthesis of 4-quinolinone 2-carboxamides as calpain inhibitors, Bioorg Med Chem Lett., 18(1):205-209.
Nema et al., 2011, Excipients and Their Role in Approved Injectable Products: Current Usage and Future Directions, PDA J Pharm Sci Technol. 65(3):287-332.
Pegorier et al., 2010, Bone Morphogenetic Protein (BMP)-4 and BMP-7 regulate differentially Transforming Growth Factor (TGF)-β1 in normal human lung fibroblasts (NHLF), Respir Res. 11:85 in 11 pages.
Pehere et al., 2012, New β-Strand Templates Constrained bt Huisgen Cycloaddition, Org Lett. 14(5):1330-1333.
Pehere et al., 2013, New cylindrical peptide assemblies defined by extended parallel β-sheets, Org Biomol Chem. 11(3):425-429.
Pehere et al., 2013, Synthesis and Extended Activity of Triazole-Containing Macrocyclic Protease Inhibitors, Chem Eur J. 19:7975-7981.
Powell et al., 1998, Compendium of Excipients for Parenteral Formulations, pDA; J Pharm Sci Technol. 52(5):238-311.
Ravulapalli et al., 2009, Distinguishing between calpain heterodimerization and homodimerization, FEBS J. 276(4):973-982.
Rotstein et al., 2014, Spirocyclic hypervalent iodine(III)-mediated radiofluorination of non-activated and hindered aromatics, Nature Comm. 5:4365-4371.
Rotstein et al., 2016, Mechanistic Studies and Radiofluorination of Structurally Diverse Pharmaceuticals with Spiroyclic Iodonium(III) Ylides, Chem Sci. 7(7):4407-4417.
Santos et al., 2012, Distinct Regulatory Functions of Calpain 1 and 2 during Neural Stem Cell Self-Renewal and Differentiation, PLoS One 7(3):e33468 in 12 pages.
Schád et al., 2002, A novel human small subuit of calpains, Biochem J 342(Pt 2):383-388.
Stuart et al., 2011, Molecular Modeling: A Search for a Calpain Inhibitor as a New Treatment for Cataractogenesis, J Med Chem. 54(21):7503-7522.
Walker et al., 2001, General method for the synthesis of cyclic peptidomimetic compounds, Tetrahed Letts. 42(34):5801-5804.

(56) References Cited

OTHER PUBLICATIONS

Wells et al., 2001, 1,2-Benzothiazine 1,1-Dioxide $P_2$-$P_3$ Peptide Mimetic Aldehyde Calpain I Inhibitors, J Med Chem. 44:3488-3503.
Woon et al., 2011, Structure guided development of potent reversibly binding penicillin binding protein inhibitors, ACS Med Chem Lett., 2(3):219-223 and Supporting Information, S1-S46.
Young et al., 2010, Beyond the Canonical 20 Amino Acids: Expanding the Genetic Lexicon, J Biol Chem. 285(15):11039-11044.
Donald et al., "C10 N-Acyl Modified FK-506: A Possible Hybrid Analogue of the Transition State of Peptidyl-Prolyl Cis-Trans Isomerization," Tetrahedron Letters, 1991, vol. 32 (10), pp. 1375-1378.
International Search report and Written Opinion received in PCT Application No. PCT/US2017/021285, dated Jun. 21, 2017.
Stoermer, et al., "Base Sensitivity of Arginine Alpha-Ketoamide Inhibitors of Serine Proteases," Aust. J. Chem., 2009, vol. 62(9), pp. 988-992.
Von Dobeneck, et al. "Diaminopyrrolinone," Liebigs Ann. Chem., 1976, vol. 3, pp. 476-486.

CYCLIC KETO-AMIDE COMPOUNDS AS CALPAIN MODULATORS AND METHODS OF PRODUCTION AND USE THEREOF

BACKGROUND

Field of the Invention

The present disclosure relates to small molecule calpain modulatory compounds, pharmaceutical compositions comprising the compounds, and methods of using the compounds and compositions to modulate calpain activity, including methods to treat diseases and conditions mediated at least in part by the physiologic effects of CAPN1, CAPN2 or CAPN9, or combinations thereof.

Description of the Related Art

Fibrotic disease accounts for an estimated 45% of deaths in the developed world but the development of therapies for such diseases is still in its infancy. The current treatments for fibrotic diseases, such as for idiopathic lung fibrosis, renal fibrosis, systemic sclerosis, and liver cirrhosis, are few in number and only alleviate some of the symptoms of fibrosis while failing to treat the underlying cause.

Despite the current limited understanding of the diverse etiologies responsible for these conditions, similarities in the phenotype of the affected organs, across fibrotic diseases, strongly support the existence of common pathogenic pathways. At present, it is recognized that a primary driver of fibrotic disease is a high transforming growth factor-beta (TGFβ) signaling pathway which can promote the transformation of normally functioning cells into fibrosis-promoting cells. Termed "myofibroblasts," these transformed cells can secrete large amounts of extracellular matrix proteins and matrix degrading enzymes, resulting in the formation of scar tissue and eventual organ failure. This cellular process is transformative and termed "myofibroblast differentiation" (which includes Epithelial-to-Mesenchymal Transition (EpMT) and its variations like Endothelial-to-Mesenchymal Transition (EnMT) and Fibroblast-to-Myofibroblast Transition (FMT)). This process is a major target for the treatment of fibrotic diseases. Myofibroblast differentiation has also been shown to occur within cancer cells that have been chronically exposed to high TGFβ, causing stationary epithelial cells to become motile, invasive, and metastasize. Thus, within the context of cancer, the signaling has been documented to associate with the acquisition of drug resistance, immune system evasion, and development of stem cell properties.

Despite the tremendous potential of myofibroblast differentiation-inhibiting drugs, and the numerous attempts to develop a working treatment, the data gathered thus far has yet to translate into practical therapy. This is partly due to the lack of an ideal target protein. Initial strategies to target the myofibroblast differentiation process focused on proximal inhibition of the TGFβ signaling pathway by various methods, including targeting ligand activators (e.g., alpha-v integrins), ligand-receptor interactions (e.g., using neutralizing antibodies) or TGFβ receptor kinase activity (e.g., small molecule chemical compound drugs to block signal transduction). Unfortunately, TGFβ is a pleiotropic cytokine with many physiological functions such that global suppression of TGFβ signaling was also associated with severe side effects. Additionally, current data suggests that such proximal inhibition may be vulnerable to pathologic workaround strategies (i.e., due to redundancy or compensation), that would limit the utility of such drugs. Further complicating matters is that, in cancer, TGFβ signaling early on functions as an anti-tumorigenic growth inhibitor but later becomes tumor promoting and is another reason why selective inhibition of pathogenic elements of signaling is so strongly desired. In light of these inherent limitations, current treatment strategies have refocused on identification and inhibition of critical distal events in TGFβ signaling, which in theory would preferentially target the pathologic, but not physiological functions of TGFβ signaling.

SUMMARY OF THE INVENTION

The inventors have found a series of keto-amide compounds that inhibit CAPN1, CAPN2, and/or CAPN9 and affect a chain of cellular effects so as to elicit therapeutic benefits. In some embodiments, compounds are inhibitors clapains. In some embodiments, compounds are selective and/or specific calpain inhibitors. In some embodiments, compounds are specific inhibitors of one of: CAPN1, CAPN2 or CAPN9. In some embodiments, compounds are selective inhibitors of one of: CAPN1, CAPN2 or CAPN9. In some embodiments, compounds are selective inhibitors of: CAPN1 and CAPN2, or CAPN1 and CAPN9, or CAPN2 and CAPN9. In some embodiments, compounds are effective inhibitors of CAPN1, CAPN2 and/or CAPN9.

Combination therapy through one molecule is unique in pharmacology since most drugs have only one or two enzymatic targets. Keto-amide compounds of the present invention are broadly effective in treating a host of conditions arising from fibrosis or inflammation, and specifically including those associated with myofibroblast differentiation. Accordingly, compounds of the invention are active therapeutics for a diverse set of diseases or disorders that include or that produces a symptom which include, but are not limited to: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases or disorders.

Certain embodiments of the present invention are directed toward using these keto-amide compounds to treat diseases or conditions or that produces a symptom in a subject which include, but not limited to: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases.

In certain embodiments methods are provided for alleviating or ameliorating a condition or disorder, affected at least in part by the enzymatic activity of CAPN1, CAPN2, and/or CAPN9, or mediated at least in part by the enzymatic activity of CAPN1, CAPN2, and/or CAPN1 wherein the condition includes or produces a symptom which includes: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and/or rheumatoid arthritis.

In some embodiments, the methods, compounds, and/or compositions of the present invention are used for prophylactic therapy.

In some embodiments, the CAPN1, CAPN2, and/or CAPN9 inhibiting compounds demonstrate efficacy in animal models of human disease. Specifically, in-vivo treatment of mice, rabbits, and other mammalian subjects with compounds of the present invention establish the utility of these compounds as therapeutic agents to modulate CAPN1, CAPN2, and/or CAPN9 activities in humans and thereby ameliorate corresponding medical conditions.

Some embodiments provide compounds, pharmaceutical compositions, and methods of use to inhibit myofibroblast differentiation. Some embodiments provide compounds, pharmaceutical compositions, and methods of use for inhibiting CAPN1, CAPN2, and/or CAPN9 or combinations of these enzyme activities such as CAPN1 and CAPN2, or CAPN1 and CAPN9, or CAPN2 and CAPN9. Some embodiments provide methods for treatment of diseases and disorders by inhibiting CAPN1, CAPN2, and/or CAPN9 or combinations of these enzymatic activities.

Certain embodiments provide novel small molecules that are specific or selective inhibitors of CAPN1, CAPN2, and/or CAPN9 activity, or selective inhibitors of combinations of CAPN1, CAPN2 and CAPN9 activities, e.g., selective inhibitors of CAPN1 and CAPN2, or CAPN1 and CAPN9, or CAPN2 and CAPN9.

In certain embodiments, the compound has a structure represented by Formula I:

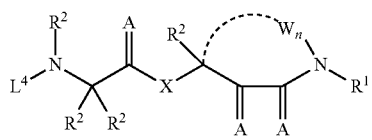

Formula I where:

n is from 1-12;

each A is independently selected from the group consisting of: O and S;

X is NH or $NR^2$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

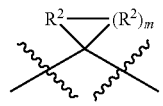

where m is 1-19, sulfonyl, substituted sulfonyl, sulfinyl, and substituted sulfinyl, wherein any two adjacent W atoms may form $CR^2=CR^2$ or C≡C;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, aminoacyl, phthalimido, and formyl;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

Some embodiments include a compound selected from the group consisting of:

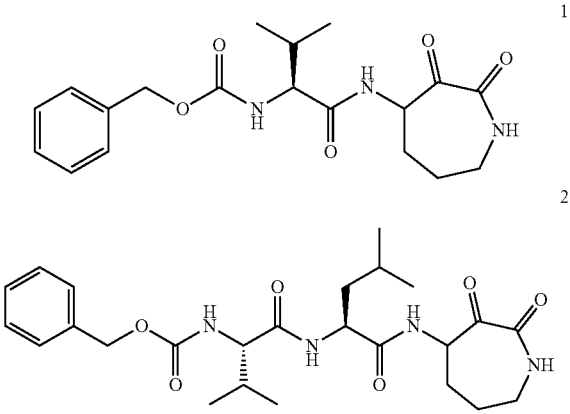

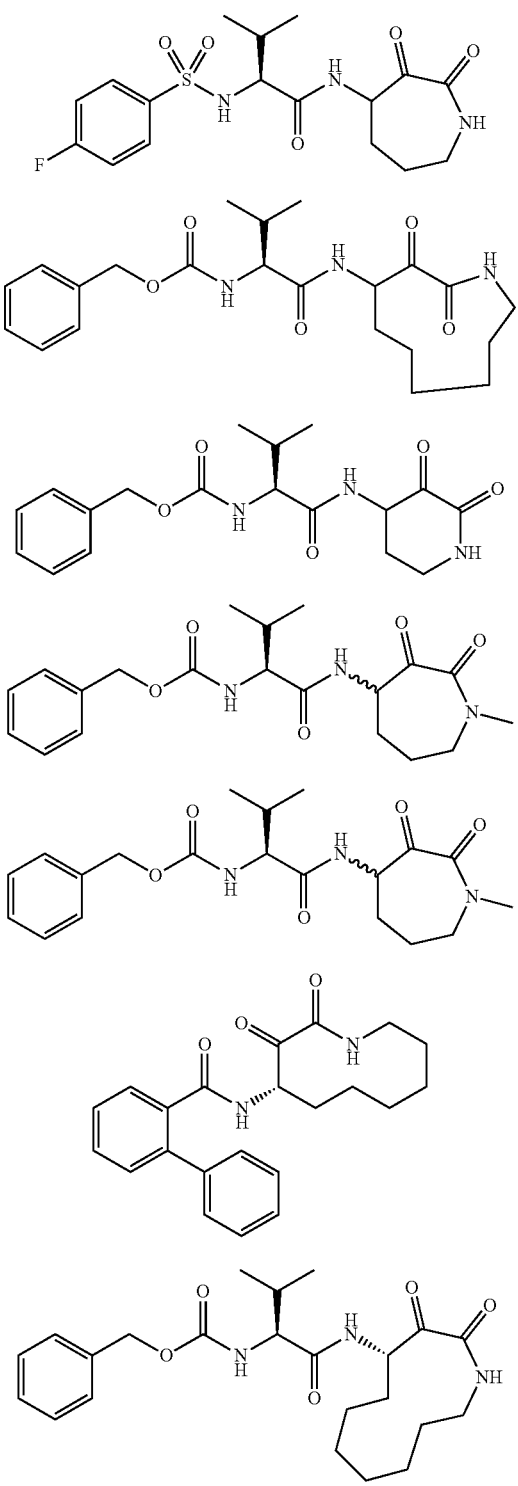

or a pharmaceutically acceptable salt thereof.

In a related aspect, pharmaceutical compositions are provided that include an effective amount of one or more compounds of Formula I-XXXII described herein and a pharmaceutically acceptable excipient.

In certain embodiments, methods are provided for inhibiting CAPN1, CAPN2 or CAPN9 that includes contacting (in vivo or in vitro) cells (including neurons/microglia/invading macrophages) with an effective amount of one or more compounds of Formula I-XXXII described herein.

In certain embodiments, methods are provided for selectively inhibiting one of: CAPN1, CAPN2, or CAPN9 that includes contacting (in vivo or in vitro) cells (including neurons/microglia/invading macrophages) with an effective amount of one or more compounds of Formula I-XXXII described herein.

In other embodiments, methods are provided for selectively inhibiting two of: CAPN1, CAPN2, or CAPN9 (e.g., CAPN1 and CAPN2, or CAPN1 and CAPN9 or CAPN2 and CAPN9) that includes contacting (in vivo or in vitro) cells (including neurons/microglia/invading macrophages) with an effective amount of one or more compounds of Formula I-XXXII described herein.

In other embodiments, methods are provided for specifically inhibiting one of: CAPN1, CAPN2, or CAPN9 that includes contacting (in vivo or in vitro) cells (including neurons/microglia/invading macrophages) with an effective amount of one or more compounds of Formula I-XXXII described herein.

In other embodiments, methods are provided for specifically inhibiting two of: CAPN1, CAPN2, or CAPN9 (e.g., CAPN1 and CAPN2, or CAPN1 and CAPN9 or CAPN2 and CAPN9) that includes contacting (in vivo or in vitro) (including neurons/microglia/invading macrophages) with an effective amount of one or more compounds of Formula I-XXXII described herein.

In an aspect, a method is provided for treating a disease or disorder affected at least in part by CAPN1, CAPN2, and/or CAPN9, where the method comprises administering to a subject in need of treatment an effective amount of one or more compounds of Formula I-XXXII, or a pharmaceutical composition comprising a pharmaceutically acceptable excipient and an effective amount of one or more compounds of Formula I-XXXII described herein.

In one aspect, an article of manufacture is provided for use in inhibiting CAPN1, CAPN2, and/or CAPN9 and treating a disease or disorder affected at least in part by CAPN1, CAPN2, and/or CAPN9, wherein the article comprises a a compound of Formula I-XXXII as provided herein. The diseases affected at least in part by CAPN1, CAPN2, and/or CAPN9 are as provided herein. In some embodiments, the article of manufacture further includes a label with instructions for using the composition to treat a disease or disorder affected at least in part by CAPN1, CAPN2, and/or CAPN9.

These and other embodiments are described in further detail herein.

DETAILED DESCRIPTION OF THE INVENTION

Utility

Compounds of the present invention inhibit calpain. Specifically, these compounds of Formula I-XXXII inhibit CAPN 1, 2, and/or 9. Such compounds are useful for the treatment or therapy of fibrotic and other diseases.

Definitions

Terms used in the claims and specification are defined as set forth below unless otherwise specified. Further, if any term or symbol used herein is not defined as set forth below, it shall have its ordinary meaning in the art.

As used herein and in the appended claims, singular articles such as "a," "an" and "the" and similar referents in the context of describing the elements (especially in the context of the following claims) are to be construed to cover both the singular and the plural, unless otherwise indicated herein or clearly contradicted by context. Recitation of ranges of values herein are merely intended to serve as a shorthand method of referring individually to each separate value falling within the range, including the upper and lower bounds of the range, unless otherwise indicated herein, and each separate value is incorporated into the specification as if it were individually recited herein. All methods described herein can be performed in any suitable order unless otherwise indicated herein or otherwise clearly contradicted by context. The use of any and all examples, or exemplary language (e.g., "such as") provided herein, is intended merely to better illuminate the embodiments and does not pose a limitation on the scope of the claims unless otherwise stated. No language in the specification should be construed as indicating any non-claimed element as essential.

Generally, reference to a certain element such as hydrogen or H is meant to include all isotopes of that element. For example, if an R group is defined to include hydrogen or H, it also includes deuterium and tritium. Compounds comprising radioisotopes such as tritium, $C^{14}$, $P^{32}$ and $S^{35}$ are thus within the scope of the present technology. Procedures for inserting such labels into the compounds of the present technology will be readily apparent to those skilled in the art based on the disclosure herein.

As used herein, "a fibrotic disease" includes, for example, liver fibrosis (alcoholic, viral, autoimmune, metabolic and hereditary chronic disease), renal fibrosis (e.g., resulting from chronic inflammation, infections or type II diabetes), lung fibrosis (idiopathic or resulting from environmental insults including toxic particles, sarcoidosis, asbestosis, hypersensitivity pneumonitis, bacterial infections including tuberculosis, medicines, etc.), interstitial fibrosis, systemic scleroderma (autoimmune disease in which many organs become fibrotic), macular degeneration (fibrotic disease of the eye), pancreatic fibrosis (resulting from, for example, alcohol abuse and chronic inflammatory disease of the pancreas), fibrosis of the spleen (from sickle cell anemia, other blood disorders) cardiac fibrosis (resulting from infection, inflammation and hypertrophy), mediastinal fibrosis, myelofibrosis, endomyocardial fibrosis, retroperitoneal fibrosis, progressive massive fibrosis, nephrogenic systemic fibrosis, fibrotic complications of surgery, especially surgical implants, injection fibrosis and secondary conditions and disease states of fibrosis. Secondary conditions and disease states which occur as a consequence of or associated with fibrosis include for example, cirrhosis, diffuse parenchymal lung disease, post-vasectomy pain syndrome and rheumatoid arthritis, among others.

The term "ameliorating" refers to any therapeutically beneficial result in the treatment of a disease state, e.g., an inflammatory disease state, including lessening in the severity or progression, remission, or cure thereof. In some embodiments, "ameliorating" includes prophylaxis of a disease state.

The term "in vitro" refers to processes that occur in a living cell growing separate from a living organism, e.g., growing in tissue culture.

The term "in vivo" refers to processes that occur in a living organism.

The term "mammal" as used herein includes both humans and non-humans and include but is not limited to humans, non-human primates, canines, felines, murines, bovines, equines, and porcines.

The term "sufficient amount" means an amount sufficient to produce a desired effect, e.g., an amount sufficient to modulate protein aggregation in a cell.

The term "therapeutically effective amount" is an amount that is effective to ameliorate a symptom of a disease. A therapeutically effective amount can, in some embodiments, be a "prophylactically effective amount" as prophylaxis can be considered therapy.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and diastereomeric mixtures, as well as the individual optical isomers can be isolated or synthesized so as to be substantially free of their enantiomeric or diastereomeric partners, and these stereoisomers are all within the scope of the present technology.

The compounds of the present technology can exist as solvates, especially hydrates. Hydrates may form during manufacture of the compounds or compositions comprising the compounds, or hydrates may form over time due to the hygroscopic nature of the compounds. Compounds of the present technology can exist as organic solvates as well, including DMF, ether, and alcohol solvates among others. The identification and preparation of any particular solvate is within the skill of the ordinary artisan of synthetic organic or medicinal chemistry.

"Subject" refers to a mammalian organism treated using a compound of the present invention. The "subject" can be a human or non-human mammalian organism.

"Tautomer" refer to alternate forms of a compound that differ in the position of a proton, such as enol-keto and imine-enamine tautomers, or the tautomeric forms of heteroaryl groups containing a ring atom attached to both a ring NH moiety and a ring =N moiety such as pyrazoles, imidazoles, benzimidazoles, triazoles, and tetrazoles.

"Treating" or "treatment" of a disease or disorder in a subject refers to 1) preventing the disease or disorder from occurring in a subject that is predisposed or does not yet display symptoms of the disease or disorder; 2) inhibiting the disease or disorder or arresting its development; or 3) ameliorating or alleviating the cause of the regression of the disease or disorder.

Unless indicated otherwise, the nomenclature of substituents that are not explicitly defined herein are arrived at by naming the terminal portion of the functionality followed by the adjacent functionality toward the point of attachment. For example, the substituent "alkoxycarbonylalkyl" refers to the group (alkoxy)-C(O)-(alkyl)-.

As used herein, the following definitions shall apply unless otherwise indicated. Further, if any term or symbol used herein is not defined as set forth below, it shall have its ordinary meaning in the art.

As used herein, "naturally occurring amino acid side chain" will be understood to be the substituent of a natural amino acid. Naturally occurring amino acids have a substituent attached to the α-carbon. Naturally occurring amino acids include the list shown below.
Charged:
Arginine—Arg—R
Lysine—Lys—K
Aspartic acid—Asp—D
Glutamic acid—Glu—E
Polar (May Participate in Hydrogen Bonds):
Glutamine—Gln—Q Asparagine—Asn—N
Histidine—His—H
Serine—Ser—S
Threonine—Thr—T
Tyrosine—Tyr—Y
Cysteine—Cys—C
Methionine—Met—M
Tryptophan—Trp—W
Hydrophobic (Normally Buried Inside the Protein Core):
Alanine—Ala—A
Isoleucine—Ile—I
Leucine—Leu—L
Phenylalanine—Phe—F
Valine—Val—V
Proline—Pro—P
Glycine—Gly—G.

As used herein, "non-naturally occurring amino acid side chain" will be understood to be the substituent of a non-naturally occurring amino acid. Non-naturally occurring amino acids have a substituent attached to the α-carbon. Non-naturally occurring amino acids include the list described below.

Non-natural amino acids include β-amino acids ($β^3$ and $β^2$), Homo-amino acids, Proline and Pyruvic acid derivatives, 3-substituted Alanine derivatives, Glycine derivatives, Ring-substituted Phenylalanine and Tyrosine Derivatives, Linear core amino acids and N-methyl amino acids. Exemplary non-natural amino acids are available from Sigma-Aldridge, listed under "unnatural amino acids & derivatives." See also, Travis S. Young and Peter G. Schultz, "Beyond the Canonical 20 Amino Acids: Expanding the Genetic Lexicon," J. Biol. Chem. 2010 285: 11039-11044.

As used herein, the phrase "modulating or inhibiting (the activity of) CAPN1, CAPN2, and/or CAPN9" refers to use of any agent capable of altering the cellular expression levels and/or biological activity of the CAPN1, CAPN2, and/or CAPN9 gene, messenger RNA, or protein. In some embodiments, an agent that modulates or inhibits the biological activity of CAPN1, CAPN2, and/or CAPN9 directly interferes with the expression (such as transcription, splicing, transport, etc.) of the gene encoding the CAPN1, CAPN2, and/or CAPN9 mRNA. In other embodiments, an agent that modulates or inhibits the activity of CAPN1, CAPN2, and/or CAPN9 directly interferes with the biological activity or production of the CAPN1, CAPN2, and/or CAPN9 proteins (such as though inhibition of translation, post-translational modifications, intracellular transport, disruption of interactions between one or more proteins, etc.). In yet other embodiments, an agent that modulates or inhibits the activity of CAPN1, CAPN2, and/or CAPN9 does not directly affect the expression level or activity of CAPN1, CAPN2, and/or CAPN9 but, instead, alters the activity or expression levels of a protein whose function directly impacts the expression or activity of CAPN1, CAPN2, and/or CAPN9 (such as, for example, calpastatin). In other embodiments, an agent may specifically inhibit one or more CAPN1, CAPN2, and/or CAPN9 enzymes. In yet other embodiments, an agent may selectively inhibit CAPN1, CAPN2, and/or CAPN9 enzymes. In yet other embodiments, an agent may both specifically and selectively inhibit one or more CAPN1, CAPN2, and/or CAPN9 enzymes. In yet other embodiments, an agent is neither a specific nor selective inhibitor for one or more CAPN1, CAPN2, and/or CAPN9 enzymes, but is still active for the inhibition of one or more of the CAPN1, CAPN2, and/or CAPN9 enzymes. Calpains are also expressed in cells other than neurons, microglia and invading macrophages. In particular, they are important in skeletal muscle and herein inhibition of calpains also refers to inhibition in these cells as well.

As used herein, an agent is said to be "specific" if it reacts or associates more frequently, more rapidly, with greater duration and/or with greater affinity with a particular target (for example, a protein, such as CAPN9, CAPN2, or CAPN1 as well as a nucleic acid encoding the same) than it does with alternative substances, especially as compared to substances that are structurally related to the target, e.g., an isoform of the target. For instance, an antibody "specifically binds" to a target protein (such as CAPN9, CAPN2, or CAPN1 if it binds with greater affinity, avidity, more readily, and/or with greater duration than it binds to other substances.

In some embodiments, an agent is "specific" for a target if a concentration of the agent that produces a maximal effect in an in vitro or in vivo target assay (e.g., a binding assay or an enzyme activity assay) produces no measurable effect in a comparable assay carried out using another substance, especially one or more substances that are structurally related to the target.

As used herein, an agent is said to be a "specific inhibitor" of CAPN1, CAPN2 or CAPN9 if it inhibits the biological activity and/or expression level of CAPN1, CAPN2 or CAPN9 without inhibiting the biological activity and/or expression level of other members of the calpain family of proteases or other members of the TRP family of calcium channels.

As used herein, an agent is an agent is said to be "selective" if it reacts or associates more frequently, more rapidly, with greater duration and/or with greater affinity with a particular target or a small set of structurally-related targets (for example, a protein, such as CAPN9, CAPN2, or CAPN1 as well as a nucleic acid encoding the same) than it does with alternative substances, especially as compared to other substances that are structurally related to the target or small set of structurally-related targets, e.g., an isoform of the target. In certain embodiments, a "selective" agent reacts similarly with multiple related targets, whereas a "specific" agent reacts with its target in a manner that is markedly differently from the way it interacts with other biological molecules. For instance, an antibody "selectively binds" to a target protein (such as CAPN9, CAPN2, or CAPN1 if it binds with greater affinity, avidity, more readily, and/or with greater duration to two related targets (e.g., CAPN9, CAPN2) than it binds to other substances.

In some embodiments, an agent is "selective" for a set of targets if a concentration of the agent that produces a maximal effect in an in vitro or in vivo assay (e.g., a binding assay or an enzyme activity assay) with a first target molecule produces a measurable effect in a comparable assay carried out using a second target molecule. In some embodiments, an agent is selective if it binds to two or more targets (especially structurally-related targets) with Kd or IC50 (or other related measures) ratios of first to second target that are within a range of 1:1 to about 1:500.

As used herein, in some embodiments, an agent is said to be a "selective inhibitor" of CAPN1, CAPN2 or CAPN9 if it can be shown to inhibit the biological activity and/or expression level of two or three of CAPN1, CAPN2 or CAPN9 (e.g., CAPN1 and CAPN2, or CAPN1 and CAPN9, or CAPN2 and CAPN9 or CAPN1, CAPN2 and CAPN9) without inhibiting the biological activity and/or expression level of level of other members of the calpain family of proteases or other members of the TRP family of calcium channels.

As used herein, the term "contacting," as used herein, includes both directly contacting cells, for example, in vivo, in vitro, or ex vivo, or indirectly contacting cells, such as, for example, by administering an agent to a subject. Further, "contacting" a cell with an agent includes administering or applying a prodrug version of the agent. In some embodiments, the cell is in a fibrotic tissue, a cancerous tissue, and/or tissue with high TGFβ signaling.

As used herein, the term "fibrosis" refers to the increased extracellular matrix protein synthesis and deposition that results in the accumulation of scar tissue. Similarly, as used herein, the term "fibrotic tissue" refers to tissue that has high levels of extracellular matrix proteins (i.e., collagen), undergone extensive remodeling (though activity of matrix metalloproteinases) and exhibits progressively diminished physiological function, due to the activity of cells that have undergone myofibroblast differentiation (such as, EMT and/or FMT). In some embodiments, the cell is in a cancerous tissue, such as in tissue that comprises at least one cancer cell. In some embodiments, the cell is in a tissue with high TGFβ signaling.

As used herein, the term "inhibit," "decrease" and grammatical derivations thereof, refers to the ability of an agent to block, partially block, interfere, reduce or deactivate a pathway or mechanism of action. Thus, one of ordinary skill in the art would appreciate that the term "inhibit" or "decrease" encompasses a complete and/or partial loss of activity, e.g., a loss in activity by at least 10%, in some embodiments, a loss in activity by at least 20%, 30%, 50%, 75%, 95%, 98%, and up to and including 100%.

As used herein, the term "expression level and/or activity of a calpain" refers to the amount of a calpain found in a cell, tissue and/or subject, and/or a function of a calpain. Such functions can include, without limitation, its protease ability, its function in modulating TGFβ signaling, its function in myofibroblast transition (such as EMT and/or FMT). In some embodiments, the expression level of a calpain refers to mRNA expression level. In other embodiments, the expression level of a calpain refers to protein expression level. In some embodiments, the myofibroblast transition is EMT (such as a TGFβ-mediated EMT). In some embodiments, at least one agent inhibits Fibroblast-to-Myofibroblast Transition (FMT). In some embodiments, the calpain is CAPN9, CAPN1, and/or CAPN2.

As used herein, the terms "prevent," "preventing," "prevention," "prophylactic treatment" and the like refer to reducing the probability of developing a disease, disorder, or condition in a subject, who does not have, but is at risk of or susceptible to developing a disease, disorder, or condition. Thus, in some embodiments, an agent can be administered prophylactically to prevent the onset of a disease, disorder, or condition, or to prevent the recurrence of a disease, disorder, or condition.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to a value can be meant to encompass variations of, in some aspects, ±100% in some aspects ±50%, in some aspects ±20%, in some aspects ±10%, in some aspects ±5%, in some aspects ±1%, in some aspects ±0.5%, and in some aspects ±0.1% from the specified amount, as such variations are appropriate to perform the disclosed methods or employ the disclosed compositions.

Unless defined otherwise, all technical and scientific terms used herein have the meaning commonly understood by a person skilled in the art to which this invention belongs.

"Alkyl" refers to monovalent saturated aliphatic hydrocarbyl groups having from 1 to 10 carbon atoms and preferably 1 to 6 carbon atoms. This term includes, by way of example, linear and branched hydrocarbyl groups such as methyl ($CH_3$—), ethyl ($CH_3CH_2$—), n-propyl ($CH_3CH_2CH_2$—), isopropyl (($CH_3)_2CH$—), n-butyl ($CH_3CH_2CH_2CH_2$—), isobutyl (($CH_3)_2CHCH_2$—), sec-butyl (($CH_3)(CH_3CH_2)CH$—), t-butyl (($CH_3)_3C$—), n-pentyl ($CH_3CH_2CH_2CH_2CH_2$—), and neopentyl (($CH_3)_3CCH_2$—). $C_x$ alkyl refers to an alkyl group having x number of carbon atoms.

"Alkenyl" refers to straight or branched hydrocarbyl groups having from 2 to 6 carbon atoms and preferably 2 to 4 carbon atoms and having at least 1 and preferably from 1 to 2 sites of unsaturation (>C=C<). Such groups are exemplified, for example, by vinyl, allyl, and but-3-en-1-yl. Included within this term are the cis and trans isomers or mixtures of these isomers. $C_x$ alkenyl refers to an alkenyl group having x number of carbon atoms.

"Alkynyl" refers to straight or branched monovalent hydrocarbyl groups having from 2 to 6 carbon atoms and preferably 2 to 3 carbon atoms and having at least 1 and preferably from 1 to 2 sites of acetylenic (—C≡C—) unsaturation. Examples of such alkynyl groups include acetylenyl (—C≡CH), and propargyl (—CH$_2$C≡CH). $C_x$ alkynyl refers to an alkynyl group having x number of carbon atoms.

"Substituted alkyl" refers to an alkyl group having from 1 to 5, preferably 1 to 3, or more preferably 1 to 2 substituents selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

In some embodiments the substituted alkyl groups include halogenated alkyl groups and particularly halogenated methyl groups such as trifluoromethyl, difluromethyl, fluoromethyl and the like.

"Cycloalkyl" or "Cyclyl alkyl" refers to a saturated or partially saturated, but not aromatic, group having from 1 to 10 ring carbon atoms and no heteroatoms. Cycloalkyl encompasses single ring or multiple condensed rings, including fused bridged and spiro ring systems. In fused ring systems, one or more of the rings can be cycloalkyl, aryl, heterocycloalkyl, or heteroaryl provided that the point of attachment is through the original non-aromatic cycloalkyl ring.

"Substituted alkenyl" refers to alkenyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxy or thiol substitution is not attached to a vinyl (unsaturated) carbon atom.

"Substituted alkynyl" refers to alkynyl groups having from 1 to 3 substituents, and preferably 1 to 2 substituents, selected from the group consisting of alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, $SO_3H$, substituted sulfonyl, sulfonyloxy, thioacyl, thiol, alkylthio, and substituted alkylthio, wherein said substituents are defined herein and with the proviso that any hydroxyl or thiol substitution is not attached to an acetylenic carbon atom.

"Ar" refers to any group which is aromatic. This group must be cyclic; however, it may contain heteroatoms or may not.

"Alkoxy" refers to the group —O-alkyl wherein alkyl is defined herein. Alkoxy includes, by way of example, methoxy, ethoxy, n-propoxy, isopropoxy, n-butoxy, t-butoxy, sec-butoxy, and n-pentoxy.

"Substituted alkoxy" refers to the group —O-(substituted alkyl) wherein substituted alkyl is defined herein. Preferred substituted alkyl groups in —O-(substituted alkyl) include halogenated alkyl groups and particularly halogenated methyl groups such as trifluoromethyl, difluromethyl, fluoromethyl and the like.

"Acyl" refers to the groups H—C(O)—, alkyl-C(O)—, substituted alkyl-C(O)—, alkenyl-C(O)—, substituted alkenyl-C(O)—, alkynyl-C(O)—, substituted alkynyl-C(O)—, cycloalkyl-C(O)—, substituted cycloalkyl-C(O)—, aryl-C(O)—, substituted aryl-C(O)—, heteroaryl-C(O)—, substituted heteroaryl-C(O)—, heterocyclic-C(O)—, and substituted heterocyclic-C(O)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(O)$—.

"Acylamino" refers to the groups —$NR^{30}$C(O)alkyl, —$NR^{30}$C(O)substituted alkyl, —$NR^{30}$C(O)cycloalkyl, —$NR^{30}$C(O)substituted cycloalkyl, —$NR^{30}$C(O)alkenyl, —$NR^{30}$C(O)substituted alkenyl, alkoxy, substituted alkoxy-$NR^{30}$C(O)alkynyl, —$NR^{30}$C(O)substituted alkynyl, —$NR^{30}$C(O)aryl, —$NR^{30}$C(O)substituted aryl, —$NR^{30}$C(O)heteroaryl, —$NR^{30}$C(O)substituted heteroaryl, —$NR^{30}$C(O)heterocyclic, and —$NR^{30}$C(O)substituted heterocyclic wherein $R^{30}$ is hydrogen or alkyl and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl" refers to the groups H—C(N)—, alkyl-C(N)—, substituted alkyl-C(N)—, alkenyl-C(N)—, substituted alkenyl-C(N)—, alkynyl-C(N)—, substituted alkynyl-C(N)—, cycloalkyl-C(N)—, substituted cycloalkyl-C(N)—, aryl-C(N)—, substituted aryl-C(N)—, heteroaryl-C(N)—, substituted heteroaryl-C(N)—, heterocyclic-C(N)—, and substituted heterocyclic-C(N)—, wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein. Acyl includes the "acetyl" group $CH_3C(N)$—.

"Acyloxy" refers to the groups alkyl-C(O)O—, substituted alkyl-C(O)O—, alkenyl-C(O)O—, substituted alkenyl-C(O)O—, alkynyl-C(O)O—, substituted alkynyl-C(O)O—, aryl-C(O)O—, substituted aryl-C(O)O—, cycloalkyl-C(O)O—, substituted cycloalkyl-C(O)O—, heteroaryl-C(O)O—, substituted heteroaryl-C(O)O—, heterocyclic-C(O)O—, and substituted heterocyclic-C(O)O— wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Amino" refers to the group —$NH_2$.

"Substituted amino" refers to the group —$NR^{31}R^{32}$ where $R^{31}$ and $R^{32}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, substituted heterocyclic, and substituted sulfonyl and wherein $R^{31}$ and $R^{32}$ are optionally joined, together with the nitrogen bound thereto to form a heterocyclic or substituted heterocyclic group, provided that $R^{31}$ and $R^{32}$ are both not hydrogen, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic, and substituted heterocyclic are as defined herein. When $R^{31}$ is hydrogen and $R^{32}$ is alkyl, the substituted amino group is sometimes referred to herein as alkylamino. When $R^{31}$ and $R^{32}$ are alkyl, the substituted amino group is sometimes referred to herein as dialkylamino. When referring to a monosubstituted amino, it is meant that either $R^{31}$ or $R^{32}$ is hydrogen but not both. When referring to a disubstituted amino, it is meant that neither $R^{31}$ nor $R^{32}$ are hydrogen.

"Aminocarbonyl" refers to the group —C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminoacyl carbonyloxy" refers to the group —C(NR$^{33}$)OR$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonyl" refers to the group —C(S)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonylamino" refers to the group —NR$^{30}$C(O)NR$^{33}$R$^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminothiocarbonylamino" refers to the group —NR$^{30}$C(S)NR$^{33}$R$^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminocarbonyloxy" refers to the group —O—C(O)NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyl" refers to the group —SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonyloxy" refers to the group —O—SO$_2$NR$^{33}$R$^{34}$ where $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Aminosulfonylamino" refers to the group —NR$^{30}$—SO$_2$NR$^{33}$R$^{34}$ where $R^{30}$ is hydrogen or alkyl and $R^{33}$ and $R^{34}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where $R^{33}$ and $R^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Amidino" refers to the group —C(=NR$^{35}$)NR$^{33}$R$^{34}$ where R$^{33}$, R$^{34}$, and R$^{35}$ are independently selected from the group consisting of hydrogen, alkyl, substituted alkyl, alkenyl, substituted alkenyl, alkoxy, substituted alkoxy, alkynyl, substituted alkynyl, aryl, substituted aryl, cycloalkyl, substituted cycloalkyl, heteroaryl, substituted heteroaryl, heterocyclic, and substituted heterocyclic and where R$^{33}$ and R$^{34}$ are optionally joined together with the nitrogen bound thereto to form a heterocyclic or substituted heterocyclic group, and wherein alkyl, substituted alkyl, alkenyl, substituted alkenyl, alkoxy, substituted alkoxy, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substituted aryl" refers to aryl groups which are substituted with 1 to 5, preferably 1 to 3, or more preferably 1 to 2 substituents selected from the group consisting of alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester) amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Aryloxy" refers to the group —O-aryl, where aryl is as defined herein, that includes, by way of example, phenoxy and naphthoxy.

"Substituted aryloxy" refers to the group —O-(substituted aryl) where substituted aryl is as defined herein.

"Arylthio" refers to the group —S-aryl, where aryl is as defined herein.

"Substituted arylthio" refers to the group —S-(substituted aryl), where substituted aryl is as defined herein.

"Carbonyl" refers to the divalent group —C(O)— which is equivalent to —C(=O)—.

"Carboxy" or "carboxyl" refers to —COOH or salts thereof.

"Carboxyl ester" or "carboxy ester" refers to the groups —C(O)O-alkyl, —C(O)O-substituted alkyl, —C(O)O-alkenyl, —C(O)O-substituted alkenyl, —C(O)O-alkynyl, —C(O)O-substituted alkynyl, —C(O)O-aryl, —C(O)O-substituted aryl, —C(O)O-cycloalkyl, —C(O)O-substituted cycloalkyl, —C(O)O-heteroaryl, —C(O)O-substituted heteroaryl, —C(O)O-heterocyclic, and —C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)amino" refers to the group —NR$^{30}$—C(O)O-alkyl, —NR$^{30}$—C(O)O-substituted alkyl, —NR$^{30}$—C(O)O-alkenyl, —NR$^{30}$—C(O)O-substituted alkenyl, —NR$^{30}$—C(O)O-alkynyl, —NR$^{30}$—C(O)O-substituted alkynyl, —NR$^{30}$—C(O)O-aryl, —NR$^{30}$—C(O)O-substituted aryl, —NR$^{30}$—C(O)O-cycloalkyl, —NR$^{30}$—C(O)O-substituted cycloalkyl, —NR$^{30}$—C(O)O-heteroaryl, —NR$^{30}$—C(O)O-substituted heteroaryl, —NR$^{30}$—C(O)O-heterocyclic, and —NR$^{30}$—C(O)O-substituted heterocyclic wherein R$^{30}$ is alkyl or hydrogen, and wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"(Carboxyl ester)oxy" refers to the group —O—C(O)O-alkyl, —O—C(O)O-substituted alkyl, —O—C(O)O-alkenyl, —O—C(O)O-substituted alkenyl, —O—C(O)O-alkynyl, —O—C(O)O-substituted alkynyl, —O—C(O)O-aryl, —O—C(O)O-substituted aryl, —O—C(O)O-cycloalkyl, —O—C(O)O-substituted cycloalkyl, —O—C(O)O-heteroaryl, —O—C(O)O-substituted heteroaryl, —O—C(O)O-heterocyclic, and —O—C(O)O-substituted heterocyclic wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic, and substituted heterocyclic are as defined herein.

"Cyano" refers to the group —C≡N.

"Cycloalkyl" refers to a saturated or unsaturated but nonaromatic cyclic alkyl groups of from 3 to 10 carbon atoms having single or multiple cyclic rings including fused, bridged, and spiro ring systems. C$_x$ cycloalkyl refers to a cycloalkyl group having x number of ring carbon atoms. Examples of suitable cycloalkyl groups include, for instance, adamantyl, cyclopropyl, cyclobutyl, cyclopentyl, and cyclooctyl. One or more the rings can be aryl, heteroaryl, or heterocyclic provided that the point of attachment is through the non-aromatic, non-heterocyclic ring saturated carbocyclic ring. "Substituted cycloalkyl" refers to a cycloalkyl group having from 1 to 5 or preferably 1 to 3 substituents selected from the group consisting of oxo, thione, alkyl, substituted alkyl, alkenyl, substituted alkenyl, alkynyl, substituted alkynyl, alkoxy, substituted alkoxy, acyl, acylamino, aminocarbonylamino, acyloxy, amino, substituted amino, aminocarbonyl, aminothiocarbonyl, aminocarbonylamino, aminothiocarbonylamino, aminocarbonyloxy, aminosulfonyl, aminosulfonyloxy, aminosulfonylamino, amidino, aryl, substituted aryl, aryloxy, substituted aryloxy, arylthio, substituted arylthio, carboxyl, carboxyl ester, (carboxyl ester)amino, (carboxyl ester)oxy, cyano, cycloalkyl, substituted cycloalkyl, cycloalkyloxy, substituted cycloalkyloxy, cycloalkylthio, substituted cycloalkylthio, guanidino, substituted guanidino, halo, hydroxy, heteroaryl, substituted heteroaryl, heteroaryloxy, substituted heteroaryloxy, heteroarylthio, substituted heteroarylthio, heterocyclic, substituted heterocyclic, heterocyclyloxy, substituted heterocyclyloxy, heterocyclylthio, substituted heterocyclylthio, nitro, SO$_3$H, substituted sulfonyl, sulfonyloxy, thioacyl, thiol, alkylthio, and substituted alkylthio, wherein said substituents are defined herein.

"Cycloalkyloxy" refers to —O-cycloalkyl.

"Substituted cycloalkyloxy" refers to —O-(substituted cycloalkyl).

"Cycloalkylthio" refers to —S-cycloalkyl.

"Substituted cycloalkylthio" refers to —S-(substituted cycloalkyl).

"Ethylene glycol" refers to the group —O—CH$_2$CH$_2$—O-E, wherein E is either H or CH$_3$.

"Guanidino" refers to the group —NHC(=NH)NH$_2$.

"Substituted guanidino" refers to —NR$^{36}$C(=NR$^{36}$)N(R$^{36}$)$_2$ where each R$^{36}$ is independently selected from the group consisting of hydrogen, alkyl, substituted alkyl, aryl, substituted aryl, heteroaryl, substituted heteroaryl, heterocyclic, and substituted heterocyclic and two $R^{36}$ groups attached to a common guanidino nitrogen atom are optionally joined together with the nitrogen bound thereto to form a heterocyclic or substituted heterocyclic group, provided that at least one $R^{36}$ is not hydrogen, and wherein said substituents are as defined herein.

"Halo" or "halogen" refers to fluoro, chloro, bromo and iodo and preferably is fluoro or chloro.

"Hydroxy" or "hydroxyl" refers to the group —OH.

"Heteroaryl" refers to an aromatic group of from 1 to 10 carbon atoms and 1 to 4 heteroatoms selected from the group consisting of oxygen, nitrogen and sulfur within the ring. Such heteroaryl groups can have a single ring (e.g., pyridinyl or furyl) or multiple condensed rings (e.g., indolizinyl or benzothienyl) wherein the condensed rings may or may not be aromatic and/or contain a heteroatom provided that the point of attachment is through an atom of the aromatic heteroaryl group. In one embodiment, the nitrogen and/or the sulfur ring atom(s) of the heteroaryl group are optionally oxidized to provide for the N-oxide (N→O), sulfinyl, or sulfonyl moieties. Preferred heteroaryls include 5 or 6 membered heteroaryls such as pyridinyl, pyrrolyl, indolyl, thiophenyl, and furanyl.

"Substituted heteroaryl" refers to heteroaryl groups that are substituted with from 1 to 5, preferably 1 to 3, or more preferably 1 to 2 substituents selected from the group consisting of the same group of substituents defined for substituted aryl.

"Heteroaryloxy" refers to —O-heteroaryl.

"Substituted heteroaryloxy" refers to the group —O-(substituted heteroaryl).

"Heteroarylthio" refers to the group —S-heteroaryl.

"Substituted heteroarylthio" refers to the group —S-(substituted heteroaryl).

"Heterocycle" or "heterocyclic" or "heterocycloalkyl" or "heterocyclyl" refers to a saturated or partially saturated, but not aromatic, group having from 1 to 10 ring carbon atoms and from 1 to 4 ring heteroatoms selected from the group consisting of nitrogen, sulfur, or oxygen. $C_x$ cycloalkyl refers to a heterocycloalkyl group having x number of ring atoms including the ring heteroatoms. Heterocycle encompasses single ring or multiple condensed rings, including fused bridged and spiro ring systems. In fused ring systems, one or more the rings can be cycloalkyl, aryl or heteroaryl provided that the point of attachment is through the non-aromatic ring. In one embodiment, the nitrogen and/or sulfur atom(s) of the heterocyclic group are optionally oxidized to provide for the N-oxide, sulfinyl, sulfonyl moieties.

"Substituted heterocyclic" or "substituted heterocycloalkyl" or "substituted heterocyclyl" refers to heterocyclyl groups that are substituted with from 1 to 5 or preferably 1 to 3 of the same substituents as defined for substituted cycloalkyl.

"Heterocyclyloxy" refers to the group —O-heterocycyl.

"Substituted heterocyclyloxy" refers to the group —O-(substituted heterocycyl).

"Heterocyclylthio" refers to the group —S-heterocycyl.

"Substituted heterocyclylthio" refers to the group —S-(substituted heterocycyl).

Examples of heterocycle and heteroaryl include, but are not limited to, azetidine, pyrrole, imidazole, pyrazole, pyridine, pyrazine, pyrimidine, pyridazine, indolizine, isoindole, indole, dihydroindole, indazole, purine, quinolizine, isoquinoline, quinoline, phthalazine, naphthylpyridine, quinoxaline, quinazoline, cinnoline, pteridine, carbazole, carboline, phenanthridine, acridine, phenanthroline, isothI zole, phenazine, isoxazole, phenoxazine, phenothI zine, imidazolidine, imidazoline, piperidine, piperazine, indoline, phthalimide, 1,2,3,4-tetrahydroisoquinoline, 4,5,6,7-tetrahydrobenzo[b]thiophene, thiazole, thiazolidine, thiophene, benzo[b]thiophene, morpholinyl, thiomorpholinyl (also referred to as thI morpholinyl), 1,1-dioxothiomorpholinyl, piperidinyl, pyrrolidine, and tetrahydrofuranyl.

"Nitro" refers to the group —$NO_2$.

"Oxo" refers to the atom (=O) or (—O).

"Phthalimido" refers to the group

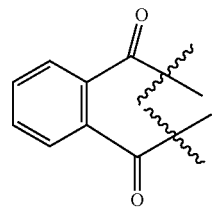

Phthalimide functional groups are well known in the art and can be generated by covalently bonding a nitrogen atom to a $C_6H_4(CO)_2$ group.

"Polyethylene glycol" refers to the group —O—($CH_2CH_2$—O)$_n$-E, wherein E is either H or $CH_3$, where n is between 2-20,000.

"Spirocyclic ring system" refers to a ring system with two rings that has a single ring carbon atom in common to both rings. Herein used the term bicyclic can incorporate up to four heteroatoms in either ring.

"Bicyclic ring system" refers to a ring system with two rings that has two ring carbon atoms in common, and which can located at any position along either ring. Herein used the term bicyclic ring system can incorporate up to four heteroatoms in either ring.

"Sulfinyl" refers to the divalent group —SO—.

"Sulfonyl" refers to the divalent group —$S(O)_2$—.

"Substituted sulfonyl" refers to the group —$SO_2$-alkyl, —$SO_2$-substituted alkyl, —$SO_2$—OH, —$SO_2$-alkenyl, —$SO_2$-substituted alkenyl, —$SO_2$-cycloalkyl, —$SO_2$-substituted cylcoalkyl, —$SO_2$-aryl, —$SO_2$-substituted aryl, —$SO_2$-heteroaryl, —$SO_2$-substituted heteroaryl, —$SO_2$-heterocyclic, —$SO_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfonyl includes groups such as methyl-$SO_2$—, phenyl-$SO_2$—, and 4-methylphenyl-$SO_2$—. Preferred substituted alkyl groups on the substituted alkyl-$SO_2$— include halogenated alkyl groups and particularly halogenated methyl groups such as trifluoromethyl, difluromethyl, fluoromethyl and the like.

"Substituted sulfinyl" refers to the group —SO-alkyl, —SO-substituted alkyl, —SO-alkenyl, —SO-substituted alkenyl, —SO-cycloalkyl, —SO-substituted cylcoalkyl, —SO-aryl, —SO-substituted aryl, —SO-heteroaryl, —SO-substituted heteroaryl, —SO-heterocyclic, —SO-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein. Substituted sulfinyl includes groups such as methyl-SO—, phenyl-SO—, and 4-methylphenyl-SO—. Preferred substituted alkyl groups on the substituted alkyl-SO— include halogenated alkyl groups and particularly halogenated methyl groups such as trifluoromethyl, difluromethyl, fluoromethyl and the like.

"Sulfonyloxy" or "substituted sulfonyloxy" refers to the group —OSO$_2$-alkyl, —OSO$_2$-substituted alkyl, —OSO$_2$—OH, —OSO$_2$-alkenyl, —OSO$_2$-substituted alkenyl, —OSO$_2$-cycloalkyl, —OSO$_2$-substituted cylcoalkyl, —OSO$_2$-aryl, —OSO$_2$-substituted aryl, —OSO$_2$-heteroaryl, —OSO$_2$-substituted heteroaryl, —OSO$_2$-heterocyclic, —OSO$_2$-substituted heterocyclic, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Substitution" or "substitution" generally refers groups which are covalently bonded to an atom to replace a hydrogen atom. The atom in this general context can be a carbon atom or a heteroatom, for example a nitrogen atom.

"Thioacyl" refers to the groups H—C(S)—, alkyl-C(S)—, substituted alkyl-C(S)—, alkenyl-C(S)—, substituted alkenyl-C(S)—, alkynyl-C(S)—, substituted alkynyl-C(S)—, cycloalkyl-C(S)—, substituted cycloalkyl-C(S)—, aryl-C(S)—, substituted aryl-C(S)—, heteroaryl-C(S)—, substituted heteroaryl-C(S)—, heterocyclic-C(S)—, and substituted heterocyclic-C(S)—, wherein alkyl, substituted alkyl, alkenyl, substituted alkenyl, alkynyl, substituted alkynyl, cycloalkyl, substituted cycloalkyl, aryl, substituted aryl, heteroaryl, substituted heteroaryl, heterocyclic and substituted heterocyclic are as defined herein.

"Mercapto" or "thiol" refers to the group —SH.

"Formyl" refers to the group —C(O)H.

"Thiocarbonyl" refers to the divalent group —C(S)— which is equivalent to —C(=S)—.

"Thione" refers to the atom (=S).

"Alkylthio" refers to the group —S-alkyl wherein alkyl is as defined herein.

"Substituted alkylthio" refers to the group —S-(substituted alkyl) wherein substituted alkyl is as defined herein. Preferred substituted alkyl groups on —S-(substituted alkyl) include halogenated alkyl groups and particularly halogenated methyl groups such as trifluoromethyl, difluoromethyl, fluoromethyl and the like.

Stereoisomers of compounds (also known as optical isomers) include all chiral, diastereomeric, and racemic forms of a structure, unless the specific stereochemistry is expressly indicated. Thus, compounds used in the present technology include enriched or resolved optical isomers at any or all asymmetric atoms as are apparent from the depictions. Both racemic and d or l enriched stereomeric mixtures, as well as the individual optical isomers can be isolated or synthesized so as to be substantially free of their enantiomeric or diastereomeric partners, and these stereoisomers are all within the scope of the present technology.

The compounds of the present technology may exist as solvates, especially hydrates. Hydrates may form during manufacture of the compounds or compositions comprising the compounds, or hydrates may form over time due to the hygroscopic nature of the compounds. Compounds of the present technology may exist as organic solvates as well, including DMF, ether, and alcohol solvates among others. The identification and preparation of any particular solvate is within the skill of the ordinary artisan of synthetic organic or medicinal chemistry.

"Tautomer" refer to alternate forms of a compound that differ in the position of a proton, such as enol-keto and imine-enamine tautomers, or the tautomeric forms of heteroaryl groups containing a ring atom attached to both a ring —NH— moiety and a ring =N— moiety such as pyrazoles, imidazoles, benzimidazoles, triazoles, and tetrazoles.

Herein any substituted functional group is substituted at from one to three different positions, and those one to three substituting groups are capable of each independently being substituted at one to three positions, wherein any and each substituting group is independently selected from the group consisting of: halogen, hydroxyl, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, acyl, acylamino, aminocarbonylamino, aminoacyl, acyloxy, amino, substituted amino, aminocarbonyl, aminothiocarbonyl, aminoacyl carbonyloxy, aminocarbonylamino, aminothiocarbonylamino, aminocarbonyloxy, aminosulfonyl, aminosulfonyloxy, aminosulfonylamino, amidino, $C_1$-$C_8$ alkoxy, substituted $C_1$-$C_8$ alkoxy, $C_3$-$C_7$ aryl, substituted $C_3$-$C_7$ aryl, $C_3$-$C_7$ aryloxy, substituted $C_3$-$C_7$ aryloxy, $C_3$-$C_7$ arylthio, substituted $C_3$-$C_7$ arylthio, carboxyl, carboxyl ester, (carboxyl ester)amino, (carboxyl ester)oxy, $C_3$-$C_{10}$ cycloalkyl, substituted $C_3$-$C_{10}$ cycloalkyl, $C_3$-$C_7$ heterocycloalkyl, guanidino, substituted guanidino, $C_3$-$C_7$ heteroaryloxy, $C_3$-$C_7$ substituted heteroaryloxy, $C_3$-$C_7$ heteroarylthio, $C_3$-$C_7$ substituted heteroarylthio, sulfonyl, substituted sulfonyl, sulfinyl, substituted sulfinyl, sulfonyloxy, substituted sulfonyloxy, thioacyl, alkylthio, substituted alkylthio, $C_3$-$C_7$ heteroaryl, and substituted $C_3$-$C_7$ heteroaryl.

Herein any and all heteroaryl and heterocycloalkyl substituents may contain up to four heteroatoms selected from the group consisting of: O, N, and S.

It is understood that in all substituted groups defined above, polymers arrived at by defining substituents with further substituents to themselves (e.g., substituted aryl having a substituted aryl group as a substituent which is itself substituted with a substituted aryl group, etc.) are not intended for inclusion herein. In such cases, the maximum number of such substituents is three. That is to say that each of the above definitions is constrained by a limitation that each functional group is substituted (at from one to three positions) and that any and all of those substituent groups may be substituted one more time (at from one to three positions).

It is understood that the above definitions are not intended to include impermissible substitution patterns (e.g., methyl substituted with 5 fluoro groups). Such impermissible substitution patterns are well known to the skilled artisan.

Throughout this application, the text refers to various embodiments of the present compounds, compositions, and methods. The various embodiments described are meant to provide a variety of illustrative examples and should not be construed as descriptions of alternative species. Rather, it should be noted that the descriptions of various embodiments provided herein may be of overlapping scope. The embodiments discussed herein are merely illustrative and are not meant to limit the scope of the present technology.

Compound numbering used herein is merely for convenience and meant for the specific section, scheme, or table in which they appear. They should not be construed or confused with the same numberings, if any, used in other sections, schemes, or tables.

Compounds of the Present Technology

The present technology is directed to compounds, compositions, and methods of using said compounds or compositions to inhibit CAPN1, CAPN2, and/or CAPN9. Also provided are methods useful in order treating diseases or disorders which are affected at least in part by CAPN1, CAPN2, and/or CAPN9.

In one aspect, the present technology provides for one or more compounds of a core structure of a mono- or di-amino acid or tri-amino acid wherein the compounds may be substituted by one or more organic functional groups at the C-terminus, N-terminus, and/or the side-chain.

In some embodiments, the invention is a compound comprising Formula II:

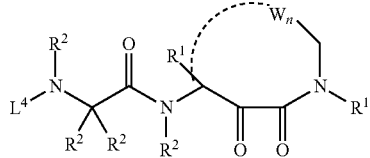

Formula II where:

n is from 1-11;

X is NH or $NR^2$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

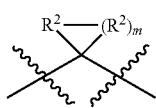

where m is 1-19, sulfonyl, substituted sulfonyl, sulfinyl, and substituted sulfinyl, wherein any two adjacent W atoms may form $CR^2$=$CR^2$ or C≡C;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, aminoacyl, phthalimido, and formyl;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula III:

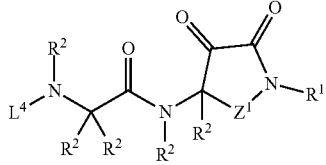

Formula III where:

$Z^1$ is selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

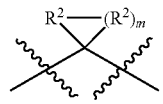

where m is 1-19, sulfonyl, substituted sulfonyl, sulfinyl, and substituted sulfinyl;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

or a tautomer and/or a pharmaceutically acceptable salt thereof.

In some embodiments, the invention is a compound comprising Formula IV:

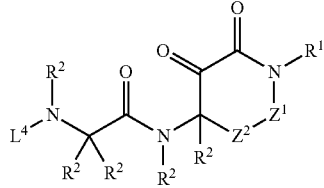

Formula IV where:

$Z^1$ and $Z^2$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

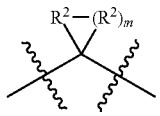

where m is 1-19, sulfonyl, substituted sulfonyl, sulfinyl, and substituted sulfinyl, wherein any two adjacent W atoms may form $CR^2=CR^2$ or $C\equiv C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula V:

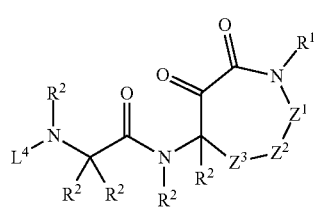

Formula V where:

$Z^1$, $Z^2$, and $Z^3$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

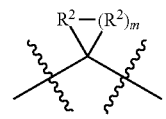

where m is 1-19, sulfonyl, substituted sulfonyl, sulfinyl, and substituted sulfinyl, wherein any two adjacent W atoms may form $CR^2=CR^2$ or $C\equiv C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula VI:

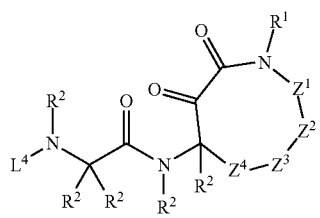

Formula VI where:

$Z^1$, $Z^2$, $Z^3$, and $Z^4$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

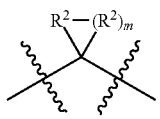

where m is 1-19, sulfonyl, substituted sulfonyl, sulfinyl, and substituted sulfinyl, wherein any two adjacent W atoms may form $CR^2=CR^2$ or $C\equiv C$;

each $R^1$ is independently is selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula VII:

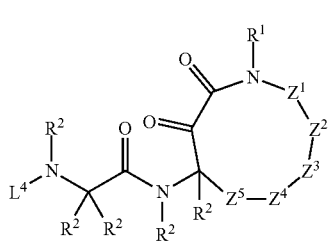

Formula VII where:

$Z^1$, $Z^2$, $Z^3$, $Z^4$, and $Z^5$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

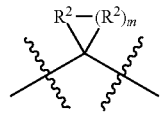

where m is 1-19, sulfonyl, substituted sulfonyl, sulfinyl, and substituted sulfinyl, wherein any two adjacent W atoms may form $CR^2=CR^2$ or $C\equiv C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula VIII:

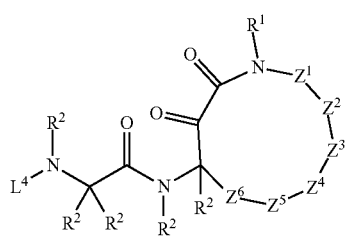

Formula VIII where:

$Z^1$, $Z^2$, $Z^3$, $Z^4$, $Z^5$, and $Z^6$ are each independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

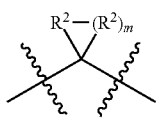

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula IX:

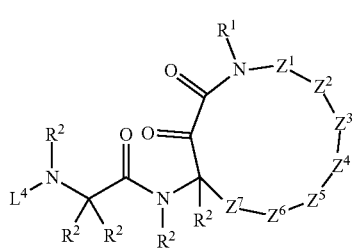

Formula IX where:

$Z^1$, $Z^2$, $Z^3$, $Z^4$, $Z^5$, $Z^6$, and $Z^7$ are each independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

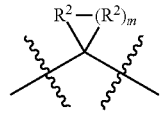

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula X:

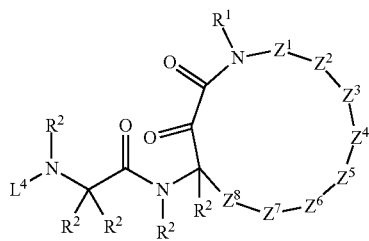

Formula X where:

$Z^1$, $Z^2$, $Z^3$, $Z^4$, $Z^5$, $Z^6$, $Z^7$, and $Z^8$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

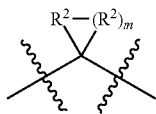

where m is 1-19, sulfonyl, substituted sulfonyl, sulfinyl, and substituted sulfinyl, wherein any two adjacent W atoms may form $CR^2=CR^2$ or $C\equiv C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XI:

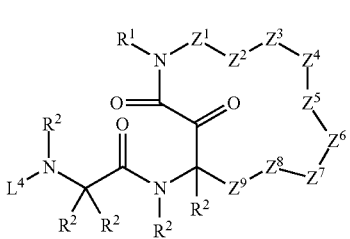

Formula XI where:

$Z^1$, $Z^2$, $Z^3$, $Z^4$, $Z^5$, $Z^6$, $Z^7$, $Z^8$ and $Z^9$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

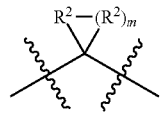

where m is 1-19, sulfonyl, substituted sulfonyl, sulfinyl, and substituted sulfinyl, wherein any two adjacent W atoms may form $CR^2=CR^2$ or $C\equiv C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XII:

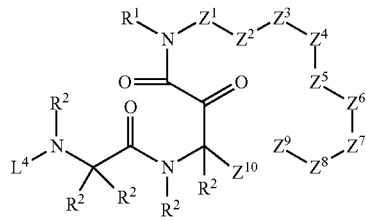

Formula XII where:

$Z^1$, $Z^2$, $Z^3$, $Z^4$, $Z^5$, $Z^6$, $Z^7$, $Z^8$, $Z^9$ and $Z^{10}$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

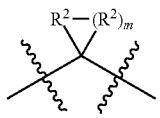

where m is 1-19, sulfonyl, substituted sulfonyl, sulfinyl, and substituted sulfinyl, wherein any two adjacent W atoms may form $CR^2=CR^2$ or $C≡C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XIII:

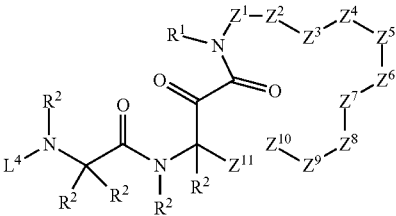

Formula XIII where:

$Z^1$, $Z^2$, $Z^3$, $Z^4$, $Z^5$, $Z^6$, $Z^7$, $Z^8$, $Z^9$, $Z^{10}$ and $Z^{11}$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

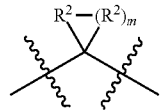

where m is 1-19, sulfonyl, substituted sulfonyl, sulfinyl, and substituted sulfinyl, wherein any two adjacent W atoms may form $CR^2=CR^2$ or $C≡C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XIX:

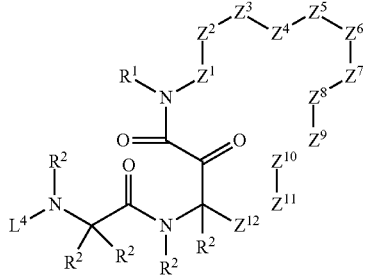

Formula XIV where:

$Z^1, Z^2, Z^3, Z^4, Z^5, Z^6, Z^7, Z^8, Z^9, Z^{10}, Z^{11}$ and $Z^{12}$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

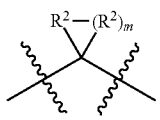

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XV:

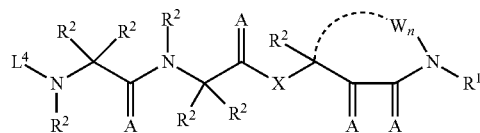

Formula XV where:

n is from 1-12;

each A is independently selected from the group consisting of: O and S;

X is NH or $NR^2$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

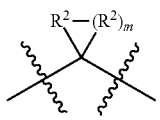

where m is 1-19, sulfonyl, substituted sulfonyl, sulfinyl, and substituted sulfinyl, wherein any two adjacent W atoms may form $CR^2$=$CR^2$ or C≡C;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, aminoacyl, phthalimido, and formyl;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XVI:

Formula XVI

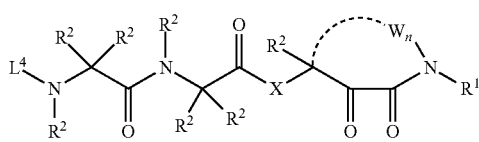

where:

n is from 1-12;

X is NH or $NR^2$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

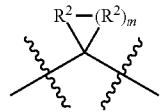

where m is 1-19, sulfonyl, substituted sulfonyl, sulfinyl, and substituted sulfinyl, wherein any two adjacent W atoms may form $CR^2$=$CR^2$ or C≡C;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, aminoacyl, phthalimido, and formyl;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XVII:

Formula XVII

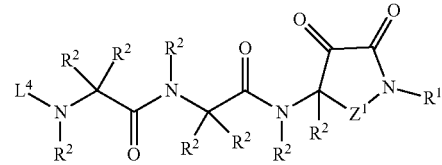

where:

is selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

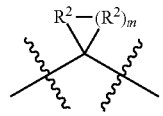

where m is 1-19, sulfonyl, substituted sulfonyl, sulfinyl, and substituted sulfinyl;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

or a tautomer and/or a pharmaceutically acceptable salt thereof.

In some embodiments, the invention is a compound comprising Formula XVIII:

Formula XVIII

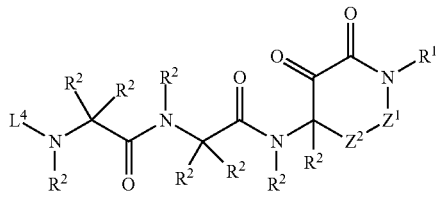

where:

$Z^1$ and $Z^2$ are each independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

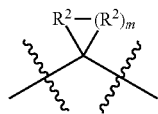

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XIX:

Formula XIX

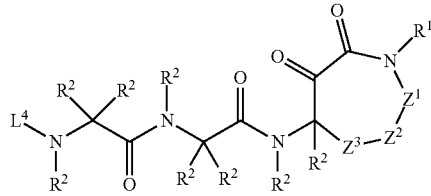

where:

$Z^1$, $Z^2$, and $Z^3$ are each independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

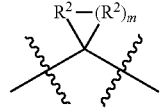

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently is selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XX:

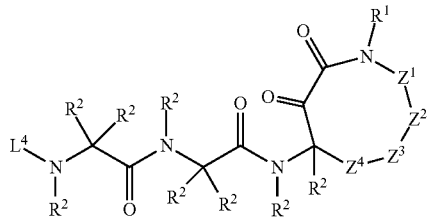

Formula XX where:

$Z^1$, $Z^2$, $Z^3$, and $Z^4$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

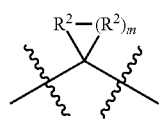

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXI:

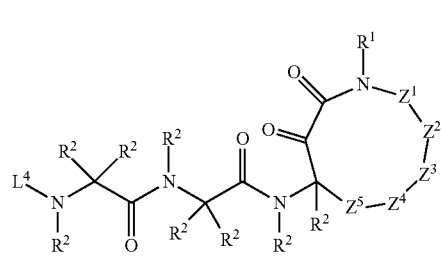

Formula XXI where:

$Z^1$, $Z^2$, $Z^3$, $Z^4$, and $Z^5$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

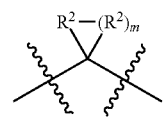

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXII:

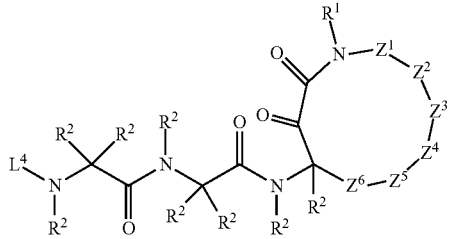

Formula XXII where:

$Z^1$, $Z^2$, $Z^3$, $Z^4$, $Z^5$, and $Z^6$ are each independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

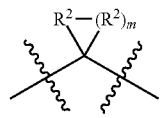

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXIII:

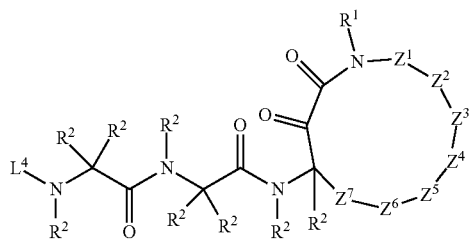

Formula XXIII where:

$Z^1$, $Z^2$, $Z^3$, $Z^4$, $Z^5$, $Z^6$, and $Z^7$ are each independently selected from the group consisting of: $CH_2$, $C(R^2)_2$, $CHR^2$, O, NH, $NR^2$, C(=O), C(=S), S, S(=O), S(=O)$_2$, —C—, —CH—, a $C_3$-$C_{12}$ spirocyclic group of

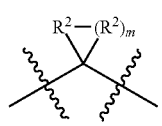

where m is 1-19, sulfonyl, substituted sulfonyl, sulfinyl, and substituted sulfinyl, wherein any two adjacent W atoms may form $CR^2=CR^2$ or $C≡C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXIV:

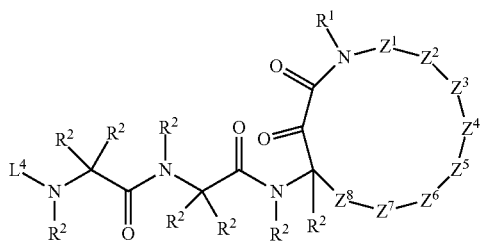

Formula XXIV where:
$Z^1$, $Z^2$, $Z^3$, $Z^4$, $Z^5$, $Z^6$, $Z^7$, and $Z^8$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

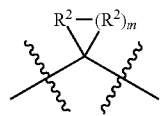

where m is 1-19, sulfonyl, substituted sulfonyl, sulfinyl, and substituted sulfinyl, wherein any two adjacent W atoms may form $CR^2=CR^2$ or $C≡C$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXV:

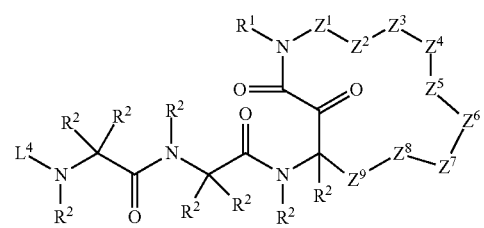

Formula XXV where:

$Z^1$, $Z^2$, $Z^3$, $Z^4$, $Z^5$, $Z^6$, $Z^7$, $Z^8$ and $Z^9$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

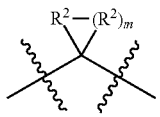

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXVI:

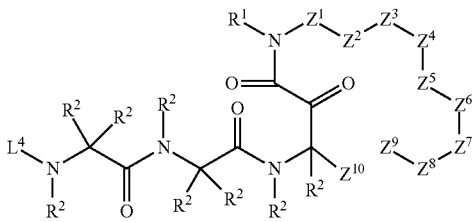

Formula XXVI where:

$Z^1$, $Z^2$, $Z^3$, $Z^4$, $Z^5$, $Z^6$, $Z^7$, $Z^8$, $Z^9$ and $Z^{10}$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

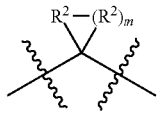

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXVII:

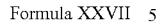

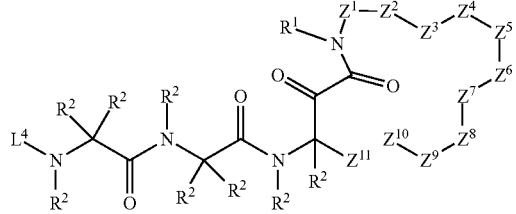

where:
$Z^1, Z^2, Z^3, Z^4, Z^5, Z^6, Z^7, Z^8, Z^9$ and $Z^{10}$ and $Z^{11}$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

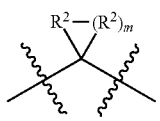

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXVIII:

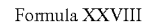

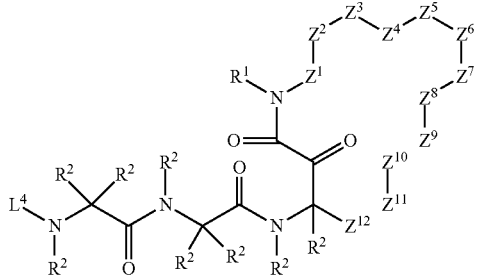

where:
$Z^1, Z^2, Z^3, Z^4, Z^5, Z^6, Z^7, Z^8, Z^9$ and $Z^{10}$, $Z^{11}$ and $Z^{12}$ are each independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

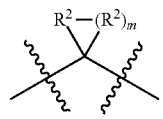

where m is 1-19, sulfonyl, substituted sulfonyl, sulfinyl, and substituted sulfinyl, wherein any two adjacent W atoms may form $CR^2$=$CR^2$ or C≡C;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

In some embodiments, the invention is a compound comprising Formula XXIX:

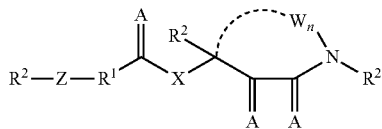

Formula XXIX where:

n is from 1-12;

each A is independently selected from the group consisting of: O and S;

X is NH or $NR^2$;

each $R^1$ is independently selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

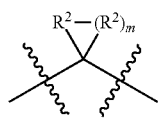

where m is 1-19, sulfonyl, substituted sulfonyl, sulfinyl, and substituted sulfinyl, wherein any two adjacent W atoms may form $CR^2$=$CR^2$ or C≡C;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

Z is selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_1$-$C_8$ alkoxy, substituted $C_1$-$C_8$ alkoxy, substituted amino, alkylthio, substituted alkylthio, O, NH, $NR^2$, S, and a covalent bond;

or a tautomer and/or a pharmaceutically acceptable salt thereof.

In some embodiments, the invention is a compound comprising Formula XXX:

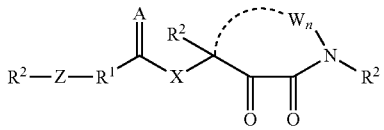

Formula XXX where:

n is from 1-12;

each A is independently selected from the group consisting of: O and S;

X is NH or $NR^2$;

each $R^1$ is independently selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

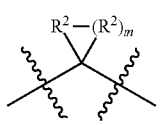

where m is 1-19, sulfonyl, substituted sulfonyl, sulfinyl, and substituted sulfinyl, wherein any two adjacent W atoms may form $CR^2$=$CR^2$ or C≡C;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

Z is selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_1$-$C_8$ alkoxy, substituted $C_1$-$C_8$ alkoxy, substituted amino, alkylthio, substituted alkylthio, O, NH, $NR^2$, S, and a covalent bond;

or a tautomer and/or a pharmaceutically acceptable salt thereof.

In some embodiments, the invention is a compound comprising Formula XXXI:

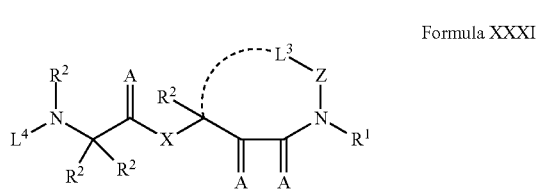

Formula XXXI where:

each A is independently selected from the group consisting of: O and S;

X is NH or $NR^2$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^3$ is a group containing 1-8 atoms and is selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_1$-$C_8$ alkoxy, substituted $C_1$-$C_8$ alkoxy, amino, substituted amino, alkylthio, substituted alkylthio, sulfonyl, $C(R^2)_2$, $CHR^2$, O, NH, $NR^2$, S, substituted sulfonyl, sulfinyl, and substituted sulfinyl;

Z is selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_1$-$C_8$ alkoxy, substituted $C_1$-$C_8$ alkoxy, substituted amino, alkylthio, substituted alkylthio, sulfonyl, $C(R^2)_2$, $CHR^2$, O, NH, $NR^2$, S, substituted sulfonyl, sulfinyl, substituted sulfinyl, and a covalent bond;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, aminoacyl, phthalimido, and formyl;

wherein each and any atom of $L^3$ and Z are capable of being covalently bonded to the same or other $R^2$ functional groups such that a bicyclic or spirocyclic ring system is formed;

or a tautomer and/or a pharmaceutically acceptable salt thereof.

In some embodiments, the invention is a compound comprising Formula XXXII:

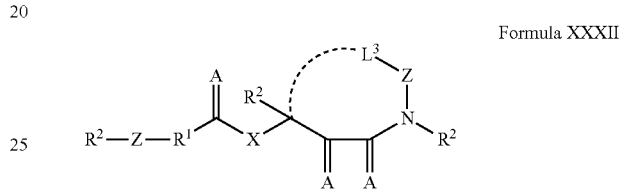

Formula XXXII where:

each A is independently selected from the group consisting of: O and S;

X is NH or $NR^2$;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^3$ is a group containing 1-8 atoms and is selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_1$-$C_8$ alkoxy, substituted $C_1$-$C_8$ alkoxy, amino, substituted amino, alkylthio, substituted alkylthio, sulfonyl, $C(R^2)_2$, $CHR^2$, O, NH, $NR^2$, S, substituted sulfonyl, sulfinyl, and substituted sulfinyl;

Z is selected from the group consisting of: $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_1$-$C_8$ alkoxy, substituted $C_1$-$C_8$ alkoxy, substituted amino, alkylthio, substituted alkylthio, sulfonyl, $C(R^2)_2$, $CHR^2$, O, NH, $NR^2$, S, substituted sulfonyl, sulfinyl, substituted sulfinyl, and a covalent bond;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO-ethylene glycol, —CO-polyethylene glycol, substituted sulfonyl, substituted sulfinyl, thioacyl, aminoacyl, phthalimido, and formyl;

wherein each and any atom of $L^3$ and Z are capable of being covalently bonded to the same or other $R^2$ functional groups such that a bicyclic or spirocyclic ring system is formed;

or a tautomer and/or a pharmaceutically acceptable salt thereof.

In one aspect, the present technology provides two or more compounds of Formula I-XXXII described herein.

In some embodiments, the compound is of Formula II-XXVIII, wherein $R^1$ is H.

In some embodiments, the compound is of Formula II-XXVIII, wherein $R^1$ is H and all $N$—$R^2$ are N—H.

In some embodiments, the compound is of Formula II, wherein W contains a heteroatom.

In some embodiments, the compound is of Formula II, wherein W contains an oxygen heteroatom. In some embodiments, the compound is of Formula II, wherein W contains a sulfur heteroatom. In some embodiments, the compound is of Formula II, wherein W contains a nitrogen heteroatom.

In some embodiments, the compound is of Formula II, wherein W contains sulfonyl functional group.

In some embodiments, the compound is of Formula II, wherein $R^1$ is an alkyl functional group.

In some embodiments, the compound is of Formula II, wherein $R^1$ is an aromatic functional group.

In some embodiments, the compound is of Formula III, wherein $R^1$ is an alkyl functional group.

In some embodiments, the compound is of Formula III, wherein Z is nitrogen.

In some embodiments, the compound is of Formula III, wherein Z is $CH_2$.

In some embodiments, the compound is of Formula III, wherein one $R^2$ on the

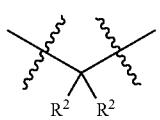

carbon atom is H and the other is $CH(CH_3)_2$.

In some embodiments, the compound is of Formula III, wherein one $R^2$ on the

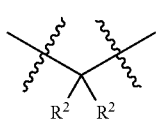

carbon atom is H and the other is $CH_2$—$CH(CH_3)_2$.

In some embodiments, the compound is of Formula III, wherein one $R^2$ on the

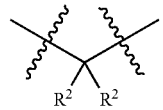

carbon atom is H and the other is Ar.

In some embodiments, the compound is of Formula III, wherein one $L^4$ forms a carbamate functional group.

In some embodiments, the compound is of Formula III, wherein one $L^4$ forms a sulfamate functional group.

In some embodiments, the compound is of Formula III, wherein one $L^4$ is —$C(O)C(CH_3)_3$.

In some embodiments, the compound is of Formula III, wherein one $L^4$ is —$C(O)C(CH_3)_3$.

In some embodiments, the compound is of Formula IV, wherein $Z^1$ is $CH_2$ and $R^1$ is H.

In some embodiments, the compound is of Formula IV, wherein $Z^1$ is $CH_2$, $Z^2$ is $CH_2$, and $R^1$ is H.

In some embodiments, the compound is of Formula IV, wherein $Z^1$ is $CH_2$, $Z^2$ is O, and $R^1$ is H.

In some embodiments, the compound is of Formula V, wherein $Z^1$ is $CH_2$, $Z^2$ is NH, and $R^1$ is H.

In some embodiments, the compound is of Formula VI, wherein $Z^1$ is $CH_2$, $Z^2$ is NH, and $R^1$ is H.

In some embodiments, the compound is of Formula III-XIVIV, wherein $R^1$ is H, both $N$—$R^2$ are N—H, and $L^4$ is

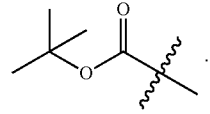

In some embodiments, the compound is of Formula III-XIVIV, wherein $R^1$ is H, both $N$—$R^2$ are N—H, and $L^4$ is

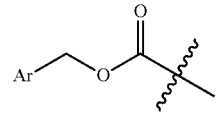

In some embodiments, the compound is of Formula III-XIVIV, wherein $R^1$ is H, both $N$—$R^2$ are N—H, and $L^4$ is

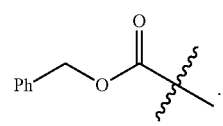 [SMILES: *C(=O)OCc1ccccc1]

In some embodiments, the compound is of Formula III-XIVIV, wherein $R^1$ is H, both $N$—$R^2$ are N—H, and $L^4$ is

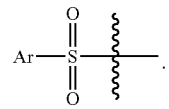

In some embodiments, the compound is of Formula III-XIVIV, wherein $R^1$ is H, both N—$R^2$ are N—H, one $R^2$ of

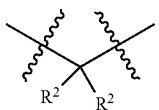

is H and the other is

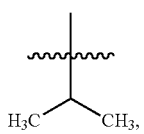

and $L^4$ is

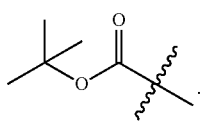 [SMILES: *C(=O)OC(C)(C)C]

In some embodiments, the compound is of Formula III-XIVIV, wherein $R^1$ is H, both N—$R^2$ are N—H, one $R^2$ of

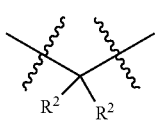

is H and the other is

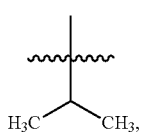

and $L^4$ is

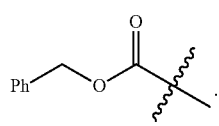 [SMILES: *C(=O)OCc1ccccc1]

In some embodiments, the compound is of Formula III-XIVIV, wherein $R^1$ is H, both N—$R^2$ are N—H, one $R^2$ of

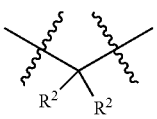

is H and the other is

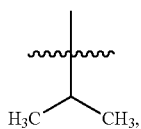

and $L^4$ is

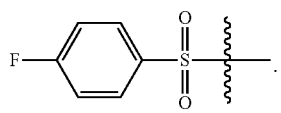 [SMILES: *S(=O)(=O)c1ccc(F)cc1]

In some embodiments, the compound is of Formula III, wherein $R^1$ is H, both N—$R^2$ are N—H, one $R^2$ of

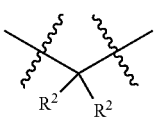

is H and the other is

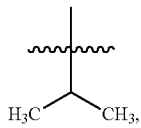

and $L^4$ is

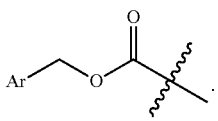

In some embodiments, the compound is of Formula III, wherein $R^1$ is H, both N—$R^2$ are N—H, one $R^2$ of

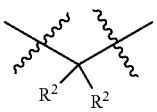

is H and the other is

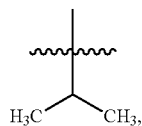

and L⁴ is

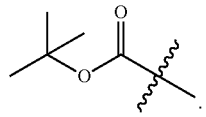 [SMILES: *C(=O)OC(C)(C)C]

In some embodiments, the compound is of Formula III, wherein R¹ is H, both N—R² are N—H, one R² of

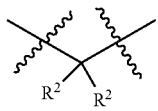

is H and the other is

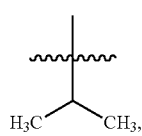

and L⁴ is

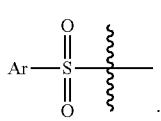

In some embodiments, the compound is of Formula IV, wherein R¹ is H, both N—R² are N—H, one R² of

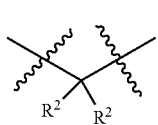

is H and the other is

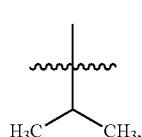

and L⁴ is

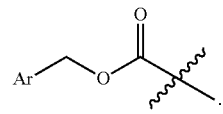

In some embodiments, the compound is of Formula IV, wherein R¹ is H, both N—R² are N—H, one R² of

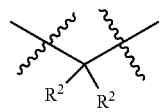

is H and the other is

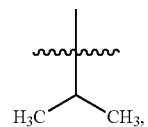

and L⁴ is

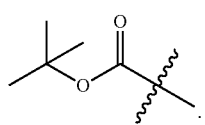

In some embodiments, the compound is of Formula IV, wherein R¹ is H, both N—R² are N—H, one R² of

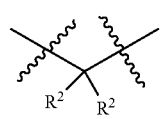

is H and the other is

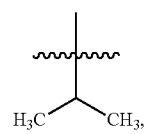

and L⁴ is

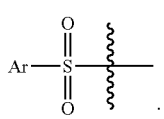

In some embodiments, the compound is of Formula V, wherein R¹ is H, both N—R² are N—H, one R² of

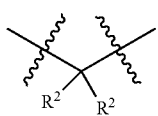

is H and the other is

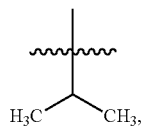

and $L^4$ is

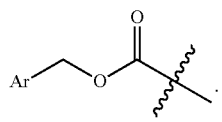

In some embodiments, the compound is of Formula V, wherein $R^1$ is H, both N—$R^2$ are N—H, one $R^2$ of

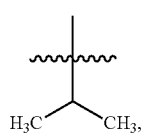

is H and the other is

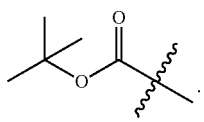 [SMILES: *C(=O)OC(C)(C)C]

and $L^4$ is

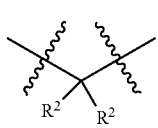

In some embodiments, the compound is of Formula V, wherein $R^1$ is H, both N—$R^2$ are N—H, one $R^2$ of is H and the other is and $L^4$ is

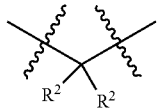

In some embodiments, the compound is of Formula VI, wherein $R^1$ is H, both N—$R^2$ are N—H, one $R^2$ of is H and the other is and $L^4$ is

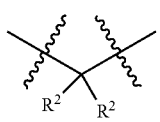

In some embodiments, the compound is of Formula VI, wherein $R^1$ is H, both N—$R^2$ are N—H, one $R^2$ of is H and the other is

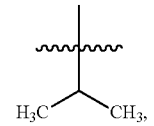

and $L^4$ is

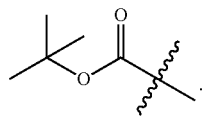 [SMILES: *C(=O)OC(C)(C)C]

In some embodiments, the compound is of Formula VI, wherein $R^1$ is H, both N—$R^2$ are N—H, one $R^2$ of

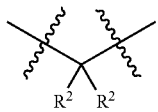

is H and the other is

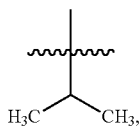

and $L^4$ is

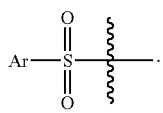

In some embodiments, the compound is of Formula VII, wherein $R^1$ is H, both N—$R^2$ are N—H, one $R^2$ of

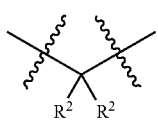

is H and the other is

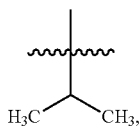

and $L^4$ is

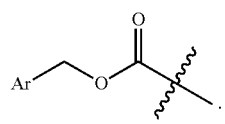

In some embodiments, the compound is of Formula VII, wherein $R^1$ is H, both N—$R^2$ are N—H, one $R^2$ of

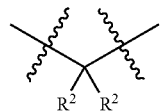

is H and the other is

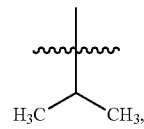

and $L^4$ is

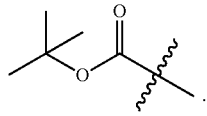 [SMILES: *C(=O)OC(C)(C)C]

In some embodiments, the compound is of Formula VII, wherein $R^1$ is H, both N—$R^2$ are N—H, one $R^2$ of

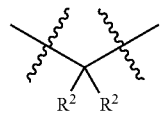

is H and the other is

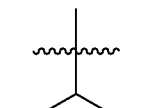

and $L^4$ is

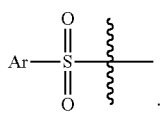

In some embodiments, the compound is of Formula III-XIV, wherein $R^1$ is H, both N—$R^2$ are N—H, one $R^2$ of

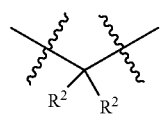

is H and the other is

![structure: isopropyl group with CH3, CH3]

and L⁴ is

![structure: tert-butyl ester linker]

In some embodiments, the compound is of Formula III-XIV, wherein R¹ is H, both N—R² are N—H, one R² of ![structure: CR²R² branching]

is H and the other is

![structure: isopropyl group with CH3, CH3]

and L⁴ is

![structure: benzyl ester linker, Ph-O-C(O)-]

In some embodiments, the compound is of Formula III-XIV, wherein R¹ is H, both N—R² are N—H, one R² of ![structure: CR²R² branching]

is H and the other is

![structure: isopropyl group with CH3, CH3]

and L⁴ is

![structure: 4-fluorophenylsulfonyl linker]

In some embodiments, the compound is of Formula III-XIV, wherein R¹ is H, both N—R² are N—H, one R² of ![structure: CR²R² branching]

is H and the other is selected from the group consisting of:

![structures: vinyl, allyl, cyclopropyl, ethynyl]

![structures: cyanomethyl, imidazole, pyrrole, pyrrole]

![structures: pyrazole, isothiazole, and thiophene]

and L⁴ is

![structure: tert-butyl ester linker]

In some embodiments, the compound is of Formula III-XIV, wherein R¹ is H, both N—R² are N—H, one R² of

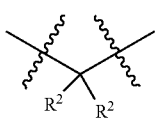

is H and the other is selected from the group consisting of:

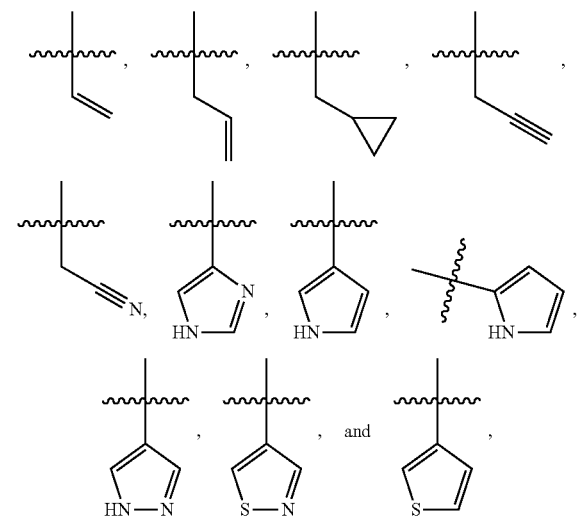

and L⁴ is

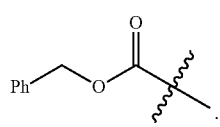

In some embodiments, the compound is of Formula III-XIV, wherein R¹ is H, both N—R² are N—H, one R² of

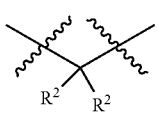

is H and the other is selected from the group consisting of:

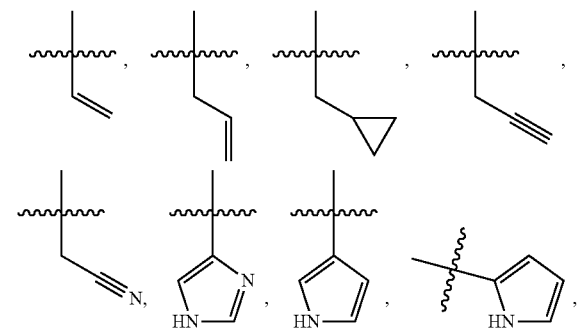

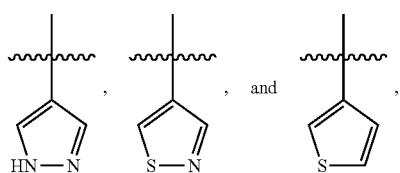

and L⁴ is

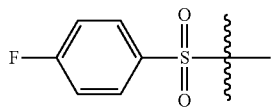

In some embodiments, the compound is of Formula XV-XXVIII, wherein R¹ is H, all N—R² are N—H, and L⁴ is

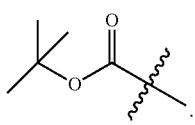

In some embodiments, the compound is of Formula XV-XXVIII, wherein R¹ is H, all N—R² are N—H, and L⁴ is

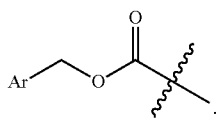

In some embodiments, the compound is of Formula XV-XXVIII, wherein R¹ is H, all N—R² are N—H, is

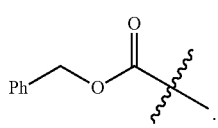 [SMILES: *C(=O)OCc1ccccc1]

In some embodiments, the compound is of Formula XV-XXVIII, wherein R¹ is H, all N—R² are N—H, and L⁴ is

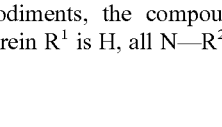

In some embodiments, the compound is of Formula XV-XXVIII, wherein R¹ is H, all N—R² are N—H, two R² of the two

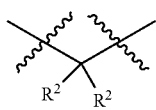

groups on separate carbon atoms are H and one of the other two R² groups is

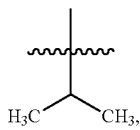

and L⁴ is

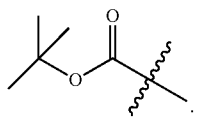 [SMILES: *C(=O)OC(C)(C)C]

In some embodiments, the compound is of Formula XV-XXVIII, wherein R¹ is H, all N—R² are N—H, two R² of the two

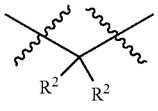

groups on separate carbon atoms are H and one of the other two R² groups is

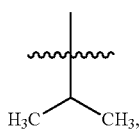

and L⁴ is

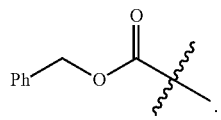

In some embodiments, the compound is of Formula XV-XXVIII, wherein R¹ is H, all N—R² are N—H, two R² of the two

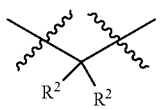

groups on separate carbon atoms are H and one of the other two R² groups is

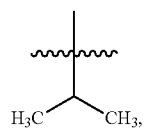

and L⁴ is

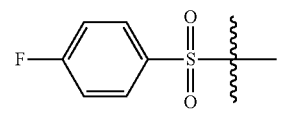

In some embodiments, the compound is of Formula XIII, wherein R¹ is H, all N—R² are N—H, two R² of the two

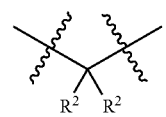

groups on separate carbon atoms are H and one of the other two R² groups is

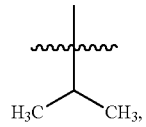

and L⁴ is

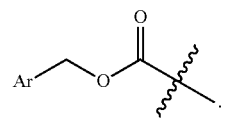

In some embodiments, the compound is of Formula XIII, wherein R¹ is H, all N—R² are N—H, two R² of the two

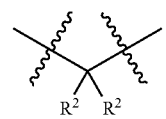

groups on separate carbon atoms are H and one of the other two R² groups is

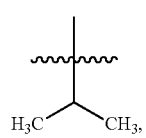

and L⁴ is

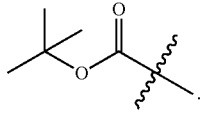

In some embodiments, the compound is of Formula XIII, wherein R¹ is H, all N—R² are N—H, two R² of the two

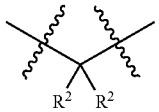

groups on separate carbon atoms are H and one of the other two R² groups is

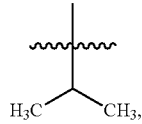

and L⁴ is

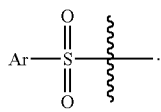

In some embodiments, the compound is of Formula XIV, wherein R¹ is H, all N—R² are N—H, two R² of the two

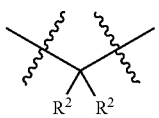

groups on separate carbon atoms are H and one of the other two R² groups is

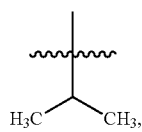

and L⁴ is

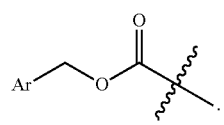

In some embodiments, the compound is of Formula XIV, wherein R¹ is H, both N—R² are N—H, two R² of the two

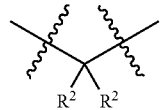

groups on separate carbon atoms are H and one of the other two R² groups is

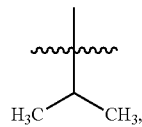

and L⁴ is

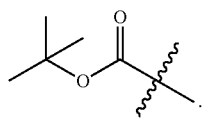 [SMILES: *C(=O)OC(C)(C)C]

In some embodiments, the compound is of Formula XIV, wherein R¹ is H, all N—R² are N—H, two R² of the two

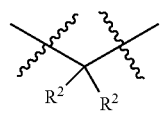

groups on separate carbon atoms are H and one of the other two R² groups is

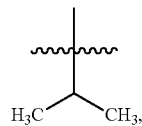

and L⁴ is

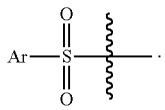

In some embodiments, the compound is of Formula XV, wherein R¹ is H, all N—R² are N—H, two R² of the two

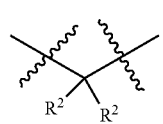

groups on separate carbon atoms are H and one of the other two R² groups is

73

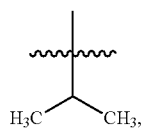

and L$^4$ is

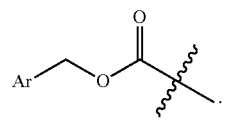

In some embodiments, the compound is of Formula XV, wherein R$^1$ is H, all N—R$^2$ are N—H, two R$^2$ of the two

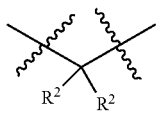

groups on separate carbon atoms are H and one of the other two R$^2$ groups is

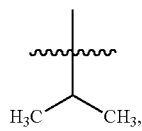

and L$^4$ is

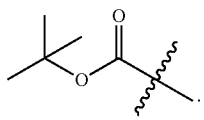 [SMILES: *C(=O)OC(C)(C)C]

In some embodiments, the compound is of Formula XV, wherein R$^1$ is H, all N—R$^2$ are N—H, two R$^2$ of the two

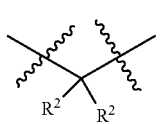

groups on separate carbon atoms are H and one of the other two R$^2$ groups is

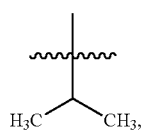

74 and L$^4$ is

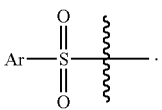

In some embodiments, the compound is of Formula XVI, wherein R$^1$ is H, all N—R$^2$ are N—H, two R$^2$ of the two

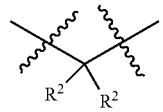

groups on separate carbon atoms are H and one of the other two R$^2$ groups is

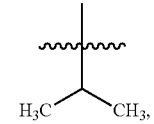

and L$^4$ is

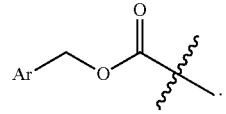

In some embodiments, the compound is of Formula XVI, wherein R$^1$ is H, all N—R$^2$ are N—H, one R$^2$ of

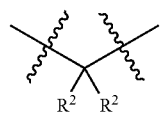

is H and the other is

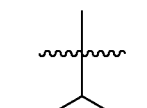

and L$^4$ is

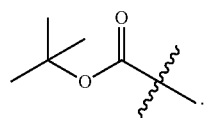 [SMILES: *C(=O)OC(C)(C)C]

In some embodiments, the compound is of Formula XVI, wherein R$^1$ is H, all N—R$^2$ are N—H, two R$^2$ of the two

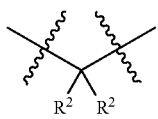

groups on separate carbon atoms are H and one of the other two R² groups is

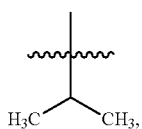

and L⁴ is

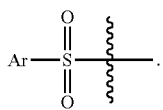

In some embodiments, the compound is of Formula XVII, wherein R¹ is H, all N—R² are N—H, two R² of the two

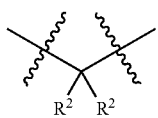

groups on separate carbon atoms are H and one of the other two R² groups is

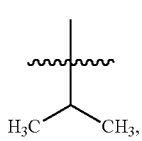

and L⁴ is

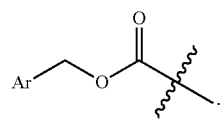

In some embodiments, the compound is of Formula XVII, wherein R¹ is H, all N—R² are N—H, two R² of the two

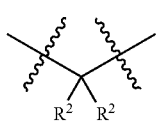

groups on separate carbon atoms are H and one of the other two R² groups is

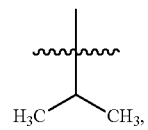

and L⁴ is

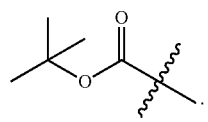 [SMILES: *C(=O)OC(C)(C)C]

In some embodiments, the compound is of Formula XVII, wherein R¹ is H, all N—R² are N—H, two R² of the two

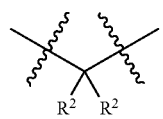

groups on separate carbon atoms are H and one of the other two R² groups is

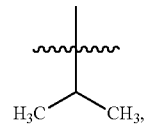

and L⁴ is

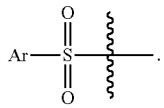

In some embodiments, the compound is of Formula XV-XXVIII, wherein R¹ is H, all N—R² are N—H, two R² of the two

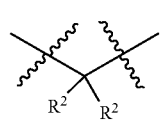

groups on separate carbon atoms are H and one of the other two R² groups is

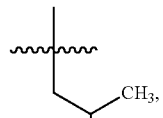

and L⁴ is

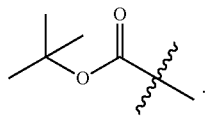 [SMILES: *C(=O)OC(C)(C)C]

In some embodiments, the compound is of Formula XV-XXVIII, wherein R¹ is H, all N—R² are N—H, two R² of the two

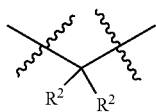

groups on separate carbon atoms are H and one of the other two R² groups is

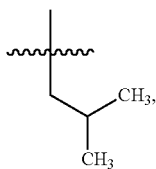 [SMILES: *CC(C)C]

and L⁴ is

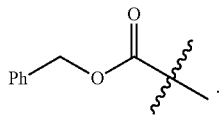

In some embodiments, the compound is of Formula XV-XXVIII, wherein R¹ is H, all N—R² are N—H, two R² of the two

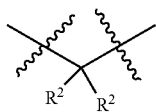

groups on separate carbon atoms are H and one of the other two R² groups is

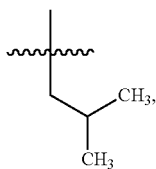 [SMILES: *CC(C)C]

and L⁴ is

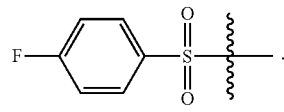 [SMILES: *S(=O)(=O)c1ccc(F)cc1]

In some embodiments, the compound is of Formula XV-XXVIII, wherein R¹ is H, all N—R² are N—H, two R² of the two

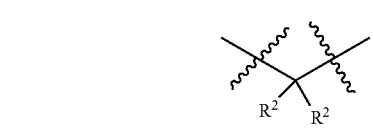

groups on separate carbon atoms are H and one of the other two R² groups is selected from the group consisting of:

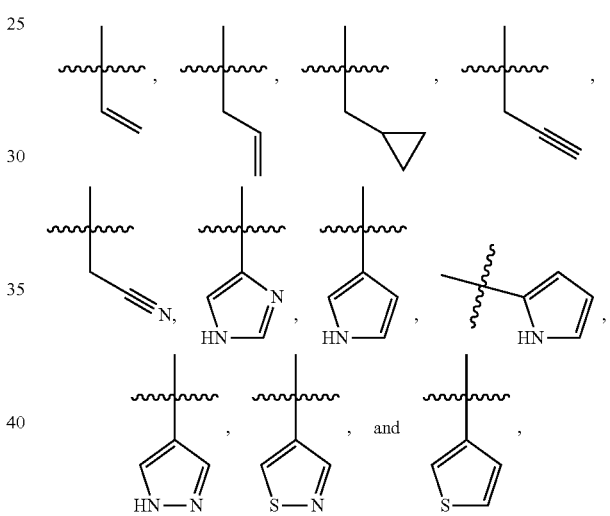

and L⁴ is

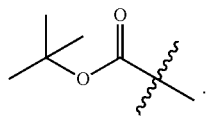 [SMILES: *C(=O)OC(C)(C)C]

In some embodiments, the compound is of Formula XV-XXVIII, wherein R¹ is H, all N—R² are N—H, two R² of the two

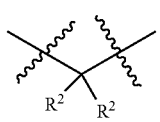

groups on separate carbon atoms are H and one of the other two R² groups is selected from the group consisting of:

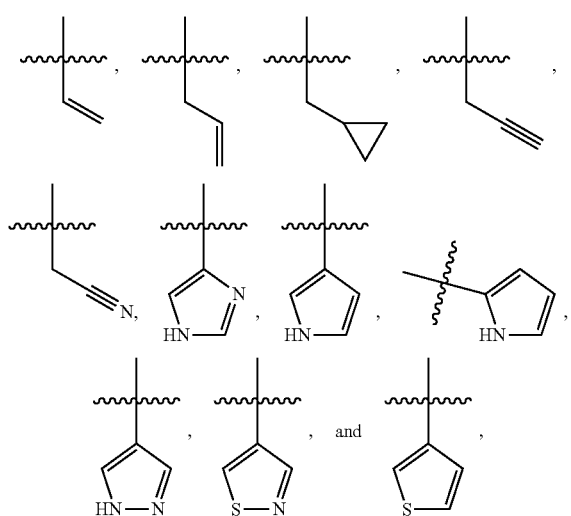

and L⁴ is

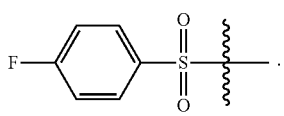

In some embodiments, the compound is of Formula XV-XXVIII, wherein R¹ is H, all N—R² are N—H, two R² of the two

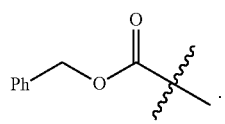 [SMILES: *C(=O)OCc1ccccc1]

groups on separate carbon atoms are H and one of the other two R² groups is selected from the group consisting of:

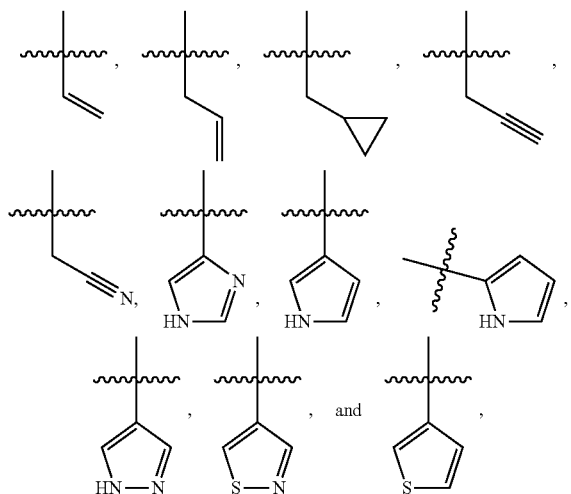

and L⁴ is

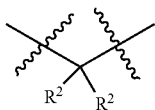

In some embodiments, the present technology includes a compound which is selected from the compound of the tables below:

TABLE 1

FiveRings

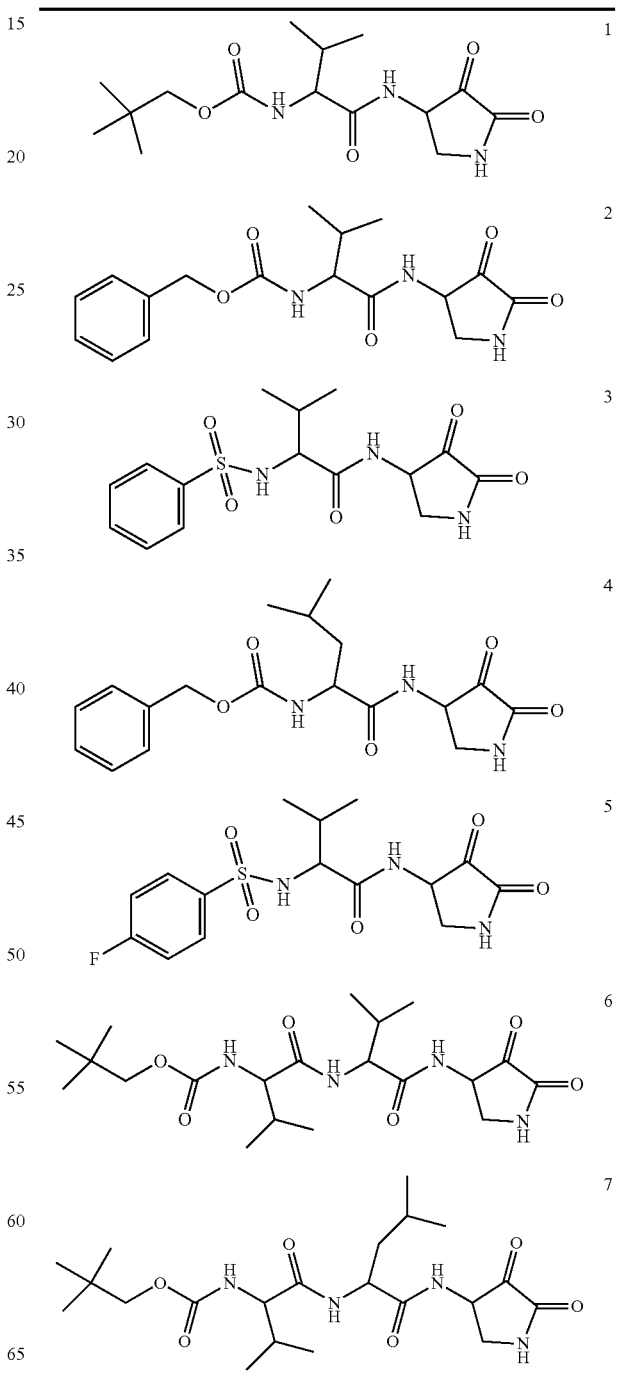

TABLE 1-continued
FiveRings
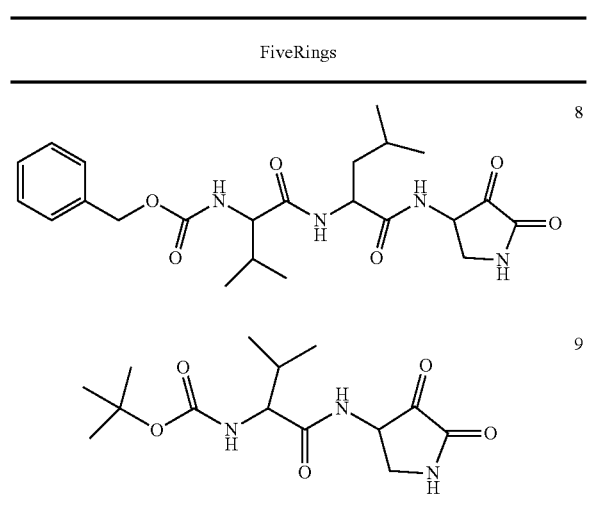
TABLE 2
SixRings
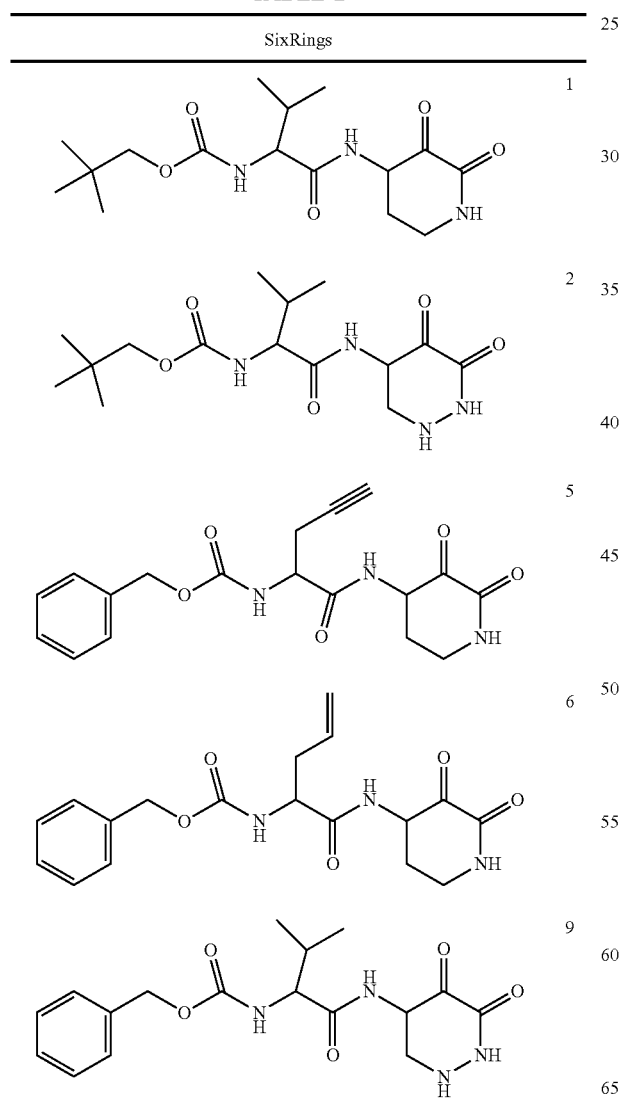
TABLE 2-continued
SixRings
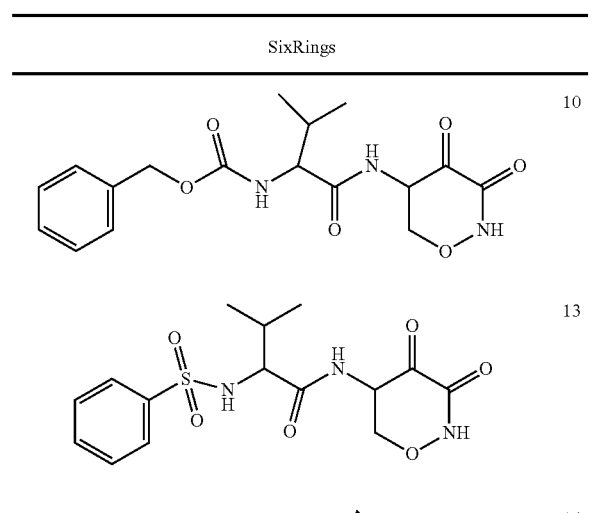
TABLE 2-continued
SixRings
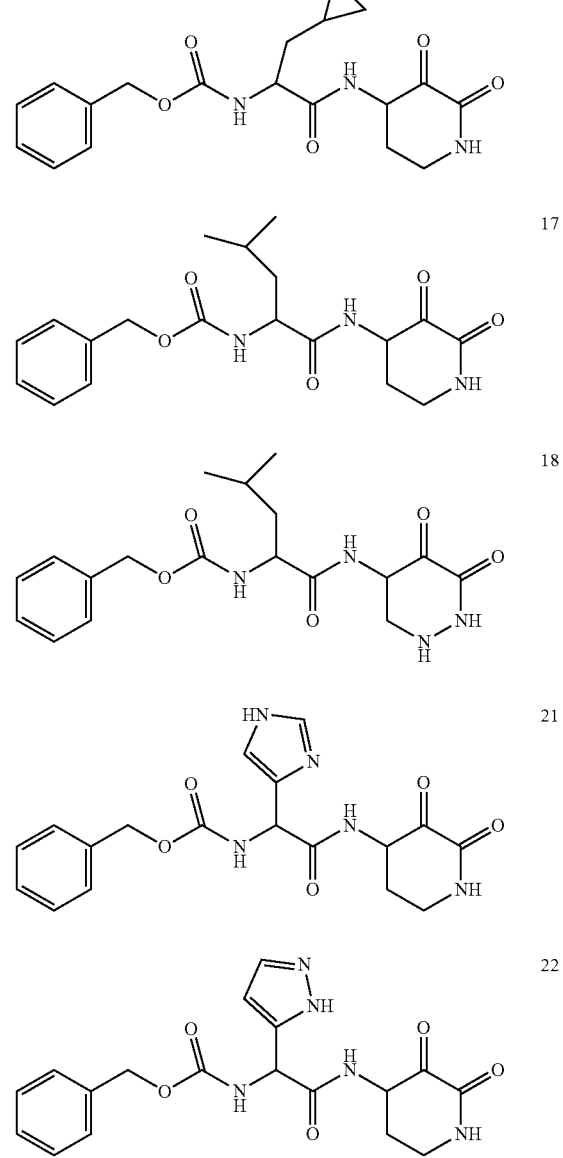

TABLE 2-continued
SixRings
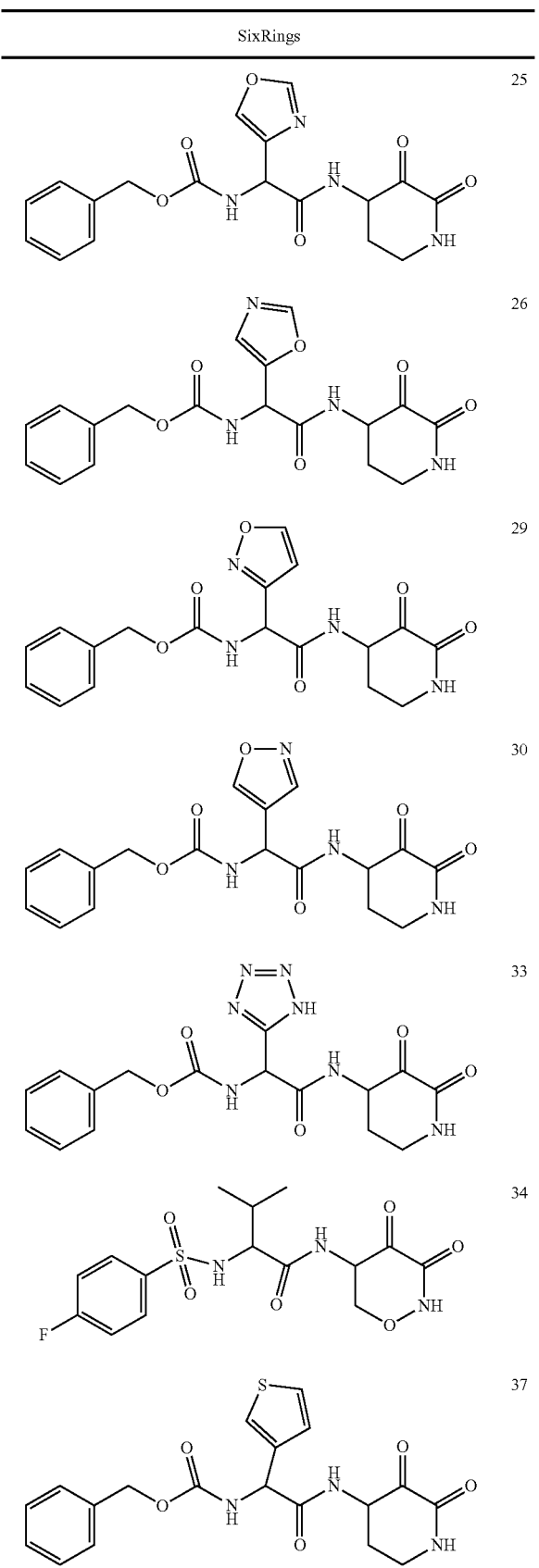
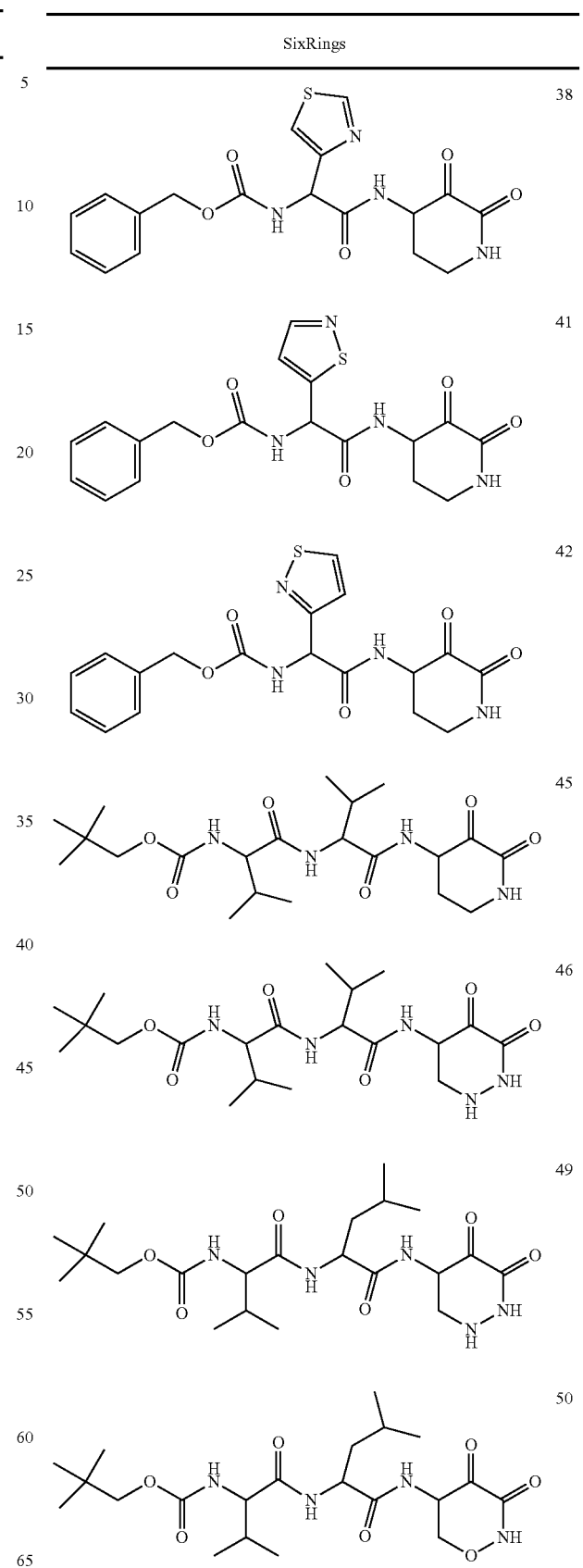

TABLE 2-continued
SixRings
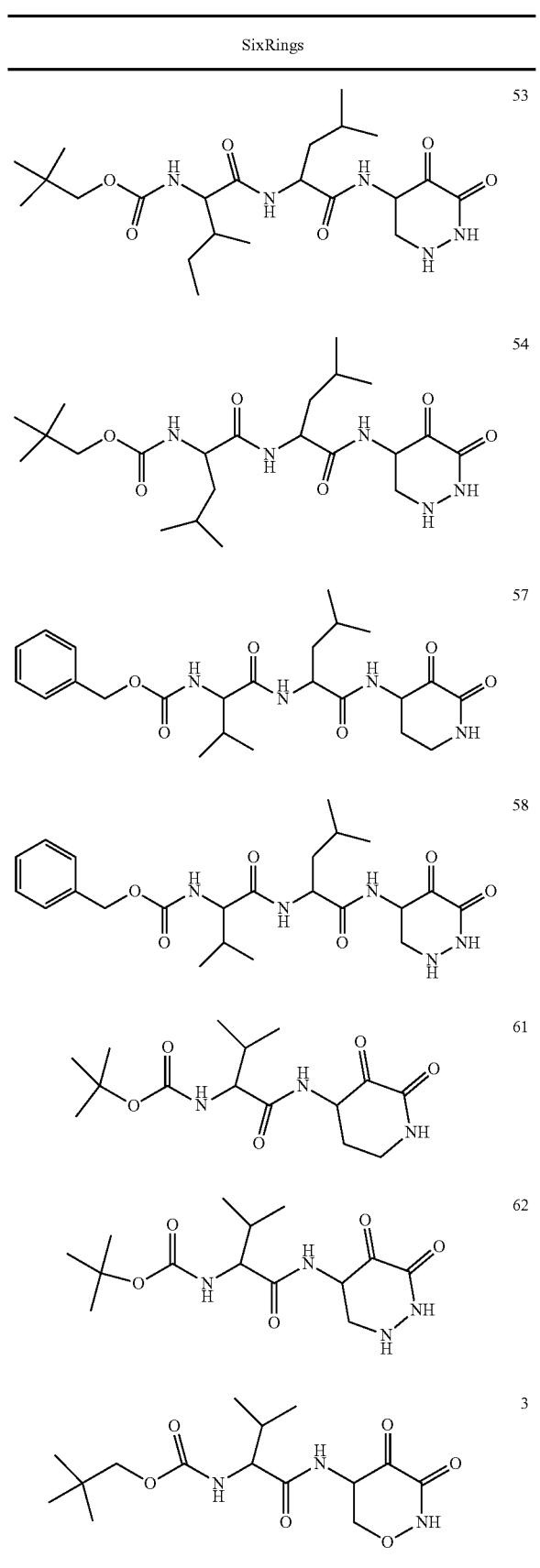
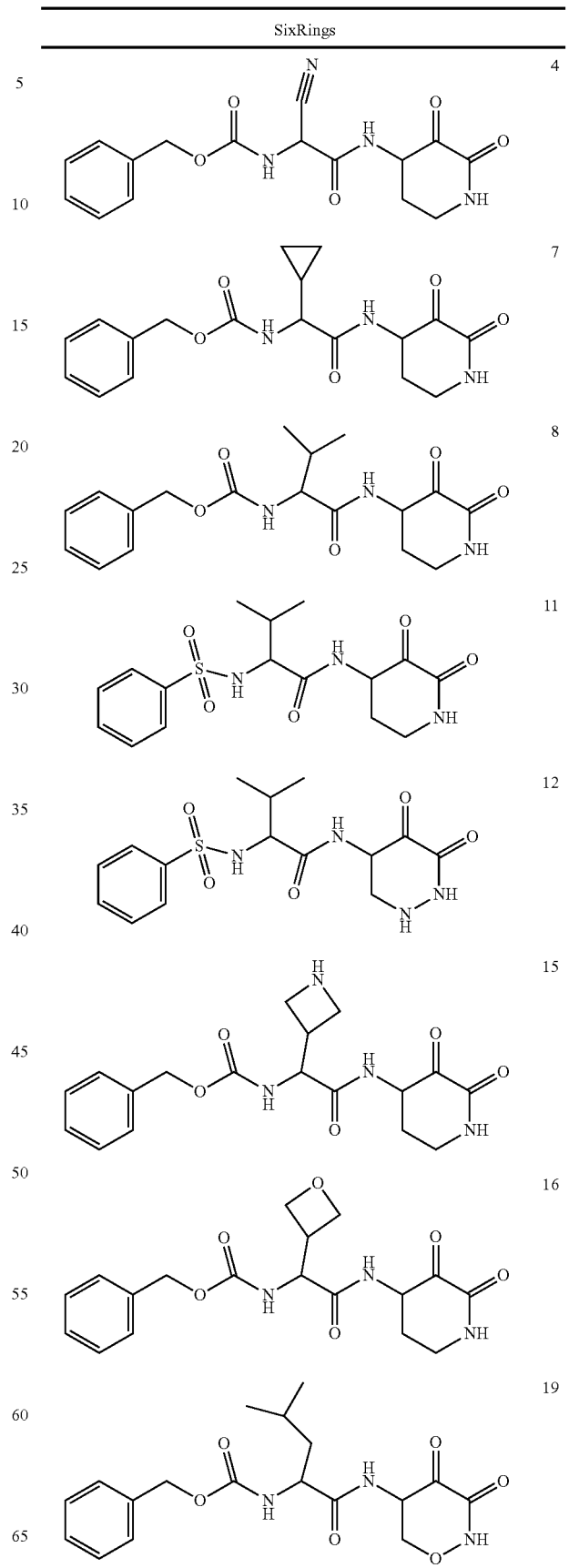

TABLE 2-continued
SixRings
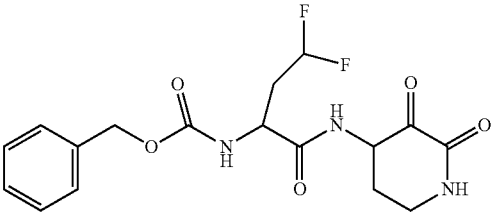 [SMILES: O=C(NC(CC(F)F)C(=O)NC1CCNC(=O)C1=O)OCc1ccccc1] 20
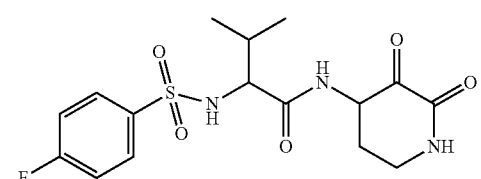 23
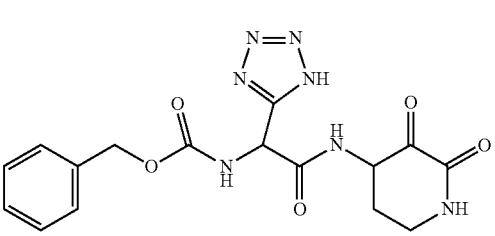 [SMILES: O=C(NC(C(=O)NC1CCNC(=O)C1=O)c1nnn[nH]1)OCc1ccccc1] 24
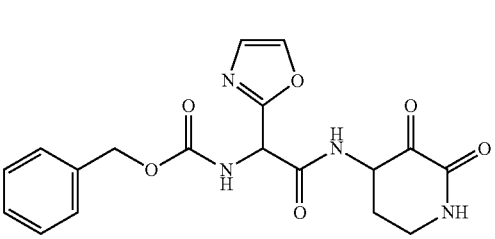 [SMILES: O=C(NC(C(=O)NC1CCNC(=O)C1=O)c1ncco1)OCc1ccccc1] 27
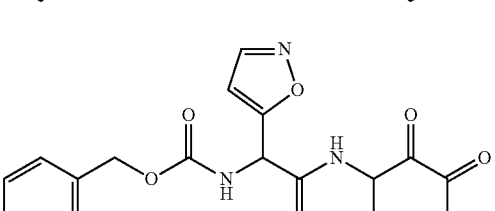 28
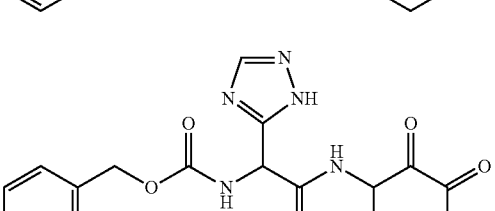 31
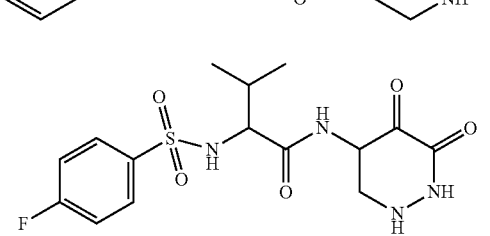 32
TABLE 2-continued
SixRings
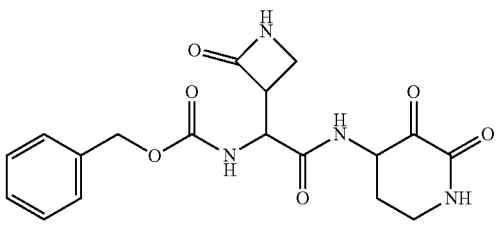 [SMILES: O=C(NC(C(=O)NC1CCNC(=O)C1=O)C1CNC1=O)OCc1ccccc1] 35
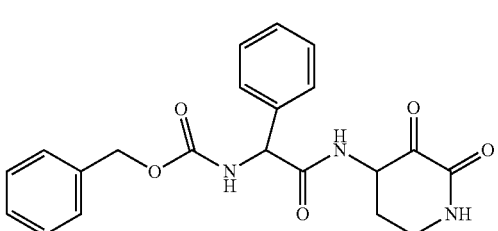 36
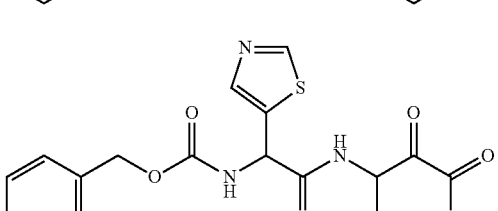 39
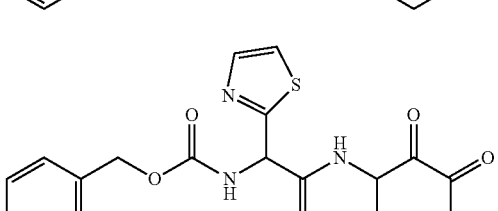 40
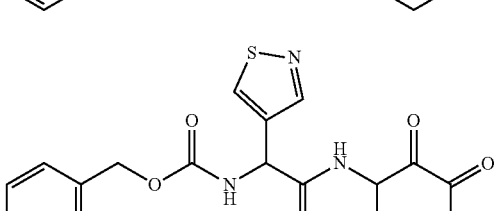 43
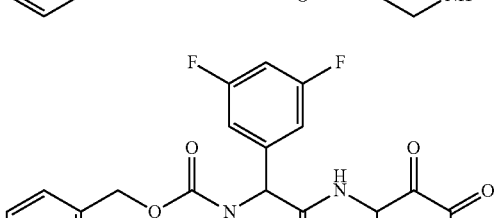 44
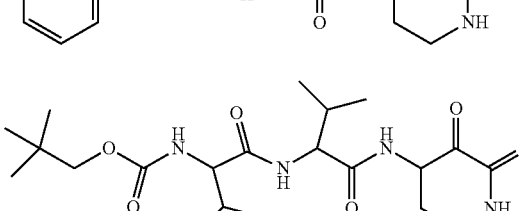 47

TABLE 2-continued
SixRings
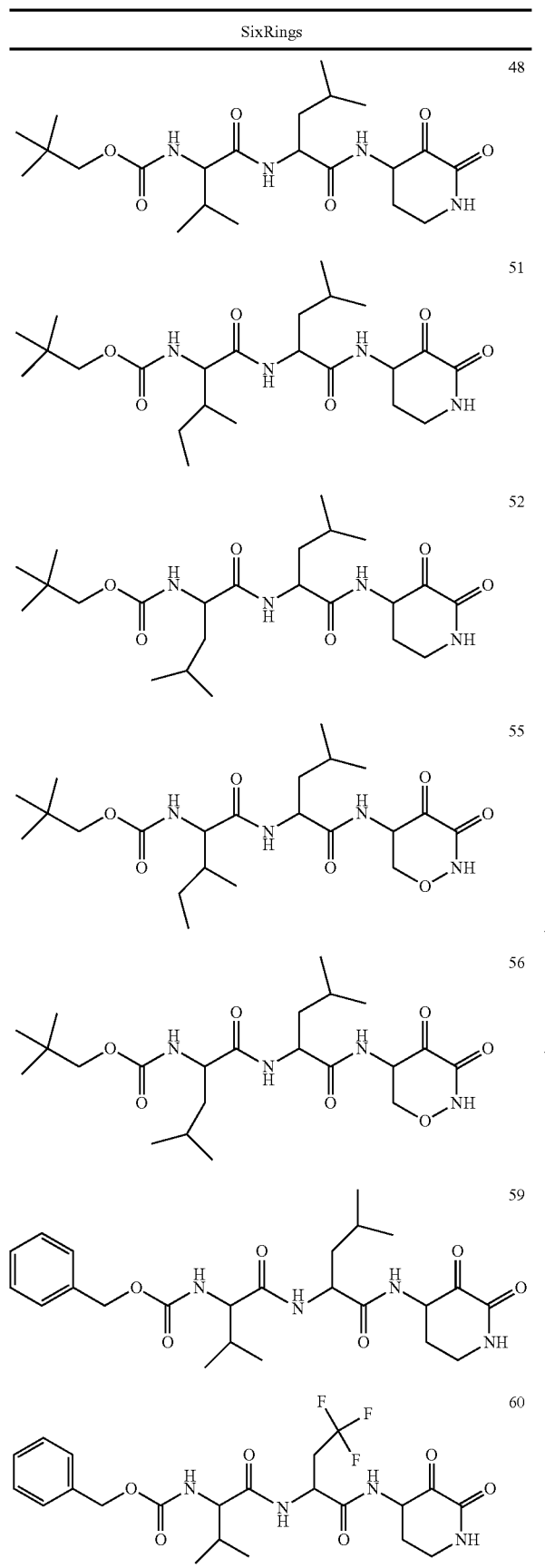
TABLE 2-continued
SixRings
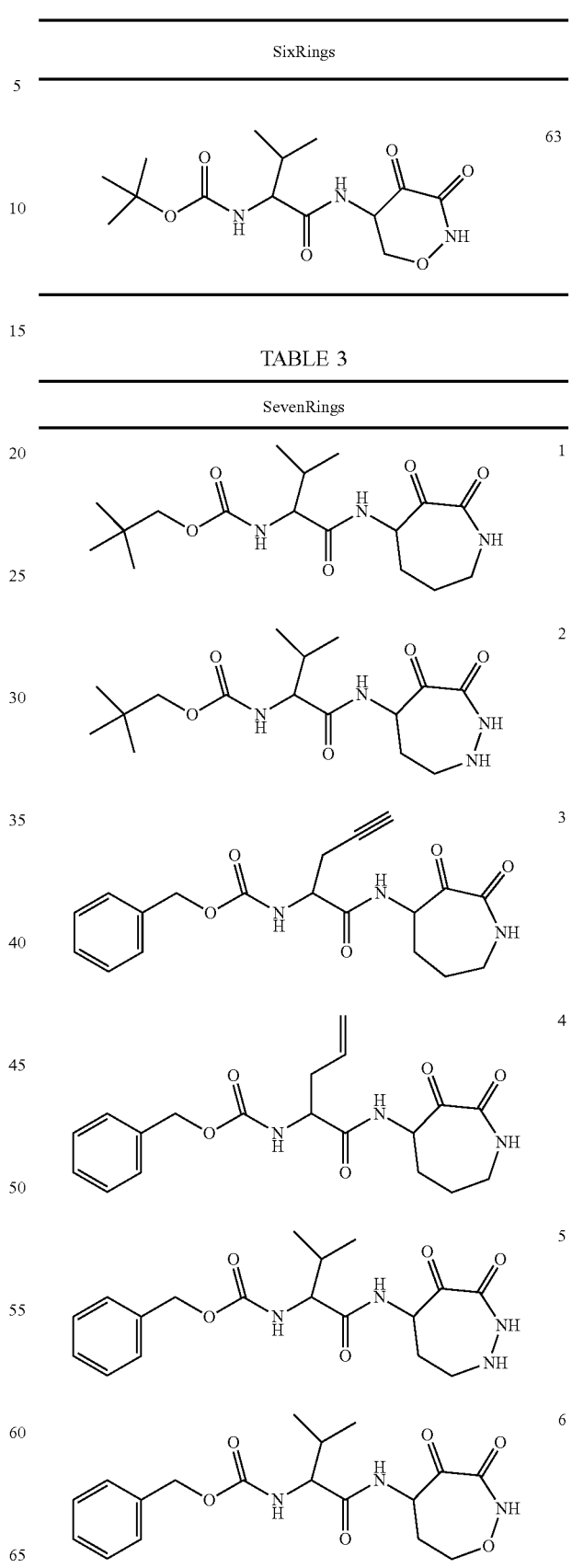
TABLE 3
SevenRings TABLE 3-continued
SevenRings
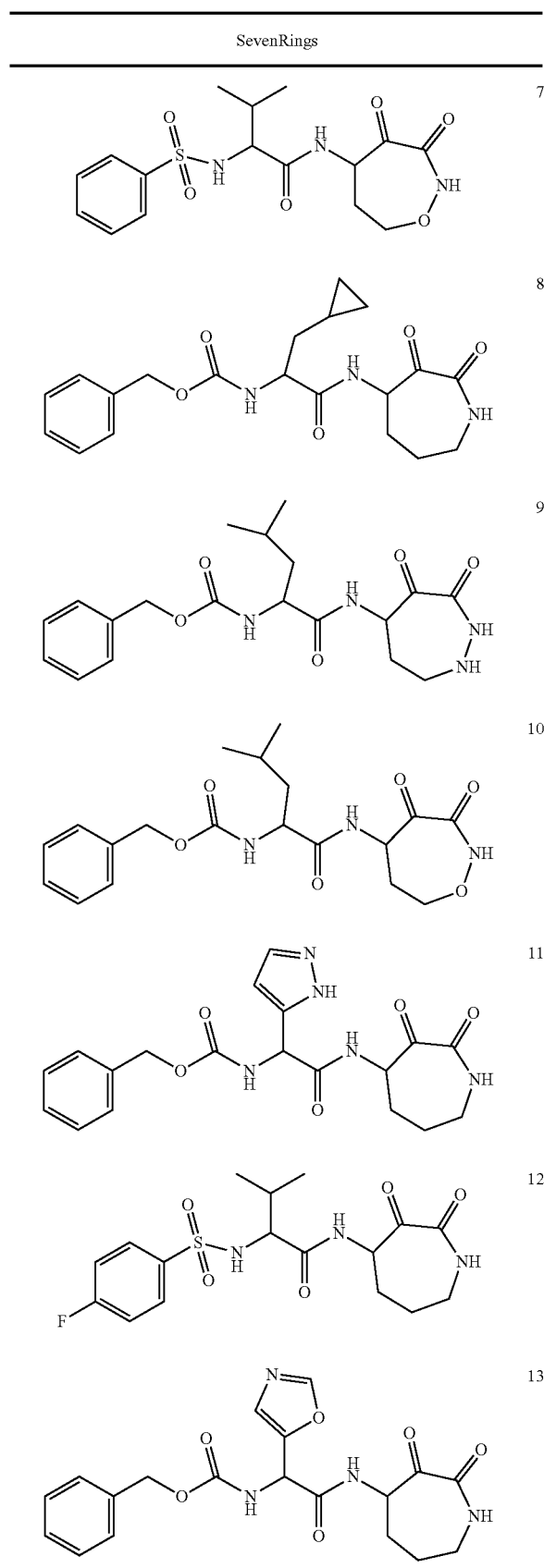
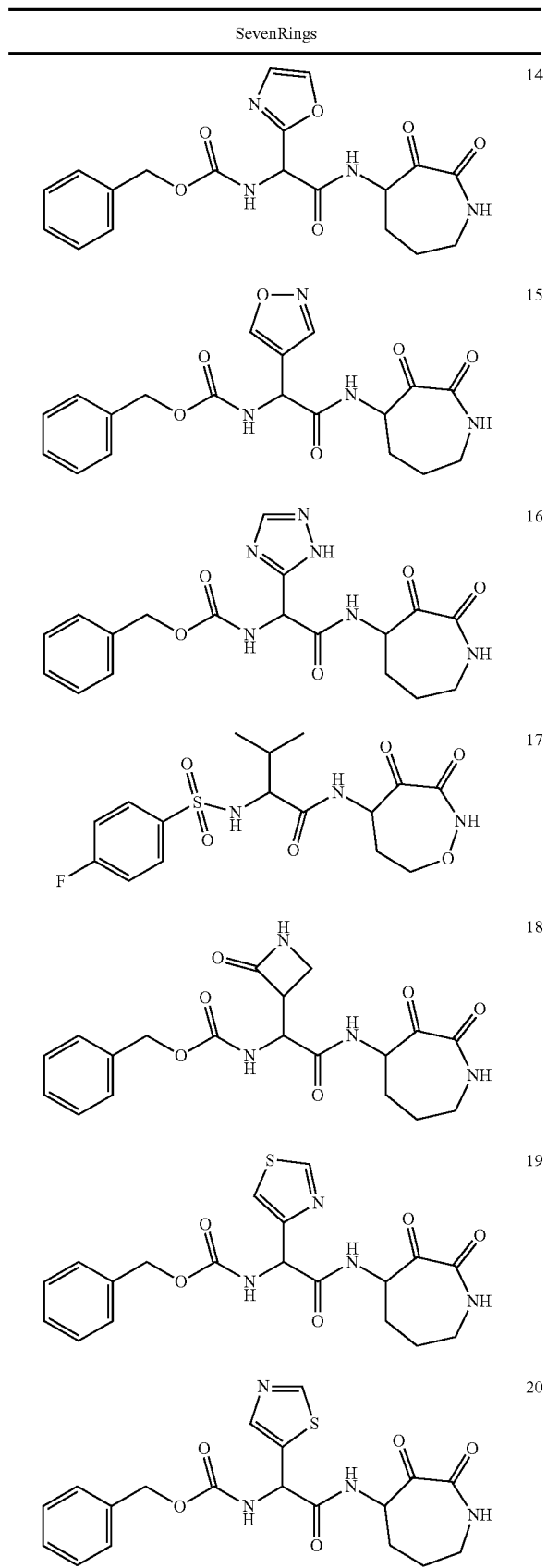

TABLE 3-continued
SevenRings
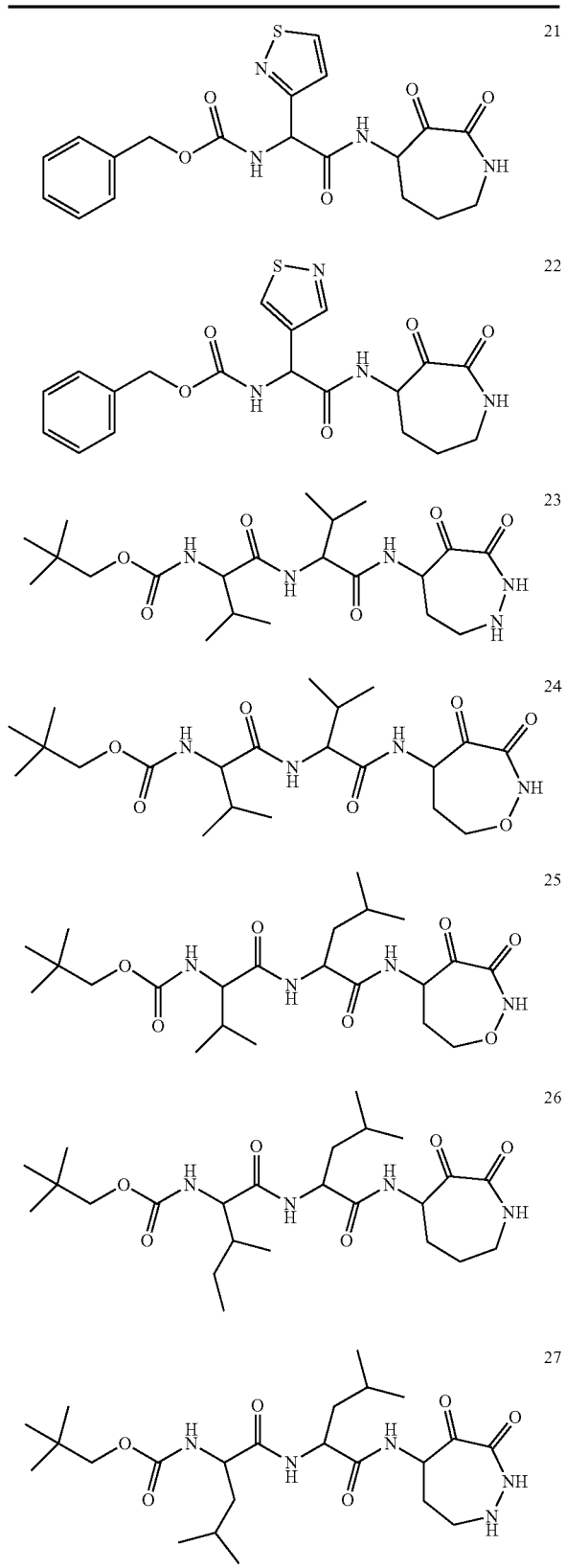
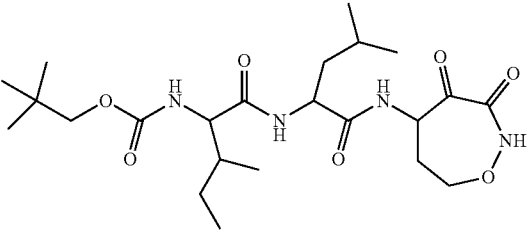 [SMILES: CCC(C)C(NC(=O)OCC(C)(C)C)C(=O)NC(CC(C)C)C(=O)NC1CCONC(=O)C1=O]
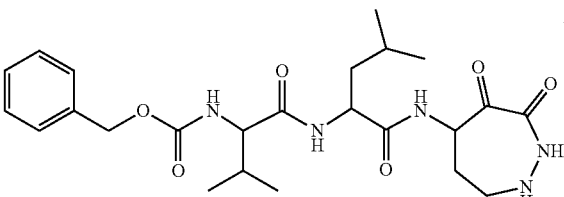
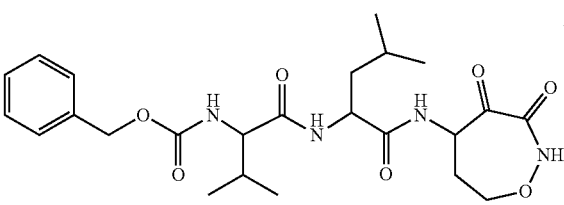 [SMILES: CC(C)CC(NC(=O)C(NC(=O)OCc1ccccc1)C(C)C)C(=O)NC1CCONC(=O)C1=O]
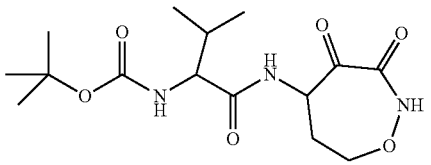 [SMILES: CC(C)C(NC(=O)OC(C)(C)C)C(=O)NC1CCONC(=O)C1=O]
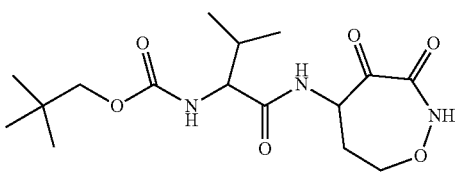 [SMILES: CC(C)C(NC(=O)OCC(C)(C)C)C(=O)NC1CCONC(=O)C1=O]
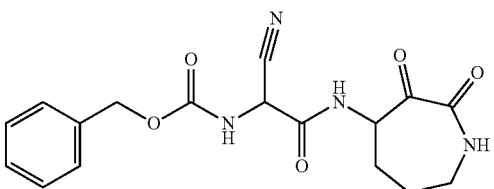
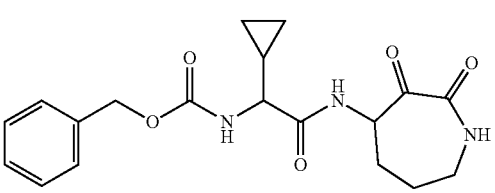 [SMILES: O=C(NC(C(=O)NC1CCCNC(=O)C1=O)C1CC1)OCc1ccccc1]
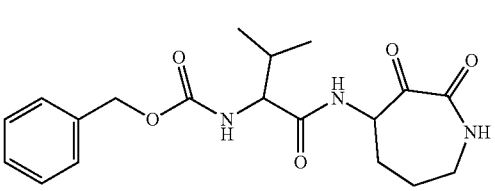 [SMILES: CC(C)C(NC(=O)OCc1ccccc1)C(=O)NC1CCCNC(=O)C1=O]

TABLE 3-continued
SevenRings
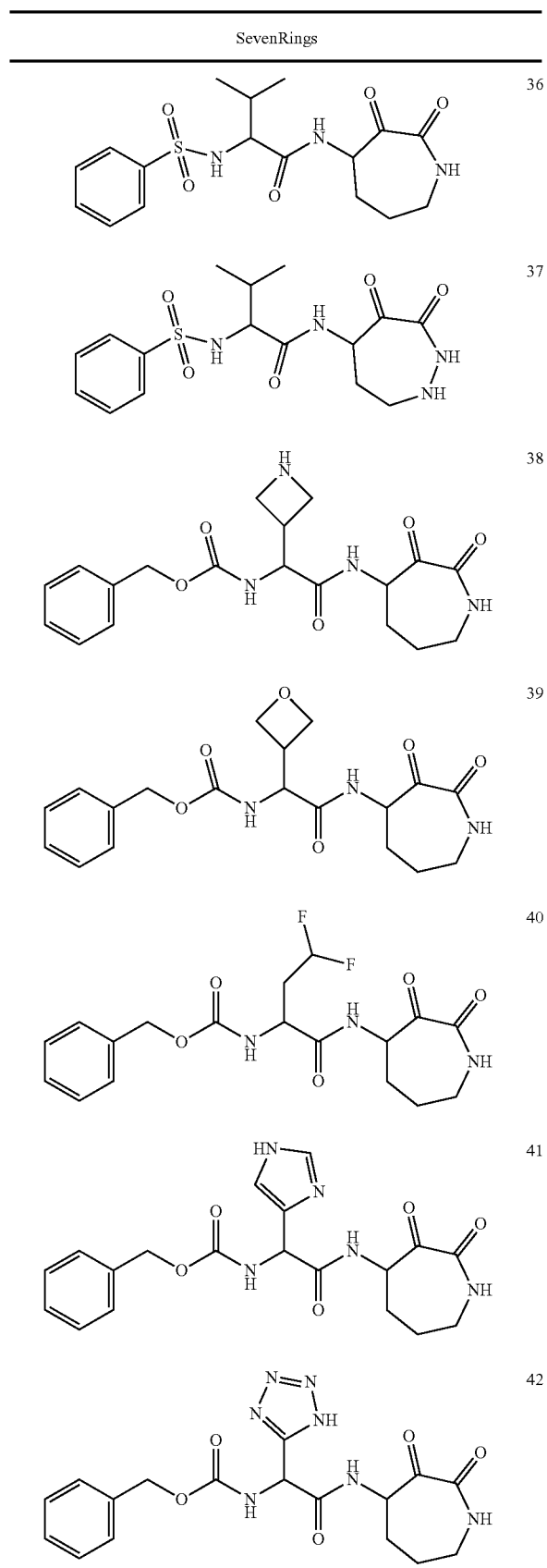
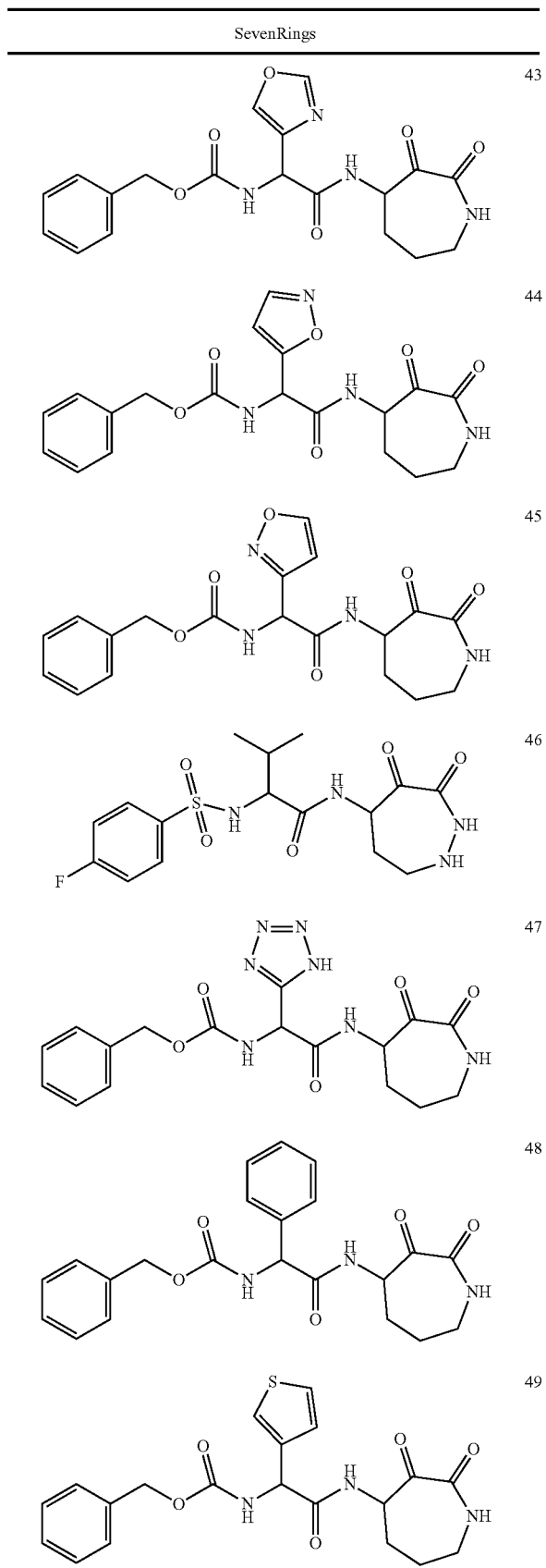

TABLE 3-continued
SevenRings
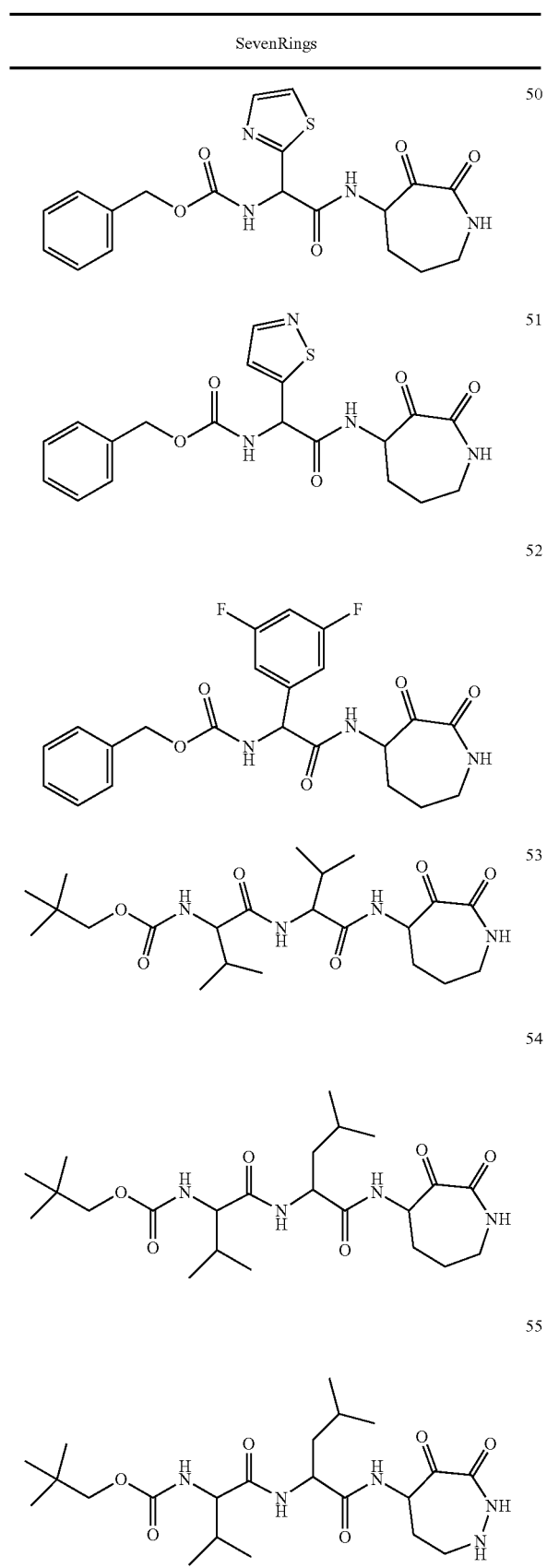
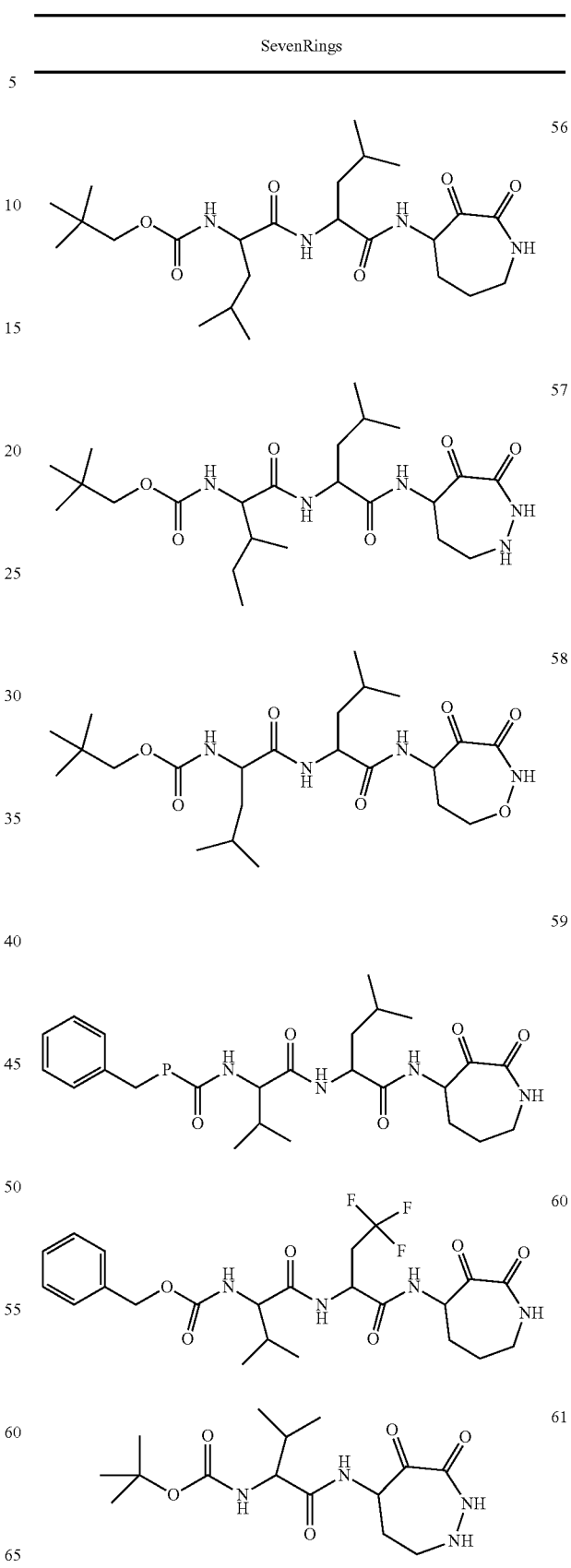

TABLE 4
EightRings
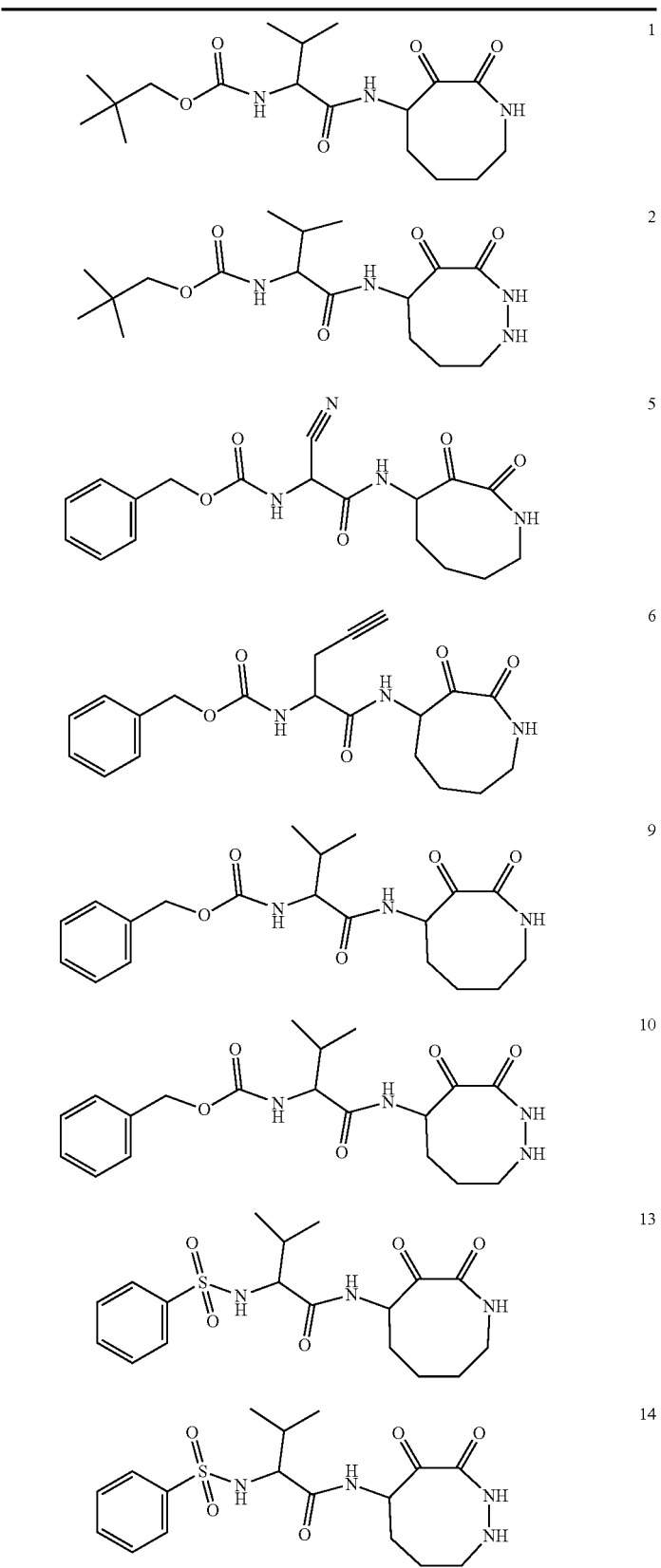

TABLE 4-continued
EightRings
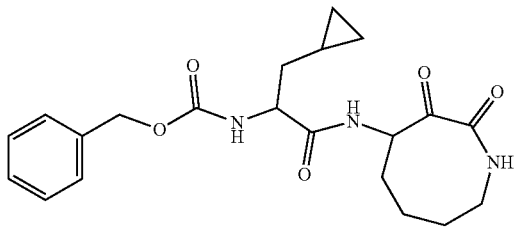 [SMILES: O=C(NC(CC1CC1)C(=O)NC1CCCCNC(=O)C1=O)OCc1ccccc1] 17
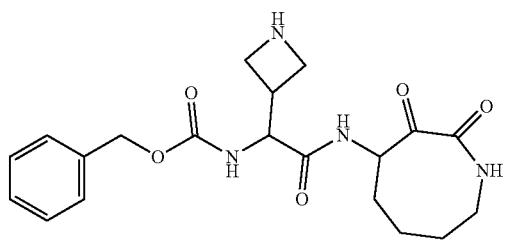 [SMILES: O=C(NC(C(=O)NC1CCCCNC(=O)C1=O)C1CNC1)OCc1ccccc1] 18
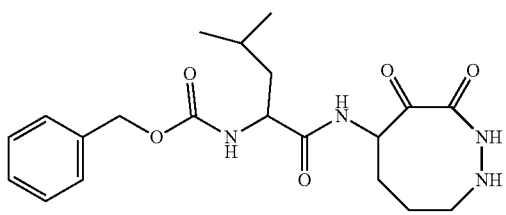 [SMILES: CC(C)CC(NC(=O)OCc1ccccc1)C(=O)NC1CCCNNC(=O)C1=O] 21
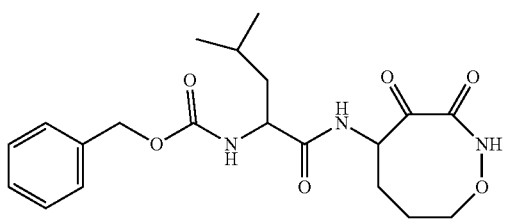 [SMILES: CC(C)CC(NC(=O)OCc1ccccc1)C(=O)NC1CCCONC(=O)C1=O] 22
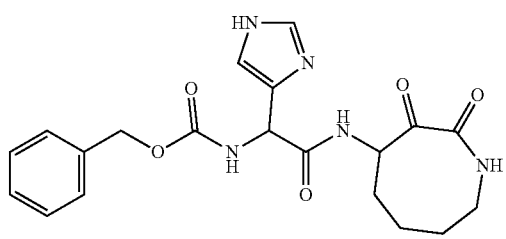 [SMILES: O=C(NC(C(=O)NC1CCCCNC(=O)C1=O)c1c[nH]cn1)OCc1ccccc1] 25
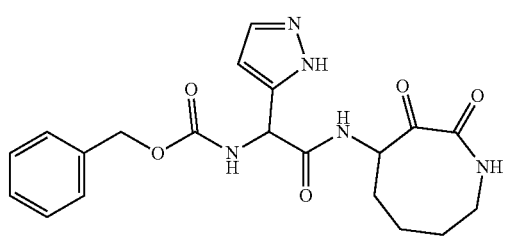 [SMILES: O=C(NC(C(=O)NC1CCCCNC(=O)C1=O)c1ccn[nH]1)OCc1ccccc1] 26

TABLE 4-continued
EightRings
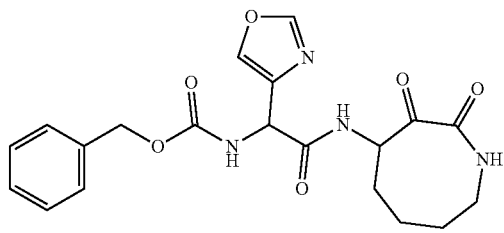 [SMILES: O=C(NC(C(=O)NC1CCCCNC(=O)C1=O)c1cocn1)OCc1ccccc1]
29
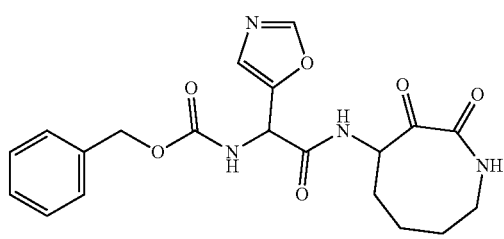
30
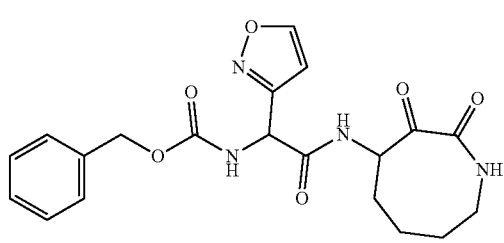 [SMILES: O=C(NC(C(=O)NC1CCCCNC(=O)C1=O)c1ccon1)OCc1ccccc1]
33
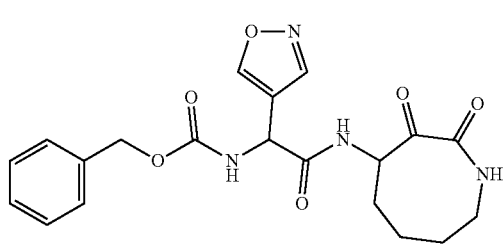 [SMILES: O=C(NC(C(=O)NC1CCCCNC(=O)C1=O)c1cnoc1)OCc1ccccc1]
34
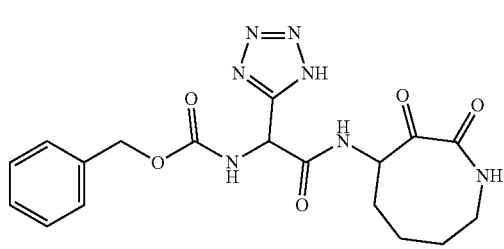 [SMILES: O=C(NC(C(=O)NC1CCCCNC(=O)C1=O)c1nnn[nH]1)OCc1ccccc1]
37
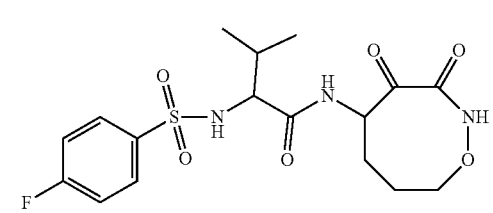 [SMILES: CC(C)C(NS(=O)(=O)c1ccc(F)cc1)C(=O)NC1CCCONC(=O)C1=O]
38

TABLE 4-continued
EightRings
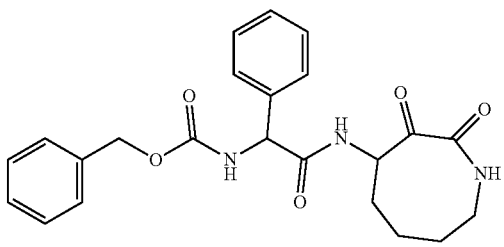 [SMILES: O=C(NC(C(=O)NC1CCCCNC(=O)C1=O)c1ccccc1)OCc1ccccc1]
41
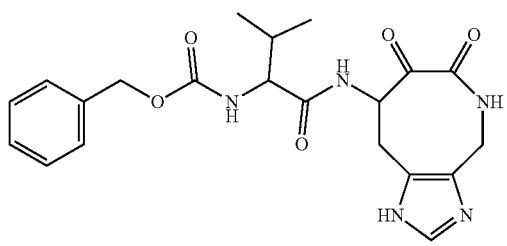
42
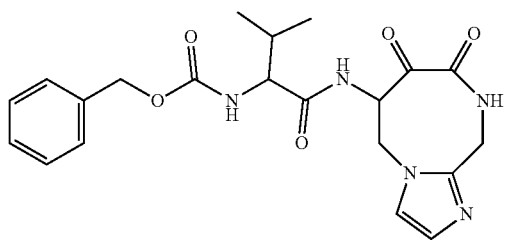 [SMILES: CC(C)C(NC(=O)OCc1ccccc1)C(=O)NC1Cn2ccnc2CNC(=O)C1=O]
45
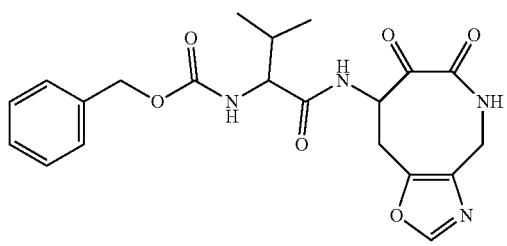 [SMILES: CC(C)C(NC(=O)OCc1ccccc1)C(=O)NC1Cc2ocnc2CNC(=O)C1=O]
46
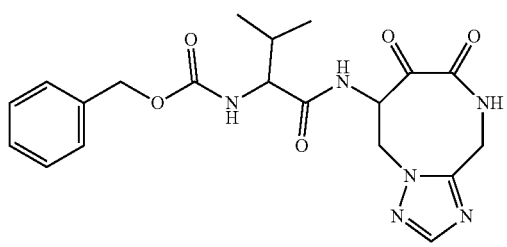 [SMILES: CC(C)C(NC(=O)OCc1ccccc1)C(=O)NC1Cn2ncnc2CNC(=O)C1=O]
49
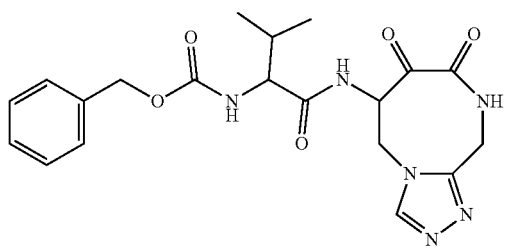 [SMILES: CC(C)C(NC(=O)OCc1ccccc1)C(=O)NC1Cn2cnnc2CNC(=O)C1=O]
50

TABLE 4-continued
EightRings
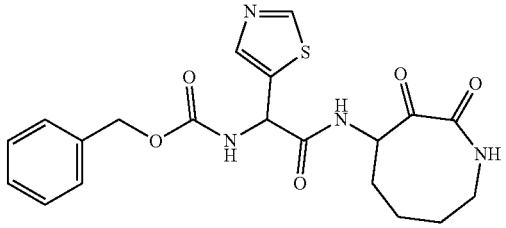 53
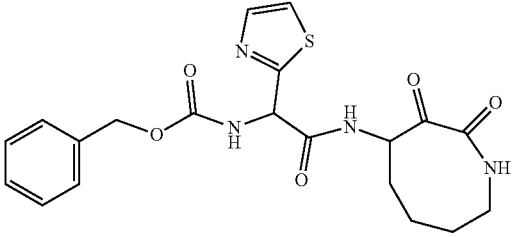 [SMILES: O=C(NC(C(=O)NC1CCCCNC(=O)C1=O)c1nccs1)OCc1ccccc1] 54
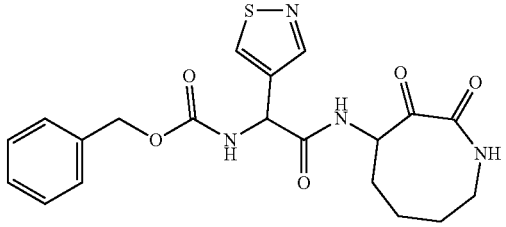 [SMILES: O=C(NC(C(=O)NC1CCCCNC(=O)C1=O)c1cnsc1)OCc1ccccc1] 57
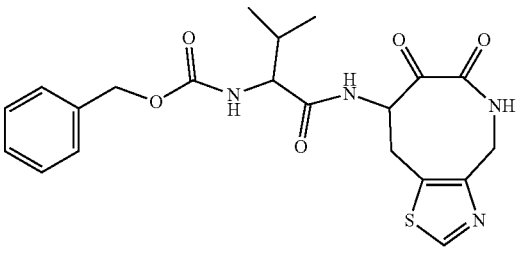 [SMILES: CC(C)C(NC(=O)OCc1ccccc1)C(=O)NC1Cc2scnc2CNC(=O)C1=O] 58
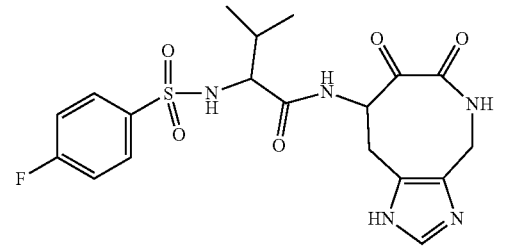 [SMILES: CC(C)C(NS(=O)(=O)c1ccc(F)cc1)C(=O)NC1Cc2[nH]cnc2CNC(=O)C1=O] 61
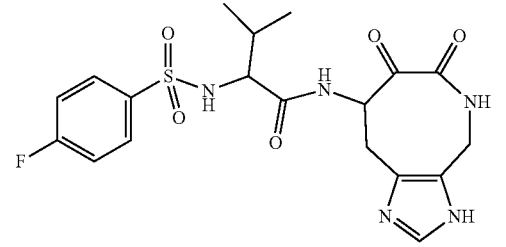 [SMILES: CC(C)C(NS(=O)(=O)c1ccc(F)cc1)C(=O)NC1Cc2nc[nH]c2CNC(=O)C1=O] 62

TABLE 4-continued
EightRings
| | |
|---|---|
| 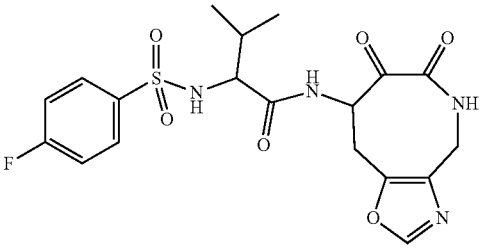 [SMILES: CC(C)C(NS(=O)(=O)c1ccc(F)cc1)C(=O)NC1Cc2ocnc2CNC(=O)C1=O] | 65 |
| 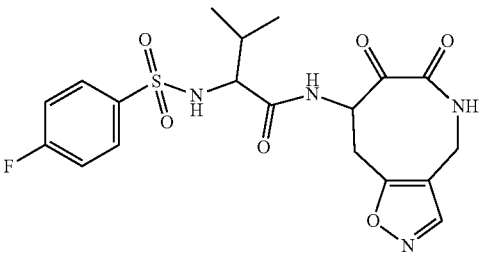 [SMILES: CC(C)C(NS(=O)(=O)c1ccc(F)cc1)C(=O)NC1Cc2oncc2CNC(=O)C1=O] | 66 |
| 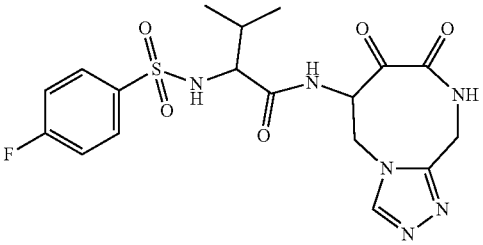 [SMILES: CC(C)C(NS(=O)(=O)c1ccc(F)cc1)C(=O)NC1Cn2cnnc2CNC(=O)C1=O] | 69 |
| 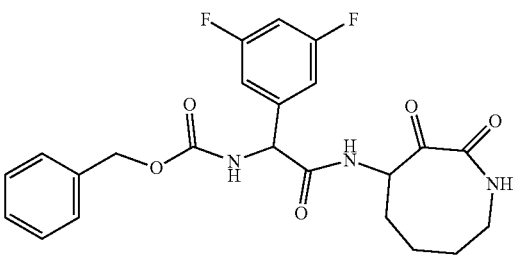 [SMILES: O=C(NC(C(=O)NC1CCCCNC(=O)C1=O)c1cc(F)cc(F)c1)OCc1ccccc1] | 70 |
| 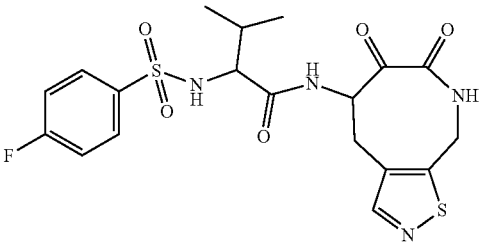 [SMILES: CC(C)C(NS(=O)(=O)c1ccc(F)cc1)C(=O)NC1Cc2cnsc2CNC(=O)C1=O] | 73 |
| 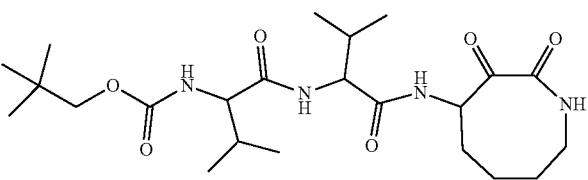 [SMILES: CC(C)C(NC(=O)OCC(C)(C)C)C(=O)NC(C(=O)NC1CCCCNC(=O)C1=O)C(C)C] | 74 |

TABLE 4-continued
EightRings
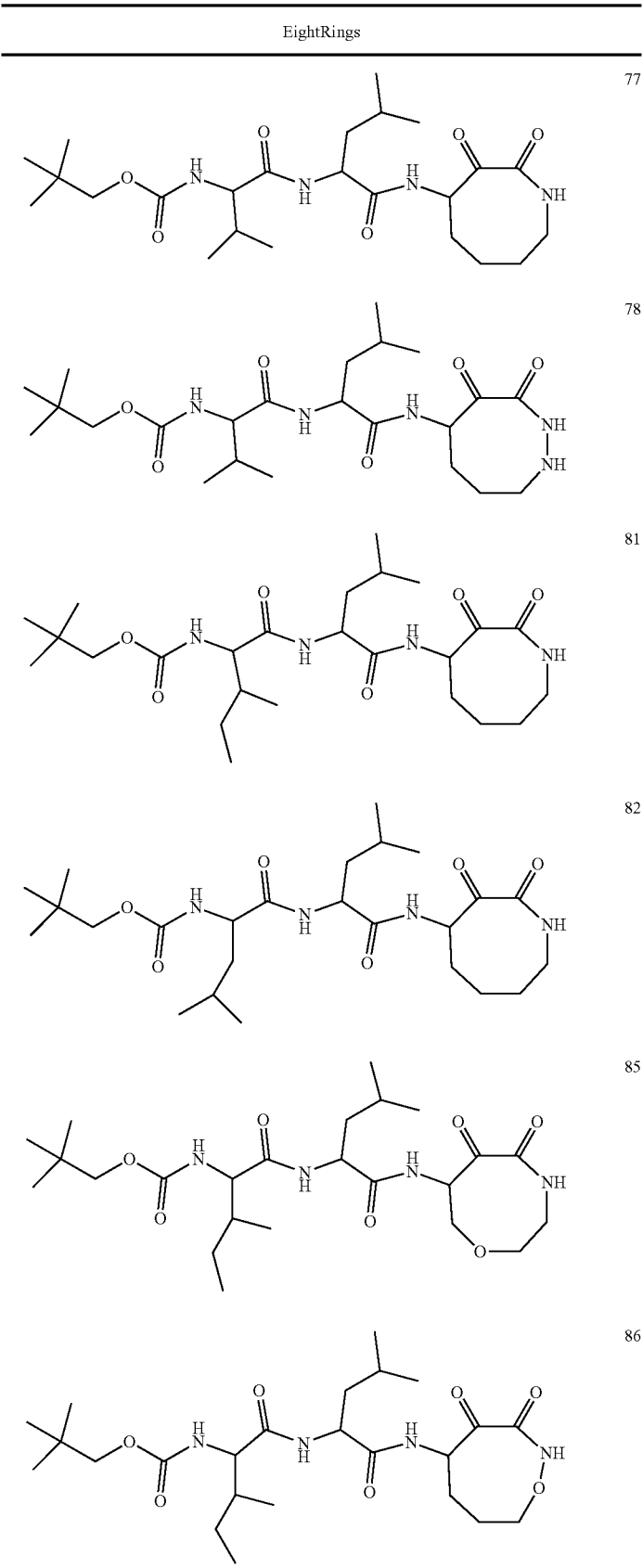

TABLE 4-continued
EightRings
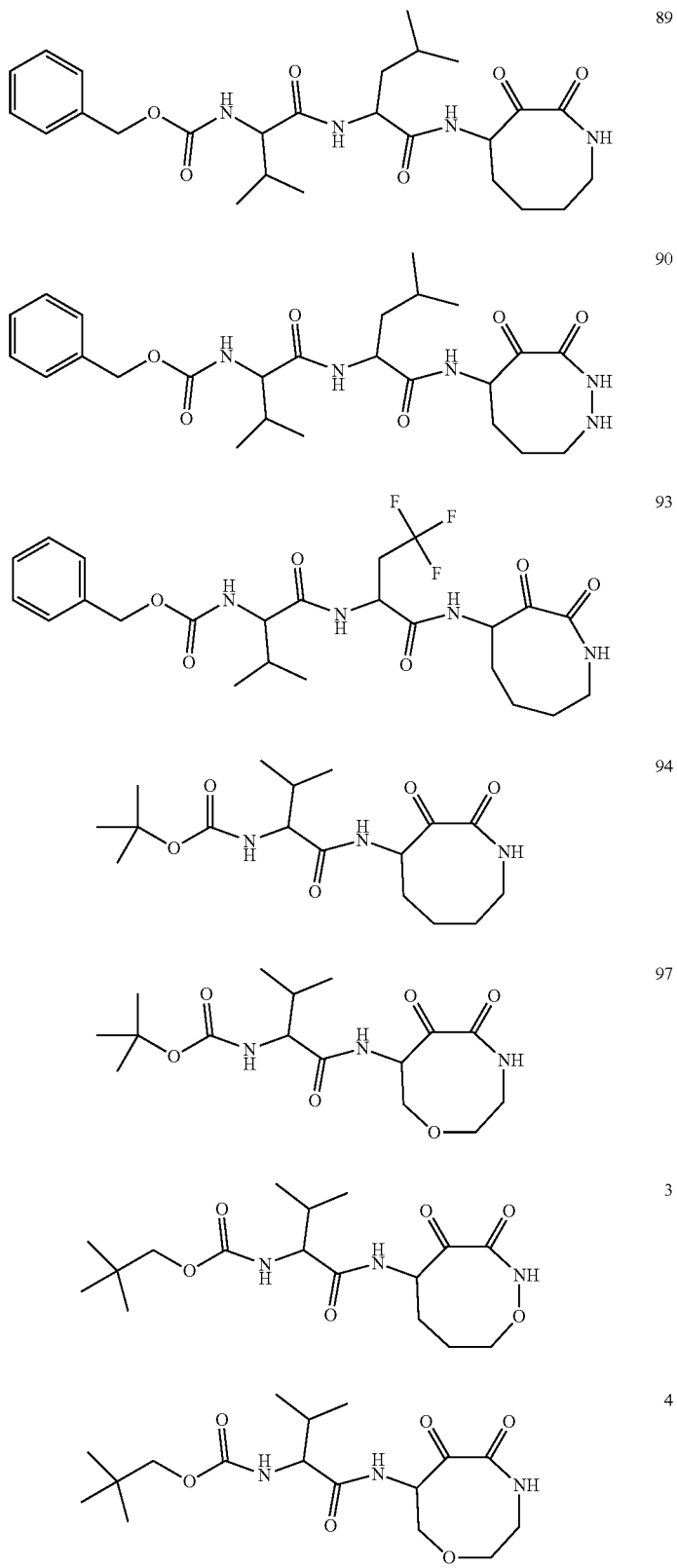

TABLE 4-continued
EightRings
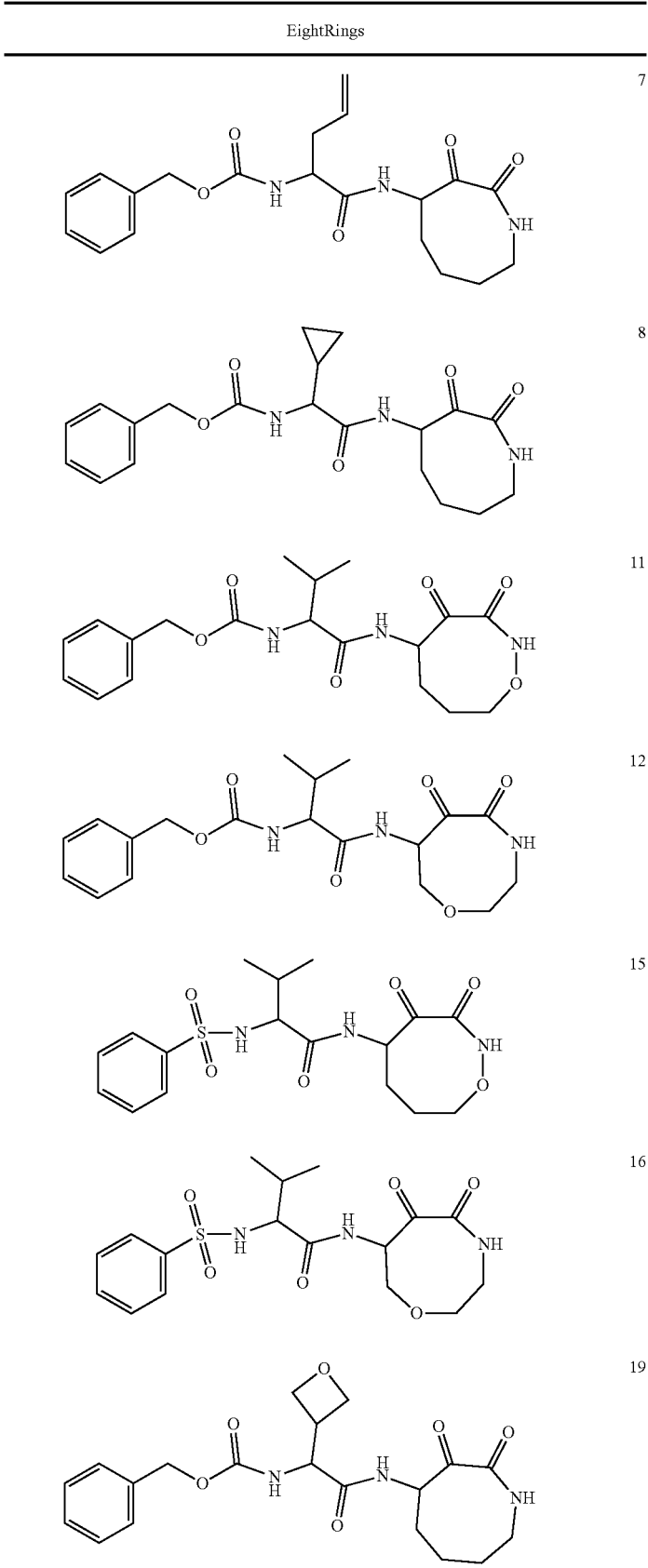
7
8
11
12
15
16
19

TABLE 4-continued
EightRings
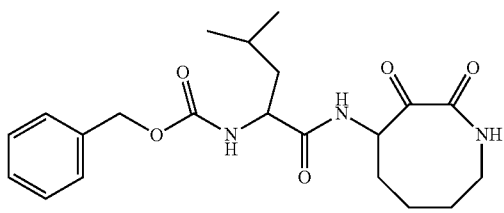 [SMILES: CC(C)CC(NC(=O)OCc1ccccc1)C(=O)NC1CCCCNC(=O)C1=O]
20
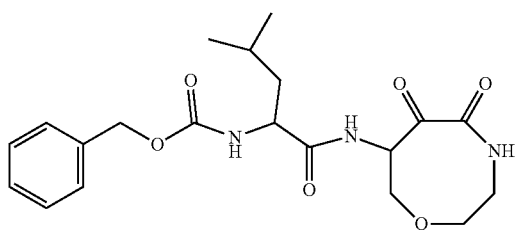 [SMILES: CC(C)CC(NC(=O)OCc1ccccc1)C(=O)NC1COCCNC(=O)C1=O]
23
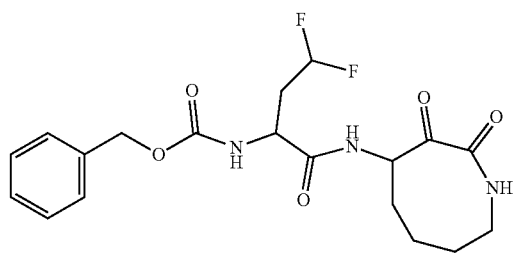 [SMILES: O=C(NC(CC(F)F)C(=O)NC1CCCCNC(=O)C1=O)OCc1ccccc1]
24
27
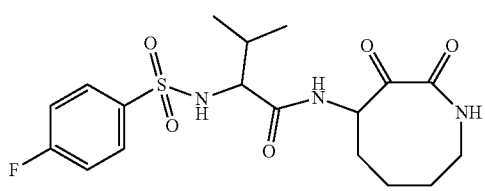 [SMILES: CC(C)C(NS(=O)(=O)c1ccc(F)cc1)C(=O)NC1CCCCNC(=O)C1=O]
28
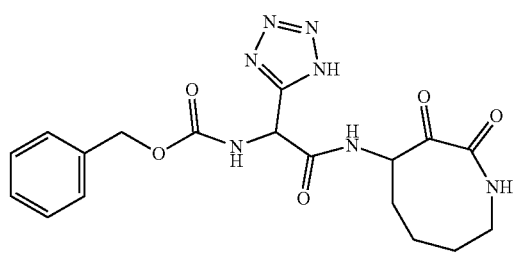 [SMILES: O=C(NC(C(=O)NC1CCCCNC(=O)C1=O)c1nnn[nH]1)OCc1ccccc1]
31
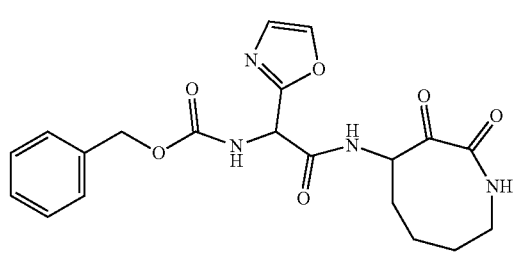 [SMILES: O=C(NC(C(=O)NC1CCCCNC(=O)C1=O)c1ncco1)OCc1ccccc1]

TABLE 4-continued
EightRings
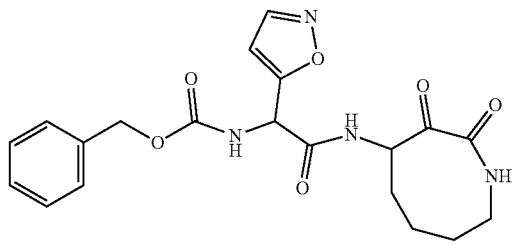 [SMILES: O=C(NC(C(=O)NC1CCCCNC(=O)C1=O)c1ccno1)OCc1ccccc1]
32
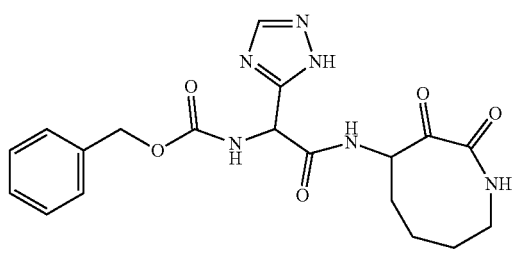 [SMILES: O=C(NC(C(=O)NC1CCCCNC(=O)C1=O)c1ncn[nH]1)OCc1ccccc1]
35
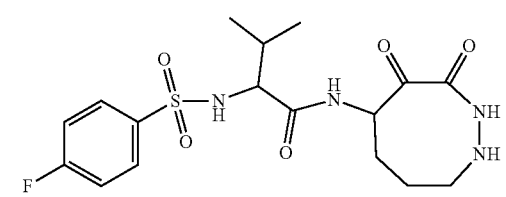 [SMILES: CC(C)C(NS(=O)(=O)c1ccc(F)cc1)C(=O)NC1CCCNNC(=O)C1=O]
36
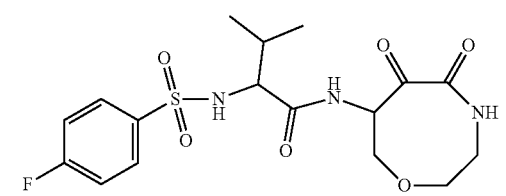 [SMILES: CC(C)C(NS(=O)(=O)c1ccc(F)cc1)C(=O)NC1COCCNC(=O)C1=O]
39
40
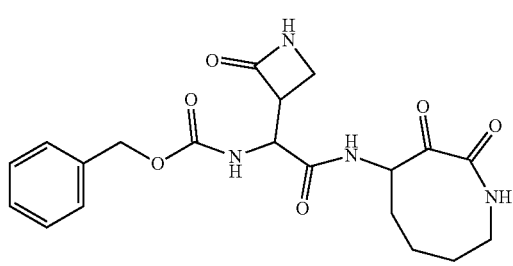 [SMILES: O=C(NC(C(=O)NC1CCCCNC(=O)C1=O)C1CNC1=O)OCc1ccccc1]
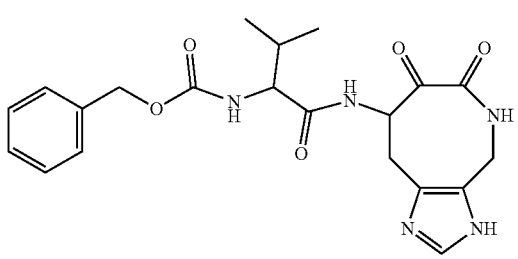 [SMILES: CC(C)C(NC(=O)OCc1ccccc1)C(=O)NC1Cc2nc[nH]c2CNC(=O)C1=O]
43

TABLE 4-continued
EightRings
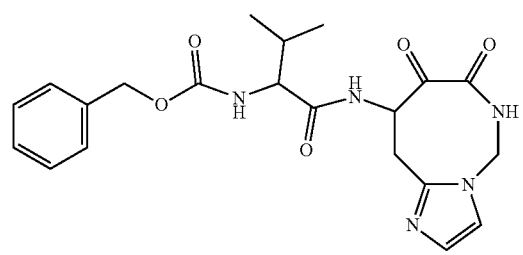 [SMILES: CC(C)C(NC(=O)OCc1ccccc1)C(=O)NC1Cc2nccn2CNC(=O)C1=O]
44
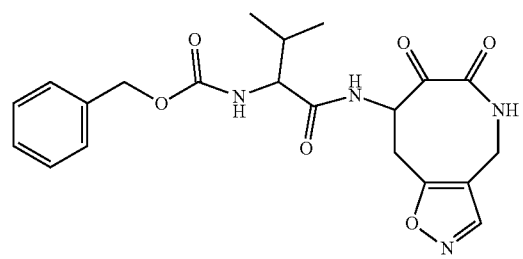 [SMILES: CC(C)C(NC(=O)OCc1ccccc1)C(=O)NC1Cc2oncc2CNC(=O)C1=O]
47
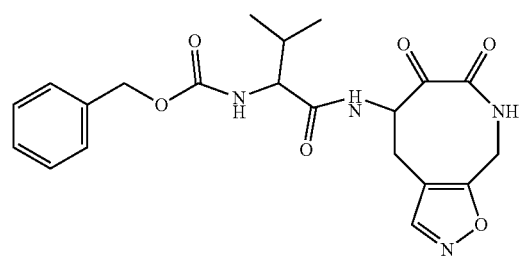 [SMILES: CC(C)C(NC(=O)OCc1ccccc1)C(=O)NC1Cc2cnoc2CNC(=O)C1=O]
48
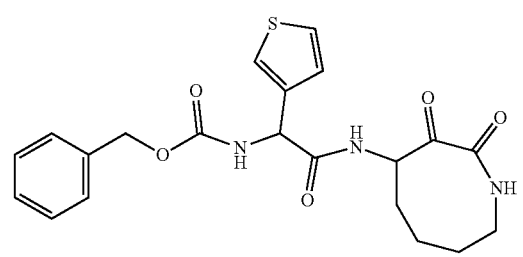 [SMILES: O=C(NC(C(=O)NC1CCCCNC(=O)C1=O)c1ccsc1)OCc1ccccc1]
51
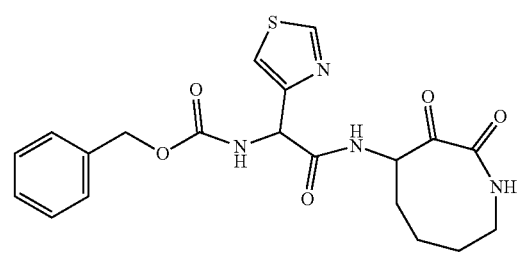 [SMILES: O=C(NC(C(=O)NC1CCCCNC(=O)C1=O)c1cscn1)OCc1ccccc1]
52
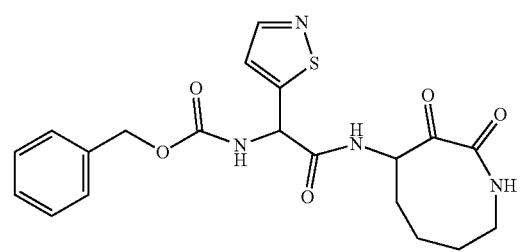 [SMILES: O=C(NC(C(=O)NC1CCCCNC(=O)C1=O)c1ccns1)OCc1ccccc1]
55

TABLE 4-continued
EightRings
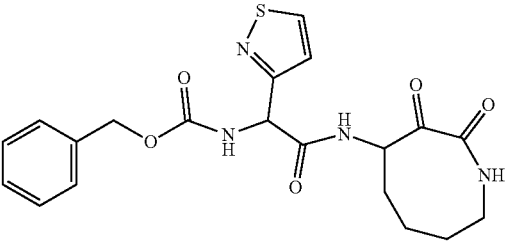 [SMILES: O=C(NC(C(=O)NC1CCCCNC(=O)C1=O)c1ccsn1)OCc1ccccc1] 56
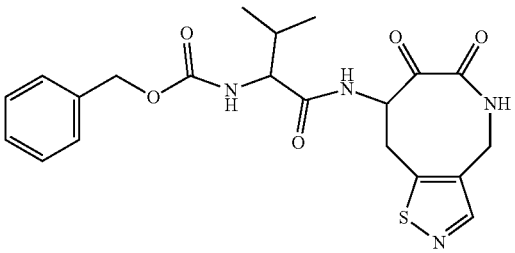 59
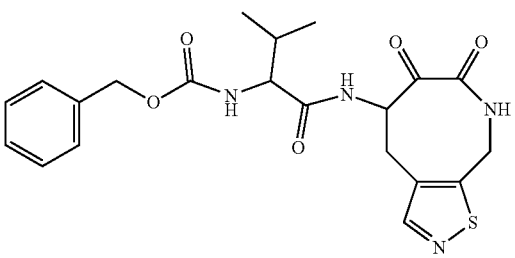 [SMILES: CC(C)C(NC(=O)OCc1ccccc1)C(=O)NC1Cc2cnsc2CNC(=O)C1=O] 60
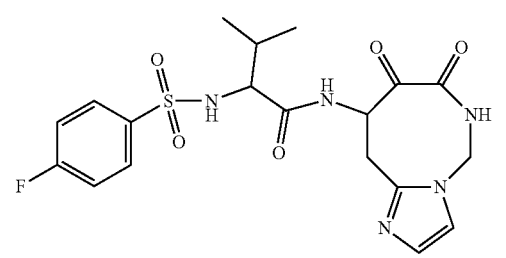 [SMILES: CC(C)C(NS(=O)(=O)c1ccc(F)cc1)C(=O)NC1Cc2nccn2CNC(=O)C1=O] 63
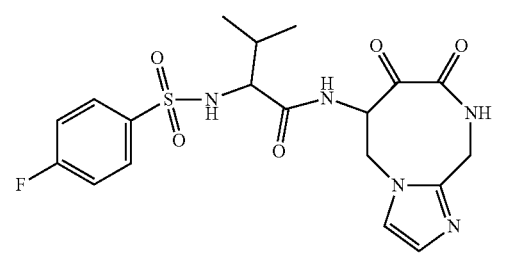 [SMILES: CC(C)C(NS(=O)(=O)c1ccc(F)cc1)C(=O)NC1Cn2ccnc2CNC(=O)C1=O] 64
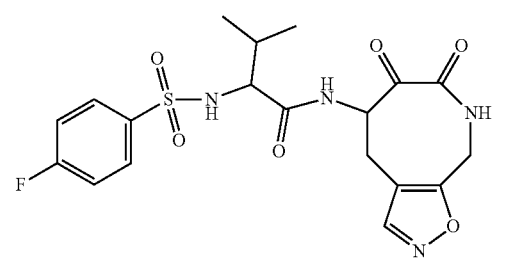 [SMILES: CC(C)C(NS(=O)(=O)c1ccc(F)cc1)C(=O)NC1Cc2cnoc2CNC(=O)C1=O] 67

TABLE 4-continued

EightRings

| | |
|---|---|
| (structure) | 68 |
| (structure) | 71 |
| (structure) | 72 |
| (structure) | 75 |
| (structure) | 76 |
| (structure) | 79 |
| (structure) | 80 |

TABLE 4-continued
EightRings
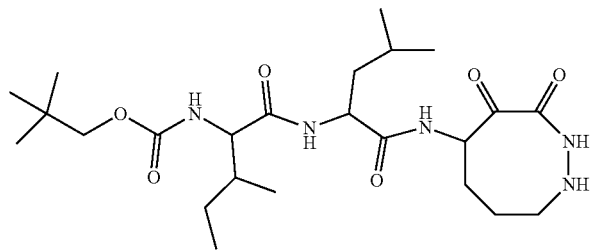 [SMILES: CCC(C)C(NC(=O)OCC(C)(C)C)C(=O)NC(CC(C)C)C(=O)NC1CCCNNC(=O)C1=O]
83
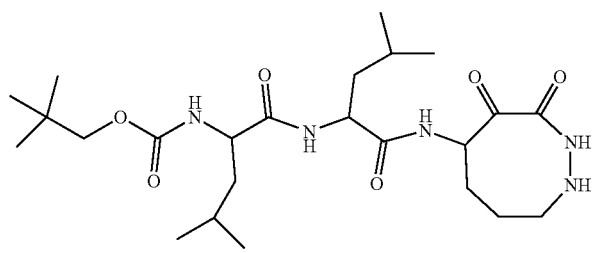 [SMILES: CC(C)CC(NC(=O)OCC(C)(C)C)C(=O)NC(CC(C)C)C(=O)NC1CCCNNC(=O)C1=O]
84
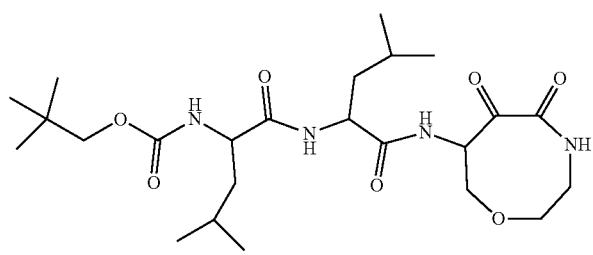 [SMILES: CC(C)CC(NC(=O)OCC(C)(C)C)C(=O)NC(CC(C)C)C(=O)NC1COCCNC(=O)C1=O]
87
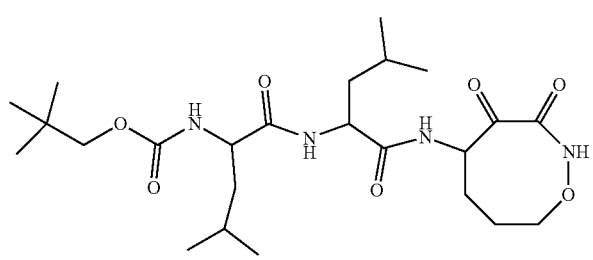 [SMILES: CC(C)CC(NC(=O)OCC(C)(C)C)C(=O)NC(CC(C)C)C(=O)NC1CCCONC(=O)C1=O]
88
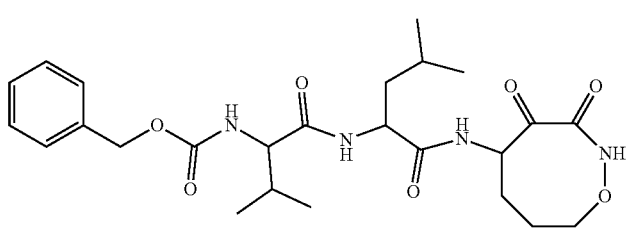 [SMILES: CC(C)CC(NC(=O)C(NC(=O)OCc1ccccc1)C(C)C)C(=O)NC1CCCONC(=O)C1=O]
91
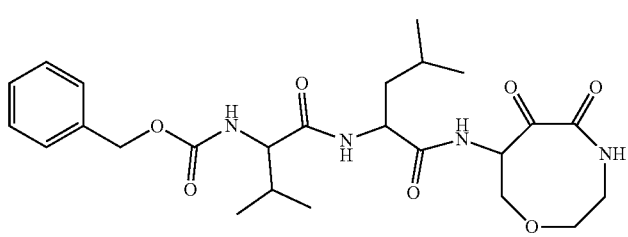 [SMILES: CC(C)CC(NC(=O)C(NC(=O)OCc1ccccc1)C(C)C)C(=O)NC1COCCNC(=O)C1=O]
92

TABLE 4-continued

EightRings

| | |
|---|---|
| (structure) | 95 |
| (structure) | 96 |

TABLE 5

NineRings

| | |
|---|---|
| (structure) | 1 |
| (structure) | 2 |
| (structure) | 5 |
| (structure) | 6 |
| (structure) | 9 |

TABLE 5-continued
NineRings
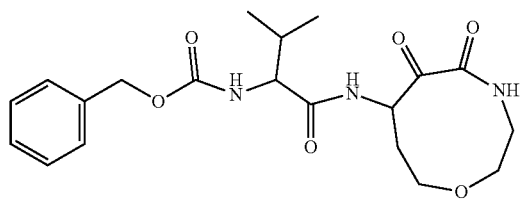 [SMILES: CC(C)C(NC(=O)OCc1ccccc1)C(=O)NC1CCOCCNC(=O)C1=O]
10
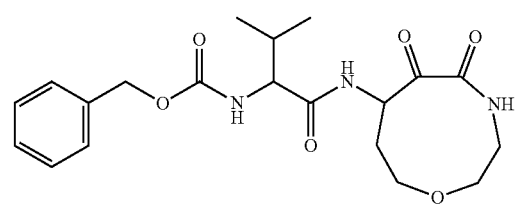 [SMILES: CC(C)C(NC(=O)OCc1ccccc1)C(=O)NC1CCOCCNC(=O)C1=O]
13
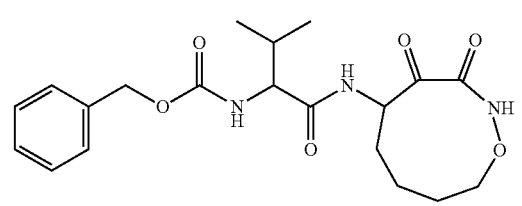
14
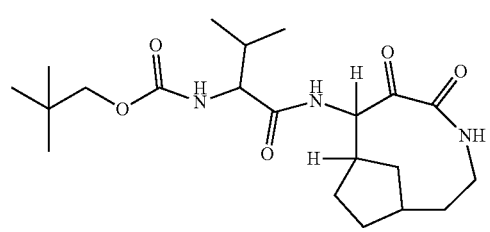 [SMILES: CC(C)C(NC(=O)OCC(C)(C)C)C(=O)NC1C(=O)C(=O)NCCC2CCC1C2]
17
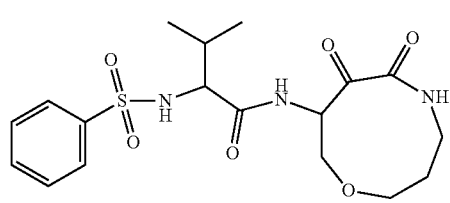 [SMILES: CC(C)C(NS(=O)(=O)c1ccccc1)C(=O)NC1COCCCNC(=O)C1=O]
18
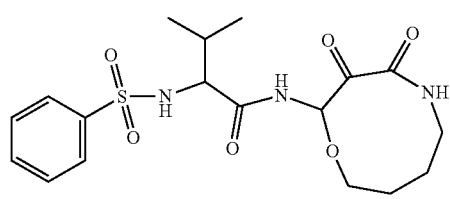 [SMILES: CC(C)C(NS(=O)(=O)c1ccccc1)C(=O)NC1OCCCCNC(=O)C1=O]
21
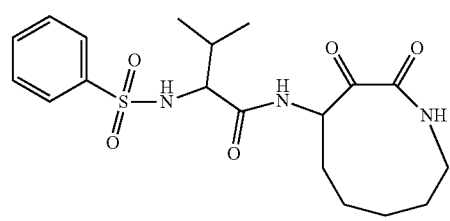 [SMILES: CC(C)C(NS(=O)(=O)c1ccccc1)C(=O)NC1CCCCCNC(=O)C1=O]
22

TABLE 5-continued
NineRings
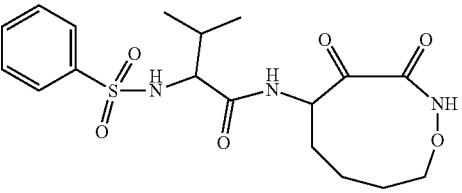 [SMILES: CC(C)C(NS(=O)(=O)c1ccccc1)C(=O)NC1CCCCONC(=O)C1=O]
25
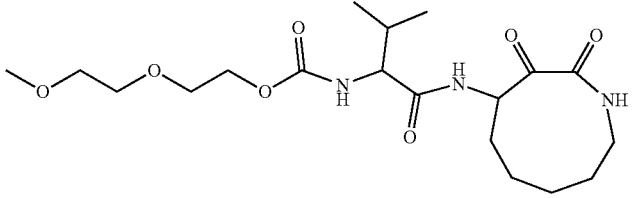 [SMILES: COCCOCCOC(=O)NC(C(=O)NC1CCCCCNC(=O)C1=O)C(C)C]
26
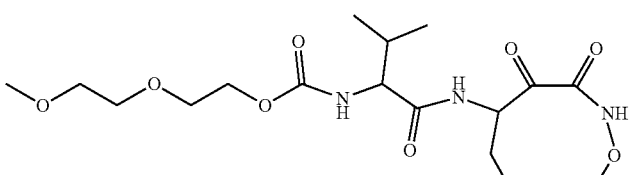
29
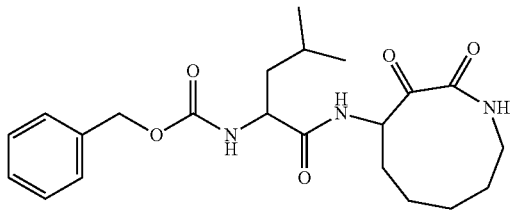 [SMILES: CC(C)CC(NC(=O)OCc1ccccc1)C(=O)NC1CCCCCNC(=O)C1=O]
30
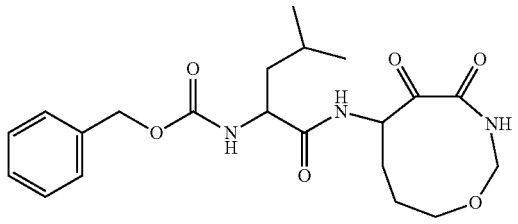 [SMILES: CC(C)CC(NC(=O)OCc1ccccc1)C(=O)NC1CCCOCNC(=O)C1=O]
33

34
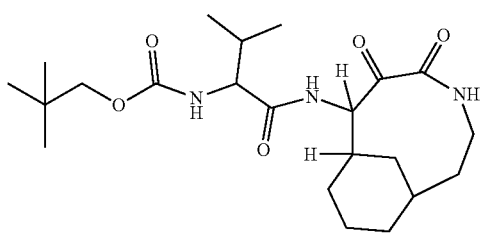 [SMILES: CC(C)C(NC(=O)OCC(C)(C)C)C(=O)NC1C(=O)C(=O)NCCC2CCCC1C2]
37

TABLE 5-continued
NineRings
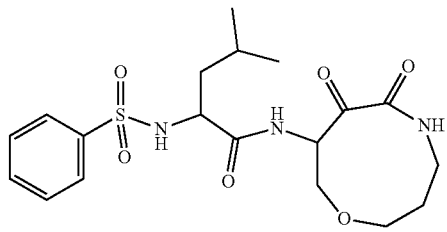 [SMILES: CC(C)CC(NS(=O)(=O)c1ccccc1)C(=O)NC1COCCCNC(=O)C1=O]
38
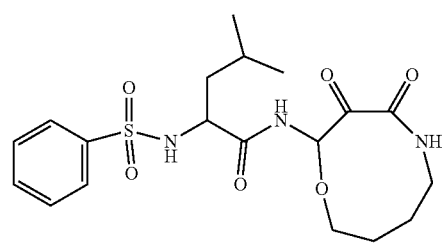 [SMILES: CC(C)CC(NS(=O)(=O)c1ccccc1)C(=O)NC1OCCCCNC(=O)C1=O]
41
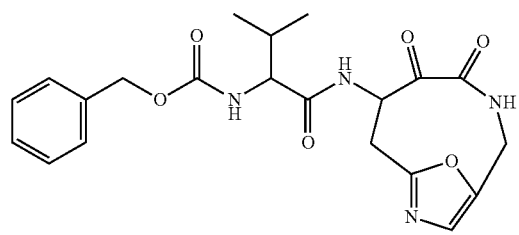 [SMILES: CC(C)C(NC(=O)OCc1ccccc1)C(=O)NC1Cc2ncc(o2)CNC(=O)C1=O]
42
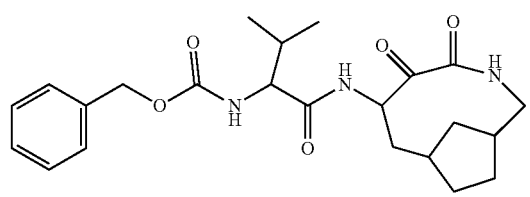 [SMILES: CC(C)C(NC(=O)OCc1ccccc1)C(=O)NC1CC2CCC(CNC(=O)C1=O)C2]
45
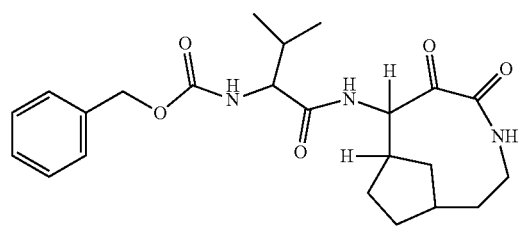 [SMILES: CC(C)C(NC(=O)OCc1ccccc1)C(=O)NC1C(=O)C(=O)NCCC2CCC1C2]
46
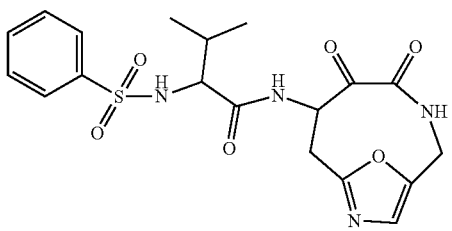 [SMILES: CC(C)C(NS(=O)(=O)c1ccccc1)C(=O)NC1CC2=NC=C(CNC(=O)C1=O)O2]
49

TABLE 5-continued
NineRings
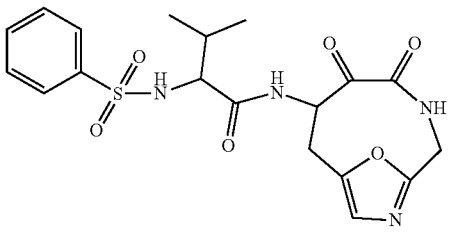 [SMILES: CC(C)C(NS(=O)(=O)c1ccccc1)C(=O)NC1CC2=CN=C(CNC(=O)C1=O)O2] 50
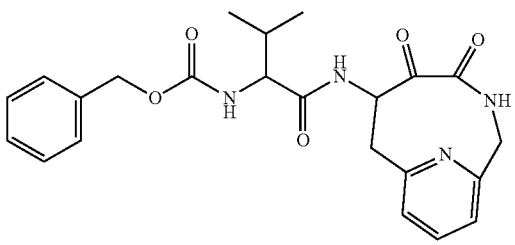 [SMILES: CC(C)C(NC(=O)OCc1ccccc1)C(=O)NC1Cc2cccc(n2)CNC(=O)C1=O] 53
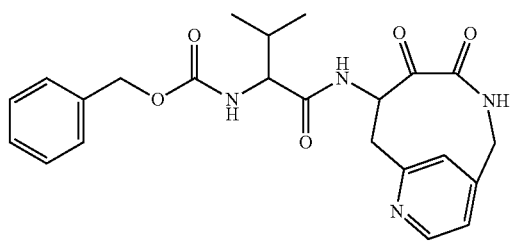 [SMILES: CC(C)C(NC(=O)OCc1ccccc1)C(=O)NC1Cc2cc(ccn2)CNC(=O)C1=O] 54
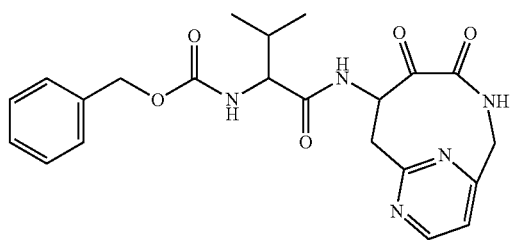 [SMILES: CC(C)C(NC(=O)OCc1ccccc1)C(=O)NC1Cc2nccc(n2)CNC(=O)C1=O] 57
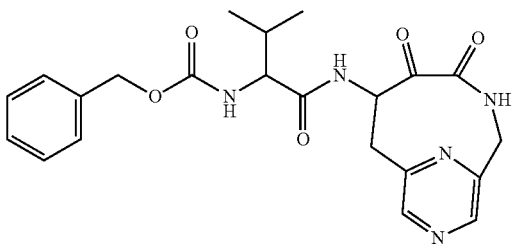 [SMILES: CC(C)C(NC(=O)OCc1ccccc1)C(=O)NC1Cc2cncc(n2)CNC(=O)C1=O] 58
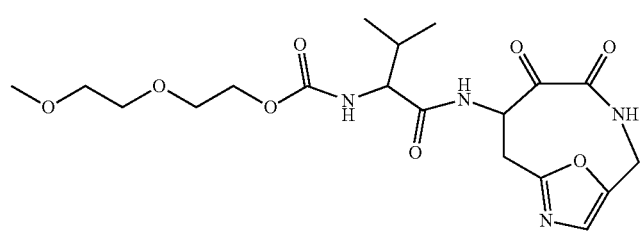 [SMILES: COCCOCCOC(=O)NC(C(=O)NC1CC2=NC=C(CNC(=O)C1=O)O2)C(C)C] 61

TABLE 5-continued
NineRings
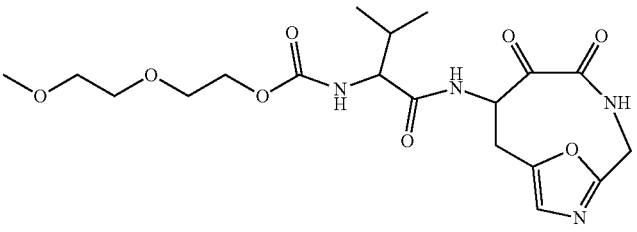 [SMILES: COCCOCCOC(=O)NC(C(=O)NC1CC2=CN=C(CNC(=O)C1=O)O2)C(C)C]
62
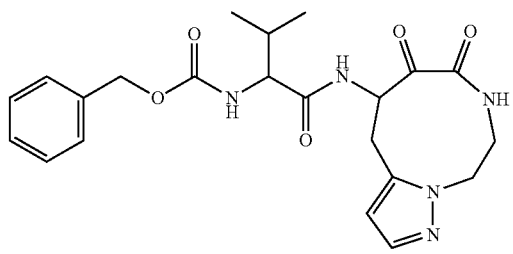 [SMILES: CC(C)C(NC(=O)OCc1ccccc1)C(=O)NC1Cc2ccnn2CCNC(=O)C1=O]
65
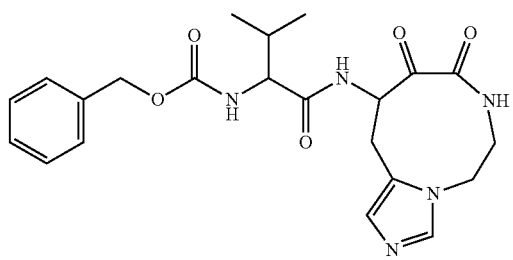 [SMILES: CC(C)C(NC(=O)OCc1ccccc1)C(=O)NC1Cc2cncn2CCNC(=O)C1=O]
66
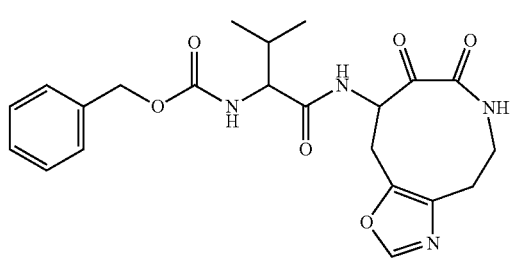 [SMILES: CC(C)C(NC(=O)OCc1ccccc1)C(=O)NC1Cc2ocnc2CCNC(=O)C1=O]
69
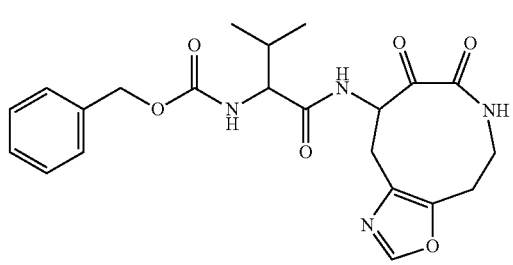 [SMILES: CC(C)C(NC(=O)OCc1ccccc1)C(=O)NC1Cc2ncoc2CCNC(=O)C1=O]
70
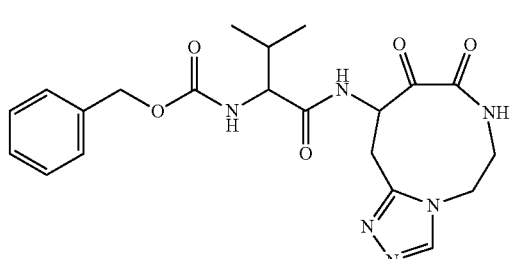
73

TABLE 5-continued
NineRings
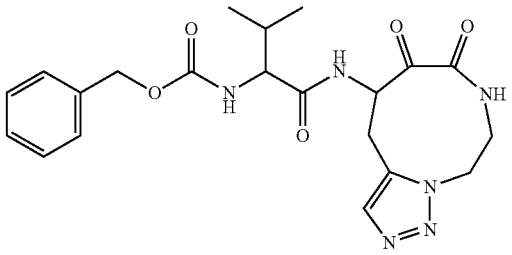 [SMILES: CC(C)C(NC(=O)OCc1ccccc1)C(=O)NC1Cc2cnnn2CCNC(=O)C1=O]
74
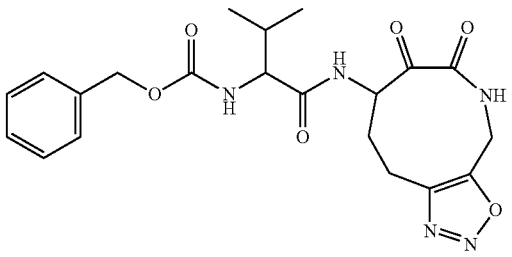 [SMILES: CC(C)C(NC(=O)OCc1ccccc1)C(=O)NC1CCc2nnoc2CNC(=O)C1=O]
77
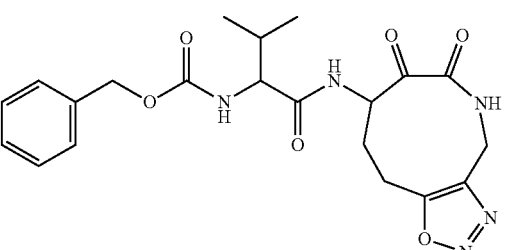
78
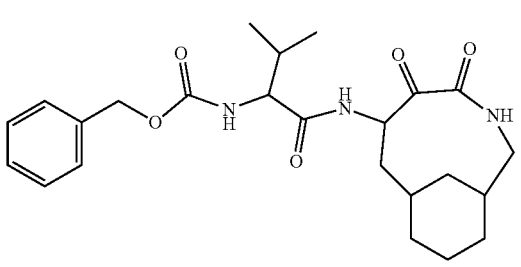 [SMILES: CC(C)C(NC(=O)OCc1ccccc1)C(=O)NC1CC2CCCC(CNC(=O)C1=O)C2]
81
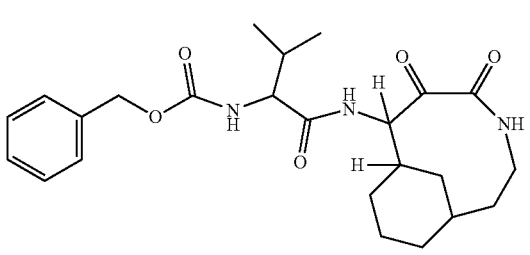 [SMILES: CC(C)C(NC(=O)OCc1ccccc1)C(=O)NC1C(=O)C(=O)NCCC2CCCC1C2]
82
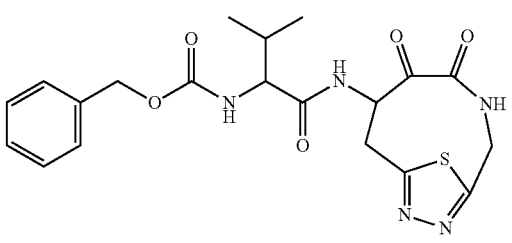 [SMILES: CC(C)C(NC(=O)OCc1ccccc1)C(=O)NC1CC2=NN=C(CNC(=O)C1=O)S2]
85

TABLE 5-continued
NineRings
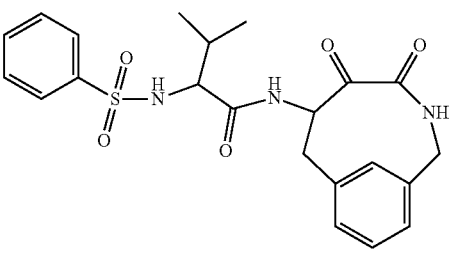 [SMILES: CC(C)C(NS(=O)(=O)c1ccccc1)C(=O)NC1Cc2cccc(c2)CNC(=O)C1=O] 86
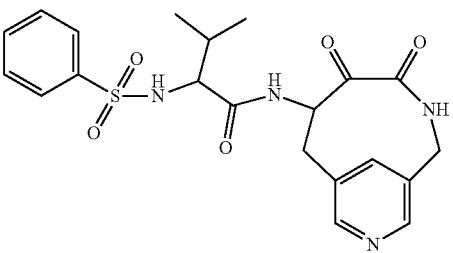 [SMILES: CC(C)C(NS(=O)(=O)c1ccccc1)C(=O)NC1Cc2cncc(c2)CNC(=O)C1=O] 89
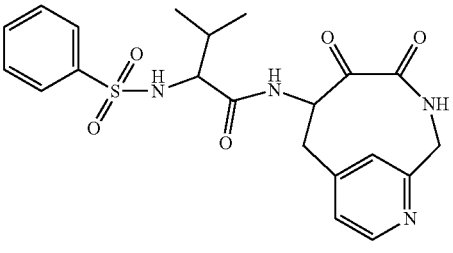 [SMILES: CC(C)C(NS(=O)(=O)c1ccccc1)C(=O)NC1Cc2ccnc(c2)CNC(=O)C1=O] 90
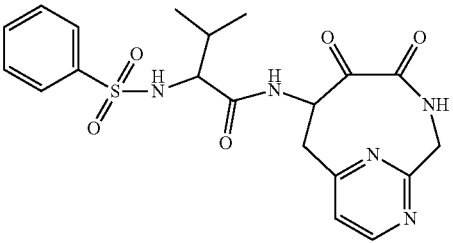 [SMILES: CC(C)C(NS(=O)(=O)c1ccccc1)C(=O)NC1Cc2ccnc(n2)CNC(=O)C1=O] 93
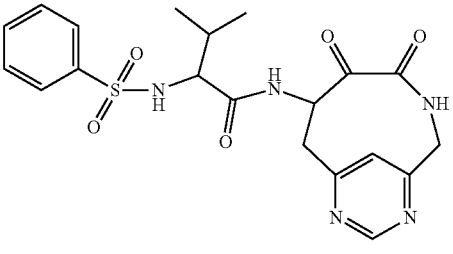 [SMILES: CC(C)C(NS(=O)(=O)c1ccccc1)C(=O)NC1Cc2cc(ncn2)CNC(=O)C1=O] 94
97

TABLE 5-continued
NineRings
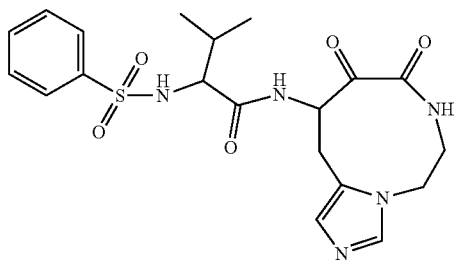 [SMILES: CC(C)C(NS(=O)(=O)c1ccccc1)C(=O)NC1Cc2cncn2CCNC(=O)C1=O]
98
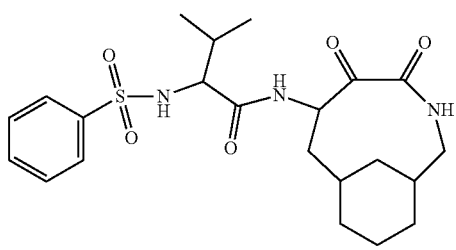 [SMILES: CC(C)C(NS(=O)(=O)c1ccccc1)C(=O)NC1CC2CCCC(CNC(=O)C1=O)C2]
101
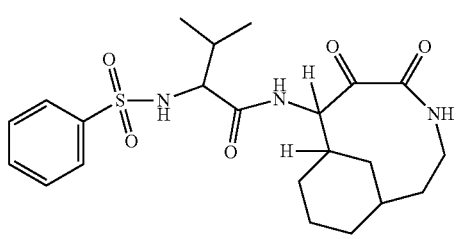 [SMILES: CC(C)C(NS(=O)(=O)c1ccccc1)C(=O)NC1C(=O)C(=O)NCCC2CCCC1C2]
102
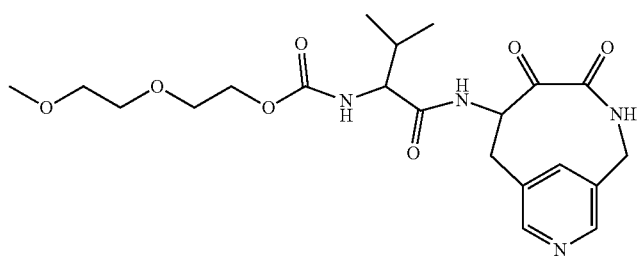 [SMILES: COCCOCCOC(=O)NC(C(=O)NC1Cc2cncc(c2)CNC(=O)C1=O)C(C)C]
105
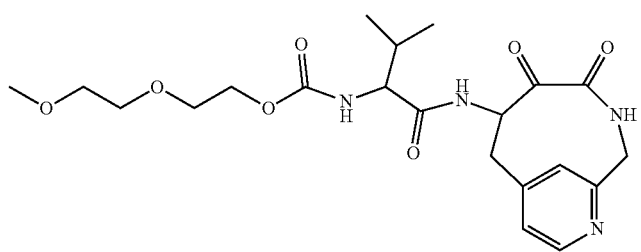 [SMILES: COCCOCCOC(=O)NC(C(=O)NC1Cc2ccnc(c2)CNC(=O)C1=O)C(C)C]
106
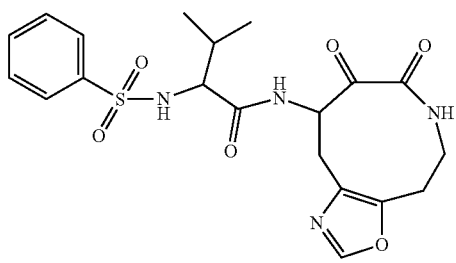 [SMILES: CC(C)C(NS(=O)(=O)c1ccccc1)C(=O)NC1Cc2ncoc2CCNC(=O)C1=O]
109

TABLE 5-continued

NineRings

| | |
|---|---|
| (structure) | 110 |
| (structure) | 113 |
| (structure) | 114 |
| (structure) | 117 |
| (structure) | 118 |
| (structure) | 121 |

TABLE 5-continued
NineRings
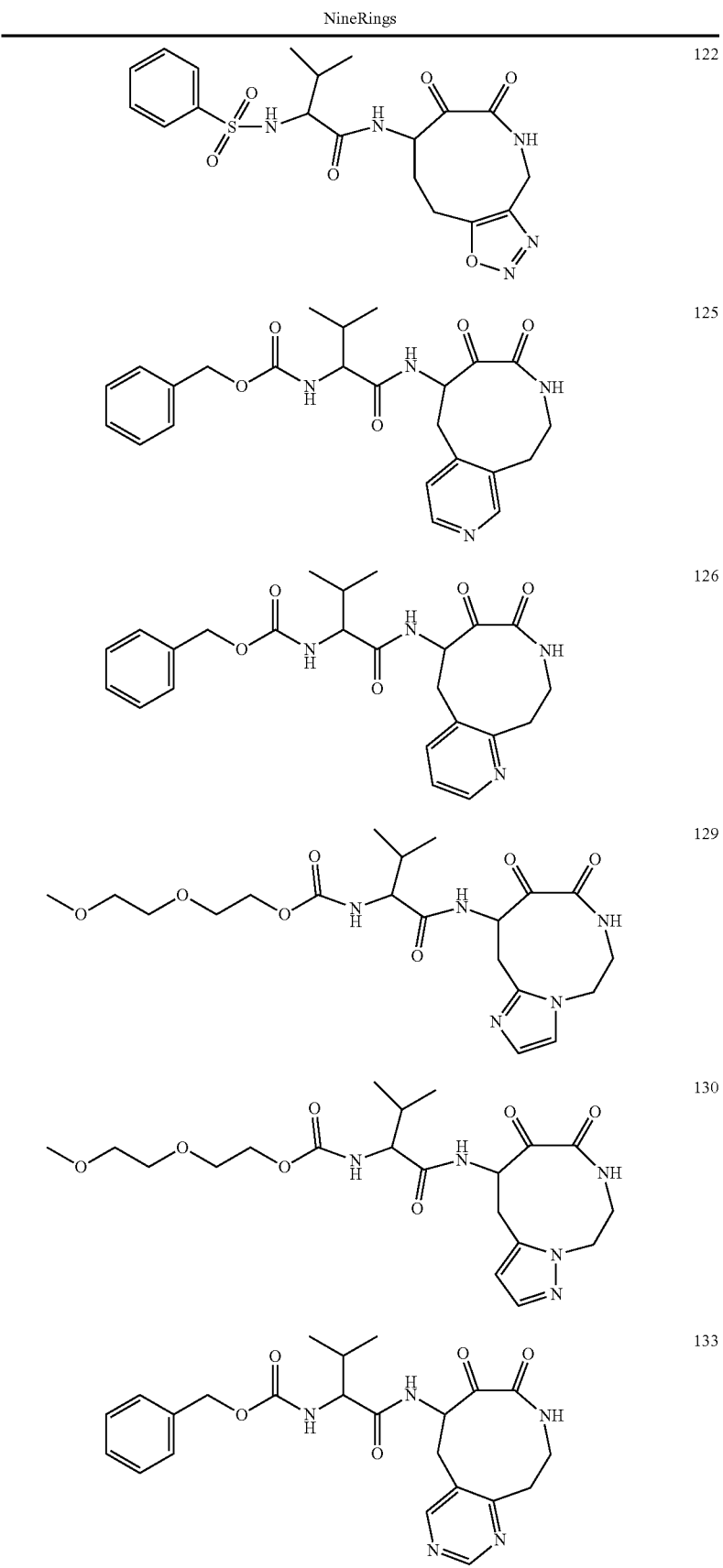

TABLE 5-continued
NineRings
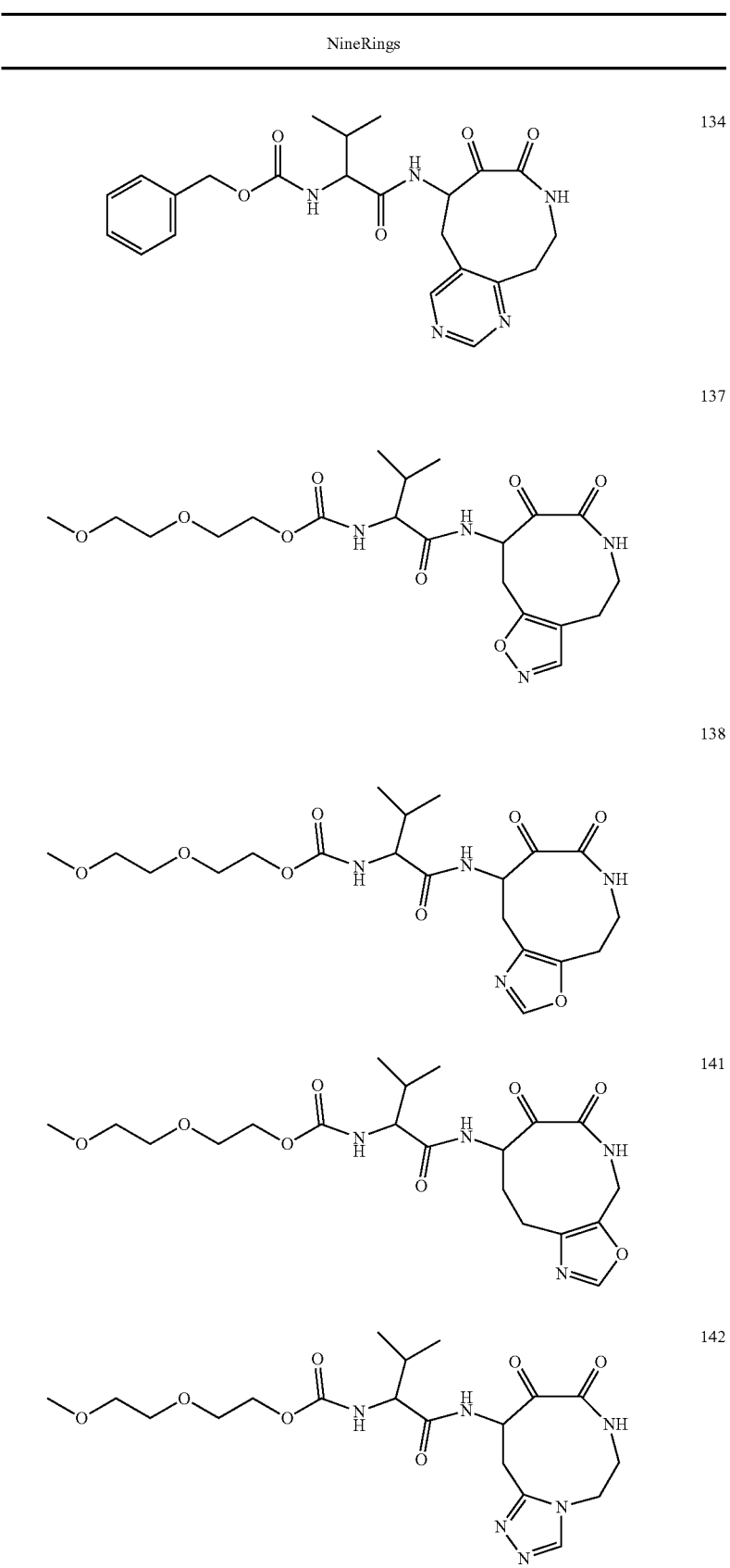
134
137
138
141
142

TABLE 5-continued
NineRings
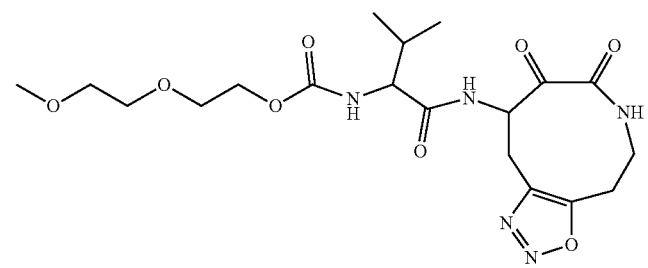 [SMILES: COCCOCCOC(=O)NC(C(=O)NC1Cc2nnoc2CCNC(=O)C1=O)C(C)C]
145
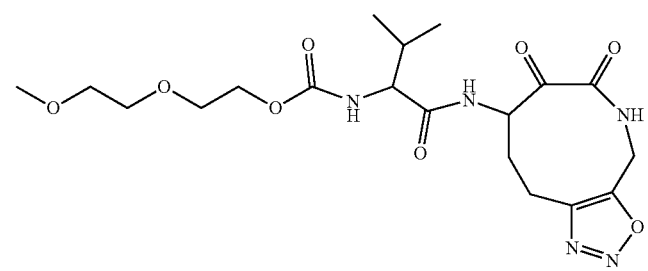 [SMILES: COCCOCCOC(=O)NC(C(=O)NC1CCc2nnoc2CNC(=O)C1=O)C(C)C]
146
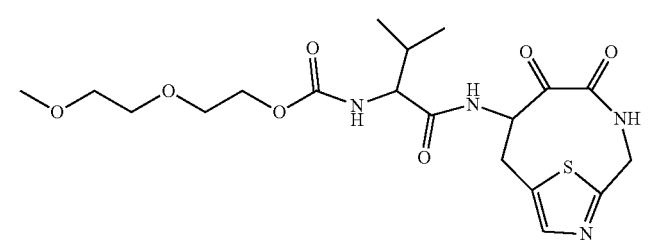 [SMILES: COCCOCCOC(=O)NC(C(=O)NC1CC2=CN=C(CNC(=O)C1=O)S2)C(C)C]
149
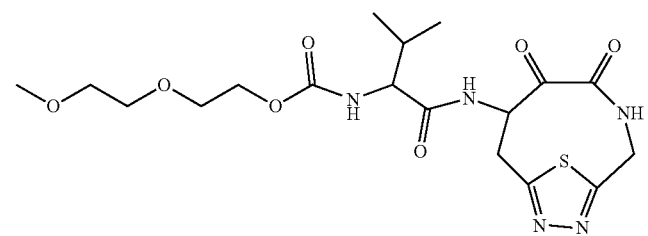 [SMILES: COCCOCCOC(=O)NC(C(=O)NC1CC2=NN=C(CNC(=O)C1=O)S2)C(C)C]
150
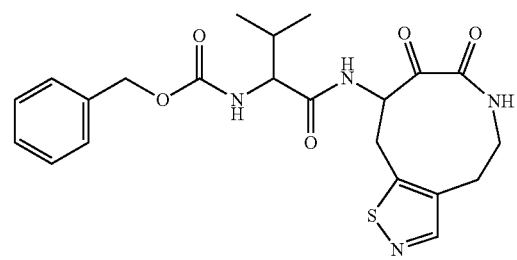 [SMILES: CC(C)C(NC(=O)OCc1ccccc1)C(=O)NC1Cc2sncc2CCNC(=O)C1=O]
153
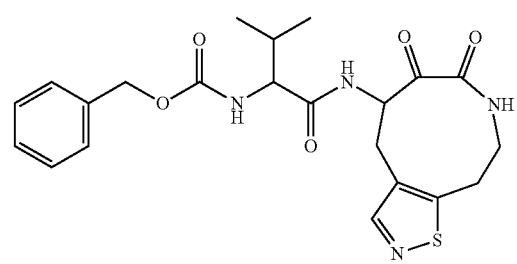 [SMILES: CC(C)C(NC(=O)OCc1ccccc1)C(=O)NC1Cc2cnsc2CCNC(=O)C1=O]
154

TABLE 5-continued
NineRings
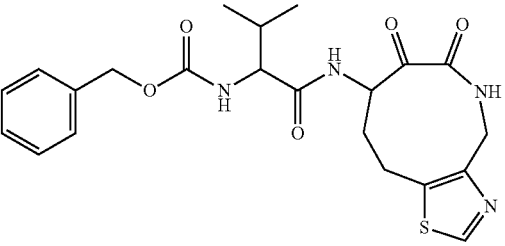 [SMILES: CC(C)C(NC(=O)OCc1ccccc1)C(=O)NC1CCc2scnc2CNC(=O)C1=O] 157
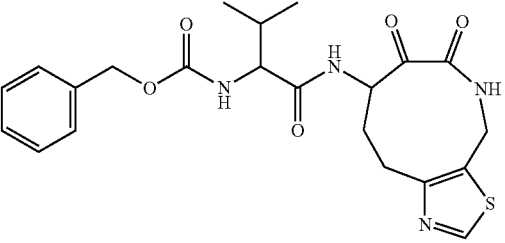 [SMILES: CC(C)C(NC(=O)OCc1ccccc1)C(=O)NC1CCc2ncsc2CNC(=O)C1=O] 158
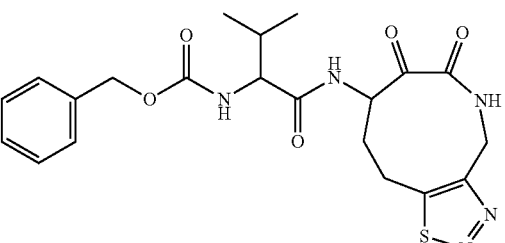 161
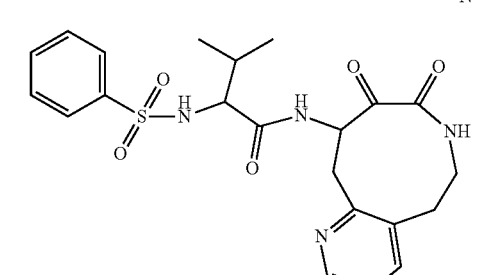 162
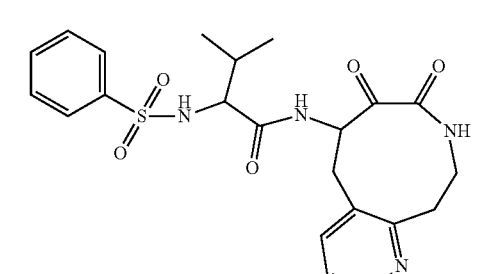 165
166

TABLE 5-continued
NineRings
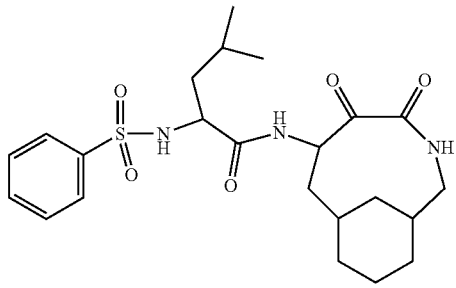 [SMILES: CC(C)CC(NS(=O)(=O)c1ccccc1)C(=O)NC1CC2CCCC(CNC(=O)C1=O)C2]
169
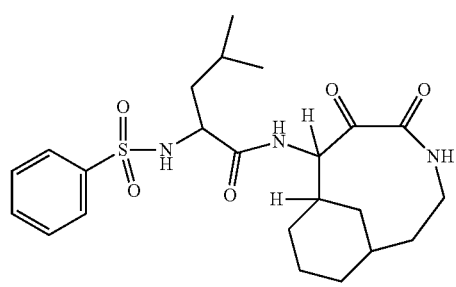 [SMILES: CC(C)CC(NS(=O)(=O)c1ccccc1)C(=O)NC1C(=O)C(=O)NCCC2CCCC1C2]
170
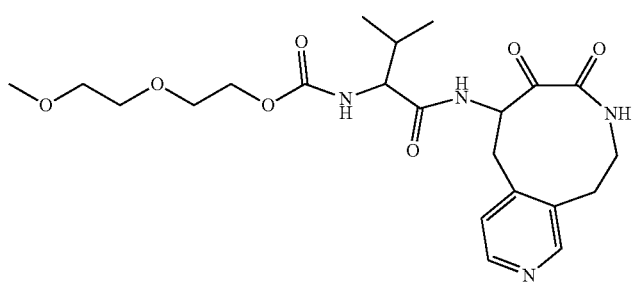 [SMILES: COCCOCCOC(=O)NC(C(=O)NC1Cc2ccncc2CCNC(=O)C1=O)C(C)C]
173
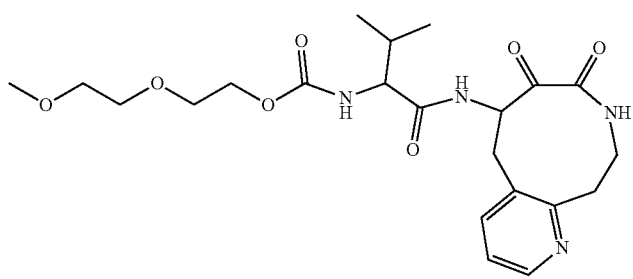 [SMILES: COCCOCCOC(=O)NC(C(=O)NC1Cc2cccnc2CCNC(=O)C1=O)C(C)C]
174
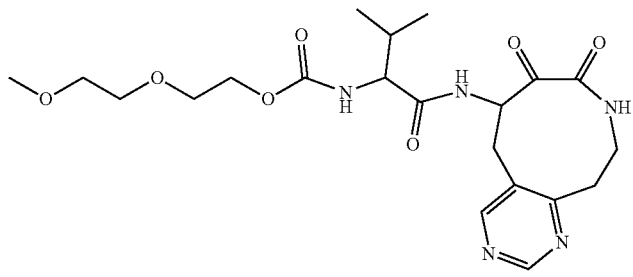 [SMILES: COCCOCCOC(=O)NC(C(=O)NC1Cc2cncnc2CCNC(=O)C1=O)C(C)C]
177

TABLE 5-continued
NineRings
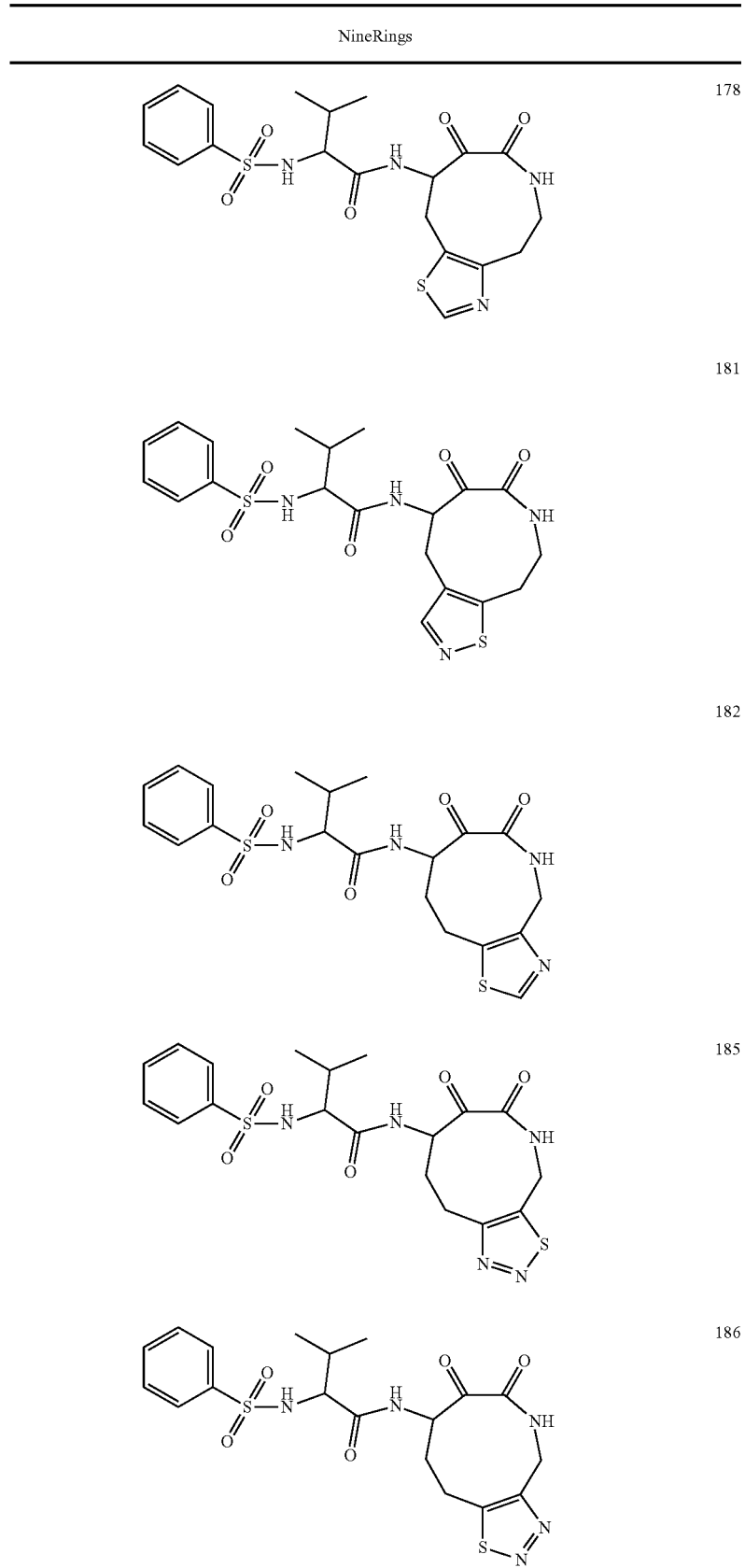
178
181
182
185
186

TABLE 5-continued
NineRings
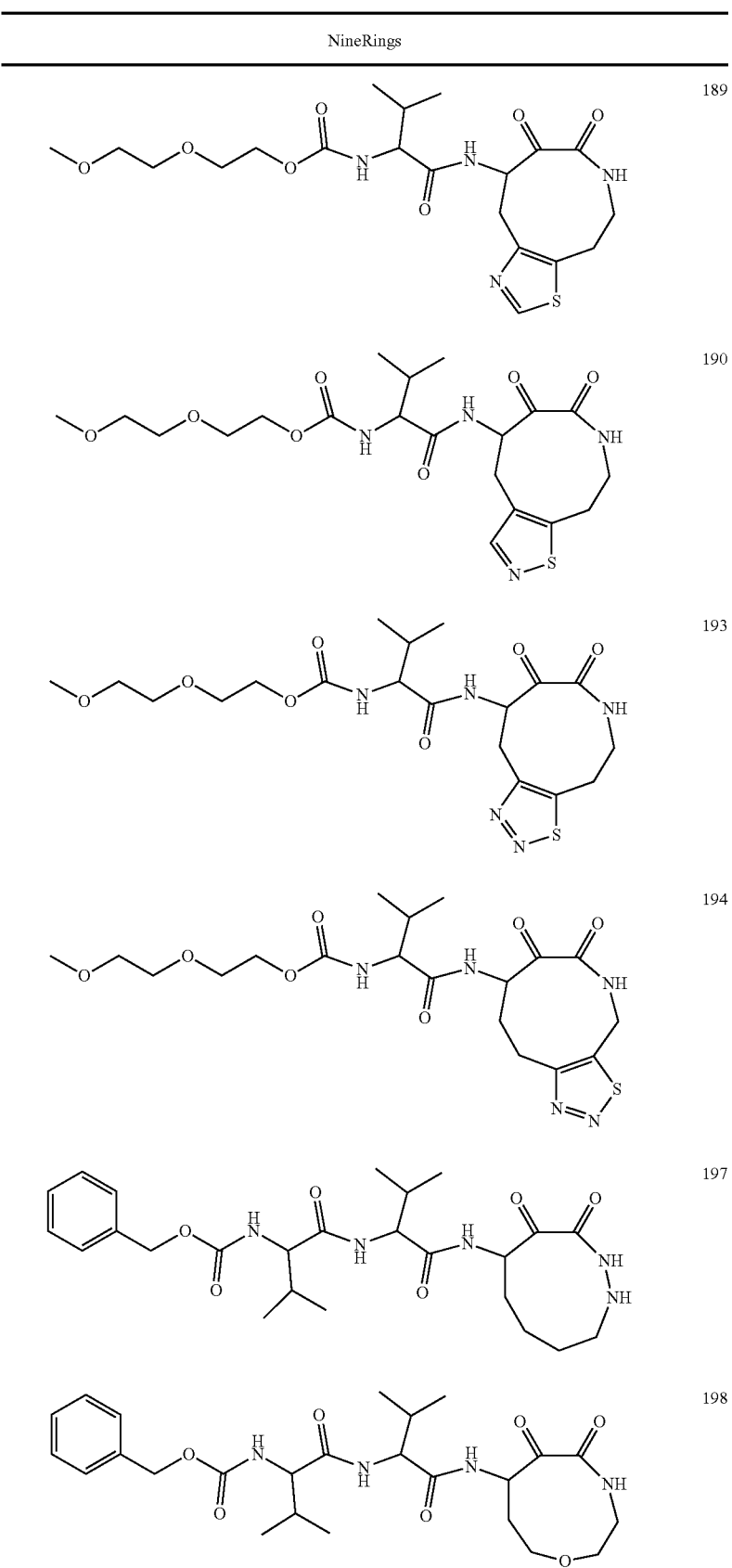

TABLE 5-continued
NineRings
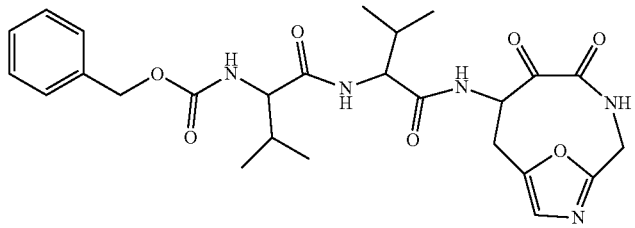 [SMILES: CC(C)C(NC(=O)OCc1ccccc1)C(=O)NC(C(=O)NC1CC2=CN=C(CNC(=O)C1=O)O2)C(C)C]
201
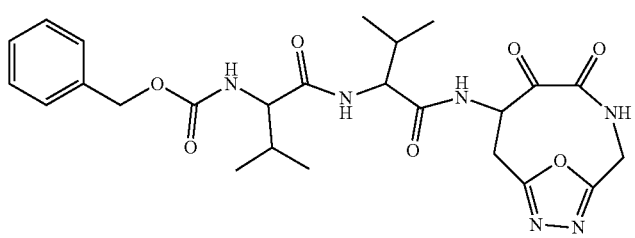 [SMILES: CC(C)C(NC(=O)OCc1ccccc1)C(=O)NC(C(=O)NC1CC2=NN=C(CNC(=O)C1=O)O2)C(C)C]
202
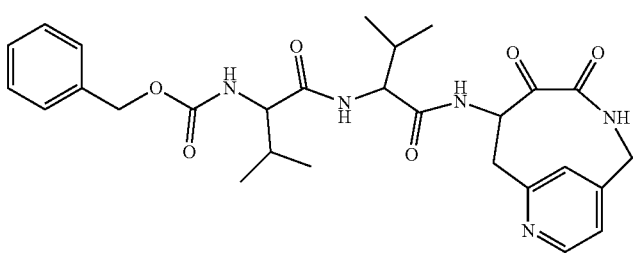 [SMILES: CC(C)C(NC(=O)OCc1ccccc1)C(=O)NC(C(=O)NC1Cc2cc(ccn2)CNC(=O)C1=O)C(C)C]
205
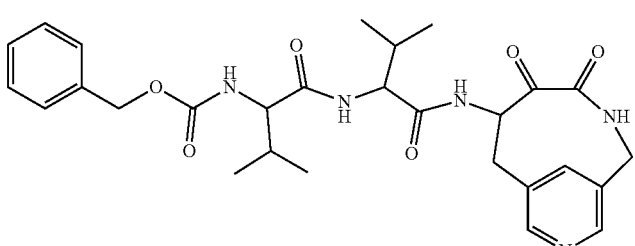
206
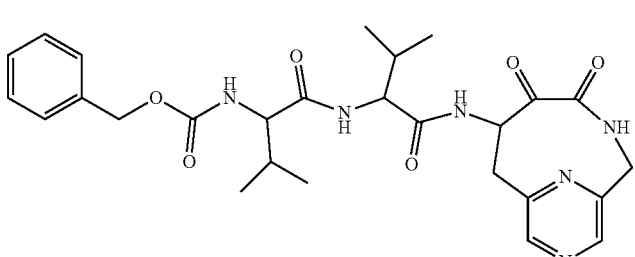
209
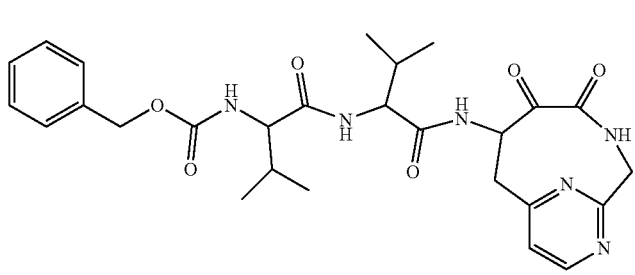 [SMILES: CC(C)C(NC(=O)OCc1ccccc1)C(=O)NC(C(=O)NC1Cc2ccnc(n2)CNC(=O)C1=O)C(C)C]
210

TABLE 5-continued
NineRings
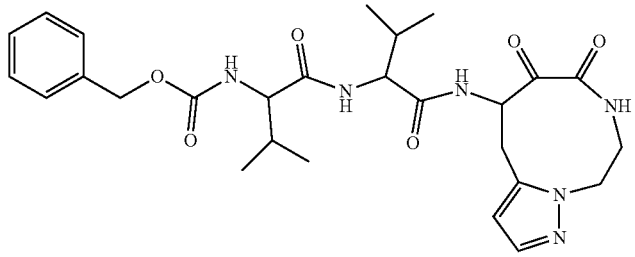 [SMILES: CC(C)C(NC(=O)OCc1ccccc1)C(=O)NC(C(=O)NC1Cc2ccnn2CCNC(=O)C1=O)C(C)C]
213
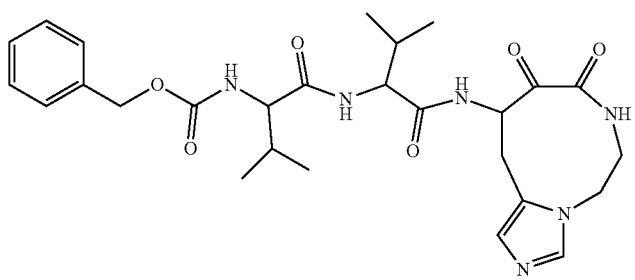 [SMILES: CC(C)C(NC(=O)OCc1ccccc1)C(=O)NC(C(=O)NC1Cc2cncn2CCNC(=O)C1=O)C(C)C]
214
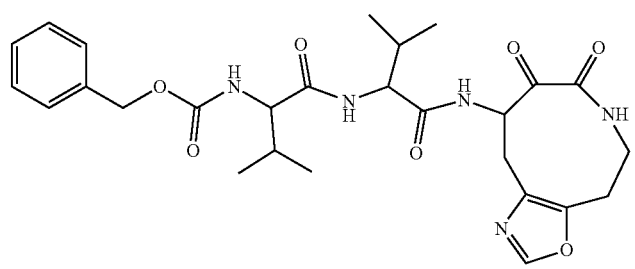 [SMILES: CC(C)C(NC(=O)OCc1ccccc1)C(=O)NC(C(=O)NC1Cc2ncoc2CCNC(=O)C1=O)C(C)C]
217
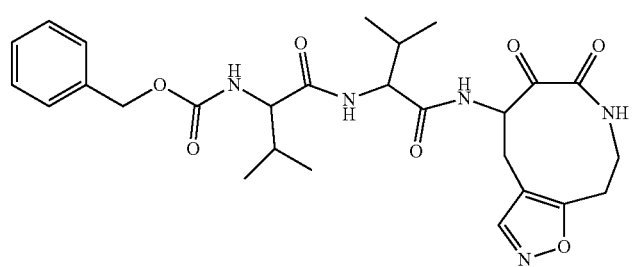 [SMILES: CC(C)C(NC(=O)OCc1ccccc1)C(=O)NC(C(=O)NC1Cc2cnoc2CCNC(=O)C1=O)C(C)C]
218
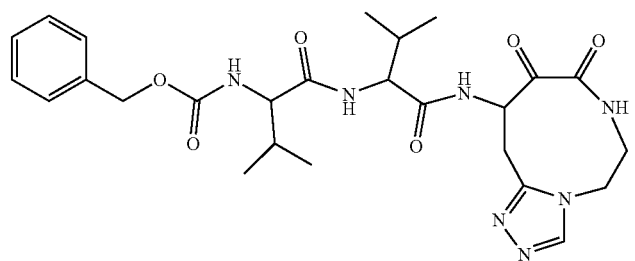 [SMILES: CC(C)C(NC(=O)OCc1ccccc1)C(=O)NC(C(=O)NC1Cc2nncn2CCNC(=O)C1=O)C(C)C]
221

TABLE 5-continued
NineRings
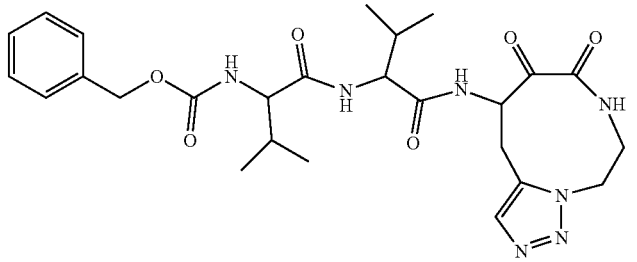 [SMILES: CC(C)C(NC(=O)OCc1ccccc1)C(=O)NC(C(=O)NC1Cc2cnnn2CCNC(=O)C1=O)C(C)C]
222
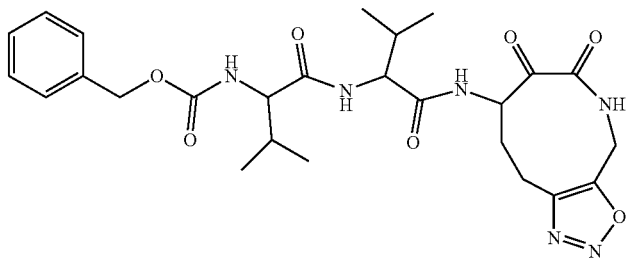 [SMILES: CC(C)C(NC(=O)OCc1ccccc1)C(=O)NC(C(=O)NC1CCc2nnoc2CNC(=O)C1=O)C(C)C]
225
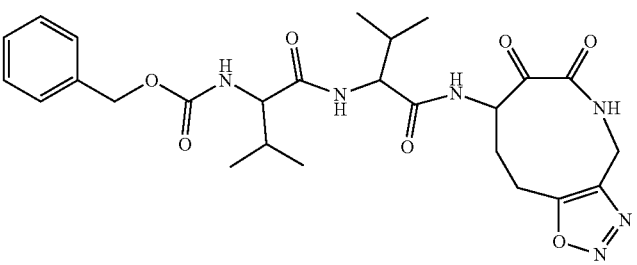 [SMILES: CC(C)C(NC(=O)OCc1ccccc1)C(=O)NC(C(=O)NC1CCc2onnc2CNC(=O)C1=O)C(C)C]
226
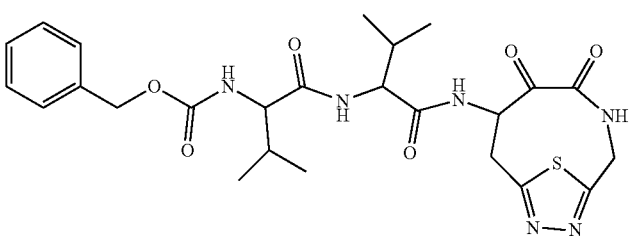 [SMILES: CC(C)C(NC(=O)OCc1ccccc1)C(=O)NC(C(=O)NC1CC2=NN=C(CNC(=O)C1=O)S2)C(C)C]
229
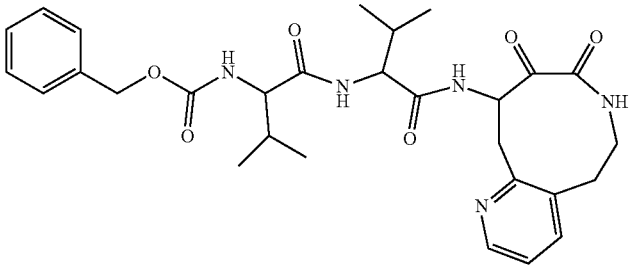 [SMILES: CC(C)C(NC(=O)OCc1ccccc1)C(=O)NC(C(=O)NC1Cc2ncccc2CCNC(=O)C1=O)C(C)C]
230
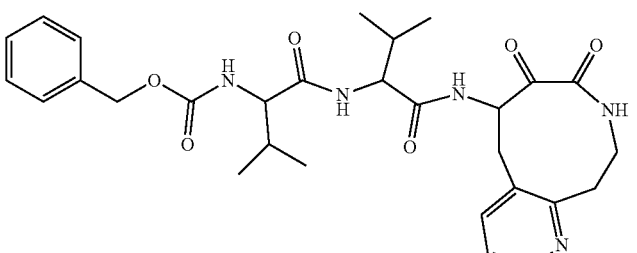
233

TABLE 5-continued
NineRings
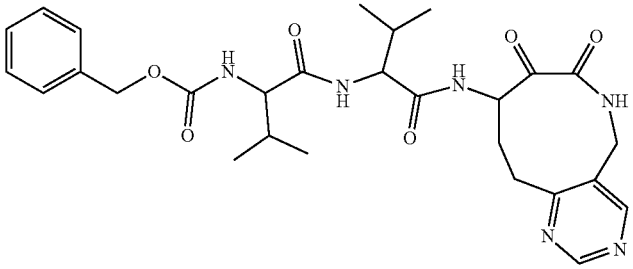 [SMILES: CC(C)C(NC(=O)OCc1ccccc1)C(=O)NC(C(=O)NC1CCc2ncncc2CNC(=O)C1=O)C(C)C]
234
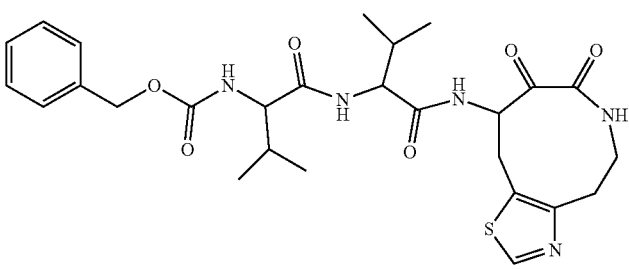 [SMILES: CC(C)C(NC(=O)OCc1ccccc1)C(=O)NC(C(=O)NC1Cc2scnc2CCNC(=O)C1=O)C(C)C]
237
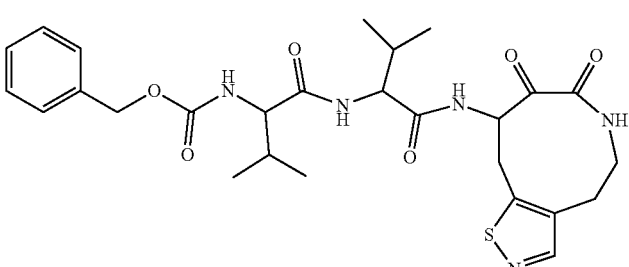
238
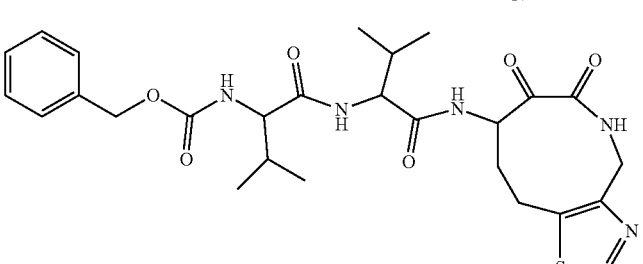
241
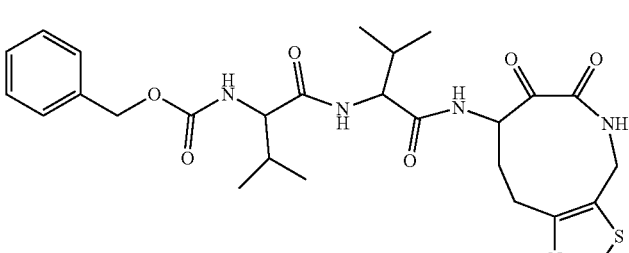
242
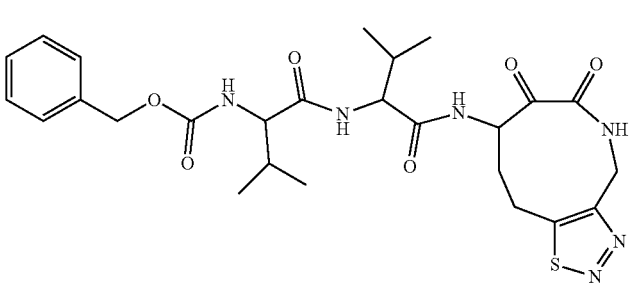 [SMILES: CC(C)C(NC(=O)OCc1ccccc1)C(=O)NC(C(=O)NC1CCc2snnc2CNC(=O)C1=O)C(C)C]
245

TABLE 5-continued
NineRings
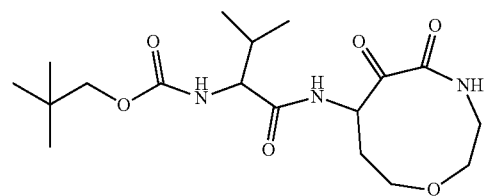 [SMILES: CC(C)C(NC(=O)OCC(C)(C)C)C(=O)NC1CCOCCNC(=O)C1=O]
3
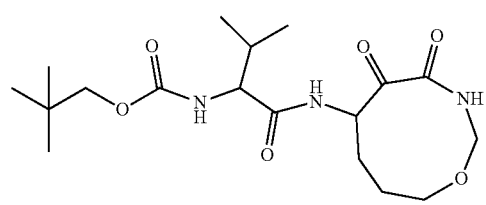 [SMILES: CC(C)C(NC(=O)OCC(C)(C)C)C(=O)NC1CCCOCNC(=O)C1=O]
4
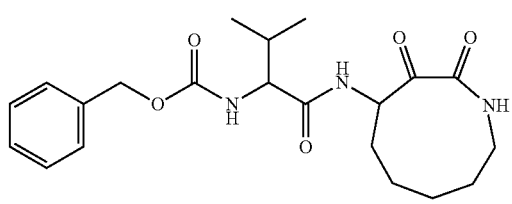 [SMILES: CC(C)C(NC(=O)OCc1ccccc1)C(=O)NC1CCCCCNC(=O)C1=O]
7
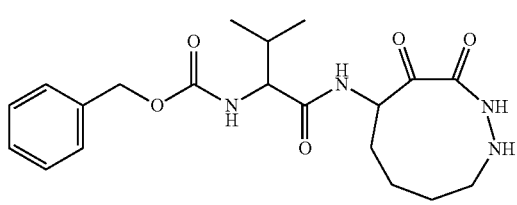 [SMILES: CC(C)C(NC(=O)OCc1ccccc1)C(=O)NC1CCCCNNC(=O)C1=O]
8
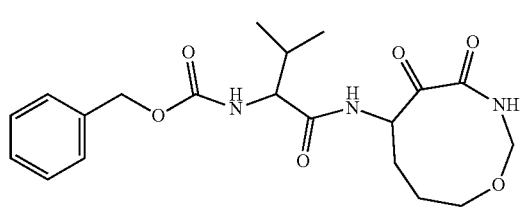 [SMILES: CC(C)C(NC(=O)OCc1ccccc1)C(=O)NC1CCCOCNC(=O)C1=O]
11
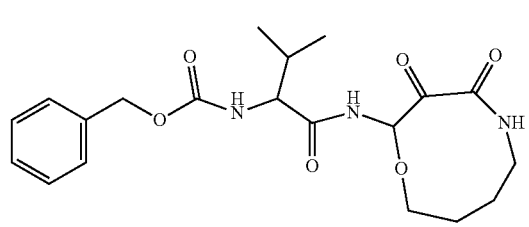 [SMILES: CC(C)C(NC(=O)OCc1ccccc1)C(=O)NC1OCCCCNC(=O)C1=O]
12
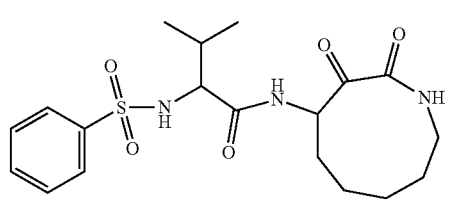 [SMILES: CC(C)C(NS(=O)(=O)c1ccccc1)C(=O)NC1CCCCCNC(=O)C1=O]
15

TABLE 5-continued

NineRings

/ 175
TABLE 5-continued
NineRings
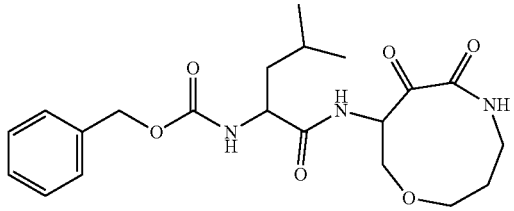 [SMILES: CC(C)CC(NC(=O)OCc1ccccc1)C(=O)NC1COCCCNC(=O)C1=O]
31
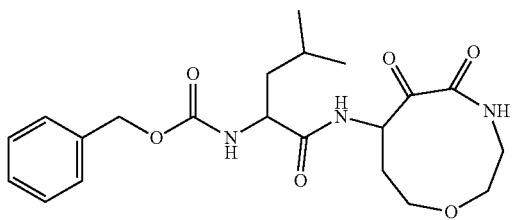 [SMILES: CC(C)CC(NC(=O)OCc1ccccc1)C(=O)NC1CCOCCNC(=O)C1=O]
32
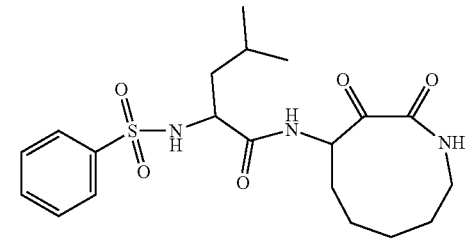 [SMILES: CC(C)CC(NS(=O)(=O)c1ccccc1)C(=O)NC1CCCCCNC(=O)C1=O]
35
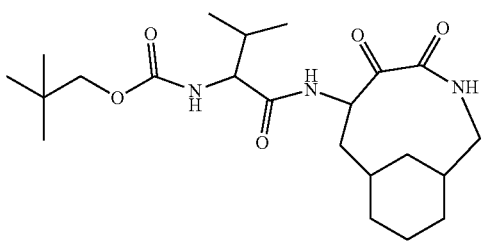 [SMILES: CC(C)C(NC(=O)OCC(C)(C)C)C(=O)NC1CC2CCCC(CNC(=O)C1=O)C2]
36
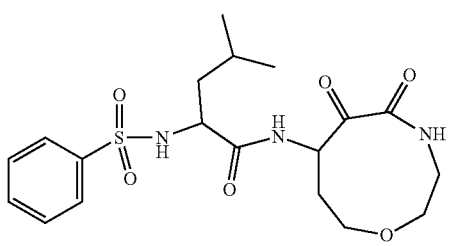 [SMILES: CC(C)CC(NS(=O)(=O)c1ccccc1)C(=O)NC1CCOCCNC(=O)C1=O]
39
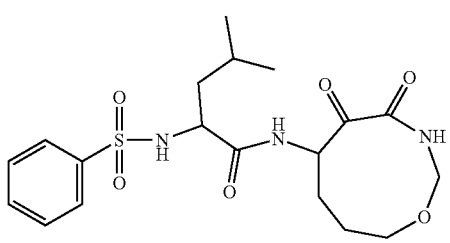 [SMILES: CC(C)CC(NS(=O)(=O)c1ccccc1)C(=O)NC1CCCOCNC(=O)C1=O]
40

TABLE 5-continued
NineRings
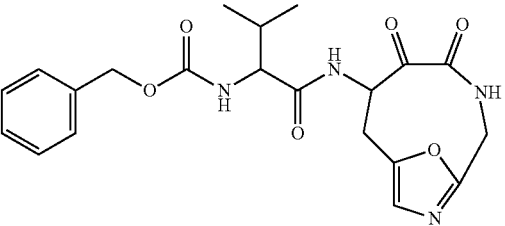 [SMILES: CC(C)C(NC(=O)OCc1ccccc1)C(=O)NC1CC2=CN=C(CNC(=O)C1=O)O2] 43
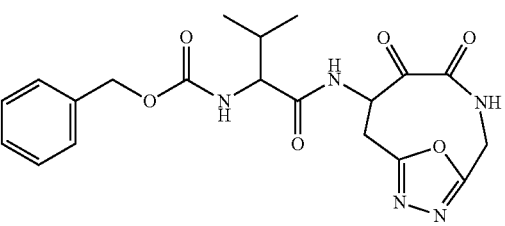 [SMILES: CC(C)C(NC(=O)OCc1ccccc1)C(=O)NC1CC2=NN=C(CNC(=O)C1=O)O2] 44
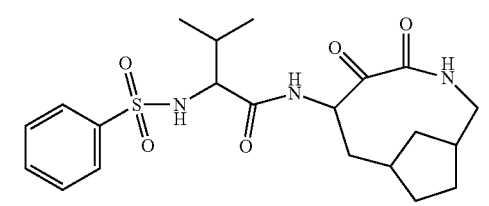 [SMILES: CC(C)C(NS(=O)(=O)c1ccccc1)C(=O)NC1CC2CCC(CNC(=O)C1=O)C2] 47
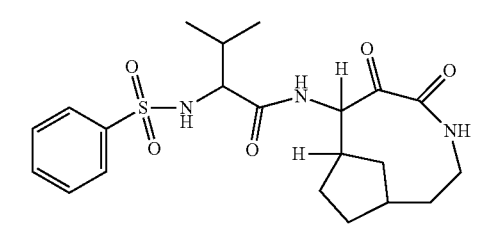 [SMILES: CC(C)C(NS(=O)(=O)c1ccccc1)C(=O)NC1C(=O)C(=O)NCCC2CCC1C2] 48
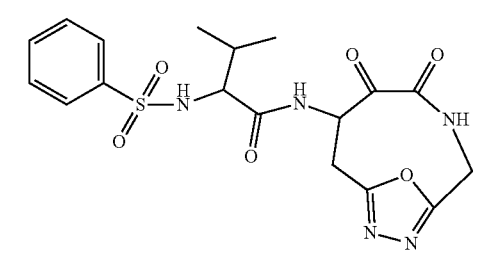 [SMILES: CC(C)C(NS(=O)(=O)c1ccccc1)C(=O)NC1CC2=NN=C(CNC(=O)C1=O)O2] 51
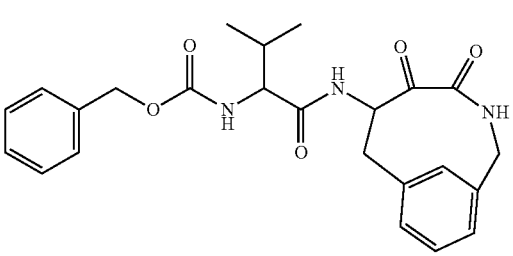 [SMILES: CC(C)C(NC(=O)OCc1ccccc1)C(=O)NC1Cc2cccc(c2)CNC(=O)C1=O] 52

TABLE 5-continued

NineRings

55

56

59

60

63

64

TABLE 5-continued

NineRings

| | |
|---|---|
| (structure) | 67 |
| (structure) | 68 |
| (structure) | 71 |
| (structure) | 72 |
| (structure) | 75 |
| (structure) | 76 |

TABLE 5-continued
NineRings
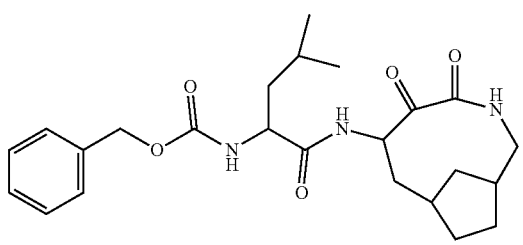 [SMILES: CC(C)CC(NC(=O)OCc1ccccc1)C(=O)NC1CC2CCC(CNC(=O)C1=O)C2]
79
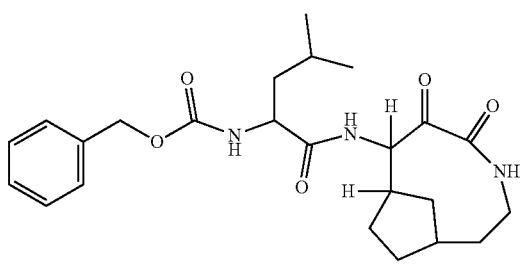 [SMILES: CC(C)CC(NC(=O)OCc1ccccc1)C(=O)NC1C(=O)C(=O)NCCC2CCC1C2]
80
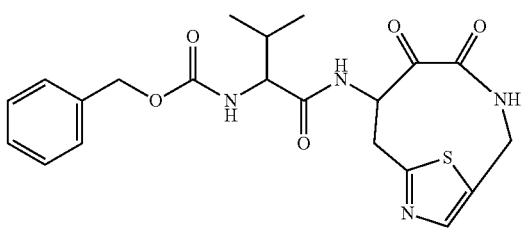 [SMILES: CC(C)C(NC(=O)OCc1ccccc1)C(=O)NC1Cc2ncc(s2)CNC(=O)C1=O]
83
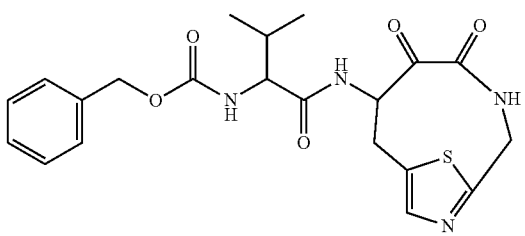 [SMILES: CC(C)C(NC(=O)OCc1ccccc1)C(=O)NC1Cc2cnc(s2)CNC(=O)C1=O]
84
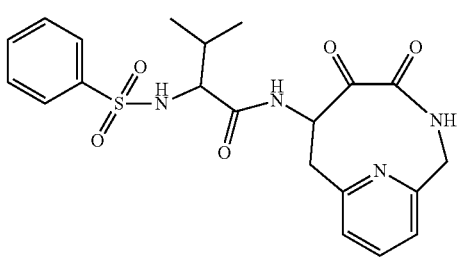 [SMILES: CC(C)C(NS(=O)(=O)c1ccccc1)C(=O)NC1Cc2cccc(n2)CNC(=O)C1=O]
87
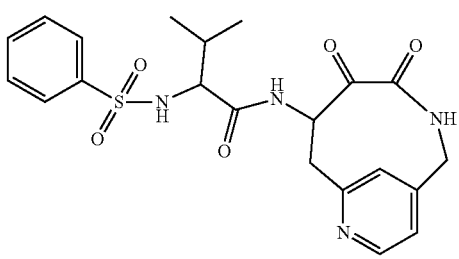 [SMILES: CC(C)C(NS(=O)(=O)c1ccccc1)C(=O)NC1Cc2cc(ccn2)CNC(=O)C1=O]
88

TABLE 5-continued
NineRings
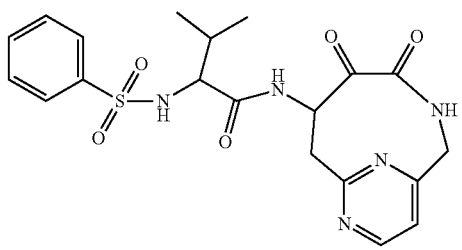 [SMILES: CC(C)C(NS(=O)(=O)c1ccccc1)C(=O)NC1Cc2nccc(n2)CNC(=O)C1=O]
91
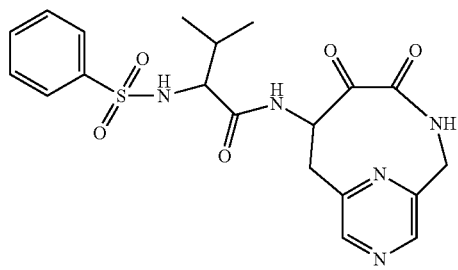 [SMILES: CC(C)C(NS(=O)(=O)c1ccccc1)C(=O)NC1Cc2cncc(n2)CNC(=O)C1=O]
92
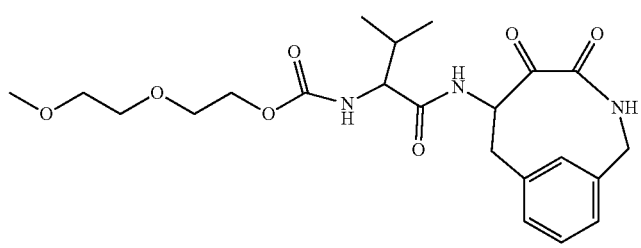 [SMILES: COCCOCCOC(=O)NC(C(=O)NC1Cc2cccc(c2)CNC(=O)C1=O)C(C)C]
95
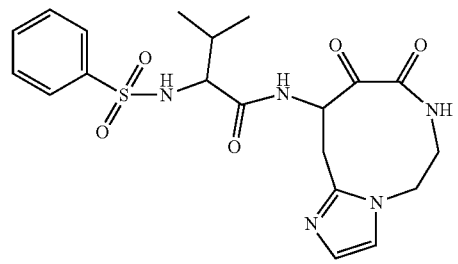 [SMILES: CC(C)C(NS(=O)(=O)c1ccccc1)C(=O)NC1Cc2nccn2CCNC(=O)C1=O]
96
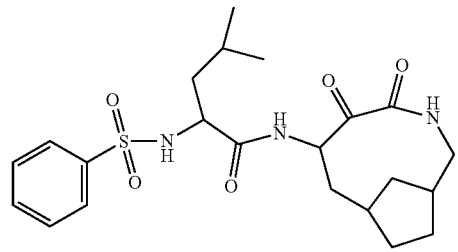 [SMILES: CC(C)CC(NS(=O)(=O)c1ccccc1)C(=O)NC1CC2CCC(CNC(=O)C1=O)C2]
99
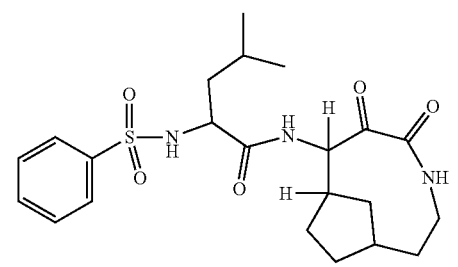 [SMILES: CC(C)CC(NS(=O)(=O)c1ccccc1)C(=O)NC1C(=O)C(=O)NCCC2CCC1C2]
100

TABLE 5-continued
NineRings
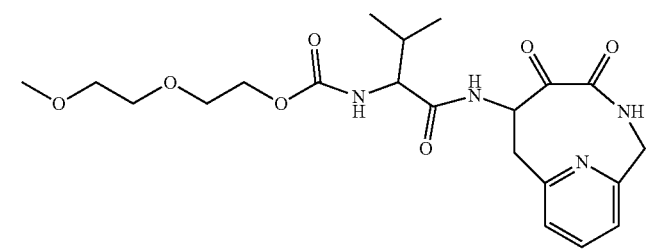 [SMILES: COCCOCCOC(=O)NC(C(=O)NC1Cc2cccc(n2)CNC(=O)C1=O)C(C)C]
103
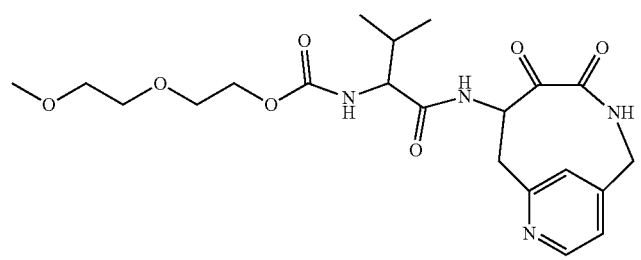
104
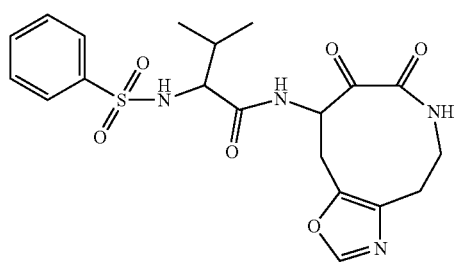 [SMILES: CC(C)C(NS(=O)(=O)c1ccccc1)C(=O)NC1Cc2ocnc2CCNC(=O)C1=O]
107
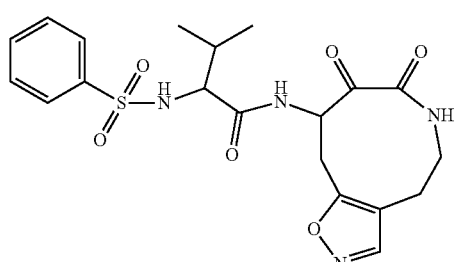
108
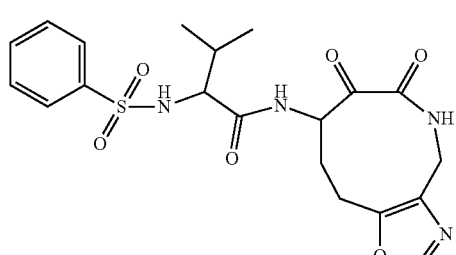
111
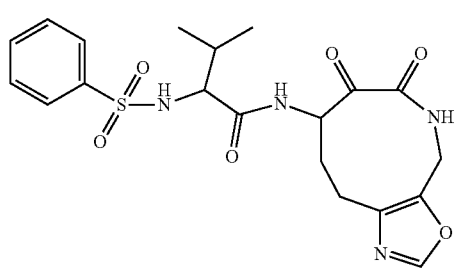 [SMILES: CC(C)C(NS(=O)(=O)c1ccccc1)C(=O)NC1CCc2ncoc2CNC(=O)C1=O]
112

TABLE 5-continued
NineRings
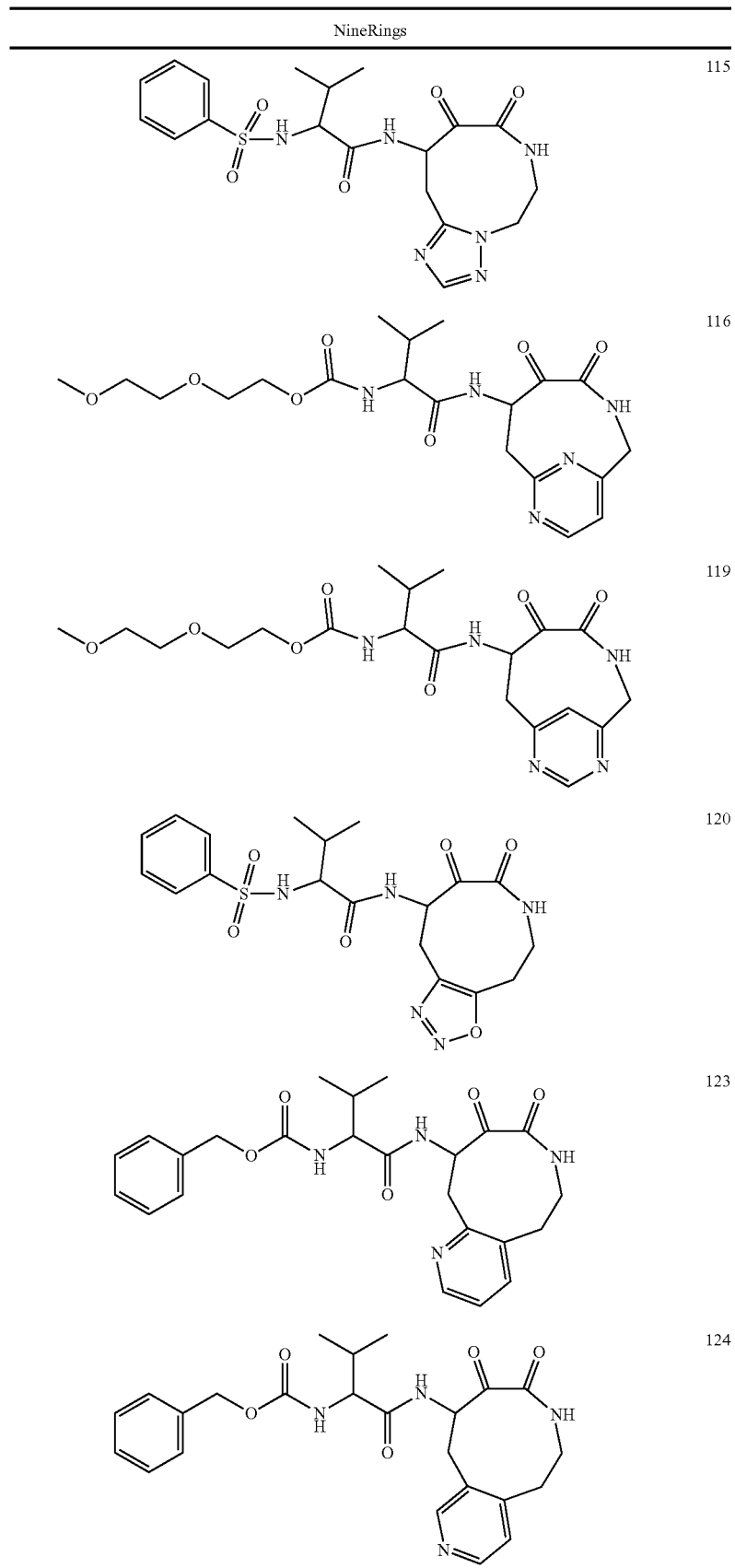

TABLE 5-continued
NineRings
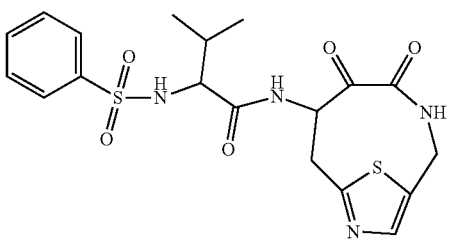 [SMILES: CC(C)C(NS(=O)(=O)c1ccccc1)C(=O)NC1CC2=NC=C(CNC(=O)C1=O)S2]
127
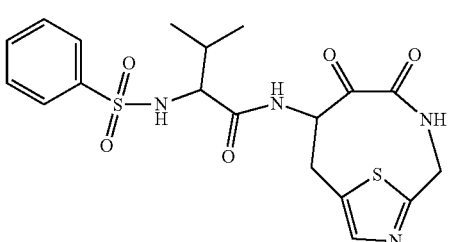
128
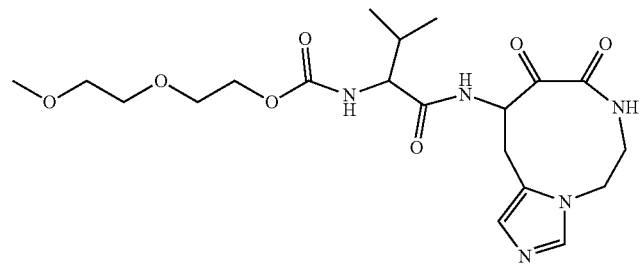 [SMILES: COCCOCCOC(=O)NC(C(=O)NC1Cc2cncn2CCNC(=O)C1=O)C(C)C]
131
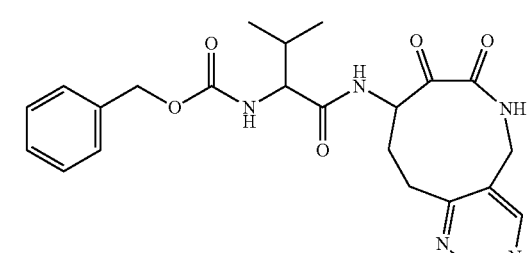
132
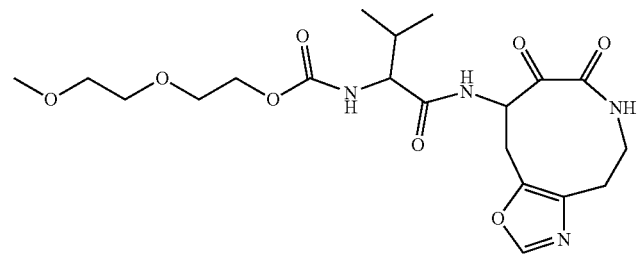 [SMILES: COCCOCCOC(=O)NC(C(=O)NC1Cc2ocnc2CCNC(=O)C1=O)C(C)C]
135
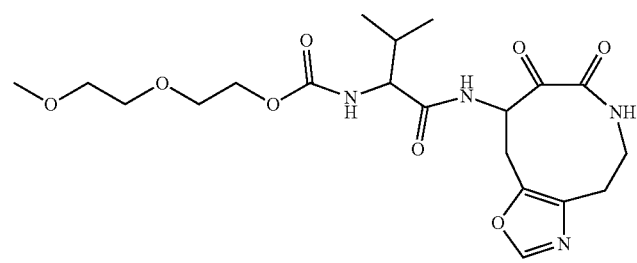 [SMILES: COCCOCCOC(=O)NC(C(=O)NC1Cc2ocnc2CCNC(=O)C1=O)C(C)C]
136

TABLE 5-continued
NineRings
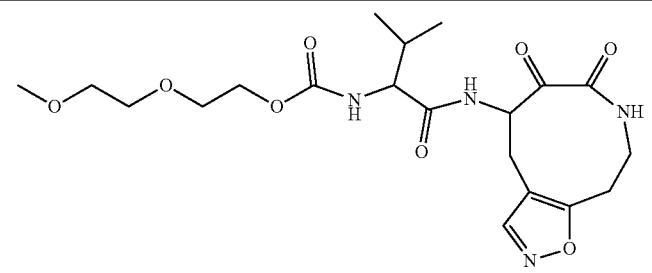
139
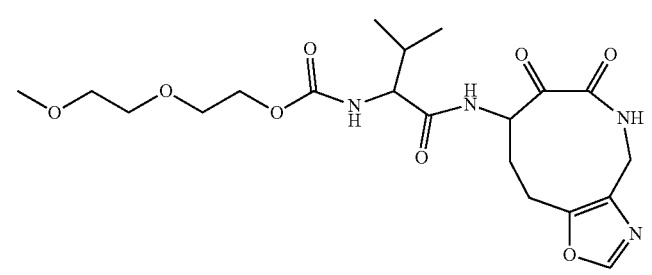 [SMILES: COCCOCCOC(=O)NC(C(=O)NC1CCc2ocnc2CNC(=O)C1=O)C(C)C]
140
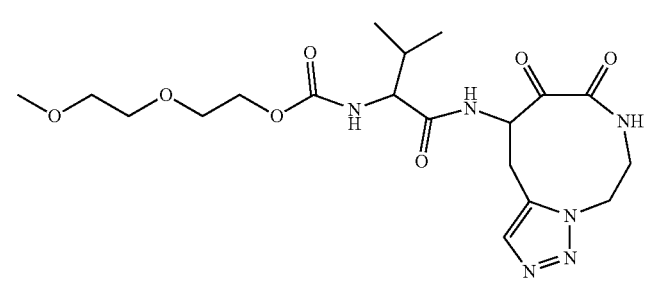
143
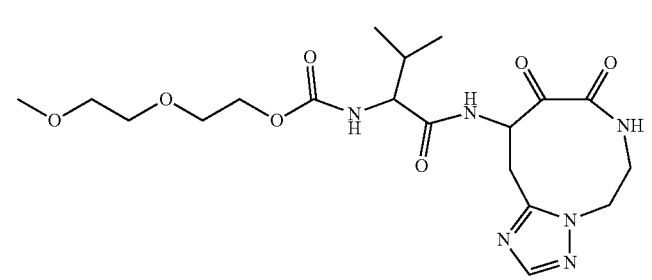 [SMILES: COCCOCCOC(=O)NC(C(=O)NC1Cc2ncnn2CCNC(=O)C1=O)C(C)C]
144
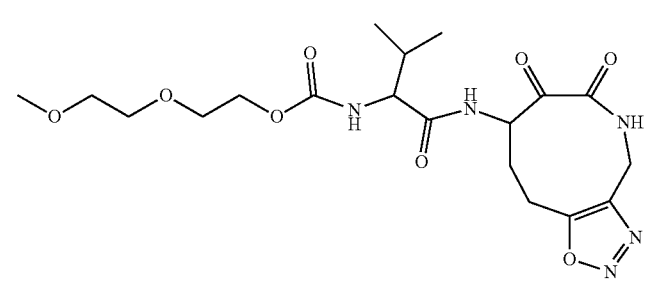 [SMILES: COCCOCCOC(=O)NC(C(=O)NC1CCc2onnc2CNC(=O)C1=O)C(C)C]
147
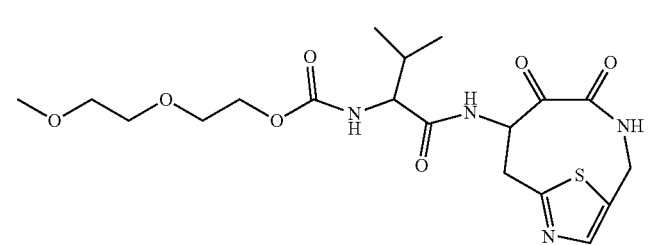 [SMILES: COCCOCCOC(=O)NC(C(=O)NC1CC2=NC=C(CNC(=O)C1=O)S2)C(C)C]
148

TABLE 5-continued
NineRings
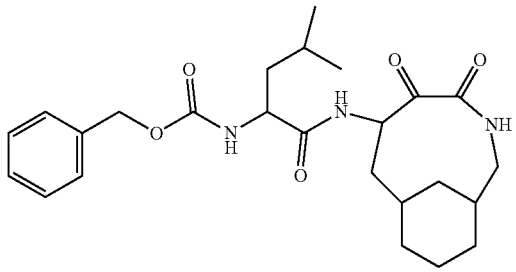 [SMILES: CC(C)CC(NC(=O)OCc1ccccc1)C(=O)NC1CC2CCCC(CNC(=O)C1=O)C2]
151
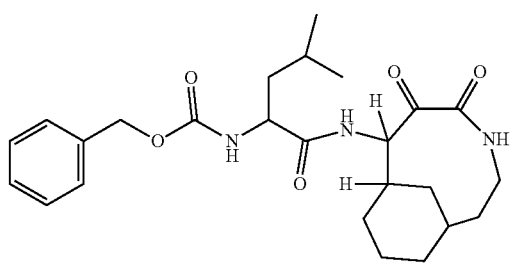 [SMILES: CC(C)CC(NC(=O)OCc1ccccc1)C(=O)NC1C(=O)C(=O)NCCC2CCCC1C2]
152
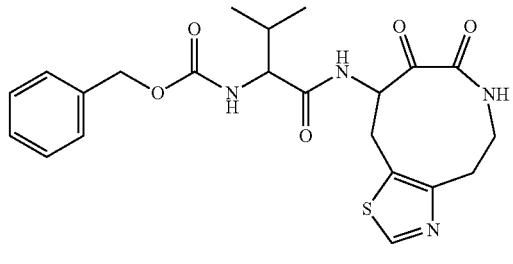
155
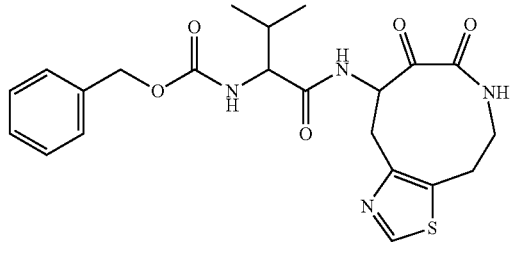
156
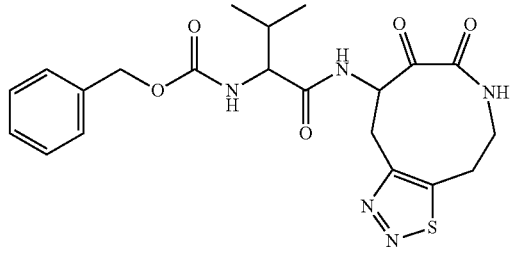
159
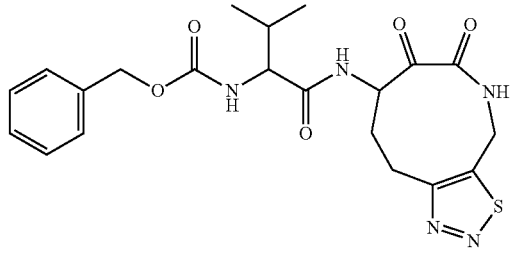
160

TABLE 5-continued
NineRings
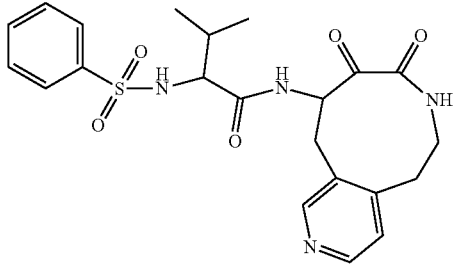 [SMILES: CC(C)C(NS(=O)(=O)c1ccccc1)C(=O)NC1Cc2cnccc2CCNC(=O)C1=O]
163
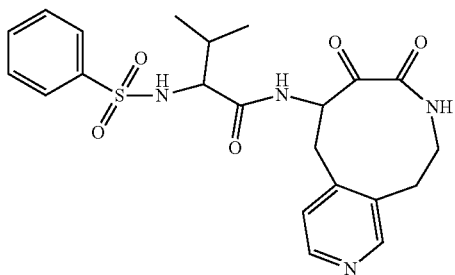 [SMILES: CC(C)C(NS(=O)(=O)c1ccccc1)C(=O)NC1Cc2ccncc2CCNC(=O)C1=O]
164
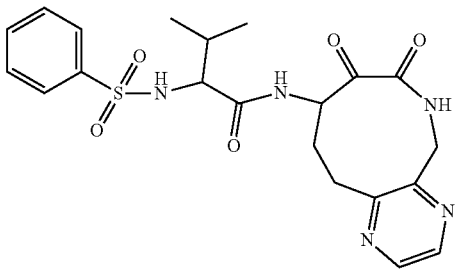 [SMILES: CC(C)C(NS(=O)(=O)c1ccccc1)C(=O)NC1CCc2nccnc2CNC(=O)C1=O]
167
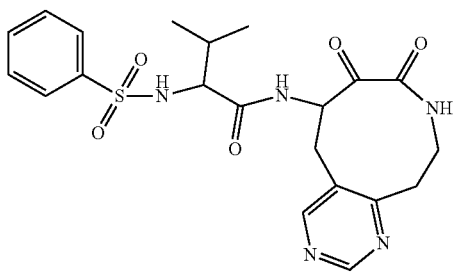 [SMILES: CC(C)C(NS(=O)(=O)c1ccccc1)C(=O)NC1Cc2cncnc2CCNC(=O)C1=O]
168
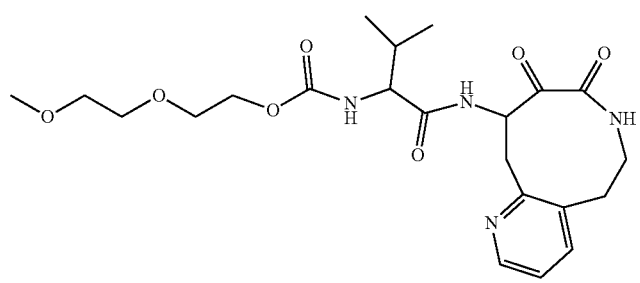 [SMILES: COCCOCCOC(=O)NC(C(=O)NC1Cc2ncccc2CCNC(=O)C1=O)C(C)C]
171

TABLE 5-continued
NineRings
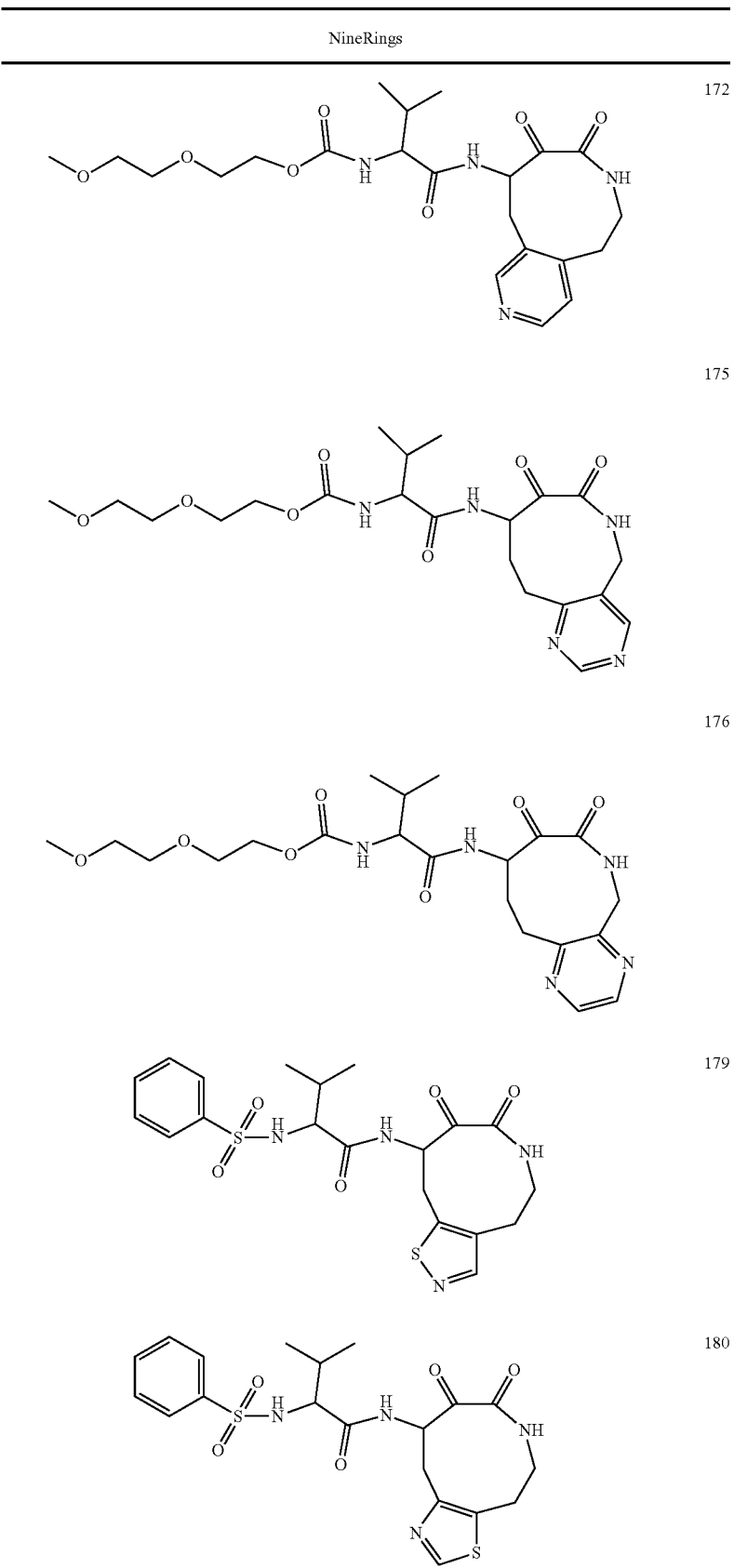
172
175
176
179
180

TABLE 5-continued
NineRings
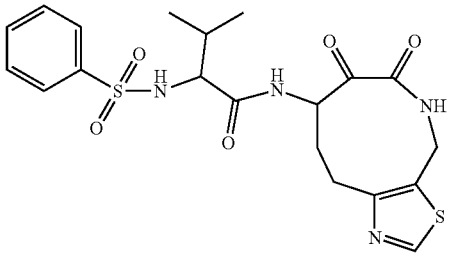 [SMILES: CC(C)C(NS(=O)(=O)c1ccccc1)C(=O)NC1CCc2ncsc2CNC(=O)C1=O]
183
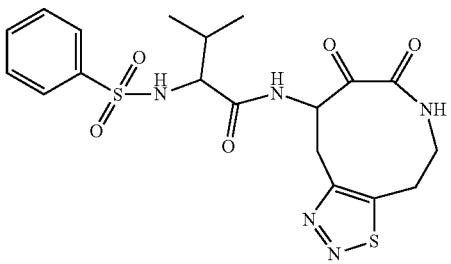 [SMILES: CC(C)C(NS(=O)(=O)c1ccccc1)C(=O)NC1Cc2nnsc2CCNC(=O)C1=O]
184
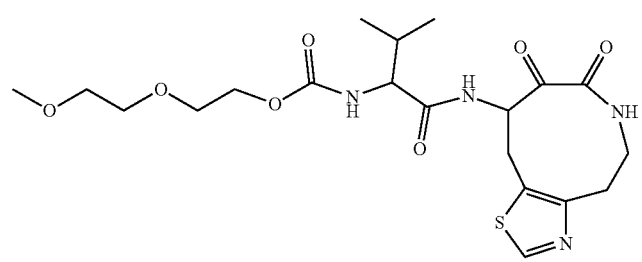 [SMILES: COCCOCCOC(=O)NC(C(=O)NC1Cc2scnc2CCNC(=O)C1=O)C(C)C]
187
188
191
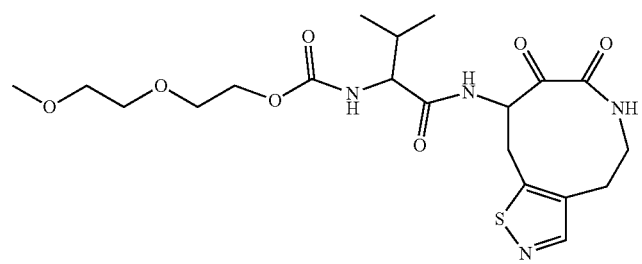 [SMILES: COCCOCCOC(=O)NC(C(=O)NC1Cc2sncc2CCNC(=O)C1=O)C(C)C]
192
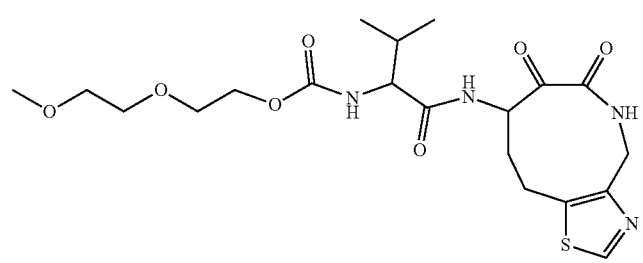 [SMILES: COCCOCCOC(=O)NC(C(=O)NC1CCc2scnc2CNC(=O)C1=O)C(C)C]

TABLE 5-continued
NineRings
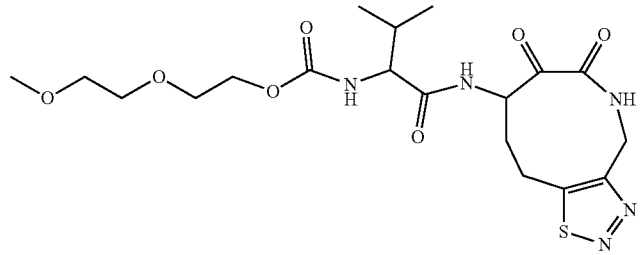 [SMILES: COCCOCCOC(=O)NC(C(=O)NC1CCc2snnc2CNC(=O)C1=O)C(C)C]
195
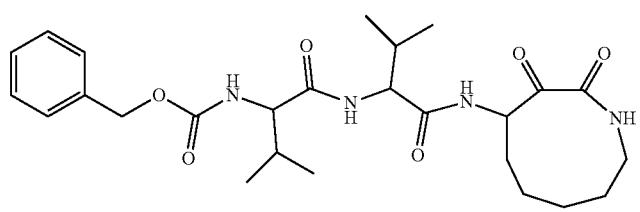 [SMILES: CC(C)C(NC(=O)OCc1ccccc1)C(=O)NC(C(=O)NC1CCCCCNC(=O)C1=O)C(C)C]
196
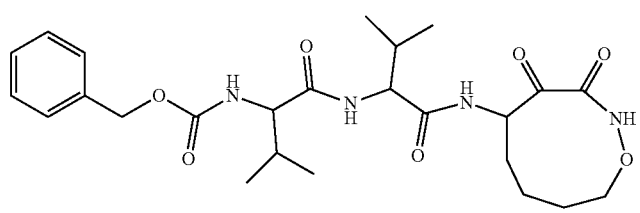 [SMILES: CC(C)C(NC(=O)OCc1ccccc1)C(=O)NC(C(=O)NC1CCCCONC(=O)C1=O)C(C)C]
199
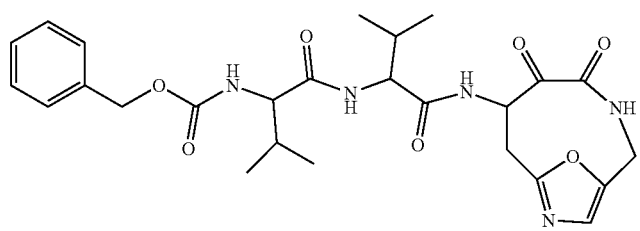 [SMILES: CC(C)C(NC(=O)OCc1ccccc1)C(=O)NC(C(=O)NC1CC2=NC=C(CNC(=O)C1=O)O2)C(C)C]
200
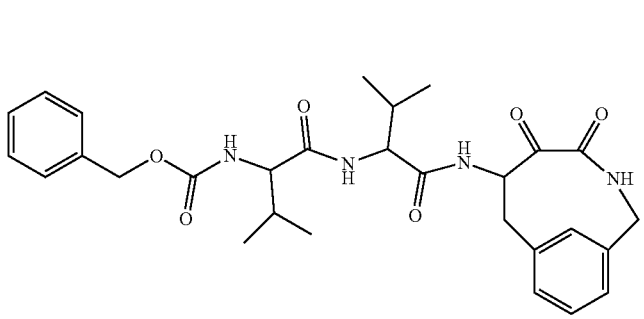 [SMILES: CC(C)C(NC(=O)OCc1ccccc1)C(=O)NC(C(=O)NC1Cc2cccc(c2)CNC(=O)C1=O)C(C)C]
203
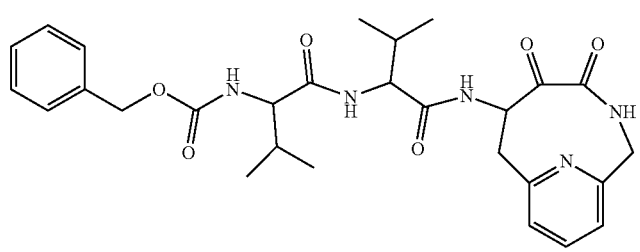
204

TABLE 5-continued
NineRings
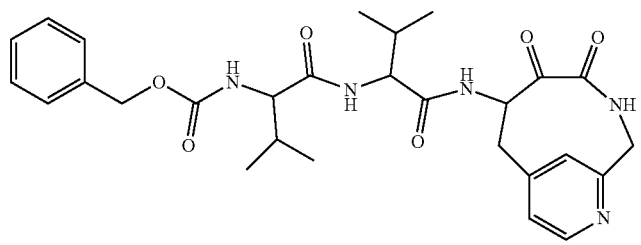 [SMILES: CC(C)C(NC(=O)OCc1ccccc1)C(=O)NC(C(=O)NC1Cc2ccnc(c2)CNC(=O)C1=O)C(C)C]
207
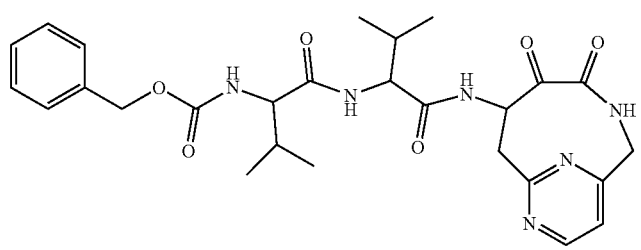 [SMILES: CC(C)C(NC(=O)OCc1ccccc1)C(=O)NC(C(=O)NC1Cc2nccc(n2)CNC(=O)C1=O)C(C)C]
208
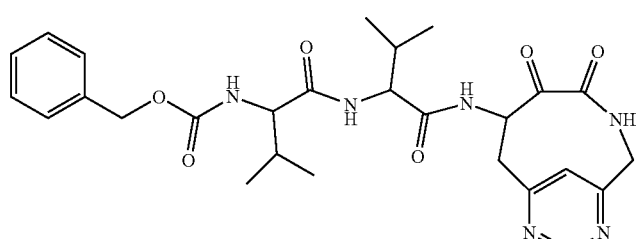
211
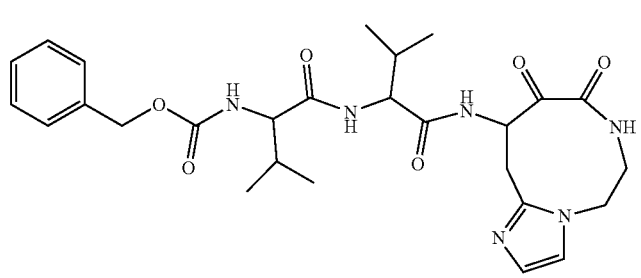 [SMILES: CC(C)C(NC(=O)OCc1ccccc1)C(=O)NC(C(=O)NC1Cc2nccn2CCNC(=O)C1=O)C(C)C]
212
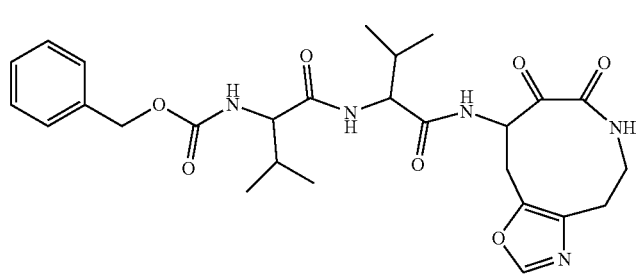 [SMILES: CC(C)C(NC(=O)OCc1ccccc1)C(=O)NC(C(=O)NC1Cc2ocnc2CCNC(=O)C1=O)C(C)C]
215
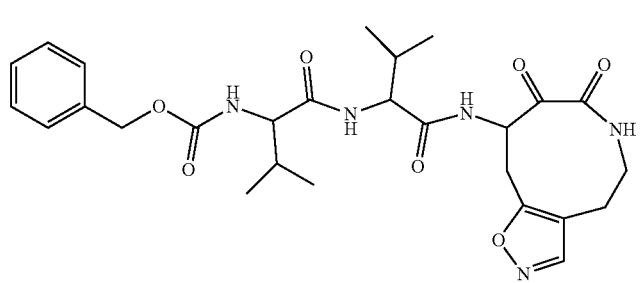 [SMILES: CC(C)C(NC(=O)OCc1ccccc1)C(=O)NC(C(=O)NC1Cc2oncc2CCNC(=O)C1=O)C(C)C]
216

TABLE 5-continued
NineRings
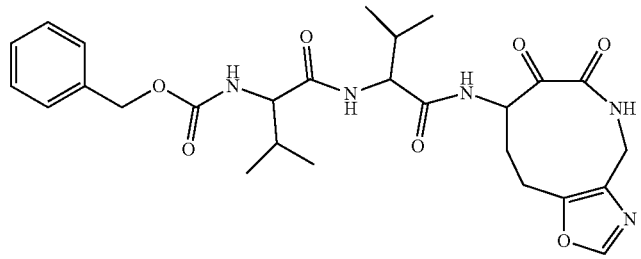 [SMILES: CC(C)C(NC(=O)OCc1ccccc1)C(=O)NC(C(=O)NC1CCc2ocnc2CNC(=O)C1=O)C(C)C]
219
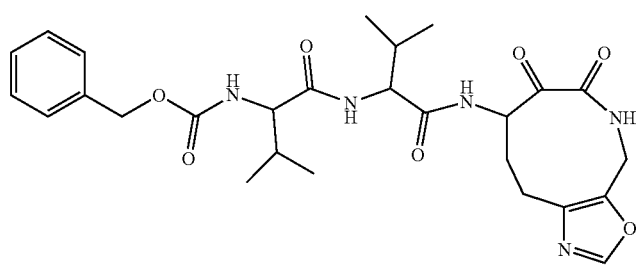 [SMILES: CC(C)C(NC(=O)OCc1ccccc1)C(=O)NC(C(=O)NC1CCc2ncoc2CNC(=O)C1=O)C(C)C]
220
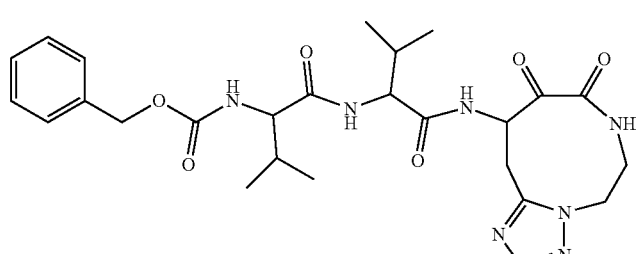
223
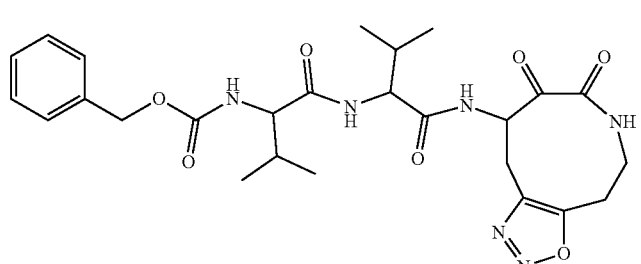
224
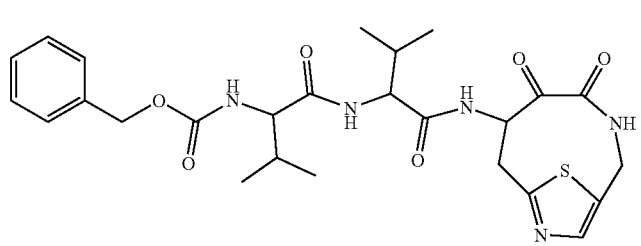 [SMILES: CC(C)C(NC(=O)OCc1ccccc1)C(=O)NC(C(=O)NC1CC2=NC=C(CNC(=O)C1=O)S2)C(C)C]
227
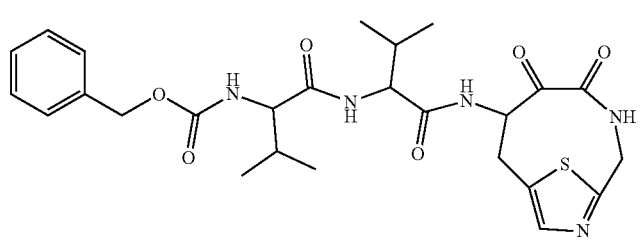 [SMILES: CC(C)C(NC(=O)OCc1ccccc1)C(=O)NC(C(=O)NC1CC2=CN=C(CNC(=O)C1=O)S2)C(C)C]
228

TABLE 5-continued
NineRings
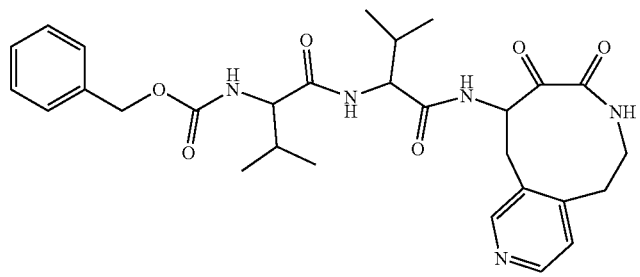 [SMILES: CC(C)C(NC(=O)OCc1ccccc1)C(=O)NC(C(=O)NC1Cc2cnccc2CCNC(=O)C1=O)C(C)C]
231
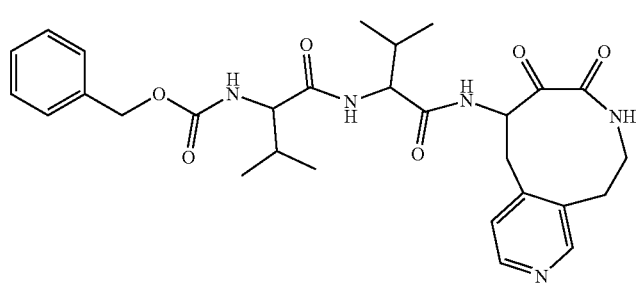 [SMILES: CC(C)C(NC(=O)OCc1ccccc1)C(=O)NC(C(=O)NC1Cc2ccncc2CCNC(=O)C1=O)C(C)C]
232
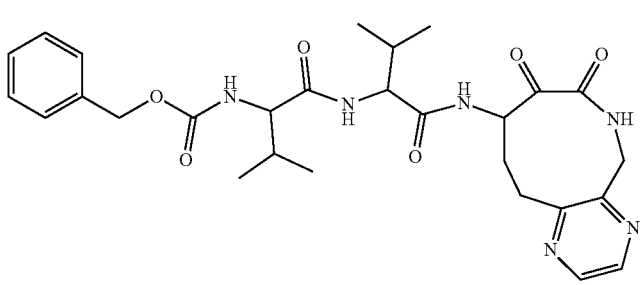 [SMILES: CC(C)C(NC(=O)OCc1ccccc1)C(=O)NC(C(=O)NC1CCc2nccnc2CNC(=O)C1=O)C(C)C]
235
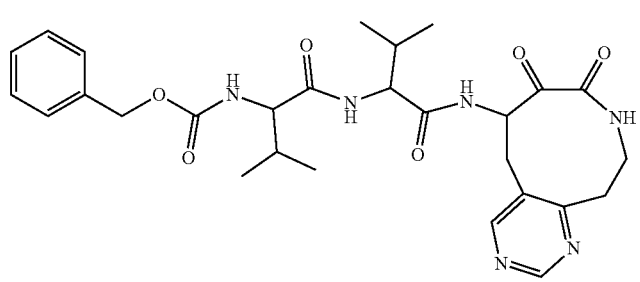 [SMILES: CC(C)C(NC(=O)OCc1ccccc1)C(=O)NC(C(=O)NC1Cc2cncnc2CCNC(=O)C1=O)C(C)C]
236
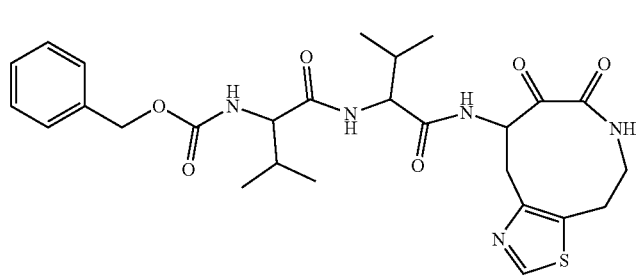 [SMILES: CC(C)C(NC(=O)OCc1ccccc1)C(=O)NC(C(=O)NC1Cc2ncsc2CCNC(=O)C1=O)C(C)C]
239

TABLE 5-continued

NineRings

TABLE 6-continued
TenRings
| | |
|---|---|
| 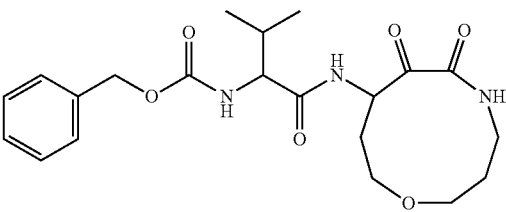 | 6 |
| 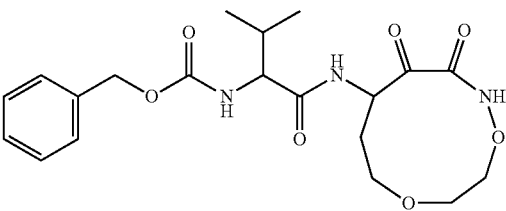 [SMILES: CC(C)C(NC(=O)OCc1ccccc1)C(=O)NC1CCOCCCNC(=O)C1=O] | 9 |
| 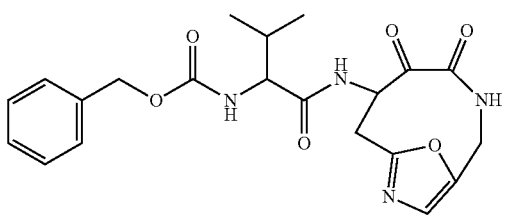 [SMILES: CC(C)C(NC(=O)OCc1ccccc1)C(=O)NC1CC2=NC=C(CNC(=O)C1=O)O2] | 10 |
| 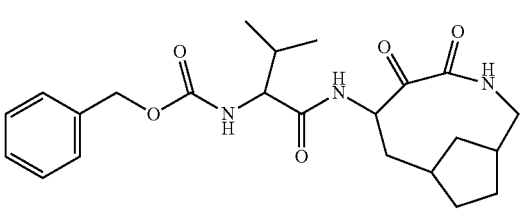 [SMILES: CC(C)C(NC(=O)OCc1ccccc1)C(=O)NC1CC2CCC(CNC(=O)C1=O)C2] | 13 |
| 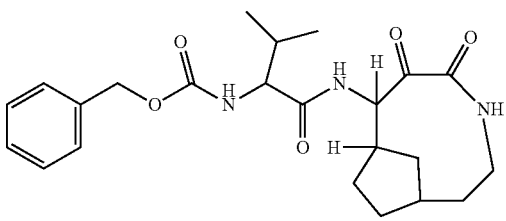 [SMILES: CC(C)C(NC(=O)OCc1ccccc1)C(=O)NC1C(=O)C(=O)NCCC2CCC1C2] | 14 |
| 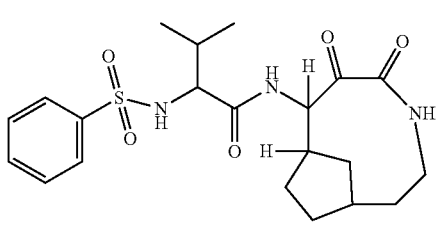 [SMILES: CC(C)C(NS(=O)(=O)c1ccccc1)C(=O)NC1C(=O)C(=O)NCCC2CCC1C2] | 17 |
| 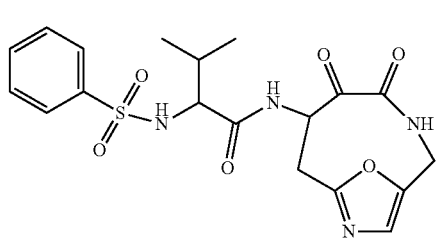 [SMILES: CC(C)C(NS(=O)(=O)c1ccccc1)C(=O)NC1CC2=NC=C(CNC(=O)C1=O)O2] | 18 |

TABLE 6-continued

TenRings

TABLE 6-continued
TenRings
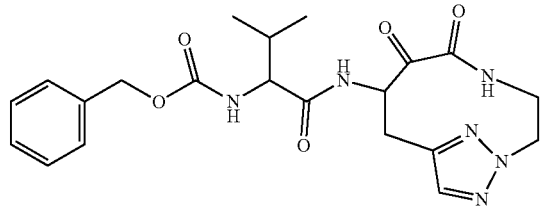 [SMILES: CC(C)C(NC(=O)OCc1ccccc1)C(=O)NC1Cc2cnn(n2)CCNC(=O)C1=O] 34
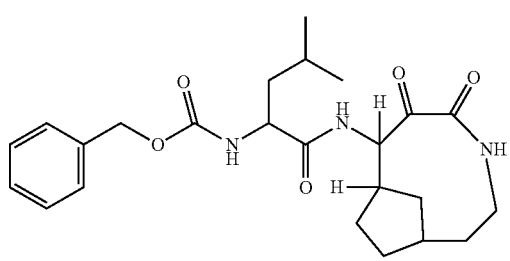 [SMILES: CC(C)CC(NC(=O)OCc1ccccc1)C(=O)NC1C(=O)C(=O)NCCC2CCC1C2] 37
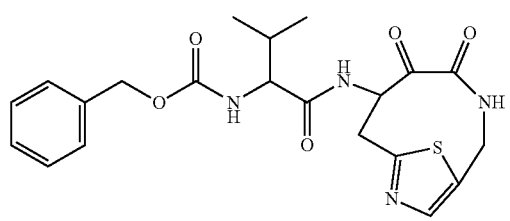 38
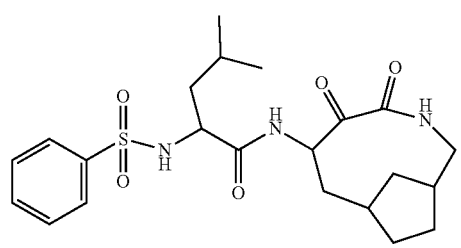 [SMILES: CC(C)CC(NS(=O)(=O)c1ccccc1)C(=O)NC1CC2CCC(CNC(=O)C1=O)C2] 41
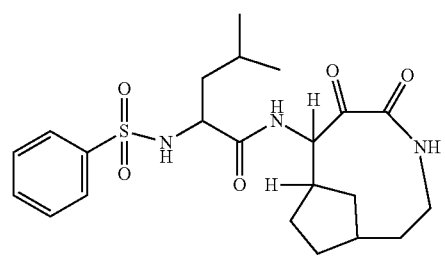 [SMILES: CC(C)CC(NS(=O)(=O)c1ccccc1)C(=O)NC1C(=O)C(=O)NCCC2CCC1C2] 42
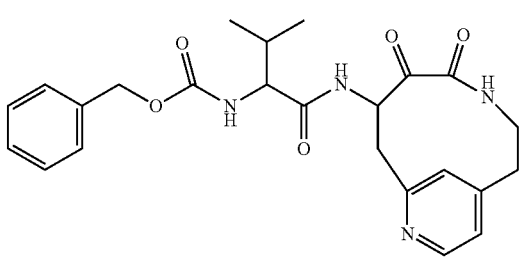 [SMILES: CC(C)C(NC(=O)OCc1ccccc1)C(=O)NC1Cc2cc(ccn2)CCNC(=O)C1=O] 45

TABLE 6-continued
TenRings
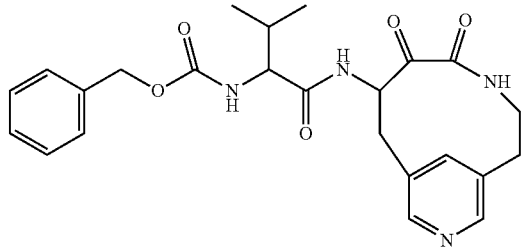 [SMILES: CC(C)C(NC(=O)OCc1ccccc1)C(=O)NC1Cc2cncc(c2)CCNC(=O)C1=O]
46
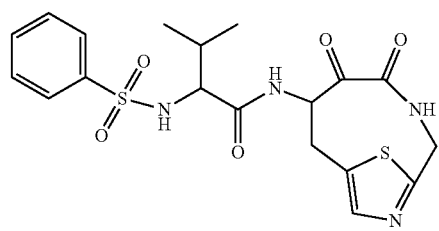 [SMILES: CC(C)C(NS(=O)(=O)c1ccccc1)C(=O)NC1CC2=CN=C(CNC(=O)C1=O)S2]
49
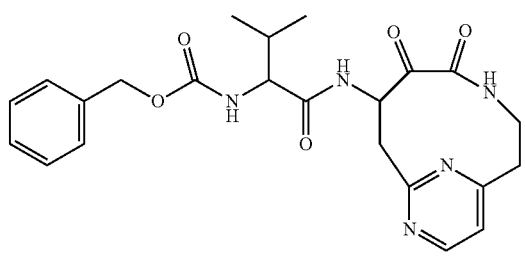 [SMILES: CC(C)C(NC(=O)OCc1ccccc1)C(=O)NC1Cc2nccc(n2)CCNC(=O)C1=O]
50
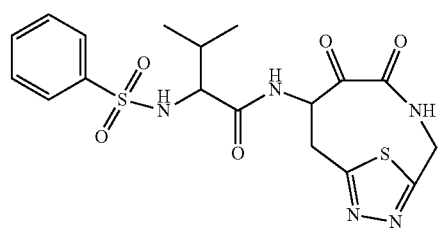 [SMILES: CC(C)C(NS(=O)(=O)c1ccccc1)C(=O)NC1CC2=NN=C(CNC(=O)C1=O)S2]
53
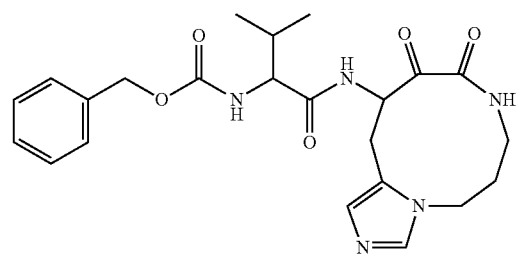
54
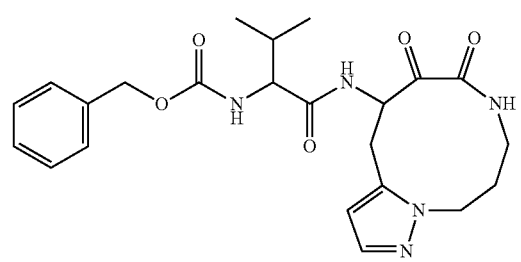 [SMILES: CC(C)C(NC(=O)OCc1ccccc1)C(=O)NC1Cc2ccnn2CCCNC(=O)C1=O]
57

TABLE 6-continued

TenRings

TABLE 6-continued
TenRings
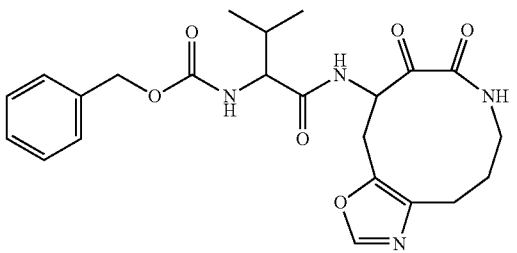 70
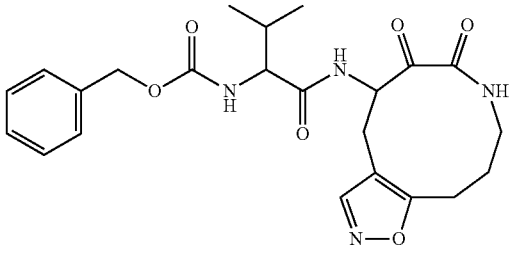 73
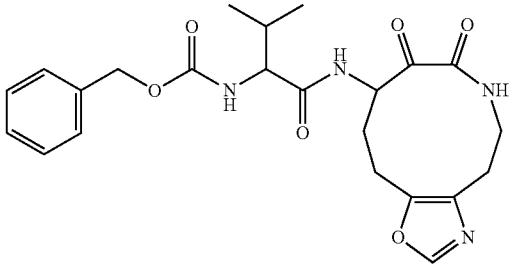 74
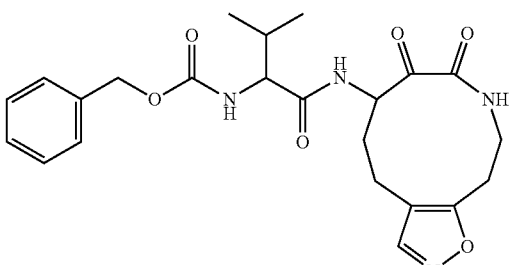 77
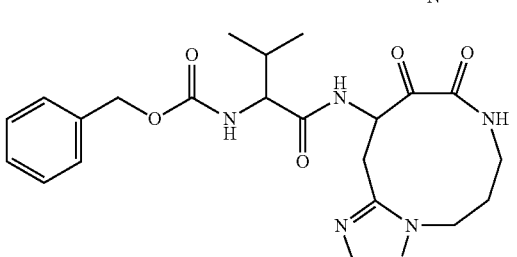 78
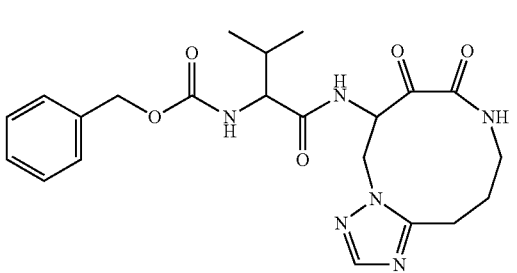 [SMILES: CC(C)C(NC(=O)OCc1ccccc1)C(=O)NC1Cn2ccnc2CCCNC(=O)C1=O] 81

TABLE 6-continued

TenRings

82

85

86

89

90

93

TABLE 6-continued
TenRings
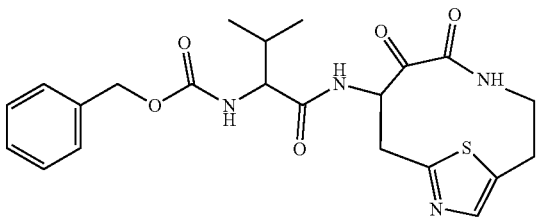 [SMILES: CC(C)C(NC(=O)OCc1ccccc1)C(=O)NC1CC2=NC=C(CCNC(=O)C1=O)S2]
94
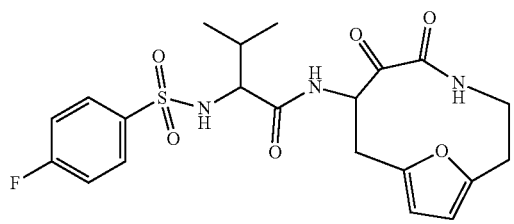 [SMILES: CC(C)C(NS(=O)(=O)c1ccc(F)cc1)C(=O)NC1CC2=CC=C(CCNC(=O)C1=O)O2]
97
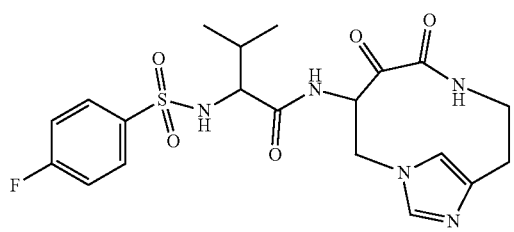 [SMILES: CC(C)C(NS(=O)(=O)c1ccc(F)cc1)C(=O)NC1Cn2cnc(c2)CCNC(=O)C1=O]
98
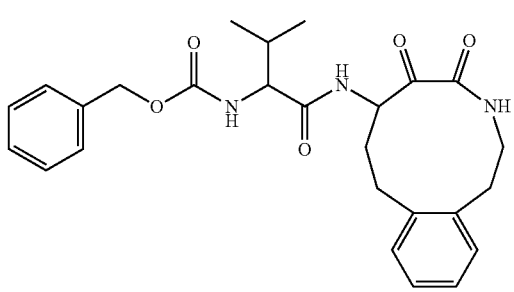 [SMILES: CC(C)C(NC(=O)OCc1ccccc1)C(=O)NC1CCc2ccccc2CCNC(=O)C1=O]
101
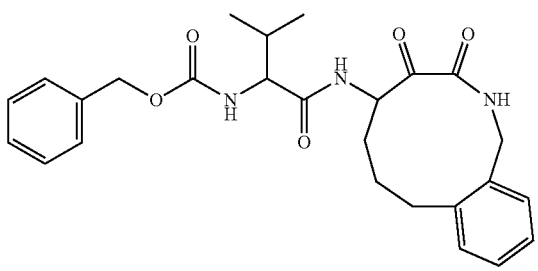
102
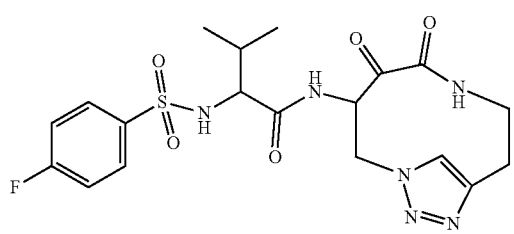 [SMILES: CC(C)C(NS(=O)(=O)c1ccc(F)cc1)C(=O)NC1Cn2cc(nn2)CCNC(=O)C1=O]
105

TABLE 6-continued
TenRings
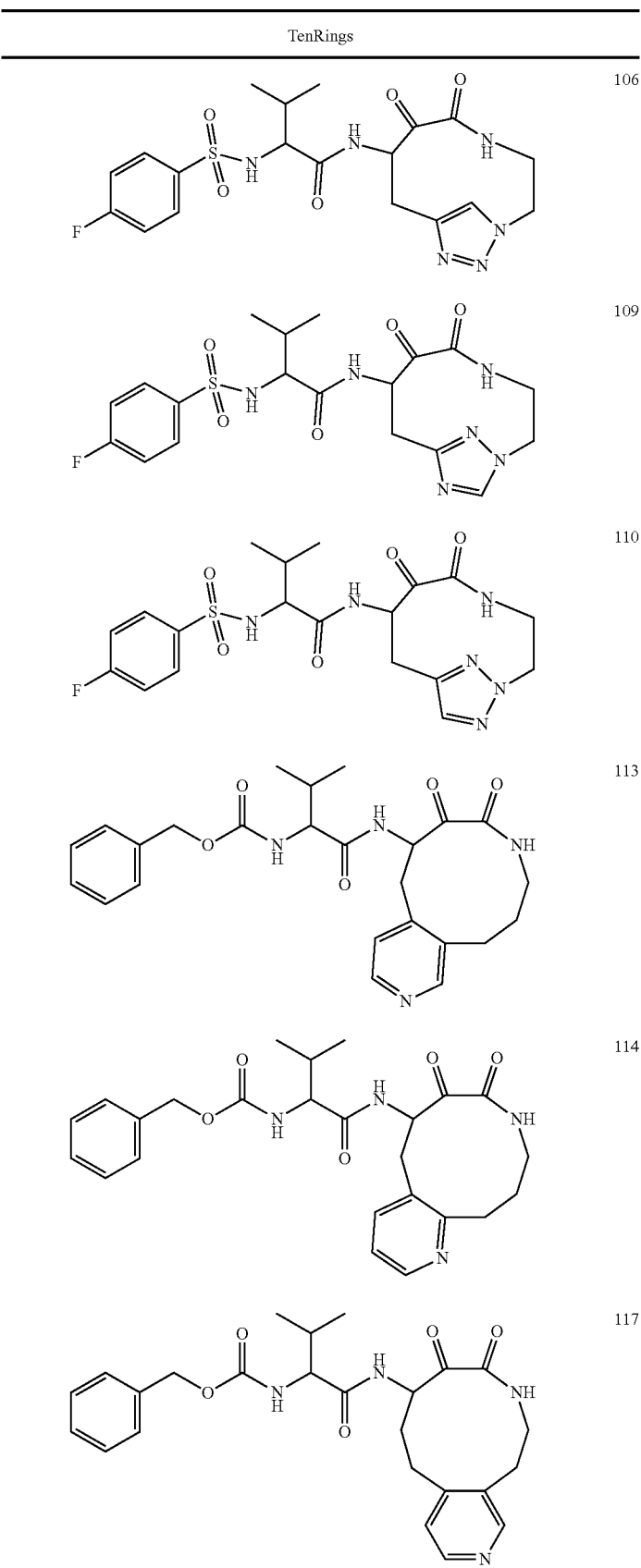

TABLE 6-continued
TenRings
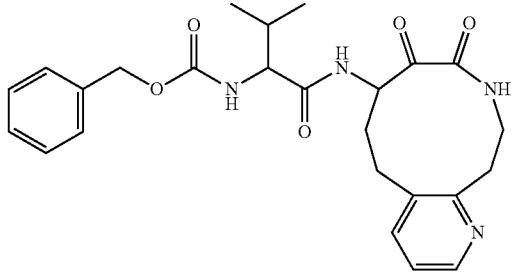 [SMILES: CC(C)C(NC(=O)OCc1ccccc1)C(=O)NC1CCc2cccnc2CCNC(=O)C1=O]
118
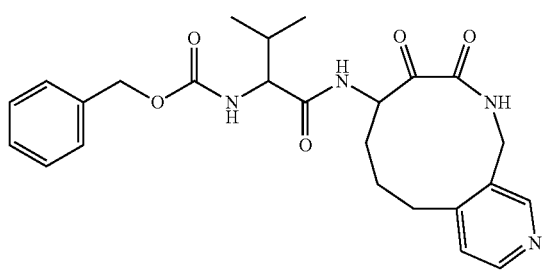 [SMILES: CC(C)C(NC(=O)OCc1ccccc1)C(=O)NC1CCCc2ccncc2CNC(=O)C1=O]
121
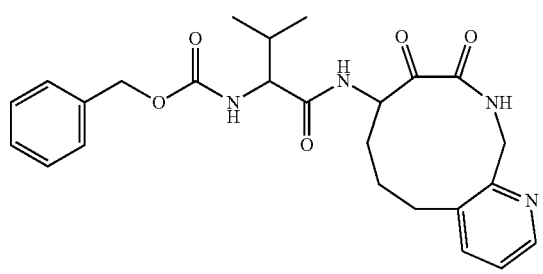 [SMILES: CC(C)C(NC(=O)OCc1ccccc1)C(=O)NC1CCCc2cccnc2CNC(=O)C1=O]
122
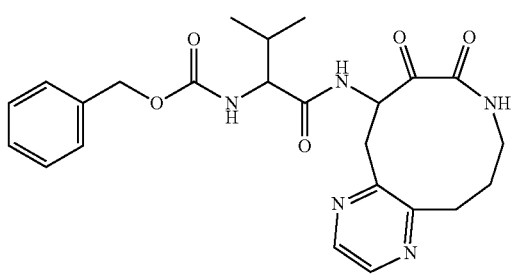 [SMILES: CC(C)C(NC(=O)OCc1ccccc1)C(=O)NC1Cc2nccnc2CCCNC(=O)C1=O]
125
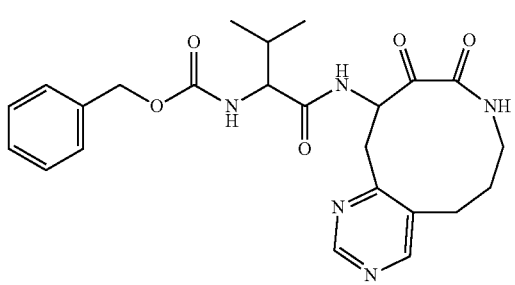 [SMILES: CC(C)C(NC(=O)OCc1ccccc1)C(=O)NC1Cc2ncncc2CCCNC(=O)C1=O]
126

TABLE 6-continued
TenRings
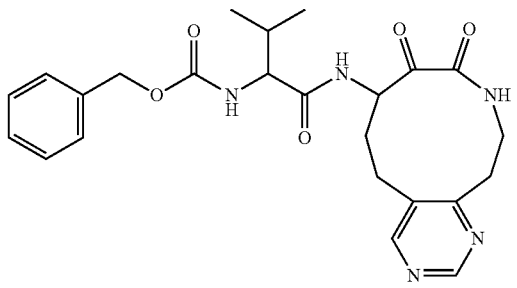 [SMILES: CC(C)C(NC(=O)OCc1ccccc1)C(=O)NC1CCc2cncnc2CCNC(=O)C1=O]
129
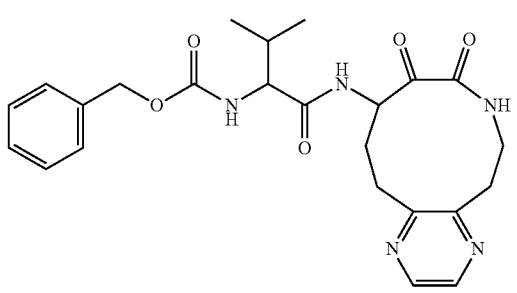 [SMILES: CC(C)C(NC(=O)OCc1ccccc1)C(=O)NC1CCc2nccnc2CCNC(=O)C1=O]
130
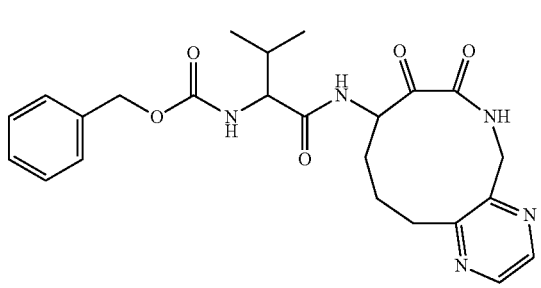 [SMILES: CC(C)C(NC(=O)OCc1ccccc1)C(=O)NC1CCCc2nccnc2CNC(=O)C1=O]
133
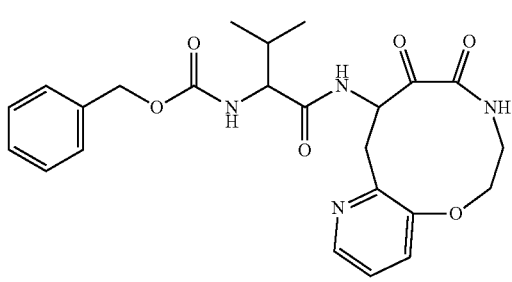 [SMILES: CC(C)C(NC(=O)OCc1ccccc1)C(=O)NC1Cc2ncccc2OCCNC(=O)C1=O]
134
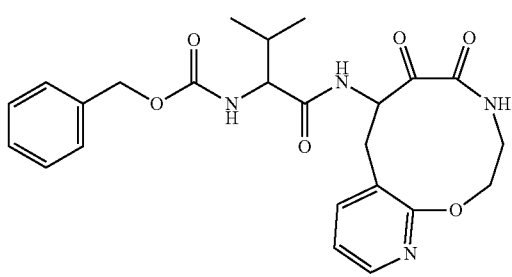
137

TABLE 6-continued
TenRings
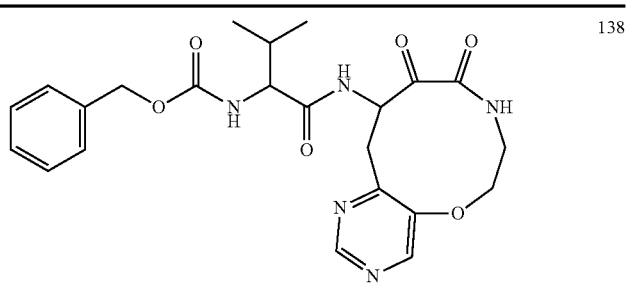
138
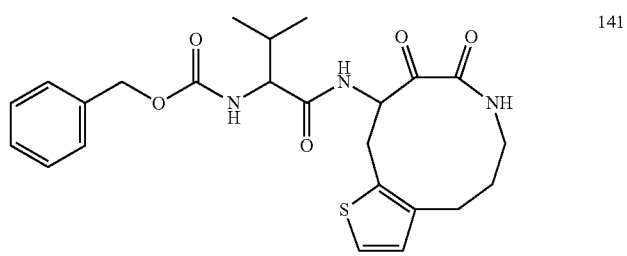
141
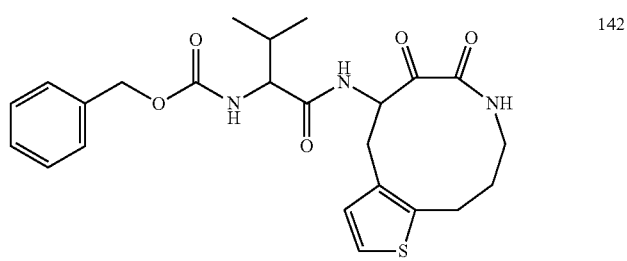
142
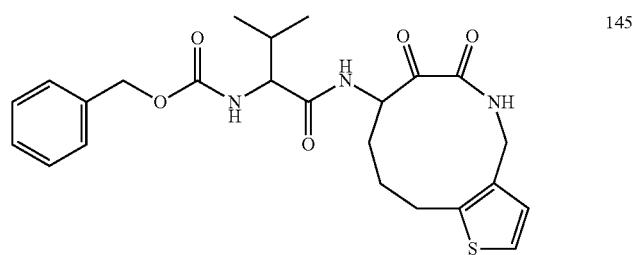
145
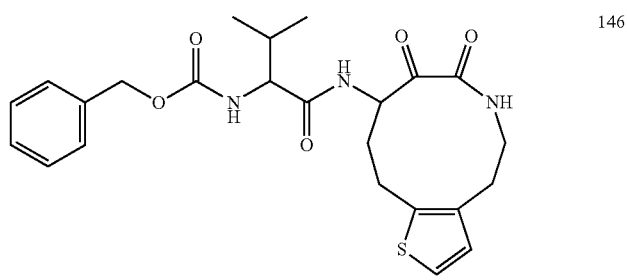
146
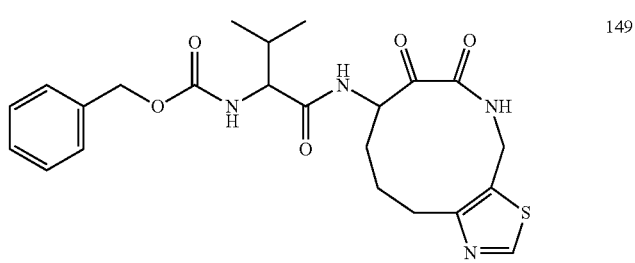
149

TABLE 6-continued
TenRings
| | |
|---|---|
|  | 150 |
| 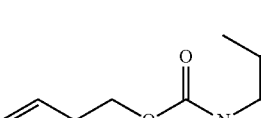 | 153 |
| 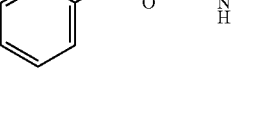 | 154 |
|  | 157 |
| 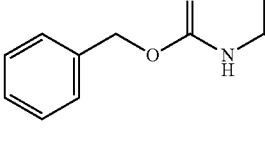 | 158 |
|  | 161 |

TABLE 6-continued
TenRings
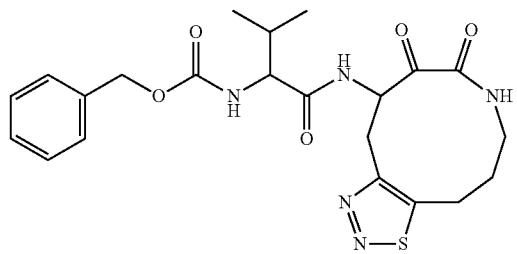 [SMILES: CC(C)C(NC(=O)OCc1ccccc1)C(=O)NC1Cc2ccsc2CCCNC(=O)C1=O]
162
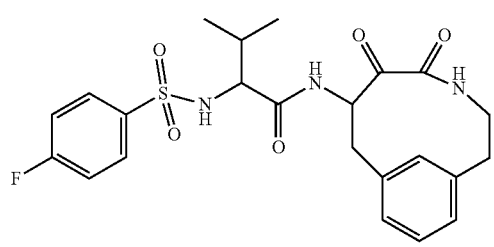 [SMILES: CC(C)C(NS(=O)(=O)c1ccc(F)cc1)C(=O)NC1Cc2cccc(c2)CCNC(=O)C1=O]
165
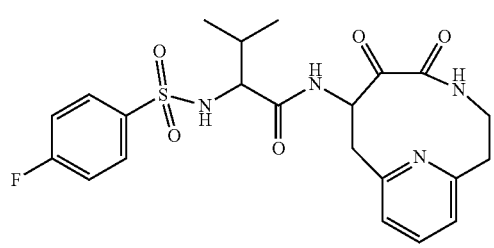 [SMILES: CC(C)C(NS(=O)(=O)c1ccc(F)cc1)C(=O)NC1Cc2cccc(n2)CCNC(=O)C1=O]
166
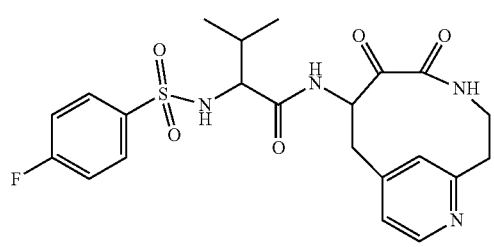
169
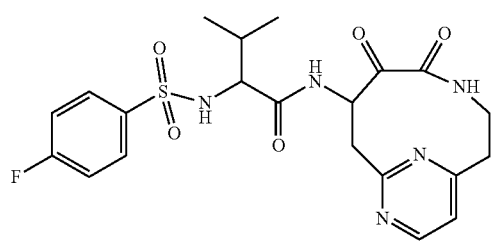 [SMILES: CC(C)C(NS(=O)(=O)c1ccc(F)cc1)C(=O)NC1Cc2nccc(n2)CCNC(=O)C1=O]
170
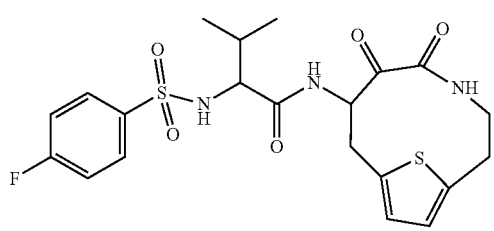 [SMILES: CC(C)C(NS(=O)(=O)c1ccc(F)cc1)C(=O)NC1CC2=CC=C(CCNC(=O)C1=O)S2]
173

TABLE 6-continued
TenRings
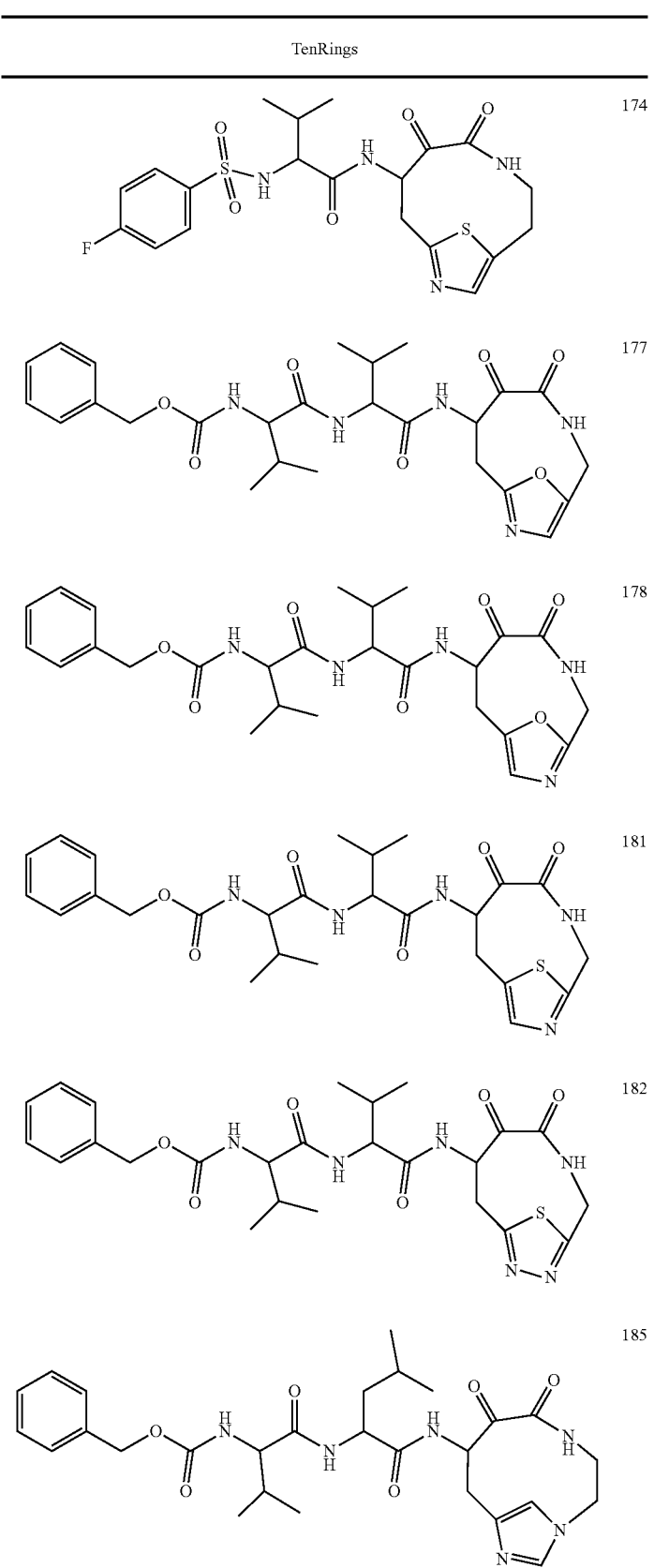

TABLE 6-continued
TenRings
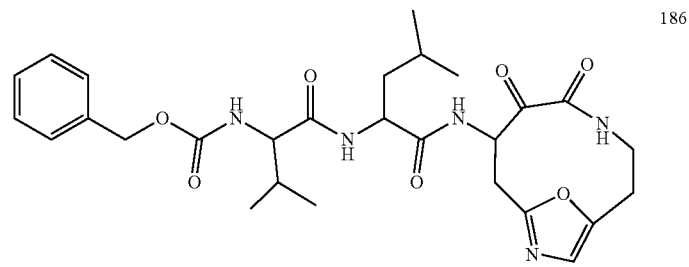
186
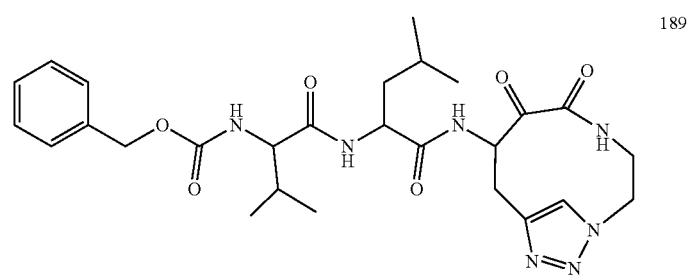
189
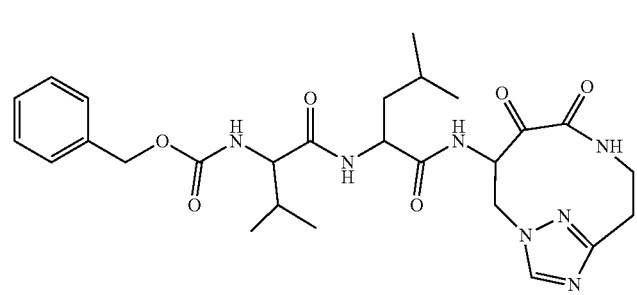 [SMILES: CC(C)CC(NC(=O)C(NC(=O)OCc1ccccc1)C(C)C)C(=O)NC1Cn2cnc(n2)CCNC(=O)C1=O]
190
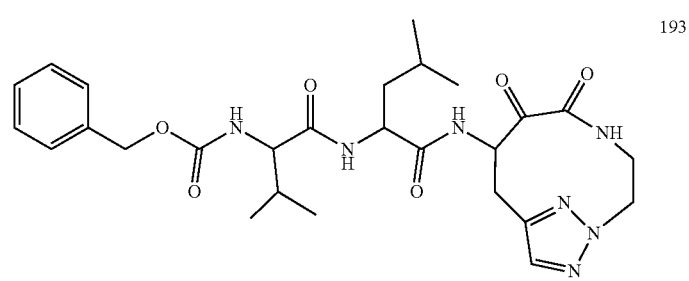
193
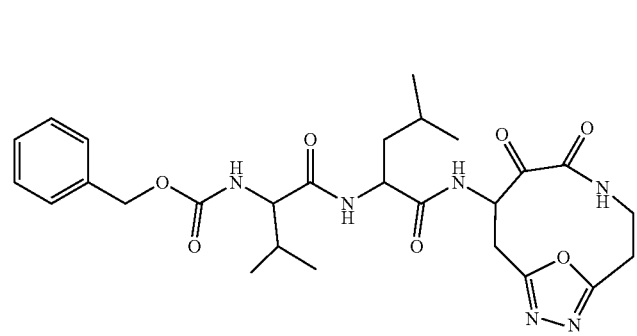 [SMILES: CC(C)CC(NC(=O)C(NC(=O)OCc1ccccc1)C(C)C)C(=O)NC1CC2=NN=C(CCNC(=O)C1=O)O2]
194

TABLE 6-continued
TenRings
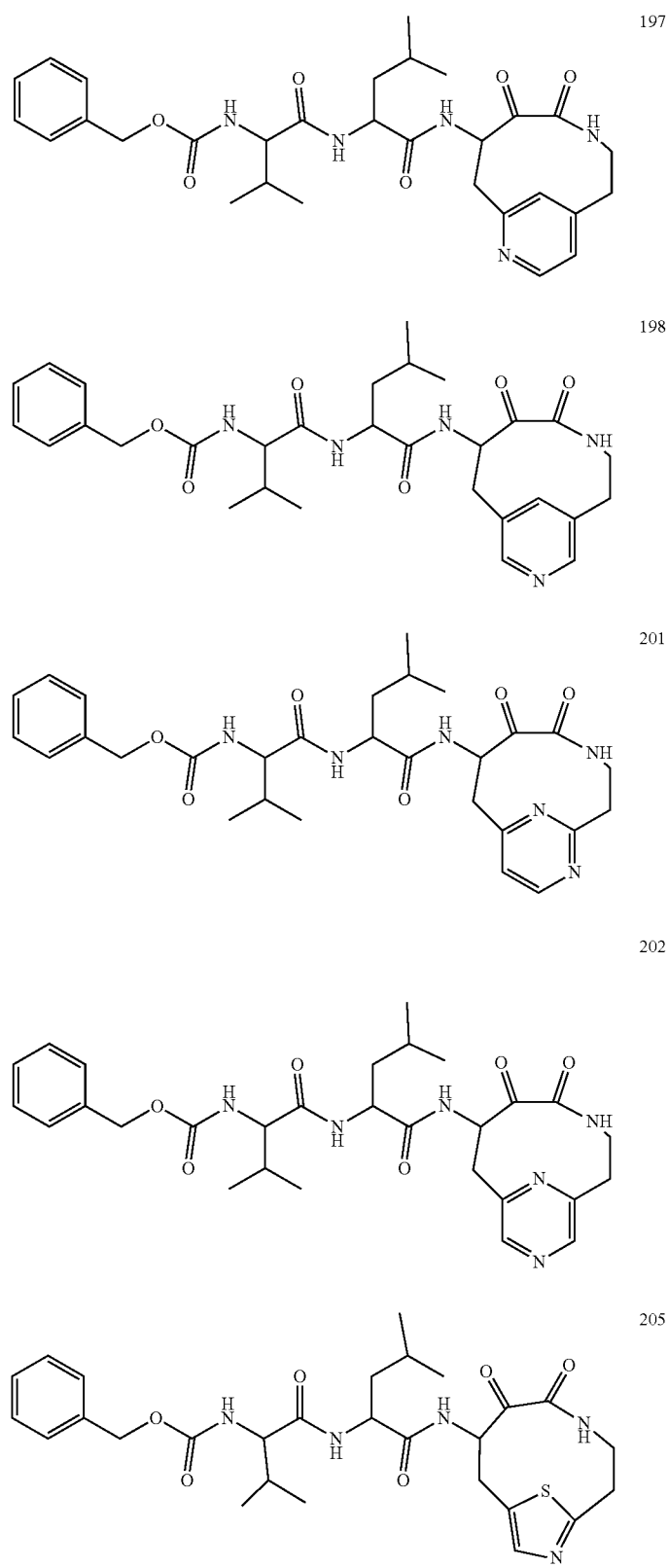
197
198
201
202
205

TABLE 6-continued
TenRings
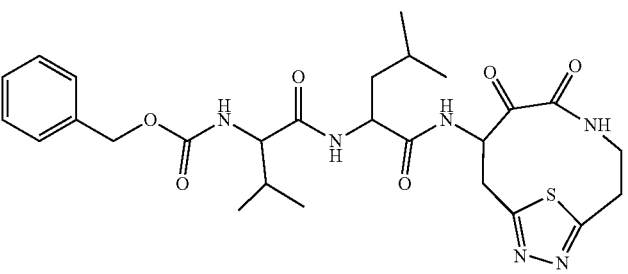 [SMILES: CC(C)CC(NC(=O)C(NC(=O)OCc1ccccc1)C(C)C)C(=O)NC1CC2=NN=C(CCNC(=O)C1=O)S2]
206
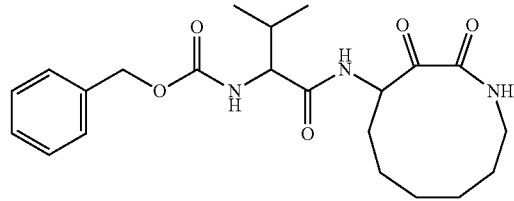
3
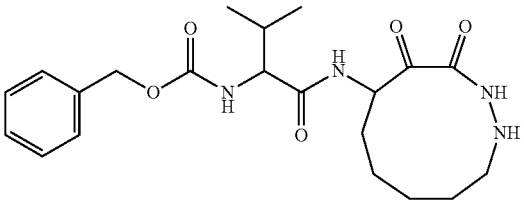 [SMILES: CC(C)C(NC(=O)OCc1ccccc1)C(=O)NC1CCCCCNNC(=O)C1=O]
4
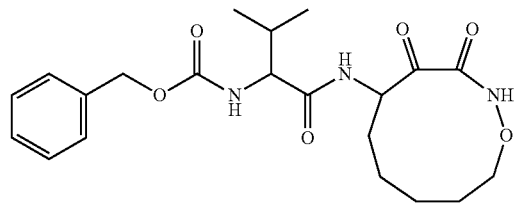 [SMILES: CC(C)C(NC(=O)OCc1ccccc1)C(=O)NC1CCCCCONC(=O)C1=O]
7
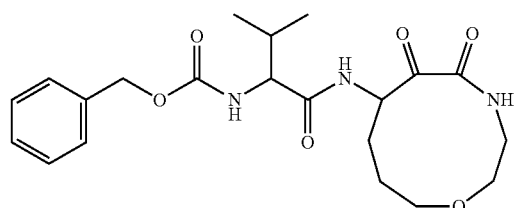
8
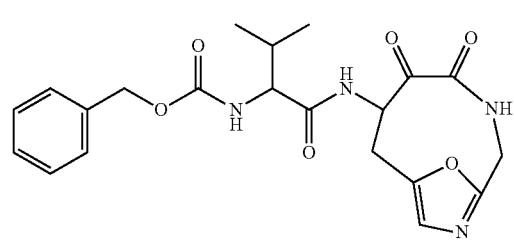 [SMILES: CC(C)C(NC(=O)OCc1ccccc1)C(=O)NC1Cc2cnc(o2)CNC(=O)C1=O]
11
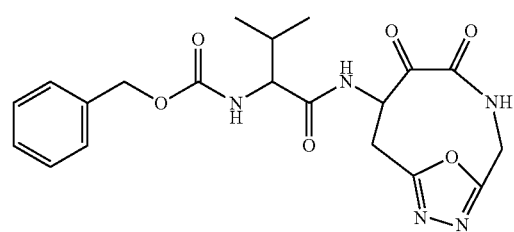 [SMILES: CC(C)C(NC(=O)OCc1ccccc1)C(=O)NC1Cc2nnc(o2)CNC(=O)C1=O]
12

TABLE 6-continued
TenRings
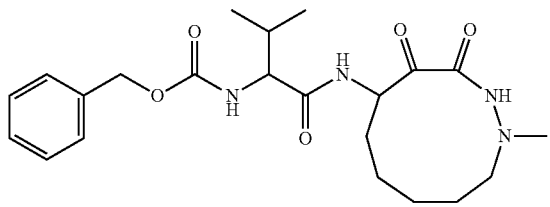 [SMILES: CC(C)C(NC(=O)OCc1ccccc1)C(=O)NC1CCCCCN(C)NC(=O)C1=O] 15
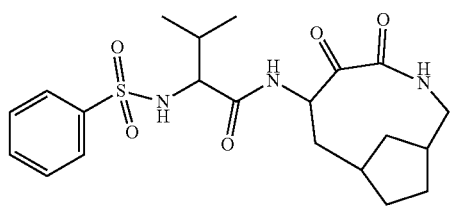 [SMILES: CC(C)C(NS(=O)(=O)c1ccccc1)C(=O)NC1CC2CCC(CNC(=O)C1=O)C2] 16
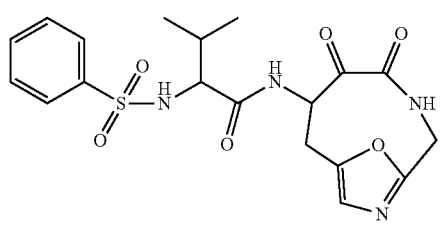 [SMILES: CC(C)C(NS(=O)(=O)c1ccccc1)C(=O)NC1CC2=CN=C(CNC(=O)C1=O)O2] 19
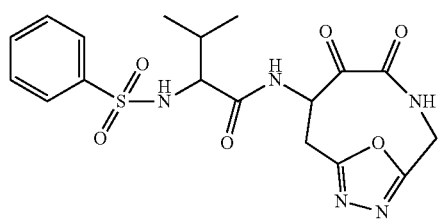 20
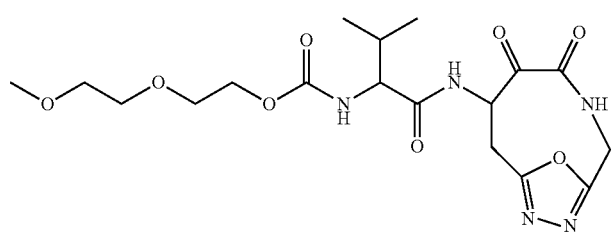 [SMILES: COCCOCCOC(=O)NC(C(=O)NC1Cc2nnc(o2)CNC(=O)C1=O)C(C)C] 23
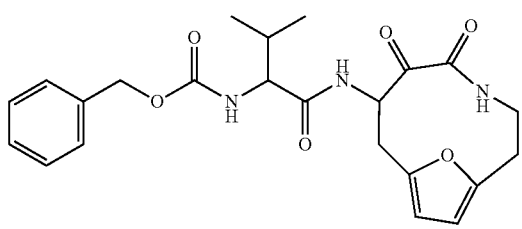 [SMILES: CC(C)C(NC(=O)OCc1ccccc1)C(=O)NC1CC2=CC=C(CCNC(=O)C1=O)O2] 24
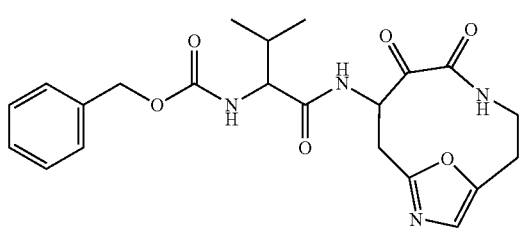 [SMILES: CC(C)C(NC(=O)OCc1ccccc1)C(=O)NC1CC2=NC=C(CCNC(=O)C1=O)O2] 27

TABLE 6-continued
TenRings
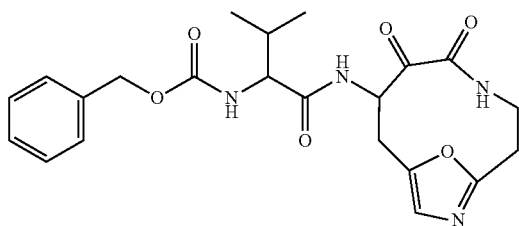
28
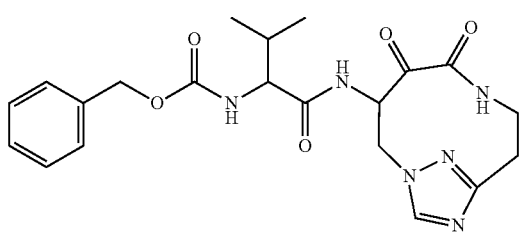 [SMILES: CC(C)C(NC(=O)OCc1ccccc1)C(=O)NC1Cn2cnc(n2)CCNC(=O)C1=O]
31
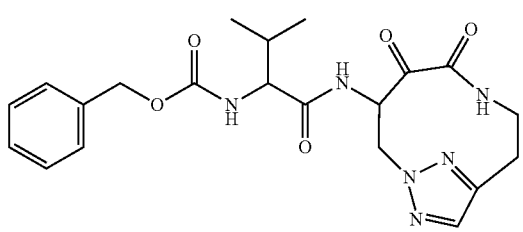 [SMILES: CC(C)C(NC(=O)OCc1ccccc1)C(=O)NC1Cn2ncc(n2)CCNC(=O)C1=O]
32
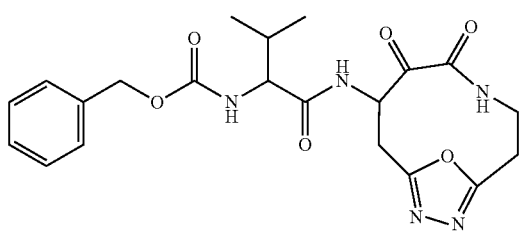 [SMILES: CC(C)C(NC(=O)OCc1ccccc1)C(=O)NC1CC2=NN=C(CCNC(=O)C1=O)O2]
35
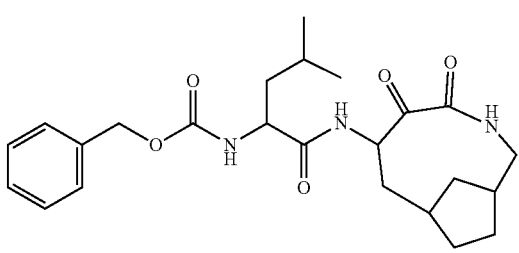 [SMILES: CC(C)CC(NC(=O)OCc1ccccc1)C(=O)NC1CC2CCC(CNC(=O)C1=O)C2]
36
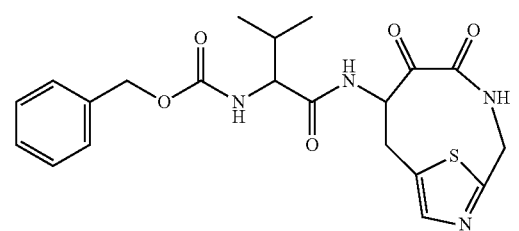 [SMILES: CC(C)C(NC(=O)OCc1ccccc1)C(=O)NC1Cc2nnc(s2)CNC(=O)C1=O]
39

TABLE 6-continued
TenRings
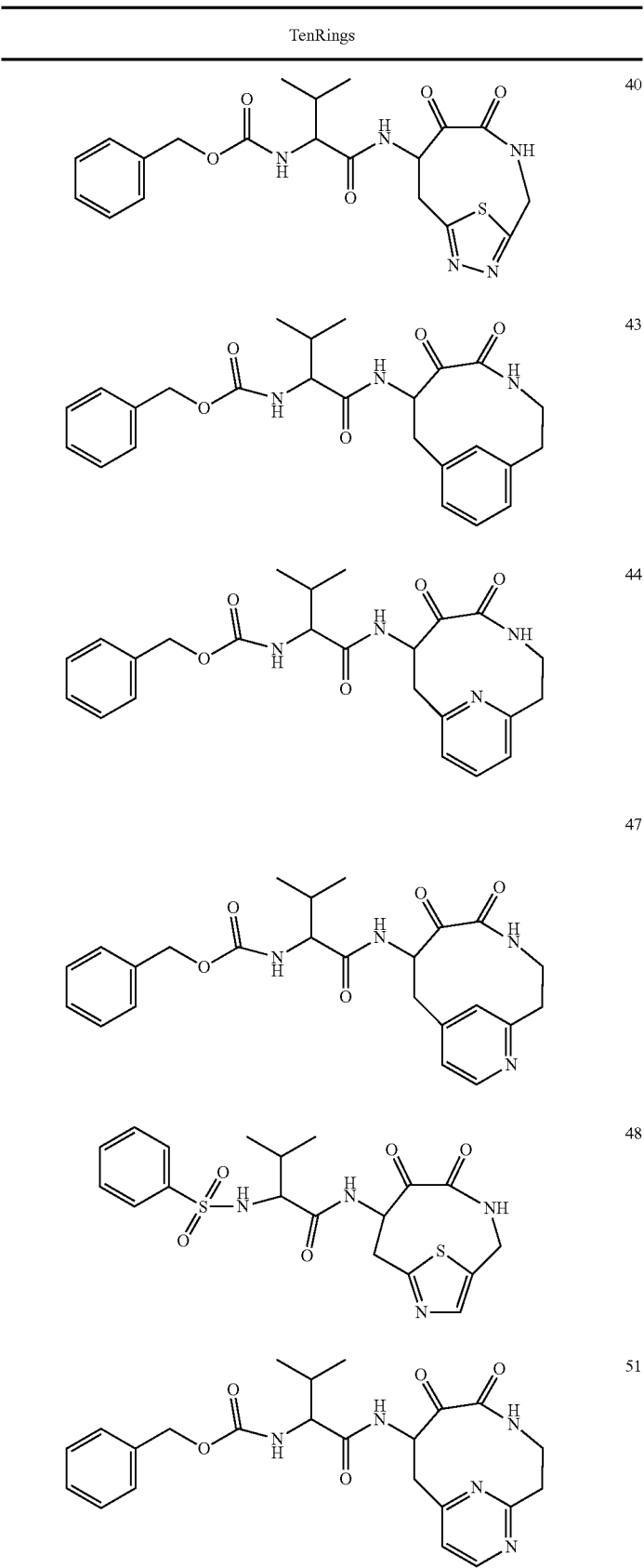

TABLE 6-continued
TenRings
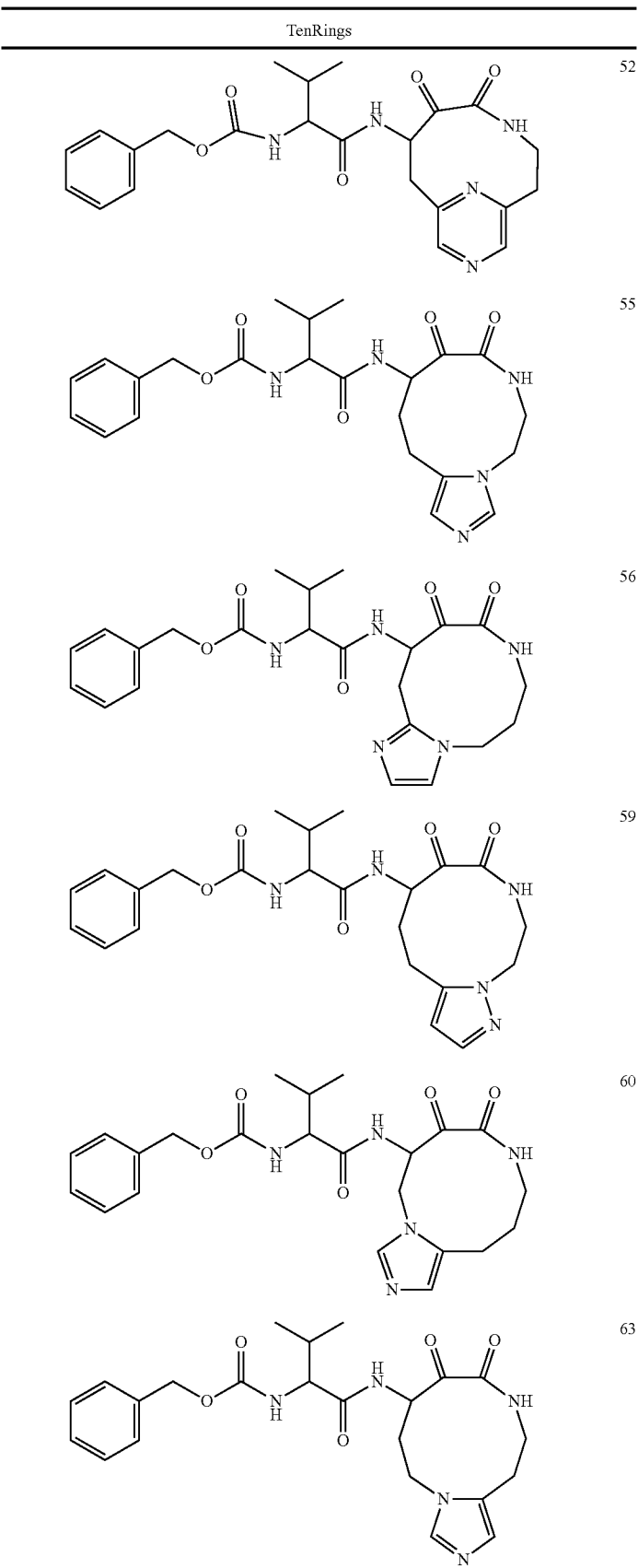

TABLE 6-continued
TenRings
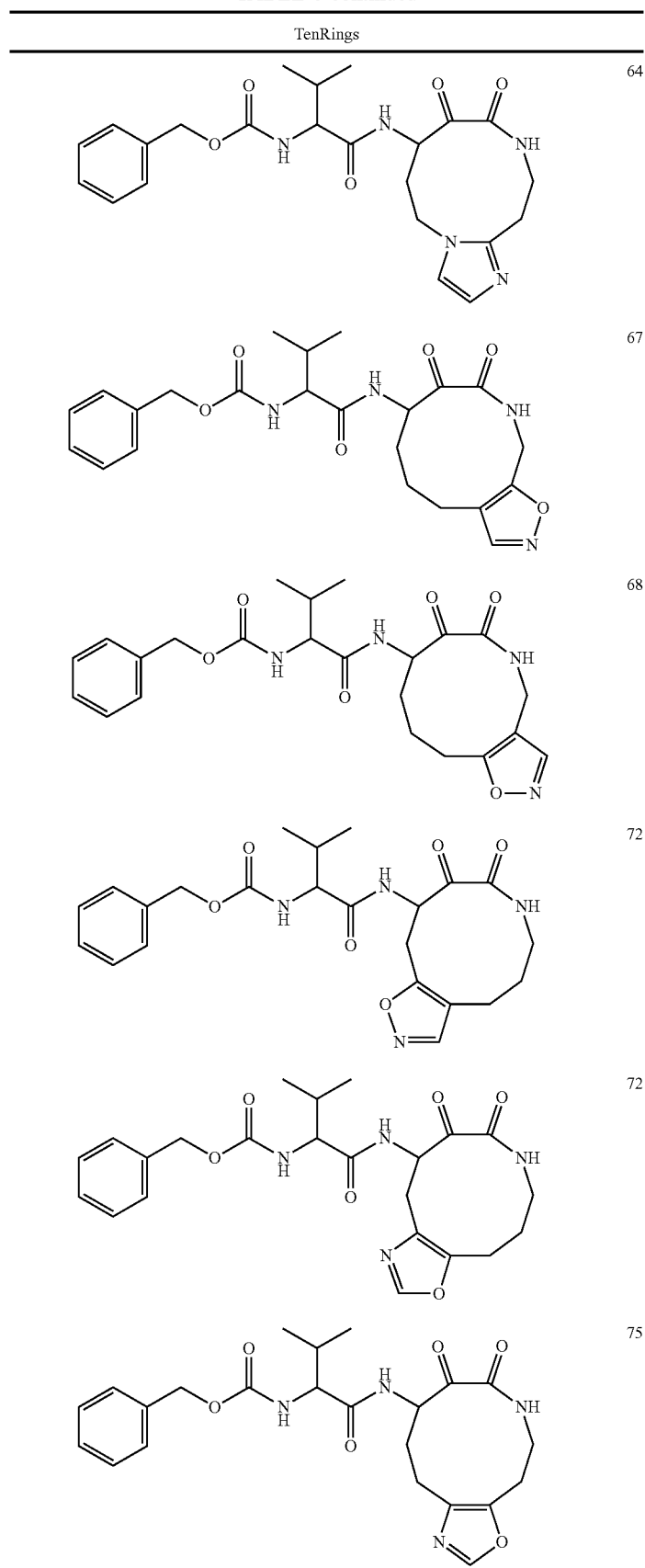
64
67
68
72
72
75

TABLE 6-continued
TenRings
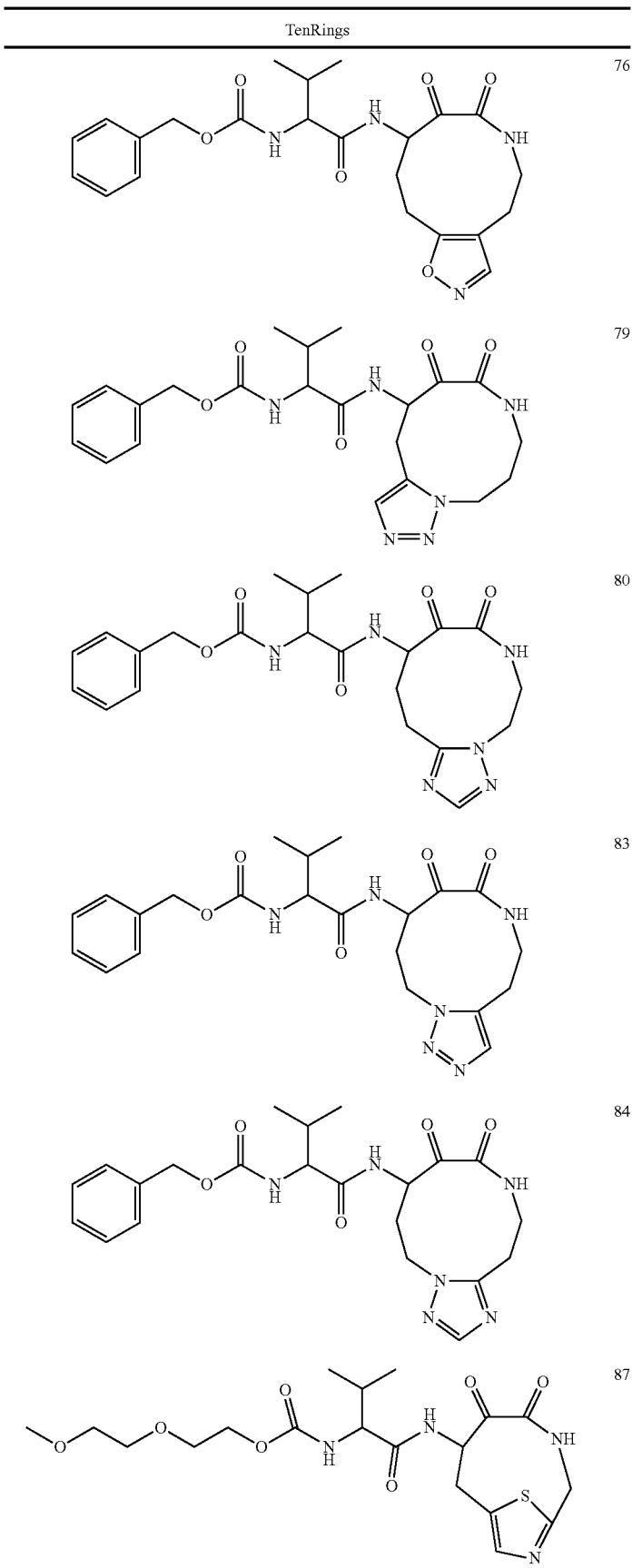

TABLE 6-continued
TenRings
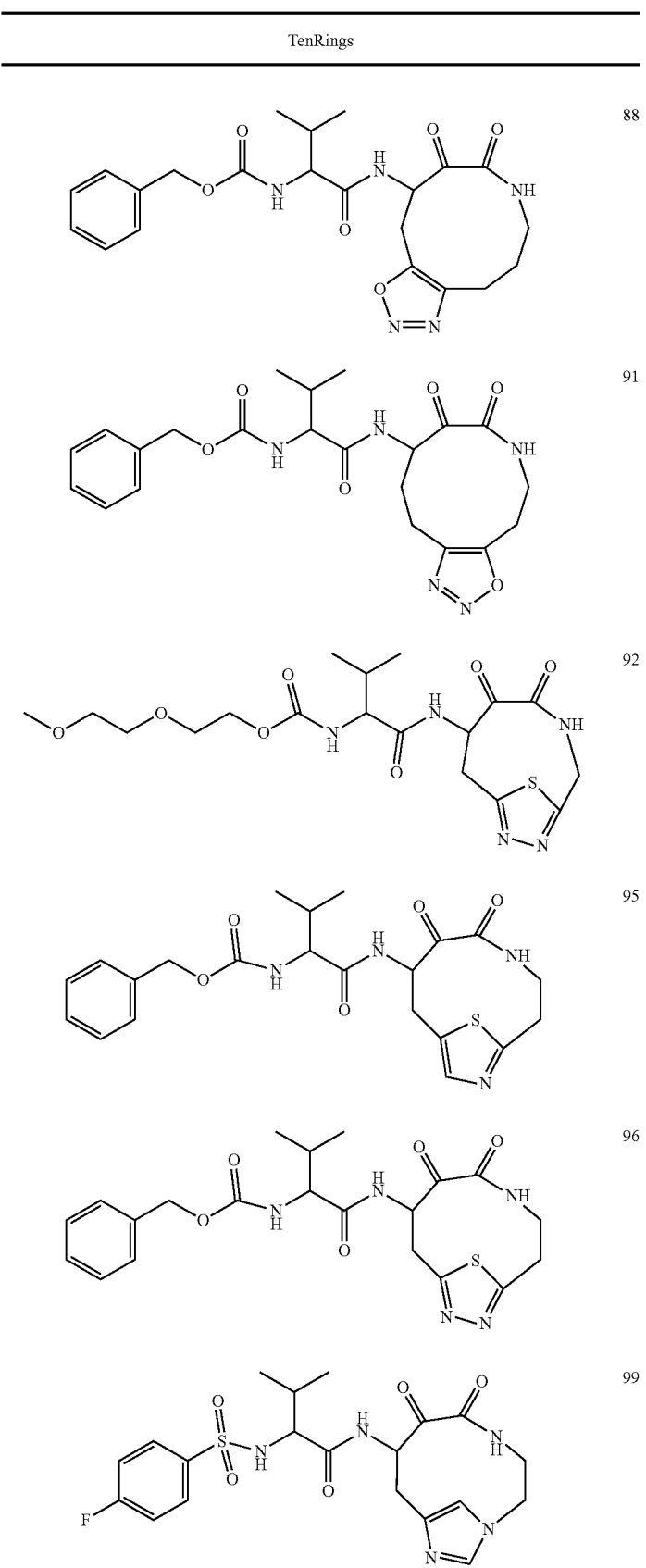

TABLE 6-continued
TenRings
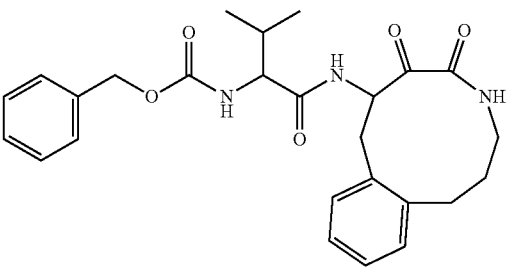 [SMILES: CC(C)C(NC(=O)OCc1ccccc1)C(=O)NC1Cc2ccccc2CCCNC(=O)C1=O]
100
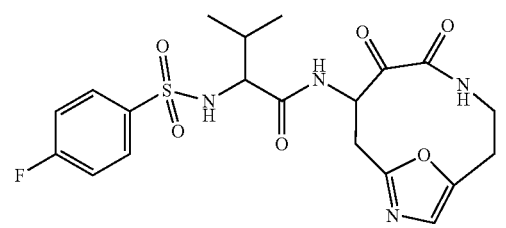 [SMILES: CC(C)C(NS(=O)(=O)c1ccc(F)cc1)C(=O)NC1CC2=NC=C(CCNC(=O)C1=O)O2]
103
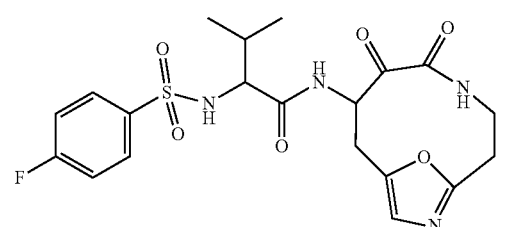
104
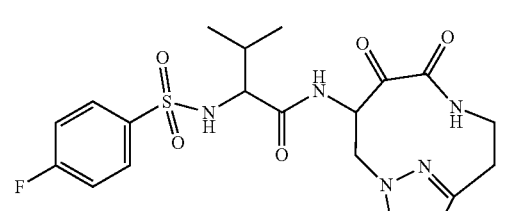
107
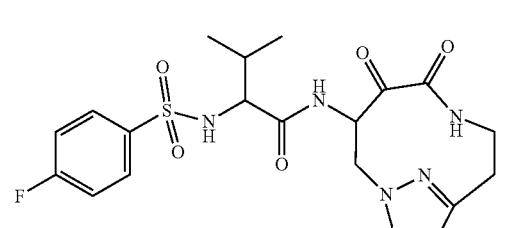
108
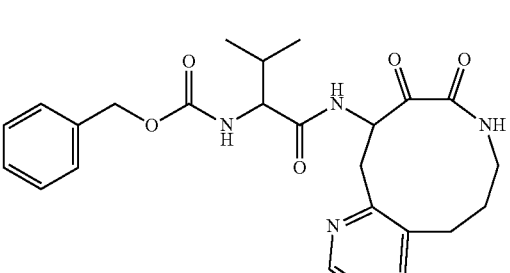
111

TABLE 6-continued
TenRings
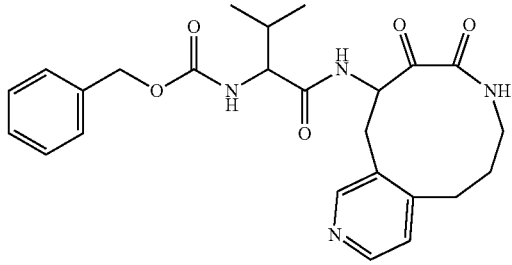
112
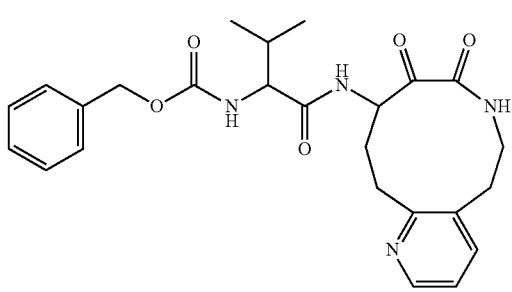 [SMILES: CC(C)C(NC(=O)OCc1ccccc1)C(=O)NC1CCc2ncccc2CCNC(=O)C1=O]
115
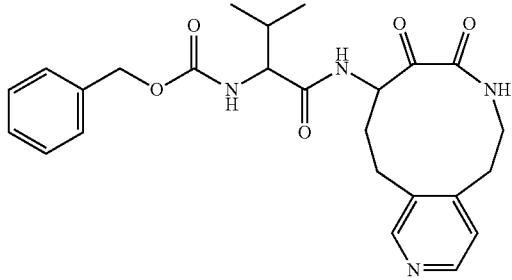 [SMILES: CC(C)C(NC(=O)OCc1ccccc1)C(=O)NC1CCc2cnccc2CCNC(=O)C1=O]
116
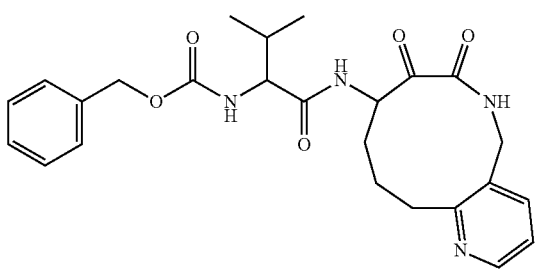
119
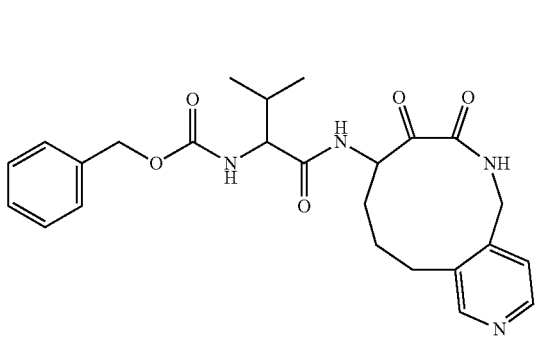 [SMILES: CC(C)C(NC(=O)OCc1ccccc1)C(=O)NC1CCCc2cnccc2CNC(=O)C1=O]
120

TABLE 6-continued
TenRings
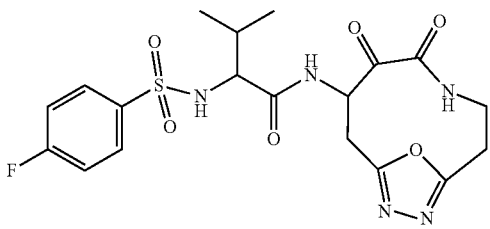 [SMILES: CC(C)C(NS(=O)(=O)c1ccc(F)cc1)C(=O)NC1CC2=NN=C(CCNC(=O)C1=O)O2]
123
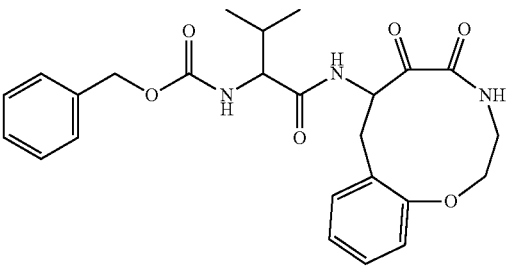 [SMILES: CC(C)C(NC(=O)OCc1ccccc1)C(=O)NC1Cc2ccccc2OCCNC(=O)C1=O]
124
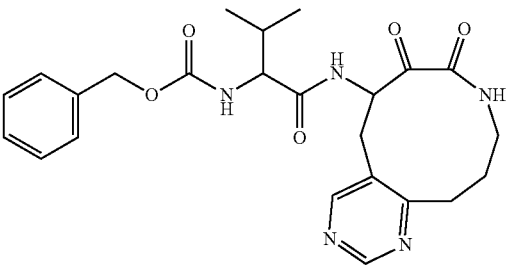 [SMILES: CC(C)C(NC(=O)OCc1ccccc1)C(=O)NC1Cc2cncnc2CCCNC(=O)C1=O]
127
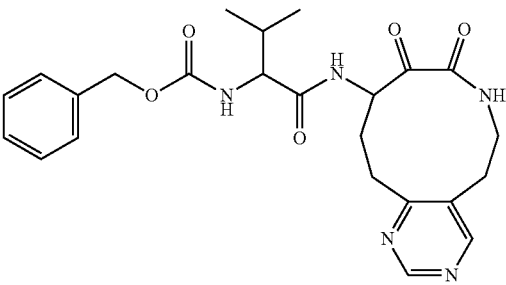 [SMILES: CC(C)C(NC(=O)OCc1ccccc1)C(=O)NC1CCc2ncncc2CCNC(=O)C1=O]
128
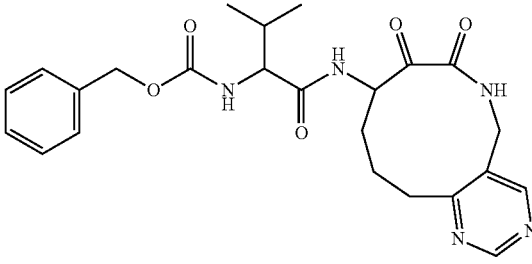
131
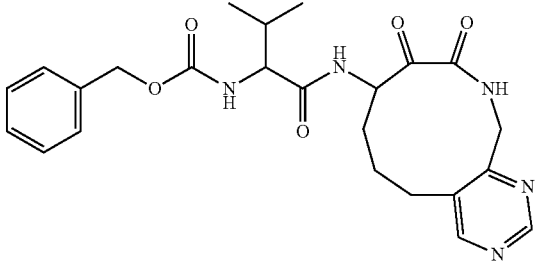 [SMILES: CC(C)C(NC(=O)OCc1ccccc1)C(=O)NC1CCCc2cncnc2CNC(=O)C1=O]
132

TABLE 6-continued
TenRings
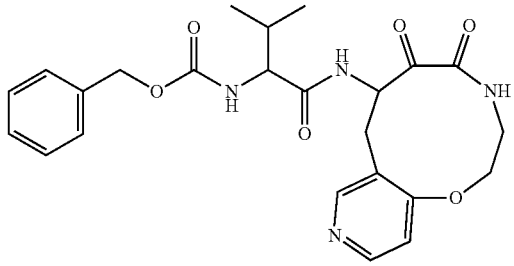
135
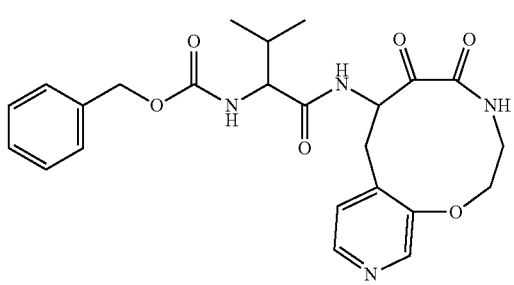 [SMILES: CC(C)C(NC(=O)OCc1ccccc1)C(=O)NC1Cc2ccncc2OCCNC(=O)C1=O]
136
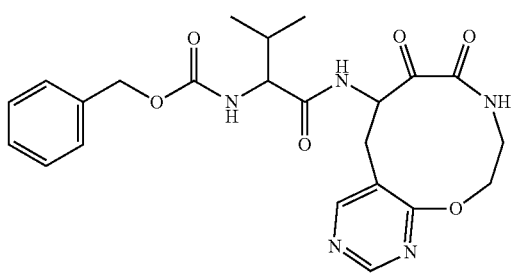 [SMILES: CC(C)C(NC(=O)OCc1ccccc1)C(=O)NC1Cc2cncnc2OCCNC(=O)C1=O]
139
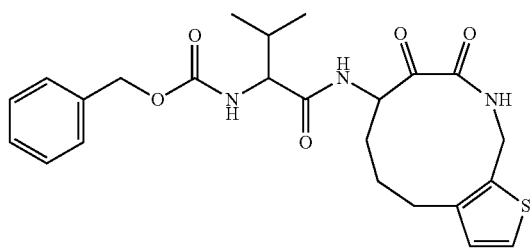 [SMILES: CC(C)C(NC(=O)OCc1ccccc1)C(=O)NC1CCCc2ccsc2CNC(=O)C1=O]
140
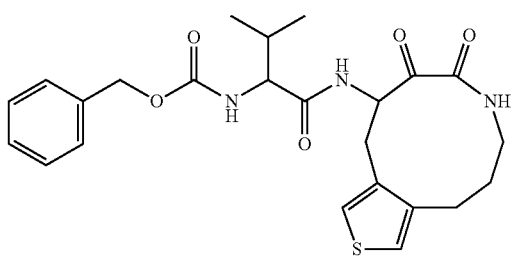 [SMILES: CC(C)C(NC(=O)OCc1ccccc1)C(=O)NC1Cc2cscc2CCCNC(=O)C1=O]
143
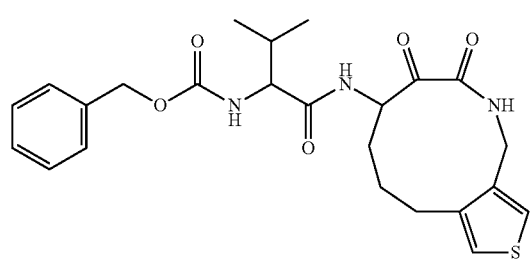 [SMILES: CC(C)C(NC(=O)OCc1ccccc1)C(=O)NC1CCCc2cscc2CNC(=O)C1=O]
144

TABLE 6-continued
TenRings
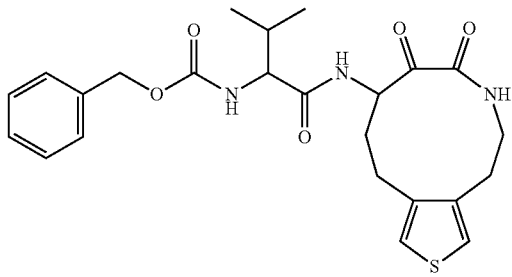 [SMILES: CC(C)C(NC(=O)OCc1ccccc1)C(=O)NC1CCc2cscc2CCNC(=O)C1=O]
147
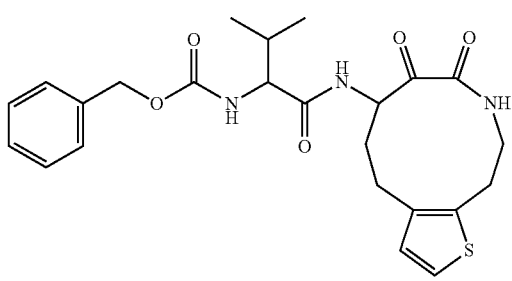 [SMILES: CC(C)C(NC(=O)OCc1ccccc1)C(=O)NC1CCc2ccsc2CCNC(=O)C1=O]
148
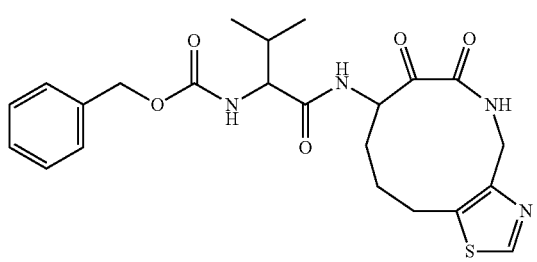
151
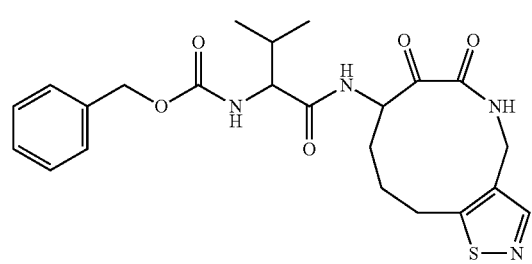 [SMILES: CC(C)C(NC(=O)OCc1ccccc1)C(=O)NC1CCCc2sncc2CNC(=O)C1=O]
152
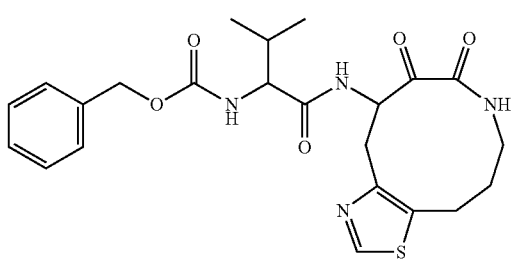
155
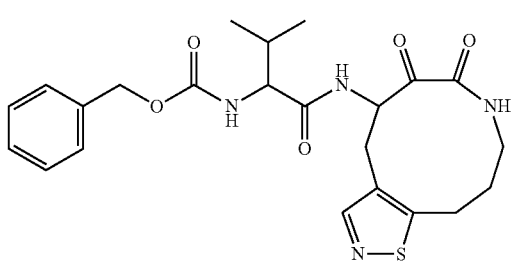
156

TABLE 6-continued
TenRings
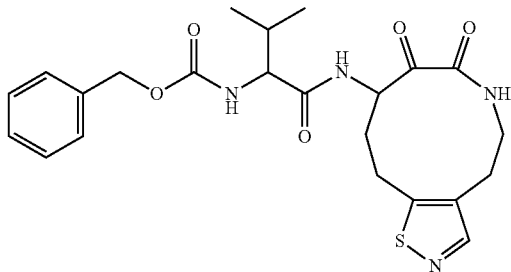 [SMILES: CC(C)C(NC(=O)OCc1ccccc1)C(=O)NC1CCc2sncc2CCNC(=O)C1=O]
159
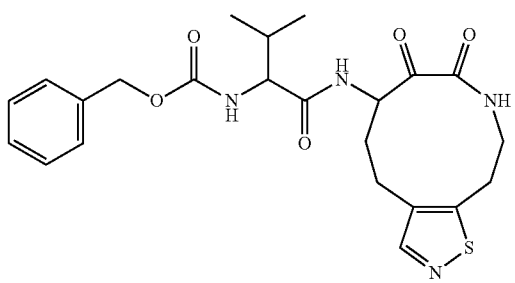
160
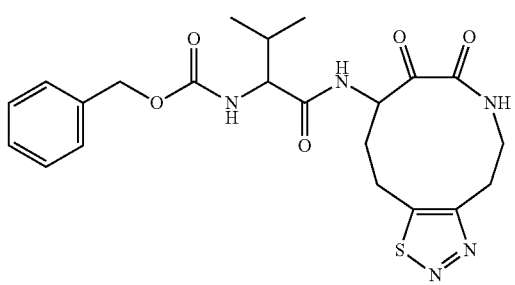
163
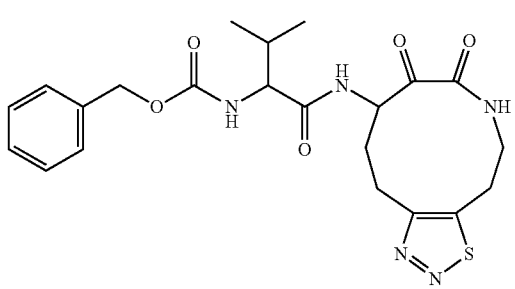 [SMILES: CC(C)C(NC(=O)OCc1ccccc1)C(=O)NC1CCc2nnsc2CCNC(=O)C1=O]
164
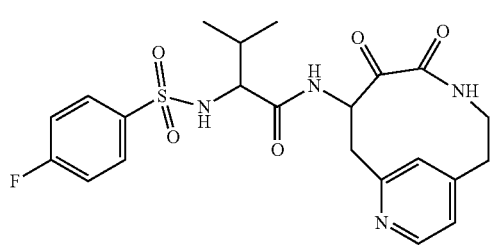 [SMILES: CC(C)C(NS(=O)(=O)c1ccc(F)cc1)C(=O)NC1Cc2cc(ccn2)CCNC(=O)C1=O]
167

TABLE 6-continued
TenRings
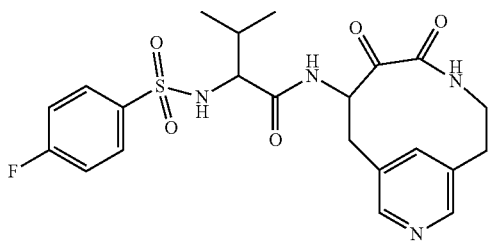
168
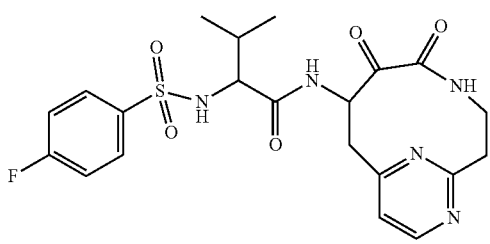 [SMILES: CC(C)C(NS(=O)(=O)c1ccc(F)cc1)C(=O)NC1Cc2ccnc(n2)CCNC(=O)C1=O]
171
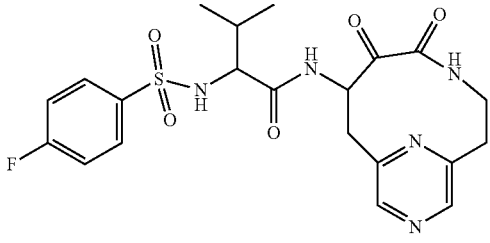
172
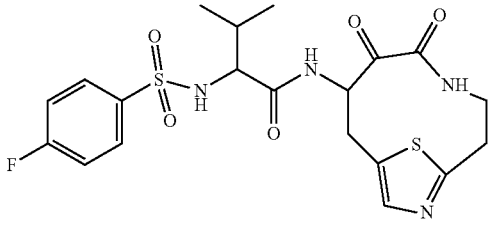 [SMILES: CC(C)C(NS(=O)(=O)c1ccc(F)cc1)C(=O)NC1CC2=CN=C(CCNC(=O)C1=O)S2]
175
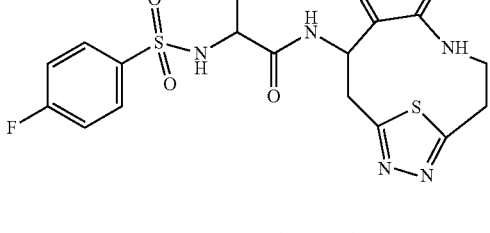
176
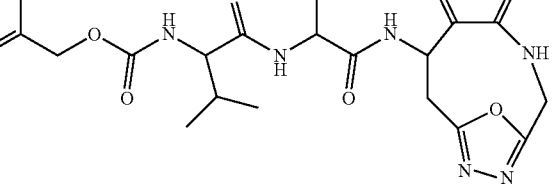
179

TABLE 6-continued
TenRings
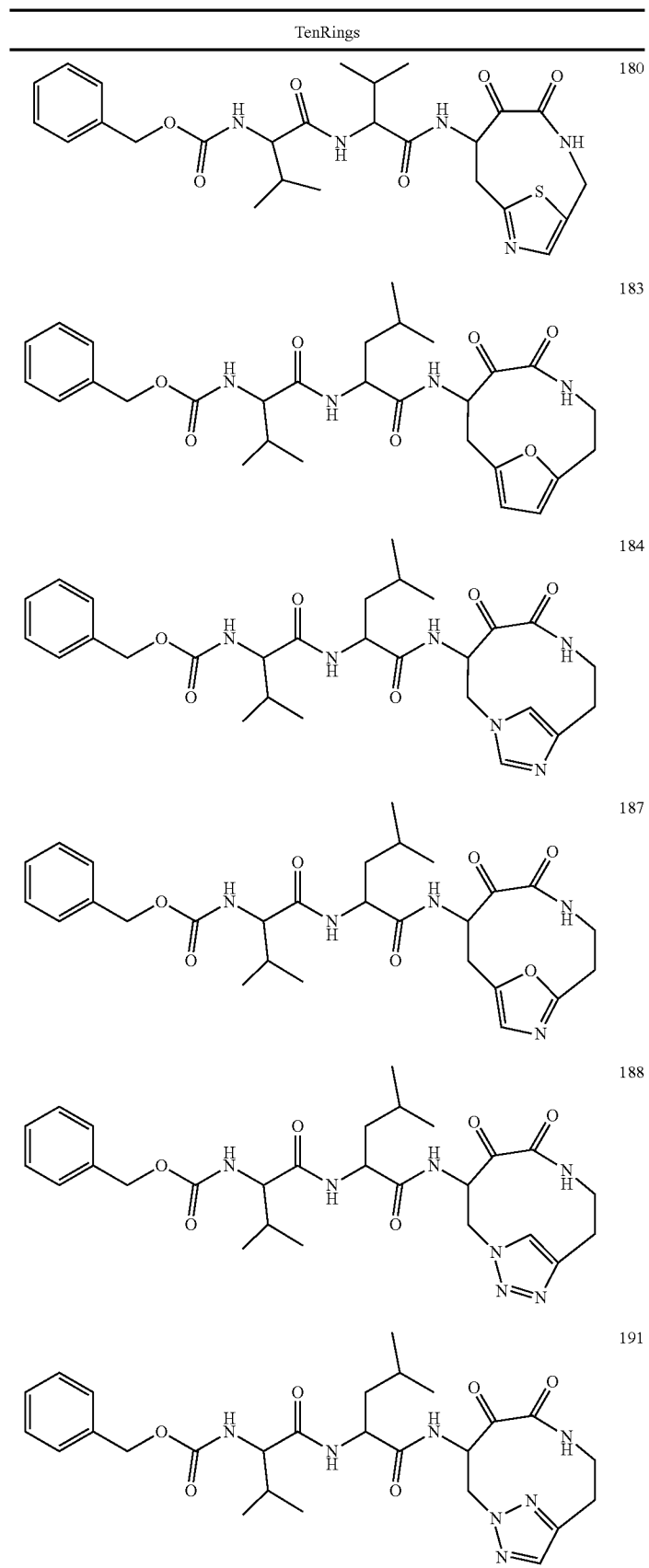

TABLE 6-continued
TenRings
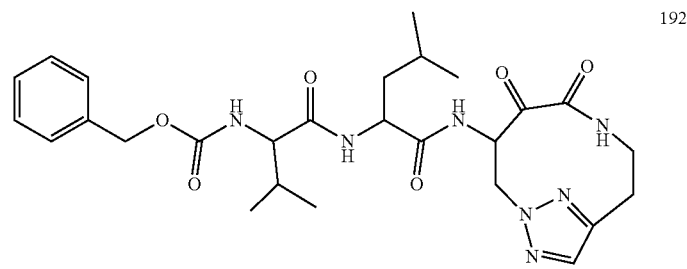
192
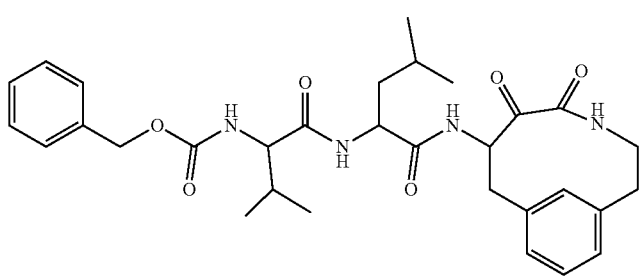 [SMILES: CC(C)CC(NC(=O)C(NC(=O)OCc1ccccc1)C(C)C)C(=O)NC1Cc2cccc(c2)CCNC(=O)C1=O]
195
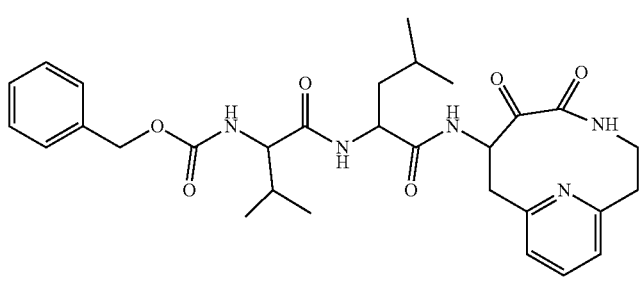 [SMILES: CC(C)CC(NC(=O)C(NC(=O)OCc1ccccc1)C(C)C)C(=O)NC1Cc2cccc(n2)CCNC(=O)C1=O]
196
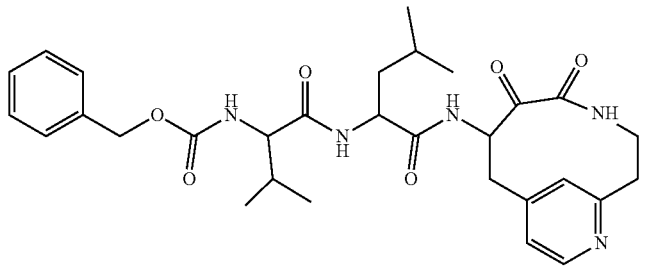 [SMILES: CC(C)CC(NC(=O)C(NC(=O)OCc1ccccc1)C(C)C)C(=O)NC1Cc2ccnc(c2)CCNC(=O)C1=O]
199
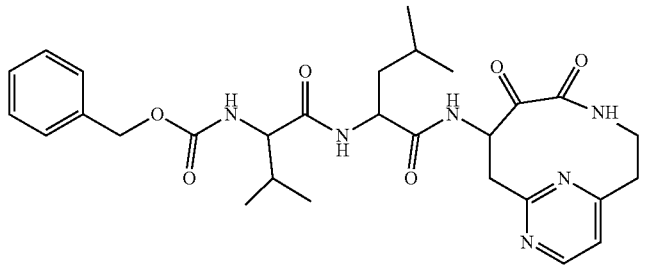
200

TABLE 6-continued
TenRings
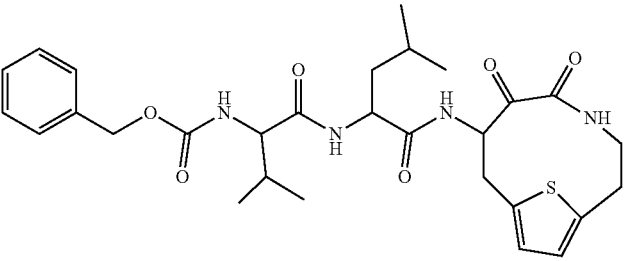 [SMILES: CC(C)CC(NC(=O)C(NC(=O)OCc1ccccc1)C(C)C)C(=O)NC1CC2=CC=C(CCNC(=O)C1=O)S2]
203
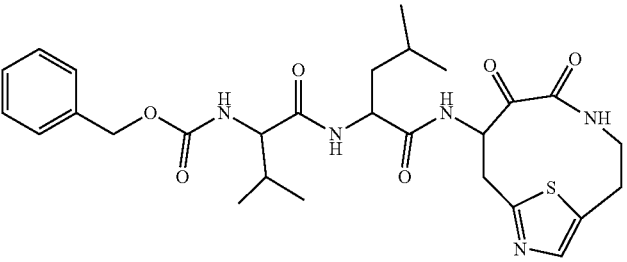 [SMILES: CC(C)CC(NC(=O)C(NC(=O)OCc1ccccc1)C(C)C)C(=O)NC1CC2=NC=C(CCNC(=O)C1=O)S2]
204
TABLE 7
ElevenRings
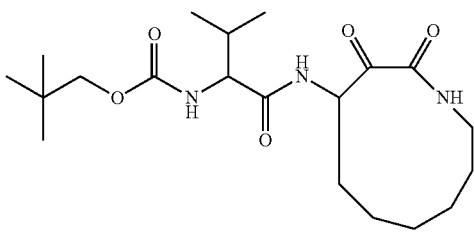 [SMILES: CC(C)C(NC(=O)OCC(C)(C)C)C(=O)NC1CCCCCCNC(=O)C1=O]
1
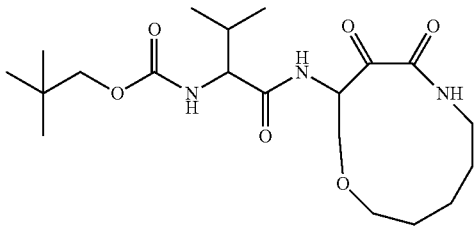
2
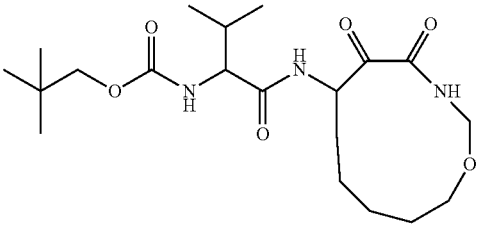 [SMILES: CC(C)C(NC(=O)OCC(C)(C)C)C(=O)NC1CCCCCOCNC(=O)C1=O]
5

TABLE 7-continued

ElevenRings

| | |
|---|---|
| [structure] | 6 |
| [structure] | 9 |
| [structure] | 10 |
| [structure] | 13 |
| [structure] | 14 |
| [structure] | 17 |

TABLE 7-continued
ElevenRings
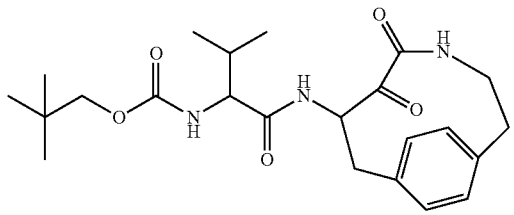 [SMILES: CC(C)C(NC(=O)OCC(C)(C)C)C(=O)NC1Cc2ccc(cc2)CCNC(=O)C1=O]
18
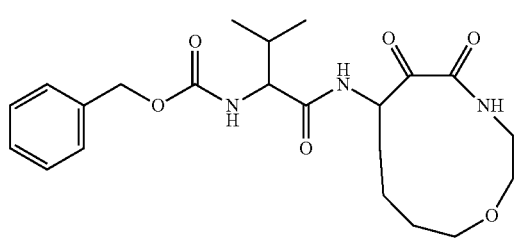 [SMILES: CC(C)C(NC(=O)OCc1ccccc1)C(=O)NC1CCCCOCCNC(=O)C1=O]
21
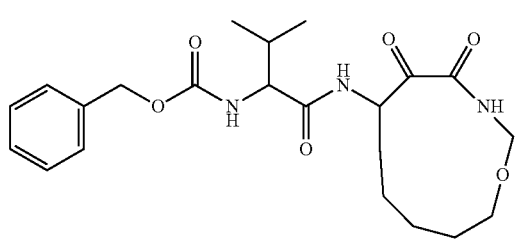 [SMILES: CC(C)C(NC(=O)OCc1ccccc1)C(=O)NC1CCCCCOCNC(=O)C1=O]
22
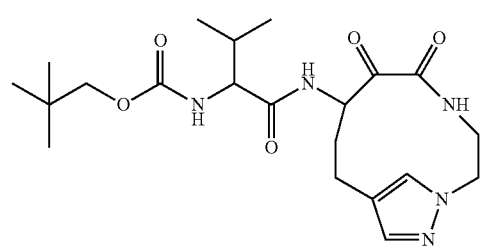 [SMILES: CC(C)C(NC(=O)OCC(C)(C)C)C(=O)NC1CCc2cnn(c2)CCNC(=O)C1=O]
25
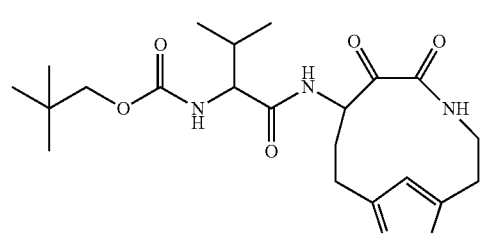
26
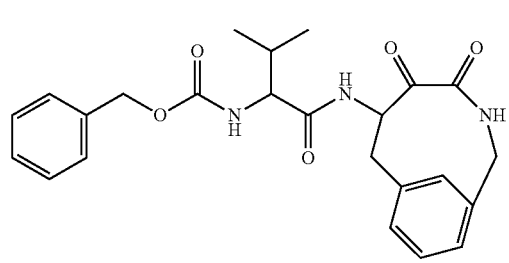
29

TABLE 7-continued
ElevenRings
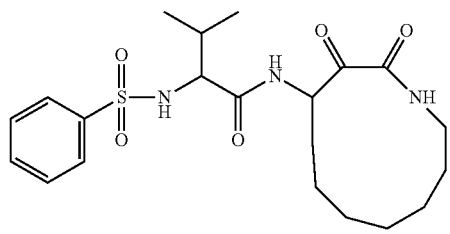
30
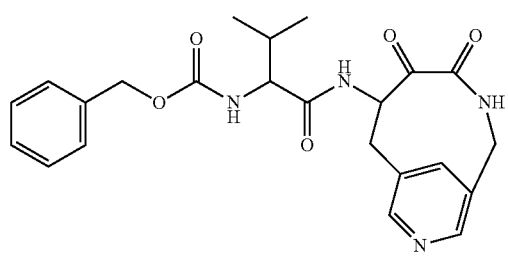 [SMILES: CC(C)C(NC(=O)OCc1ccccc1)C(=O)NC1Cc2cncc(c2)CNC(=O)C1=O]
33
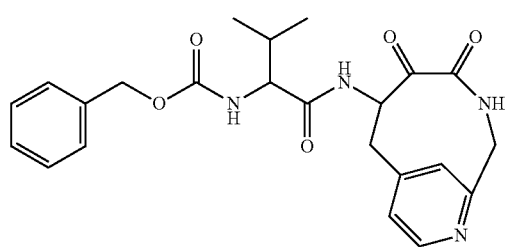 [SMILES: CC(C)C(NC(=O)OCc1ccccc1)C(=O)NC1Cc2ccnc(c2)CNC(=O)C1=O]
34
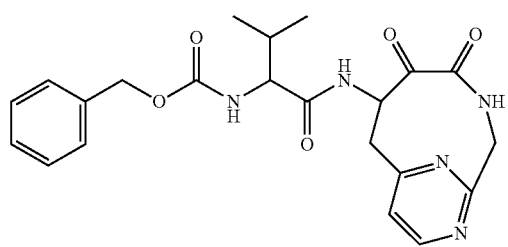
37
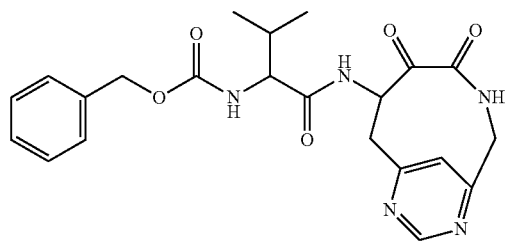
38
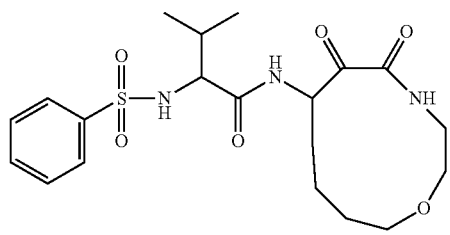 [SMILES: CC(C)C(NS(=O)(=O)c1ccccc1)C(=O)NC1CCCCOCCNC(=O)C1=O]
41

TABLE 7-continued
ElevenRings
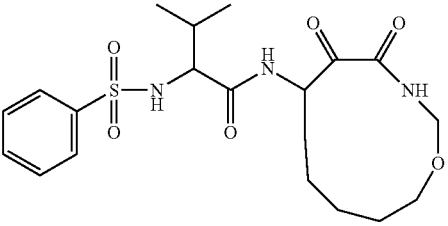 [SMILES: CC(C)C(NS(=O)(=O)c1ccccc1)C(=O)NC1CCCCCOCNC(=O)C1=O] 42
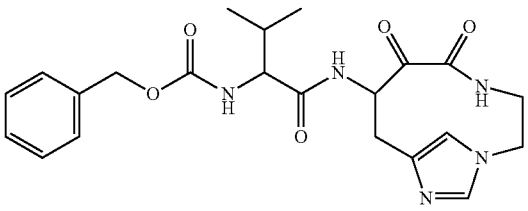 [SMILES: CC(C)C(NC(=O)OCc1ccccc1)C(=O)NC1Cc2cn(cn2)CCNC(=O)C1=O] 45
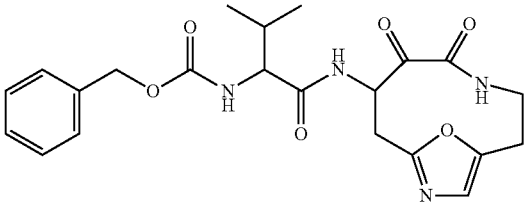 [SMILES: CC(C)C(NC(=O)OCc1ccccc1)C(=O)NC1CC2=NC=C(CCNC(=O)C1=O)O2] 46
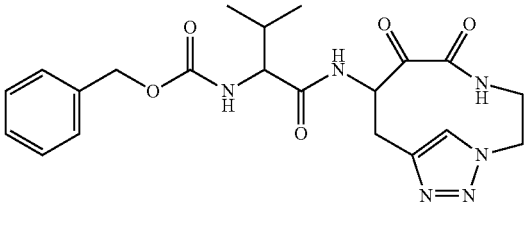 [SMILES: CC(C)C(NC(=O)OCc1ccccc1)C(=O)NC1Cc2cn(nn2)CCNC(=O)C1=O] 49
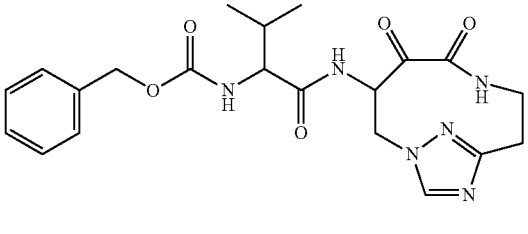 [SMILES: CC(C)C(NC(=O)OCc1ccccc1)C(=O)NC1Cn2cnc(n2)CCNC(=O)C1=O] 50
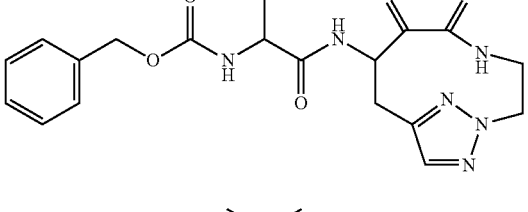 53
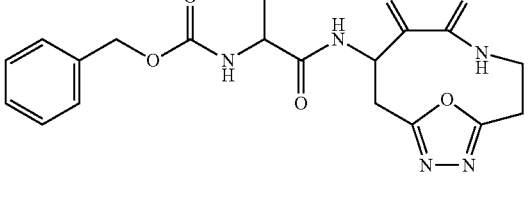 54

TABLE 7-continued
ElevenRings
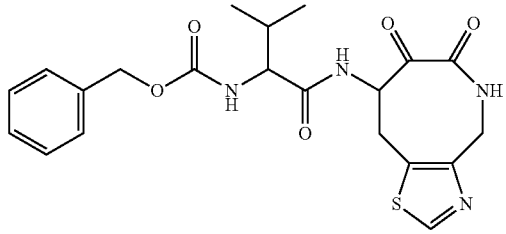 57
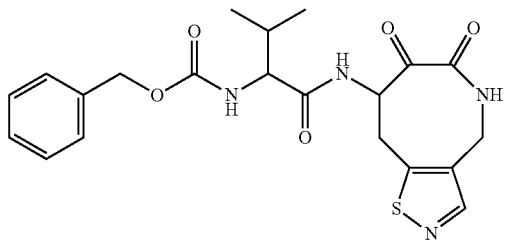 58
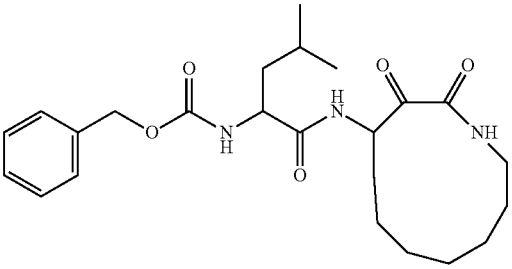 [SMILES: CC(C)CC(NC(=O)OCc1ccccc1)C(=O)NC1CCCCCCCNC(=O)C1=O] 61
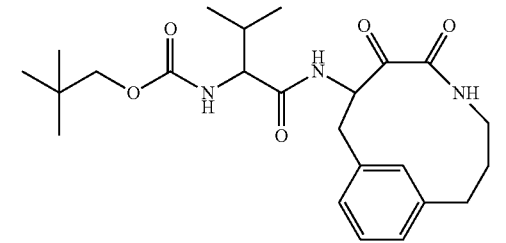 [SMILES: CC(C)C(NC(=O)OCC(C)(C)C)C(=O)NC1Cc2cccc(c2)CCCNC(=O)C1=O] 62
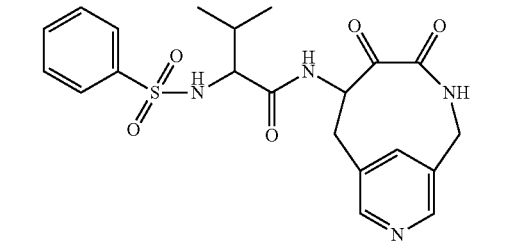 [SMILES: CC(C)C(NS(=O)(=O)c1ccccc1)C(=O)NC1Cc2cncc(c2)CNC(=O)C1=O] 65
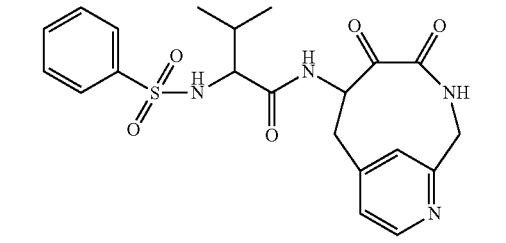 [SMILES: CC(C)C(NS(=O)(=O)c1ccccc1)C(=O)NC1Cc2ccnc(c2)CNC(=O)C1=O] 66

TABLE 7-continued
ElevenRings
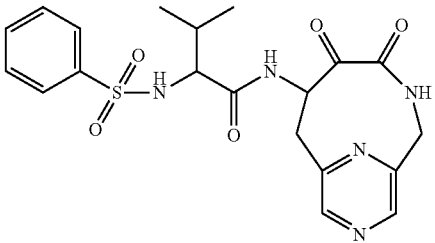 [SMILES: CC(C)C(NS(=O)(=O)c1ccccc1)C(=O)NC1Cc2cncc(n2)CNC(=O)C1=O]
69
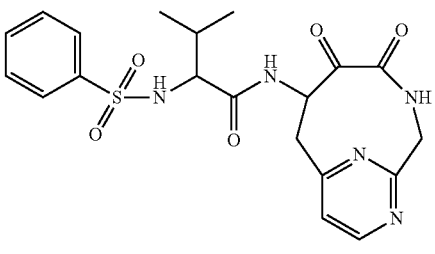 [SMILES: CC(C)C(NS(=O)(=O)c1ccccc1)C(=O)NC1Cc2ccnc(n2)CNC(=O)C1=O]
70
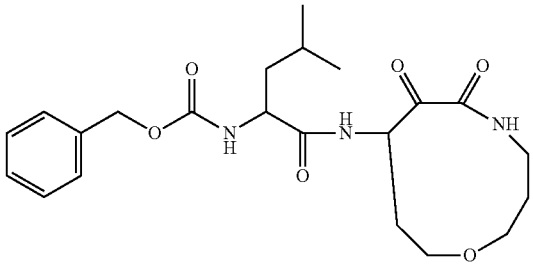 [SMILES: CC(C)CC(NC(=O)OCc1ccccc1)C(=O)NC1CCOCCCNC(=O)C1=O]
73
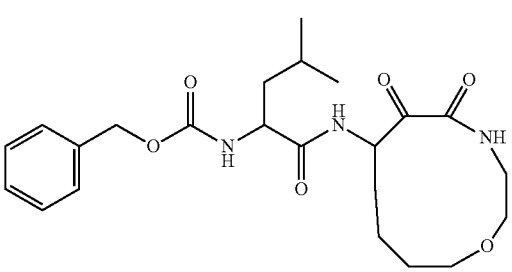 [SMILES: CC(C)CC(NC(=O)OCc1ccccc1)C(=O)NC1CCCCOCCNC(=O)C1=O]
74
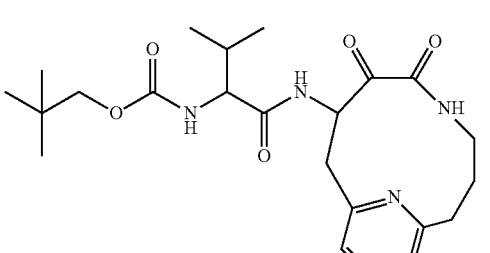
77
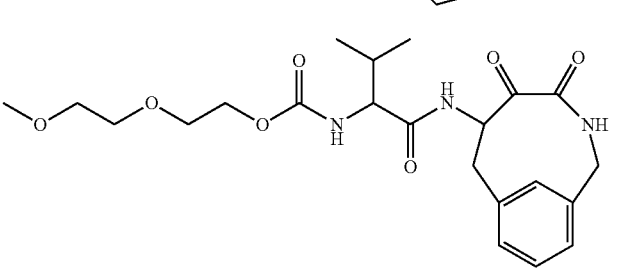
78

TABLE 7-continued
ElevenRings
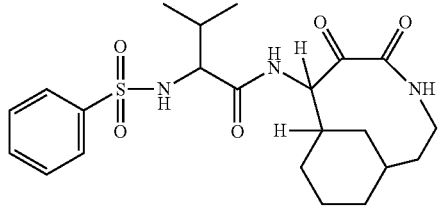 [SMILES: CC(C)C(NS(=O)(=O)c1ccccc1)C(=O)NC1C(=O)C(=O)NCCC2CCCC1C2]
81
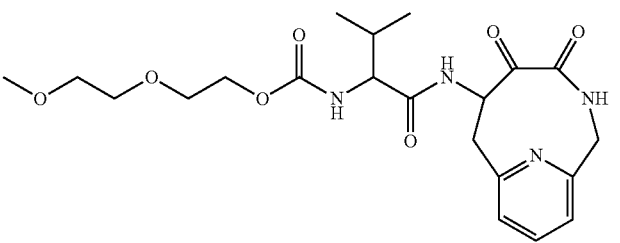 [SMILES: COCCOCCOC(=O)NC(C(=O)NC1Cc2cccc(n2)CNC(=O)C1=O)C(C)C]
82
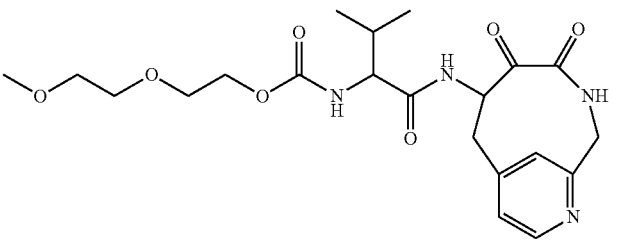 [SMILES: COCCOCCOC(=O)NC(C(=O)NC1Cc2ccnc(c2)CNC(=O)C1=O)C(C)C]
85
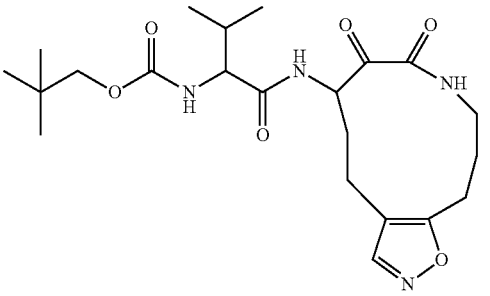 [SMILES: CC(C)C(NC(=O)OCC(C)(C)C)C(=O)NC1CCc2cnoc2CCCNC(=O)C1=O]
86
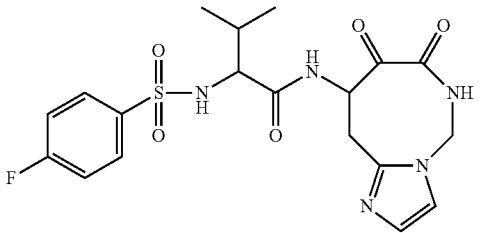 [SMILES: CC(C)C(NS(=O)(=O)c1ccc(F)cc1)C(=O)NC1Cc2nccn2CNC(=O)C1=O]
89
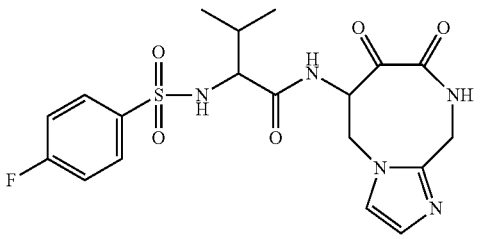 [SMILES: CC(C)C(NS(=O)(=O)c1ccc(F)cc1)C(=O)NC1Cn2ccnc2CNC(=O)C1=O]
90

TABLE 7-continued
ElevenRings
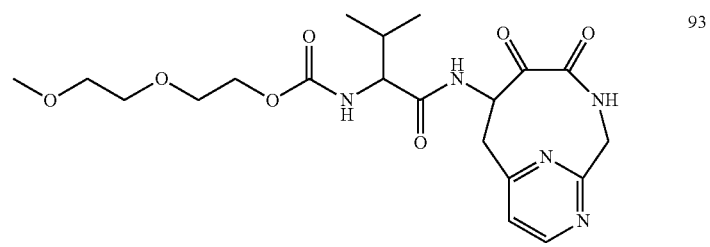
93
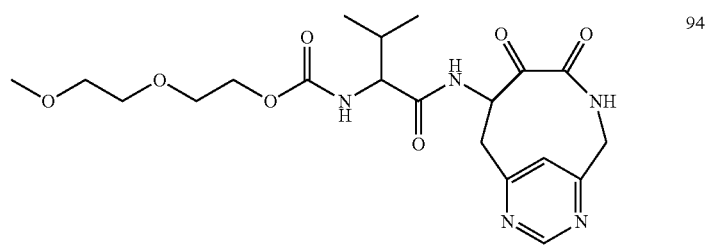
94
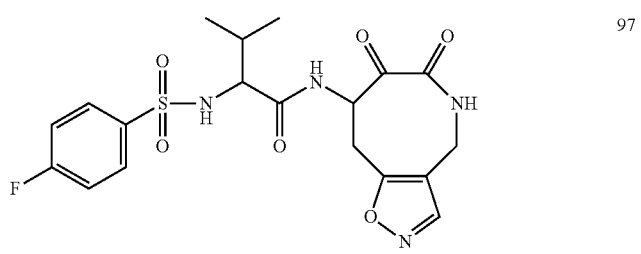
97
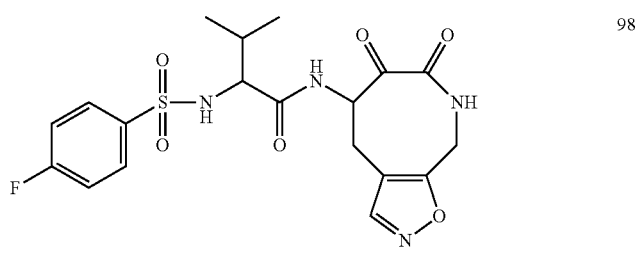
98
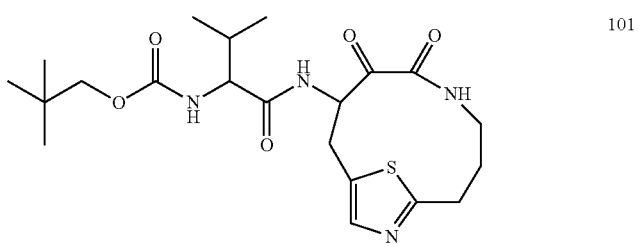
101
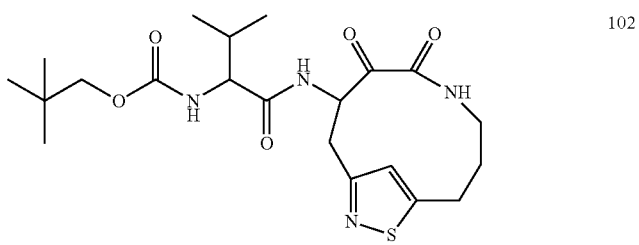
102

TABLE 7-continued
ElevenRings
105
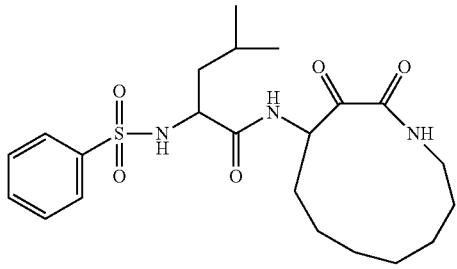
106
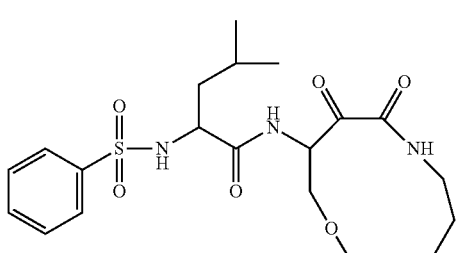
109
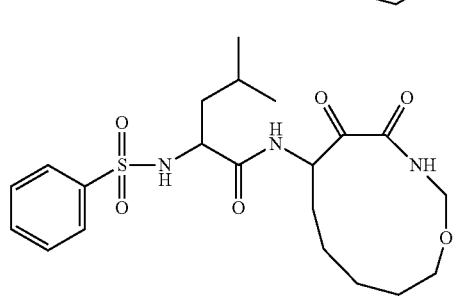
110
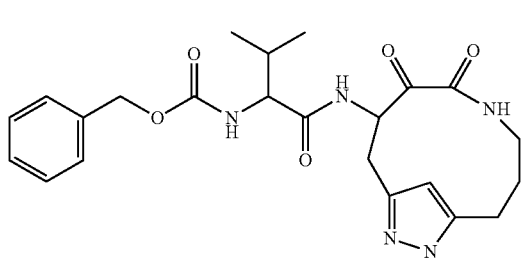
113
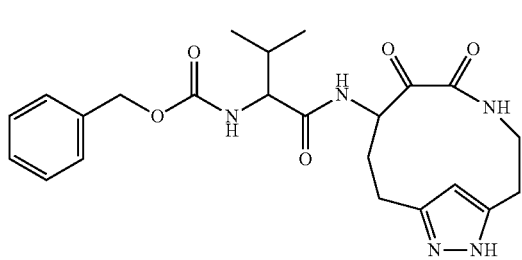 [SMILES: CC(C)C(NC(=O)OCc1ccccc1)C(=O)NC1CCc2cc([nH]n2)CCNC(=O)C1=O]
114
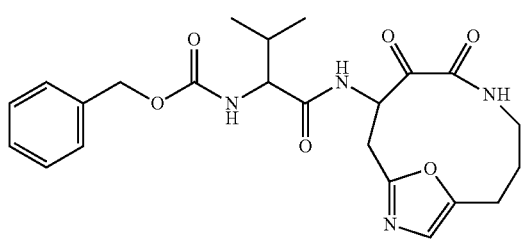 [SMILES: CC(C)C(NC(=O)OCc1ccccc1)C(=O)NC1CC2=NC=C(CCCNC(=O)C1=O)O2]

TABLE 7-continued
ElevenRings
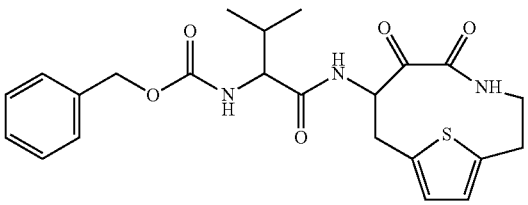 [SMILES: CC(C)C(NC(=O)OCc1ccccc1)C(=O)NC1CC2=CC=C(CCNC(=O)C1=O)S2]
117
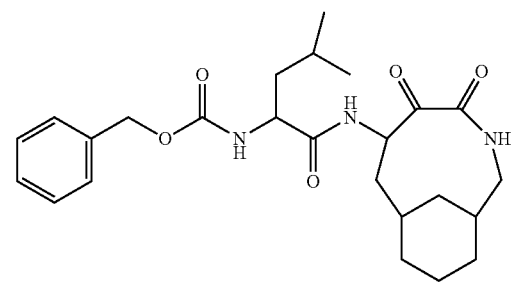 [SMILES: CC(C)CC(NC(=O)OCc1ccccc1)C(=O)NC1CC2CCCC(CNC(=O)C1=O)C2]
118
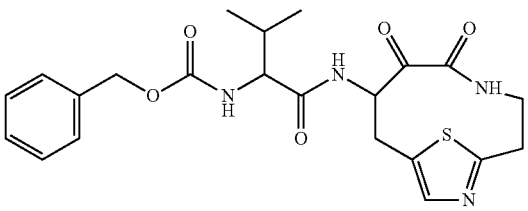 [SMILES: CC(C)C(NC(=O)OCc1ccccc1)C(=O)NC1CC2=CN=C(CCNC(=O)C1=O)S2]
121
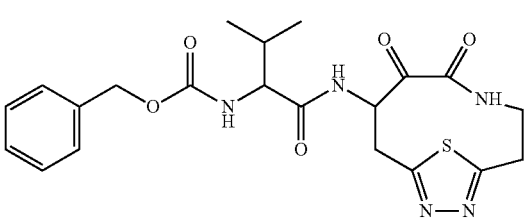 [SMILES: CC(C)C(NC(=O)OCc1ccccc1)C(=O)NC1CC2=NN=C(CCNC(=O)C1=O)S2]
122
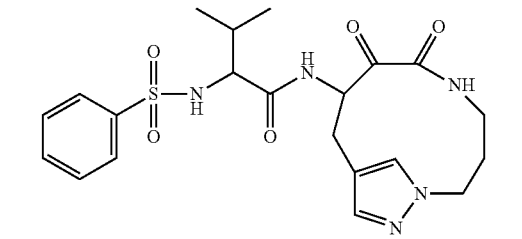 [SMILES: CC(C)C(NS(=O)(=O)c1ccccc1)C(=O)NC1Cc2cnn(c2)CCCNC(=O)C1=O]
125
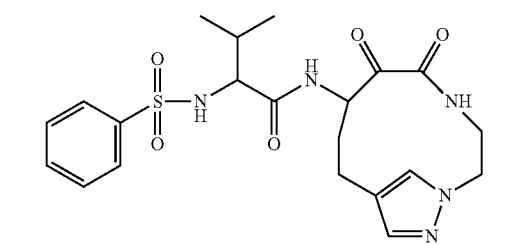 [SMILES: CC(C)C(NS(=O)(=O)c1ccccc1)C(=O)NC1CCc2cnn(c2)CCNC(=O)C1=O]
126

TABLE 7-continued

ElevenRings

| | |
|---|---|
| [structure of compound 129] | 129 |
| [structure of compound 130] | 130 |
| [structure of compound 133] | 133 |
| [structure of compound 134] | 134 |
| [structure of compound 137] | 137 |
| [structure of compound 138] | 138 |

TABLE 7-continued
ElevenRings
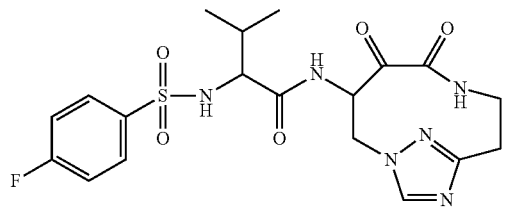 [SMILES: CC(C)C(NS(=O)(=O)c1ccc(F)cc1)C(=O)NC1Cn2cnc(n2)CCNC(=O)C1=O]
141
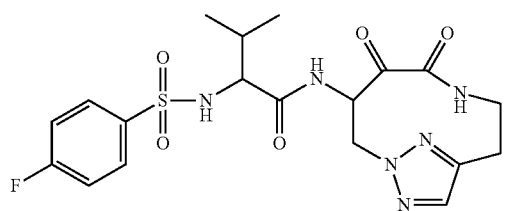 [SMILES: CC(C)C(NS(=O)(=O)c1ccc(F)cc1)C(=O)NC1Cn2ncc(n2)CCNC(=O)C1=O]
142
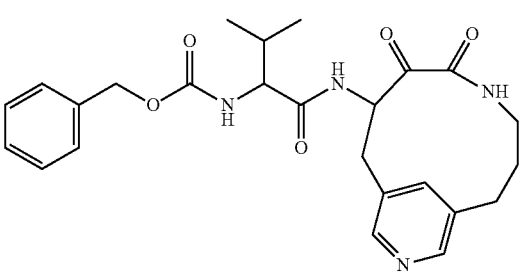 [SMILES: CC(C)C(NC(=O)OCc1ccccc1)C(=O)NC1Cc2cncc(c2)CCCNC(=O)C1=O]
145
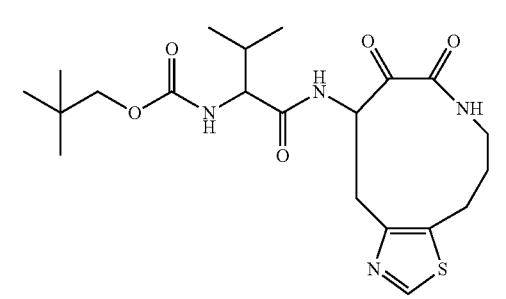 [SMILES: CC(C)C(NC(=O)OCC(C)(C)C)C(=O)NC1CCc2ncsc2CCCNC(=O)C1=O]
146
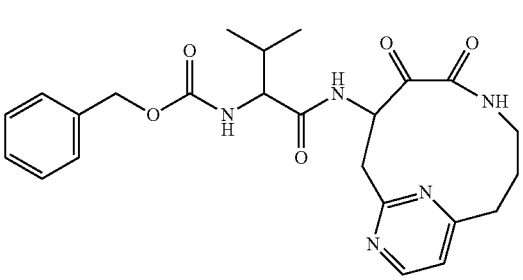 [SMILES: CC(C)C(NC(=O)OCc1ccccc1)C(=O)NC1Cc2nccc(n2)CCCNC(=O)C1=O]
149
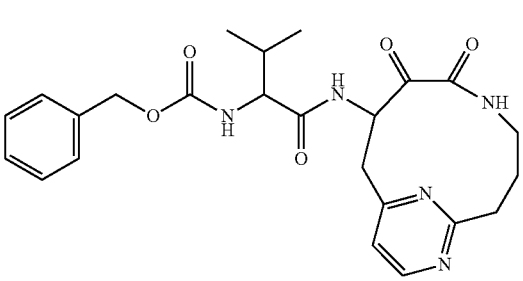 [SMILES: CC(C)C(NC(=O)OCc1ccccc1)C(=O)NC1Cc2ccnc(n2)CCCNC(=O)C1=O]
150

TABLE 7-continued
ElevenRings
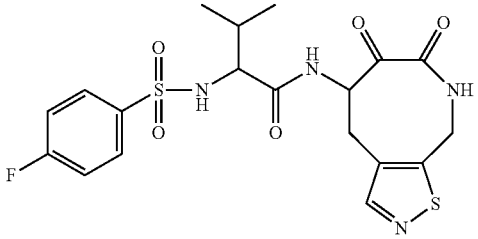
153
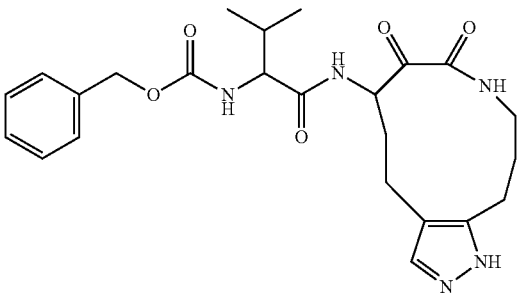 [SMILES: CC(C)C(NC(=O)OCc1ccccc1)C(=O)NC1CCc2cn[nH]c2CCCNC(=O)C1=O]
154
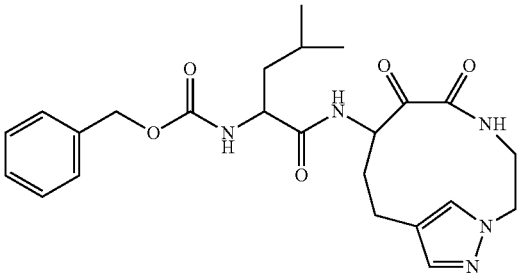 [SMILES: CC(C)CC(NC(=O)OCc1ccccc1)C(=O)NC1CCc2cnn(c2)CCNC(=O)C1=O]
157
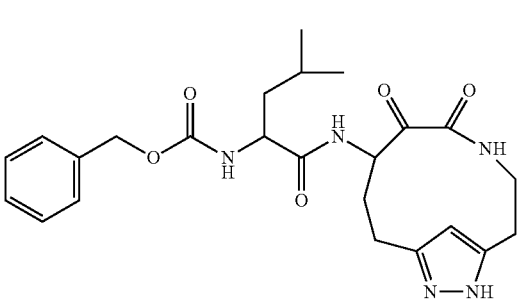 [SMILES: CC(C)CC(NC(=O)OCc1ccccc1)C(=O)NC1CCc2cc([nH]n2)CCNC(=O)C1=O]
158
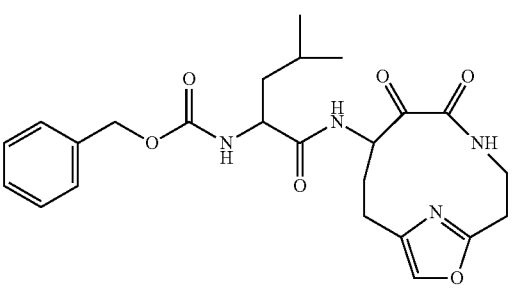 [SMILES: CC(C)CC(NC(=O)OCc1ccccc1)C(=O)NC1CCc2coc(n2)CCNC(=O)C1=O]
161

TABLE 7-continued
ElevenRings
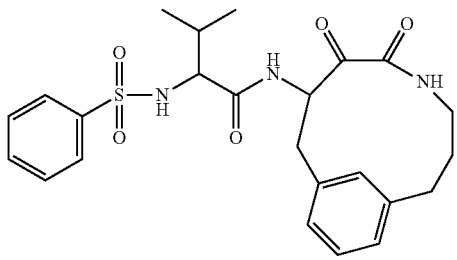 [SMILES: CC(C)C(NS(=O)(=O)c1ccccc1)C(=O)NC1Cc2cccc(c2)CCCNC(=O)C1=O] 162
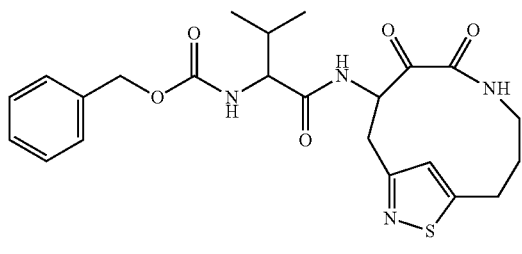 [SMILES: CC(C)C(NC(=O)OCc1ccccc1)C(=O)NC1Cc2cc(sn2)CCCNC(=O)C1=O] 165
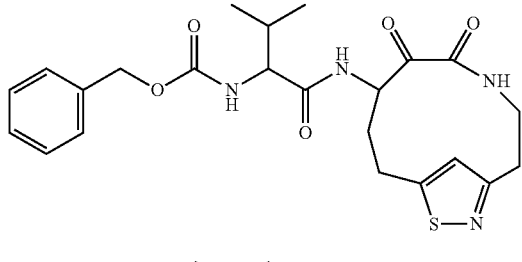 166
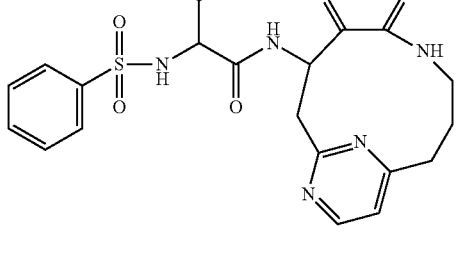 169
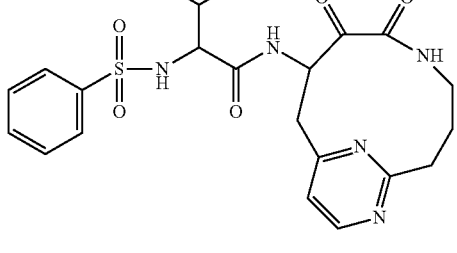 170
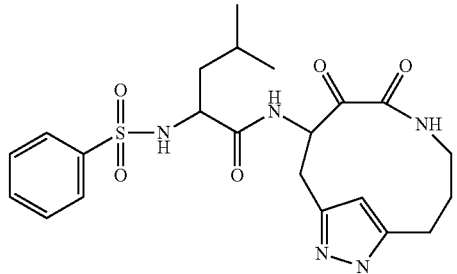 173

TABLE 7-continued
ElevenRings
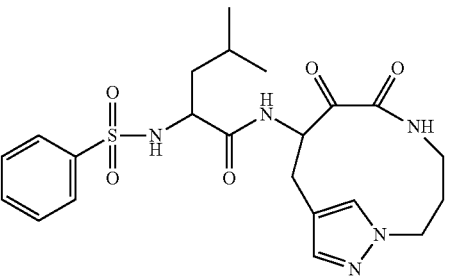 [SMILES: CC(C)CC(NS(=O)(=O)c1ccccc1)C(=O)NC1Cc2cnn(c2)CCCNC(=O)C1=O]
174
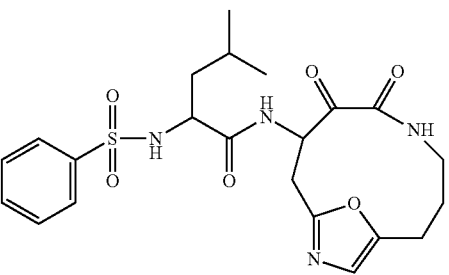 [SMILES: CC(C)CC(NS(=O)(=O)c1ccccc1)C(=O)NC1CC2=NC=C(CCCNC(=O)C1=O)O2]
177
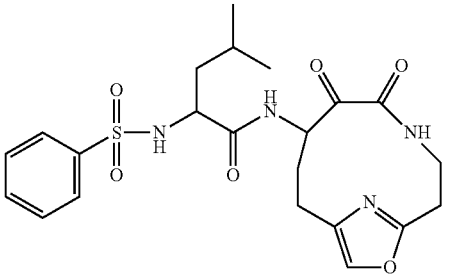 [SMILES: CC(C)CC(NS(=O)(=O)c1ccccc1)C(=O)NC1CCc2coc(n2)CCNC(=O)C1=O]
178
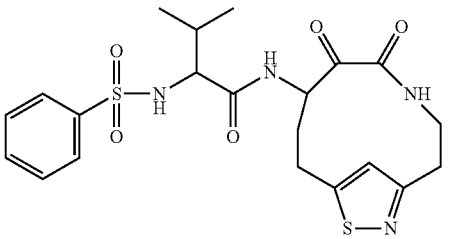 [SMILES: CC(C)C(NS(=O)(=O)c1ccccc1)C(=O)NC1CCc2cc(ns2)CCNC(=O)C1=O]
181
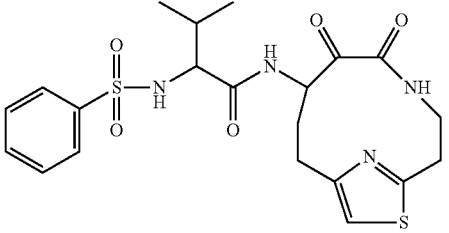 [SMILES: CC(C)C(NS(=O)(=O)c1ccccc1)C(=O)NC1CCc2csc(n2)CCNC(=O)C1=O]
182

TABLE 7-continued

ElevenRings

| | |
|---|---|
| [structure] | 185 |
| [structure] | 186 |
| [structure] | 189 |
| [structure] | 190 |
| [structure] | 193 |

TABLE 7-continued
ElevenRings
| | |
|---|---|
| 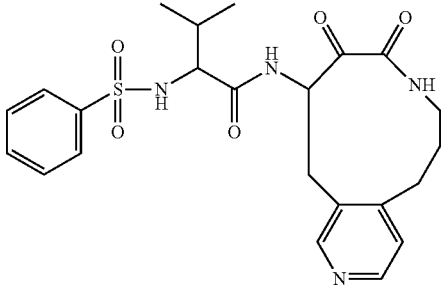 [SMILES: CC(C)C(NS(=O)(=O)c1ccccc1)C(=O)NC1CCc2cnccc2CCCNC(=O)C1=O] | 194 |
| 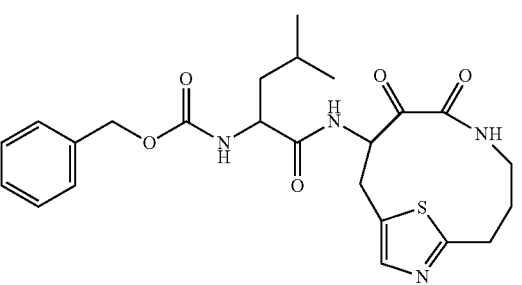 [SMILES: CC(C)CC(NC(=O)OCc1ccccc1)C(=O)NC1CC2=CN=C(CCCNC(=O)C1=O)S2] | 197 |
| 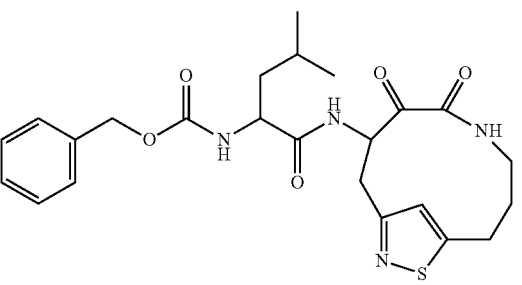 [SMILES: CC(C)CC(NC(=O)OCc1ccccc1)C(=O)NC1Cc2cc(sn2)CCCNC(=O)C1=O] | 198 |
| 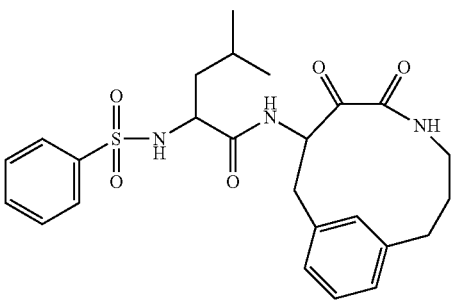 [SMILES: CC(C)CC(NS(=O)(=O)c1ccccc1)C(=O)NC1Cc2cccc(c2)CCCNC(=O)C1=O] | 201 |
| 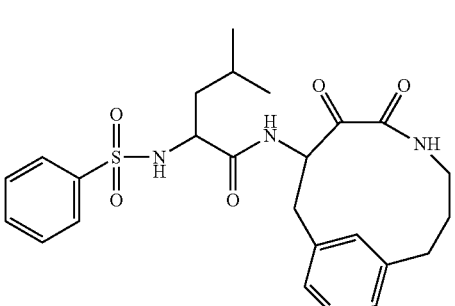 | 202 |

TABLE 7-continued
ElevenRings
205
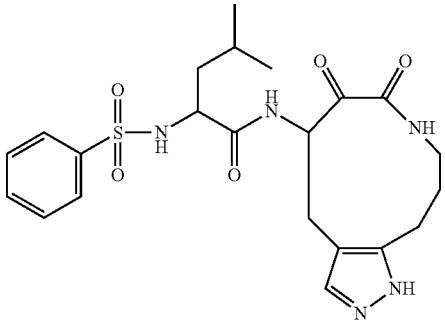 [SMILES: CC(C)CC(NS(=O)(=O)c1ccccc1)C(=O)NC1CCc2cn[nH]c2CCCNC(=O)C1=O]
206
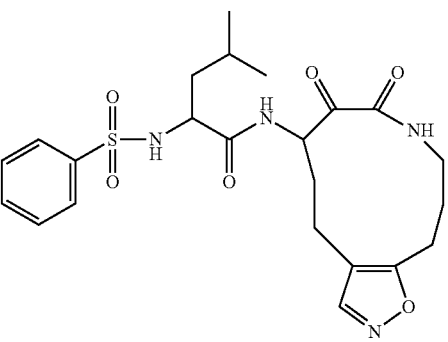 [SMILES: CC(C)CC(NS(=O)(=O)c1ccccc1)C(=O)NC1CCc2cnoc2CCCNC(=O)C1=O]
209
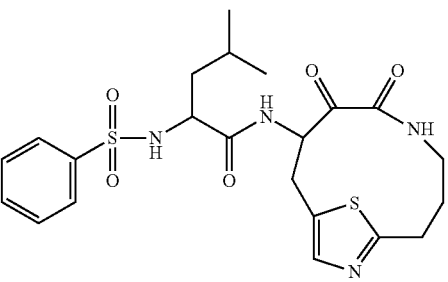 [SMILES: CC(C)CC(NS(=O)(=O)c1ccccc1)C(=O)NC1CC2=CN=C(CCCNC(=O)C1=O)S2]
210
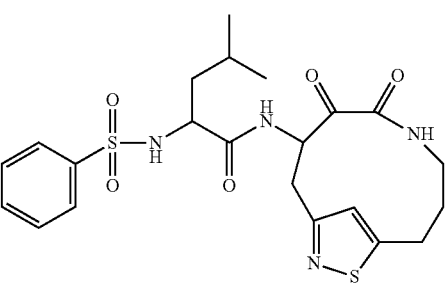 [SMILES: CC(C)CC(NS(=O)(=O)c1ccccc1)C(=O)NC1Cc2cc(sn2)CCCNC(=O)C1=O]
213
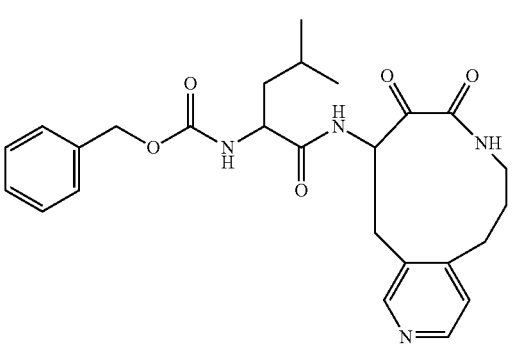 [SMILES: CC(C)CC(NC(=O)OCc1ccccc1)C(=O)NC1CCc2cnccc2CCCNC(=O)C1=O]

TABLE 7-continued
ElevenRings
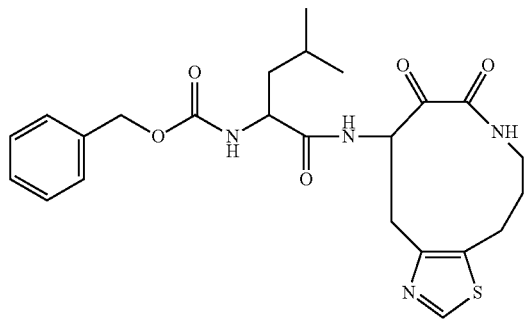 [SMILES: CC(C)CC(NC(=O)OCc1ccccc1)C(=O)NC1CCc2ncsc2CCCNC(=O)C1=O]
214
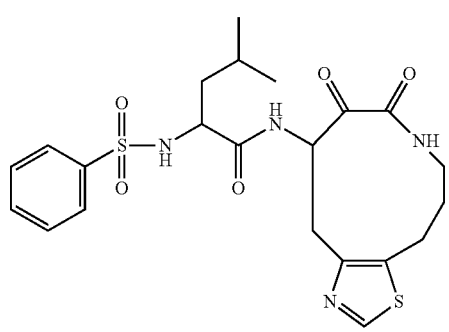 [SMILES: CC(C)CC(NS(=O)(=O)c1ccccc1)C(=O)NC1CCc2ncsc2CCCNC(=O)C1=O]
217
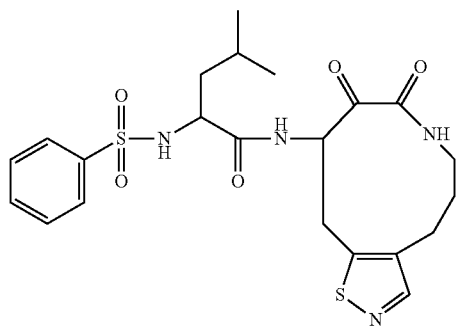 [SMILES: CC(C)CC(NS(=O)(=O)c1ccccc1)C(=O)NC1CCc2sncc2CCCNC(=O)C1=O]
218
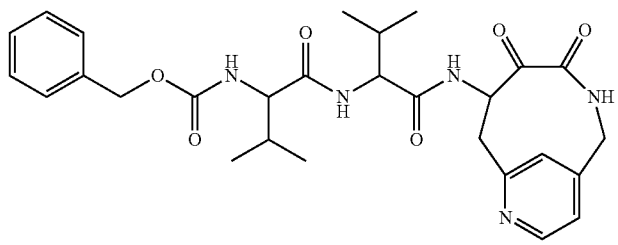
221
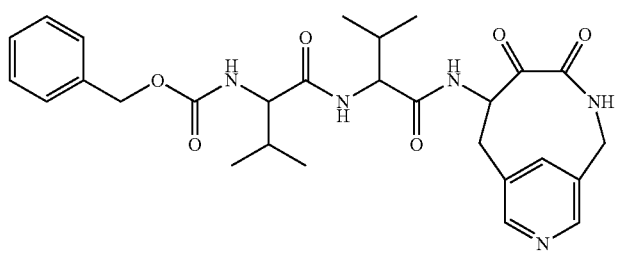 [SMILES: CC(C)C(NC(=O)OCc1ccccc1)C(=O)NC(C(=O)NC1Cc2cncc(c2)CNC(=O)C1=O)C(C)C]
222

TABLE 7-continued
ElevenRings
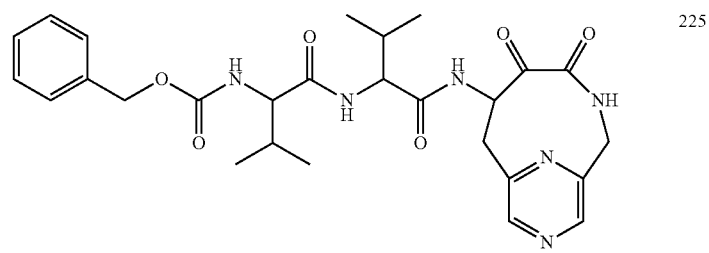
225
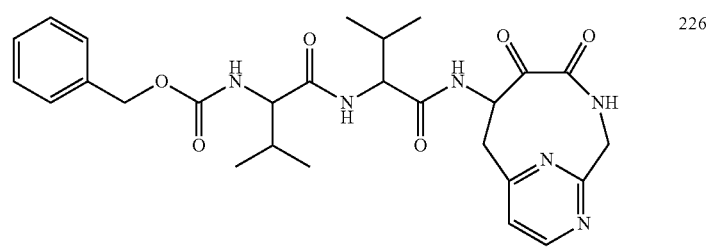
226
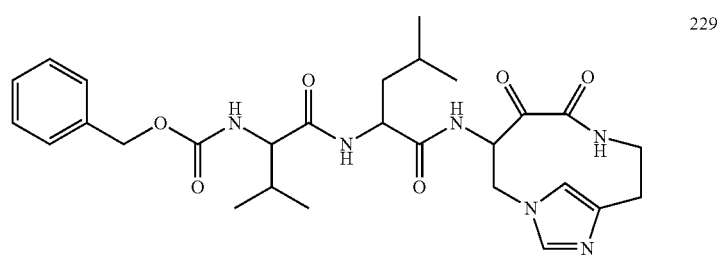
229
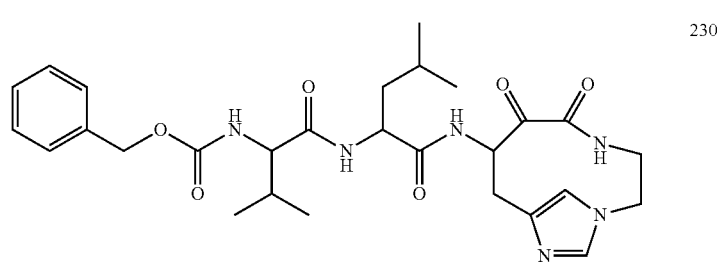
230
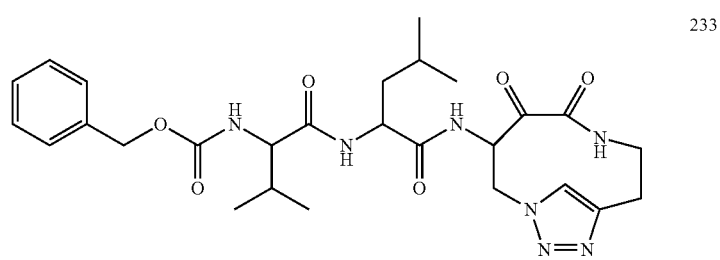
233
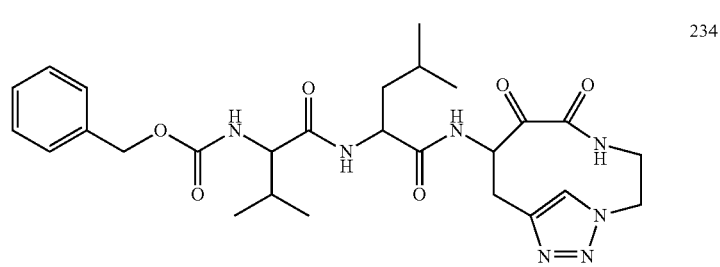
234

TABLE 7-continued
ElevenRings
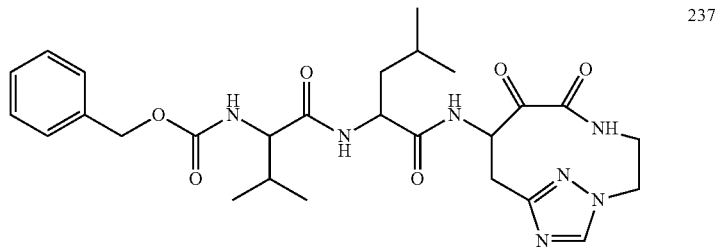
237
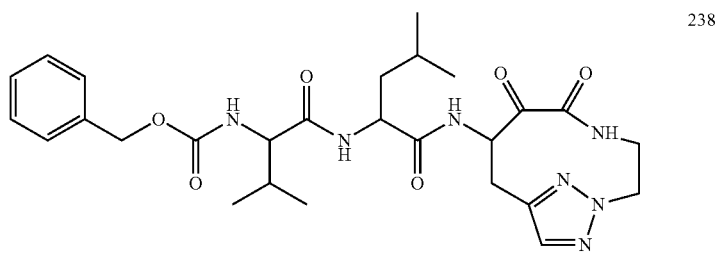
238
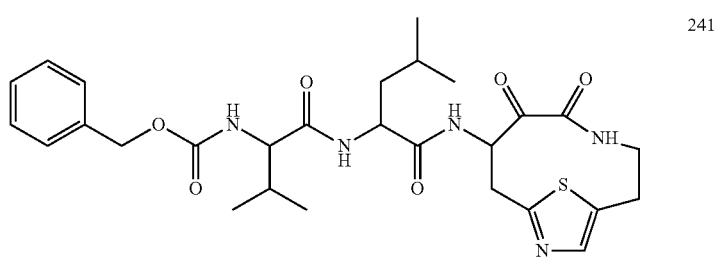
241
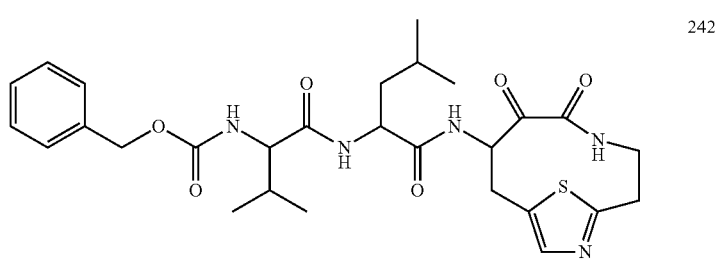
242
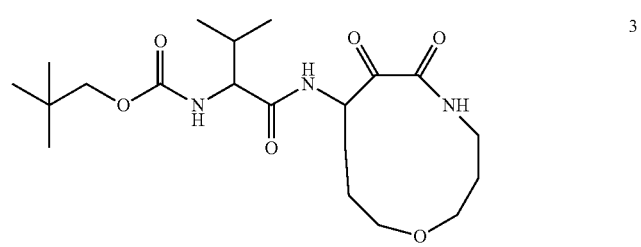
3
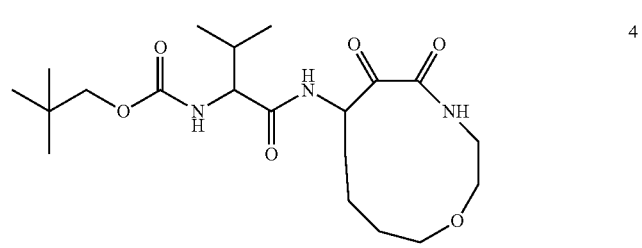
4

TABLE 7-continued
ElevenRings
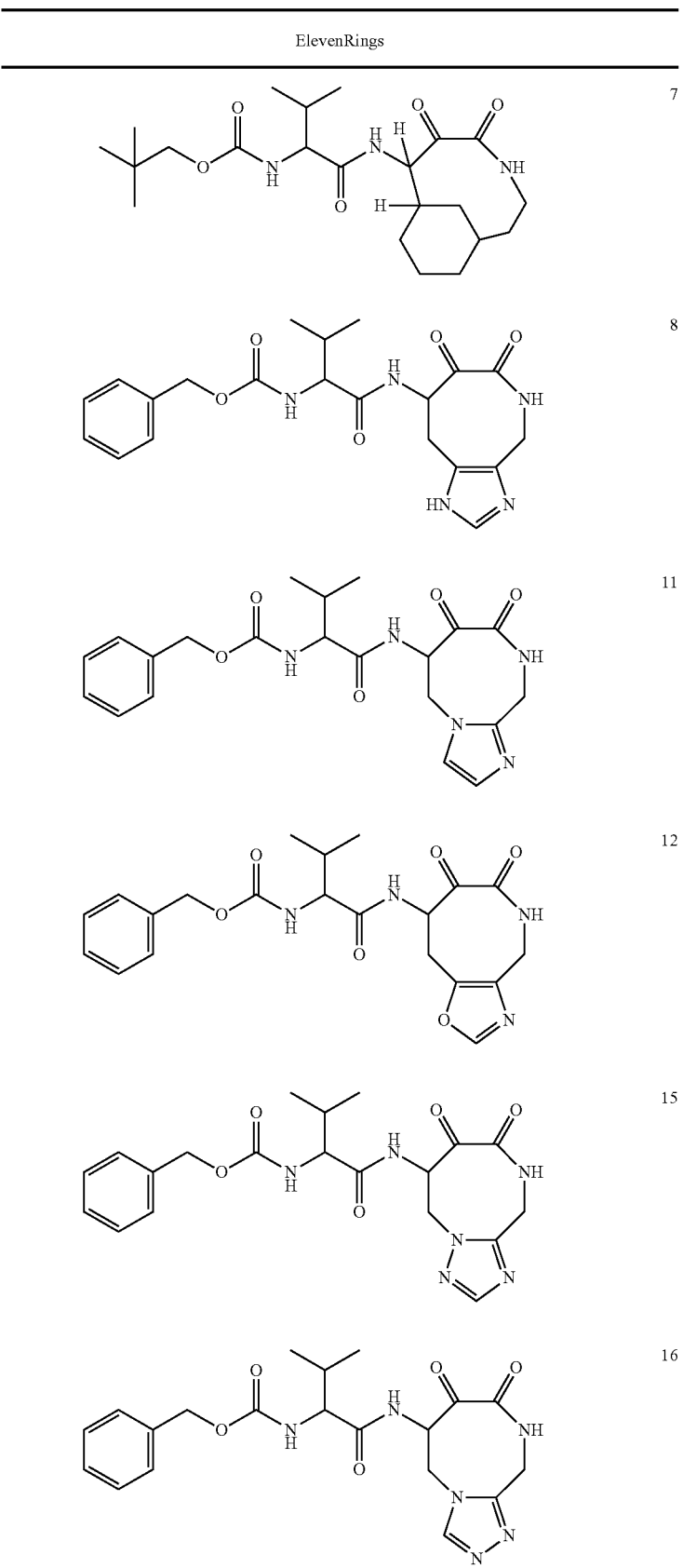

TABLE 7-continued
ElevenRings
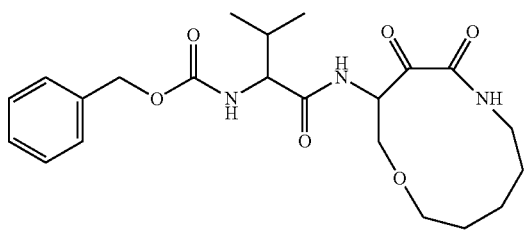 [SMILES: CC(C)C(NC(=O)OCc1ccccc1)C(=O)NC1COCCCCCNC(=O)C1=O]
19
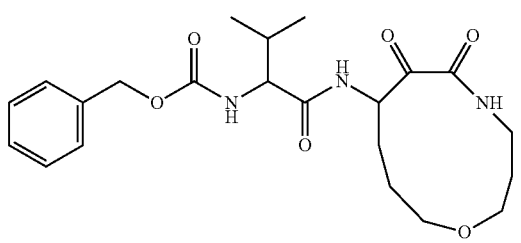 [SMILES: CC(C)C(NC(=O)OCc1ccccc1)C(=O)NC1CCCOCCCNC(=O)C1=O]
20
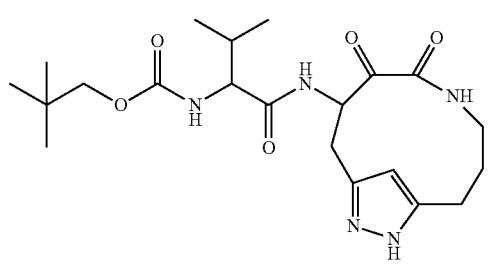 [SMILES: CC(C)C(NC(=O)OCC(C)(C)C)C(=O)NC1Cc2cc([nH]n2)CCCNC(=O)C1=O]
23
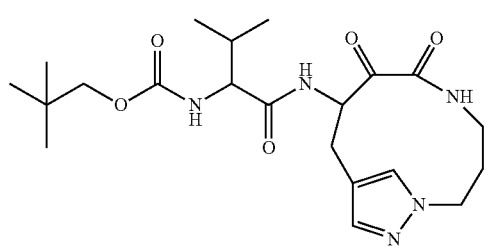 [SMILES: CC(C)C(NC(=O)OCC(C)(C)C)C(=O)NC1Cc2cnn(c2)CCCNC(=O)C1=O]
24
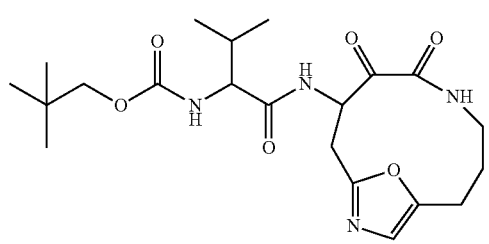 [SMILES: CC(C)C(NC(=O)OCC(C)(C)C)C(=O)NC1CC2=NC=C(CCCNC(=O)C1=O)O2]
27
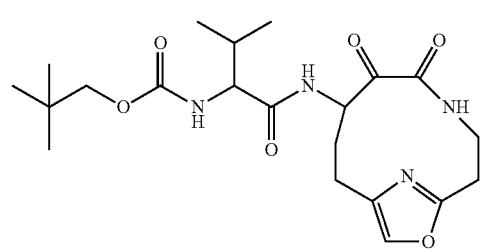 [SMILES: CC(C)C(NC(=O)OCC(C)(C)C)C(=O)NC1CCc2coc(n2)CCNC(=O)C1=O]
28

TABLE 7-continued
ElevenRings
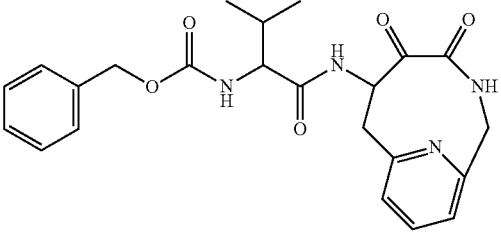 [SMILES: CC(C)C(NC(=O)OCc1ccccc1)C(=O)NC1Cc2cccc(n2)CNC(=O)C1=O]
31
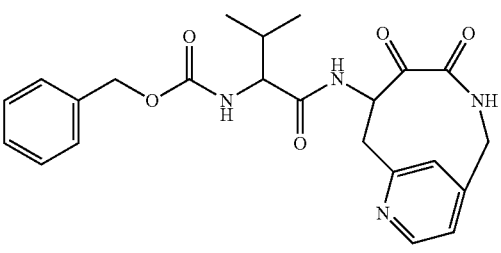 [SMILES: CC(C)C(NC(=O)OCc1ccccc1)C(=O)NC1Cc2cc(ccn2)CNC(=O)C1=O]
32
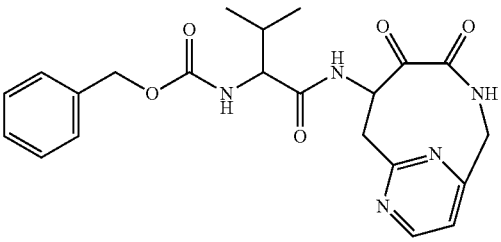 [SMILES: CC(C)C(NC(=O)OCc1ccccc1)C(=O)NC1Cc2nccc(n2)CNC(=O)C1=O]
35
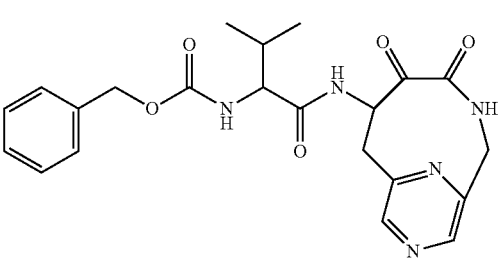 [SMILES: CC(C)C(NC(=O)OCc1ccccc1)C(=O)NC1Cc2cncc(n2)CNC(=O)C1=O]
36
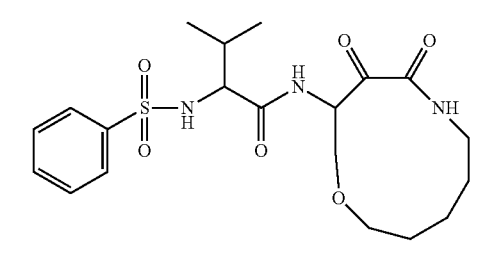 [SMILES: CC(C)C(NS(=O)(=O)c1ccccc1)C(=O)NC1COCCCCCNC(=O)C1=O]
39
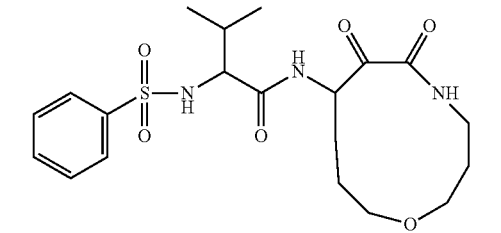 [SMILES: CC(C)C(NS(=O)(=O)c1ccccc1)C(=O)NC1CCCOCCCNC(=O)C1=O]
40

TABLE 7-continued
ElevenRings
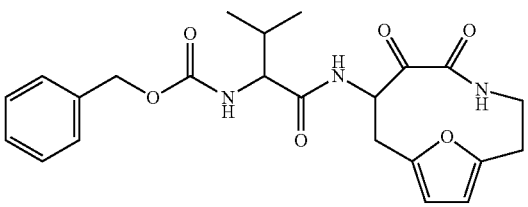 [SMILES: CC(C)C(NC(=O)OCc1ccccc1)C(=O)NC1CC2=CC=C(CCNC(=O)C1=O)O2]
43
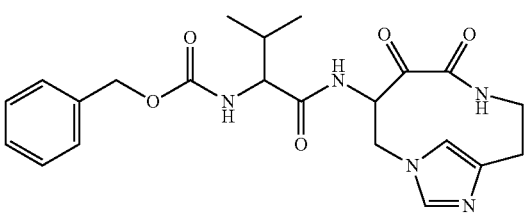 [SMILES: CC(C)C(NC(=O)OCc1ccccc1)C(=O)NC1Cn2cnc(c2)CCNC(=O)C1=O]
44
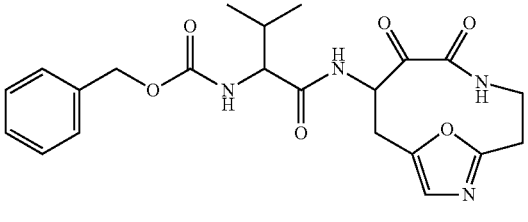 [SMILES: CC(C)C(NC(=O)OCc1ccccc1)C(=O)NC1CC2=CN=C(CCNC(=O)C1=O)O2]
47
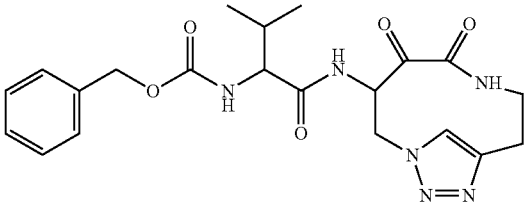 [SMILES: CC(C)C(NC(=O)OCc1ccccc1)C(=O)NC1Cn2cc(nn2)CCNC(=O)C1=O]
48
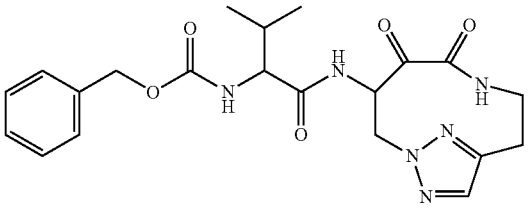 [SMILES: CC(C)C(NC(=O)OCc1ccccc1)C(=O)NC1Cn2ncc(n2)CCNC(=O)C1=O]
51
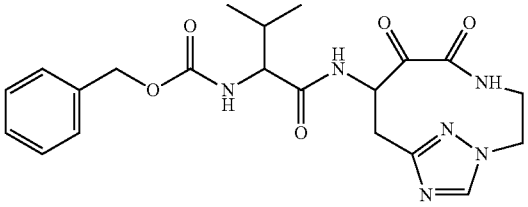 [SMILES: CC(C)C(NC(=O)OCc1ccccc1)C(=O)NC1Cc2ncn(n2)CCNC(=O)C1=O]
52
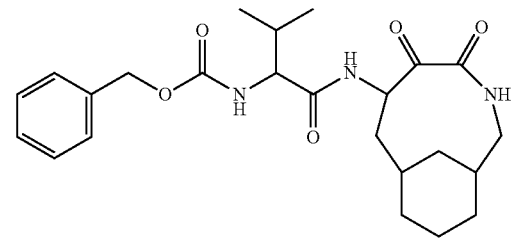 [SMILES: CC(C)C(NC(=O)OCc1ccccc1)C(=O)NC1CC2CCCC(CNC(=O)C1=O)C2]
55

TABLE 7-continued
ElevenRings
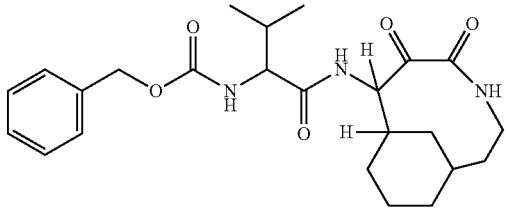 [SMILES: CC(C)C(NC(=O)OCc1ccccc1)C(=O)NC1C(=O)C(=O)NCCC2CCCC1C2]
56
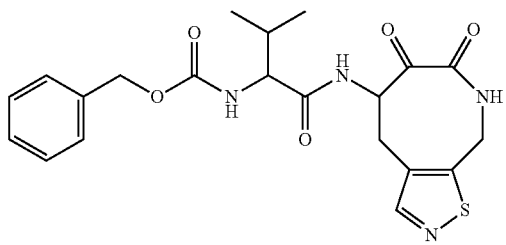
59
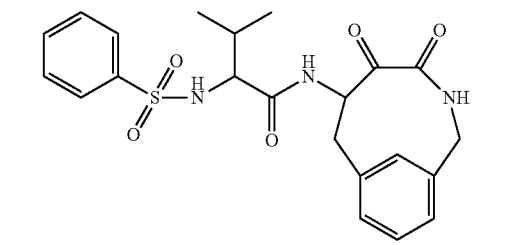 [SMILES: CC(C)C(NS(=O)(=O)c1ccccc1)C(=O)NC1Cc2cccc(c2)CNC(=O)C1=O]
60
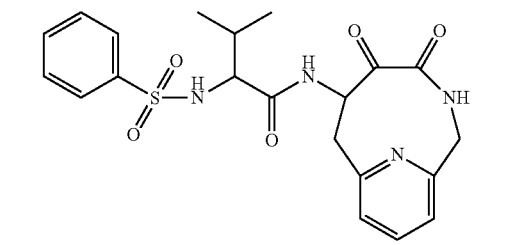 [SMILES: CC(C)C(NS(=O)(=O)c1ccccc1)C(=O)NC1Cc2cccc(n2)CNC(=O)C1=O]
63
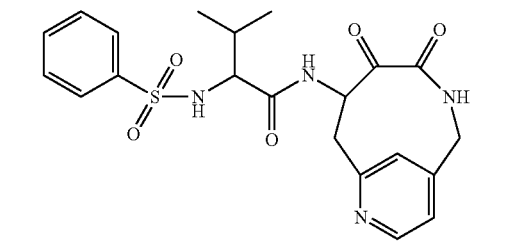 [SMILES: CC(C)C(NS(=O)(=O)c1ccccc1)C(=O)NC1Cc2cc(ccn2)CNC(=O)C1=O]
64
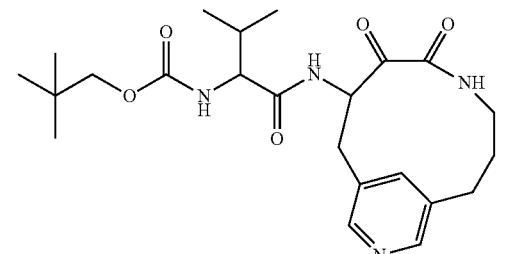 [SMILES: CC(C)C(NC(=O)OCC(C)(C)C)C(=O)NC1Cc2nccc(n2)CCCNC(=O)C1=O]
67

TABLE 7-continued

ElevenRings

68

71

72

75

76

79

TABLE 7-continued
ElevenRings
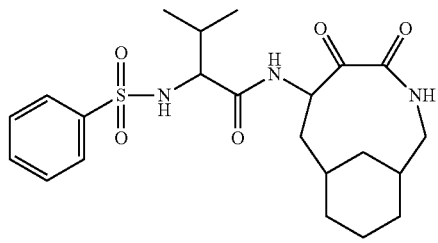 [SMILES: CC(C)C(NS(=O)(=O)c1ccccc1)C(=O)NC1CC2CCCC(CNC(=O)C1=O)C2]
80
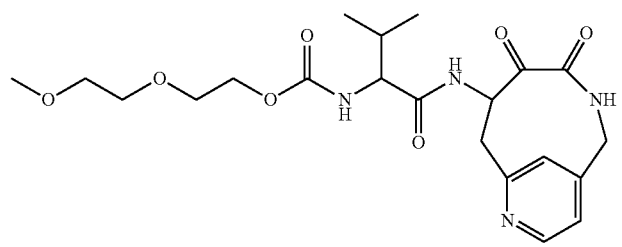 [SMILES: COCCOCCOC(=O)NC(C(=O)NC1Cc2cc(ccn2)CNC(=O)C1=O)C(C)C]
83
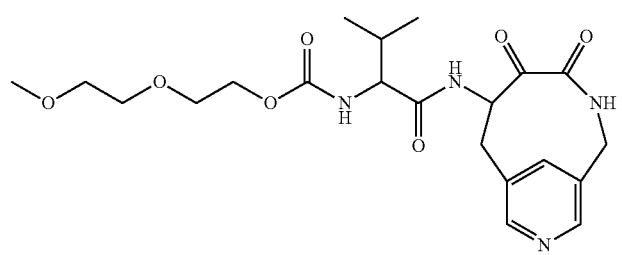 [SMILES: COCCOCCOC(=O)NC(C(=O)NC1Cc2cncc(c2)CNC(=O)C1=O)C(C)C]
84
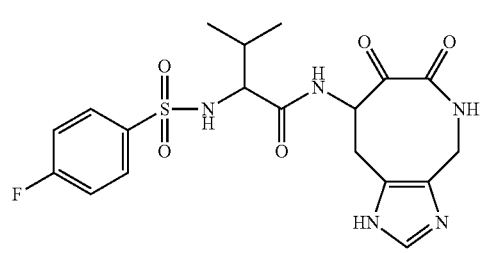 [SMILES: CC(C)C(NS(=O)(=O)c1ccc(F)cc1)C(=O)NC1Cc2[nH]cnc2CNC(=O)C1=O]
87
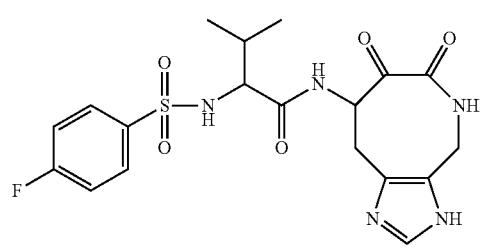 [SMILES: CC(C)C(NS(=O)(=O)c1ccc(F)cc1)C(=O)NC1Cc2nc[nH]c2CNC(=O)C1=O]
88
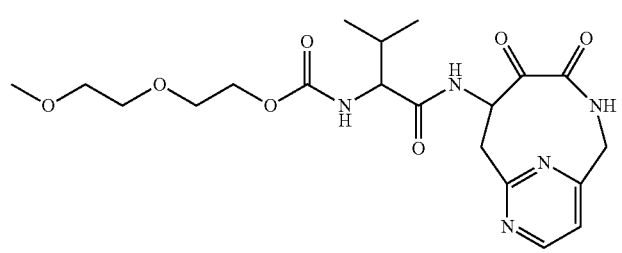 [SMILES: COCCOCCOC(=O)NC(C(=O)NC1Cc2nccc(n2)CNC(=O)C1=O)C(C)C]
91

TABLE 7-continued
ElevenRings
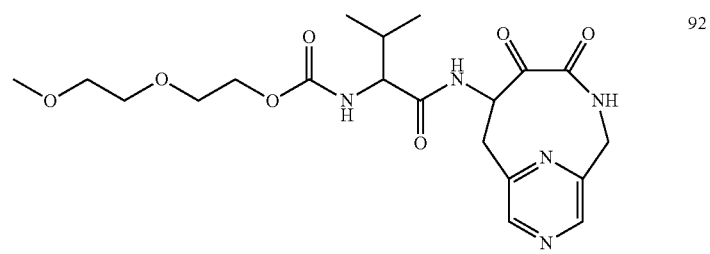
92
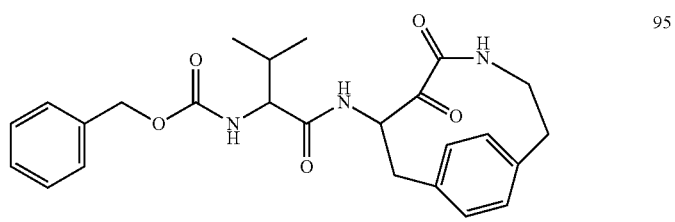
95
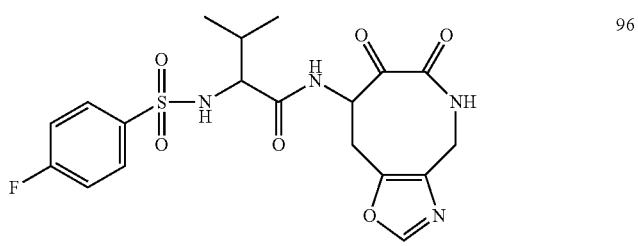
96
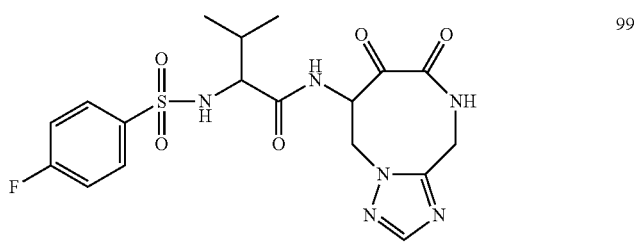
99
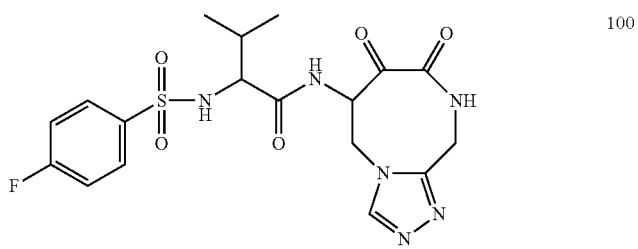
100
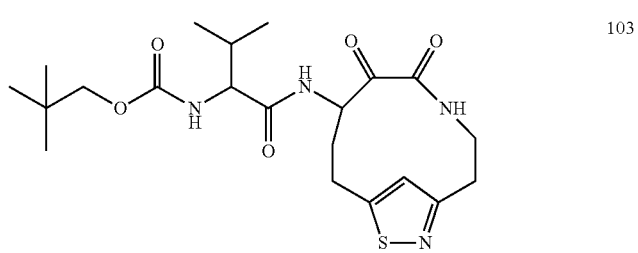
103

TABLE 7-continued
ElevenRings
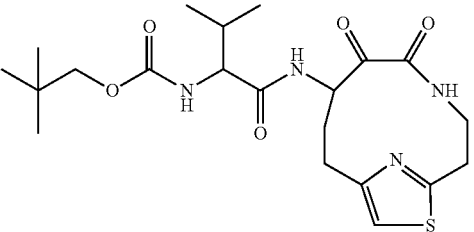 [SMILES: CC(C)C(NC(=O)OCC(C)(C)C)C(=O)NC1CCc2csc(n2)CCNC(=O)C1=O]
104
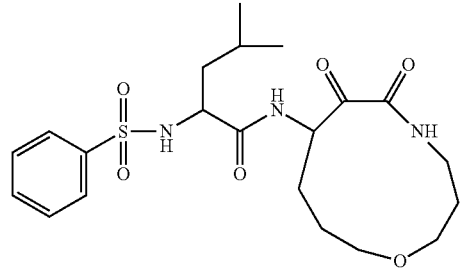 [SMILES: CC(C)CC(NS(=O)(=O)c1ccccc1)C(=O)NC1CCCOCCCNC(=O)C1=O]
107
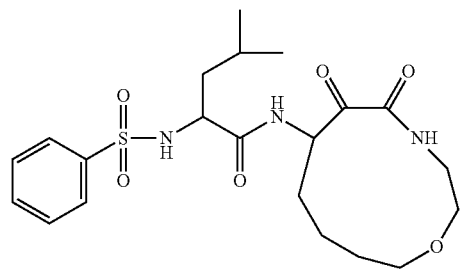 [SMILES: CC(C)CC(NS(=O)(=O)c1ccccc1)C(=O)NC1CCCCOCCNC(=O)C1=O]
108
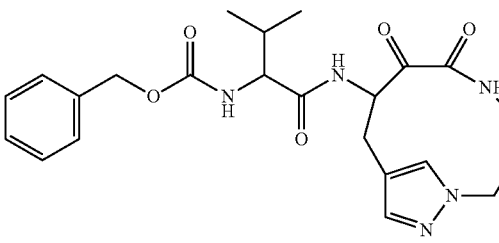
111
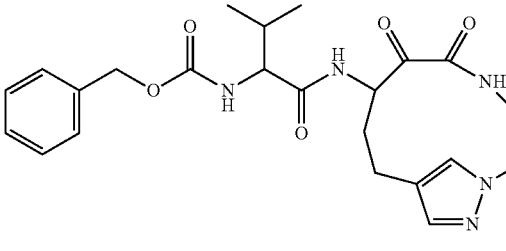
112
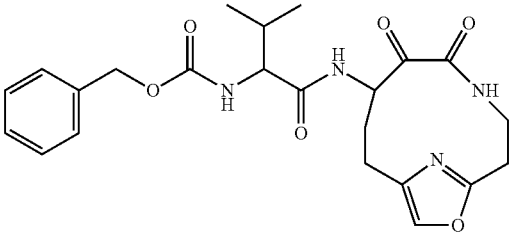 [SMILES: CC(C)C(NC(=O)OCc1ccccc1)C(=O)NC1CCc2coc(n2)CCNC(=O)C1=O]
115

TABLE 7-continued

ElevenRings

| | |
|---|---|
| (chemical structure) | 116 |
| (chemical structure) | 119 |
| (chemical structure) | 120 |
| (chemical structure) | 123 |
| (chemical structure) | 124 |
| (chemical structure) | 127 |

TABLE 7-continued
ElevenRings
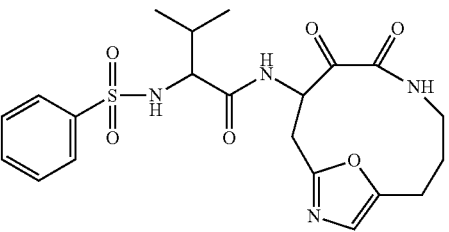 [SMILES: CC(C)C(NS(=O)(=O)c1ccccc1)C(=O)NC1CC2=NC=C(CCCNC(=O)C1=O)O2]
128
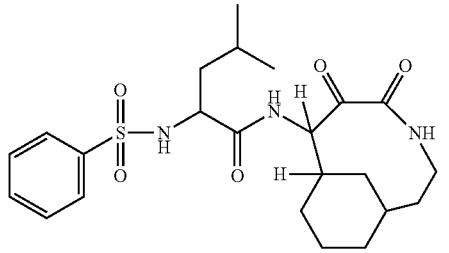 [SMILES: CC(C)CC(NS(=O)(=O)c1ccccc1)C(=O)NC1C(=O)C(=O)NCCC2CCCC1C2]
131
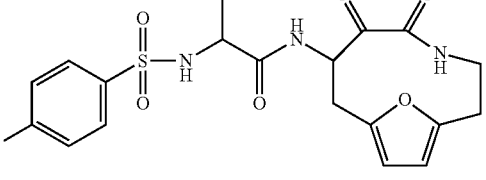
132
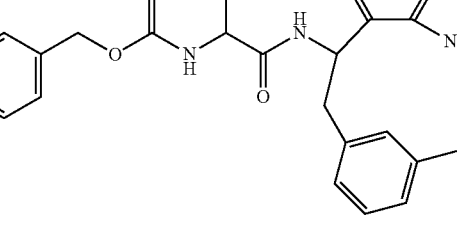
135
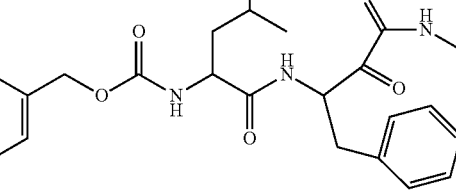
136
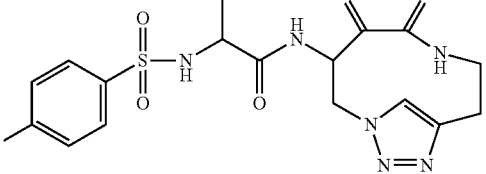
139

TABLE 7-continued
ElevenRings
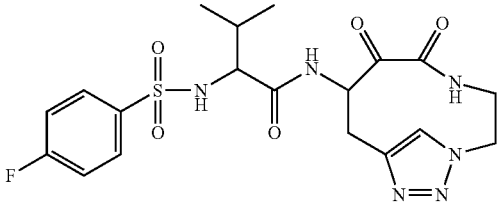 [SMILES: CC(C)C(NS(=O)(=O)c1ccc(F)cc1)C(=O)NC1Cc2cn(nn2)CCNC(=O)C1=O]
140
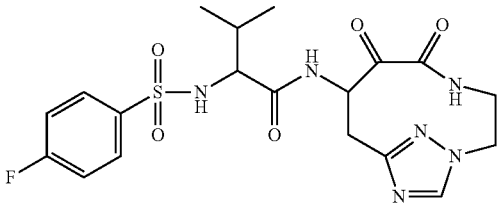
143
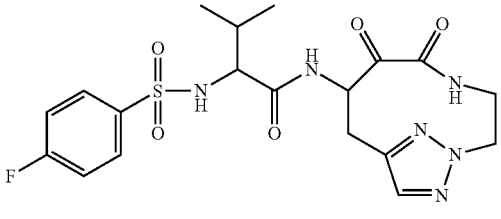 [SMILES: CC(C)C(NS(=O)(=O)c1ccc(F)cc1)C(=O)NC1Cc2cnn(n2)CCNC(=O)C1=O]
144
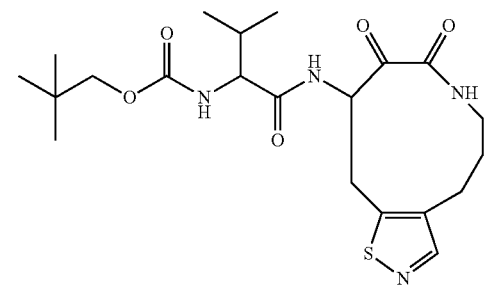 [SMILES: CC(C)C(NC(=O)OCC(C)(C)C)C(=O)NC1CCc2sncc2CCCNC(=O)C1=O]
147
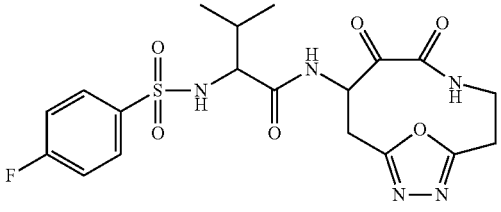 [SMILES: CC(C)C(NS(=O)(=O)c1ccc(F)cc1)C(=O)NC1CC2=NN=C(CCNC(=O)C1=O)O2]
148
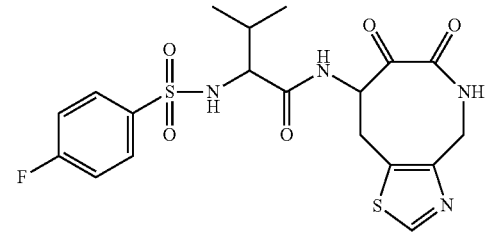 [SMILES: CC(C)C(NS(=O)(=O)c1ccc(F)cc1)C(=O)NC1Cc2scnc2CNC(=O)C1=O]
151

TABLE 7-continued
ElevenRings
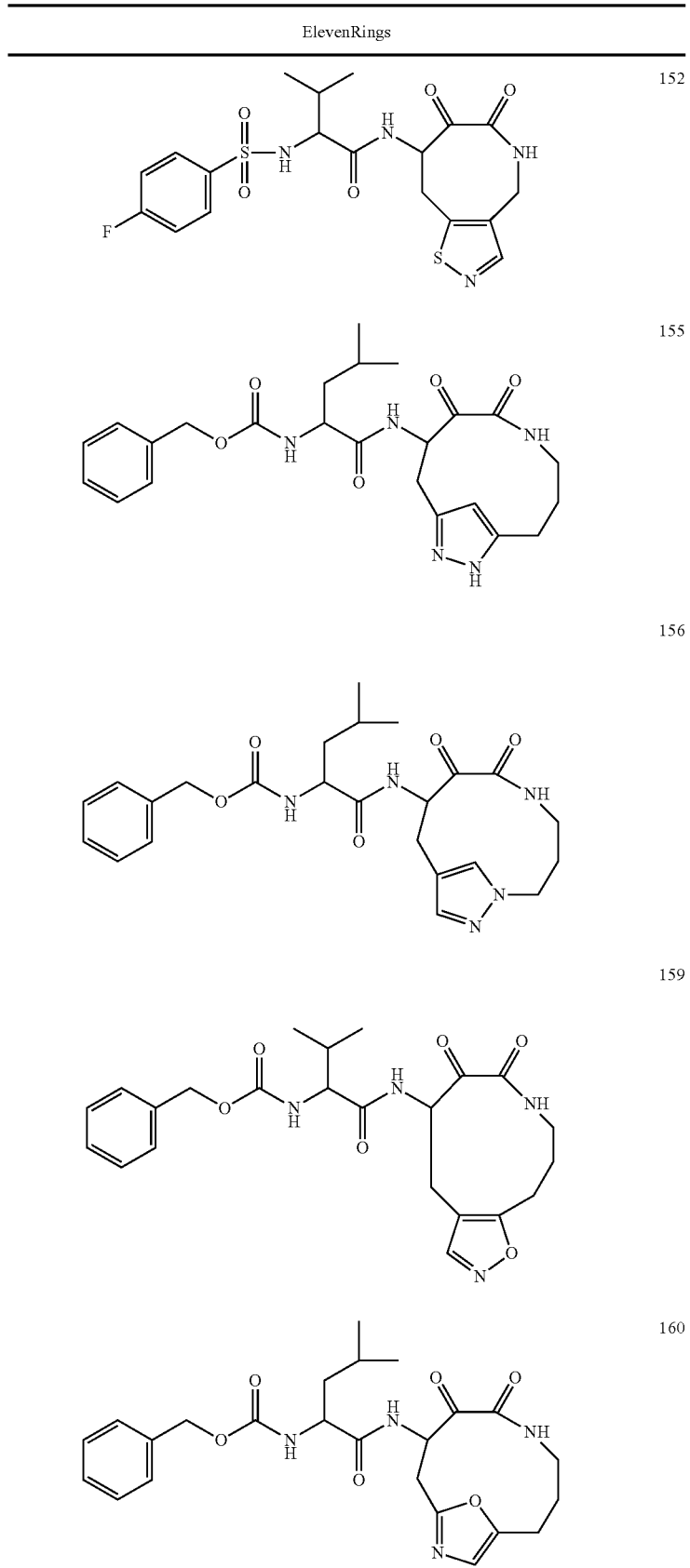

TABLE 7-continued
ElevenRings
| | |
|---|---|
| 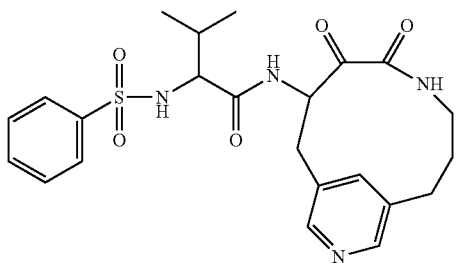 [SMILES: CC(C)C(NS(=O)(=O)c1ccccc1)C(=O)NC1Cc2cncc(c2)CCCNC(=O)C1=O] | 163 |
| 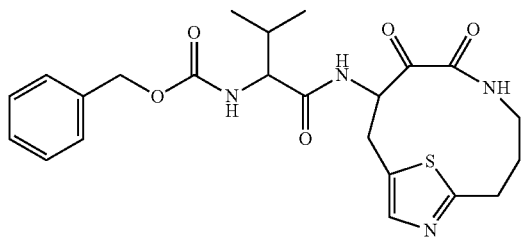 [SMILES: CC(C)C(NC(=O)OCc1ccccc1)C(=O)NC1CC2=CN=C(CCCNC(=O)C1=O)S2] | 164 |
| 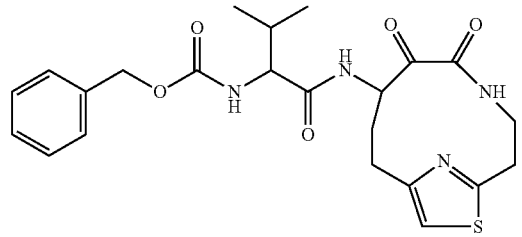 [SMILES: CC(C)C(NC(=O)OCc1ccccc1)C(=O)NC1CCc2csc(n2)CCNC(=O)C1=O] | 167 |
| 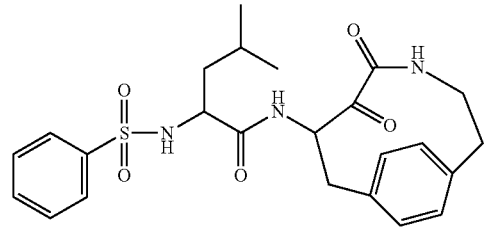 [SMILES: CC(C)CC(NS(=O)(=O)c1ccccc1)C(=O)NC1Cc2ccc(cc2)CCNC(=O)C1=O] | 168 |
| 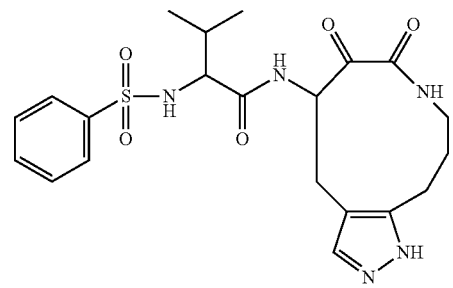 [SMILES: CC(C)C(NS(=O)(=O)c1ccccc1)C(=O)NC1CCc2cn[nH]c2CCCNC(=O)C1=O] | 171 |
| 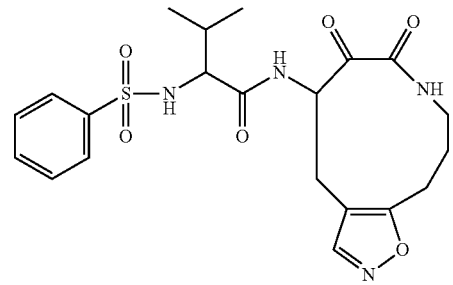 [SMILES: CC(C)C(NS(=O)(=O)c1ccccc1)C(=O)NC1CCc2cnoc2CCCNC(=O)C1=O] | 172 |

TABLE 7-continued
ElevenRings
175
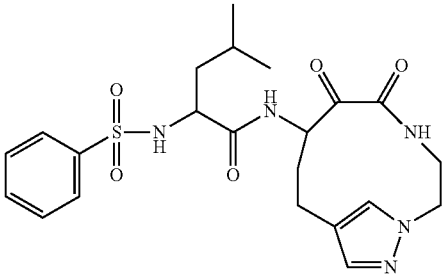 [SMILES: CC(C)CC(NS(=O)(=O)c1ccccc1)C(=O)NC1CCc2cnn(c2)CCNC(=O)C1=O]
176
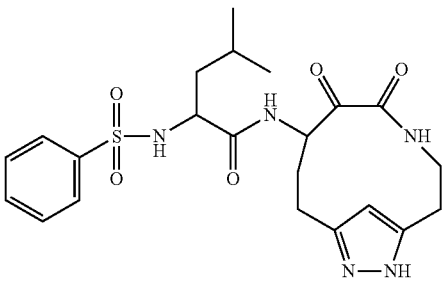 [SMILES: CC(C)CC(NS(=O)(=O)c1ccccc1)C(=O)NC1CCc2cc([nH]n2)CCNC(=O)C1=O]
179
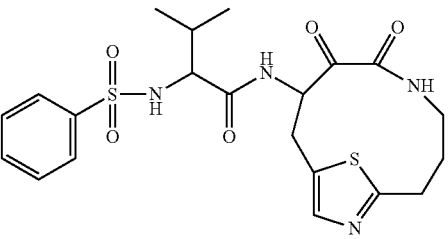 [SMILES: CC(C)C(NS(=O)(=O)c1ccccc1)C(=O)NC1CC2=CN=C(CCCNC(=O)C1=O)S2]
180
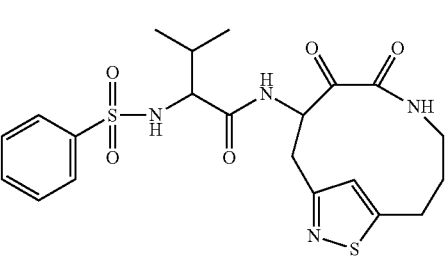 [SMILES: CC(C)C(NS(=O)(=O)c1ccccc1)C(=O)NC1Cc2cc(sn2)CCCNC(=O)C1=O]
183
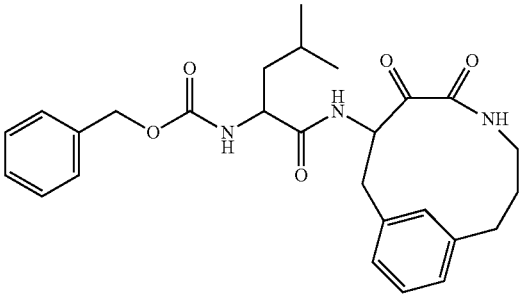 [SMILES: CC(C)CC(NC(=O)OCc1ccccc1)C(=O)NC1Cc2cccc(c2)CCCNC(=O)C1=O]

TABLE 7-continued
ElevenRings
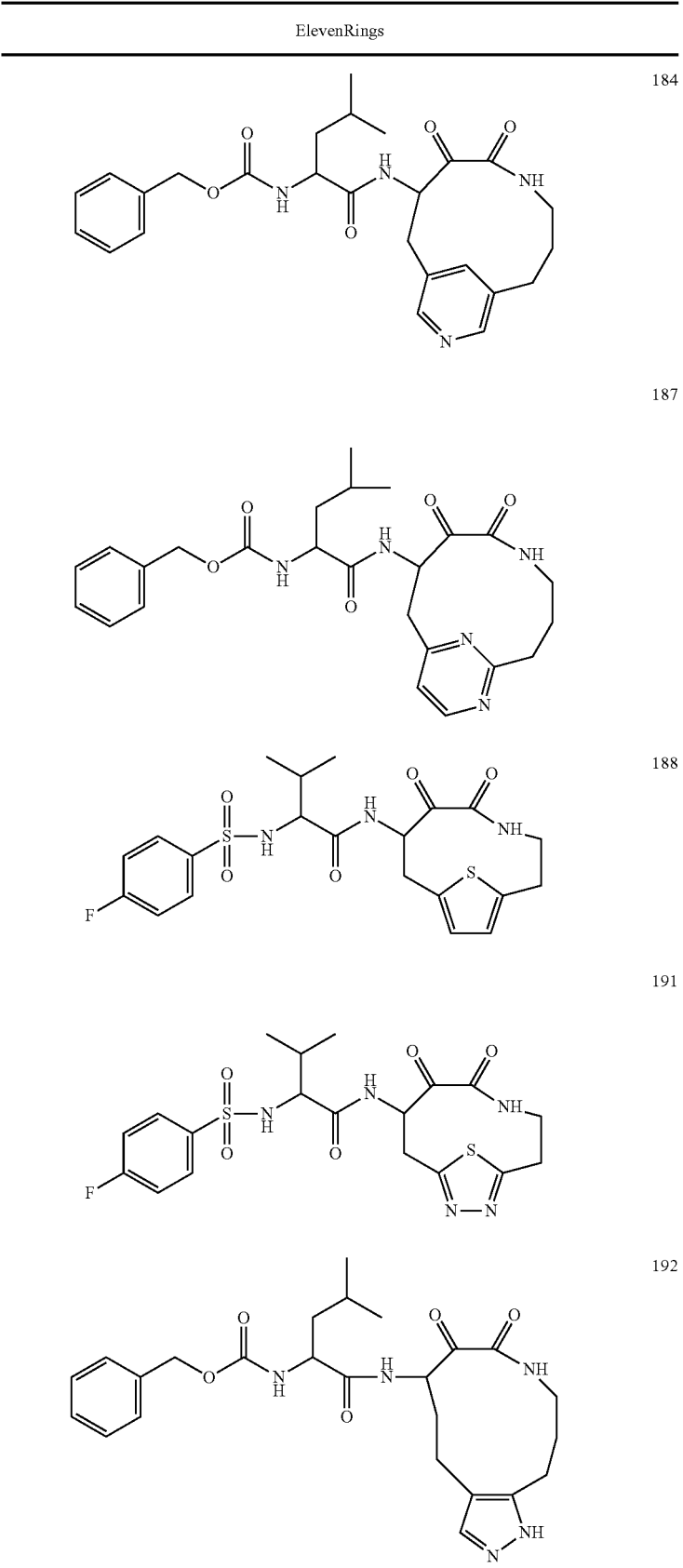
184
187
188
191
192

TABLE 7-continued
ElevenRings
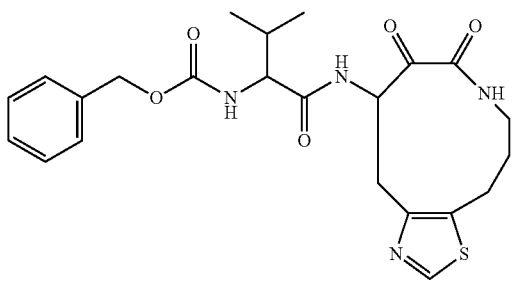 [SMILES: CC(C)C(NC(=O)OCc1ccccc1)C(=O)NC1CCc2ncsc2CCCNC(=O)C1=O]
195
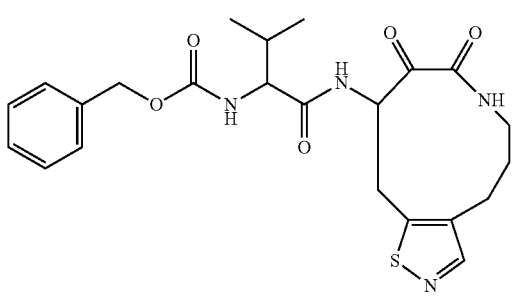 [SMILES: CC(C)C(NC(=O)OCc1ccccc1)C(=O)NC1CCc2sncc2CCCNC(=O)C1=O]
196
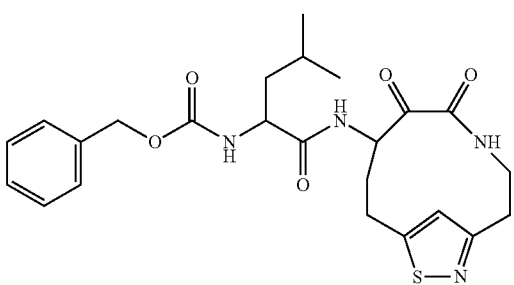 [SMILES: CC(C)CC(NC(=O)OCc1ccccc1)C(=O)NC1CCc2cc(ns2)CCNC(=O)C1=O]
199
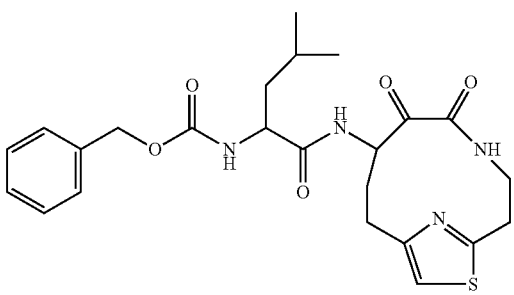 [SMILES: CC(C)CC(NC(=O)OCc1ccccc1)C(=O)NC1CCc2csc(n2)CCNC(=O)C1=O]
200
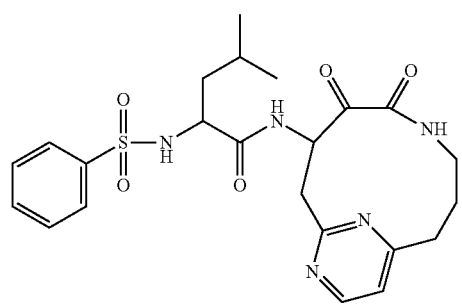 [SMILES: CC(C)CC(NS(=O)(=O)c1ccccc1)C(=O)NC1Cc2nccc(n2)CCCNC(=O)C1=O]
203

TABLE 7-continued
| ElevenRings |
|---|
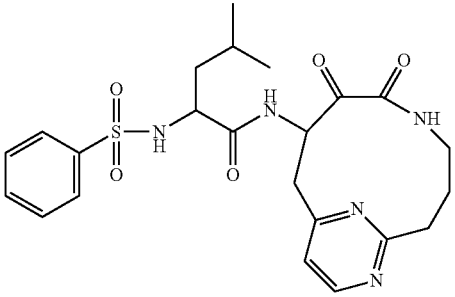 [SMILES: CC(C)CC(NS(=O)(=O)c1ccccc1)C(=O)NC1Cc2ccnc(n2)CCCNC(=O)C1=O]
204
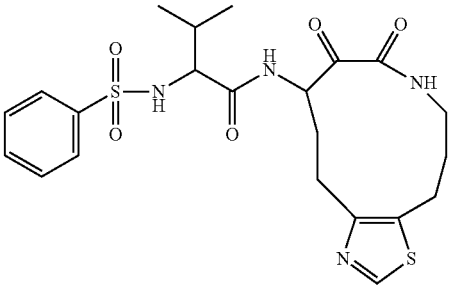 [SMILES: CC(C)C(NS(=O)(=O)c1ccccc1)C(=O)NC1CCc2ncsc2CCCNC(=O)C1=O]
207
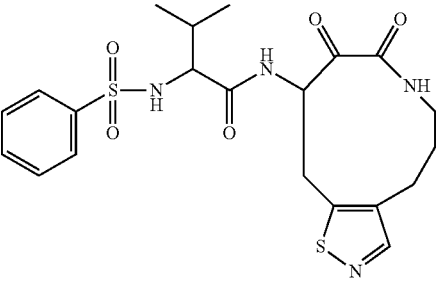 [SMILES: CC(C)C(NS(=O)(=O)c1ccccc1)C(=O)NC1CCc2sncc2CCCNC(=O)C1=O]
208
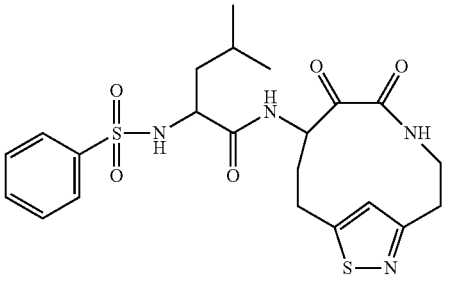 [SMILES: CC(C)CC(NS(=O)(=O)c1ccccc1)C(=O)NC1CCc2cc(ns2)CCNC(=O)C1=O]
211
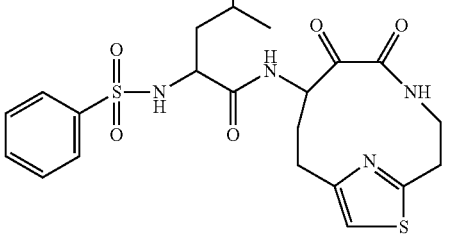
212

TABLE 7-continued
| ElevenRings |
|---|
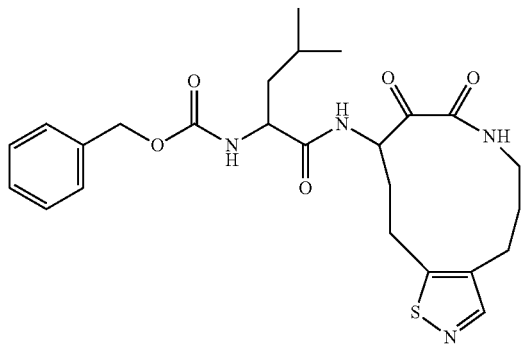 [SMILES: CC(C)CC(NC(=O)OCc1ccccc1)C(=O)NC1CCc2sncc2CCCNC(=O)C1=O]
215
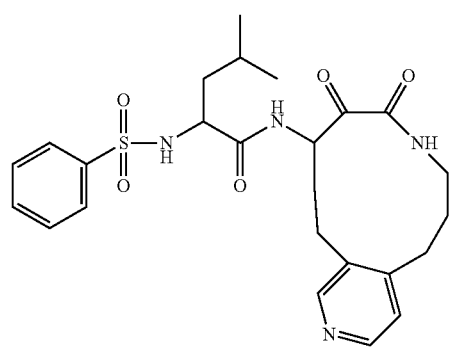 [SMILES: CC(C)CC(NS(=O)(=O)c1ccccc1)C(=O)NC1CCc2cnccc2CCCNC(=O)C1=O]
216
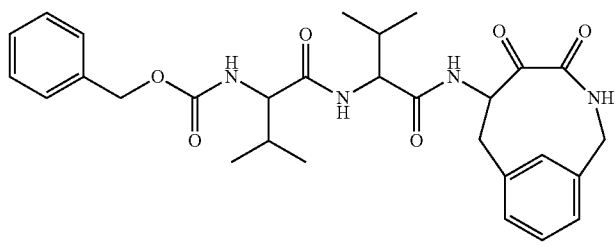 [SMILES: CC(C)C(NC(=O)OCc1ccccc1)C(=O)NC(C(=O)NC1Cc2cccc(c2)CNC(=O)C1=O)C(C)C]
219
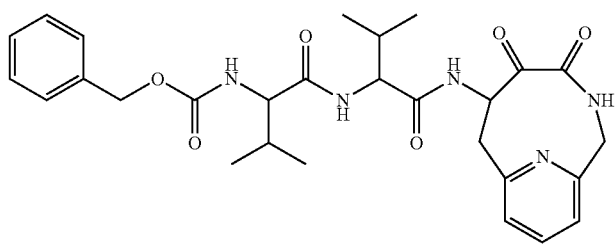 [SMILES: CC(C)C(NC(=O)OCc1ccccc1)C(=O)NC(C(=O)NC1Cc2cccc(n2)CNC(=O)C1=O)C(C)C]
220
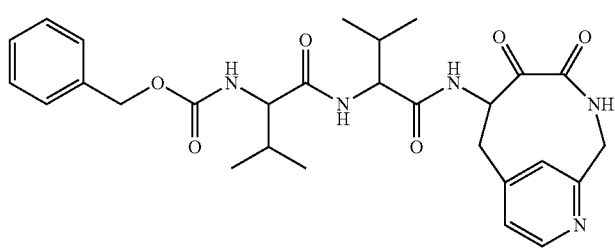 [SMILES: CC(C)C(NC(=O)OCc1ccccc1)C(=O)NC(C(=O)NC1Cc2ccnc(c2)CNC(=O)C1=O)C(C)C]
223

TABLE 7-continued
ElevenRings
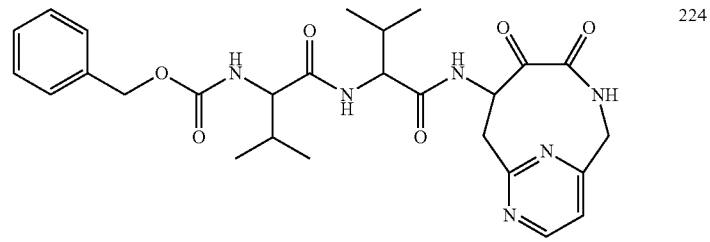
224
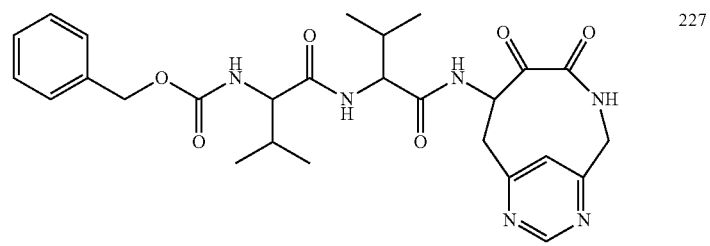
227
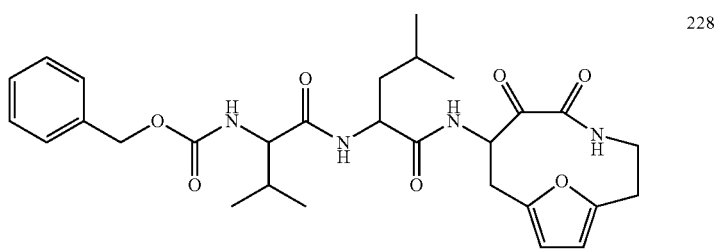
228
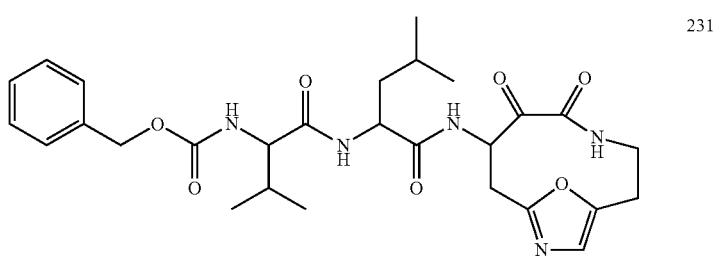
231
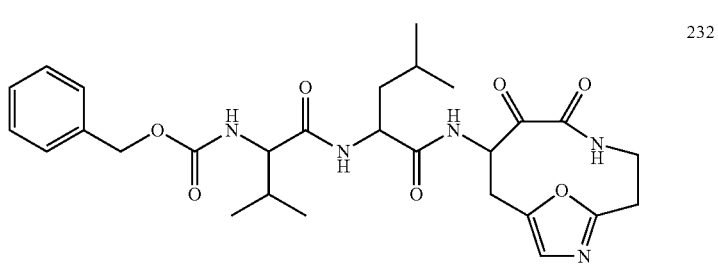
232
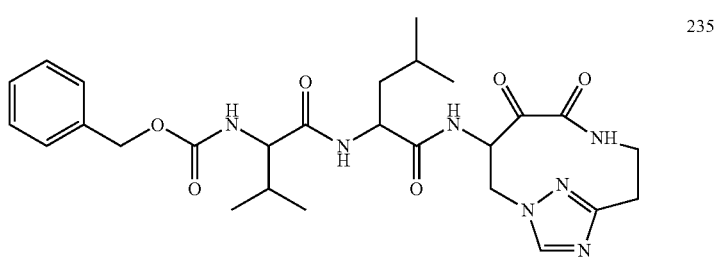
235

TABLE 7-continued
ElevenRings
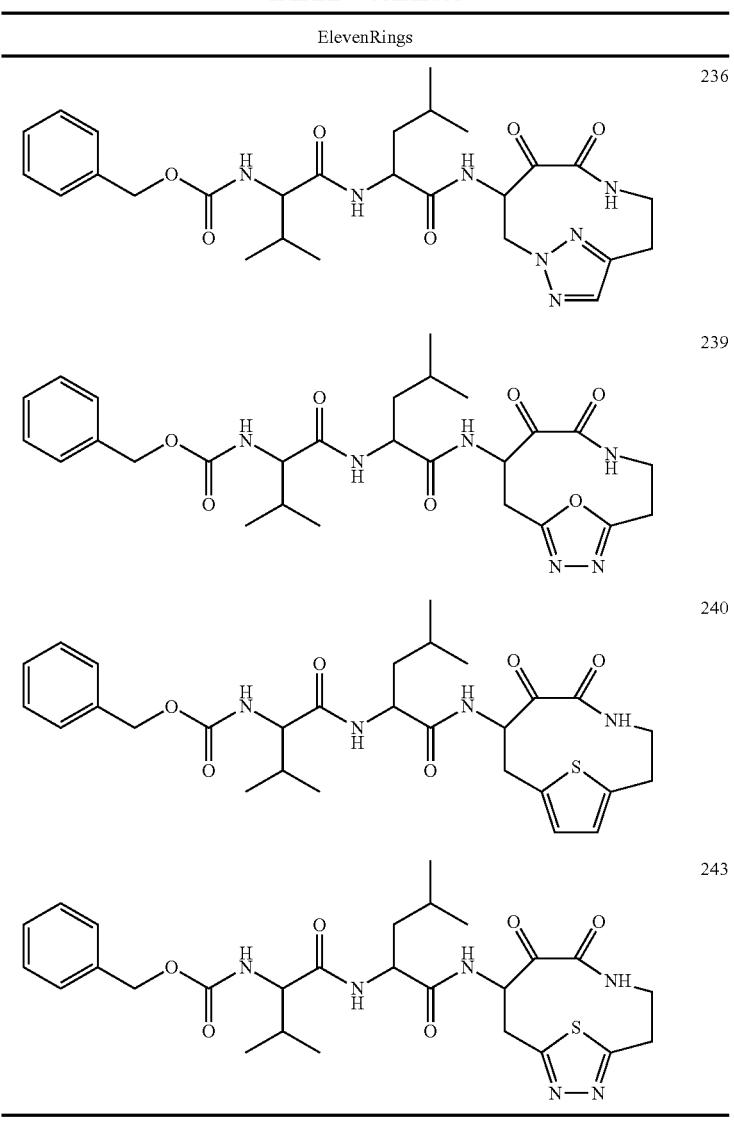
TABLE 8
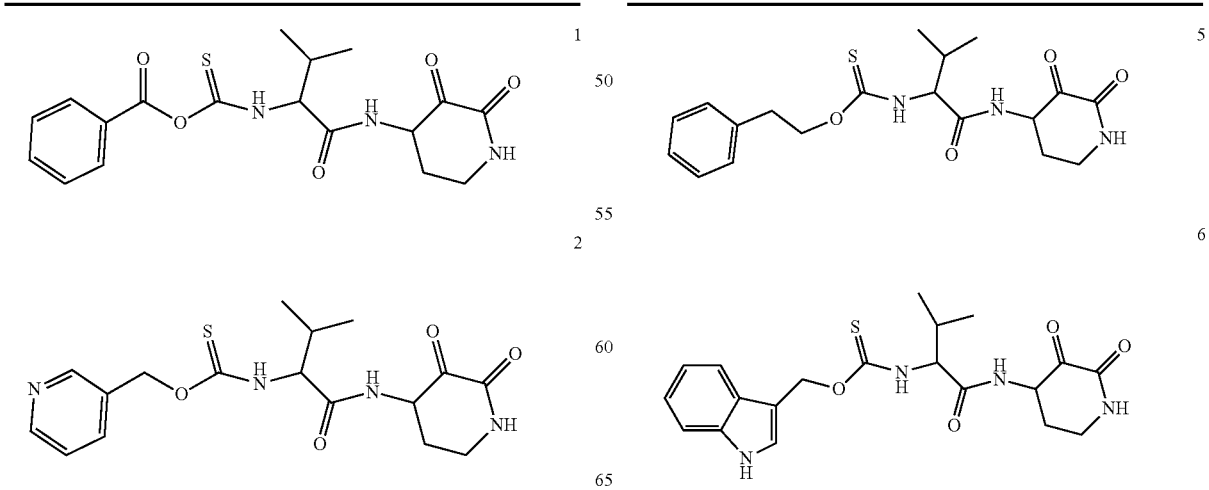

TABLE 8-continued
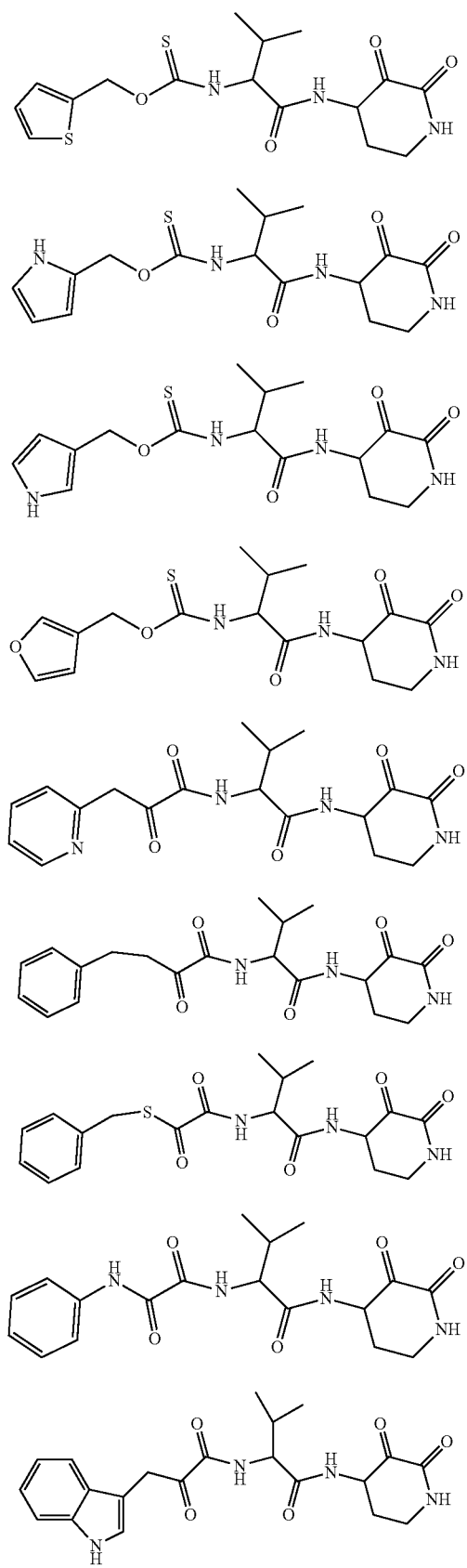
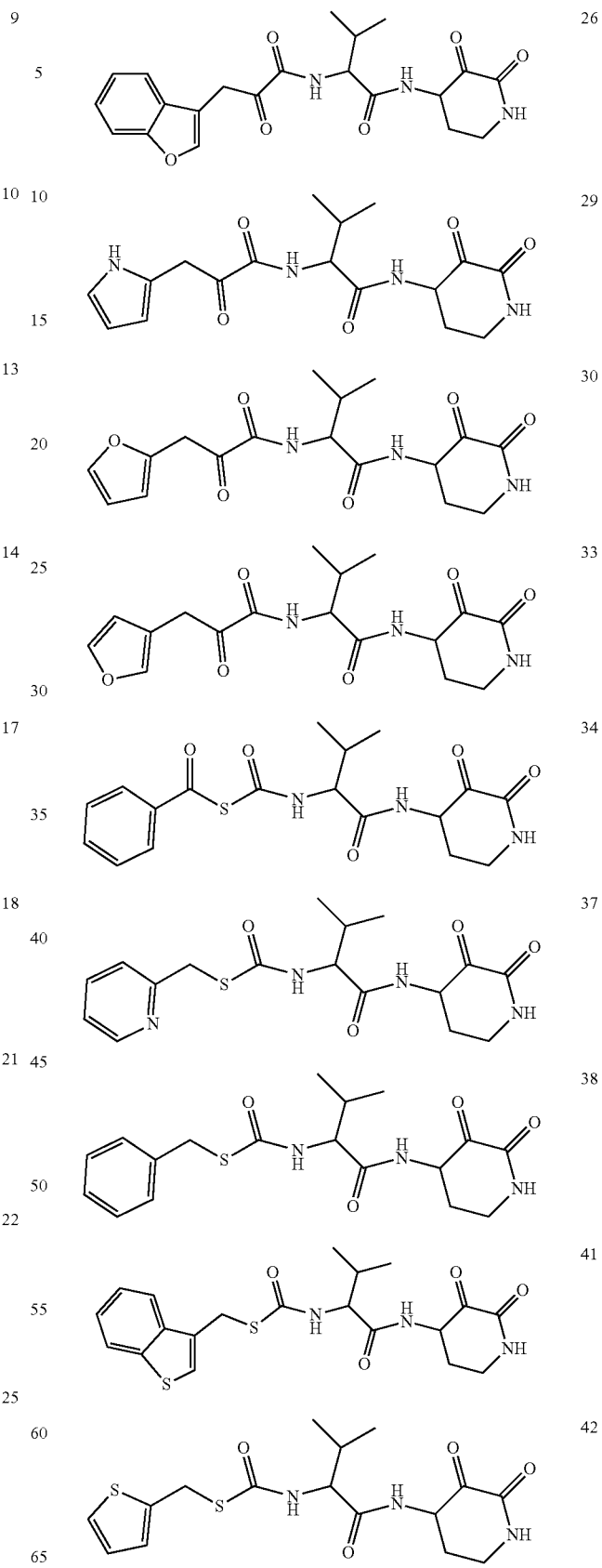

TABLE 8-continued
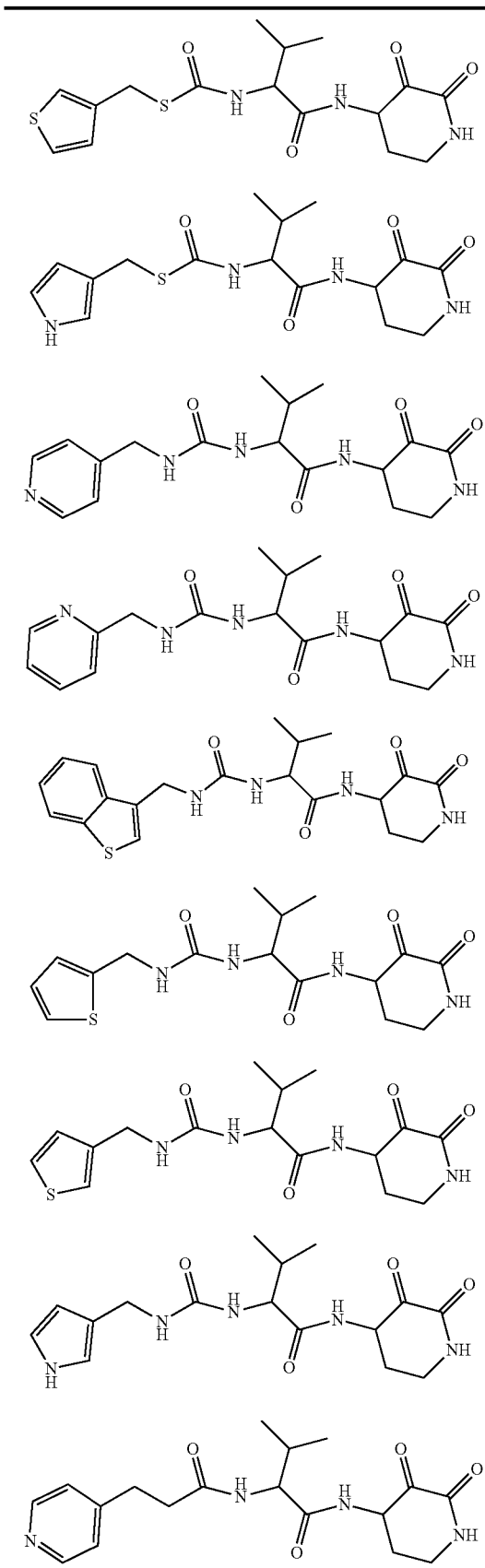
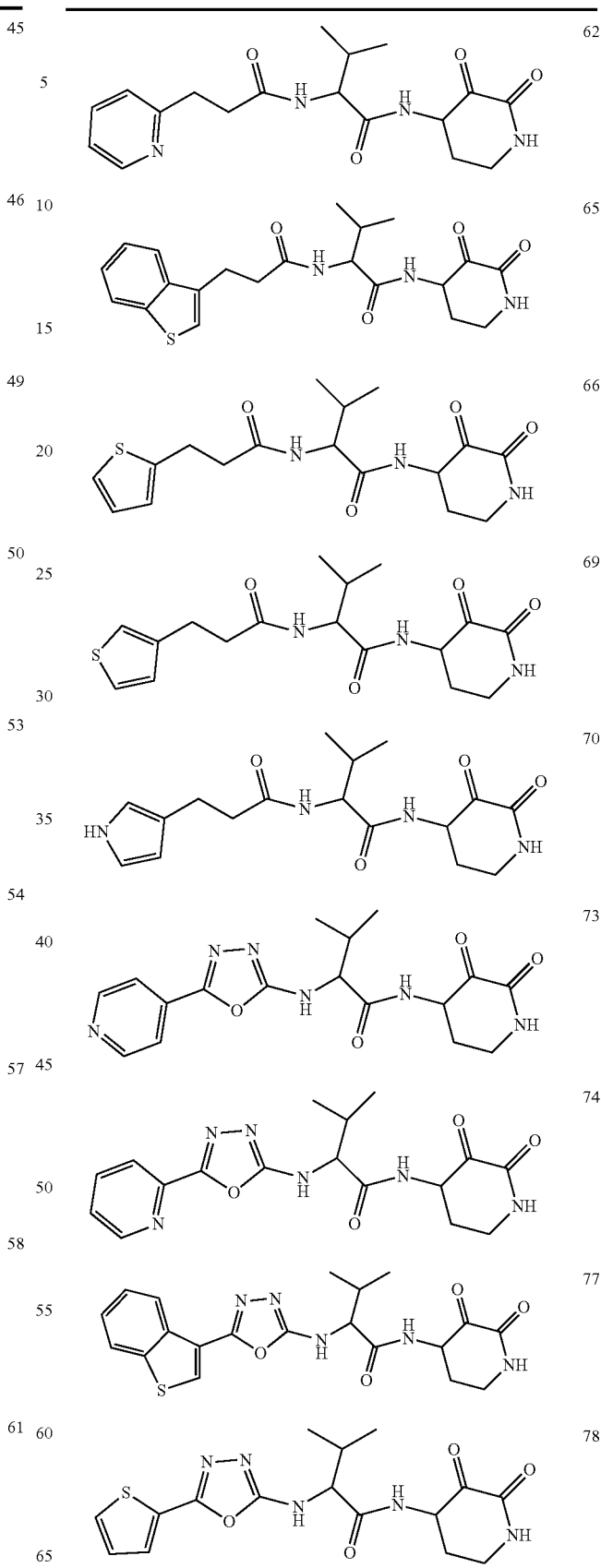

TABLE 8-continued
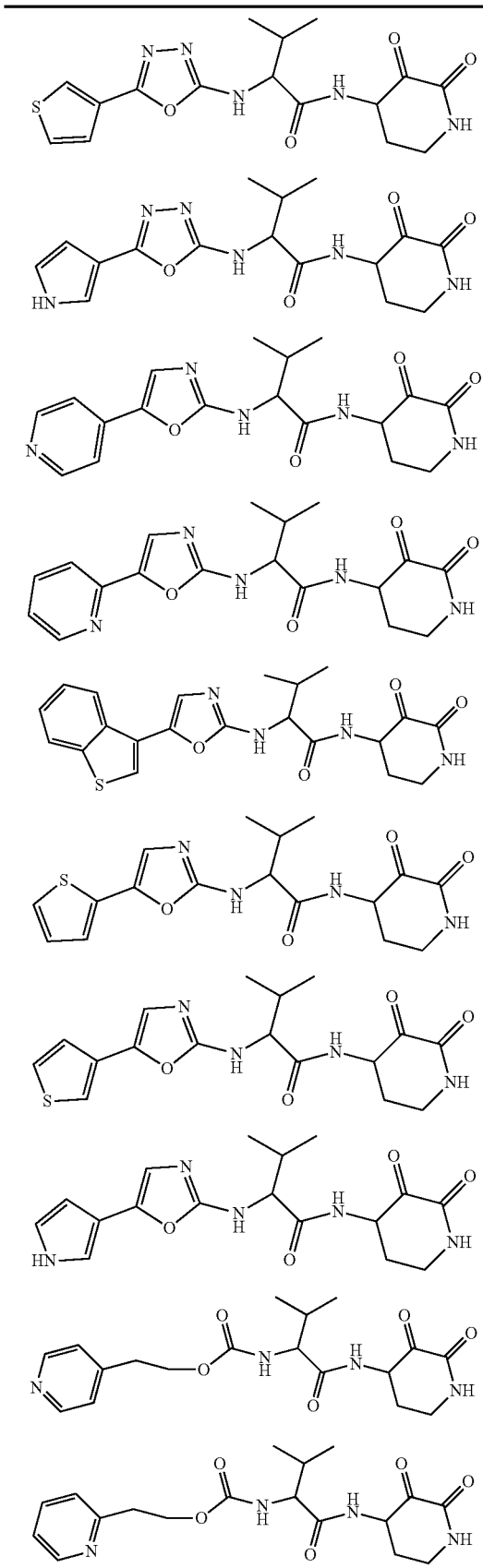
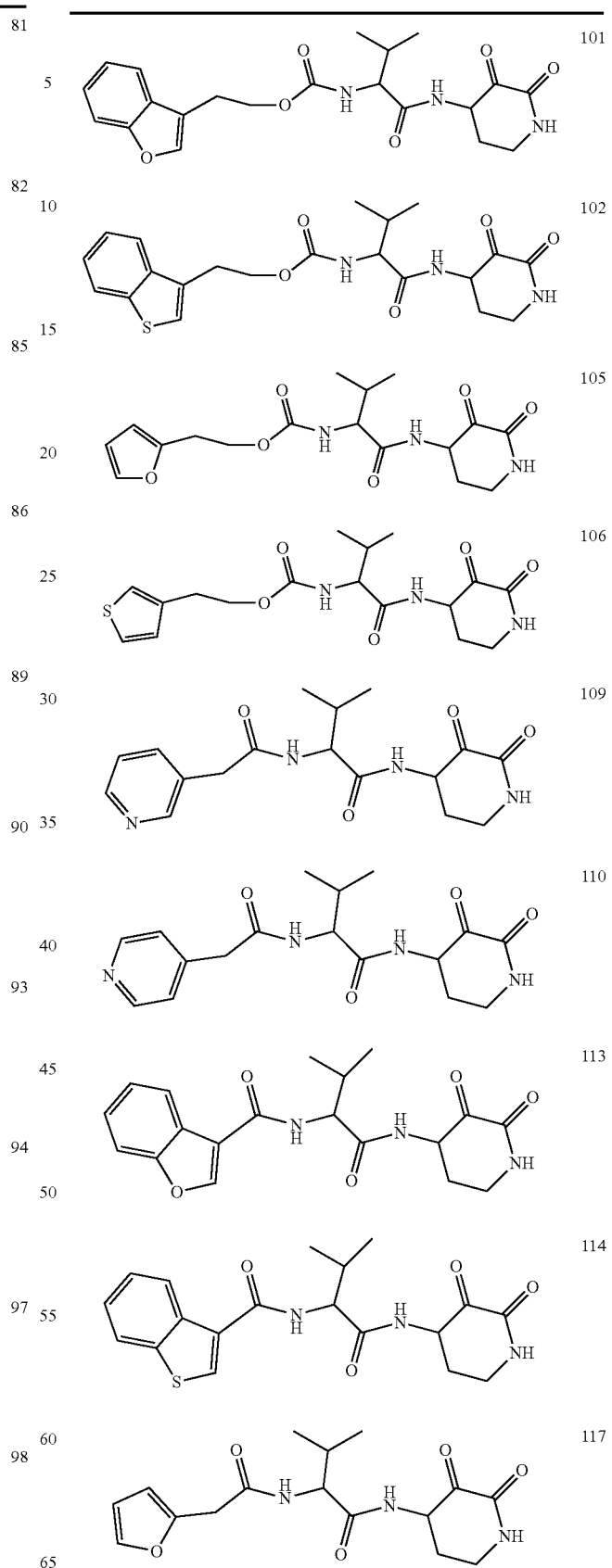

TABLE 8-continued
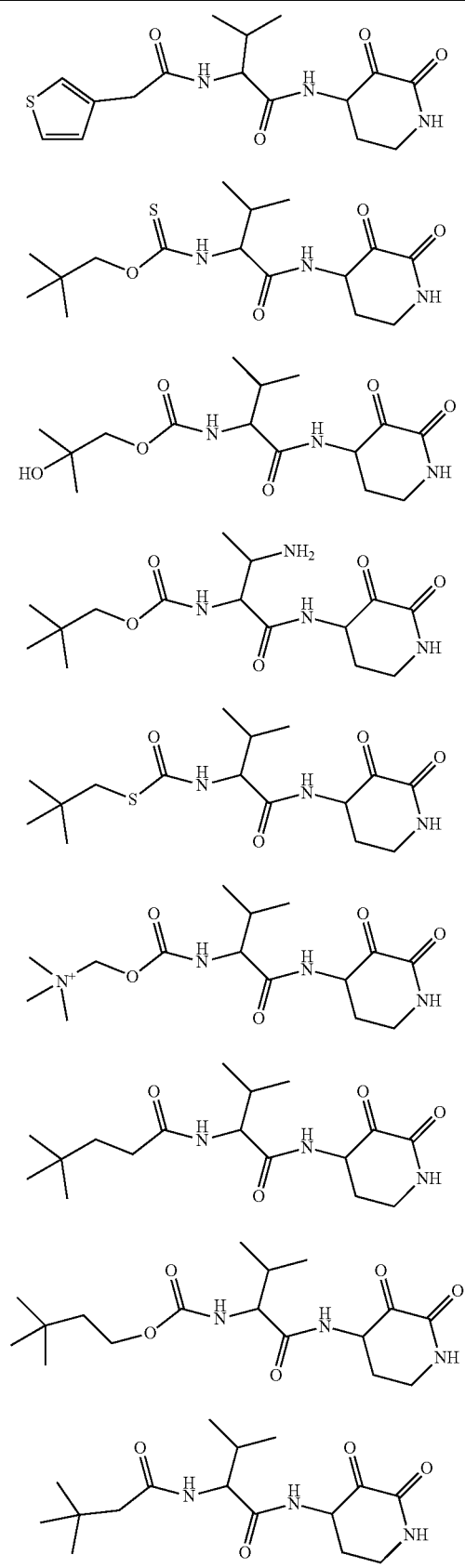
TABLE 8-continued
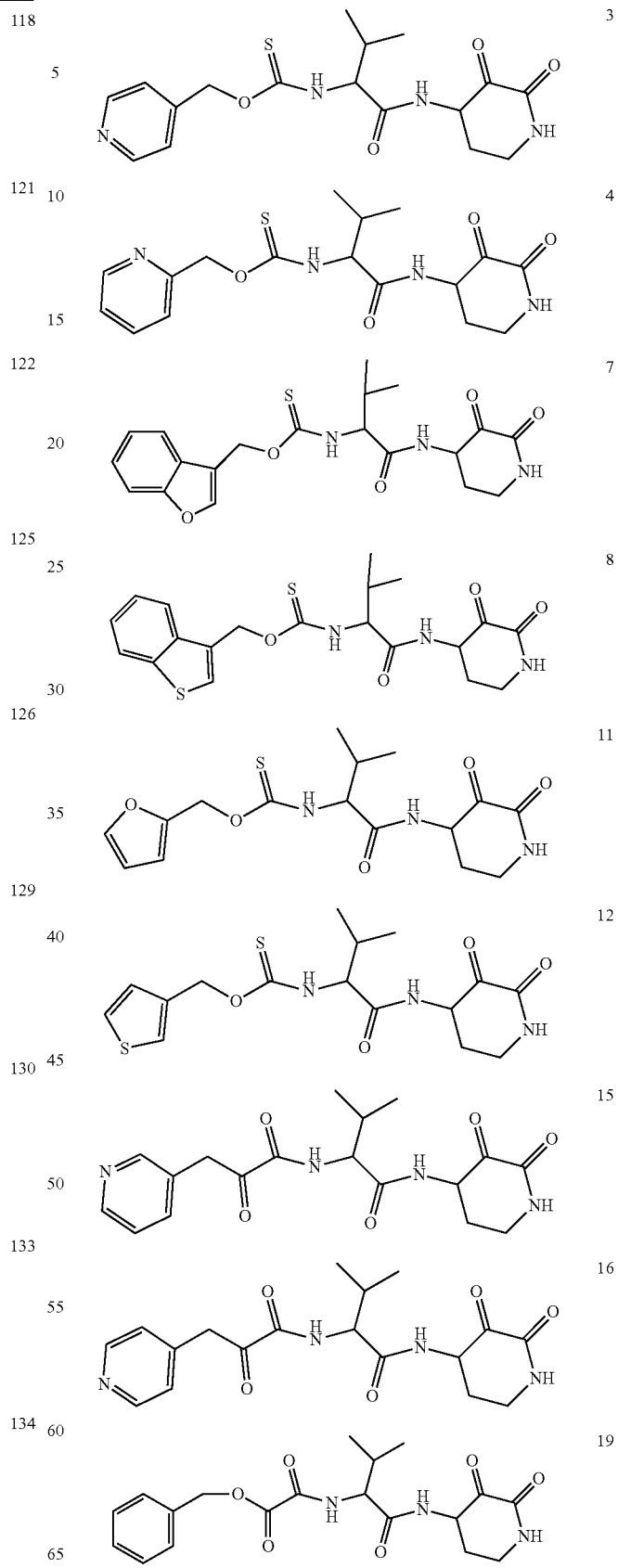

TABLE 8-continued
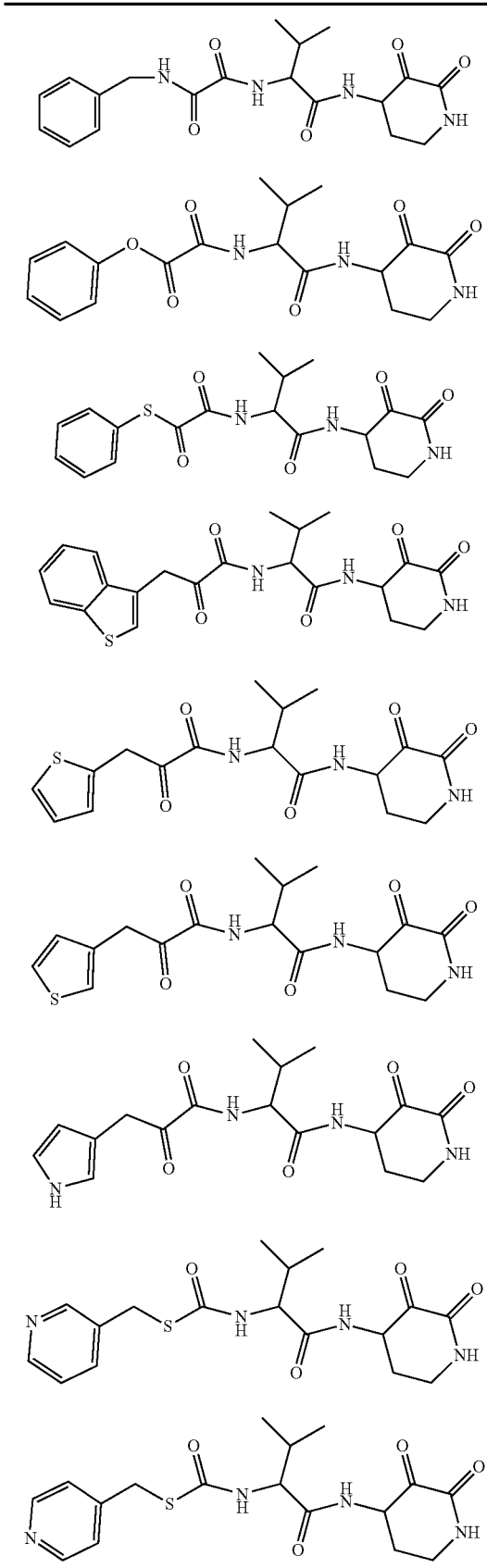
TABLE 8-continued
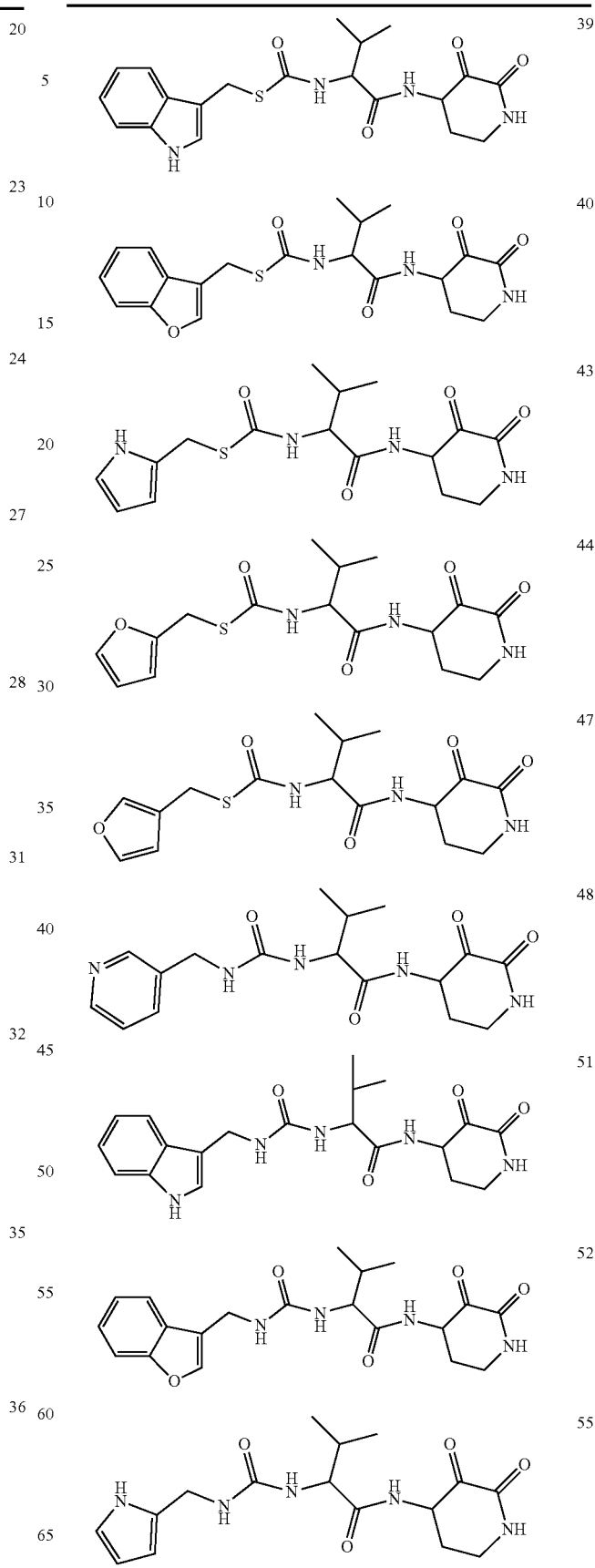

TABLE 8-continued
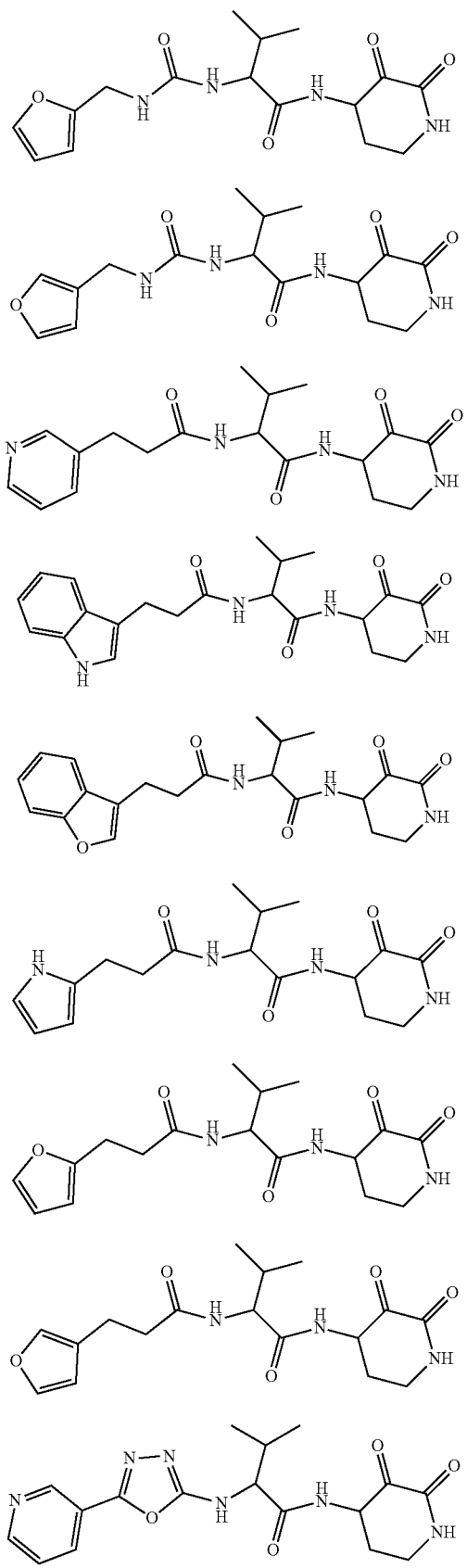
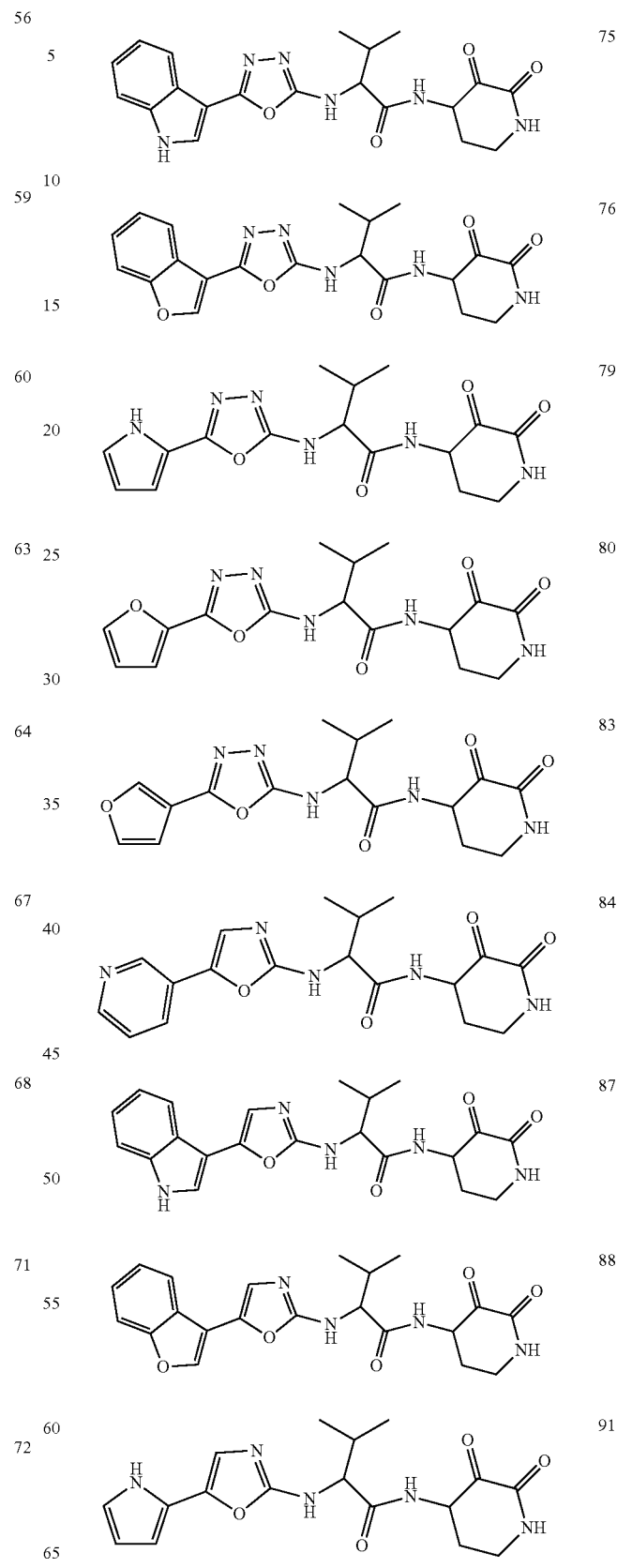

TABLE 8-continued
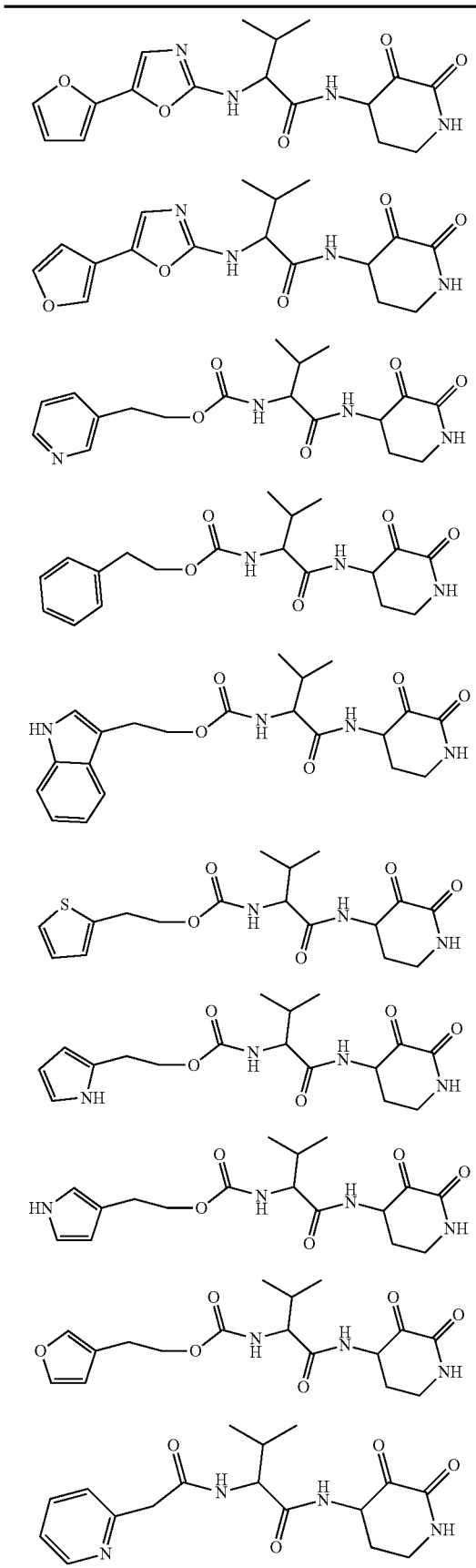
TABLE 8-continued
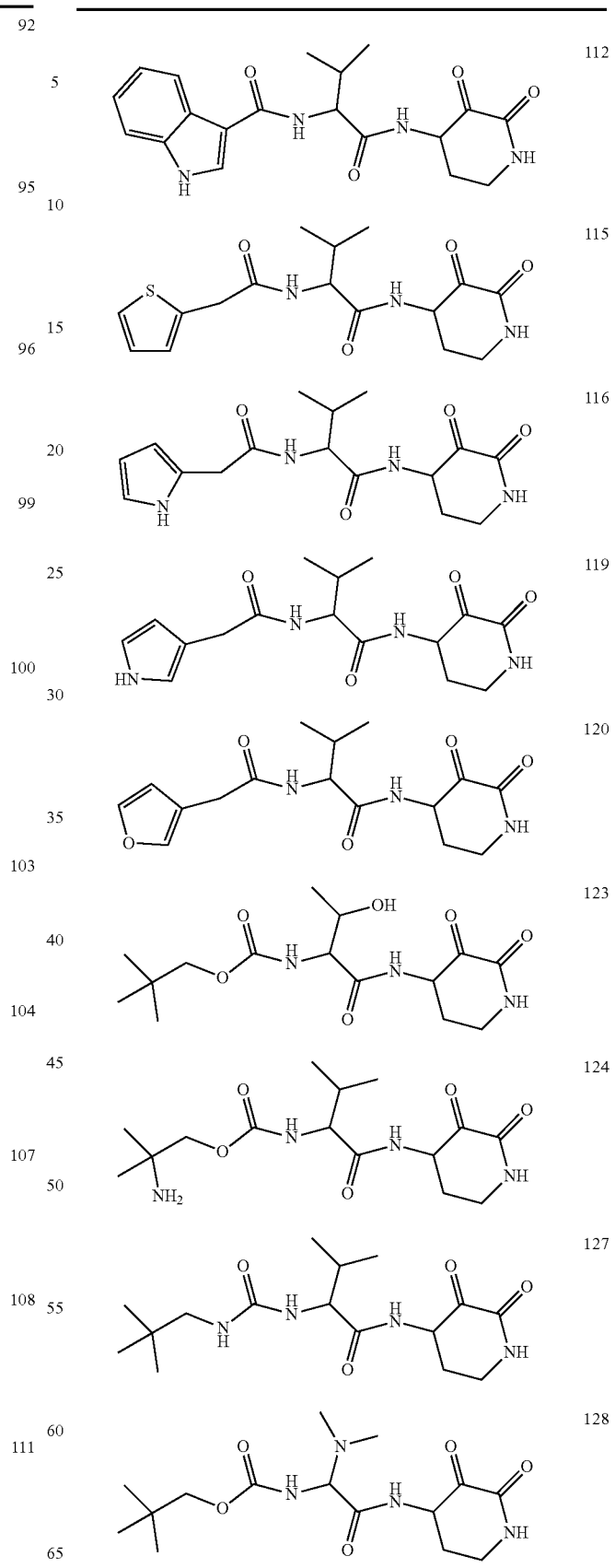

TABLE 8-continued
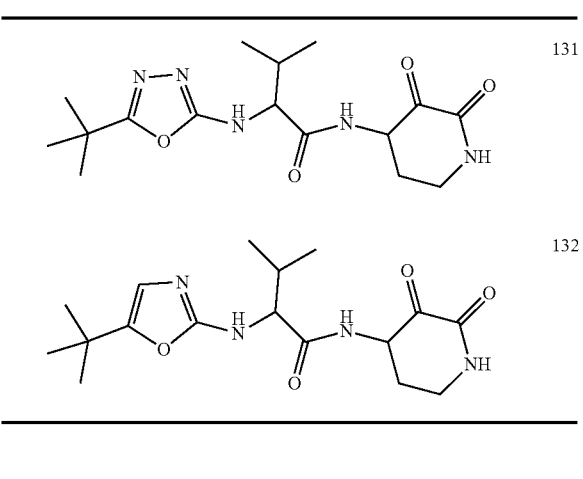
TABLE 9
TwelveRings
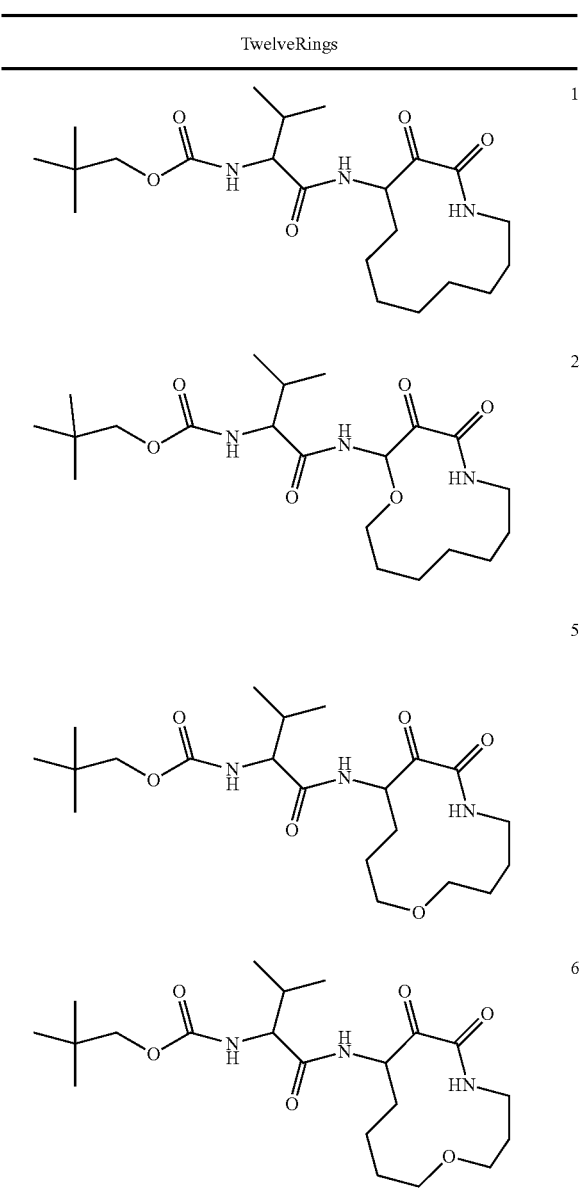
TABLE 9-continued
TwelveRings
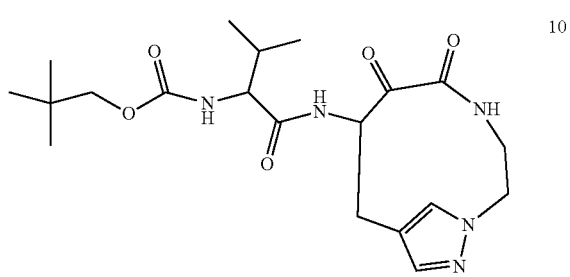
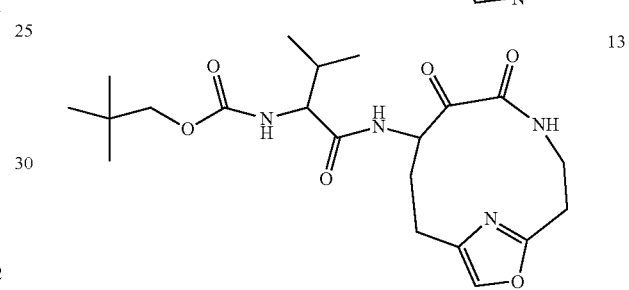
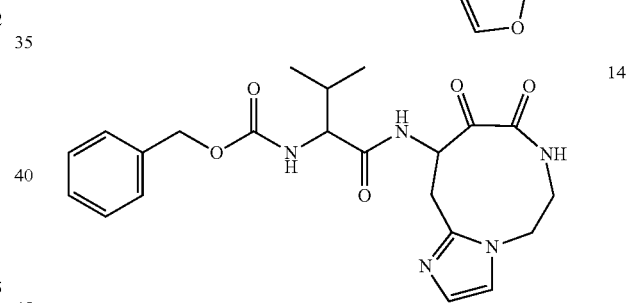
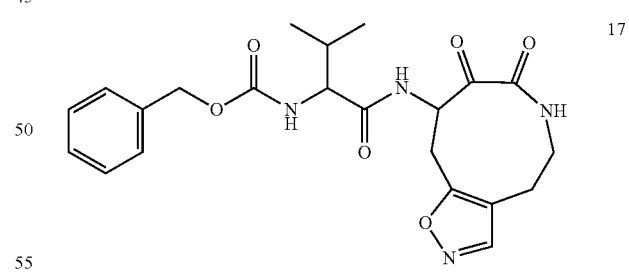
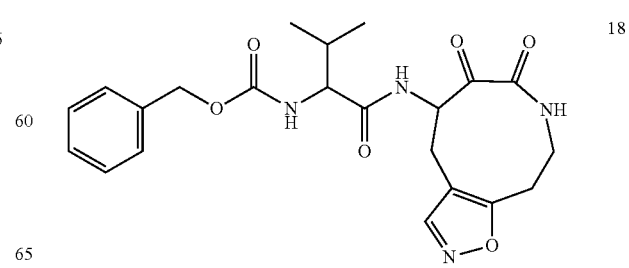

TABLE 9-continued
TwelveRings
21
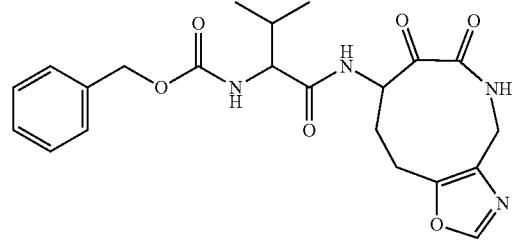
22
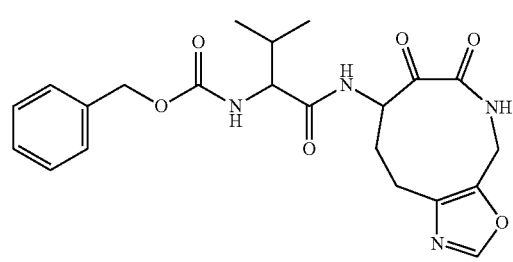
25
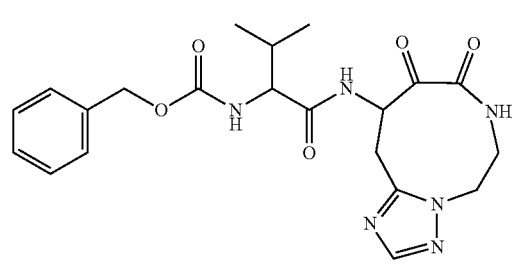
26
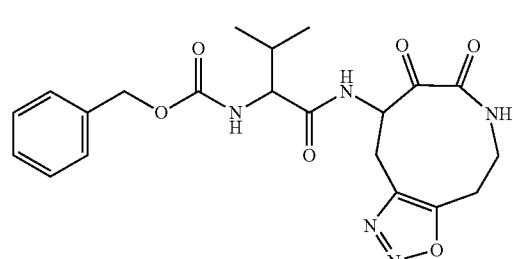
29
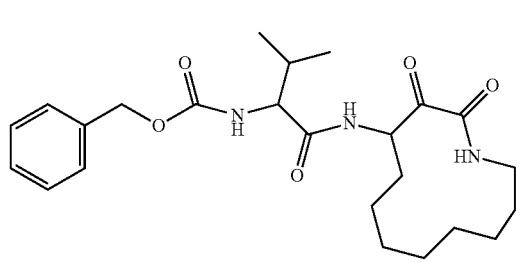 [SMILES: CC(C)C(NC(=O)OCc1ccccc1)C(=O)NC1CCCCCCCCNC(=O)C1=O]
30
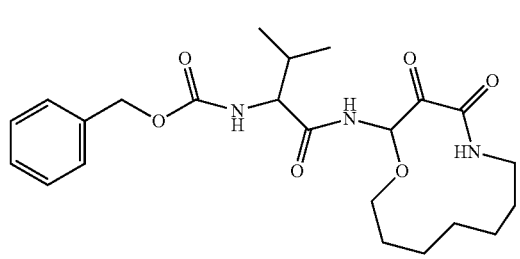 [SMILES: CC(C)C(NC(=O)OCc1ccccc1)C(=O)NC1OCCCCCCCNC(=O)C1=O]
TABLE 9-continued
TwelveRings
33
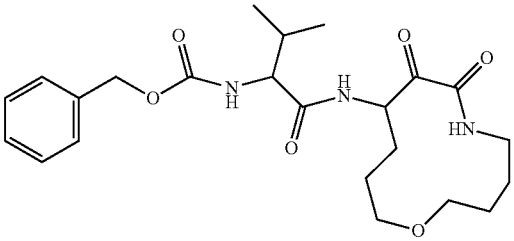 [SMILES: CC(C)C(NC(=O)OCc1ccccc1)C(=O)NC1CCCOCCCCNC(=O)C1=O]
34
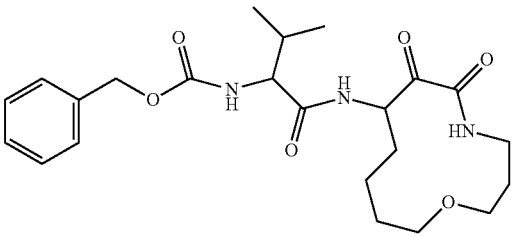 [SMILES: CC(C)C(NC(=O)OCc1ccccc1)C(=O)NC1CCCCOCCCNC(=O)C1=O]
37
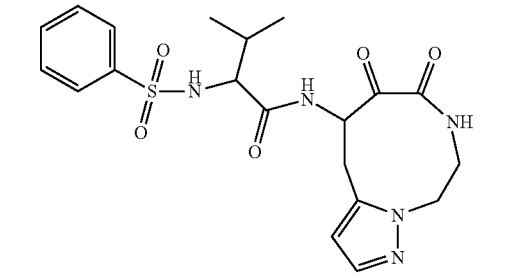 [SMILES: CC(C)C(NS(=O)(=O)c1ccccc1)C(=O)NC1Cc2ccnn2CCNC(=O)C1=O]
38
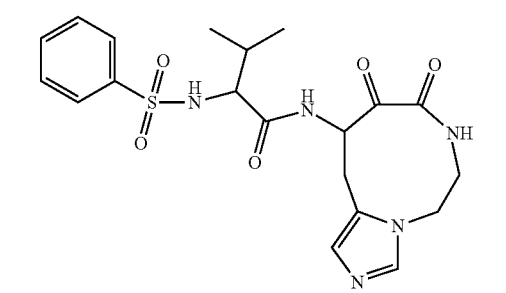 [SMILES: CC(C)C(NS(=O)(=O)c1ccccc1)C(=O)NC1Cc2cncn2CCNC(=O)C1=O]
41
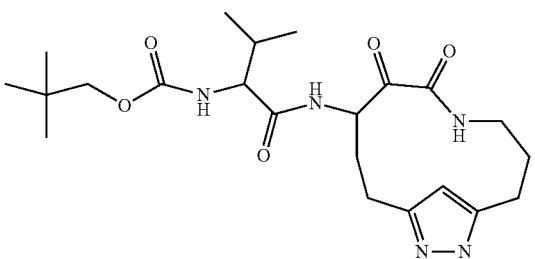 [SMILES: CC(C)C(NC(=O)OCC(C)(C)C)C(=O)NC1CCc2cnn(c2)CCCNC(=O)C1=O]
42
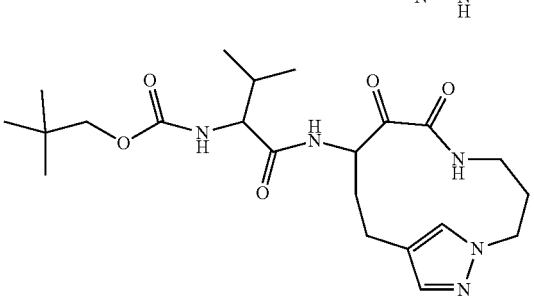

TABLE 9-continued
TwelveRings
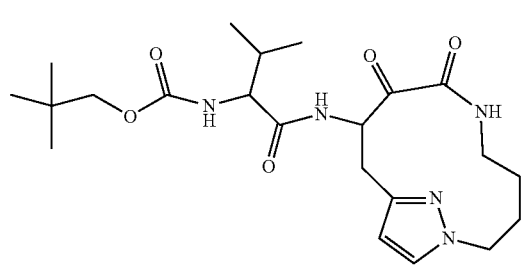 [SMILES: CC(C)C(NC(=O)OCC(C)(C)C)C(=O)NC1Cc2ccn(n2)CCCCNC(=O)C1=O]
45
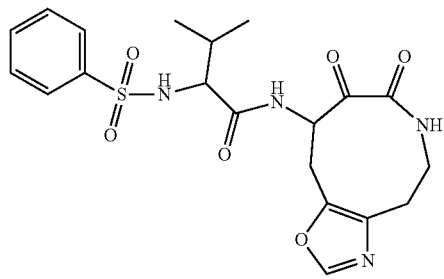 [SMILES: CC(C)C(NS(=O)(=O)c1ccccc1)C(=O)NC1Cc2ocnc2CCNC(=O)C1=O]
46
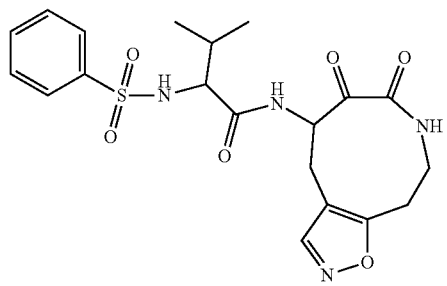 [SMILES: CC(C)C(NS(=O)(=O)c1ccccc1)C(=O)NC1Cc2cnoc2CCNC(=O)C1=O]
49
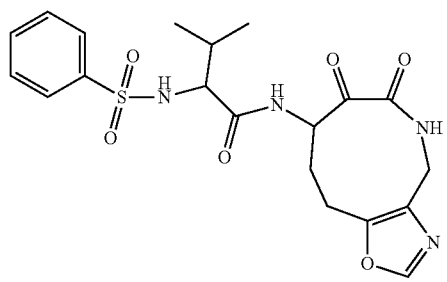 [SMILES: CC(C)C(NS(=O)(=O)c1ccccc1)C(=O)NC1CCc2ocnc2CNC(=O)C1=O]
50
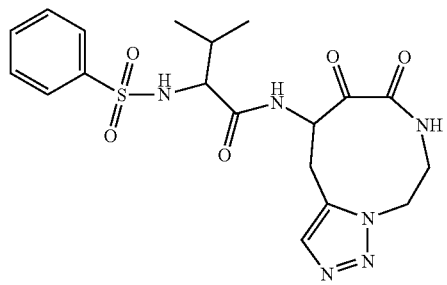 [SMILES: CC(C)C(NS(=O)(=O)c1ccccc1)C(=O)NC1Cc2cnnn2CCNC(=O)C1=O]
53
TABLE 9-continued
TwelveRings
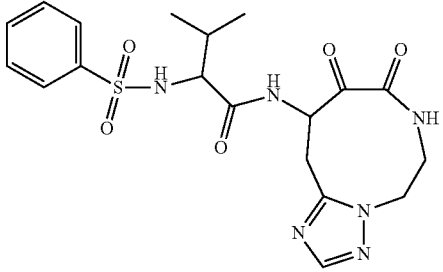 [SMILES: CC(C)C(NS(=O)(=O)c1ccccc1)C(=O)NC1Cc2ncnn2CCNC(=O)C1=O]
54
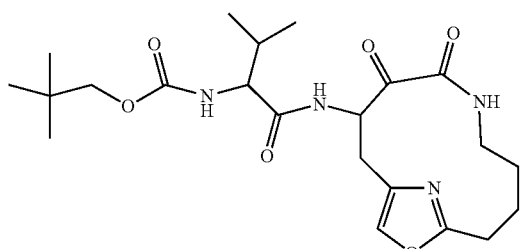
57
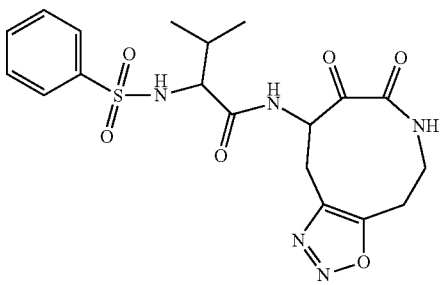 [SMILES: CC(C)C(NS(=O)(=O)c1ccccc1)C(=O)NC1Cc2nnoc2CCNC(=O)C1=O]
58
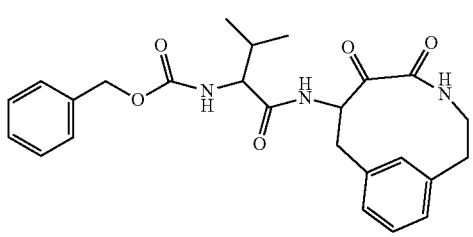 [SMILES: CC(C)C(NC(=O)OCc1ccccc1)C(=O)NC1Cc2cccc(c2)CCNC(=O)C1=O]
61
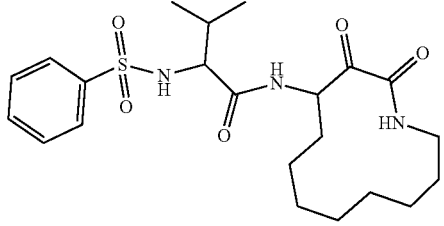 [SMILES: CC(C)C(NS(=O)(=O)c1ccccc1)C(=O)NC1CCCCCCCCNC(=O)C1=O]
62
65

TABLE 9-continued
TwelveRings
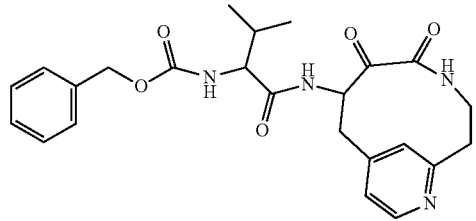 [SMILES: CC(C)C(NC(=O)OCc1ccccc1)C(=O)NC1Cc2ccnc(c2)CCNC(=O)C1=O]
66
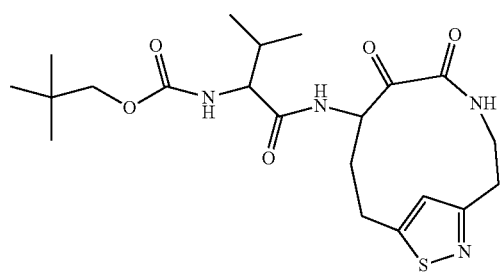 [SMILES: CC(C)C(NC(=O)OCC(C)(C)C)C(=O)NC1CCc2cc(ns2)CCNC(=O)C1=O]
69
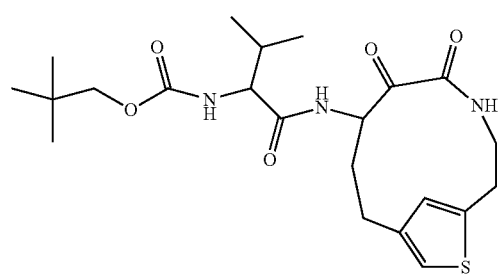 [SMILES: CC(C)C(NC(=O)OCC(C)(C)C)C(=O)NC1CCc2csc(c2)CCNC(=O)C1=O]
70
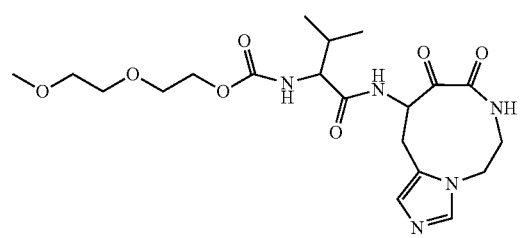 [SMILES: COCCOCCOC(=O)NC(C(=O)NC1Cc2cncn2CCNC(=O)C1=O)C(C)C]
73
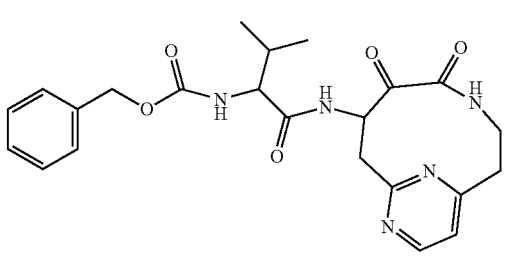 [SMILES: CC(C)C(NC(=O)OCc1ccccc1)C(=O)NC1Cc2nccc(n2)CCNC(=O)C1=O]
74
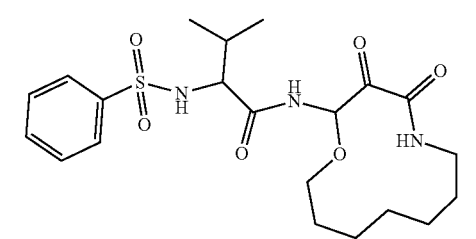 [SMILES: CC(C)C(NS(=O)(=O)c1ccccc1)C(=O)NC1OCCCCCCCNC(=O)C1=O]
77
TABLE 9-continued
TwelveRings
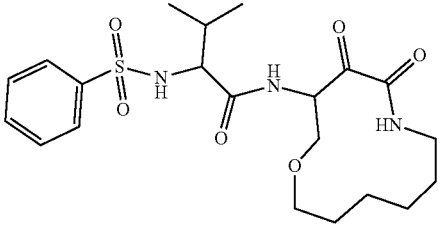 [SMILES: CC(C)C(NS(=O)(=O)c1ccccc1)C(=O)NC1COCCCCCCNC(=O)C1=O]
78
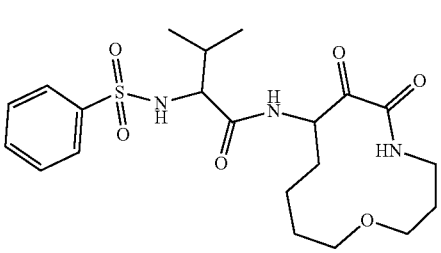 [SMILES: CC(C)C(NS(=O)(=O)c1ccccc1)C(=O)NC1CCCCOCCCNC(=O)C1=O]
81
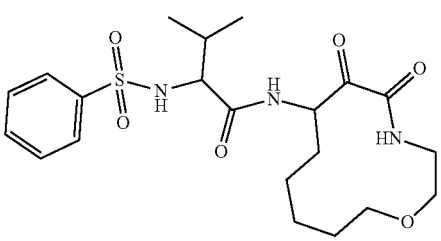 [SMILES: CC(C)C(NS(=O)(=O)c1ccccc1)C(=O)NC1CCCCCOCCNC(=O)C1=O]
82
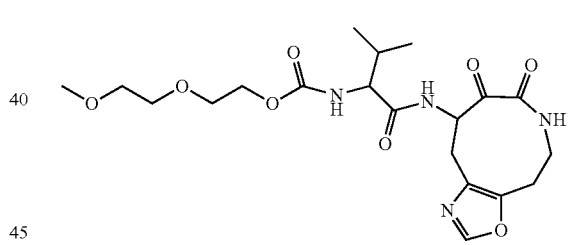
85
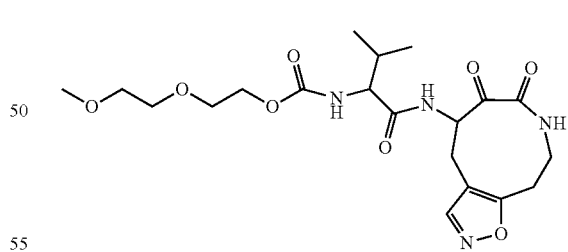
86
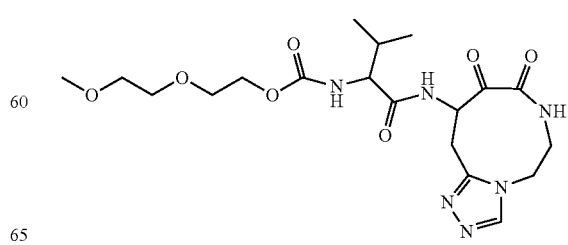
89

TABLE 9-continued
TwelveRings
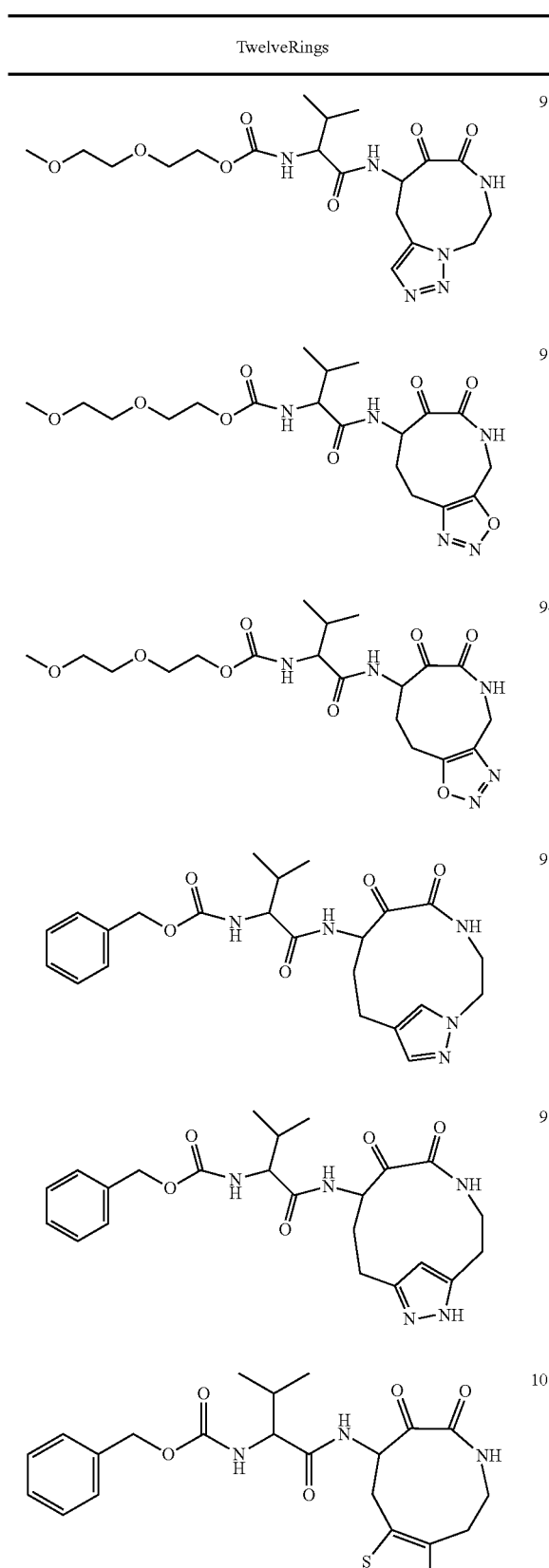
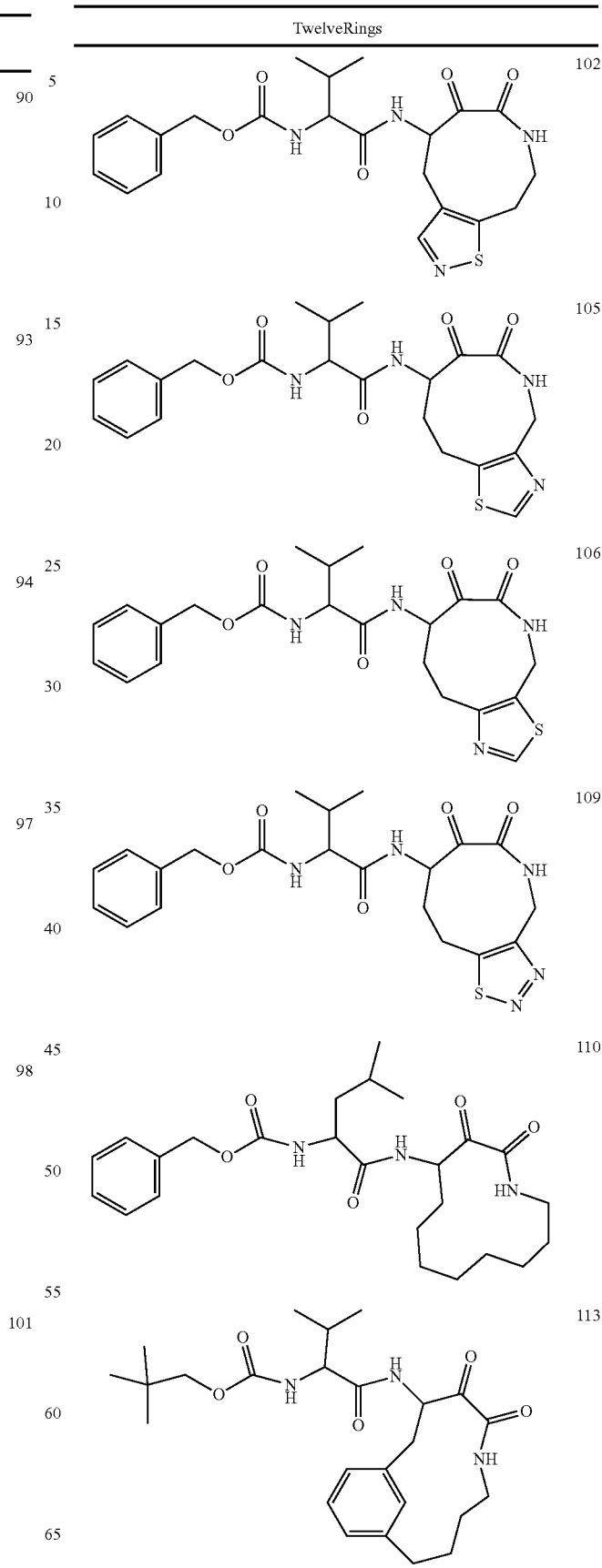

TABLE 9-continued
TwelveRings
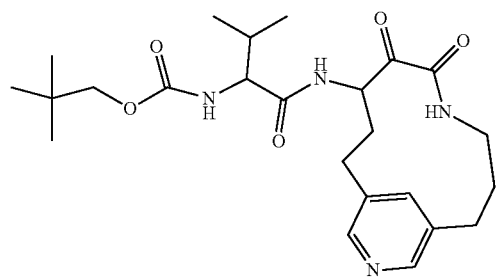 [SMILES: CC(C)C(NC(=O)OCC(C)(C)C)C(=O)NC1CCc2cncc(c2)CCCNC(=O)C1=O]
114
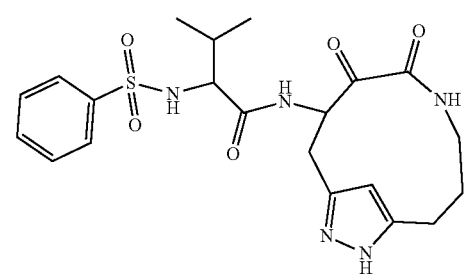 [SMILES: CC(C)C(NS(=O)(=O)c1ccccc1)C(=O)NC1Cc2cc([nH]n2)CCCNC(=O)C1=O]
117
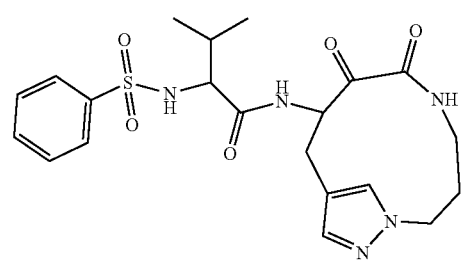 [SMILES: CC(C)C(NS(=O)(=O)c1ccccc1)C(=O)NC1Cc2cnn(c2)CCCNC(=O)C1=O]
118
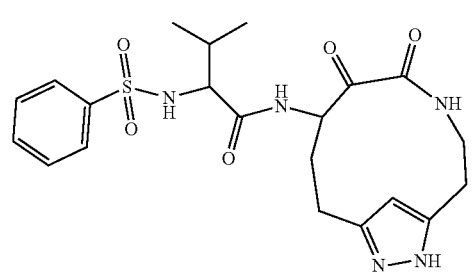 [SMILES: CC(C)C(NS(=O)(=O)c1ccccc1)C(=O)NC1CCc2cc([nH]n2)CCNC(=O)C1=O]
121
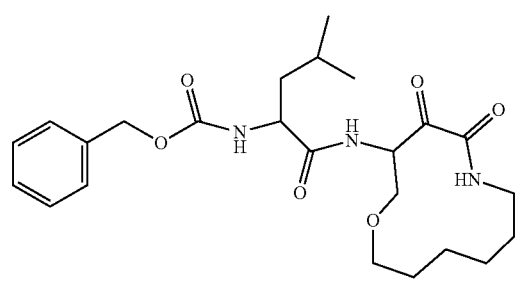 [SMILES: CC(C)CC(NC(=O)OCc1ccccc1)C(=O)NC1COCCCCCCNC(=O)C1=O]
122
TABLE 9-continued
TwelveRings
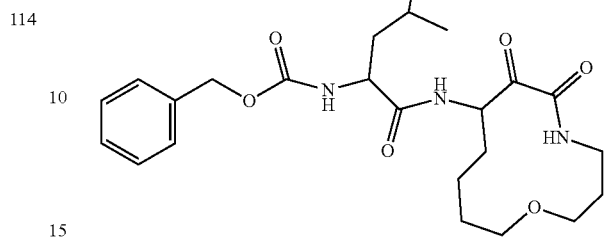
125
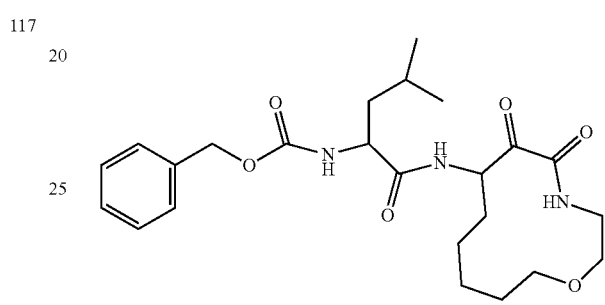
126
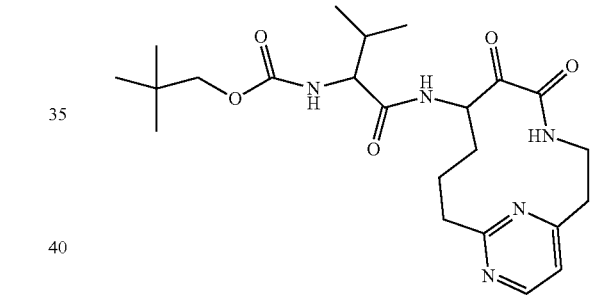
129
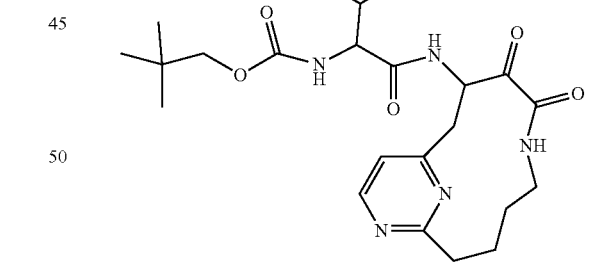
130
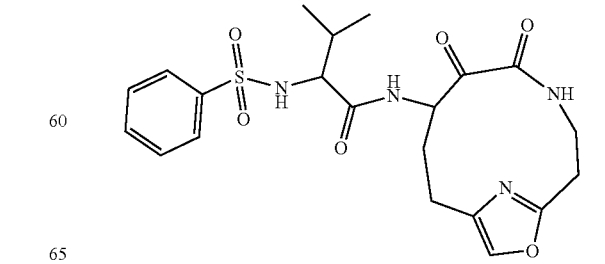
133

TABLE 9-continued
TwelveRings
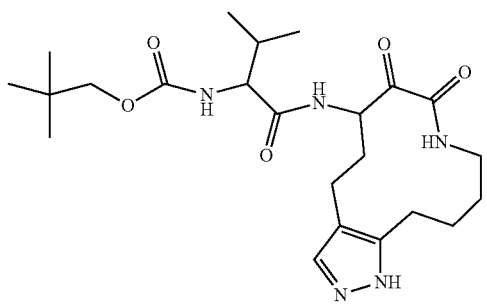 [SMILES: CC(C)C(NC(=O)OCC(C)(C)C)C(=O)NC1CCc2cn[nH]c2CCCCNC(=O)C1=O]
134
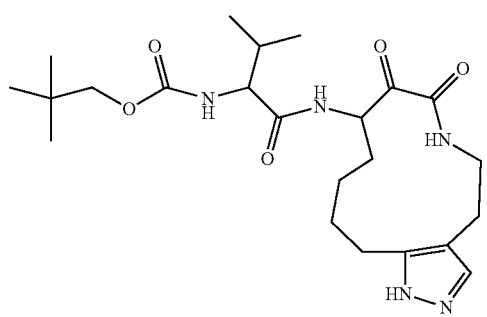 [SMILES: CC(C)C(NC(=O)OCC(C)(C)C)C(=O)NC1CCCCc2[nH]ncc2CCNC(=O)C1=O]
137
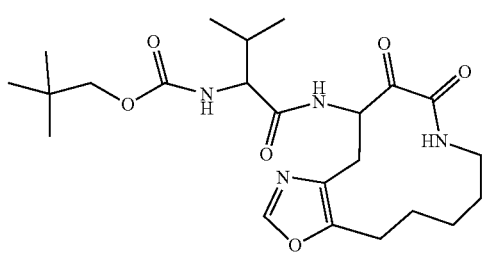 [SMILES: CC(C)C(NC(=O)OCC(C)(C)C)C(=O)NC1Cc2ncoc2CCCCCNC(=O)C1=O]
138
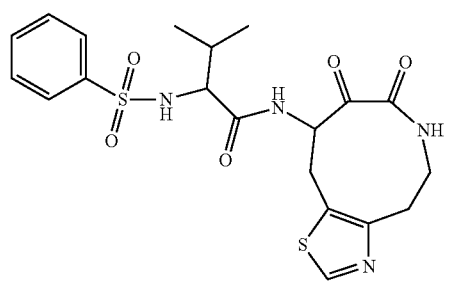 [SMILES: CC(C)C(NS(=O)(=O)c1ccccc1)C(=O)NC1Cc2scnc2CCNC(=O)C1=O]
141
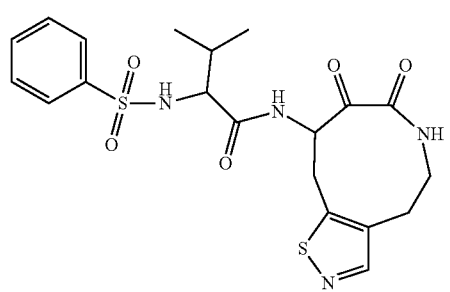 [SMILES: CC(C)C(NS(=O)(=O)c1ccccc1)C(=O)NC1Cc2sncc2CCNC(=O)C1=O]
142
TABLE 9-continued
TwelveRings
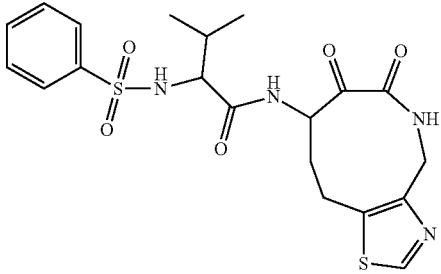 [SMILES: CC(C)C(NS(=O)(=O)c1ccccc1)C(=O)NC1CCc2scnc2CNC(=O)C1=O]
145
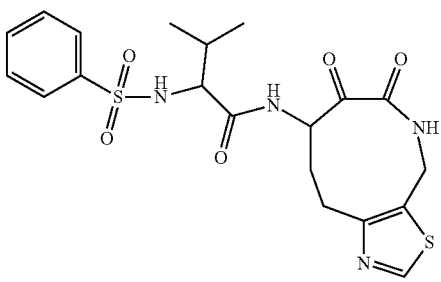 [SMILES: CC(C)C(NS(=O)(=O)c1ccccc1)C(=O)NC1CCc2ncsc2CNC(=O)C1=O]
146
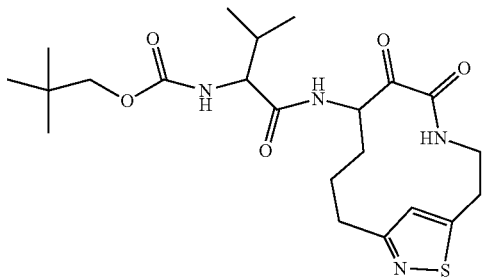 [SMILES: CC(C)C(NC(=O)OCC(C)(C)C)C(=O)NC1CCCc2cc(sn2)CCNC(=O)C1=O]
149
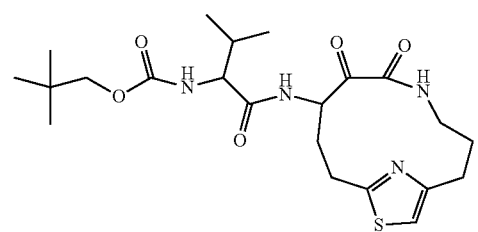 [SMILES: CC(C)C(NC(=O)OCC(C)(C)C)C(=O)NC1CCc2nc(cs2)CCCNC(=O)C1=O]
150
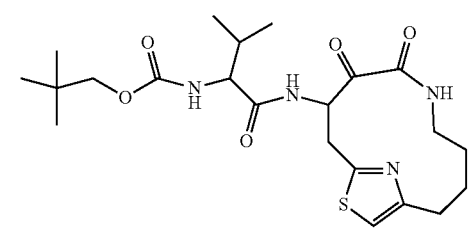 [SMILES: CC(C)C(NC(=O)OCC(C)(C)C)C(=O)NC1Cc2nc(cs2)CCCCNC(=O)C1=O]
153
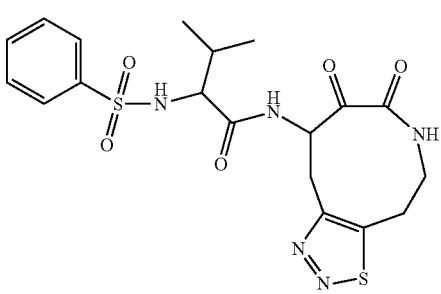 [SMILES: CC(C)C(NS(=O)(=O)c1ccccc1)C(=O)NC1Cc2nnsc2CCNC(=O)C1=O]
154

TABLE 9-continued
TwelveRings
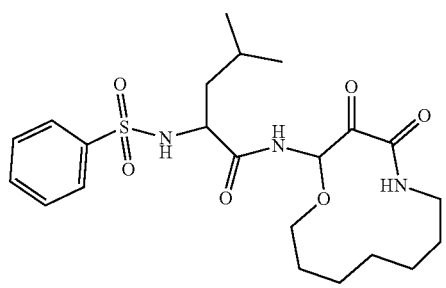 [SMILES: CC(C)CC(NS(=O)(=O)c1ccccc1)C(=O)NC1OCCCCCCCNC(=O)C1=O]
157
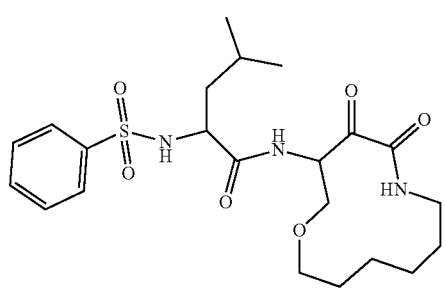 [SMILES: CC(C)CC(NS(=O)(=O)c1ccccc1)C(=O)NC1COCCCCCCNC(=O)C1=O]
158
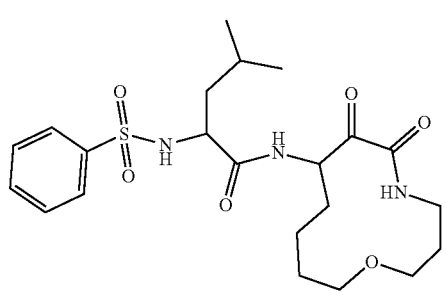 [SMILES: CC(C)CC(NS(=O)(=O)c1ccccc1)C(=O)NC1CCCCOCCCNC(=O)C1=O]
161
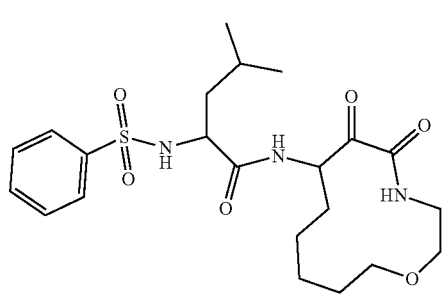 [SMILES: CC(C)CC(NS(=O)(=O)c1ccccc1)C(=O)NC1CCCCCOCCNC(=O)C1=O]
162
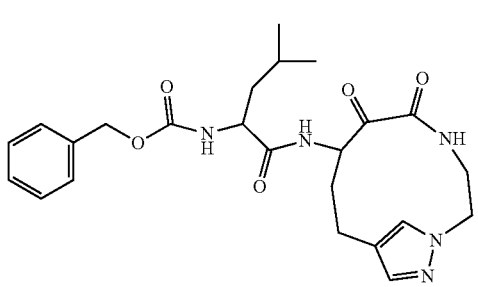 [SMILES: CC(C)CC(NC(=O)OCc1ccccc1)C(=O)NC1CCc2cnn(c2)CCNC(=O)C1=O]
165
TABLE 9-continued
TwelveRings
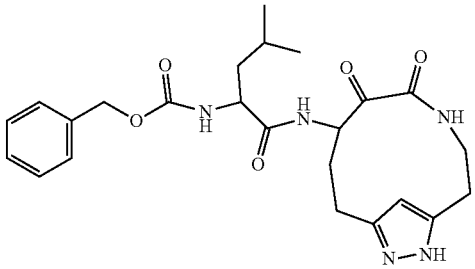 [SMILES: CC(C)CC(NC(=O)OCc1ccccc1)C(=O)NC1CCc2cc([nH]n2)CCNC(=O)C1=O]
166
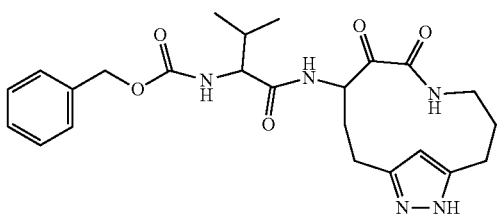 [SMILES: CC(C)C(NC(=O)OCc1ccccc1)C(=O)NC1CCc2cc([nH]n2)CCCNC(=O)C1=O]
169
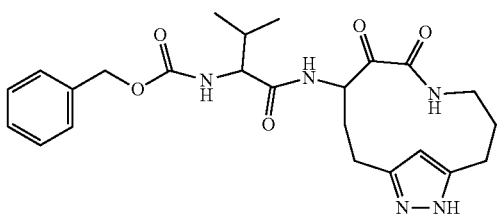 [SMILES: CC(C)C(NC(=O)OCc1ccccc1)C(=O)NC1CCc2cc([nH]n2)CCCNC(=O)C1=O]
170
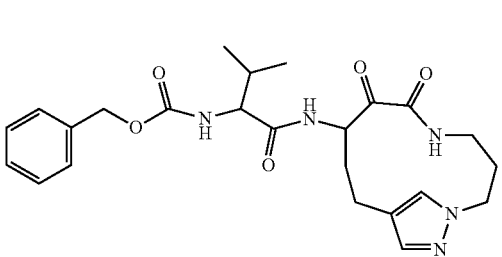 [SMILES: CC(C)C(NC(=O)OCc1ccccc1)C(=O)NC1CCc2cnn(c2)CCCNC(=O)C1=O]
173
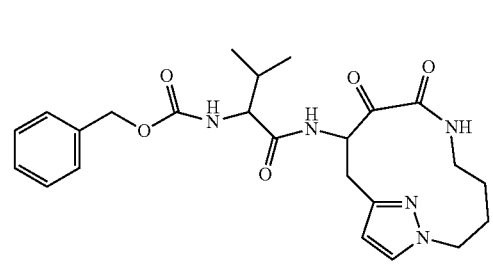 [SMILES: CC(C)C(NC(=O)OCc1ccccc1)C(=O)NC1Cc2ccn(n2)CCCCNC(=O)C1=O]
174
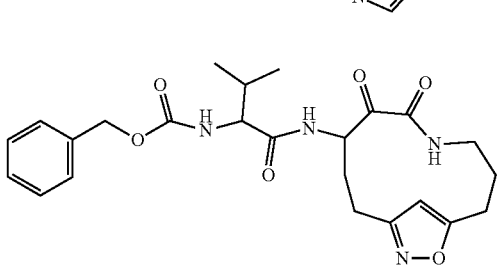
177

TABLE 9-continued
TwelveRings
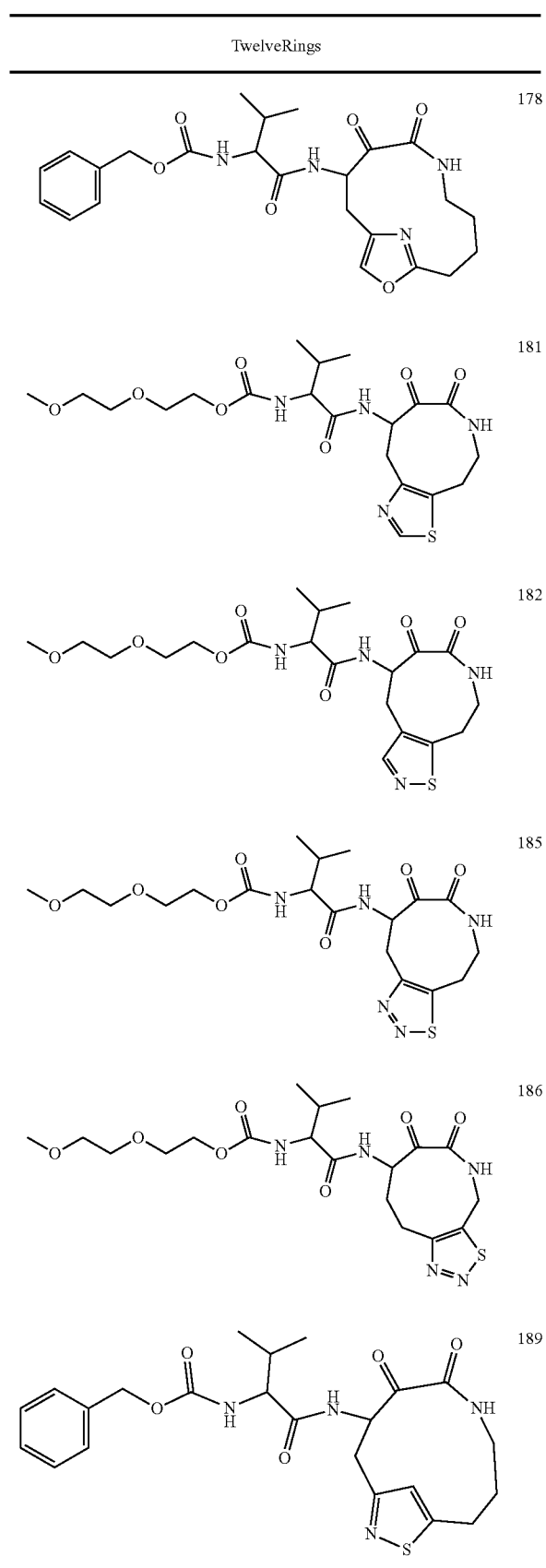

TABLE 9-continued
TwelveRings
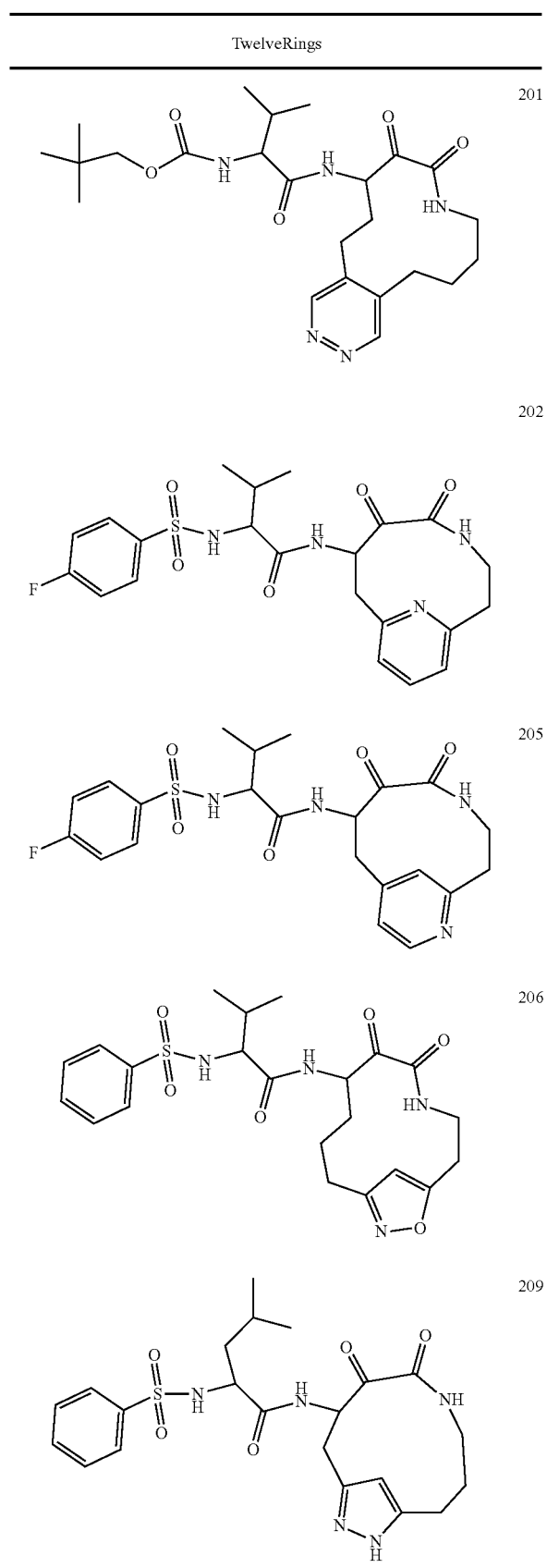
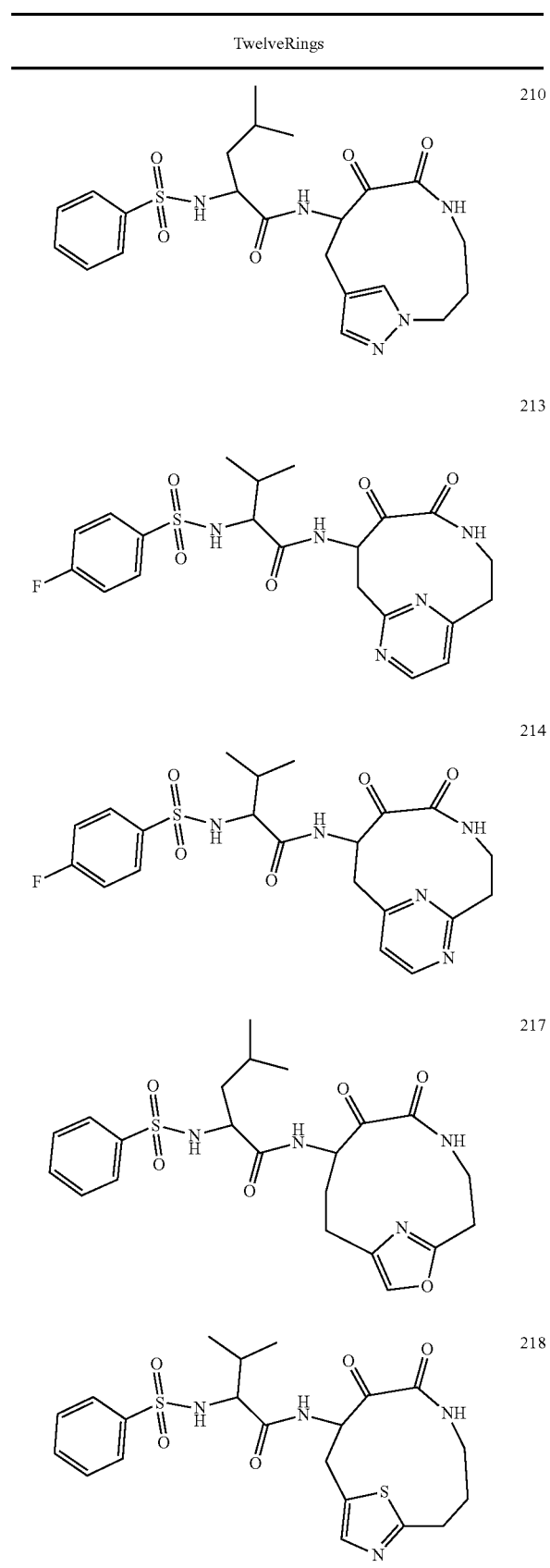

TABLE 9-continued
TwelveRings
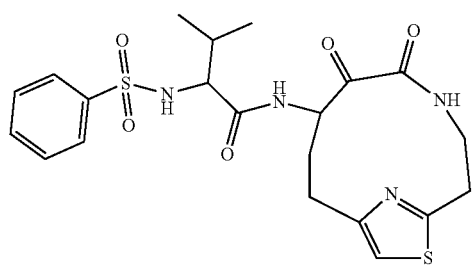 [SMILES: CC(C)C(NS(=O)(=O)c1ccccc1)C(=O)NC1CCc2csc(n2)CCNC(=O)C1=O] 221
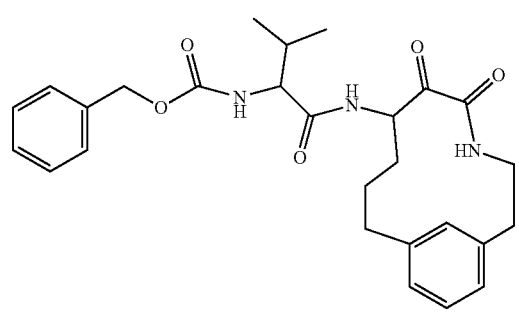 [SMILES: CC(C)C(NC(=O)OCc1ccccc1)C(=O)NC1CCCc2cccc(c2)CCNC(=O)C1=O] 222
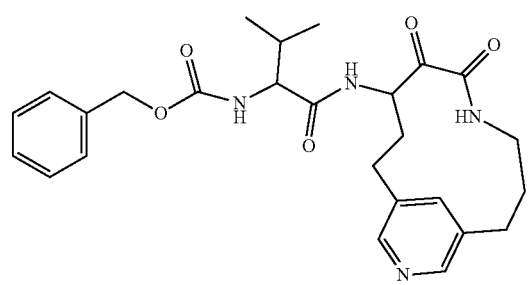 [SMILES: CC(C)C(NC(=O)OCc1ccccc1)C(=O)NC1CCc2cncc(c2)CCCNC(=O)C1=O] 225
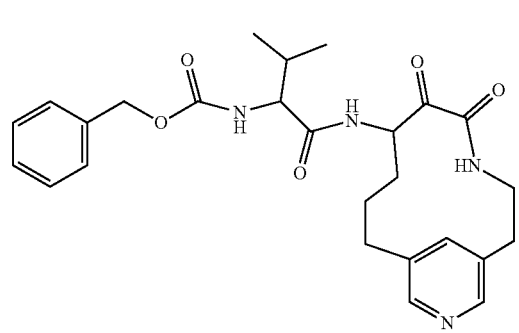 [SMILES: CC(C)C(NC(=O)OCc1ccccc1)C(=O)NC1CCCc2cncc(c2)CCNC(=O)C1=O] 226
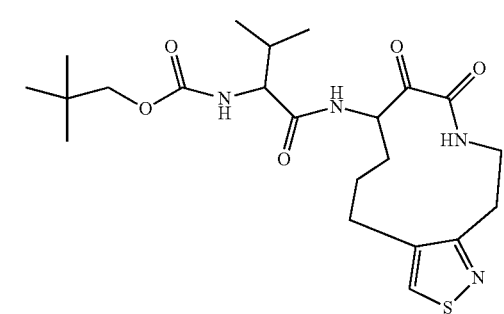 [SMILES: CC(C)C(NC(=O)OCC(C)(C)C)C(=O)NC1CCCc2csnc2CCNC(=O)C1=O] 229
TABLE 9-continued
TwelveRings
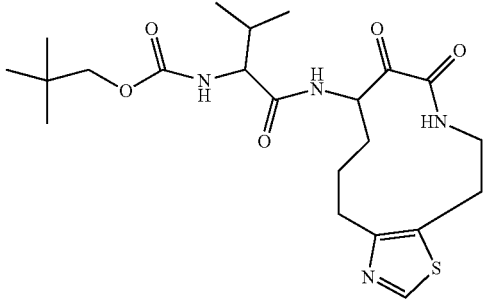 [SMILES: CC(C)C(NC(=O)OCC(C)(C)C)C(=O)NC1CCCc2ncsc2CCNC(=O)C1=O] 230
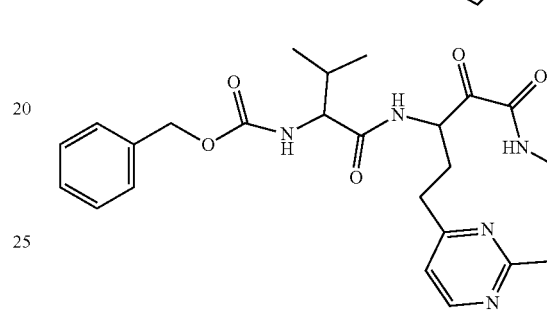 233
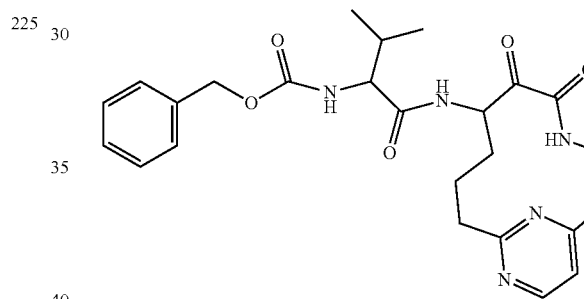 234
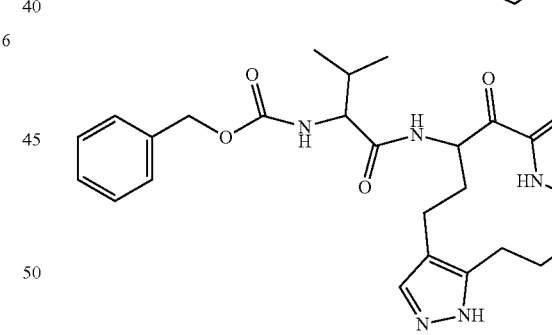 237
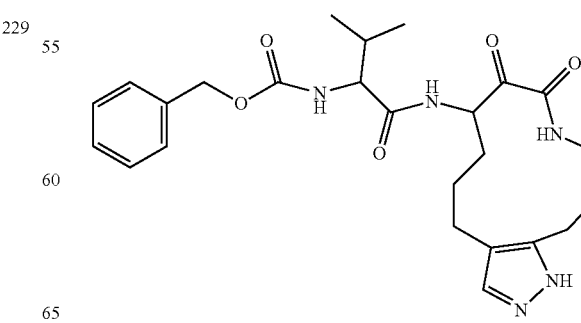 238

TABLE 9-continued
TwelveRings
241 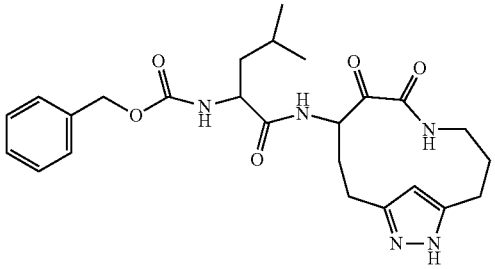 [SMILES: CC(C)CC(NC(=O)OCc1ccccc1)C(=O)NC1CCc2cc([nH]n2)CCCNC(=O)C1=O]
242 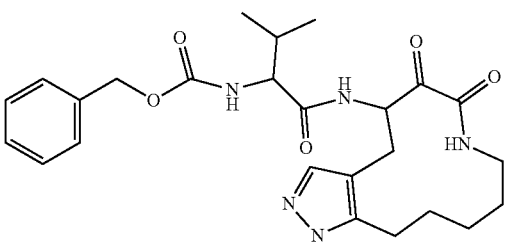 [SMILES: CC(C)C(NC(=O)OCc1ccccc1)C(=O)NC1Cc2ncoc2CCCCCNC(=O)C1=O]
245 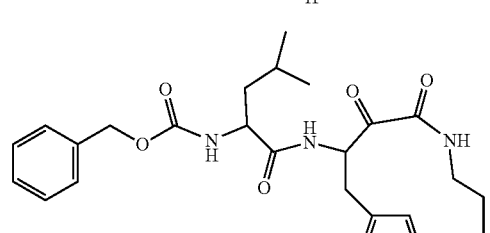
246 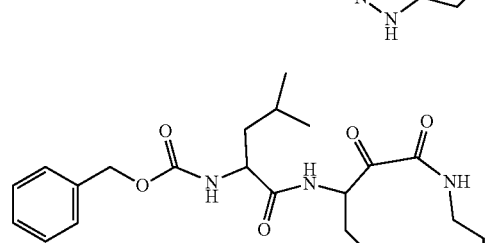
249 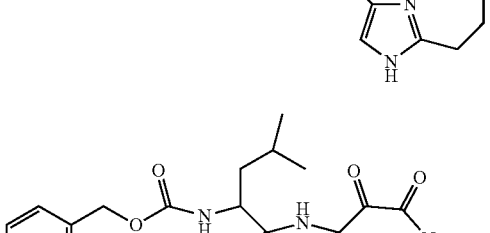
250 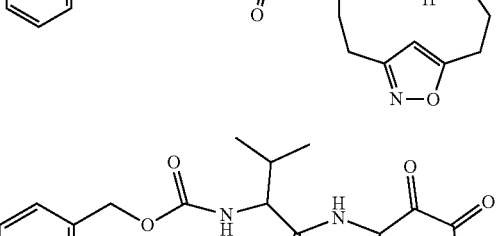
TABLE 9-continued
TwelveRings
253 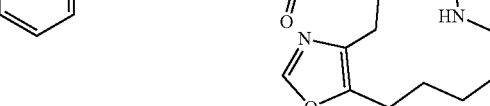
254 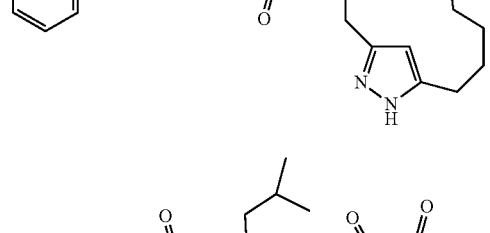
257 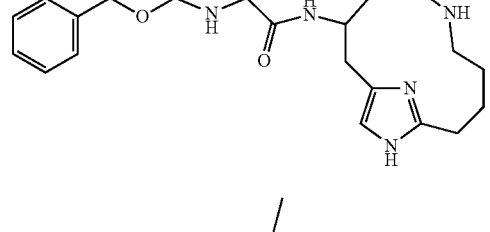
258 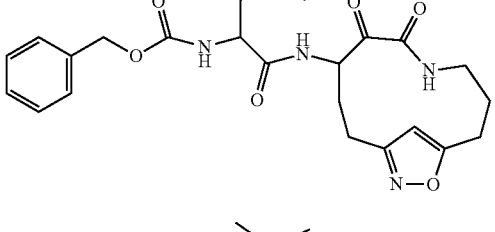
261 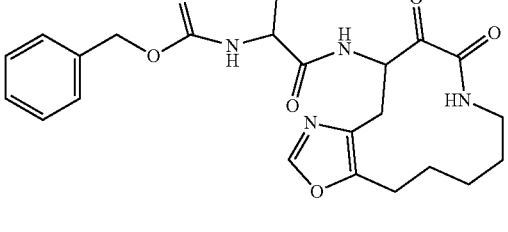

TABLE 9-continued
TwelveRings
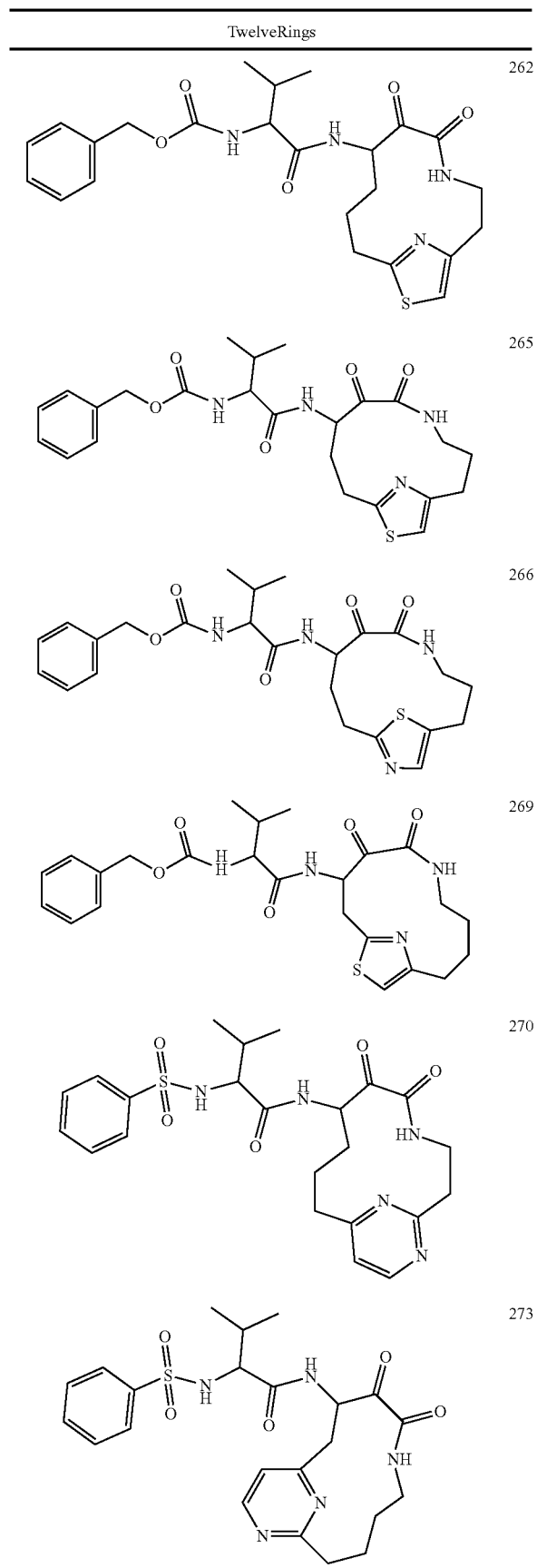
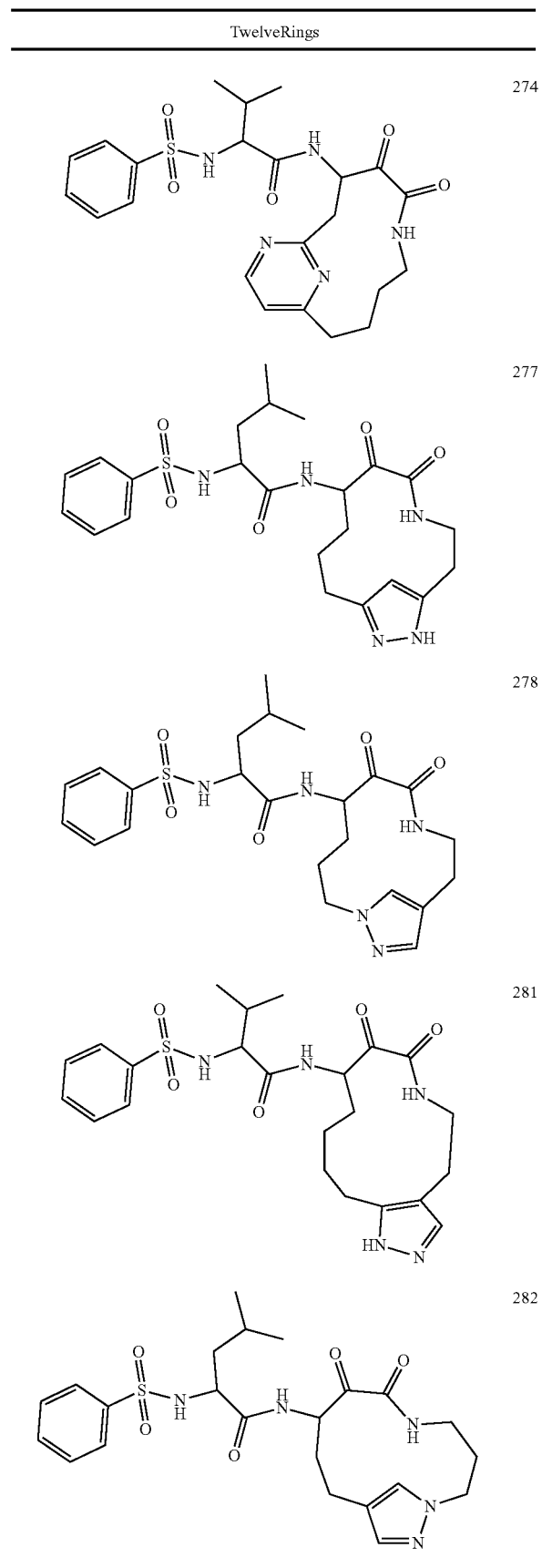

TABLE 9-continued
TwelveRings
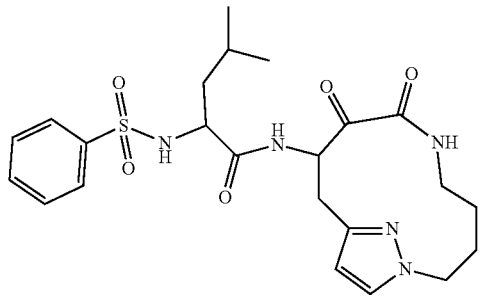 [SMILES: CC(C)CC(NS(=O)(=O)c1ccccc1)C(=O)NC1Cc2ccn(n2)CCCCNC(=O)C1=O]
285
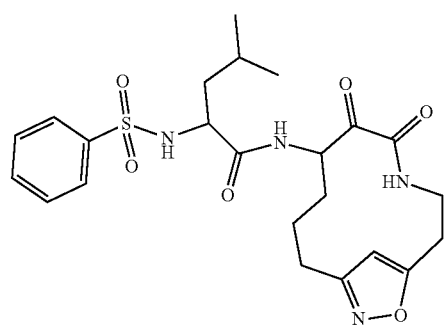 [SMILES: CC(C)CC(NS(=O)(=O)c1ccccc1)C(=O)NC1CCCc2cc(on2)CCNC(=O)C1=O]
286
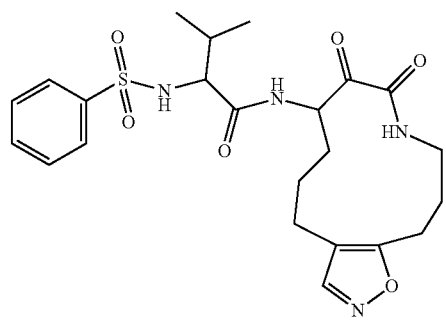 [SMILES: CC(C)C(NS(=O)(=O)c1ccccc1)C(=O)NC1CCCc2cnoc2CCCNC(=O)C1=O]
289
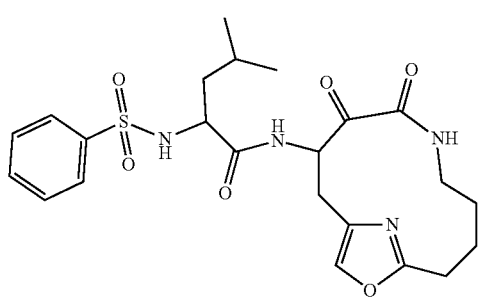 [SMILES: CC(C)CC(NS(=O)(=O)c1ccccc1)C(=O)NC1Cc2coc(n2)CCCCNC(=O)C1=O]
290
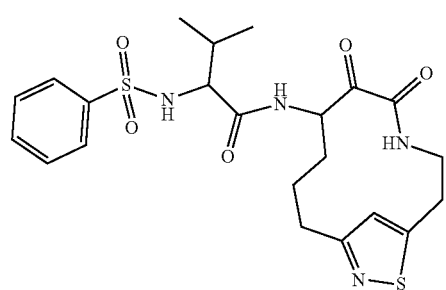 [SMILES: CC(C)C(NS(=O)(=O)c1ccccc1)C(=O)NC1CCCc2cc(sn2)CCNC(=O)C1=O]
293
TABLE 9-continued
TwelveRings
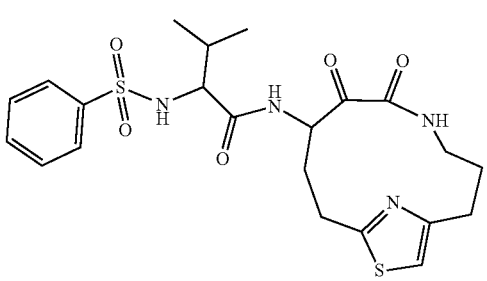 [SMILES: CC(C)C(NS(=O)(=O)c1ccccc1)C(=O)NC1CCc2nc(cs2)CCCNC(=O)C1=O]
294
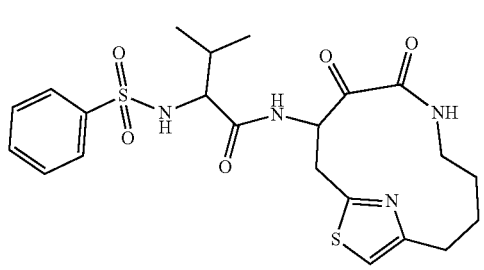 [SMILES: CC(C)C(NS(=O)(=O)c1ccccc1)C(=O)NC1Cc2nc(cs2)CCCCNC(=O)C1=O]
297
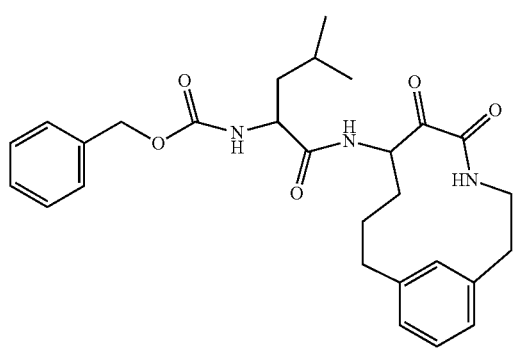 [SMILES: CC(C)CC(NC(=O)OCc1ccccc1)C(=O)NC1CCCc2cccc(c2)CCNC(=O)C1=O]
298
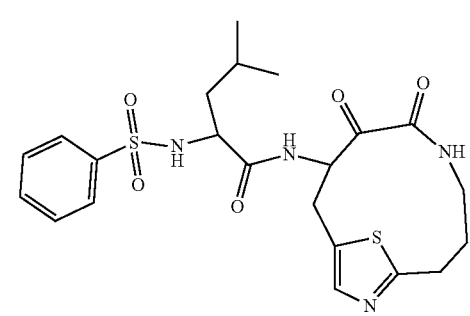 [SMILES: CC(C)CC(NS(=O)(=O)c1ccccc1)C(=O)NC1CC2=CN=C(CCCNC(=O)C1=O)S2]
301
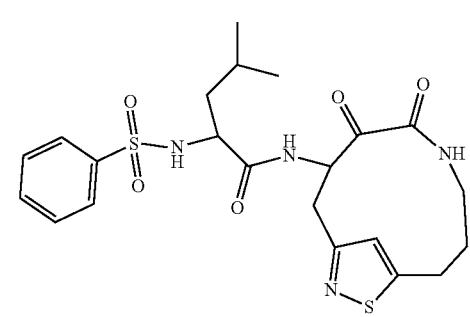 [SMILES: CC(C)CC(NS(=O)(=O)c1ccccc1)C(=O)NC1Cc2cc(sn2)CCCNC(=O)C1=O]
302

TABLE 9-continued
TwelveRings
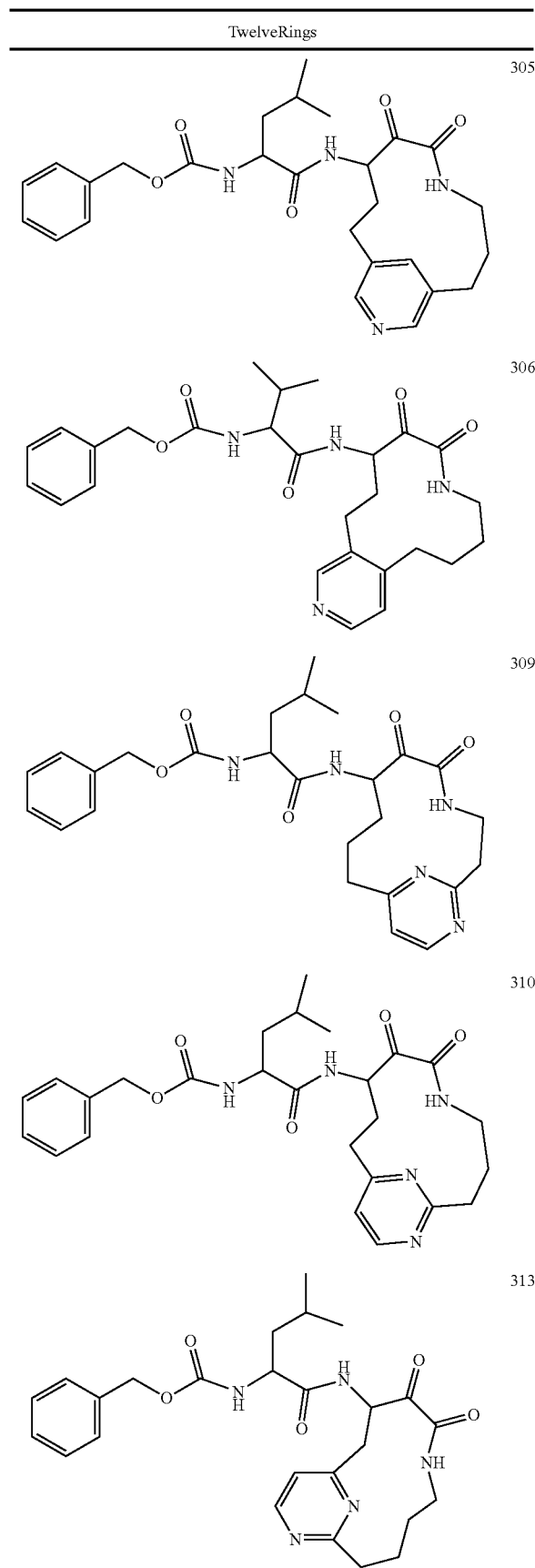
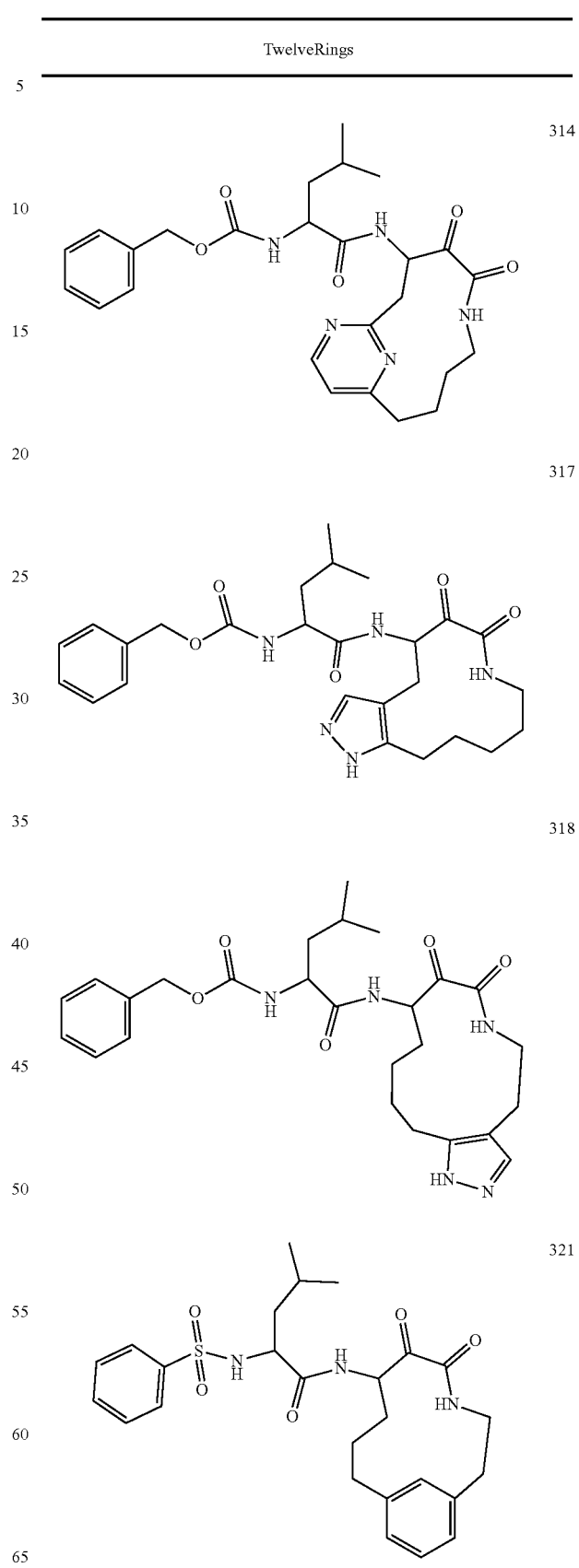

TABLE 9-continued
TwelveRings
322
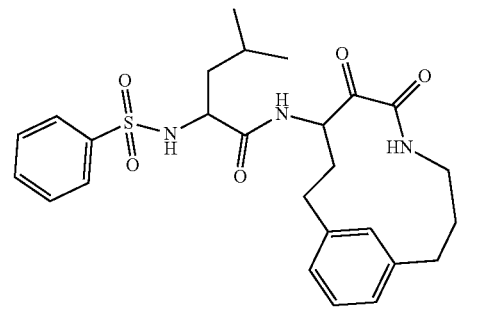 [SMILES: CC(C)CC(NS(=O)(=O)c1ccccc1)C(=O)NC1CCc2cccc(c2)CCCNC(=O)C1=O]
325
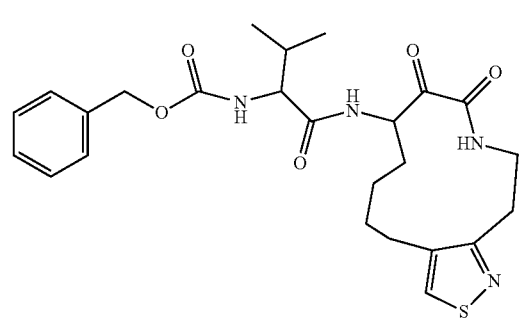 [SMILES: CC(C)C(NC(=O)OCc1ccccc1)C(=O)NC1CCCCc2csnc2CCNC(=O)C1=O]
326
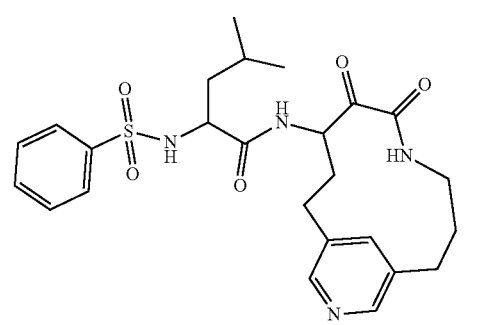 [SMILES: CC(C)CC(NS(=O)(=O)c1ccccc1)C(=O)NC1CCc2cncc(c2)CCCNC(=O)C1=O]
329
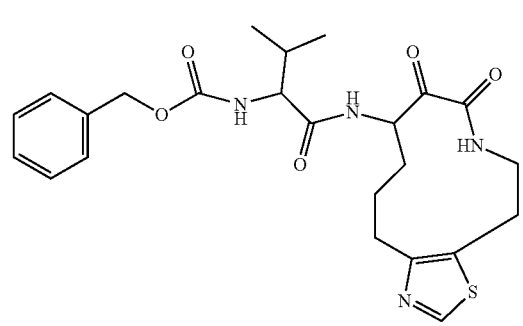 [SMILES: CC(C)C(NC(=O)OCc1ccccc1)C(=O)NC1CCCc2ncsc2CCNC(=O)C1=O]
330
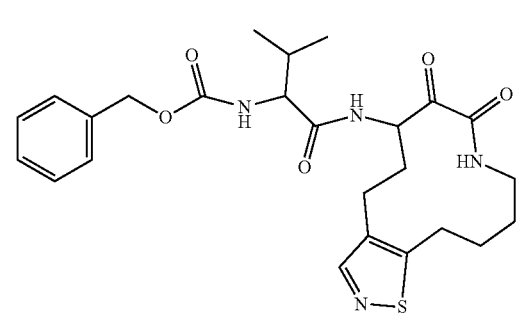 [SMILES: CC(C)C(NC(=O)OCc1ccccc1)C(=O)NC1CCc2cnsc2CCCCNC(=O)C1=O]
TABLE 9-continued
TwelveRings
333
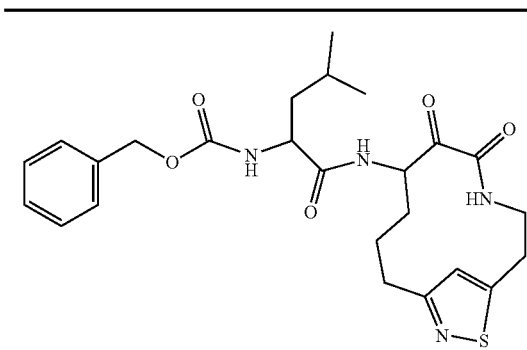
334
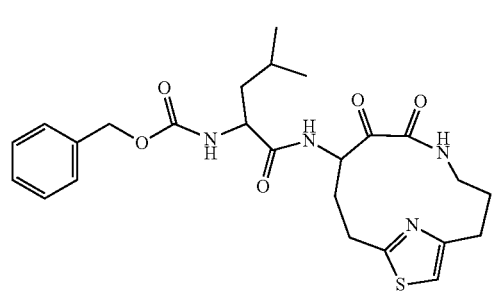 [SMILES: CC(C)CC(NC(=O)OCc1ccccc1)C(=O)NC1CCc2nc(cs2)CCCNC(=O)C1=O]
337
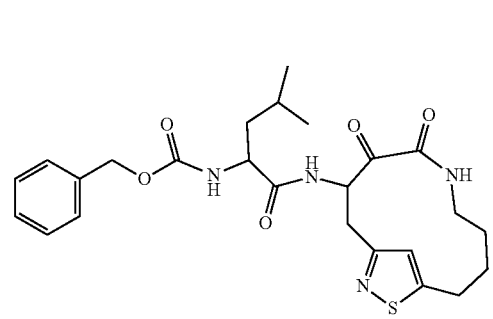 [SMILES: CC(C)CC(NC(=O)OCc1ccccc1)C(=O)NC1Cc2cc(sn2)CCCCNC(=O)C1=O]
338
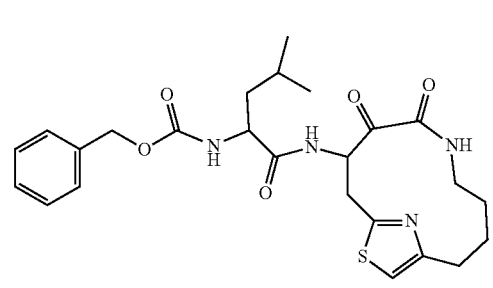 [SMILES: CC(C)CC(NC(=O)OCc1ccccc1)C(=O)NC1Cc2nc(cs2)CCCCNC(=O)C1=O]
341
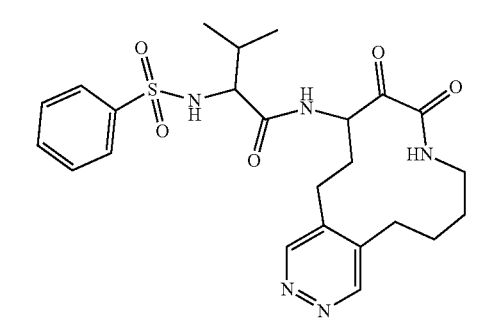 [SMILES: CC(C)C(NS(=O)(=O)c1ccccc1)C(=O)NC1CCc2cnncc2CCCCNC(=O)C1=O]

TABLE 9-continued
TwelveRings
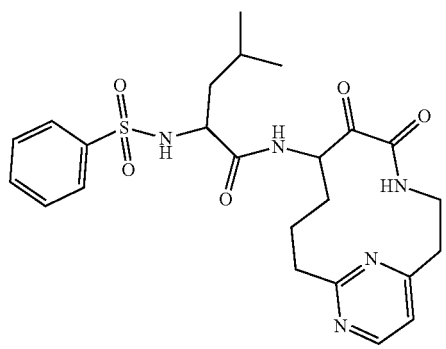 [SMILES: CC(C)CC(NS(=O)(=O)c1ccccc1)C(=O)NC1CCCc2nccc(n2)CCNC(=O)C1=O]
342
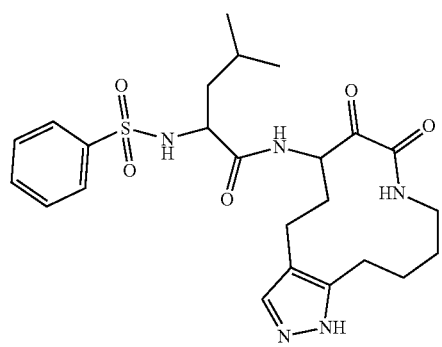 [SMILES: CC(C)CC(NS(=O)(=O)c1ccccc1)C(=O)NC1CCc2cn[nH]c2CCCCNC(=O)C1=O]
345
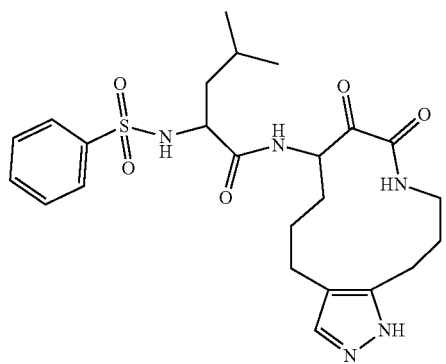 [SMILES: CC(C)CC(NS(=O)(=O)c1ccccc1)C(=O)NC1CCCc2cn[nH]c2CCCNC(=O)C1=O]
346
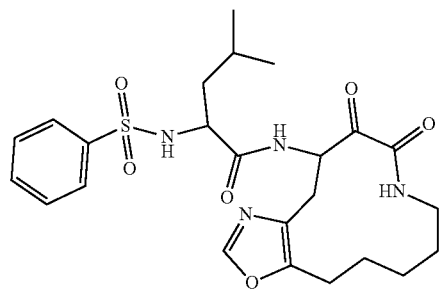 [SMILES: CC(C)CC(NS(=O)(=O)c1ccccc1)C(=O)NC1Cc2ncoc2CCCCCNC(=O)C1=O]
349
TABLE 9-continued
TwelveRings
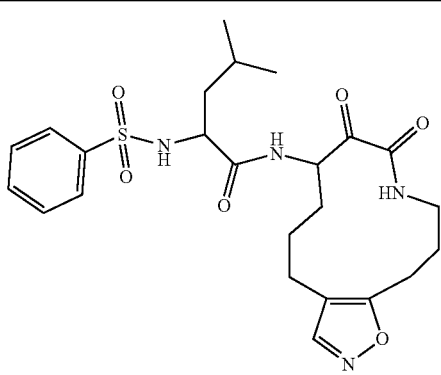
350
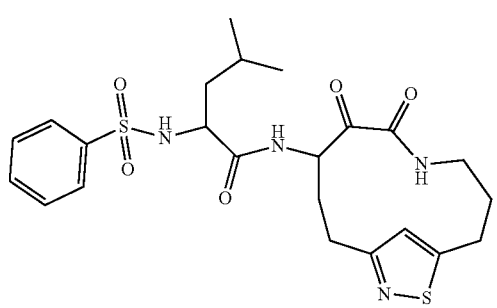 [SMILES: CC(C)CC(NS(=O)(=O)c1ccccc1)C(=O)NC1CCc2cc(sn2)CCCNC(=O)C1=O]
353
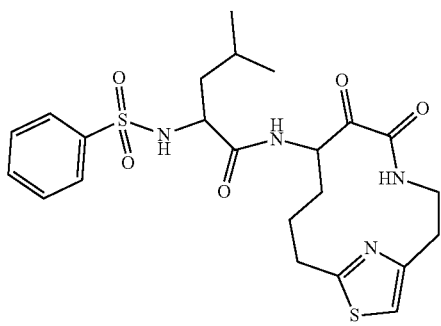 [SMILES: CC(C)CC(NS(=O)(=O)c1ccccc1)C(=O)NC1CCCc2nc(cs2)CCNC(=O)C1=O]
354
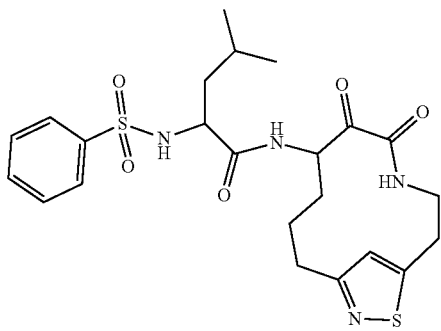 [SMILES: CC(C)CC(NS(=O)(=O)c1ccccc1)C(=O)NC1CCCc2cc(sn2)CCNC(=O)C1=O]
357

TABLE 9-continued
TwelveRings
358
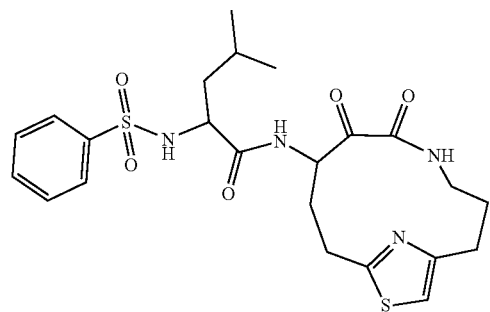 [SMILES: CC(C)CC(NS(=O)(=O)c1ccccc1)C(=O)NC1CCc2nc(cs2)CCCNC(=O)C1=O]
361
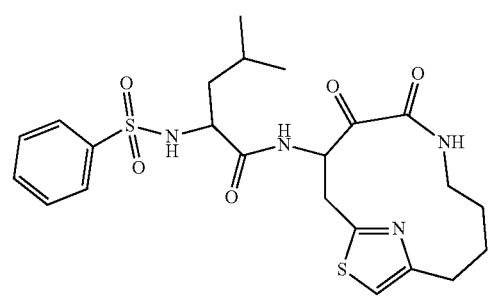 [SMILES: CC(C)CC(NS(=O)(=O)c1ccccc1)C(=O)NC1Cc2nc(cs2)CCCCNC(=O)C1=O]
362
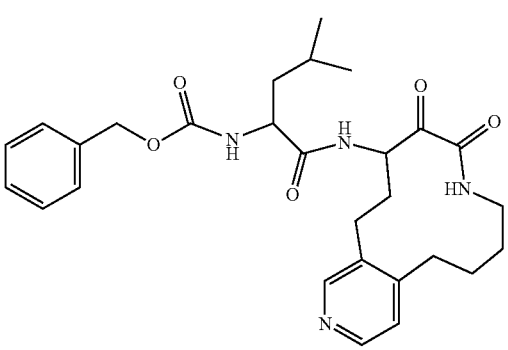 [SMILES: CC(C)CC(NC(=O)OCc1ccccc1)C(=O)NC1CCc2cnccc2CCCCNC(=O)C1=O]
365
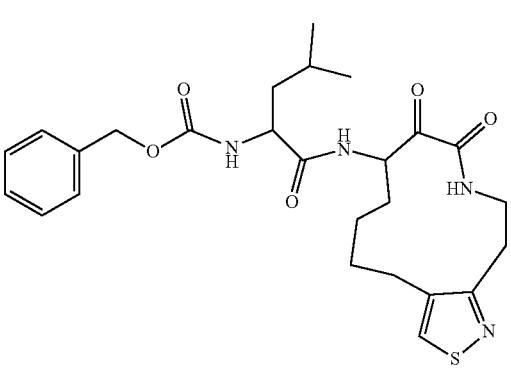 [SMILES: CC(C)CC(NC(=O)OCc1ccccc1)C(=O)NC1CCCCc2csnc2CCNC(=O)C1=O]
TABLE 9-continued
TwelveRings
366
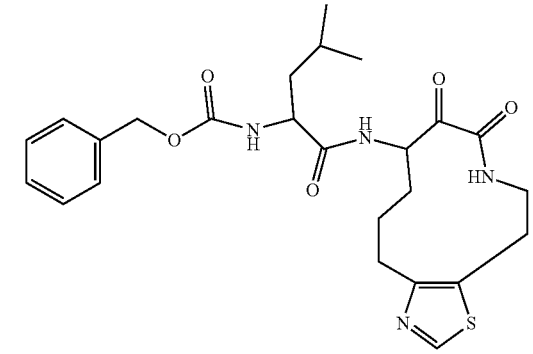 [SMILES: CC(C)CC(NC(=O)OCc1ccccc1)C(=O)NC1CCCc2ncsc2CCNC(=O)C1=O]
369
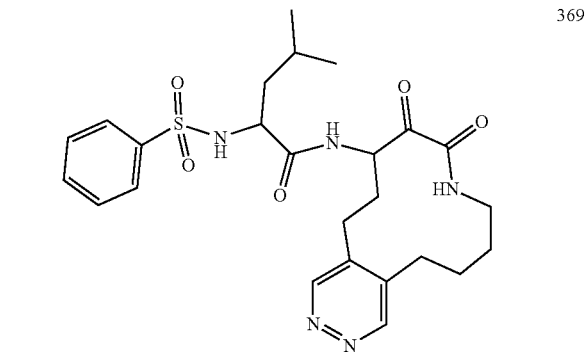
370
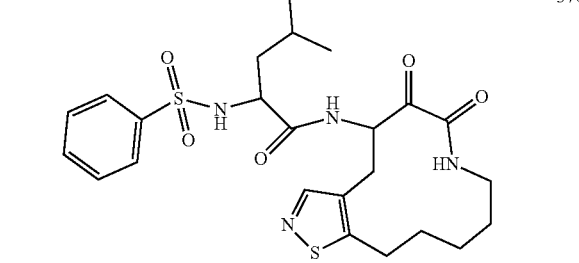
373
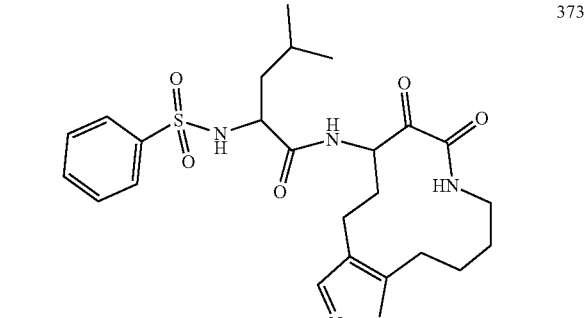
374
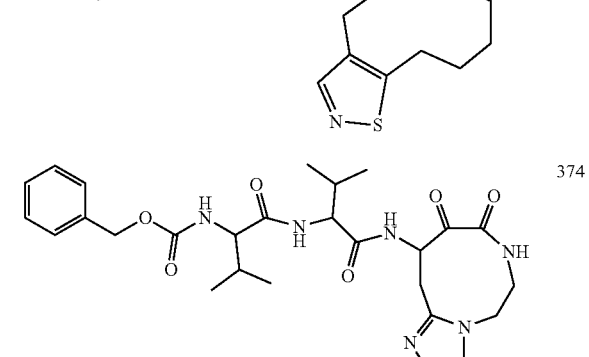

TABLE 9-continued
TwelveRings
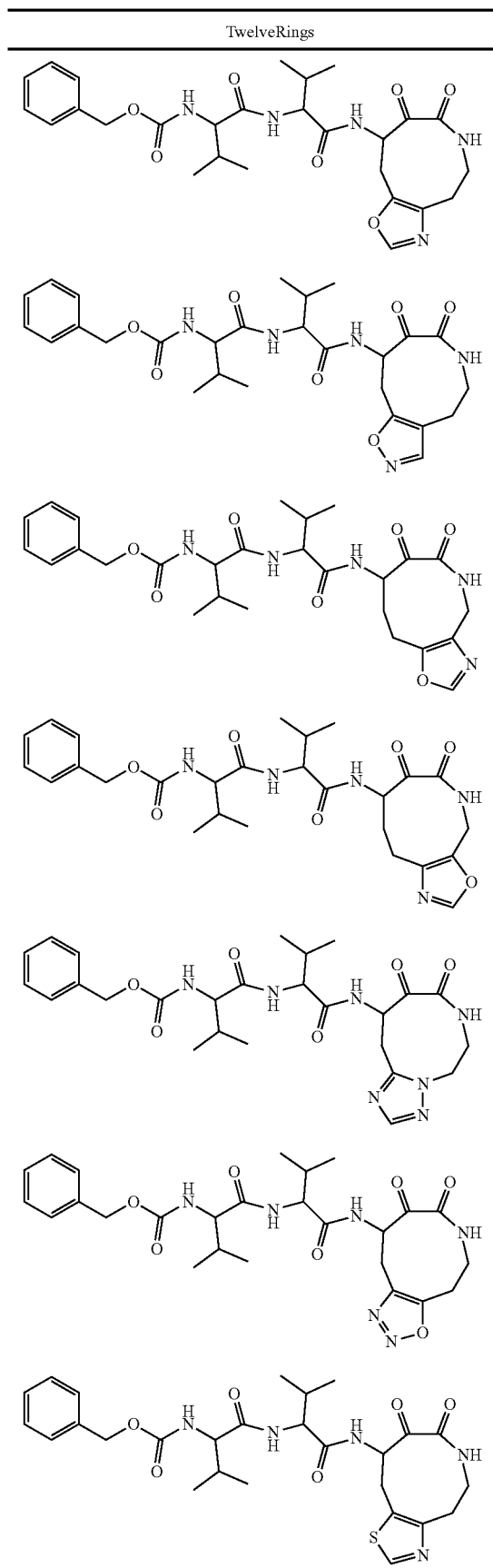
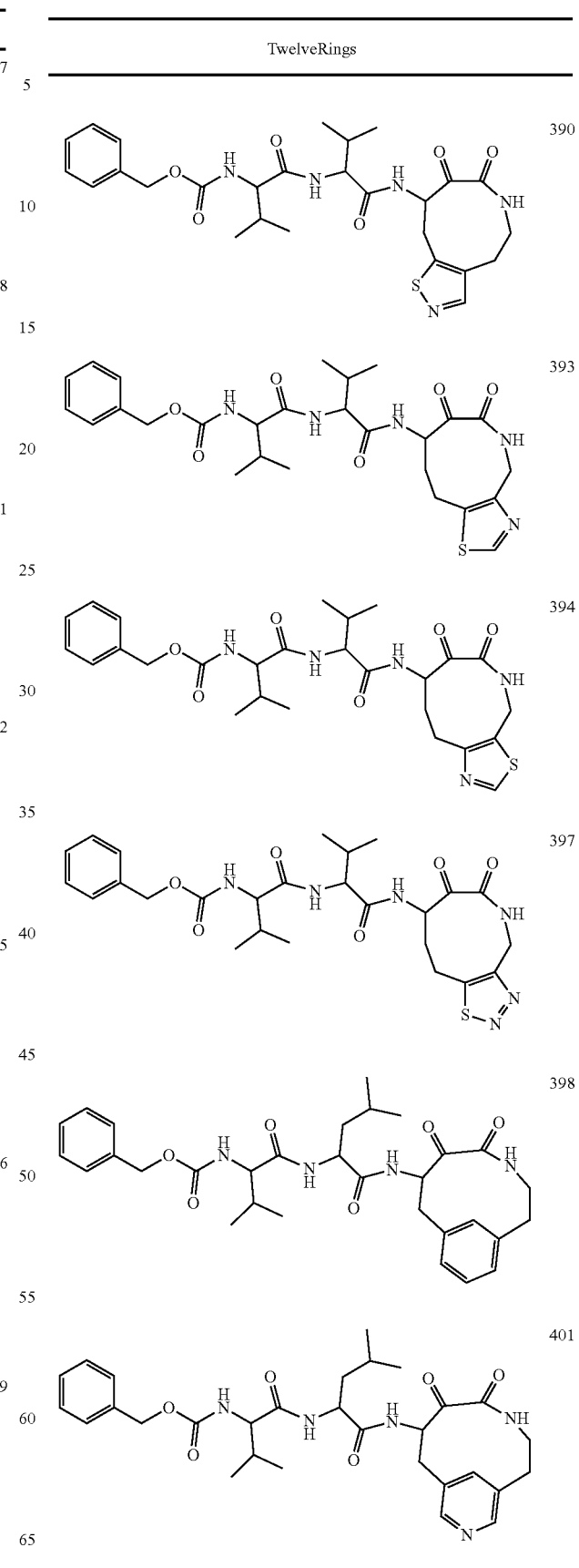

TABLE 9-continued
TwelveRings
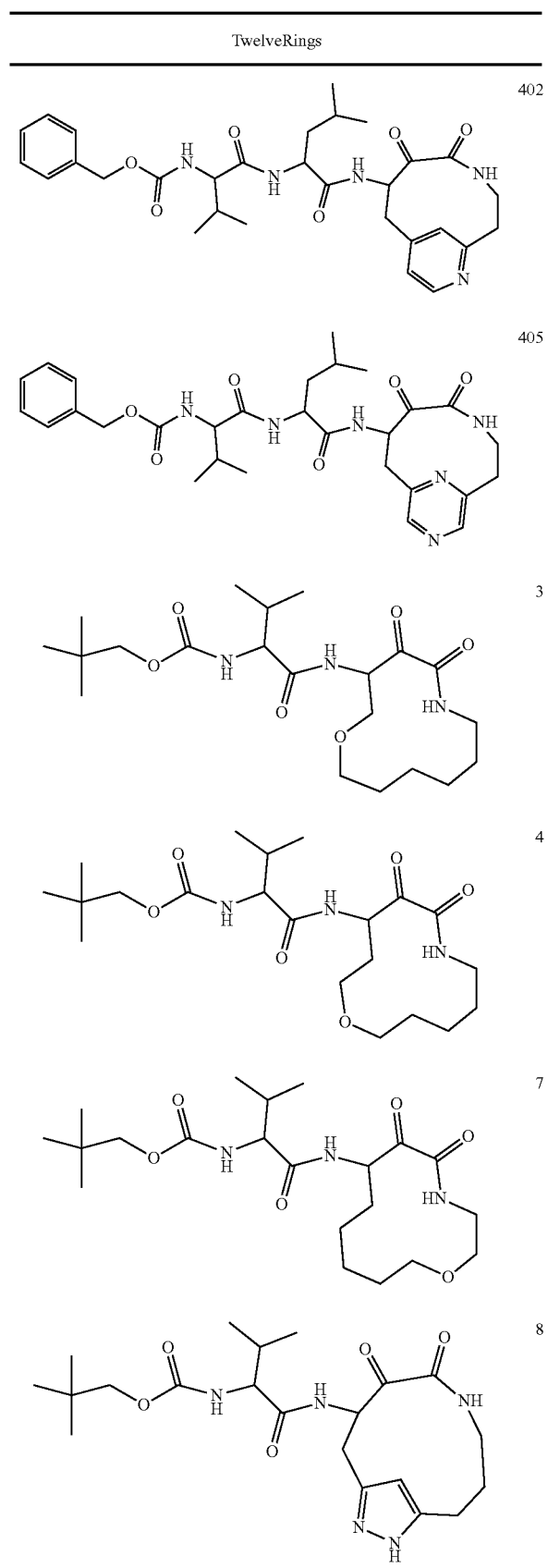
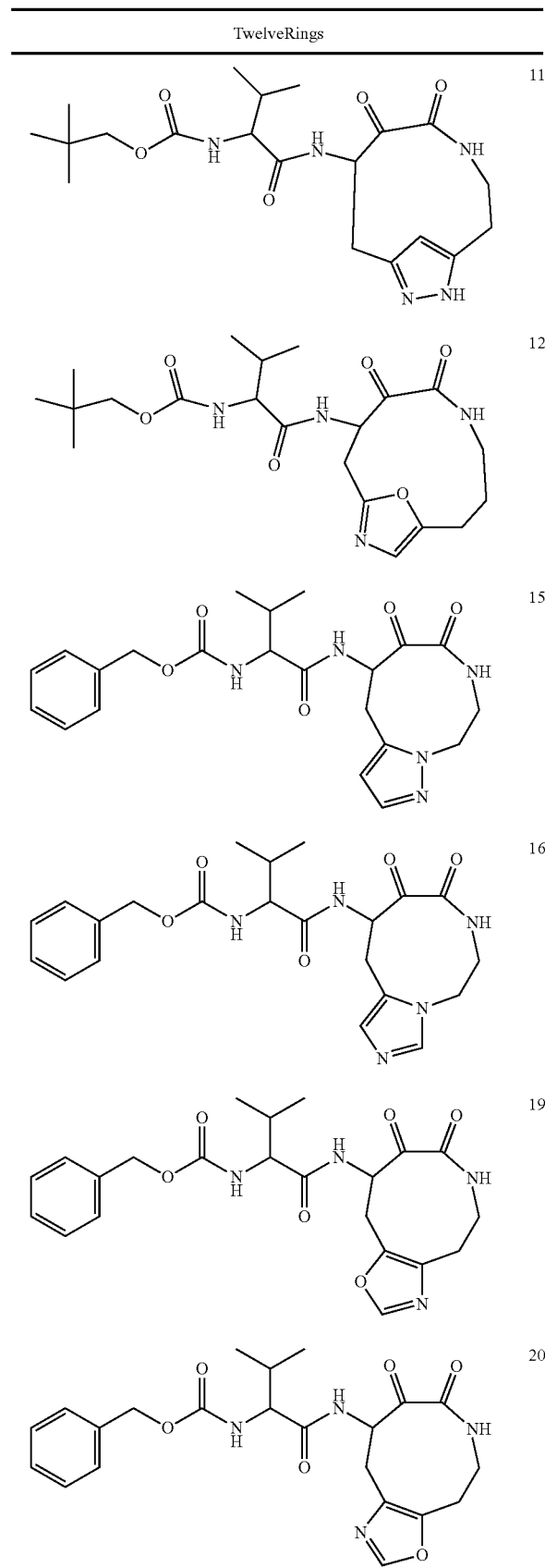

TABLE 9-continued
TwelveRings
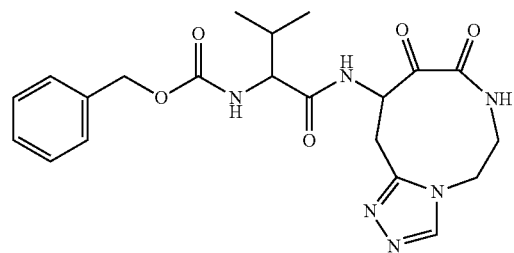 [SMILES: CC(C)C(NC(=O)OCc1ccccc1)C(=O)NC1Cc2nncn2CCNC(=O)C1=O] 23
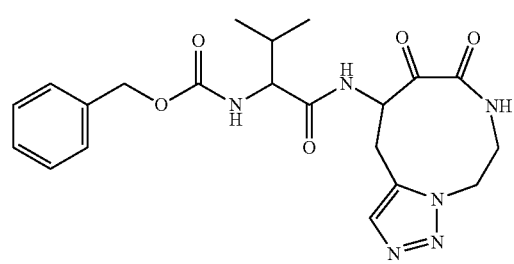 [SMILES: CC(C)C(NC(=O)OCc1ccccc1)C(=O)NC1Cc2cnnn2CCNC(=O)C1=O] 24
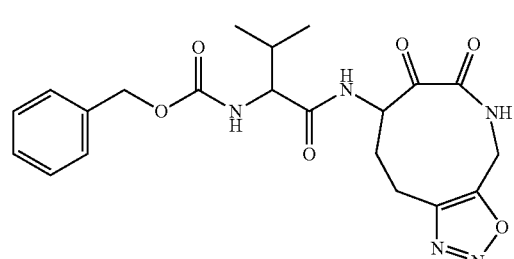 27
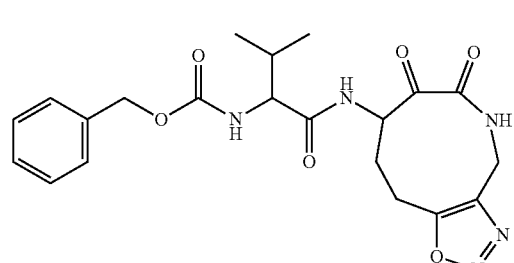 28
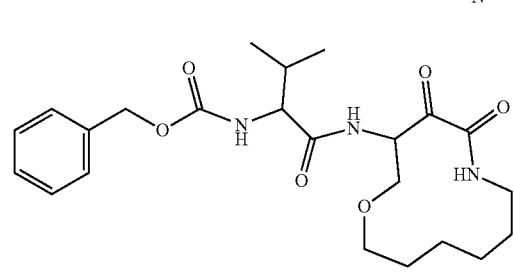 31
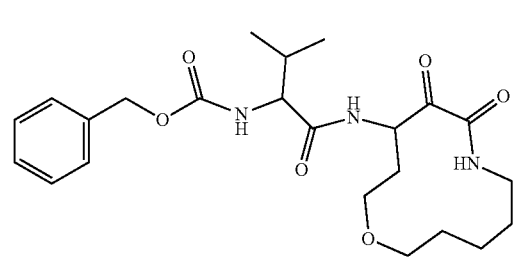 [SMILES: CC(C)C(NC(=O)OCc1ccccc1)C(=O)NC1CCOCCCCCNC(=O)C1=O] 32
TABLE 9-continued
TwelveRings
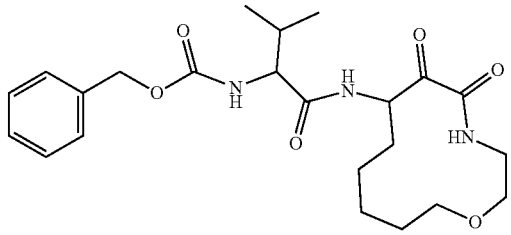 [SMILES: CC(C)C(NC(=O)OCc1ccccc1)C(=O)NC1CCCCCOCCNC(=O)C1=O] 35
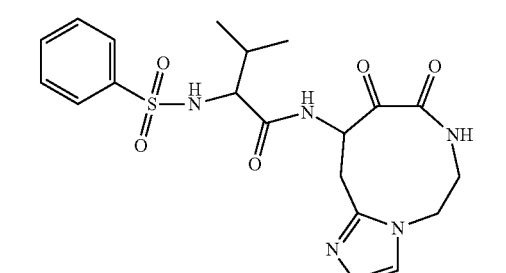 36
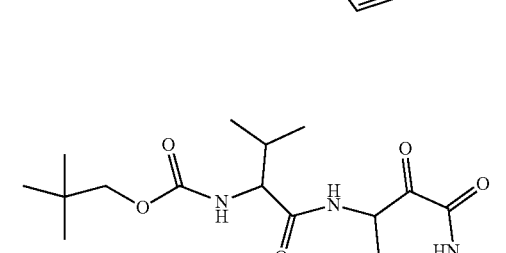 39
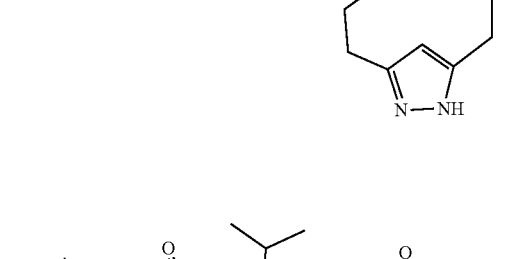 40
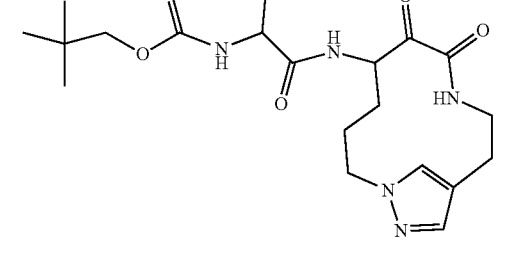 40
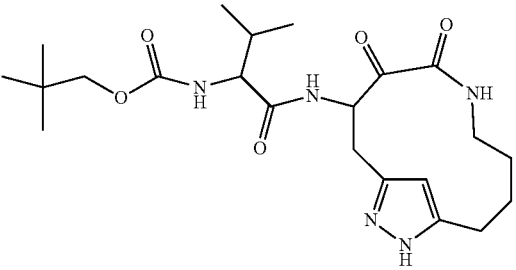 [SMILES: CC(C)C(NC(=O)OCC(C)(C)C)C(=O)NC1Cc2cc([nH]n2)CCCCNC(=O)C1=O] 43

TABLE 9-continued
TwelveRings
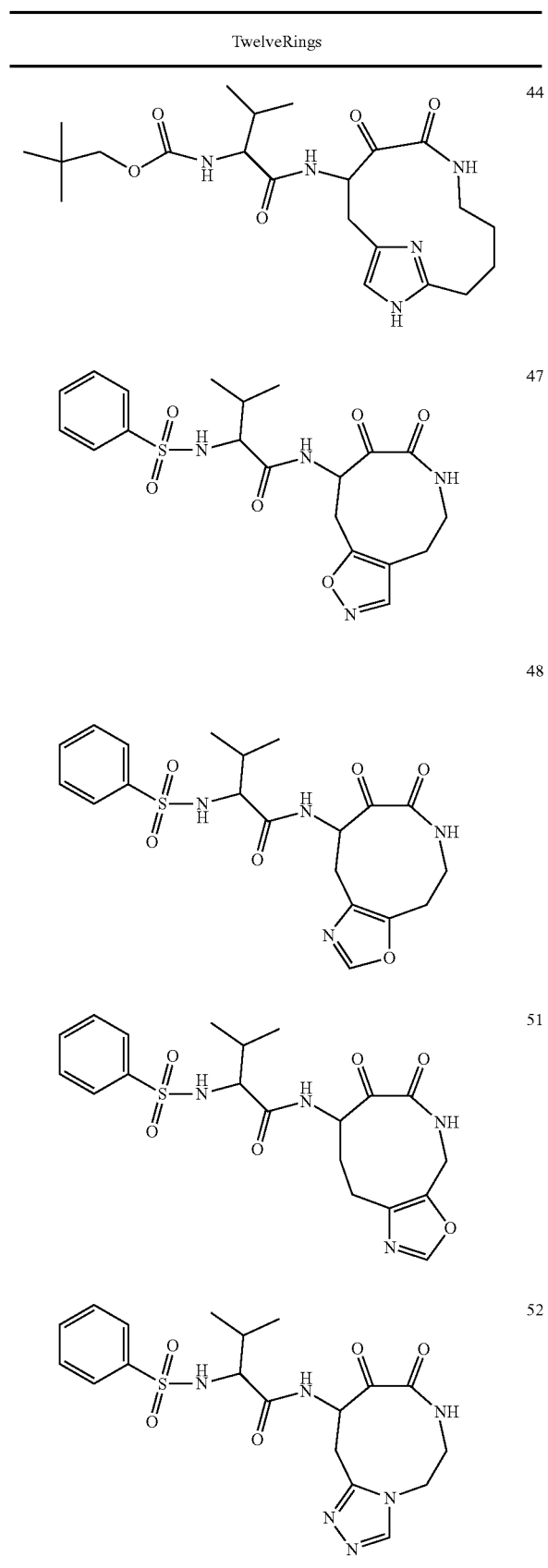
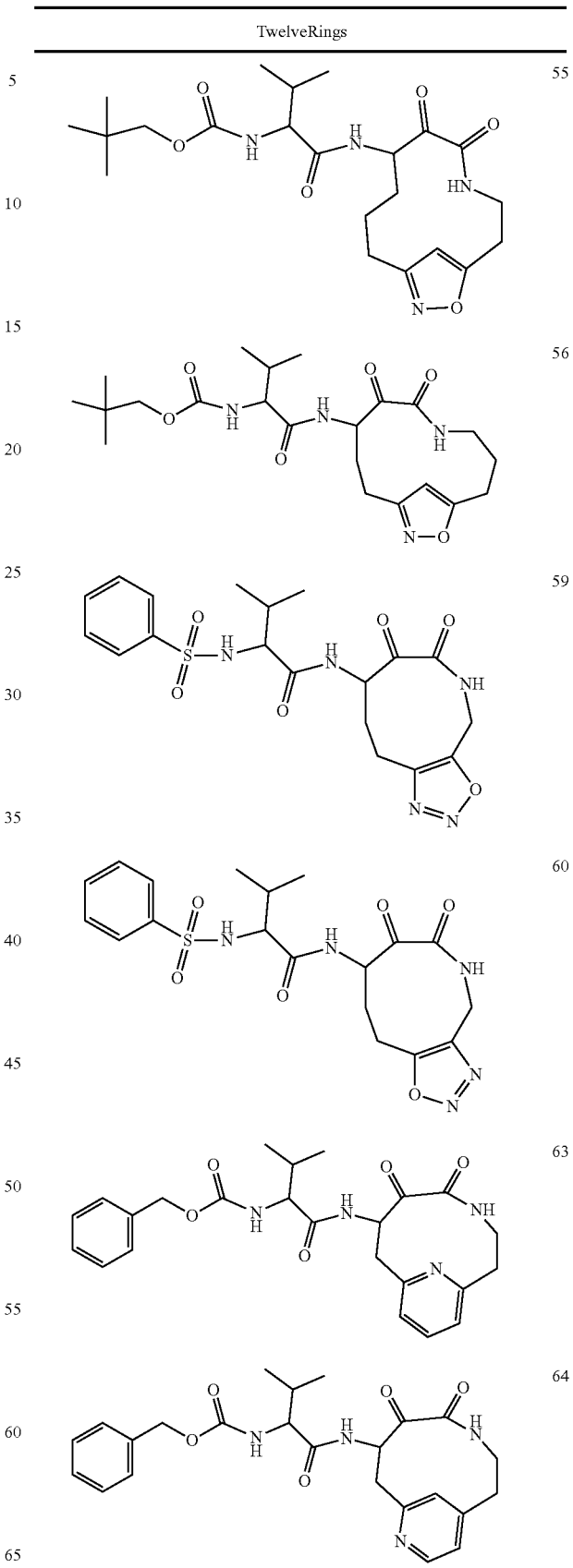

TABLE 9-continued
TwelveRings
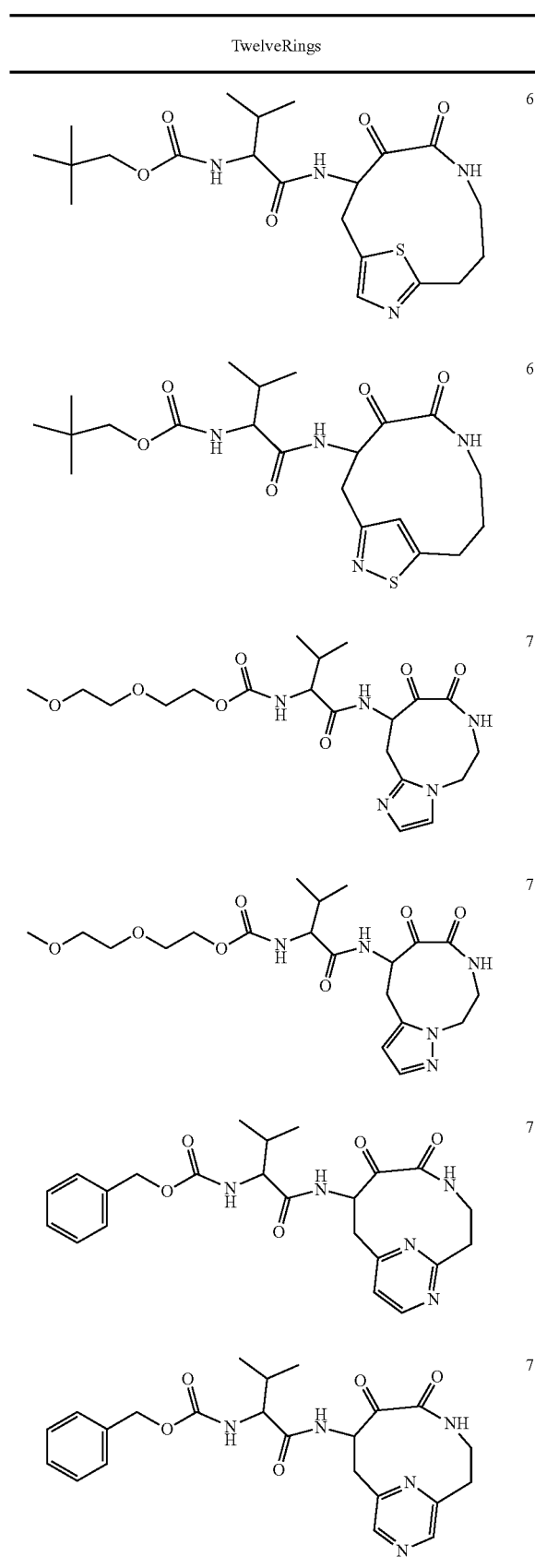
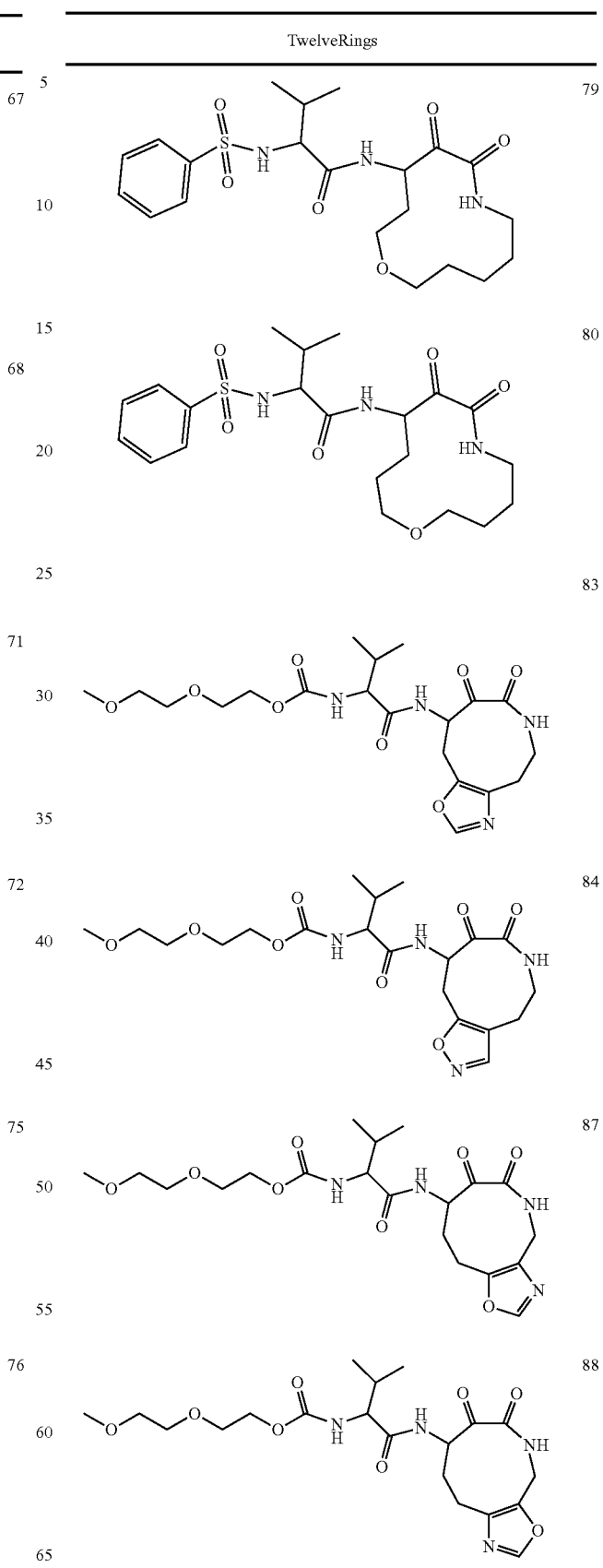

TABLE 9-continued
TwelveRings
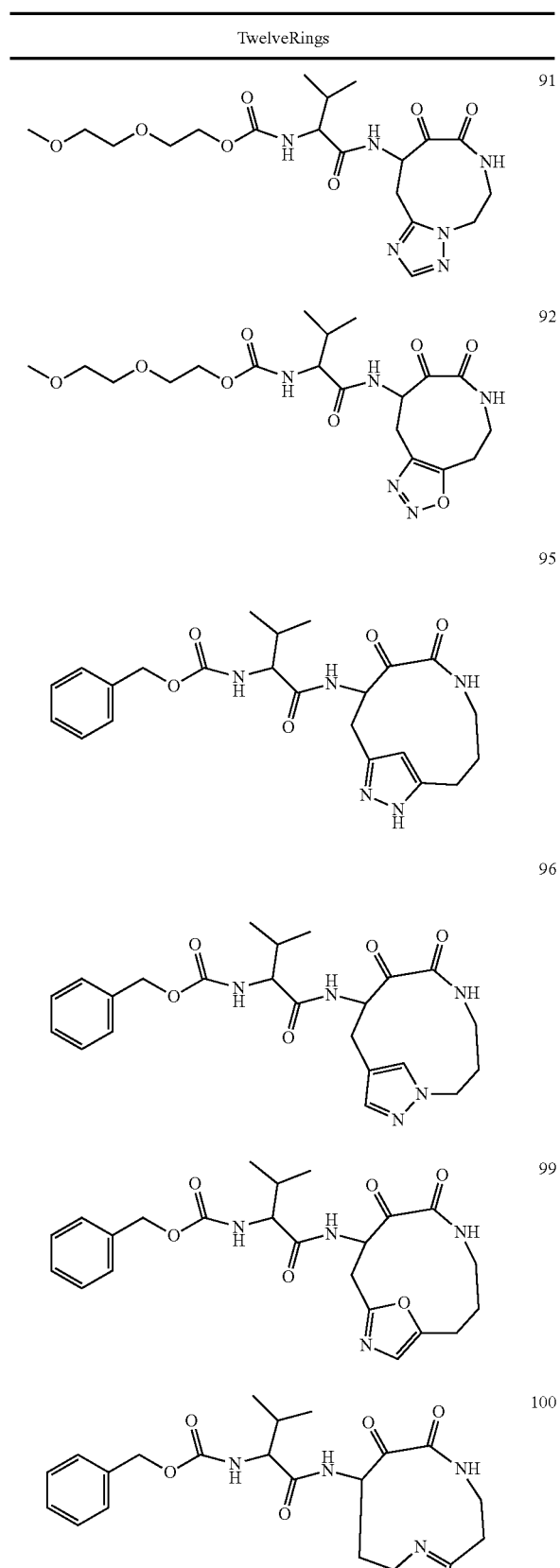
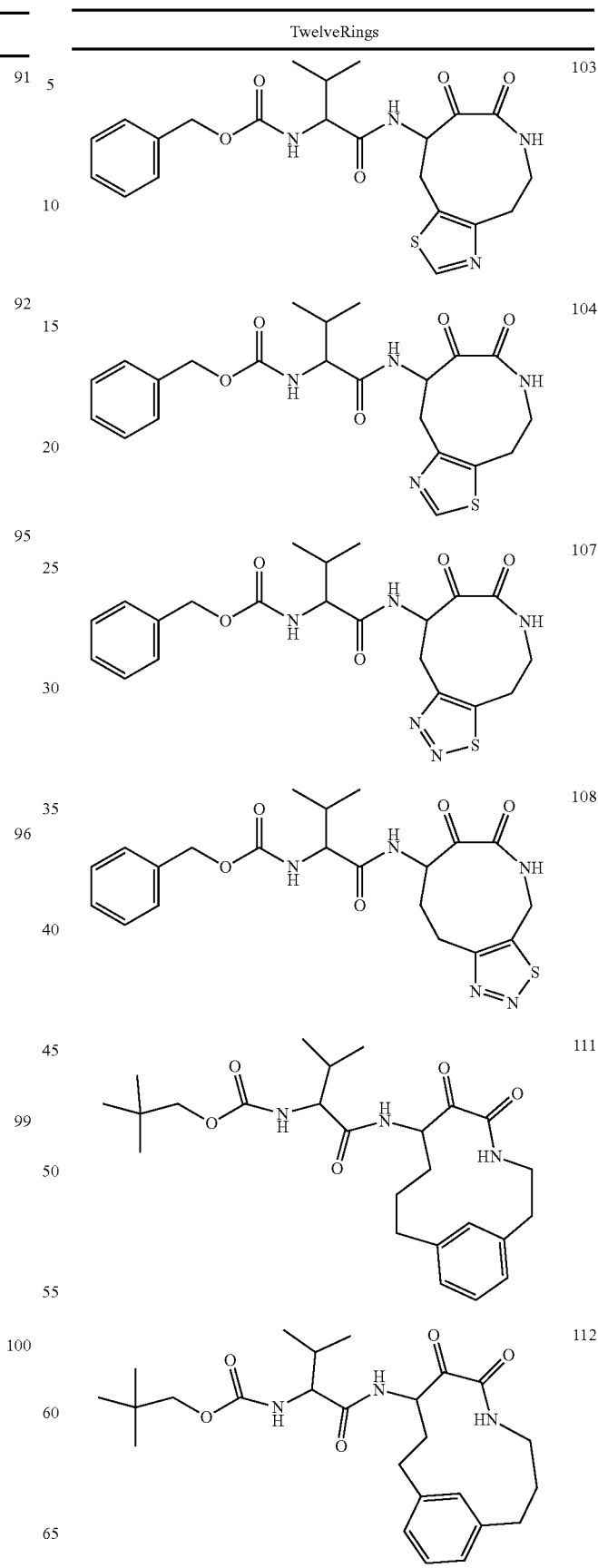

TABLE 9-continued
TwelveRings
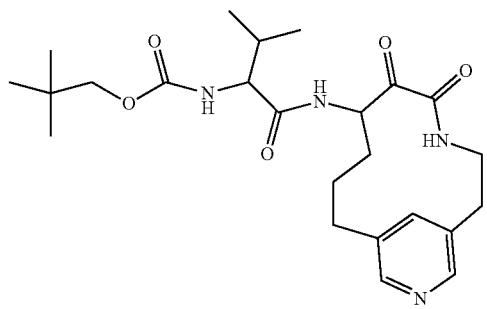 [SMILES: CC(C)C(NC(=O)OCC(C)(C)C)C(=O)NC1CCCc2cncc(c2)CCNC(=O)C1=O]
115
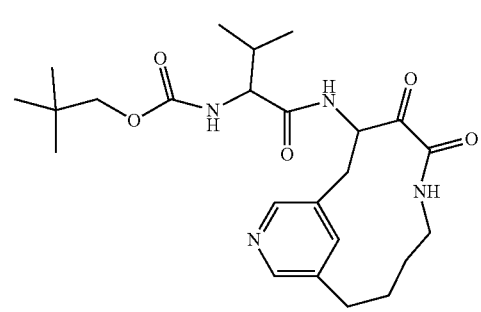 [SMILES: CC(C)C(NC(=O)OCC(C)(C)C)C(=O)NC1Cc2cncc(c2)CCCCNC(=O)C1=O]
116
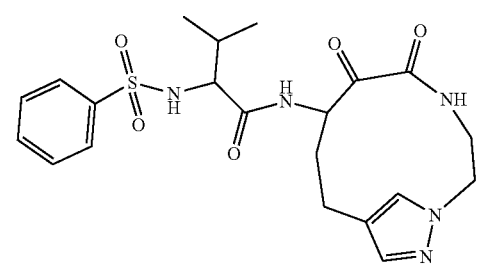 [SMILES: CC(C)C(NS(=O)(=O)c1ccccc1)C(=O)NC1CCc2cnn(c2)CCNC(=O)C1=O]
119
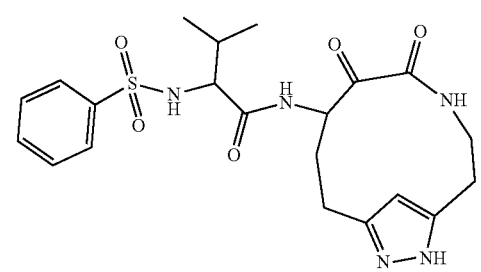 [SMILES: CC(C)C(NS(=O)(=O)c1ccccc1)C(=O)NC1CCc2cc([nH]n2)CCNC(=O)C1=O]
120
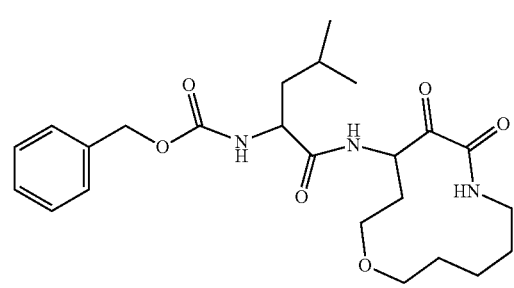 [SMILES: CC(C)CC(NC(=O)OCc1ccccc1)C(=O)NC1CCOCCCCCNC(=O)C1=O]
123
TABLE 9-continued
TwelveRings
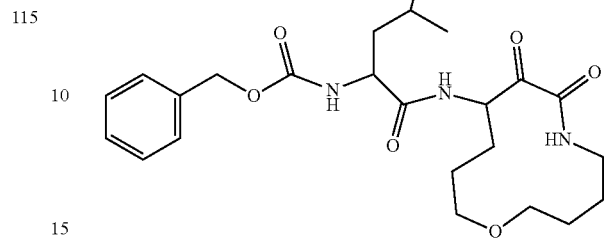
124
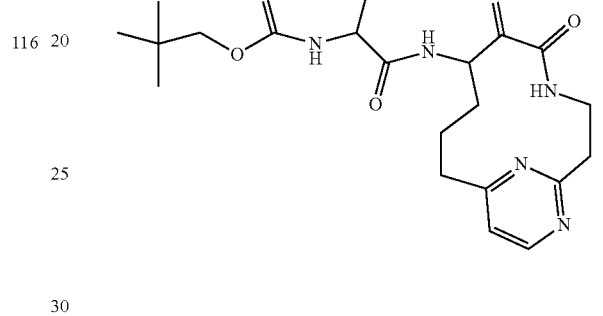
127
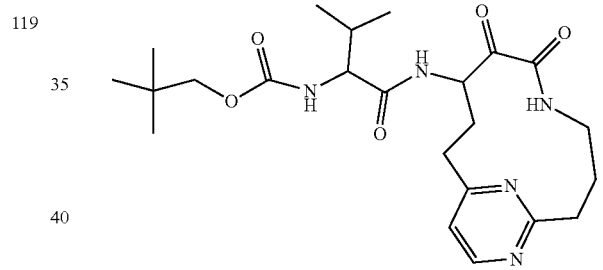
128
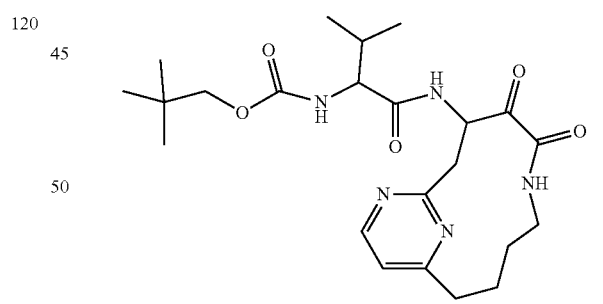
131
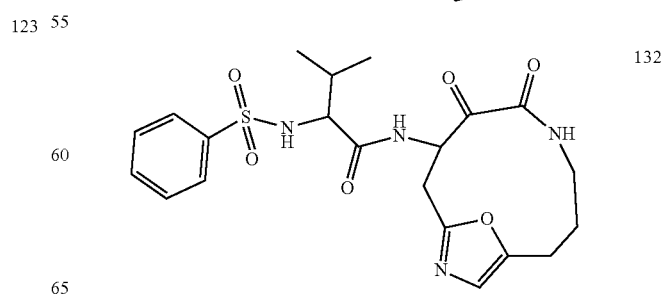
132

TABLE 9-continued
TwelveRings
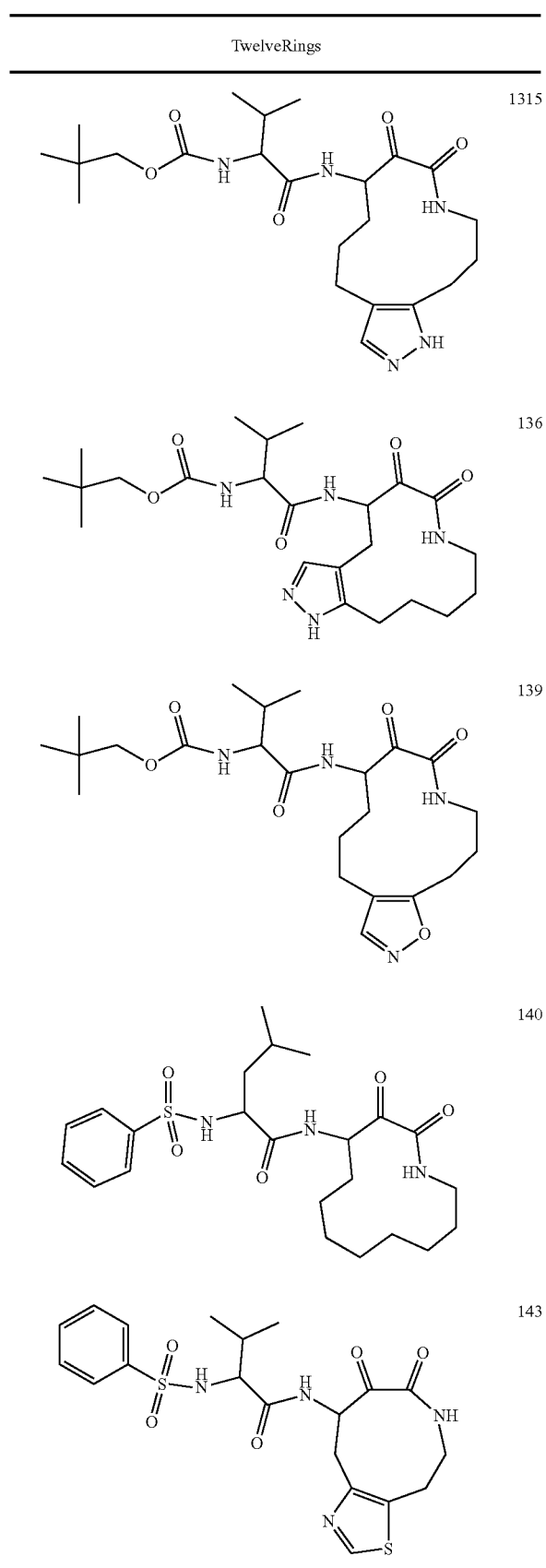
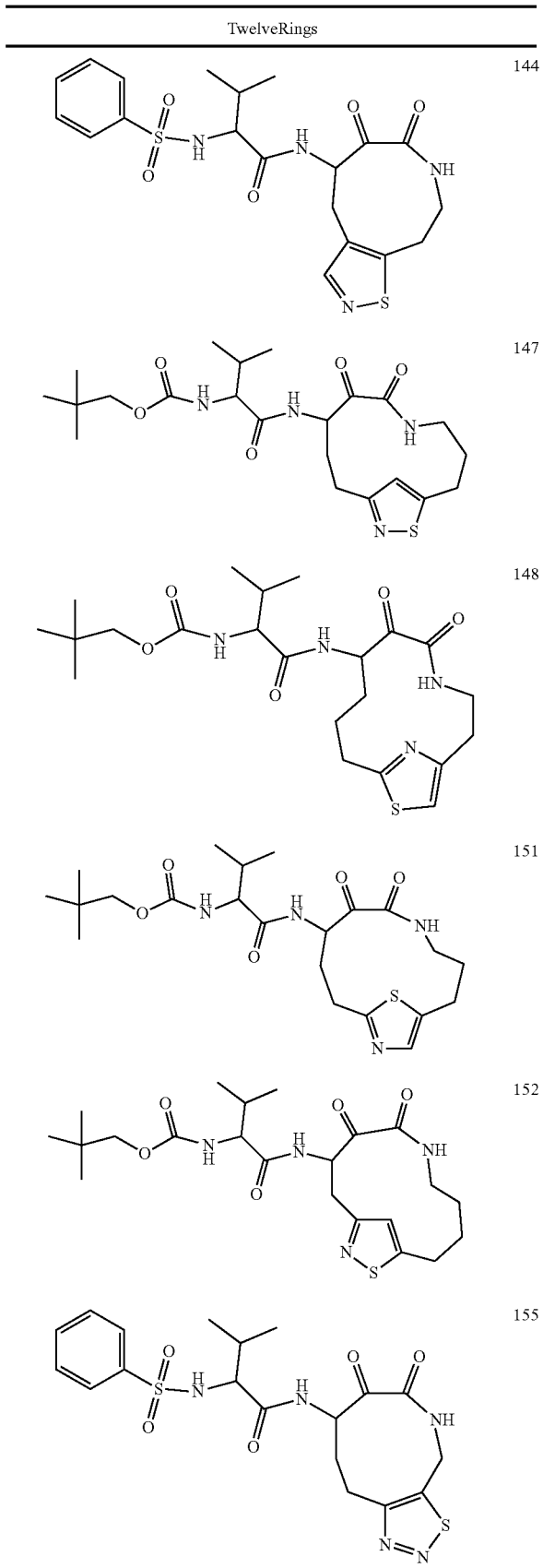

TABLE 9-continued
TwelveRings
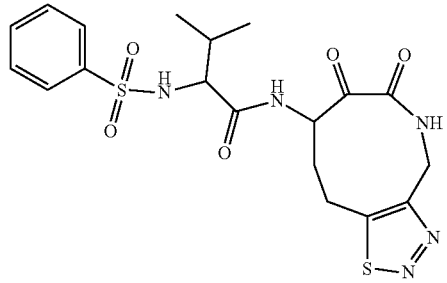 [SMILES: CC(C)C(NS(=O)(=O)c1ccccc1)C(=O)NC1CCc2snnc2CNC(=O)C1=O]
156
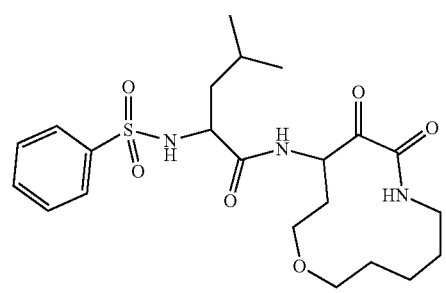 [SMILES: CC(C)CC(NS(=O)(=O)c1ccccc1)C(=O)NC1CCOCCCCCNC(=O)C1=O]
159
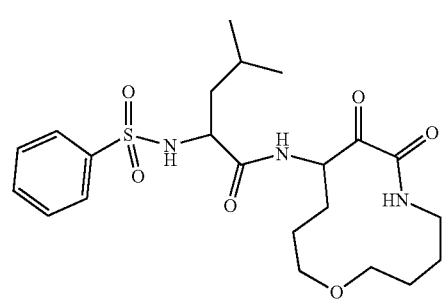 [SMILES: CC(C)CC(NS(=O)(=O)c1ccccc1)C(=O)NC1CCCOCCCCNC(=O)C1=O]
160
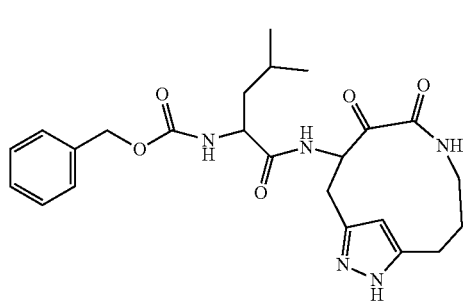 [SMILES: CC(C)CC(NC(=O)OCc1ccccc1)C(=O)NC1Cc2cc([nH]n2)CCCNC(=O)C1=O]
163
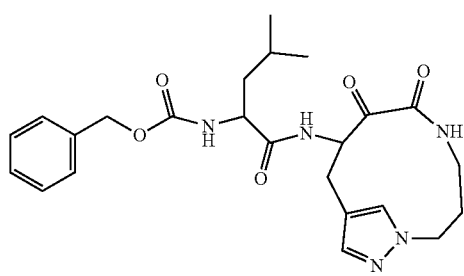 [SMILES: CC(C)CC(NC(=O)OCc1ccccc1)C(=O)NC1Cc2cnn(c2)CCCNC(=O)C1=O]
164
TABLE 9-continued
TwelveRings
167
168
171
172
175

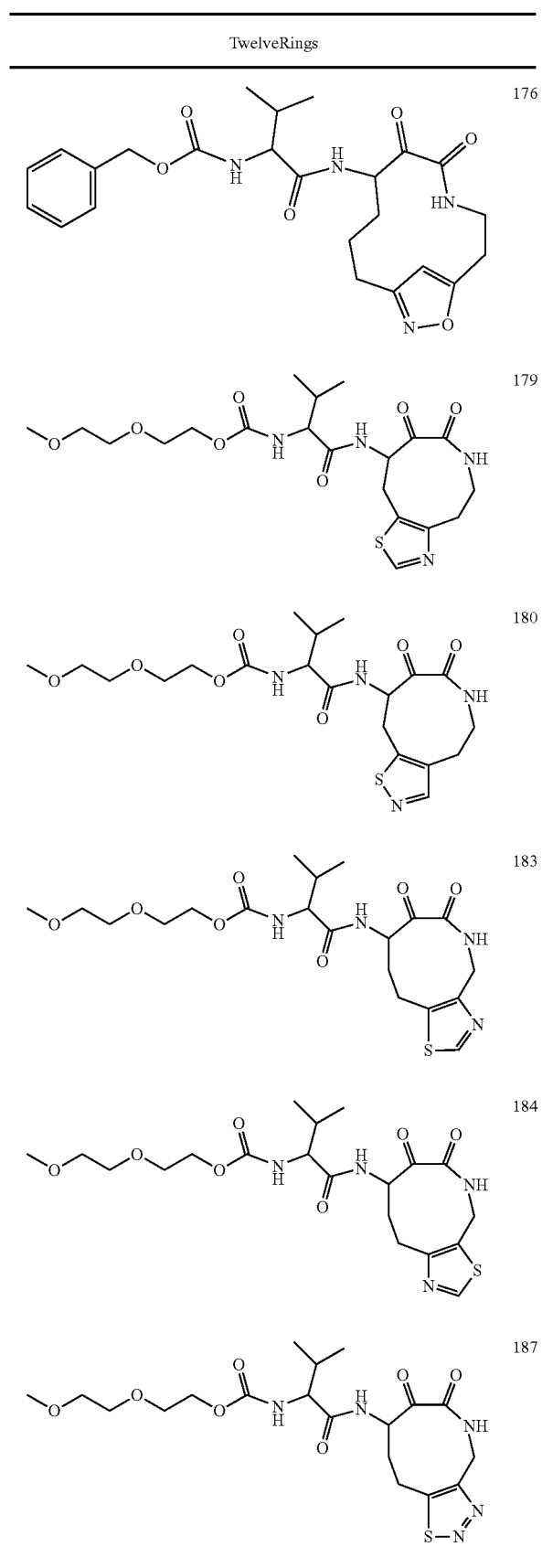
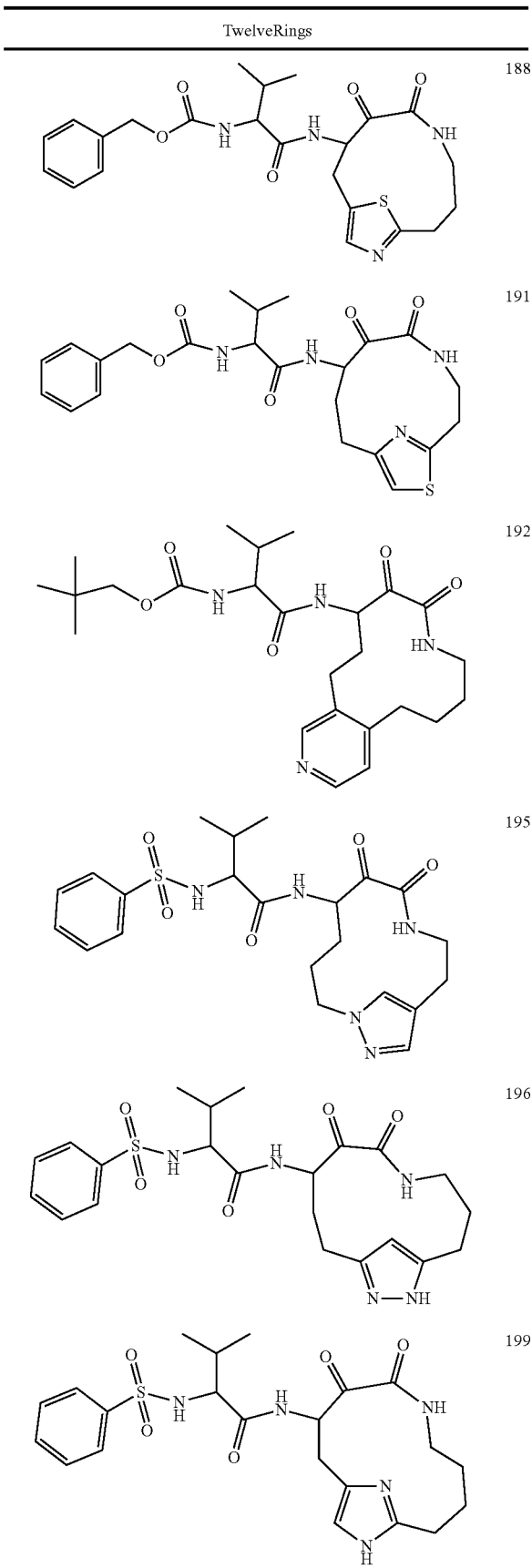

TABLE 9-continued
TwelveRings
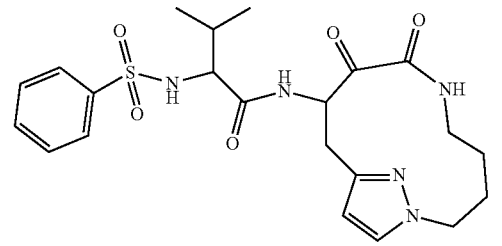 [SMILES: CC(C)C(NS(=O)(=O)c1ccccc1)C(=O)NC1Cc2ccn(n2)CCCCNC(=O)C1=O] 200
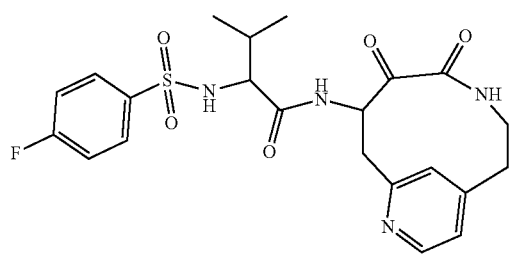 [SMILES: CC(C)C(NS(=O)(=O)c1ccc(F)cc1)C(=O)NC1Cc2cc(ccn2)CCNC(=O)C1=O] 203
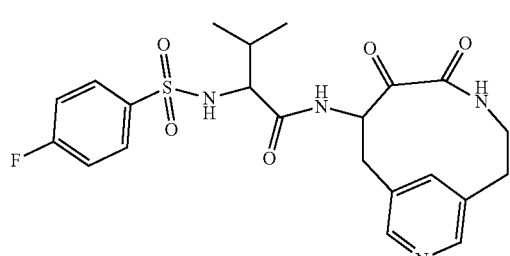 204
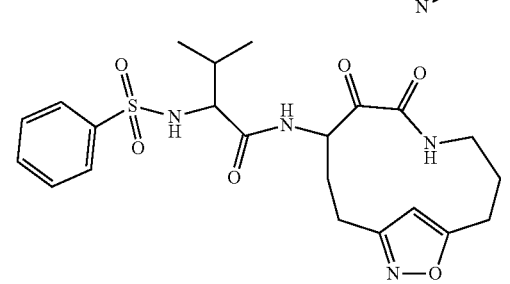 207
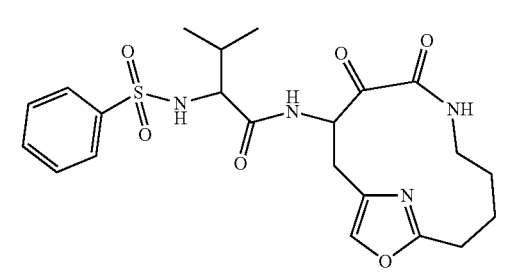 [SMILES: CC(C)C(NS(=O)(=O)c1ccccc1)C(=O)NC1Cc2coc(n2)CCCCNC(=O)C1=O] 208
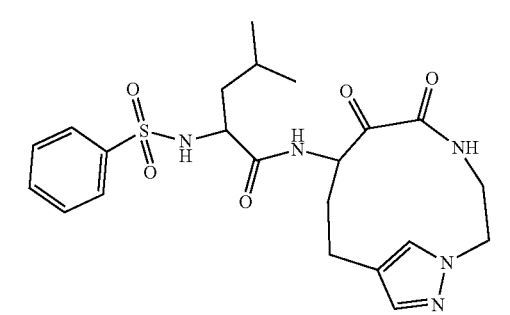 [SMILES: CC(C)CC(NS(=O)(=O)c1ccccc1)C(=O)NC1CCc2cnn(c2)CCNC(=O)C1=O] 211
TABLE 9-continued
TwelveRings
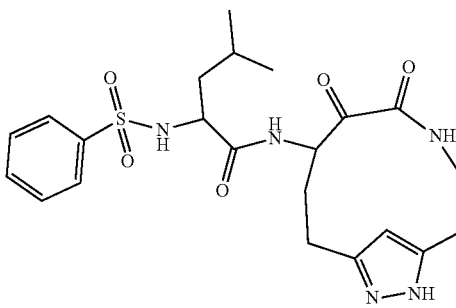 212
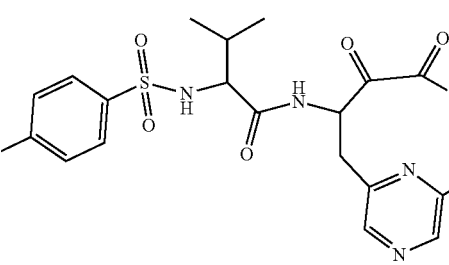 215
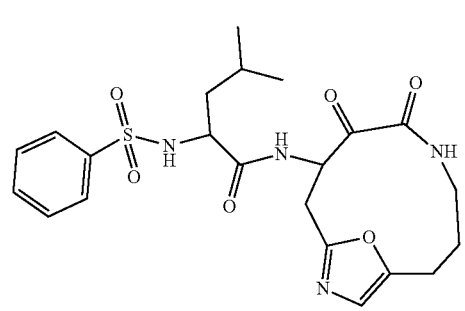 [SMILES: CC(C)CC(NS(=O)(=O)c1ccccc1)C(=O)NC1CC2=NC=C(CCCNC(=O)C1=O)O2] 216
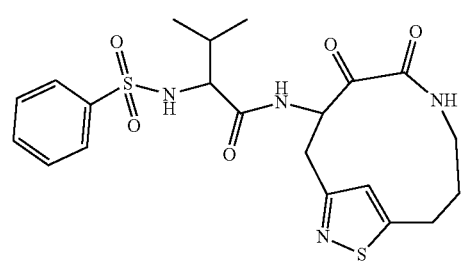 [SMILES: CC(C)C(NS(=O)(=O)c1ccccc1)C(=O)NC1Cc2cc(sn2)CCCNC(=O)C1=O] 219
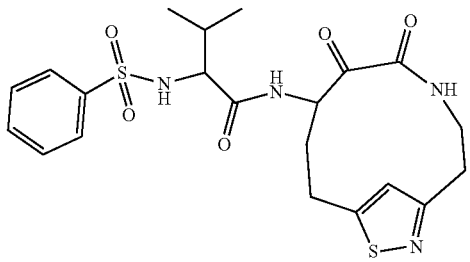 [SMILES: CC(C)C(NS(=O)(=O)c1ccccc1)C(=O)NC1CCc2cc(ns2)CCNC(=O)C1=O] 220

TABLE 9-continued

TwelveRings

TABLE 9-continued
TwelveRings
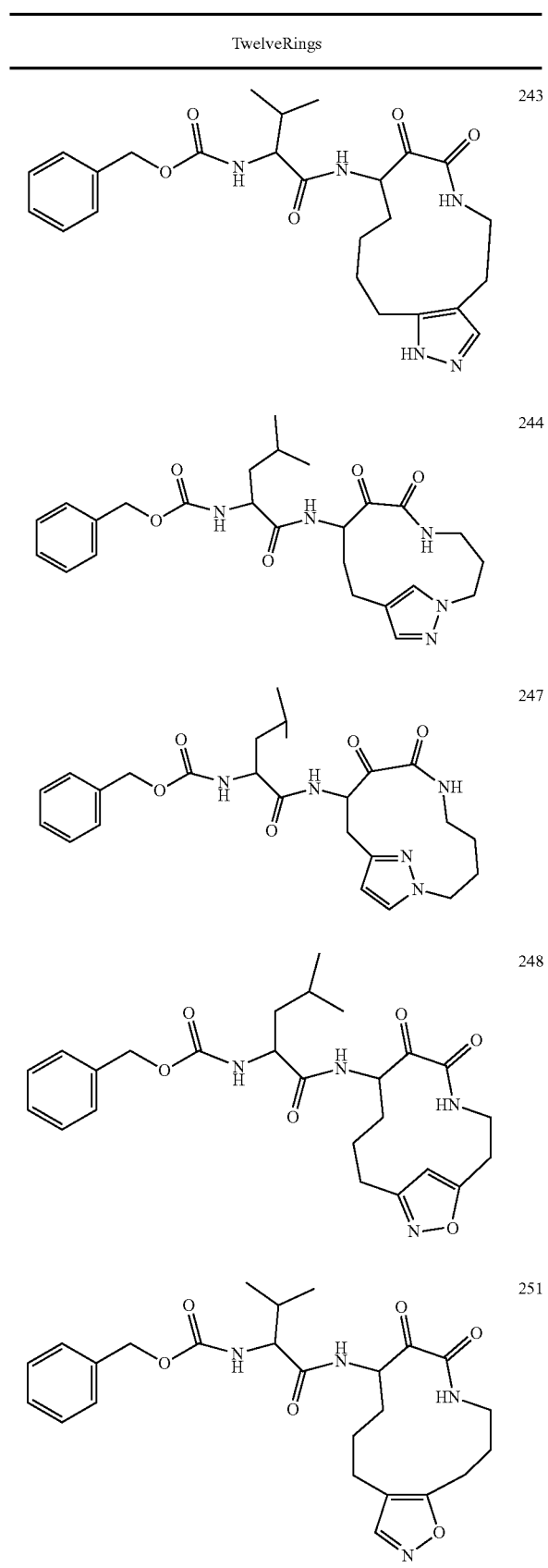
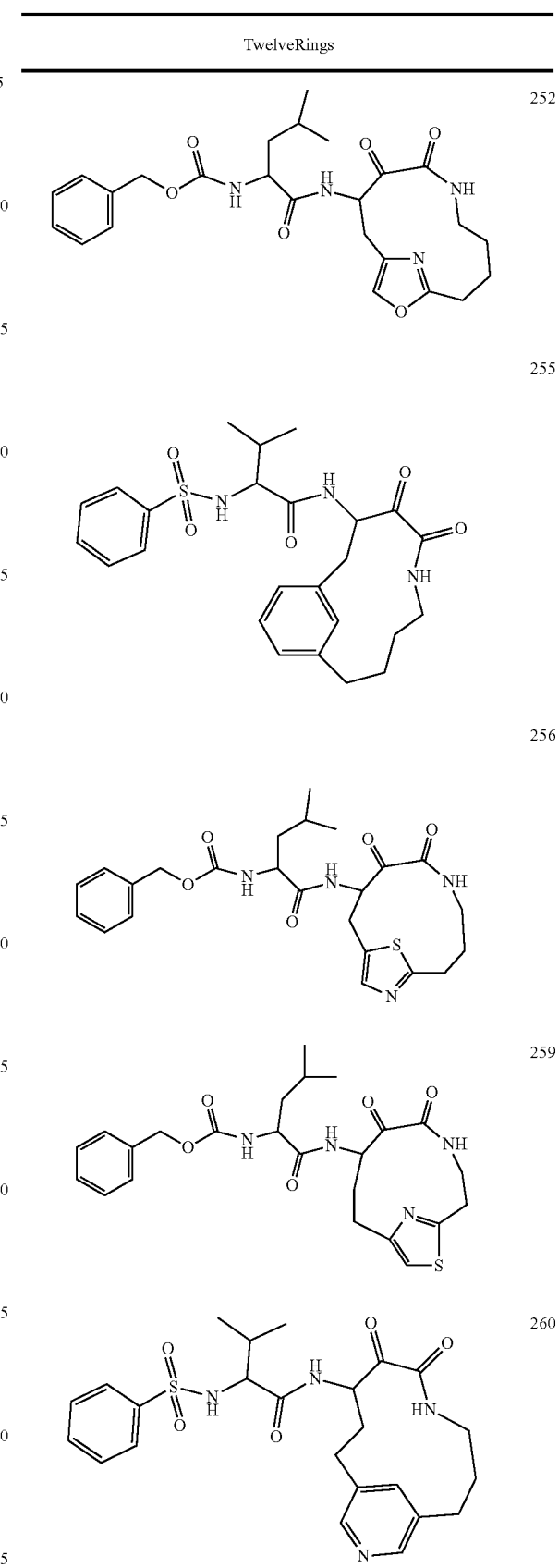

TABLE 9-continued
TwelveRings
263
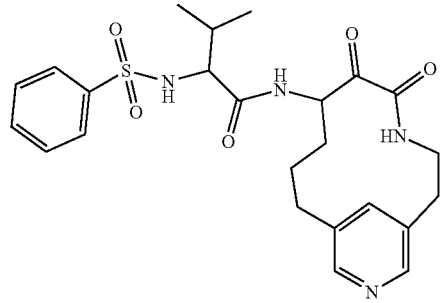 [SMILES: CC(C)C(NS(=O)(=O)c1ccccc1)C(=O)NC1CCCc2cncc(c2)CCNC(=O)C1=O]
264
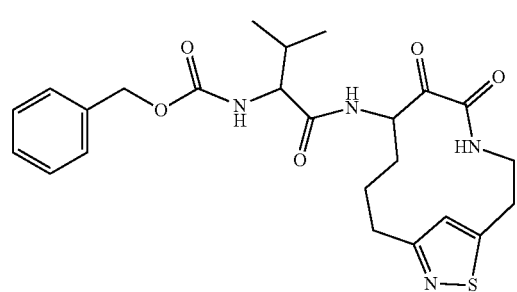
267
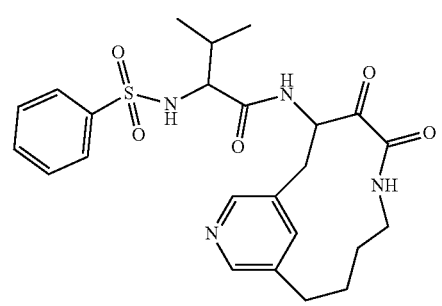 [SMILES: CC(C)C(NS(=O)(=O)c1ccccc1)C(=O)NC1Cc2cncc(c2)CCCCNC(=O)C1=O]
268
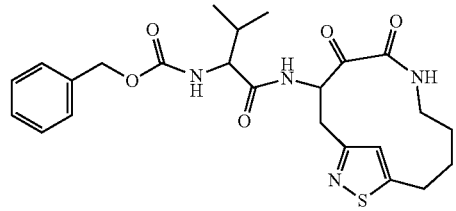 [SMILES: CC(C)C(NC(=O)OCc1ccccc1)C(=O)NC1Cc2cc(sn2)CCCCNC(=O)C1=O]
271
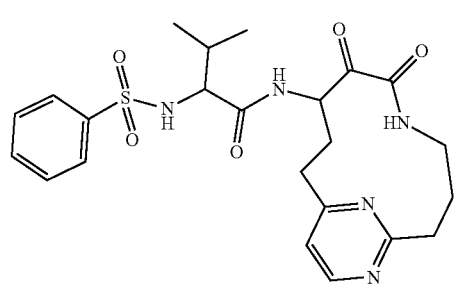 [SMILES: CC(C)C(NS(=O)(=O)c1ccccc1)C(=O)NC1CCc2ccnc(n2)CCCNC(=O)C1=O]
TABLE 9-continued
TwelveRings
272
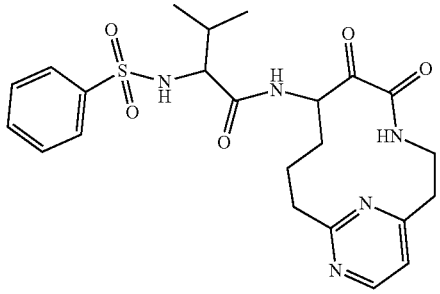 [SMILES: CC(C)C(NS(=O)(=O)c1ccccc1)C(=O)NC1CCCc2nccc(n2)CCNC(=O)C1=O]
275
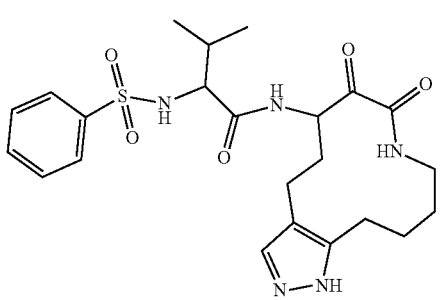 [SMILES: CC(C)C(NS(=O)(=O)c1ccccc1)C(=O)NC1CCc2cn[nH]c2CCCCNC(=O)C1=O]
276
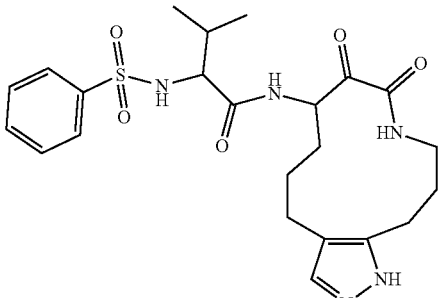
279
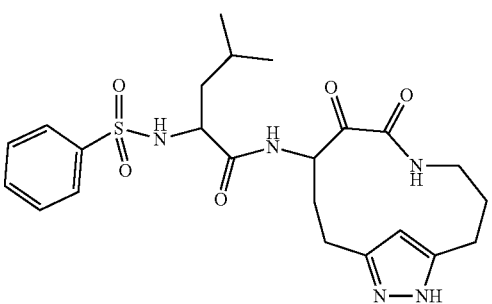 [SMILES: CC(C)CC(NS(=O)(=O)c1ccccc1)C(=O)NC1CCc2cc([nH]n2)CCCNC(=O)C1=O]
280
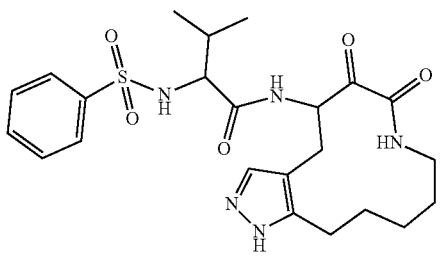 [SMILES: CC(C)C(NS(=O)(=O)c1ccccc1)C(=O)NC1Cc2cn[nH]c2CCCCCNC(=O)C1=O]

TABLE 9-continued
TwelveRings
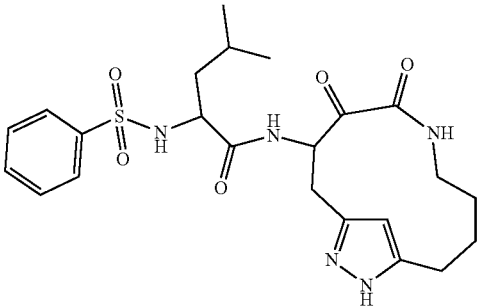 [SMILES: CC(C)CC(NS(=O)(=O)c1ccccc1)C(=O)NC1Cc2cc([nH]n2)CCCCNC(=O)C1=O] 283
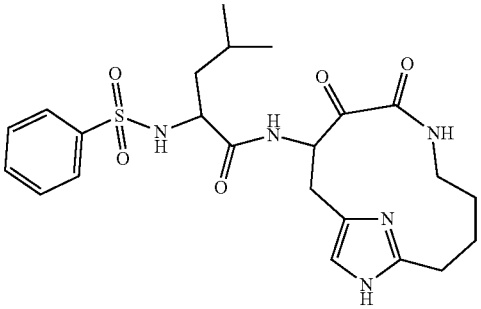 [SMILES: CC(C)CC(NS(=O)(=O)c1ccccc1)C(=O)NC1Cc2c[nH]c(n2)CCCCNC(=O)C1=O] 284
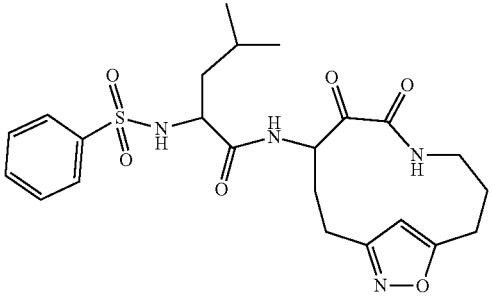 [SMILES: CC(C)CC(NS(=O)(=O)c1ccccc1)C(=O)NC1CCc2cc(on2)CCCNC(=O)C1=O] 287
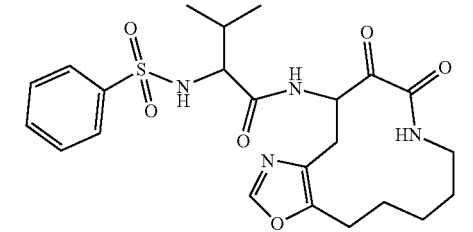 [SMILES: CC(C)C(NS(=O)(=O)c1ccccc1)C(=O)NC1Cc2ncoc2CCCCCNC(=O)C1=O] 288
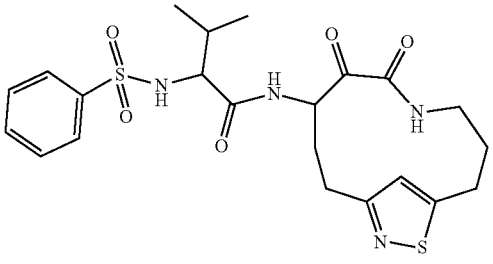 [SMILES: CC(C)C(NS(=O)(=O)c1ccccc1)C(=O)NC1CCc2cc(sn2)CCCNC(=O)C1=O] 291
TABLE 9-continued
TwelveRings
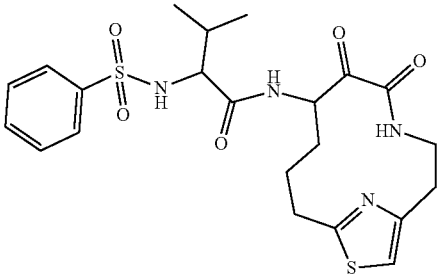 [SMILES: CC(C)C(NS(=O)(=O)c1ccccc1)C(=O)NC1CCCc2nc(cs2)CCNC(=O)C1=O] 292
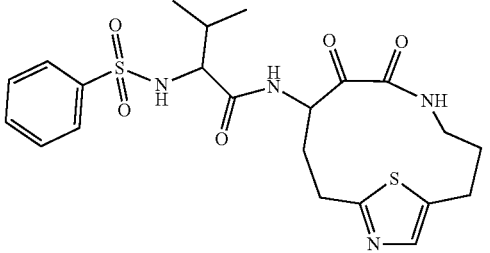 [SMILES: CC(C)C(NS(=O)(=O)c1ccccc1)C(=O)NC1CCC2=NC=C(CCCNC(=O)C1=O)S2] 295
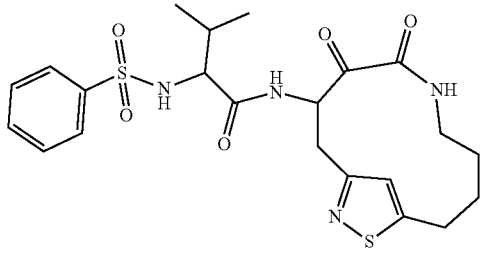 [SMILES: CC(C)C(NS(=O)(=O)c1ccccc1)C(=O)NC1Cc2cc(sn2)CCCCNC(=O)C1=O] 296
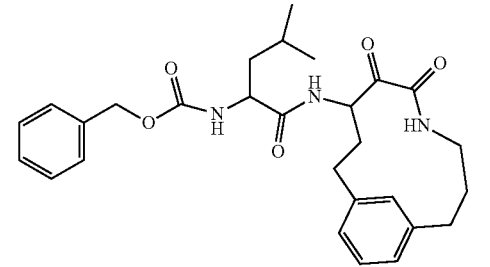 [SMILES: CC(C)CC(NC(=O)OCc1ccccc1)C(=O)NC1CCc2cccc(c2)CCCNC(=O)C1=O] 299
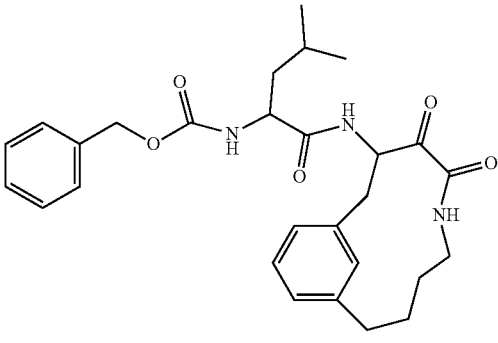 [SMILES: CC(C)CC(NC(=O)OCc1ccccc1)C(=O)NC1Cc2cccc(c2)CCCCNC(=O)C1=O] 300

TABLE 9-continued
TwelveRings
303
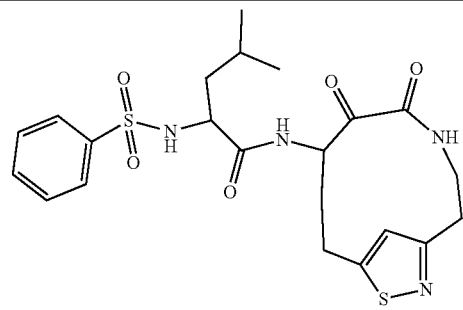
304
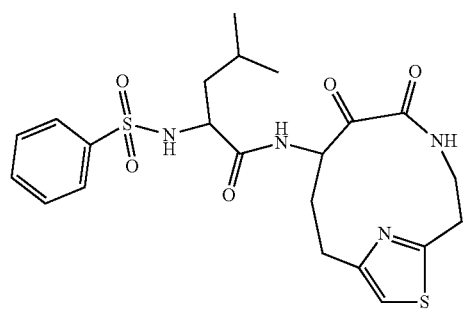 [SMILES: CC(C)CC(NS(=O)(=O)c1ccccc1)C(=O)NC1CCc2csc(n2)CCNC(=O)C1=O]
307
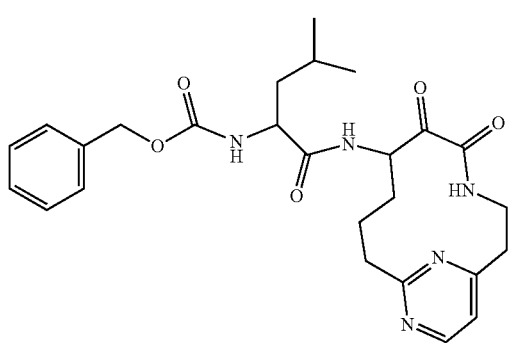 [SMILES: CC(C)CC(NC(=O)OCc1ccccc1)C(=O)NC1CCCc2nccc(n2)CCNC(=O)C1=O]
308
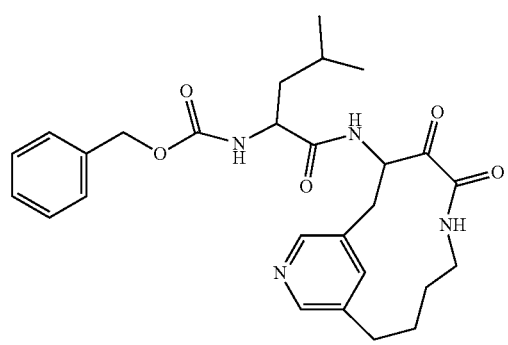 [SMILES: CC(C)CC(NC(=O)OCc1ccccc1)C(=O)NC1Cc2cncc(c2)CCCCNC(=O)C1=O]
311
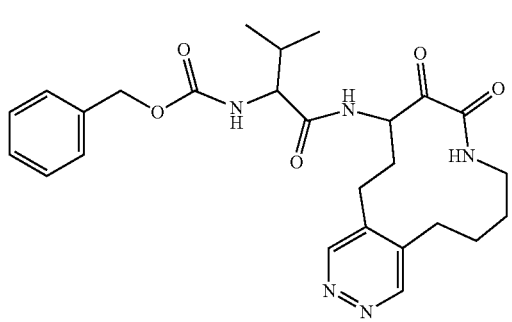 [SMILES: CC(C)C(NC(=O)OCc1ccccc1)C(=O)NC1CCc2cnncc2CCCCNC(=O)C1=O]
TABLE 9-continued
TwelveRings
312
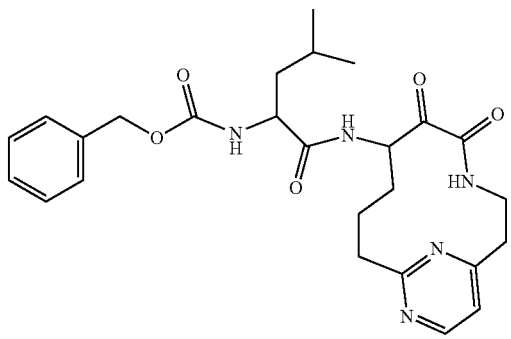 [SMILES: CC(C)CC(NC(=O)OCc1ccccc1)C(=O)NC1CCCc2nccc(n2)CCNC(=O)C1=O]
315
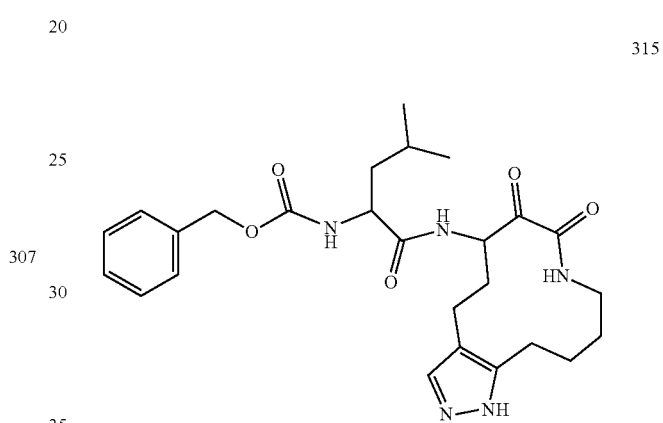
316
319
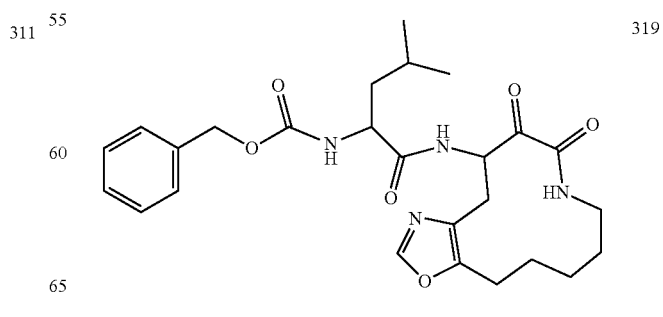

TABLE 9-continued
TwelveRings
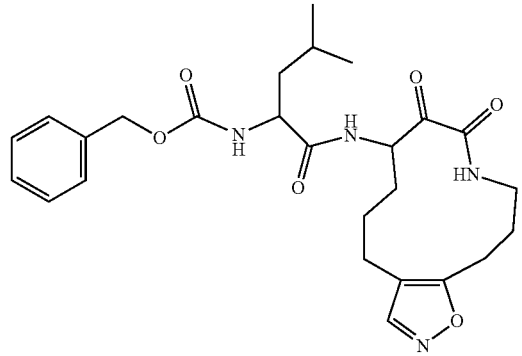 [SMILES: CC(C)CC(NC(=O)OCc1ccccc1)C(=O)NC1CCCc2cnoc2CCCNC(=O)C1=O]
320
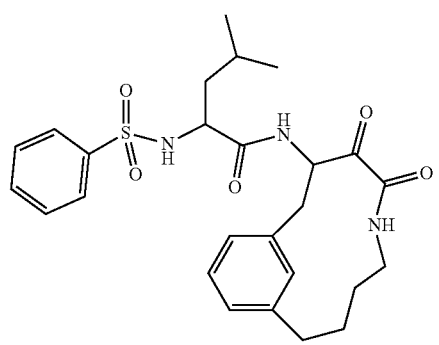 [SMILES: CC(C)CC(NS(=O)(=O)c1ccccc1)C(=O)NC1Cc2cccc(c2)CCCCNC(=O)C1=O]
323
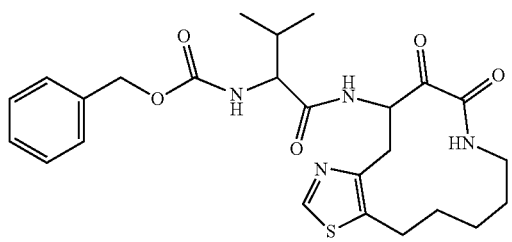 [SMILES: CC(C)C(NC(=O)OCc1ccccc1)C(=O)NC1Cc2ncsc2CCCCCNC(=O)C1=O]
324
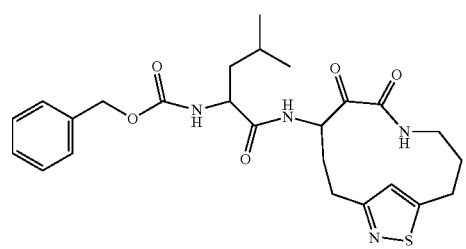 [SMILES: CC(C)CC(NC(=O)OCc1ccccc1)C(=O)NC1CCc2cc(sn2)CCCNC(=O)C1=O]
327
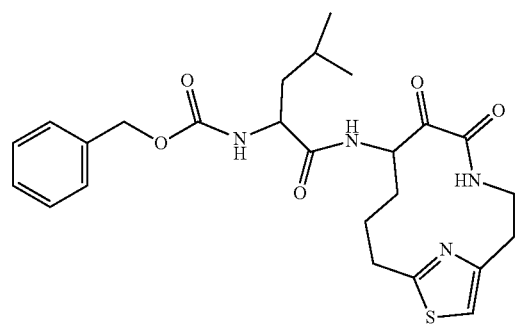 [SMILES: CC(C)CC(NC(=O)OCc1ccccc1)C(=O)NC1CCCc2nc(cs2)CCNC(=O)C1=O]
328
TABLE 9-continued
TwelveRings
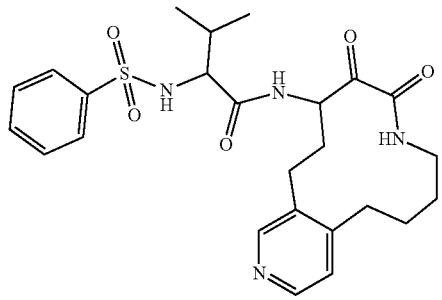 [SMILES: CC(C)C(NS(=O)(=O)c1ccccc1)C(=O)NC1CCc2cnccc2CCCCNC(=O)C1=O]
331
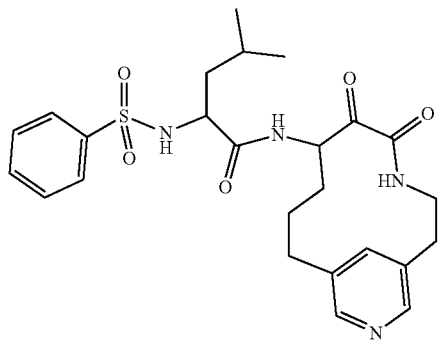 [SMILES: CC(C)CC(NS(=O)(=O)c1ccccc1)C(=O)NC1CCCc2cncc(c2)CCNC(=O)C1=O]
332
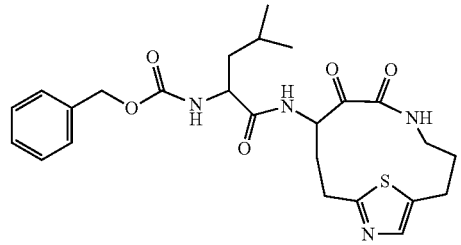 [SMILES: CC(C)CC(NC(=O)OCc1ccccc1)C(=O)NC1CCC2=NC=C(CCCNC(=O)C1=O)S2]
335
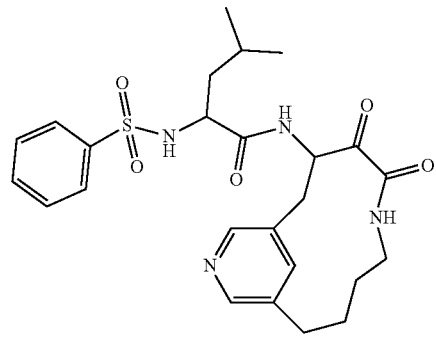 [SMILES: CC(C)CC(NS(=O)(=O)c1ccccc1)C(=O)NC1Cc2cncc(c2)CCCCNC(=O)C1=O]
336
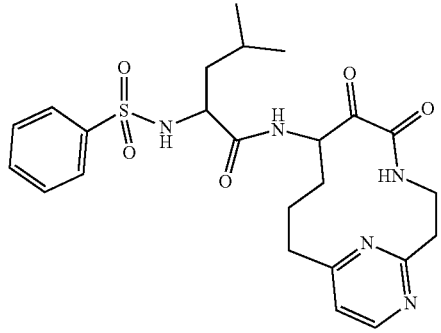 [SMILES: CC(C)CC(NS(=O)(=O)c1ccccc1)C(=O)NC1CCCc2ccnc(n2)CCNC(=O)C1=O]
339

451
TABLE 9-continued
TwelveRings
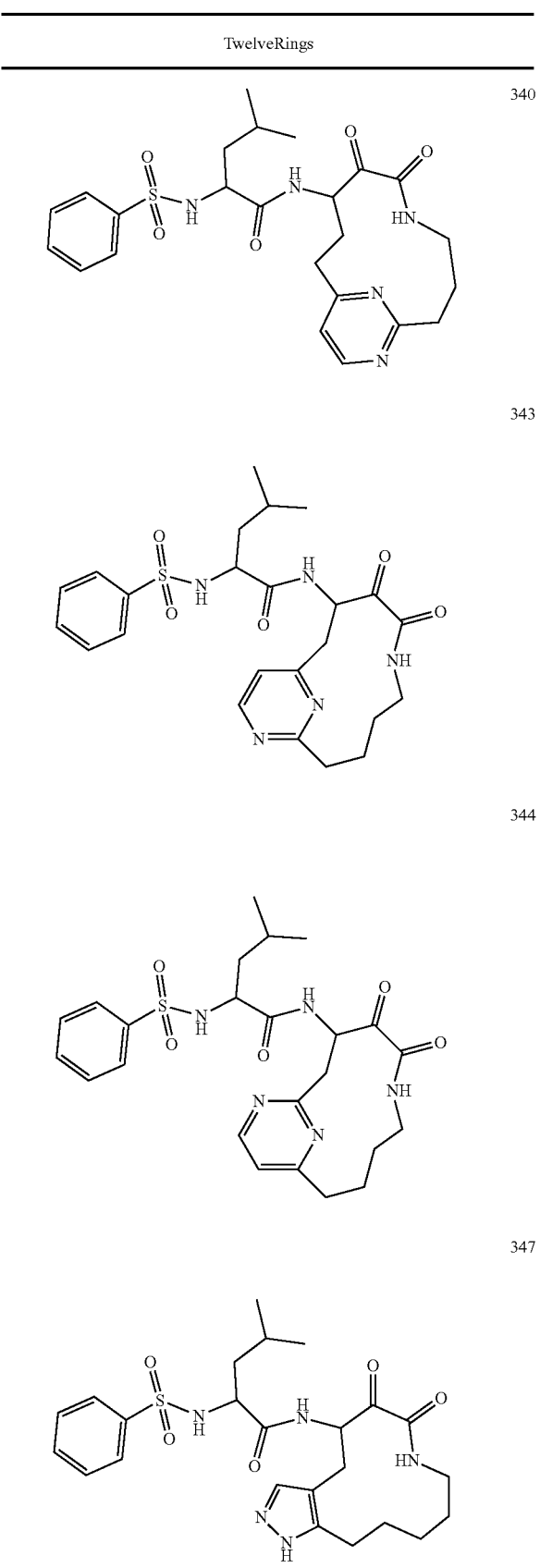
452
TABLE 9-continued
TwelveRings
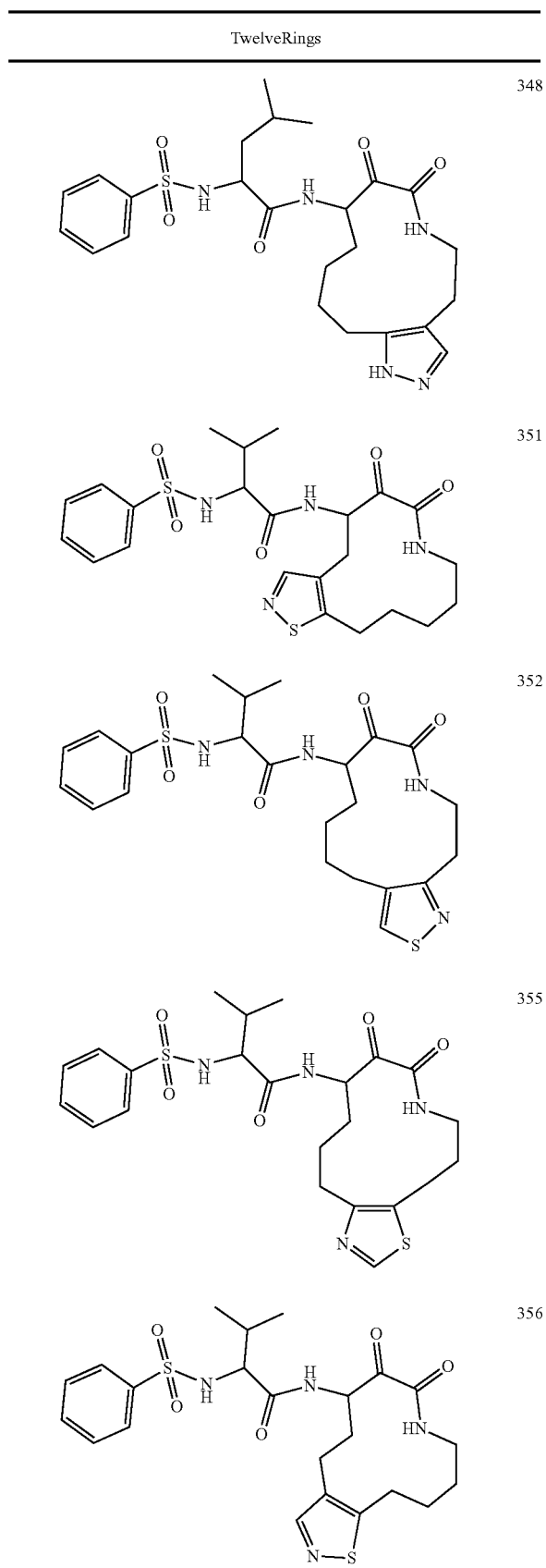

TABLE 9-continued
TwelveRings
359 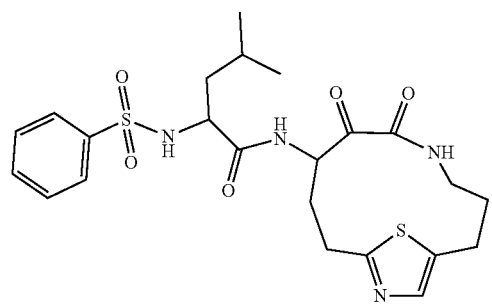 [SMILES: CC(C)CC(NS(=O)(=O)c1ccccc1)C(=O)NC1CCC2=NC=C(CCCNC(=O)C1=O)S2]
360 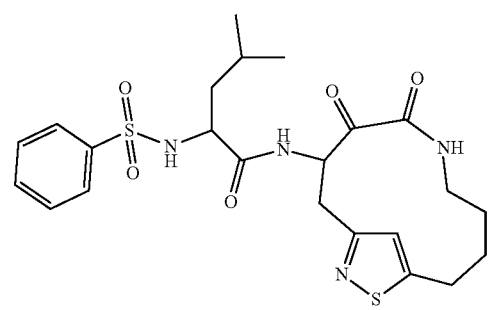 [SMILES: CC(C)CC(NS(=O)(=O)c1ccccc1)C(=O)NC1Cc2cc(sn2)CCCCNC(=O)C1=O]
363 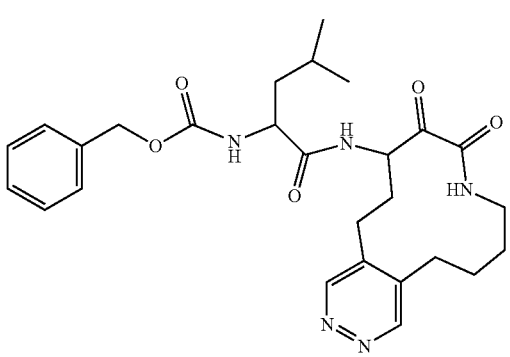 [SMILES: CC(C)CC(NC(=O)OCc1ccccc1)C(=O)NC1CCc2cnncc2CCCCNC(=O)C1=O]
364 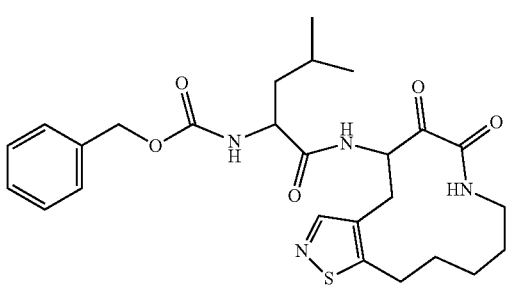 [SMILES: CC(C)CC(NC(=O)OCc1ccccc1)C(=O)NC1Cc2cnsc2CCCCCNC(=O)C1=O]
367 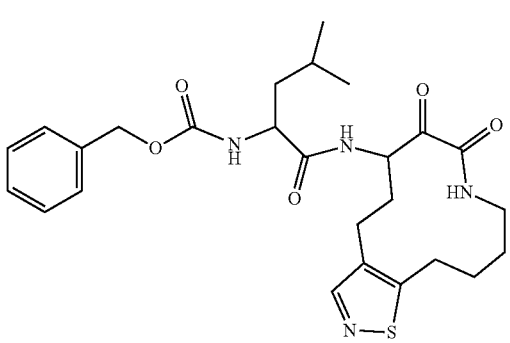 [SMILES: CC(C)CC(NC(=O)OCc1ccccc1)C(=O)NC1CCc2cnsc2CCCCNC(=O)C1=O]
TABLE 9-continued
TwelveRings
368 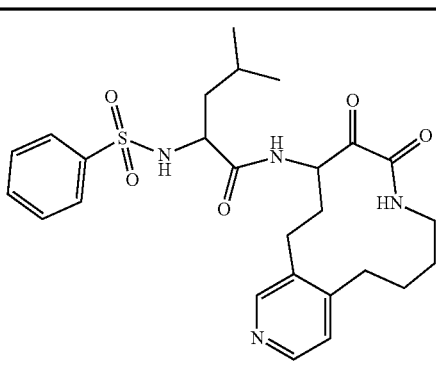
371 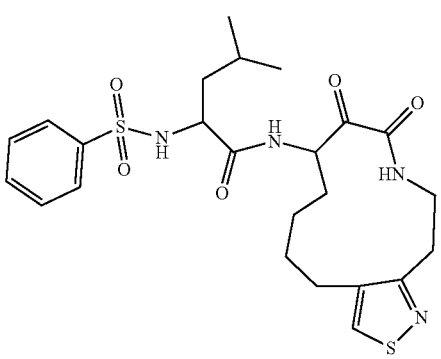 [SMILES: CC(C)CC(NS(=O)(=O)c1ccccc1)C(=O)NC1CCCCc2csnc2CCNC(=O)C1=O]
382 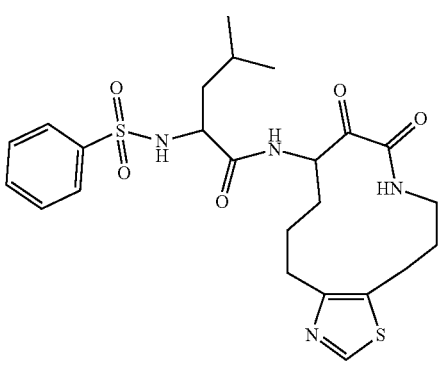 [SMILES: CC(C)CC(NS(=O)(=O)c1ccccc1)C(=O)NC1CCCc2ncsc2CCCNC(=O)C1=O]
375 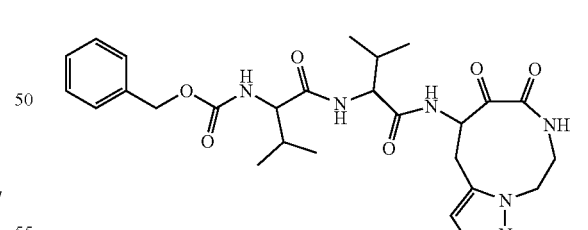
376 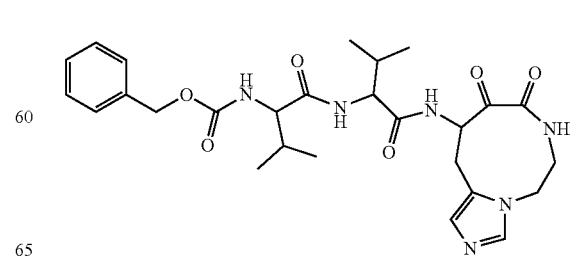

TABLE 9-continued
TwelveRings
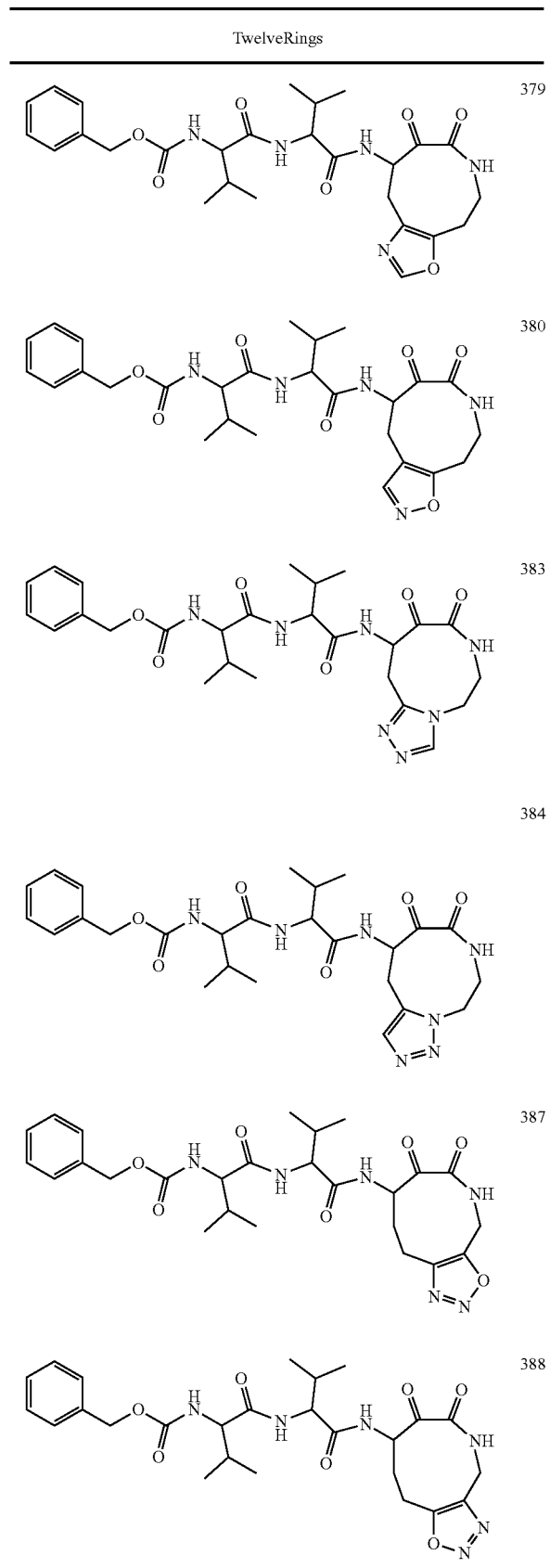
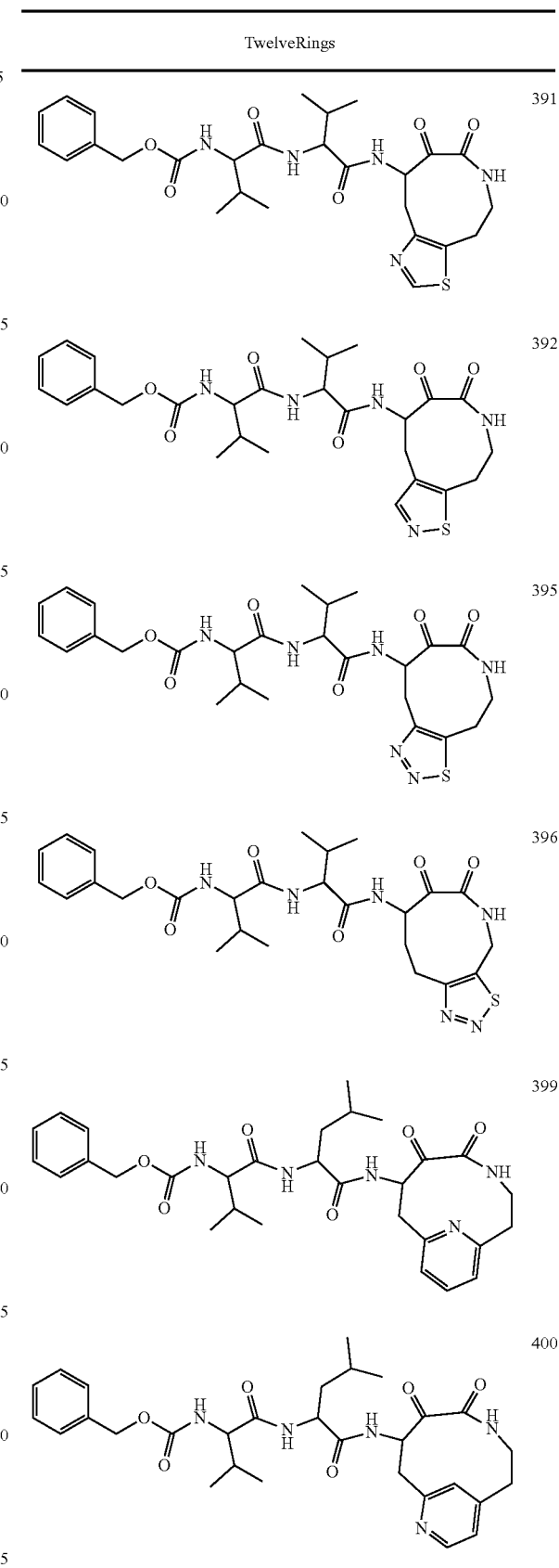

TABLE 9-continued

TwelveRings

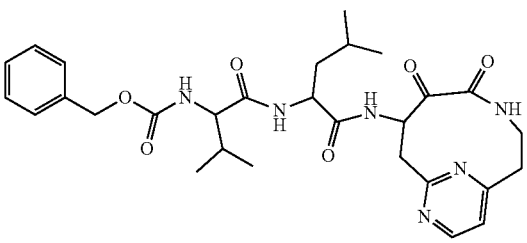 [SMILES: CC(C)CC(NC(=O)C(NC(=O)OCc1ccccc1)C(C)C)C(=O)NC1Cc2nccc(n2)CCNC(=O)C1=O]

403

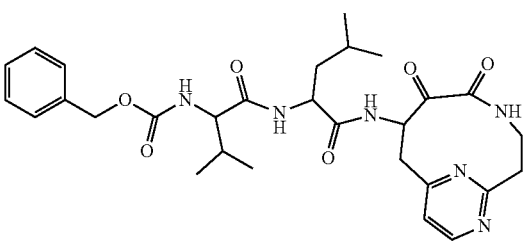 [SMILES: CC(C)CC(NC(=O)C(NC(=O)OCc1ccccc1)C(C)C)C(=O)NC1Cc2ccnc(n2)CCNC(=O)C1=O]

404 or a pharmaceutically acceptable salt thereof.

In some embodiments, the present technology is a pharmaceutical composition comprising one or more compounds disclosed herein and a pharmaceutically acceptable excipient.

In one embodiment, the compounds of the present invention or a pharmaceutically acceptable salt thereof, or a prodrug or metabolite thereof, can be administered in combination with any other pharmaceutical compound approved for treating fibrotic or myofibroblast differentiation associated diseases or disorders.

Compositions and Methods of the Present Technology

The compounds represented by Formula I-XXXII or their tautomers and/or pharmaceutically acceptable salts thereof can effectively act as CAPN1, CAPN2, and/or CAPN9 inhibitors and treat conditions affected at least in part by CAPN1, CAPN2, and/or CAPN9. In one aspect of the present technology, the present technology provides pharmaceutical compositions comprising one or more compounds of Formula I-XXXII and a pharmaceutically acceptable excipient. In another aspect of the present technology, the present technology provides a method for treating a fibrotic disease with an effective amount of one or more compound of Formula I-XXXII as provided herein.

In another aspect of the present technology, the present technology provides a method for inhibiting CAPN1, CAPN2, and/or CAPN9 and/or a method for treating a disease affected at least in part by CAPN1, CAPN2, and/or CAPN9 with an effective amount of one or more compound of Formula I-XXXII as provided herein.

The compounds of the present technology are useful in inhibiting CAPN1, CAPN2, and/or CAPN9 enzymes and/or treating disorders relating to fibrosis or myofibroblast differentiation.

In one of its method aspects, the present technology is directed to a method for inhibiting CAPN1, CAPN2, and/or CAPN9 which method comprises contacting cells (including neurons/microglia/invading macrophages) with an effective amount of one or more compound of Formula I-XXXII as described herein.

In another aspect, the present technology is directed to a method for treating a fibrotic disease, which method comprises administering to a subject an effective amount of one or more compounds of Formula I-XXXII or a pharmaceutical composition comprising a pharmaceutically acceptable excipient.

In another aspect, the present technology is directed to a method for treating a disease affected at least in part by CAPN1, CAPN2, and/or CAPN9, which method comprises administering to a subject an effective amount of one or more compounds of Formula I-XXXII or a pharmaceutical composition comprising a pharmaceutically acceptable excipient.

In an aspect, a method for inhibiting CAPN1, CAPN2, and/or CAPN9 is provided wherein the method comprises contacting cells with an effective amount of one or more compounds of Formula I-XXXII. In one aspect, the method for inhibiting CAPN1, CAPN2, and/or CAPN9 is performed in-vitro or in-vivo.

Calpains are also expressed in cells other than neurons, microglia and invading macrophages. In particular, they are important in skeletal muscle and herein inhibition of calpains also refers to inhibition in these cells as well.

Selective Inhibition

In another aspect, a method is provided for competitive binding with calpastatin (CAST), the method comprising contacting a compound of any one of claims 1-56 with CAPN1, CAPN2, and/or CAPN9 enzymes residing inside a subject. In such a method, the compound specifically inhibits one or more of the enzymes selected from the group consisting of: CAPN1, CAPN2, and CAPN9 by at least 2-fold, by at least 3-fold, by at least 4-fold, by at least 5-fold, by at least 10-fold, by at least 15-fold, by at least 20-fold, by at least 50-fold, by at least 100-fold, by at least 150-fold, by at least 200-fold, by at least 400-fold, or by at least 500-fold.

In another aspect, a method is provided for selectively inhibiting CAPN1 in the presence of CAPN2 and CAPN9, which includes contacting cells (including neurons/microglia/invading macrophages) with an effective amount of one or more compounds of Formula I-XXXII described herein.

In another aspect, a method is provided for selectively inhibiting CAPN2 in the presence of CAPN1 and CAPN9, which includes contacting cells (including neurons/microglia/invading macrophages) with an effective amount of one or more compounds of Formula I-XXXII described herein.

In another aspect, a method is provided for selectively inhibiting CAPN9 in the presence of CAPN2 and CAPN1, which includes contacting cells (including neurons/microglia/invading macrophages) with an effective amount of one or more compounds of Formula I-XXXII described herein.

In another aspect, a method is provided for selectively inhibiting CAPN1 and CAPN2 in the presence of CAPN9, which includes contacting cells (including neurons/microglia/invading macrophages) with an effective amount of one or more compounds of Formula I-XXXII described herein.

In another aspect, a method is provided for selectively inhibiting CAPN1 and CAPN9 in the presence of CAPN2, which includes contacting cells (including neurons/microglia/invading macrophages) with an effective amount of one or more compounds of Formula I-XXXII described herein.

In another aspect, a method is provided for selectively inhibiting CAPN2 and CAPN9 in the presence of CAPN1, which includes contacting cells (including neurons/microglia/invading macrophages) with an effective amount of one or more compounds of Formula I-XXXII described herein.

In another aspect, the present technology is directed to a method for treating a fibrotic disease, which method comprises administering to a subject an effective amount of one or more compounds which specifically inhibits CAPN1, CAPN2, and/or CAPN9, said compounds being selected from Formula I-XXXII or a pharmaceutical composition comprising one or more compounds from Formula I-XXXII and a pharmaceutically acceptable excipient.

In another aspect, the present technology is directed to a method for treating a disease affected at least in part by CAPN1, CAPN2, and/or CAPN9, which method comprises administering to a subject an effective amount of one or more compounds which specifically inhibits CAPN1, CAPN2, and/or CAPN9, said compounds being selected from Formula I-XXXII or a pharmaceutical composition comprising one or more compounds from Formula I-XXXII and a pharmaceutically acceptable excipient.

In another aspect, the present technology is directed to a method for treating a fibrotic disease, which method comprises administering to a subject an effective amount of one or more compounds which selectively inhibits CAPN1, CAPN2, and/or CAPN9, said compounds being selected from Formula I-XXXII or a pharmaceutical composition comprising one or more compounds from Formula I-XXXII and a pharmaceutically acceptable excipient.

In another aspect, the present technology is directed to a method for treating a disease affected at least in part by CAPN1, CAPN2, and/or CAPN9, which method comprises administering to a subject an effective amount of one or more compounds which selectively inhibits CAPN1, CAPN2, and/or CAPN9, said compounds being selected from Formula I-XXXII or a pharmaceutical composition comprising one or more compounds from Formula I-XXXII and a pharmaceutically acceptable excipient.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:5.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:10.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:20.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:50.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:100.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:200.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:250.

In another aspect, the present technology is directed to a method for treating a fibrotic disease, which method comprises administering to a subject an effective amount of one or more compounds which specifically inhibits two or more enzymes selected from the group consisting of CAPN1, CAPN2, and CAPN9 in a ratio of at least 1:1:500.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:5.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:10.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:20.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:50.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:100.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:200.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:250.

In another aspect, the present technology is directed to a method for treating a fibrotic disease, which method comprises administering to a subject an effective amount of one or more compounds which selectively inhibits two or more enzymes selected from the group consisting of CAPN1, CAPN2, and CAPN9 in a ratio of at least 1:1:500.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:5.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:10.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:20.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:50.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:100.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:200.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:250.

In another aspect, the present technology is directed to a method for treating a disease affected at least in part by CAPN1, CAPN2, and/or CAPN9, which method comprises administering to a subject an effective amount of one or more compounds which specifically inhibits two or more enzymes selected from the group consisting of CAPN1, CAPN2, and CAPN9 in a ratio of at least 1:1:500.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:5.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:10.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:20.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:50.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:100.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:200.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:250.

In another aspect, the present technology is directed to a method for treating a disease affected at least in part by CAPN1, CAPN2, and/or CAPN9, which method comprises administering to a subject an effective amount of one or more compounds which selectively inhibits two or more enzymes selected from the group consisting of CAPN1, CAPN2, and CAPN9 in a ratio of at least 1:1:500.

In another aspect, a method is provided for prophylactic therapy or treatment of a subject having a fibrotic disorder wherein said method comprising administering an effective amount of one or more compounds of Formula I-XXXII to the subject in need thereof.

In another aspect, a method is provided for prophylactic therapy or treatment of a subject having a disorder affected by CAPN1, CAPN2, and/or CAPN9 wherein said method comprising administering an effective amount of one or more compounds of Formula I-XXXII to the subject in need thereof.

In another aspect, a method for inhibiting myofibroblast differentiation (e.g., Epithelial/Endothelial-to-Mesenchymal Transition (EpMT/EnMT)) is provided wherein the method comprises contacting cells with an effective amount of one or more compounds of Formula I-XXXII disclosed herein. In one aspect, the method for inhibiting myofibroblast differentiation (e.g., Epithelial/Endothelial-to-Mesenchymal Transition (EpMT/EnMT)) is performed in-vitro or in-vivo.

In some embodiments, the present technology is a method for treating a disease or condition selected from the group consisting of or that produces a symptom selected from the group consisting of: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis diseases, wherein which method comprises administering to a subject an effective amount of one or more compounds Formula I-XXXII to a subject in need thereof.

In some embodiments, the present technology is a method for treating liver fibrosis.

In some embodiments, the present technology is a method for treating cardiac fibrosis.

In some embodiments, the present technology is a method for treating fibrosis in rheumatoid arthritis diseases.

In some embodiments, the present technology is a method for treating a condition affected by CAPN1, CAPN2, and/or CAPN9, which is in both a therapeutic and prophylactic setting for subjects. Both methods comprise administering of one or more compounds of Formula I-XXXII to a subject in need thereof.

In some embodiments, the present technology is a method for treating stiff skin syndrome.

In another aspect, the present technology is directed to a method wherein one or more compounds of Formula I-XXXII may be administered with other CAPN1, CAPN2, and/or CAPN9 inhibitor agents, such as anti-CAPN1, CAPN2, AND/OR CAPN9 antibodies or antibody fragments, CAPN1, CAPN2, and/or CAPN9 antisense, iRNA, or other small molecule CAPN1, CAPN2, and/or CAPN9 inhibitors, or in combination with other agents as described in detail herein.

Diseases and/or disorders or produced symptoms associated or affected at least in part by CAPN1, CAPN2, and/or CAPN9 include those selected from the group consisting of: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis.

In one embodiment, therapeutically effective amount is a specific amount which causes a specific physiological effect which results in the amelioration of the disorder being treated or protects against a risk associated with the disorder.

The compounds of the present technology are useful in the diagnosis and treatment of a variety of human diseases selected from the group consisting of or that produces a symptom selected from the group consisting of: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis. The compounds of the present technology are particularly useful in treating disorders arising from fibrosis and complications thereof.

In another aspect, the present technology is directed to a method wherein one or more compounds of Formula I-XXXII which are used as a means to inhibit myofibroblast differentiation (e.g., Epithelial/Endothelial-to-Mesenchymal Transition (EpMT/EnMT)). In particular, one or more of these compounds which are inhibitors of one or more (or all three) CAPN1, CAPN2, and/or CAPN9, alone or in combination with other TGFβ signaling inhibitors, could be used to treat or protect againstor reduce a symptom of a fibrotic, sclerotic or post inflammatory disease or condition including: liver fibrosis, renal fibrosis, lung fibrosis, hypersensitivity pneumonitis, interstitial fibrosis, systemic scleroderma, macular degeneration, pancreatic fibrosis, fibrosis of the spleen, cardiac fibrosis, mediastinal fibrosis, myelofibrosis, endomyocardial fibrosis, retroperitoneal fibrosis, progressive massive fibrosis, nephrogenic systemic fibrosis, fibrotic complications of surgery, chronic allograft vasculopathy and/or chronic rejection in transplanted organs, ischemic-reperfusion injury associated fibrosis, injection fibrosis, cirrhosis, diffuse parenchymal lung disease, post-vasectomy pain syndrome, and rheumatoid arthritis.

Compounds of the present technology are shown to have improved safety and potency, such as the potency of inhibiting CAPN1, CAPN2, and/or CAPN9 at low micromolar concentrations and possessing low relative cytotoxicity. In general, compounds of the present technology are shown to have potency, ameliorate, and/or possess efficacy in treating diseases or disorders which include, as a component, some form of fibrosis or inflammation.

The amount of active compound administered will vary depending upon the disease treated, the mammalian species, and the particular mode of administration, etc. Suitable doses for the compounds of the present technology can be, for example, between 0.1 mg to about 1000 mg, between 1 mg to about 500 mg, between 1 mg to about 300 mg, or between 1 mg to about 100 mg per day. Such doses can be administered once a day or more than once a day, for example 2, 3, 4, 5 or 6 times a day, but preferably 1 or 2 times per day. In some embodiments, the total dosage for a 70 kg adult is in the range of 0.001 to about 15 mg per kg weight of subject per administration or 0.01 to about 1.5 mg per kg weight of subject per administration, and such therapy can extend for a number of days, a number of weeks or months, and in some cases, years. It will be understood, however, that the specific dose level for any particular subject will depend on a variety of factors including the activity of the specific compound employed; the age, body weight, general health, sex and diet of the individual being treated; the time and route of administration; the rate of excretion; other drugs that have previously been administered; and the severity of the particular disease undergoing therapy, as is well understood by those of skill in the area.

General Synthetic Methods

The compounds of the present technology can be prepared from readily available starting materials using the following general methods and procedures. It will be appreciated that where typical or preferred process conditions (i.e., reaction temperatures, times, mole ratios of reactants, solvents, pressures, etc.) are given, other process conditions can also be used unless otherwise stated. Optimum reaction conditions may vary with the particular reactants or solvent used, but such conditions can be determined by one skilled in the art by routine optimization procedures.

Additionally, as will be apparent to those skilled in the art, conventional protecting groups may be necessary to prevent certain functional groups from undergoing undesired reactions. Suitable protecting groups for various functional groups as well as suitable conditions for protecting and deprotecting particular functional groups are well known in the art. For example, numerous protecting groups are described in T. W. Greene and P. G. M. Wuts, Protecting Groups in Organic Synthesis, Third Edition, Wiley, New York, 1999, and references cited therein.

If the compounds of the present technology contain one or more chiral centers, such compounds can be prepared or isolated as pure stereoisomers, i.e., as individual enantiomers or d(l) stereoisomers, or as stereoisomer-enriched mixtures. All such stereoisomers (and enriched mixtures) are included within the scope of the present technology, unless otherwise indicated. Pure stereoisomers (or enriched mixtures) may be prepared using, for example, optically active starting materials or stereoselective reagents well-known in the art. Alternatively, racemic mixtures of such compounds can be separated using, for example, chiral column chromatography, chiral resolving agents and the like.

The starting materials for the following reactions are generally known compounds or can be prepared by known procedures or obvious modifications thereof. For example, many of the starting materials are available from commercial suppliers such as Aldrich Chemical Co. (Milwaukee, Wis., USA), Bachem (Torrance, Calif., USA), Emka-Chemce or Sigma (St. Louis, Mo., USA). Others may be prepared by procedures, or obvious modifications thereof, described in standard reference texts such as Fieser and Fieser's Reagents for Organic Synthesis, Volumes 1-15 (John Wiley, and Sons, 1991), Rodd's Chemistry of Carbon Compounds, Volumes 1-5, and Supplementals (Elsevier Science Publishers, 1989), Organic Reactions, Volumes 1-40 (John Wiley, and Sons, 1991), March's Advanced Organic Chemistry, (John Wiley, and Sons, 5th Edition, 2001), and Larock's Comprehensive Organic Transformations (VCH Publishers Inc., 1989).

Synthesis Routes to Compounds of the Present Technology

In one general embodiment, the method involves reacting an appropriately N-protected amino acid compound with an amino-protected side-chain, as starting material, with an N,O-dimethylhydroxylamine as a coupling partner and HATU to give the Weinreb amide. It is appreciated that other suitable coupling conditions and reagents, such as HOBt and/or DMAP, may be used to form a requisite Weinreb amide. The Wenireb amide is then reduced upon treatment with DIBAL or even LAH to the corresponding aldehyde. The skilled artisan will appreciate that there are many synthetic conditions or methods by which an ester functional group can be reduced to an aldehyde and such synthetic methods are well within in the scope of the present technology disclosed. The aldehyde then undergoes a cyanohydrin reaction upon treatment with KCN, which is then hydrolyzed under acidic conditions in alcohol to the corresponding α-hydroxy ester. If the side chain nitrogen has not already been de-protected, then the next step is to de-protect and make the free amine and cyclize it with the ester to form the cyclic amide. Finally, the α-hydroxyl group is oxidized under conditions for Dess-Martin Periodinane oxidation (with hypervalent iodine) or by an oxidizing agent such as PCC (pyridinium chlorochromate). The skilled artisan will once again appreciate that there are many other oxidizing conditions and agents which are within the scope of this disclosure to oxidize the hydroxyl group. At this point, the protecting group on the nitrogen atom is de-protected (and/or another group is connected to the nitrogen atom, for example an alkyl group thru a substitution or reductive amination reaction) and then the cyclic amine is coupled to the carboxylic acid group of another appropriately N-protected amino acid to form the desired compound. Of course it is recognized that at any point during this synthesis, the keto compounds may be interchanged with thio-keto compounds as treatment with Lawesson's reagent will give the corresponding thio-carbonyl compound. This synthesis route is generally shown in Scheme 1.

In one example, the compounds of general Formula I-XXXII can be generally prepared according to representative Scheme 1:

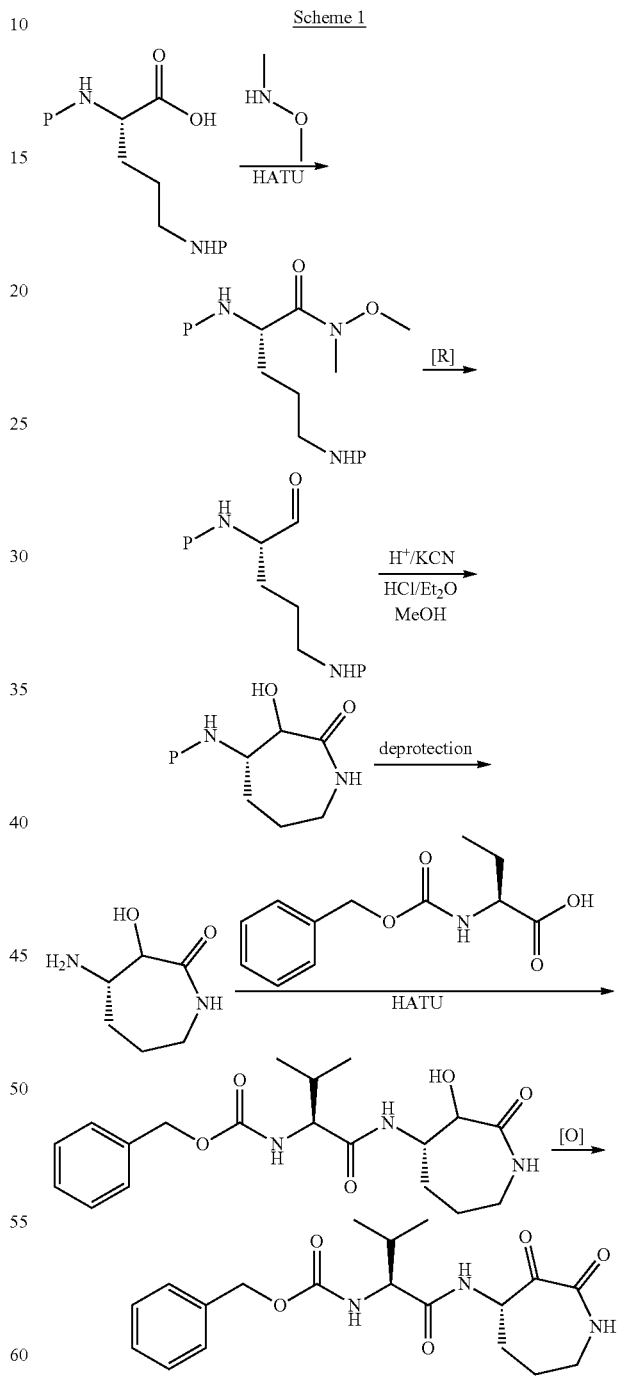

As an alternative, the skilled artisan will appreciate that these keto-amide compounds can also be prepared by converting the carboxylic acid functionality of the starting material, N-terminal protected amino acid (the side-chain may be protected as well), into an amide. In this way, the N—C bond connection to the cyclic keto-amide can be affected, optionally stereoselectively, by using the free nitrogen atom of the amide (on the C-terminus) to displace the appropriate and reactive functional group on the ring. Such functional group conversions are well known in the art and allow for complex substitution at the ring juncture. Typical substrates for displacement with the amide nitrogen are usually electrophilic in nature (though they need not be) and may include, but are not limited to: aldehydes, halides, alkenes, esters, carboxylic acids, ketones, and acid halides. Of course, either way the cyclization is affected, the skilled artisan will recognize that the requisite functional groups may be selected so that heteroatoms and multiple substituents can exist at any position of the ring. An ex In one example, the compounds of general Formula I-XXXII can also be generally prepared according to representative Scheme 2:

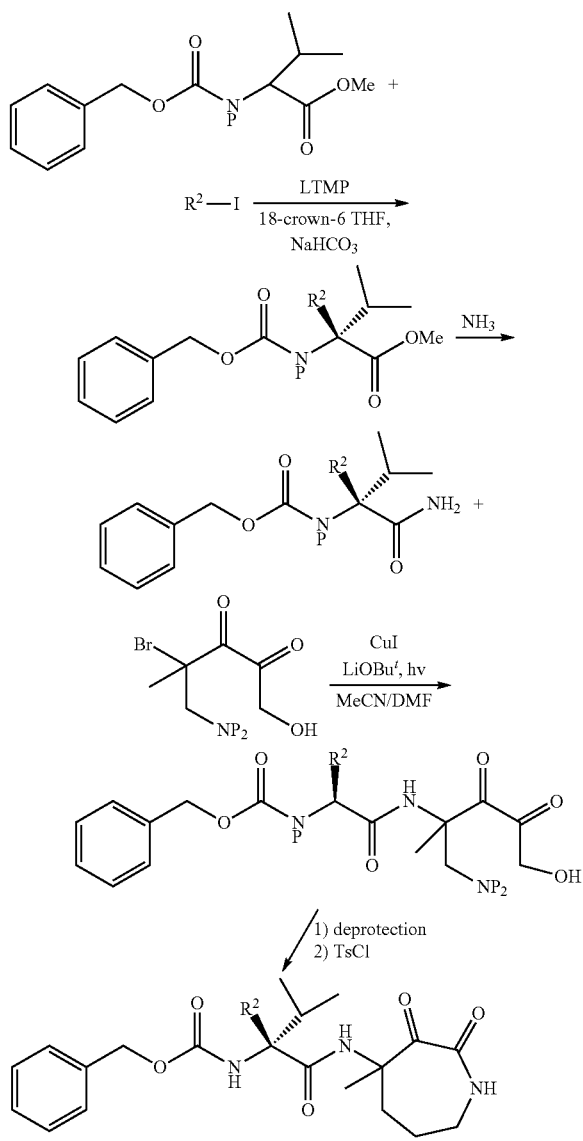

Herein it is understood that amino, keto, thio, hydroxyl, and any other necessary protecting groups and their methods of deprotection are known in the art, such as those described in T. W. Greene and P. G. M. Wuts, Protecting Groups in Organic Synthesis, Third Edition, Wiley, New York, 1999.

Alternatively, the skilled artisan will recognize that there is additional synthetic functional group modifications that can use to prepare spirocyclic and other bicyclic compounds onto the cyclic keto-amide ring.

In one example, the compounds of general Formula I-XXXII can also be generally prepared according to representative Scheme 3:

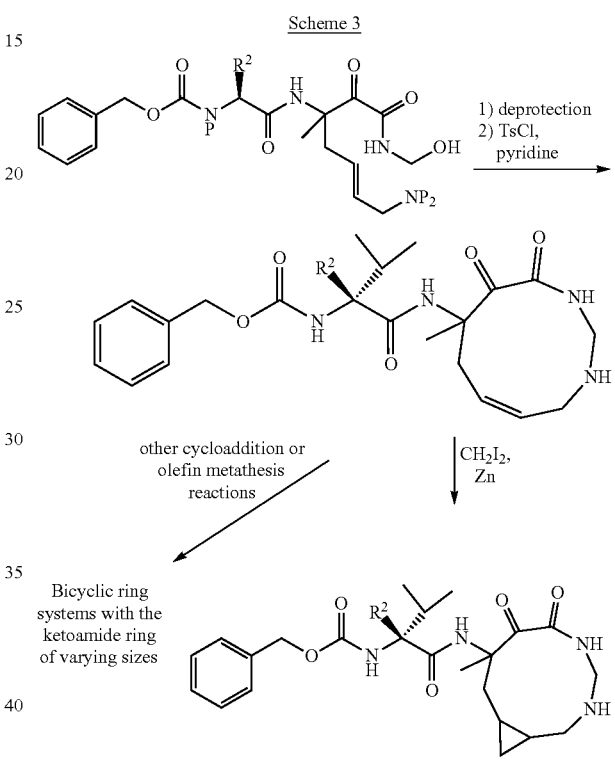

Yet in another alternative aspect, the skilled artisan will recognize that other bicyclic systems can be prepared thru similar functional group transformations with groups on the amino acid side chain or on the nitrogen atoms outside the keto-amide ring.

In one example, the compounds of general Formula I-XXXII can also be generally prepared according to representative Scheme 4:

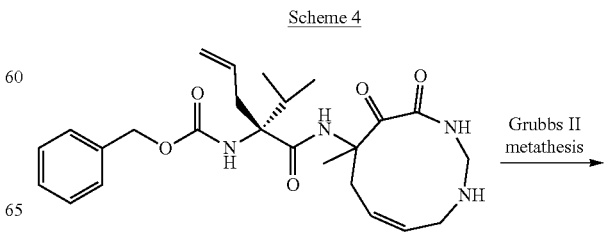

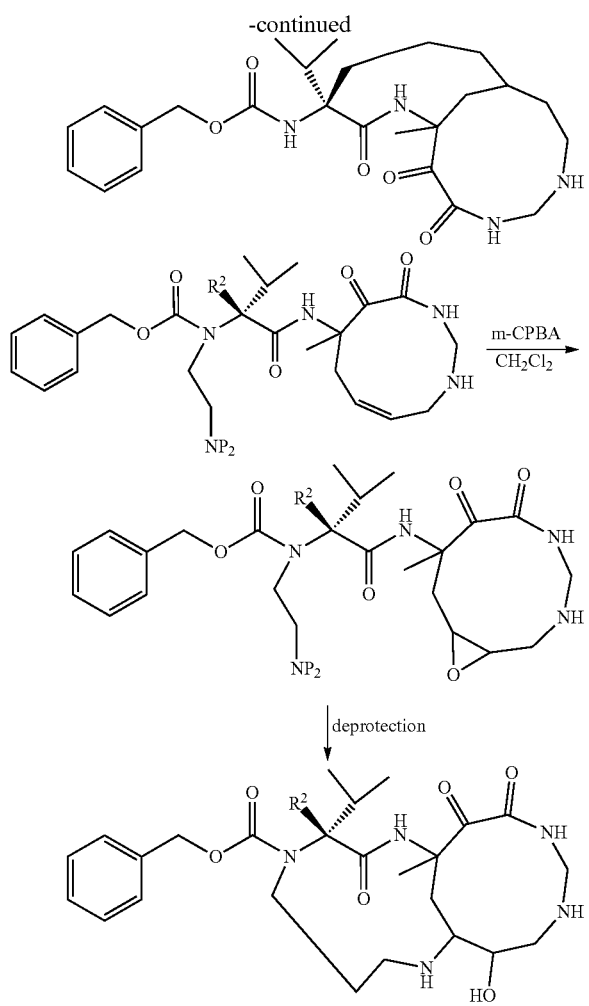

Administration and Pharmaceutical Composition

The present technology provides novel compounds possessing CAPN1, CAPN2, and/or CAPN9 inhibitory activity and, accordingly, are useful in treating conditions and/or disorders affected by (or at least in part by) CAPN1, CAPN2, and/or CAPN9. Such conditions include fibrosis and/or complications thereof.

Methods for treatment of fibrotic diseases are also encompassed by the present invention. Said methods of the invention include administering a therapeutically effective amount of any one of compounds of Formula I-XXXII. The compounds and solvates of the invention can be formulated in pharmaceutical compositions. These compositions can comprise a pharmaceutically acceptable excipient, carrier, buffer, stabilizer or other materials well known to those skilled in the art. The precise nature of the carrier or other material can depend on the route of administration, e.g. oral, intravenous, cutaneous or subcutaneous, nasal, intramuscular, intraperitoneal routes.

Pharmaceutical compositions for oral administration can be in tablet, capsule, powder or liquid form. A tablet can include a solid carrier such as gelatin or an adjuvant. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol can be included.

For intravenous, cutaneous or subcutaneous injection, or injection at the site of affliction, the active ingredient will be in the form of a parenterally acceptable aqueous solution which is pyrogen-free and has suitable pH, isotonicity and stability. Those of relevant skill in the art are well able to prepare suitable solutions using, for example, isotonic vehicles such as Sodium Chloride Injection, Ringer's Injection, Lactated Ringer's Injection. Preservatives, stabilizers, buffers, antioxidants and/or other additives can be included, as required.

A composition can be administered alone or in combination with other treatments, either simultaneously or sequentially dependent upon the condition to be treated.

In general, the compounds of the present technology will be administered in a therapeutically effective amount by any of the accepted modes of administration for agents that serve similar utilities. The actual amount of the compound of the present technology, i.e., the active ingredient, will depend upon numerous factors such as the severity of the disease to be treated, the age and relative health of the subject, the potency of the compound used, the route and form of administration, and other factors well known to the skilled artisan. The drug can be administered at least once a day, preferably once or twice a day.

An effective amount of such agents can readily be determined by routine experimentation, as can the most effective and convenient route of administration and the most appropriate formulation. Various formulations and drug delivery systems are available in the art. See, e.g., Gennaro, A. R., ed. (1995) Remington's Pharmaceutical Sciences, 18th ed., Mack Publishing Co.

A therapeutically effective dose can be estimated initially using a variety of techniques well-known in the art. Initial doses used in animal studies may be based on effective concentrations established in cell culture assays. Dosage ranges appropriate for human subjects can be determined, for example, using data obtained from animal studies and cell culture assays.

An effective amount or a therapeutically effective amount or dose of an agent, e.g., a compound of the present technology, refers to that amount of the agent or compound that results in amelioration of symptoms or a prolongation of survival in a subject. Toxicity and therapeutic efficacy of such molecules can be determined by standard pharmaceutical procedures in cell cultures or experimental animals, e.g., by determining the $LD_{50}$ (the dose lethal to 50% of the population) and the $ED_{50}$ (the dose therapeutically effective in 50% of the population). The dose ratio of toxic to therapeutic effects is therapeutic index, which can be expressed as the ratio $LD_{50}/ED_{50}$. Agents that exhibit high therapeutic indices are preferred.

The effective amount or therapeutically effective amount is the amount of the compound or pharmaceutical composition that will elicit the biological or medical response of a tissue, system, animal or human that is being sought by the researcher, veterinarian, medical doctor or other clinician. Dosages particularly fall within a range of circulating concentrations that includes the $ED_{50}$ with little or no toxicity. Dosages may vary within this range depending upon the dosage form employed and/or the route of administration utilized. The exact formulation, route of administration, dosage, and dosage interval should be chosen according to methods known in the art, in view of the specifics of a subject's condition.

Dosage amount and interval may be adjusted individually to provide plasma levels of the active moiety that are sufficient to achieve the desired effects; i.e., the minimal effective concentration (MEC). The MEC will vary for each compound but can be estimated from, for example, in vitro data and animal experiments. Dosages necessary to achieve the MEC will depend on individual characteristics and route of administration. In cases of local administration or selective uptake, the effective local concentration of the drug may not be related to plasma concentration.

The amount of agent or composition administered may be dependent on a variety of factors, including the sex, age, and weight of the subject being treated, the severity of the affliction, the manner of administration, and the judgment of the prescribing physician.

The present technology is not limited to any particular composition or pharmaceutical carrier, as such may vary. In general, compounds of the present technology will be administered as pharmaceutical compositions by any one of the following routes: oral, systemic (e.g., transdermal, intranasal or by suppository), or parenteral (e.g., intramuscular, intravenous or subcutaneous) administration. The preferred manner of administration is oral using a convenient daily dosage regimen that can be adjusted according to the degree of affliction. Compositions can take the form of tablets, pills, capsules, semisolids, powders, sustained release formulations, solutions, suspensions, elixirs, aerosols, or any other appropriate compositions. Another preferred manner for administering compounds of the present technology is inhalation.

The choice of formulation depends on various factors such as the mode of drug administration and bioavailability of the drug substance. For delivery via inhalation the compound can be formulated as liquid solution, suspensions, aerosol propellants or dry powder and loaded into a suitable dispenser for administration. There are several types of pharmaceutical inhalation devices-nebulizer inhalers, metered dose inhalers (MDI) and dry powder inhalers (DPI). Nebulizer devices produce a stream of high velocity air that causes therapeutic agents (which are formulated in a liquid form) to spray as a mist that is carried into the subject's respiratory tract. MDI's typically are formulation packaged with a compressed gas. Upon actuation, the device discharges a measured amount of therapeutic agent by compressed gas, thus affording a reliable method of administering a set amount of agent. DPI dispenses therapeutic agents in the form of a free flowing powder that can be dispersed in the subject's inspiratory air-stream during breathing by the device. In order to achieve a free flowing powder, therapeutic agent is formulated with an excipient such as lactose. A measured amount of therapeutic agent is stored in a capsule form and is dispensed with each actuation.

Pharmaceutical dosage forms of a compound of the present technology may be manufactured by any of the methods well-known in the art, such as, for example, by conventional mixing, sieving, dissolving, melting, granulating, dragee-making, tabletting, suspending, extruding, spray-drying, levigating, emulsifying, (nano/micro-) encapsulating, entrapping, or lyophilization processes. As noted above, the compositions of the present technology can include one or more physiologically acceptable inactive ingredients that facilitate processing of active molecules into preparations for pharmaceutical use.

Recently, pharmaceutical formulations have been developed especially for drugs that show poor bioavailability based upon the principle that bioavailability can be increased by increasing the surface area i.e., decreasing particle size. For example, U.S. Pat. No. 4,107,288 describes a pharmaceutical formulation having particles in the size range from 10 to 1,000 nm in which the active material is supported on a crosslinked matrix of macromolecules. U.S. Pat. No. 5,145,684 describes the production of a pharmaceutical formulation in which the drug substance is pulverized to nanoparticles (average particle size of 400 nm) in the presence of a surface modifier and then dispersed in a liquid medium to give a pharmaceutical formulation that exhibits remarkably high bioavailability.

The compositions are comprised of in general, a compound of the present technology in combination with at least one pharmaceutically acceptable excipient. Acceptable excipients are non-toxic, aid administration, and do not adversely affect therapeutic benefit of the claimed compounds. Such excipient may be any solid, liquid, semisolid or, in the case of an aerosol composition, gaseous excipient that is generally available to one of skill in the art.

Solid pharmaceutical excipients include starch, cellulose, talc, glucose, lactose, sucrose, gelatin, malt, rice, flour, chalk, silica gel, magnesium stearate, sodium stearate, glycerol monostearate, sodium chloride, dried skim milk and the like. Liquid and semisolid excipients may be selected from glycerol, propylene glycol, water, ethanol and various oils, including those of petroleum, animal, vegetable or synthetic origin, e.g., peanut oil, soybean oil, mineral oil, sesame oil, etc. Preferred liquid carriers, particularly for injectable solutions, include water, saline, aqueous dextrose, and glycols.

Compressed gases may be used to disperse a compound of the present technology in aerosol form. Inert gases suitable for this purpose are nitrogen, carbon dioxide, etc. Other suitable pharmaceutical excipients and their formulations are described in Remington's Pharmaceutical Sciences, edited by E. W. Martin (Mack Publishing Company, 18th ed., 1990).

The present compositions may, if desired, be presented in a pack or dispenser device containing one or more unit dosage forms containing the active ingredient. Such a pack or device may, for example, comprise metal or plastic foil, such as a blister pack, or glass, and rubber stoppers such as in vials. The pack or dispenser device may be accompanied by instructions for administration. Compositions comprising a compound of the present technology formulated in a compatible pharmaceutical carrier may also be prepared, placed in an appropriate container, and labeled for treatment of an indicated condition.

The amount of the compound in a formulation can vary within the full range employed by those skilled in the art. Typically, the formulation will contain, on a weight percent (wt %) basis, from about 0.01 99.99 wt % of a compound of the present technology based on the total formulation, with the balance being one or more suitable pharmaceutical excipients. Preferably, the compound is present at a level of about 1 80 wt %. Representative pharmaceutical formulations are described below.

FORMULATION EXAMPLES

The following are representative pharmaceutical formulations containing a compound of Formula I-XXXII.

Formulation Example 1

Tablet Formulation

The following ingredients are mixed intimately and pressed into single scored tablets.

| Ingredient | Quantity per tablet, mg |
| --- | --- |
| compound of this the present technology | 400 |
| cornstarch | 50 |
| croscarmellose sodium | 25 |
| lactose | 120 |
| magnesium stearate | 5 |

Formulation Example 2

Capsule Formulation

The following ingredients are mixed intimately and loaded into a hard-shell gelatin capsule.

| Ingredient | Quantity per capsule, mg |
| --- | --- |
| compound of this the present technology | 200 |
| lactose, spray-dried | 148 |
| magnesium stearate | 2 |

Formulation Example 3

Suspension Formulation

The following ingredients are mixed to form a suspension for oral administration.

| Ingredient | Amount |
| --- | --- |
| compound of this the present technology | 1.0 g |
| fumaric acid | 0.5 g |
| sodium chloride | 2.0 g |
| methyl paraben | 0.15 g |
| propyl paraben | 0.05 g |
| granulated sugar | 25.0 g |
| sorbitol (70% solution) | 13.00 g |
| Veegum K (Vanderbilt Co.) | 1.0 g |
| flavoring | 0.035 mL |
| colorings | 0.5 mg |
| distilled water | q.s. to 100 mL |

Formulation Example 4

Injectable Formulation

The following ingredients are mixed to form an injectable formulation.

| Ingredient | Amount |
| --- | --- |
| compound of this the present technology | 0.2 mg-20 mg |
| sodium acetate buffer solution, 0.4M | 2.0 mL |
| HCl (1N) or NaOH (1N) | q.s. to suitable pH |
| water (distilled, sterile) | q.s. to 20 mL |

Formulation Example 5

Suppository Formulation

A suppository of total weight 2.5 g is prepared by mixing the compound of the present technology with Witepsol® H-15 (triglycerides of saturated vegetable fatty acid; Riches-Nelson, Inc., New York), and has the following composition:

| Ingredient | Amount |
| --- | --- |
| Compound of the present technology | 500 mg |
| Witepsol ® H-15 | balance |

The following synthetic and biological examples are offered to illustrate this the present technology and are not to be construed in any way as limiting the scope of this the present technology. Unless otherwise stated, all temperatures are in degrees Celsius.

EXAMPLES

Below are examples of specific embodiments for carrying out the present invention. The examples are offered for illustrative purposes only, and are not intended to limit the scope of the present invention in any way. Efforts have been made to ensure accuracy with respect to numbers used (e.g., amounts, temperatures, etc.), but some experimental error and deviation should, of course, be allowed for.

The practice of the present invention will employ, unless otherwise indicated, conventional methods of protein chemistry, biochemistry, recombinant DNA techniques and pharmacology, within the skill of the art. Such techniques are explained fully in the literature. See, e.g., T. E. Creighton, *Proteins: Structures and Molecular Properties* (W.H. Freeman and Company, 1993); A. L. Lehninger, *Biochemistry* (Worth Publishers, Inc., current addition); Sambrook, et al., *Molecular Cloning: A Laboratory Manual* (2nd Edition, 1989); *Methods In Enzymology* (S. Colowick and N. Kaplan eds., Academic Press, Inc.); *Remington's Pharmaceutical Sciences,* 18th Edition (Easton, Pa.: Mack Publishing Company, 1990); Carey and Sundberg *Advanced Organic Chemistry* $3^{rd}$ *Ed.* (Plenum Press) Vols A and B (1992).

The present technology is further understood by reference to the following examples, which are intended to be purely exemplary of the present technology. The present technology is not limited in scope by the exemplified embodiments, which are intended as illustrations of single aspects of the present technology only. Any methods that are functionally equivalent are within the scope of the present technology. Various modifications of the present technology in addition to those described herein will become apparent to those skilled in the art from the foregoing description and accompanying figures. Such modifications fall within the scope of the appended claims.

In the examples below, the following abbreviations have the following meanings. If an abbreviation is not defined, it has its generally accepted meaning.

aq.=aqueous
LC-MS=liquid chromatography-mass spectrometry
MS=mass spectrometry
THF=tetrahydrofuran
$NaHCO_3$=sodium bicarbonate
DIEA=diisopropylethylamine
MS=mass spectrometry
NaH=sodium hydride
o/n=overnight
HATU=1-[Bis(dimethylamino)methylene]-1H-1,2,3-trI zolo[4,5-b]pyridinium 3-oxid hexafluorophosphate
r.t.=room temperature
LAH=lithium aluminum hydride
DCM=dichloromethane DMF=dimethylformamide
DMSO=dimethyl sulfoxide
equiv.=equivalent
eq.=equivalent
EtOAc=ethyl acetate
EtOH=ethanol
g=gram
h=hours
hrs.=hours
HCl=hydrochloric acid
HPLC=high-performance liquid chromatography
HOAc=acetic acid
M=molar
MeOH=methanol
mg=milligrams
mL=milliliters
mmol=millimols
mp=melting point
m/z=mass to charge ratio
NaCl=sodium chloride
Na$_2$CO$_3$=sodium carbonate
NMR=nuclear magnetic resonance
NaOH=sodium hydroxide
Na$_2$SO$_4$=sodium sulfate
TLC=thin layer chromatography
UV=ultraviolet
wt %=weight percent
μM=micromolar General Experimental Details:

Final compounds were confirmed by HPLC/MS analysis and determined to be ≥90%. $^1$H and $^{13}$C NMR spectra were recorded in CDCW (residual internal standard CHCW=δ 7.26), DMSO-d$_6$ (residual internal standard CD$_3$SOCD$_2$H=δ 2.50), methanol-d$_4$ (residual internal standard CD$_3$OD), or acetone-d$_6$ (residual internal standard CD$_3$COCD$_2$H=δ 2.05). The chemical shifts (δ) reported are given in parts per million (ppm) and the coupling constants (J) are in Hertz (Hz). The spin multiplicities are reported as s=singlet, bs=broad singlet, bm=broad multiplet=doublet, t=triplet, q=quartet, p=pentuplet, dd=doublet of doublet, ddd=doublet of doublet of doublet, dt=doublet of triplet, td=triplet of doublet, tt=triplet of triplet, and m=multiplet.

HPLC-MS analysis was carried out with gradient elution. Medium pressure liquid chromatography (MPLC) was performed with silica gel columns in both the normal phase and reverse phase.

Compounds Synthesis Procedures and Assay Data:

Example 1

Benzyl ((2S)-1-((2,3-dioxoazepan-4-yl)amino)-3-methyl-1-oxobutan-2-yl)carbamate (1)

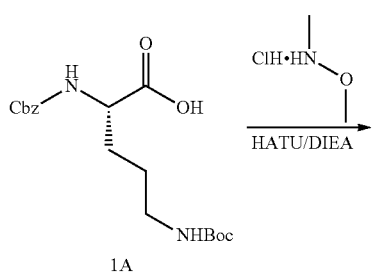

1A

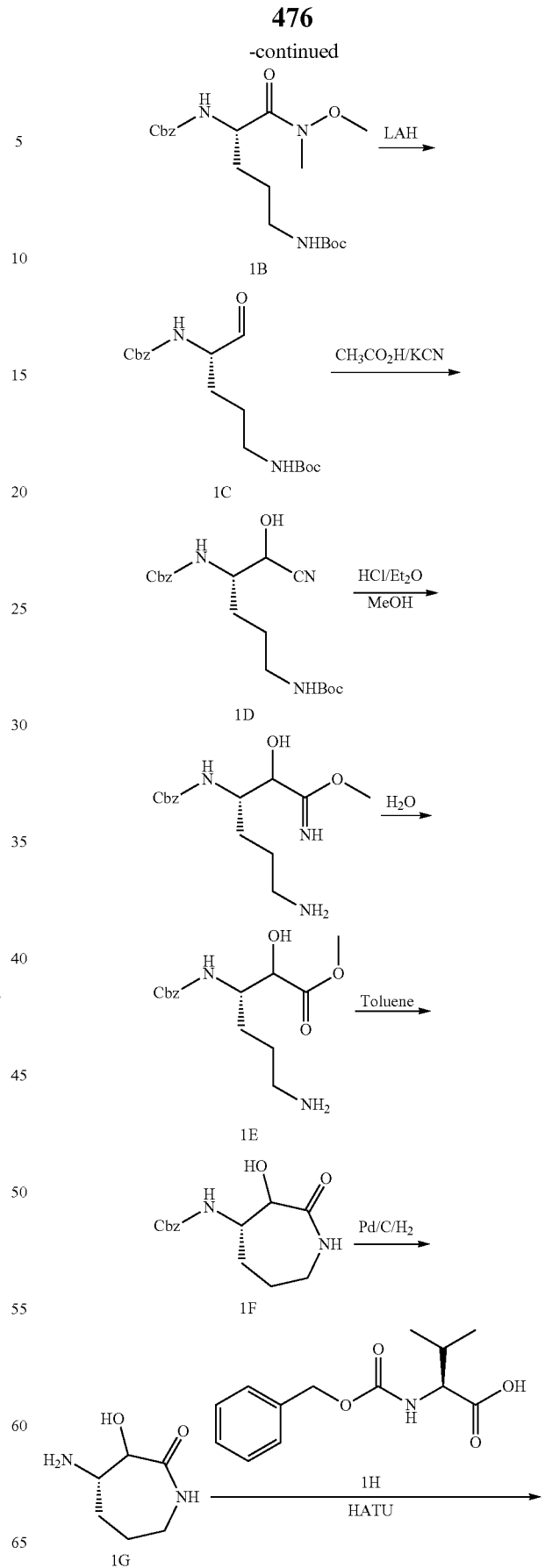

1B

1C

1D

1E

1F

1G

-continued

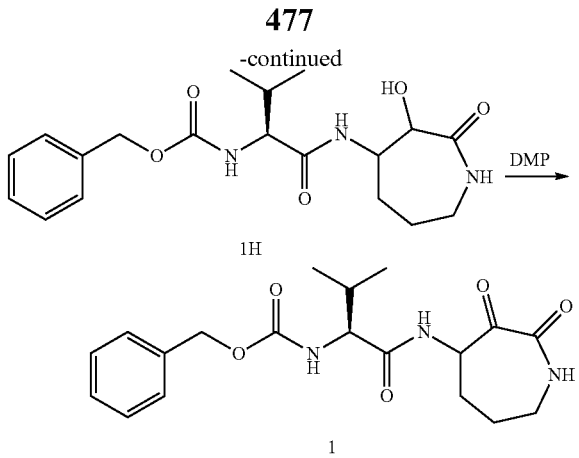

Weinreb Amide Intermediate Synthesis

Step 1: Synthesis of Compound 1B

Compound 1A (4 g, 1.0 eq.), N,O-dimethylhydroxylamine hydrochloride (1.12 g, 1.05 eq.) and HATU (4.56 g, 1.1 eq.) were combined in 30 mL DMF. The mixture was stirred at 0° C. for 5 minutes, and then DIEA (4.8 mL, 2.5 eq.) was added. The resulting mixture was stirred at rt. for 2 hrs. The mixture was diluted with 100 mL ethyl acetate and 30 mL hexane, washed with 3×60 mL water, 50 mL 1N HCl and 50 mL brine. The solvent was removed in vacuo to afford 1B (4.38 g, yield 98%) which was used without further purification.

Step 2: Synthesis of Compound 1C

Compound 1B (4.3 g, 1.0 eq.) was dissolved in 40 mL dry THF, cooled to −15° C. LAH (11.6 mL of 1.0M in THF, 1.1 eq.) was added dropwise. The resulting mixture was stirred at 0° C. for 1.5 hrs. Then the reaction was quenched with 1.5 mL ice-water. Regular work up afforded 1C (3.2 g, yield 87%) which was used immediately without further purification.

Step 3: Synthesis of Compound 1D

Compound 1C (3.2 g, 1.0 eq.) was dissolved in 25 mL MeOH. To the solution was added KCN (0.77 g, 1.3 eq.) and Acetic acid (0.66 g, 1.2 eq.). The resulting mixture was heated at 70° C. in a sealed-tube for 20 hrs. The reaction mixture was dried in vacuo and the residue was dissolved in 50 mL acetate, washed with water and brine. The crude mixture was purified on silica gel column to provide 1D (2.3 g, yield 67%).

Step 4: Synthesis of Compound 1E

A 120 mL solution of 3M HCl in Et₂O/MeOH (3:1) was cooled to −10° C. for 5 minutes under N₂. Compound 1D (2.3 g) was added. The resulting mixture was stirred at −10° C. for 1 hr, and then gradually warmed to room temperature. The mixture was then stirred at rt. overnight to form intermediate imidate. The mixture was cooled at 0° C., then added 30 mL ice-water. The reaction was stirred at rt. for 24 hrs. The solvent was removed in vacuo and the residue was adjusted pH to ~10 by adding 2M Na₂CO₃ at 0° C., then extracted with 5×30 mL CH₂Cl₂ to provide 1E (1.06 g, yield 56%) as white solid.

Step 5: Synthesis of Compound 1F

Compound 1E (1 g) was suspended in 100 mL dry toluene. The mixture was heated at reflux temperature for 18 hrs. The solvent was removed in vacuo, the residue was purified on silica gel column to provide 1F (0.21 g, yield 23%).

Step 6: Synthesis of Compound 1G

Compound 1F (200 mg) was dissolved in 20 mL MeOH, added Pd/C (10%, 40 mg). The mixture was hydrogenated at 45 psi H₂ for 4 hrs. The catalyst was removed by filtration. The solution was concentrated in vacuo to provide 1G (90 mg, yield 87%) as white solid.

Step 7: Synthesis of Compound 1J

Compound 1H (65 mg, 1.2 eq.) and HATU (108 mg, 1.3 eq.) were dissolved in 2.5 mL dry DMF, the mixture was stirred at rt. for 5 minutes. To the reaction was added DIEA (0.1 mL, 2.5 eq.) and 1G (31 mg, 1.0 eq). The resulting mixture was stirred at rt. for 18 hrs. The crude mixture was purified on preparative-HPLC to afford 1J (53 mg, yield 65%).

Step 8: Synthesis of Compound 1

Compound 1J (30 mg, 1.0 eq) was dissolved in 5 mL dry CH₂Cl₂, then added DMP (67 mg, 2.0 eq). The resulting mixture was stirred at rt. for 8 hrs. LC/MS analysis showed lots of compound 1J remained. Additional DMP (30 mg) was added to the reaction, the resulting mixture was stirred at rt. overnight. The precipitated solid was removed by filtration and discarded. The mother solution was dried in vacuo. The residue was dissolved in 3 mL MeOH and purified on HPLC to afford compound 1 (9 mg, yield 30%) as white solid. $^1$H NMR (400 MHz, CDCW); δ 7.31 (m, 5H), 6.72 (m, 1H), 6.41 (m, 1H), 5.34 (m, 1H), 5.11 (s, 2H), 4.85 (m, 1H), 4.01 (m, 1H), 3.38 (m, 1H), 3.18 (m, 1H), 2.44 (m, 1H), 2.10 (m, 1H), 1.98 (m, 1H), 1.55 (m, 2H), 0.96 (d, 3H), 0.92 (d, 3H) ppm. MS: m/z 376.3 [M+H]$^+$.

Example 2

Compounds 2-3

Benzyl ((2S)-1-(((2S)-1-((2,3-dioxoazepan-4-yl)amino)-4-methyl-1-oxopentan-2-yl)amino)-3-methyl-1-oxobutan-2-yl)carbamate (2)

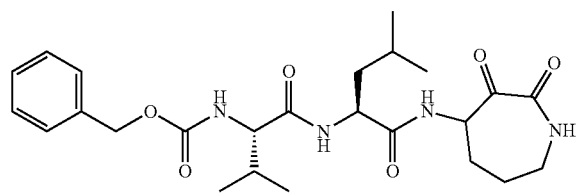

Synthesis of Compound 2

Compound 2 was prepared following the procedure of Example 1 using the corresponding carboxylic acid. $^1$H NMR (400 MHz, CDCW); δ 7.32 (m, 5H), 6.82-7.11 (m, 2H), 5.49 (m, 0.5H), 5.11 (s, 2H), 4.76 (m, 0.5H), 4.48 (m, 1H), 4.03 (m, 1H), 3.33 (m, 1H), 3.15 (m, 2H), 2.11 (m, 1H), 1.92 (m, 2H), 1.62 (m, 4H), 0.87-0.97 (m, 12H) ppm. MS: m/z 489.4 [M+H]$^+$.

479
(2S)—N-(2,3-dioxoazepan-4-yl)-2-((4-fluorophenyl)sulfonamido)-3-methylbutanamide (3)
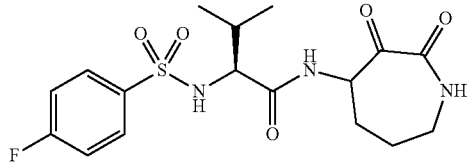
Synthesis of Compound 3
Compound 3 was prepared following the procedure of Example 1 using the corresponding carboxylic acid. $^1$H NMR (400 MHz, CD3OD); δ 7.88 (m, 2H), 7.24 (m, 2H), 4.08 (m, 1H), 3.65 (m, 2H), 3.34 (m, 1H), 3.07 (m, 1H), 1.67-1.85 (m, 2H), 1.42-1.61 (m, 2H), 0.83-0.98 (m, 6H) ppm. MS: m/z 400.3 [M+H]$^+$.
Example 3
Benzyl ((S)-1-(((S)-2,3-dioxoazecan-4-yl)amino)-3-methyl-1-oxobutan-2-yl)carbamate (4)
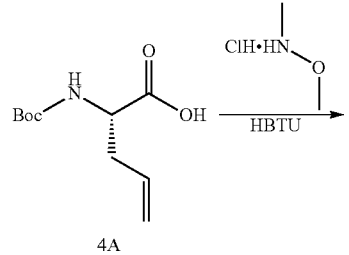
4A
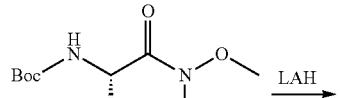
4B
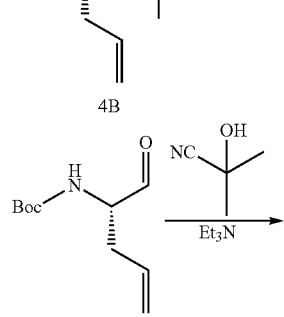
4C
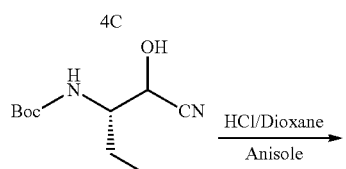
4D
480
-continued
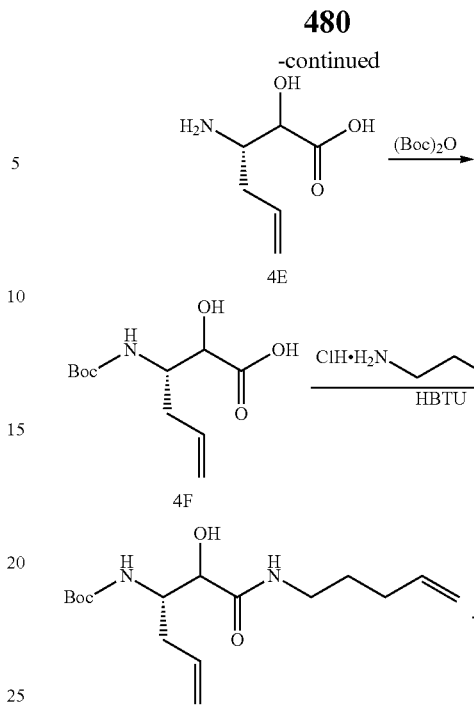
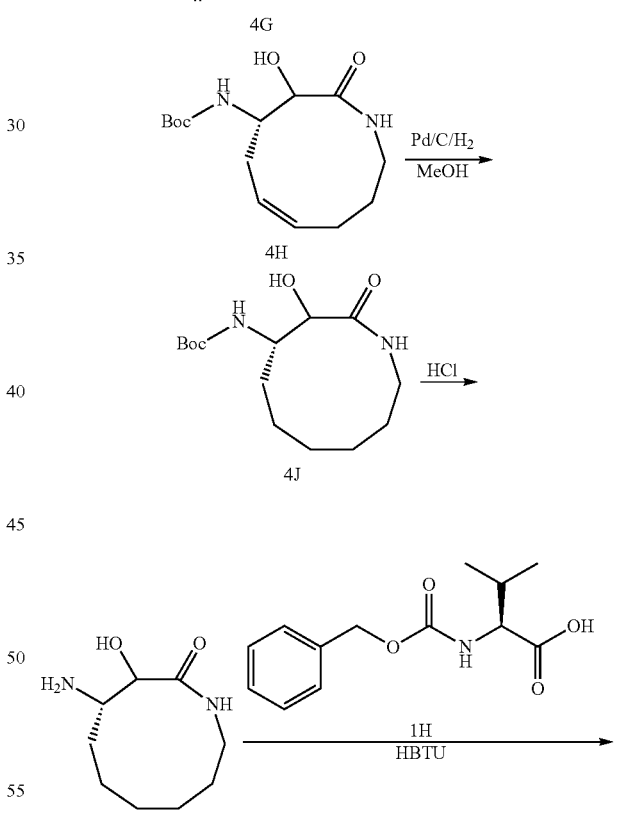

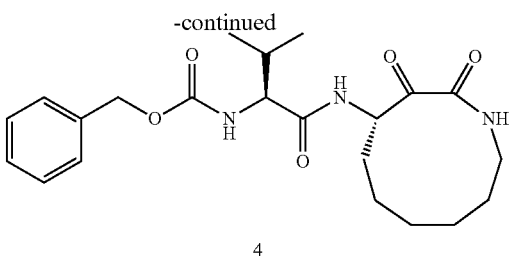

4

Step 1: Synthesis of Compound 4B

A mixture of compound 4A (8.5 g, 1.0 mmol), N-methoxymethanamine (7.7 g, 2.0 eq.), HBTU (17.3 g, 1.15 eq.) and TEA (16 g, 4.0 eq) in DMF (30 mL) was stirred at room temperature for 16 hours under $N_2$. The reaction mixture was diluted with 100 mL water, then extracted with 3×50 mL $CH_2Cl_2$. The combined organic phase was washed with 80 mL 0.5N HCl, 2×80 mL water and 50 mL saturated $NaHCO_3$, dried over $Na_2SO_4$, filtered and concentrated under reduced pressure to give compound 4B (10.5 g g, yield: ~100%) as white solid. The crude product was used in the next step without further purification.

Step 2: Synthesis of Compound 4C

Compound 4B (3.95 g, 1.0 eq.) was dissolved in dry THF (25 ml) and cooled to −78° C. under $N_2$. LAH (1M, 17.6 mL, 1.15 eq) was added dropwise. The mixture was stirred at −30° C. for 2 hrs. Then the reaction was quenched by adding $KHSO_4$ solution (0.35M, 60 mL) at −10° C. The mixture was extracted by 3×60 mL acetate. The organic phase was washed with water and brine to provide 4C (3.0, yield ~99%) which was used without further purification.

Step 3: Synthesis of Compound 4D

A solution of compound 4C (1.0 g, 1.0 eq), 2-hydroxy-2-methylpropanenitrile (855 mg, 2.0 eq.) and TEA (610 mgs, 1.2 eq.) in dry DCM (10 mL) was stirred at rt. overnight. The reaction mixture was diluted with 25 mL DCM, washed with 0.5N HCl, water and brine. The crude mixture was purified on silica gel column to afford 4D (1.08 g, yield 94.5%).

Step 4: Synthesis of Compound 4F

To a solution of compound 4D (0.97 g), anisole (600 mg) in 10 mL dioxane was added 10 mL concentrated HCl, the mixture was stirred at rt. for 30 mins, then refluxing for 1.5 hrs. The solvent was removed in vacuo to afford compound 4E as yellow solid. Compound 4E was dissolved in 10 mL water and 10 mL THF, adjusted pH to 9~10 by adding 1N NaOH and saturated $NaHCO_3$. The mixture was cooled to 0° C., then added $(Boc)_2O$. The resulting mixture was stirred at rt. overnight. THF was removed in vacuo, the residue was diluted with 10 mL water, adjusted pH ~2 by adding 1N HCl, extracted with 3×50 mL acetate to afford compound 4F (730 mg, yield 73%) which was used without purification.

Step 5: Synthesis of Compound 4G

A mixture of compound 4F (680 mg, 1.0 mmol), pent-4-en-1-amine hydrochloride (504 mg, 1.5 eq.), HBTU (1.27 g, 1.2 eq.) and TEA (1.12 g, 4.0 eq.) in DMF (7 mL) was stirred at room temperature for 16 hours under $N_2$. The reaction mixture was diluted with 20 mL water and then extracted with 3×50 mL $CH_2Cl_2$. The combined organic phase was washed with 2×10 mL 0.5N HCl, 2×20 mL water and 20 mL saturated $NaHCO_3$, dried over $Na_2SO_4$, filtered and concentrated under reduced pressure. The crude mixture was purified on silica gel column to afford compound 4G (510 mg, yield 58%).

Step 6: Synthesis of Compound 4H

Compound 4G (50 mg, 1.0 eq.) and Grubbs's $2^{nd}$ catalyst (20 mg, 0.15 eq.) in 1,2-dichloroethane (20 mL), degassed with $N_2$ for 5 mins. The mixture was heated at 90° C. for 1 hr in microwave reactor. The reaction was repeated 5 more times. The combined mixture was dried in vacuo, and directly purified on silica gel column to provide compound 4H (100 mg) contained significant amount of Cat. ligand.

Step 7: Synthesis of Compound 4J

A solution of compound 4H (100 mg) and Pd/C (40 mg, 10%) in 30 mL MeOH was hydrogenated at 50 psi for 15 hrs. The catalyst was removed, and crude product was purified on silica gel column to afford compound 4J (40 mg, yield 40%).

Step 8: Synthesis of Compound 4K

Compound 4J (40 mg) was dissolved in 2 mL dry DCM, added 2 mL 4N HCl in dioxane. The mixture was stirred at rt. for 1 hr. The solvent was removed in vacuo to afford white solid 4K (31 mg, yield 100%) as HCl salt.

Step 9: Synthesis of Compound 4L

A mixture of compound 4K (31 mg, 1.0 mmol), 1H (42 mg, 1.2 eq.), HBTU (66 mg, 1.3 eq.) and DIEA (0.1 mL, 4.0 eq) in DMF (2 mL) was stirred at room temperature for 5 hours under $N_2$. The reaction mixture was diluted with 10 mL water, then extracted with 3×50 mL $CH_2Cl_2$. The combined organic phase was washed with 2×10 mL 0.5N HCl, 2×20 mL water and 20 mL saturated $NaHCO_3$, dried over $Na_2SO_4$, filtered and concentrated under reduced pressure. The crude mixture was purified HPLC to afford compound 4L (20 mg, yield 37%).

Step 10: Synthesis of Compound 4

To a solution of compound 4L (20 mg, 1.0 eq.) in 1 ml dry DCM and 0.2 mL DMSO was added DMP (81 mg, 4.0 eq.). The resulting mixture was stirred at rt. for 3 hrs then the mixture was diluted with DCM (10 mL), quenched by adding 10% $Na_2S_2O_3$/saturated $NaHCO_3$ (v/v=1/1, ~2 mL). The organic layer was separated. The aqueous layer was extracted with DCM (5 mL×5). The combined organic layer was washed with $H_2O$ (10 mL), brine (10 mL), dried over anhydrous Na2SO4, filtered and concentrated to afford compound 4 (9 mg, yield 45.0%) as white solid. $^1$H NMR (400 MHz, DMSO-d6); δ 8.22 (t, 2H), 7.21-7.38 (m, 7H), 4.95 (s, 2H), 3.78 (m, 1H), 3.32-3.52 (m, 3H), 1.93 (m, 1H), 1.06-1.58 (m, 10H), 0.81 (m, 6H) ppm. MS: m/z 418.6 $[M+H]^+$.

Example 4

Benzyl ((2S)-1-((2,3-dioxopiperidin-4-yl)amino)-3-methyl-1-oxobutan-2-yl)carbamate (5)

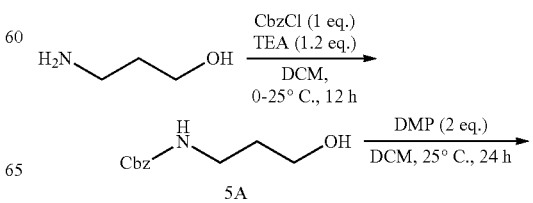

5A

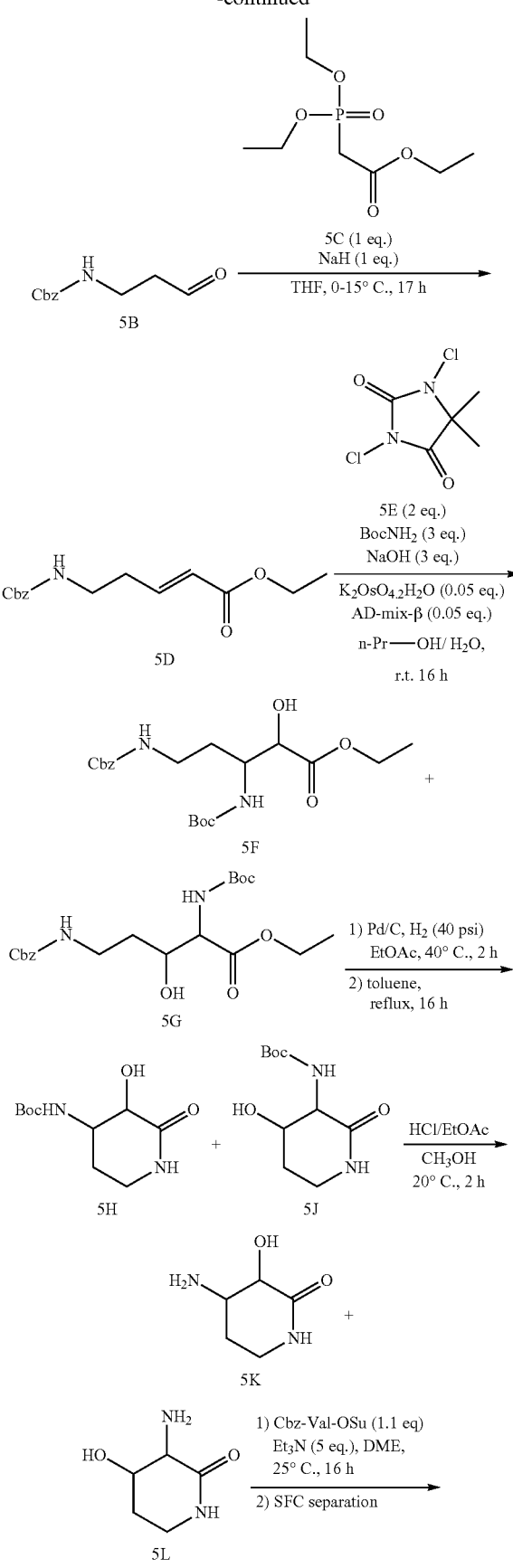

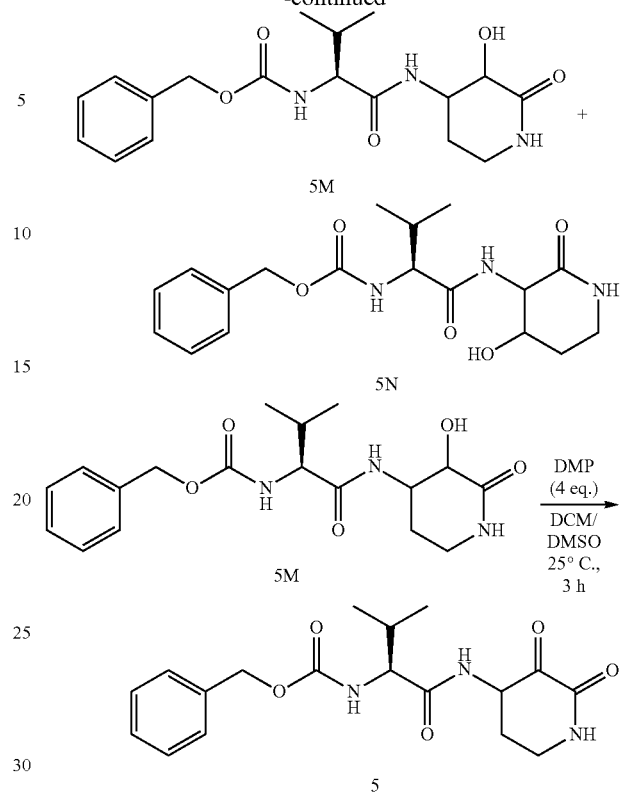

Step 1: Synthesis of Compound 5A

To a solution of 3-aminopropan-1-ol (30 g, 399.41 mmol) and TEA (66.44 mL, 479.29 mmol) in DCM (400 mL) was added the solution of CbzCl (62.5 mL, 439.35 mmol) in DCM (500 mL). The solution was stirred slowly from 0° C. to 25° C. for 12 hours. The mixture was extracted with DCM (200 mL) and washed by brine (100 mL×3). The organics was collected, dried with $Na_2SO_4$, filtered and concentrated. The mixture was washed by PE (200 mL) and EA (20 mL) to give compound 5A (60 g, yield 72%) as a white solid.

Step 2: Synthesis of Compound 5B

To a solution of compound 5A (20 g, 95.58 mmol) in DCM (500 mL) was added DMP (81.1 g, 191.16 mmol). The solution was stirred at 25° C. for 24 hours. The mixture was diluted with DCM (300 mL), quenched with a solution of 10% aq. $Na_2S_2O_3$ and 10% aq. $NaHCO_3$ (300 mL) (v/v: 1/1). The organic phase were collected and concentrated to give compound 5B (56.8 g, crude) as green oil. $^1$H NMR (DMSO-$d_6$, 400 MHz) δ 9.66 (s, 1H), 7.37-7.31 (m, 6H), 5.06-5.03 (m, 2H), 3.34-3.32 (m, 2H), 2.61-2.58 (m, 2H).

Step 3: Synthesis of Compound 5D

NaH (11 g, 274.09 mmol, 60% in oil) in THF (250 mL) was cooled to 0° C., compound 5C (54.38 mL, 274.09 mmol) was added dropwise. The reaction was stirred at 0° C. for 0.5 h, then the solution of compound 5B (56.8 g, 274.09 mmol) in THF (50 mL) was added dropwise during 0.5 h. The reaction was warmed to 10-15° C. and stirred for 16 hours. The mixture was quenched with $H_2O$ (450 mL) at 0° C., extracted with EA (400 mL). The organics were washed by brine (100 mL×5), dried with $Na_2SO_4$, filtered and concentrated. The mixture was purified by flash column (PE:EA=1:0 to 2:1) to afford Compound 5D (15 g, yield: 20%) as a white solid. $^1$H NMR (DMSO-$d_6$, 400 MHz) δ 7.38-7.32 (m, 6H), 6.90-6.82 (m, 1H), 5.91-5.83 (m, 1H), 5.02 (m, 2H), 4.14-4.09 (m, 2H), 3.17-3.07 (m, 2H), 2.38-2.33 (m, 2H), 1.23-1.18 (m, 3H).

Step 4: Synthesis of Compounds 5F and 5G

To a stirring solution of tert-butyl carbamate (11.41 g, 97.36 mmol) in n-propanol (40 ml) at room temperature was added a solution of NaOH (3.89 g, 97.36 mmol) in H$_2$O (80 mL). To this mixture was added compound 5E (12.8 g, 64.91 mmol), followed by a solution of AD-mix-β (1.26 g, 1.62 mmol) in n-propanol (20 ml), then a solution of compound 5D (9.0 g, 32.45 mmol) in n-propanol (20 ml). To this mixture was added K$_2$OsO$_4$.2H$_2$O (598 mg, 1.62 mmol). The resulting mixture was stirred at 25° C. for 16 hours. The reaction was diluted with H$_2$O (100 mL) and quenched with Na$_2$SO$_3$ (33.54 g, 266.09 mmol) and stirred at 10-15° C. for 0.5 h, then extracted with EtOAc (100 mL×3), washed with brine (100 mL) and dried over anhydrous Na$_2$SO$_4$. Filtered and concentrated to give a residue, which was purified by FCC (PE:EA=10:1 to 1:1) to give the compound 5F and 5G (5.0 g, yield: 31.8%) as a white solid. MS (ESI) m/z (M+Na$^+$) 433.1.

Step 5: Synthesis of Compounds 5H and 5J

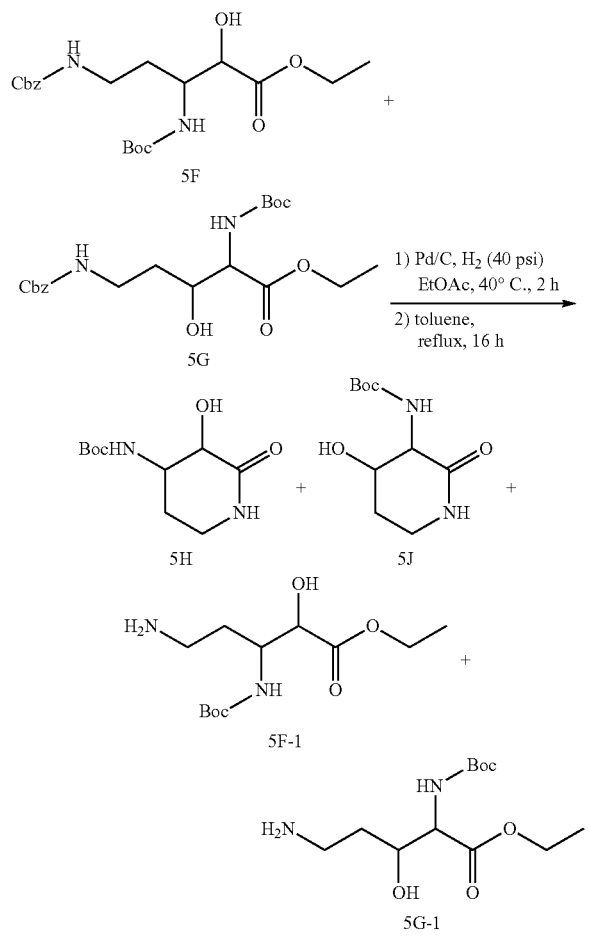

The mixture consisting of compound 5F and 5G (5.0 g, 12.18 mmol), Pd/C (2.20 g, 10% wt) and EtOAc (100 mL) was stirred at 40° C. for 2 hours under H$_2$ (40 psi) before cooling to room temperature. Filtered and the filter cake was washed with EtOAc (50 mL×3), the obtained filtrate was combined and concentrated to give the mixture of compound 5H, 5J and possible 5F-1 and 5G-1 (2.2 g, yield: 78% by 5H and 5J) as a white solid. $^1$H NMR (DMSO-d$_6$, 400 MHz) δ 7.63-7.45 (m, 1H), 7.01-6.82 (m, 1H), 5.15-5.00 (m, 1H), 3.81-3.63 (m, 1H), 3.58-3.45 (m, 1H), 3.14-2.96 (m, 2H), 1.97-1.83 (m, 1H), 1.69-1.52 (m, 1H), 1.44-1.28 (m, 9H). MS (ESI) m/z (M+2 Na$^+$) 276.0.

Step 6: Synthesis of Compounds 5H and 5J

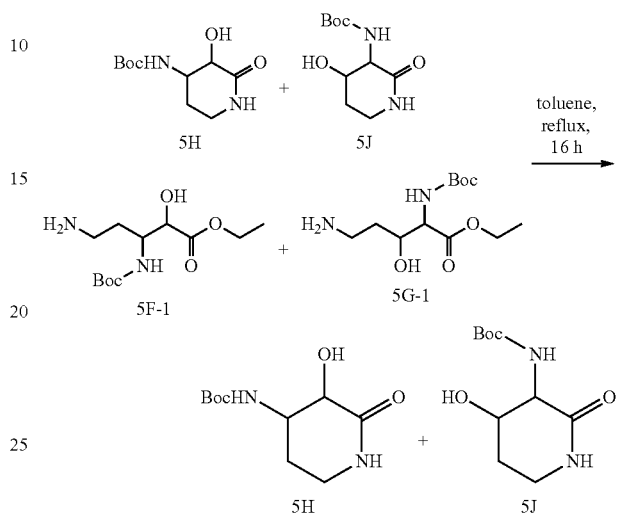

The mixture consisting of compound 5H, 5J and possible 5F-1 and 5G-1 (2.2 g) was mixed with toluene (50 mL) and stirred at 110° C. to 120° C. for 12 hours before cooling to room temperature. The toluene was removed and the residue was triturated with CH$_3$OH (10 mL) to give compound 5H and 5J (1.3 g, yield: 71%) as a white solid. $^1$H NMR (DMSO-d$_6$, 400 MHz) δ 7.60-7.44 (m, 1H), 6.98-6.83 (m, 1H), 5.12-4.98 (m, 1H), 3.81-3.63 (m, 1H), 3.52 (t, J=8.3 Hz, 1H), 3.12-2.96 (m, 2H), 1.96-1.83 (m, 1H), 1.68-1.52 (m, 1H), 1.44-1.26 (m, 9H). MS (ESI) m/z (M+2 Na$^+$) 276.0.

Step 7: Synthesis of Compounds 5K and 5L

The mixture of compound 5H and 5J (1.3 g, 5.65 mmol), HCl/EtOAc (20 mL, 4M) and MeOH (10 mL) was stirred at 20° C. for 2 hours before removing the solvent. The obtained residue was just the product 5K and 5L (1.0 g, crude, HCl) was obtained as a white solid. MS (ESI) m/z (M+H)$^+$ 130.8.

Step 8: Synthesis of Compounds 5M and 5N

The mixture consisting of Cbz-Val-OSu (2.30 g, 6.60 mmol), compound 5K and 5L (1.0 g, 6.00 mmol, HCl salt), Et$_3$N (3.4 mL, 24.0 mmol) and DME (100 mL) was stirred at 25° C. for 16 hours. The solvent was removed and the residue was diluted with HCl (2M, 25 ml) and extracted with DCM:CH$_3$OH (10:1, 80 mL×5). The organic phase was combined and washed with NaHCO$_3$ (20 mL), brine (20 mL) and concentrated to give a residue, which was purified by FCC (DCM:CH$_3$OH=1:0 to 10:1) to give the mixture of compound 5M and 5N (900 mg) as a yellow solid. The mixture (500 mg) was separated by SFC (OJ 250 mm*30 mm, 5 um), Base-EtOH (20%-20%)) to give the pure compound 5M (320 mg, yield: 31%) as a white solid. NMR (DMSO-d$_6$, 400 MHz) δ 8.16-7.93 (m, 1H), 7.61 (d, J=6.3 Hz, 1H), 7.41-7.27 (m, 5H), 7.22 (dd, J=2.8, 9.0 Hz, 1H), 5.22-5.10 (m, 1H), 5.08-4.97 (m, 2H), 3.92-3.64 (m, 3H), 3.11 (d, J=5.3 Hz, 2H), 1.98-1.84 (m, 2H), 1.71-1.50 (m, 1H), 0.93-0.77 (m, 6H). MS (ESI) m/z (M+Na$^+$) 386.1.

Step 9: Synthesis of Compound 5

The mixture consisting of compound 5M (20 mg, 55.03 umol), DMP (93.4 mg, 220.12 umol), DCM (6 mL) and DMSO (0.5 mL) was stirred at 25° C. for 3 hours before removing the solvent. The obtained residue was purified by Pre-HPLC with a Phenomenex Synergi C18 150*30 mm*4 um column (eluent: 26% to 36% (v/v) CH$_3$CN and aqueous HCl (0.05%)). The pure fractions were collected and concentrated to dryness under reduced pressure to afford the title compound 5 (6 mg, yield: 27%) as an off-white solid. $^1$H NMR (DMSO-d$_6$, 400 MHz) δ 9.09 (s, 0.45H), 8.31-8.21 (m, 0.48H), 7.57-7.44 (m, 1H), 7.41-7.25 (m, 5H), 7.20-7.09 (m, 0.53H), 7.06-6.99 (m, 0.40H), 5.10-4.97 (m, 2H), 4.25-3.81 (m, 1H), 3.22-3.10 (m, 1H), 2.88-2.75 (m, 0.59H), 2.70-2.59 (m, 0.65H), 2.56-2.52 (m, 1H), 2.35-2.24 (m, 0.5H), 2.14-1.88 (m, 1.4H), 1.55-1.13 (m, 1H), 0.95-0.76 (m, 6H). MS (ESI) m/z (M+H)$^+$ 362.0.

Example 5

Benzyl ((2S)-3-methyl-1-((1-methyl-2,3-dioxoazepan-4-yl)amino)-1-oxobutan-2-yl)carbamate (6)

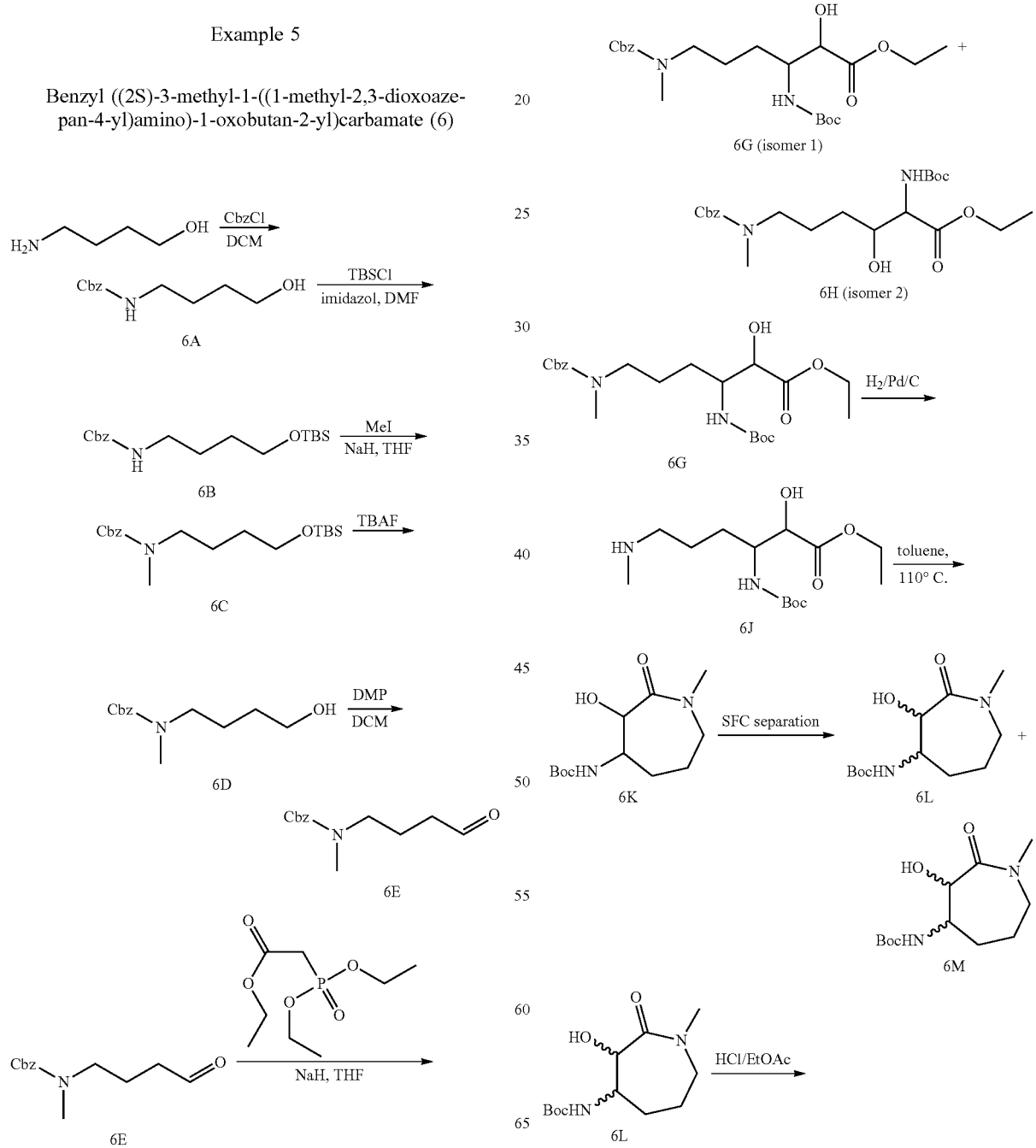

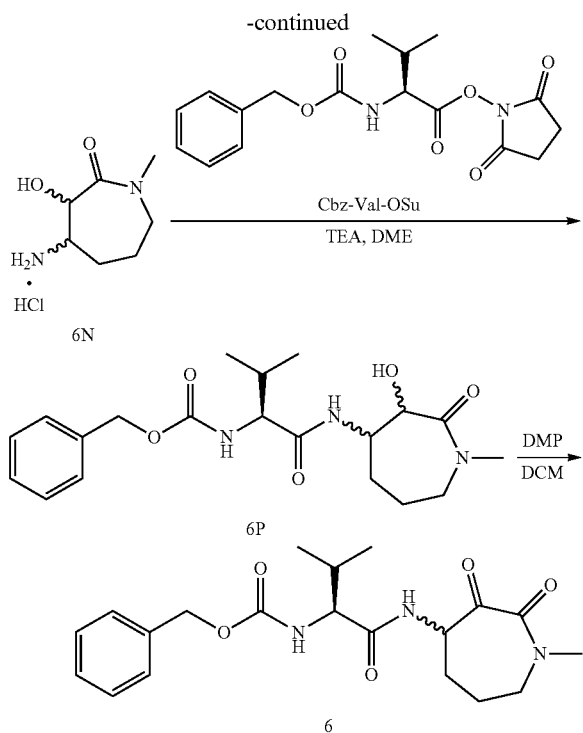

Step 1: Synthesis of Compound 6A

To a solution of 4-aminobutan-1-ol (20 g, 224.4 mmol) and CbzCl (32 mL, 224.4 mmol) in THF (200 mL) was added TEA (62.2 mL, 448.7 mmol). The mixture was stirred at 25° C. for 12 hrs. The solvent was removed in vacuo. The residue was dissolved in EtOAc (800 mL). The solution was washed with 1N HCl (800 mL). The organics were collected, washed with saturated NaHCO$_3$ (800 mL), brine (800 mL), dried with Na$_2$SO$_4$, filtered, and concentrated. The residue was washed with a solution of (PE:EA=2:1) (300 mL). The solid was filtered and collected to give compound 6A (34 g, 33.95% yield) white solid.

Step 2: Synthesis of Compound 6B

To a solution of compound 6A (24 g, 107.5 mmol) and imidazol (14.7 g, 215 mmol) in DMF (200 mL) was added TBSCl (17.9 g, 118.2 mmol) at 0° C. The mixture was stirred at 25° C. for 1 h. The mixture was washed with H$_2$O (1 L), extracted with EtOAc (500 mL×2). The organics were collected and concentrated. The residue was purified by column (PE:EA=10:1) to give compound 6B (28 g, 77.18% yield) as colorless oil. MS (ESI) m/z (M+H)$^+$ 338.1.

Step 3: Synthesis of Compound 6C

To a solution of compound 6B (45 g, 133.3 mmol) in THF (500 mL) was added NaH (10.7 g, 266.6 mmol, 60% purity) at 0° C. Then CH$_3$I (69.2 mL, 1.11 mol) was added to the mixture dropwise at 0° C. The mixture was then warmed up to 25° C. and stirred for 12 hrs. The reaction was quenched with H$_2$O (400 mL) dropwise carefully, extracted with EtOAc (800 mL). The organics were collected, washed with brine (800 mL), dried with Na$_2$SO$_4$, filtered and concentrated to give compound 6C (90 g, crude) as light yellow oil.

Step 4: Synthesis of Compound 6D

To a solution of compound 6C (10 g, 28.4 mmol) in THF (100 mL) was added TBAF (1M, 34.2 mL). The mixture was stirred at 25° C. for 3 hrs. The mixture was diluted with EtOAc (300 mL), washed with brine (300 mL×3). The organics were collected and concentrated. The residue was purified by column (PE:EA=1:1) to give compound 6D (6 g, 88.91% yield) as colorless oil. $^1$H NMR (400 MHz, DMSO-d$_6$) δ 7.40-7.17 (m, 5H), 5.06 (s, 2H), 4.45-4.35 (m, 1H), 3.50-3.36 (m, 2H), 3.30-3.13 (m, 2H), 2.95-2.65 (m, 3H), 1.55-1.47 (m, 2H), 1.44-1.36 (m, 2H).

Step 5: Synthesis of Compound 6E

To a solution of compound 6D (1 g, 4.2 mmol) in DCM (50 mL) was added DESS-MARTIN PERIODINANE (2.7 g, 6.32 mmol). The mixture was stirred at 25° C. for 12 hrs. The mixture was diluted with DCM (50 mL), quenched with a solution of 10% aq. Na$_2$S$_2$O$_3$ and 10% aq. NaHCO$_3$ (v/v=1:1) (100 mL). The organics were collected, washed with brine (100 mL), dried with Na$_2$SO$_4$, filtered and concentrated to give compound 6E (800 mg, crude) as colorless oil. $^1$H NMR (400 MHz, DMSO-d$_6$) δ 9.77-9.55 (m, 1H), 7.52-7.20 (m, 5H), 5.06 (s, 2H), 3.31-3.12 (m, 2H), 2.96-2.75 (m, 3H), 2.45-2.31 (m, 2H), 1.78-1.71 (m, 2H).

Step 6: Synthesis of Compound 6F

NaH (136 mg, 3.40 mmol, 60% purity) in THF (10 mL) was cooled to 0° C., ethyl 2-(diethoxyphosphoryl)acetate (763 mg, 3.40 mmol) was added dropwise. The mixture was stirred at 0° C. for 0.5 h. Then a solution of compound 6E (800 mg, 3.40 mmol) in THF (10 mL) was added. The mixture was stirred at 25° C. for 12 hrs. The reaction was diluted with EtOAc (50 mL), quenched with H$_2$O (30 mL). The organics were collected and concentrated. The residue was purified by column (PE:EA=2:1) to give compound 6F (500 mg, 48.24% yield) as colorless oil. $^1$H NMR (400 MHz, DMSO-d$_6$) δ 7.38-7.30 (m, 5H), 6.99-6.93 (m, 1H), 5.88-5.80 (m, 1H), 5.14 (s, 2H), 4.23-4.16 (m, 2H), 3.34-3.31 (m, 2H), 2.93 (s, 3H), 2.24-2.17 (m, 2H), 1.73-1.70 (m, 2H), 1.32-1.27 (m, 3H).

Step 7: Synthesis of Compounds 6G and 6H

To a solution of tert-butyl carbamate (4.03 g, 34.4 mmol) in n-Propanol (31 mL) was added NaOH (1.38 g, 34.38 mmol) in H$_2$O (93 mL). Then 1,3-dichloro-5,5-dimethyl-imidazolidine-2,4-dione (4.52 g, 22.92 mmol) was added, followed by addition of (DHQ)$_2$PHAL (447 mg, 0.57 mmol) in propanol (31 mL). Then a solution of compound 6F (3.5 g, 11.46 mmol) in propanol (31 mL) was added. To the mixture, K$_2$OsO$_4$.2H$_2$O (212 mg, 0.57 mmol) was added. The mixture was stirred at 25° C. for 12 hrs. Na$_2$SO$_3$ (11.85 g, 94 mmol) was added to the mixture portionwise. The mixture was stirred at 25° C. for 15 min. Then the reaction was diluted with EtOAc (200 mL), washed with H$_2$O (200 mL). The organics were collected and concentrated. The residue was purified by column (PE:EA=2:1) to give compound 6G (560 mg, 10.89% yield) as colorless oil. MS (ESI) m/z (M+Na)$^+$ 461.2. $^1$H NMR (400 MHz, DMSO-d$_6$) δ 7.40-7.29 (m, 5H), 6.37 (d, J=9.6 Hz, 1H), 5.22 (d, J=14.4 Hz, 1H), 5.06 (s, 2H), 4.11-4.02 (m, 3H), 3.82-3.79 (m, 1H), 3.27-3.19 (m, 2H), 2.85-2.81 (m, 3H), 1.55-1.35 (m, 13H), 1.19-1.15 (m, 3H). Compound 6H (620 mg, 11.93% yield) as colorless oil. MS (ESI) m/z (M+Na)$^+$ 461.2. $^1$H NMR (400 MHz, DMSO-d$_6$) δ 7.40-7.24 (m, 5H), 6.53 (d, J=9.2 Hz, 1H), 5.05 (s, 2H), 4.70 (d, J=8.4 Hz, 1H), 4.12-4.02 (m, 3H), 3.85-3.78 (m, 1H), 3.30-3.15 (m, 2H), 2.85-2.81 (m, 3H), 1.65-1.30 (m, 13H), 1.20-1.11 (m, 3H).

Step 8: Synthesis of Compound 6J

To a solution of compound 6G (560 mg, 1.28 mmol) in EtOAc (30 mL) was added wet Pd/C (170 mg, 10% purity). The mixture was stirred at 35° C. under H$_2$ at 45 psi for 12 hrs. Pd/C was filtered. The filtrate was collected and concentrated to give compound 6J (320 mg, crude) as colorless oil, which was used for the next step directly without further purification. MS (ESI) m/z (M+H)$^+$ 305.1.

Step 9: Synthesis of Compound 6K

The solution of compound 6J (320 mg, 1.05 mmol) in toluene (30 mL) was stirred at 110° C. for 12 hrs. The solvent was removed in vacuo. The residue was washed with isopropyl ethyl (3 mL). The solid was filtered and collected to afford compound 6K (80 mg, yield: 28.43%) as white solid. $^1$H NMR (400 MHz, DMSO-d$_6$) δ 6.82-6.67 (m, 1H), 4.46-4.35 (m, 1H), 3.47-3.39 (m, 1H), 3.30-3.25 (m, 1H), 1.75-1.60 (m, 3H), 1.55-1.42 (m, 1H), 1.38 (s, 9H). MS (ESI) m/z (M+H)$^+$ 259.0.

Step 10: Synthesis of Compounds 6L and 6M

Compound 6K was separated by SFC (Base-EtOH; P1: RT: 1.658 min; P2: RT: 2.555 min) to afford compound 6L (50 mg, yield: 62.50%) as light yellow oil. MS (ESI) m/z (M+H)$^+$ 258.9. Compound 6M (30 mg, yield: 37.46%) as white solid. MS (ESI) m/z (M+H)$^+$ 258.9.

Step 11: Synthesis of Compound 6N

Compound 6L (50 mg, 193.57 umol) in HCl/EtOAc (4M, 5 mL) was stirred at 25° C. for 1 h. The solvent was removed in vacuo to give 6N (30 mg, crude) as colorless oil, which was used directly for the next step. MS (ESI) m/z (M+H)$^+$ 158.9.

Step 12: Synthesis of Compound 6P

To a solution of Cbz-Val-OSu (54 mg, 0.15 mmol) and 6N (30 mg, 0.15 mmol) in DME (5 mL) was added TEA (0.1 mL, 0.7 mmol). The mixture was stirred at 25° C. for 12 hrs. The solvent was removed in vacuo. The residue was purified by prep-HPLC (HCl) to give 6P (27 mg, yield: 44.76%) as white solid. $^1$H NMR (400 MHz, DMSO-d$_6$) δ 7.98 (d, J=8.0 Hz, 1H), 7.38-7.30 (m, 5H), 7.18 (d, J=8.8 Hz, 1H), 5.04 (s, 2H), 4.63-4.42 (m, 1H), 4.26 (d, J=8.8 Hz, 1H), 3.93-3.88 (m, 1H), 3.61-3.42 (m, 2H), 3.31-3.26 (m, 1H), 2.94 (s, 3H), 1.95-1.91 (m, 1H), 1.74-1.50 (m, 4H), 0.87-0.82 (m, 6H). MS (ESI) m/z (M+H)$^+$ 392.1.

Step 13: Synthesis of Compound 6

To a solution of compound 6P (110 mg, 0.28 mmol) in DCM (40 mL) was added DESS-MARTIN PERIODINANE (537 mg, 1.26 mmol). The mixture was stirred at 30° C. for 36 hrs. The reaction was quenched with a solution of 10% aq. Na$_2$SO$_3$ and 10% aq. NaHCO$_3$ (v/v=1/1) (50 mL). The organics were collected, washed with brine (50 mL). The organics were collected, dried with Na$_2$SO$_4$, filtered and concentrated. The residue was washed with CH$_3$CN (3 mL). The solid was filtered, collected and dried in vacuo to afford compound 6 (61.3 mg, 53.72% yield) as white solid. $^1$H NMR (400 MHz, DMSO-d$_6$) δ 8.34 (d, J=6.8 Hz, 1H), 7.58-7.08 (m, 6H), 5.15-4.96 (m, 2H), 4.64-4.49 (m, 1H), 4.16-3.85 (m, 1H), 3.45-3.34 (m, 1H), 3.30-3.19 (m, 1H), 3.04-2.87 (m, 3H), 2.04-1.60 (m, 5H), 0.95-0.75 (m, 6H). MS (ESI) m/z (M+H)$^+$ 390.2.

Example 6

Benzyl ((2S)-3-methyl-1-((1-methyl-2,3-dioxoazepan-4-yl)amino)-1-oxobutan-2-yl)carbamate (7)

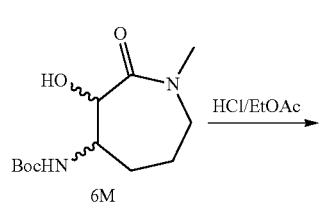

Step 1: Synthesis of Compound 7A

Compound 7A was prepared following the procedure of compound 6N. Compound 7A (22 mg, crude) was obtained as a white solid.

Step 2: Synthesis of Compound 7B

Compound 7B was prepared following the procedure of compound 6P. Compound 7B (19 mg, yield 42.94%) was obtained as a white solid. $^1$H NMR (400 MHz, DMSO-d$_6$) δ 7.85 (d, J=8.0 Hz, 1H), 7.37-7.31 (m, 5H), 7.19 (d, J=9.2 Hz, 1H), 5.03 (s, 2H), 4.49-4.37 (m, 1H), 4.25-4.14 (m, 1H), 3.91-3.79 (m, 1H), 3.63-3.39 (m, 2H), 3.31-3.17 (m, 1H), 2.94 (s, 3H), 2.00-1.86 (m, 1H), 1.84-1.36 (m, 4H), 0.90-0.83 (m, 6H). MS (ESI) m/z (M+H)$^+$ 392.1.

Step 3: Synthesis of Compound 7

Compound 7 was prepared following the procedure of compound 6. Compound 7 (60.1 mg, yield 53.72%) was obtained as a white solid. $^1$H NMR (400 MHz, DMSO-d$_6$) δ 8.43-8.23 (m, 1H), 7.48-7.05 (m, 6H), 5.14-4.86 (m, 2H), 4.58-4.36 (m, 1H), 4.05-3.80 (m, 1H), 3.41-3.34 (m, 1H), 3.28-3.14 (m, 1H), 3.01-2.85 (m, 3H), 2.03-1.58 (m, 5H), 0.94-0.65 (m, 6H). MS (ESI) m/z (M+H)$^+$ 390.2.

Example 7

(S)—N-(2,3-dioxoazecan-4-yl)-[1,1'-biphenyl]-2-carboxamide (8)

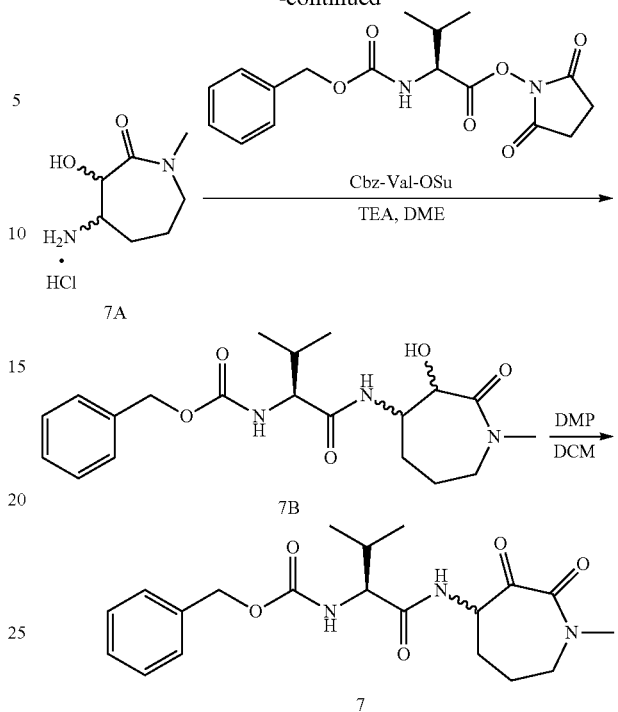

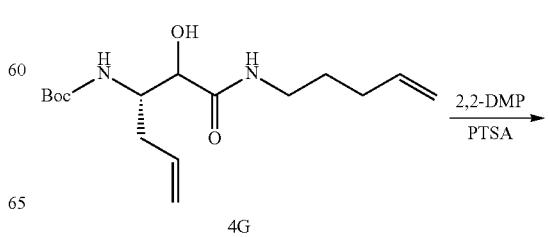

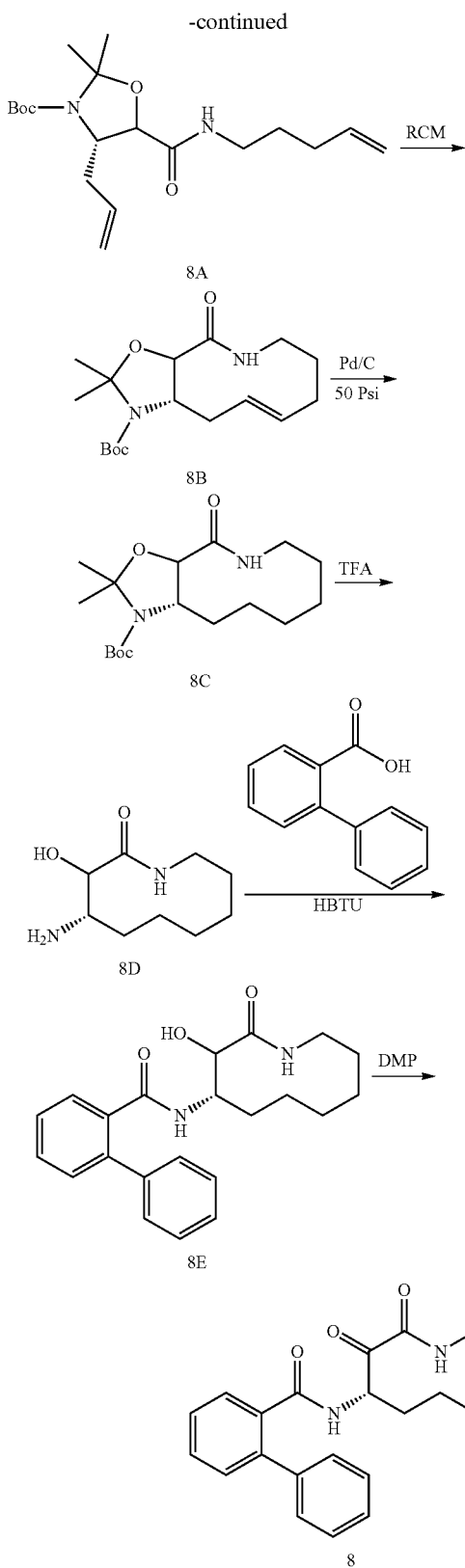

under N₂. The reaction was concentrated to give a residue, the residue was dissolved in DCM (30 mL), added sat. NaHCO₃ solution (30 mL), and extracted with DCM (10 mL), the organic phase was concentrated to give a residue. The residue was purified by column chromatography (SiO₂, Petroleum ether/Ethyl acetate=10/1~5/1). Compound 8A (550 mg, yield: 40.64%) was obtained as a yellow oil. ¹H NMR (400 MHz, CDCl₃) δ 6.58 (br s, 1H), 5.92-5.63 (m, 2H), 5.25-4.93 (m, 4H), 4.58-4.17 (m, 2H), 3.40-3.24 (m, 2H), 2.21-2.01 (m, 2H), 1.79-1.39 (m, 19H).

Step 2: Synthesis of Compound 8B

To a solution of compound 8A (600 mg, 1.70 mmol) in DCE (600 mL) was added Zhan catalyst 1B (187 mg, 255.00 umol). The mixture was stirred at 95° C. for 16 hrs. The reaction was concentrated to give a residue. The residue was purified by column chromatography (SiO₂, Petroleum ether/Ethyl acetate=10/1 to 2/1). Compound 8B (200 mg, yield: 12.69%) was obtained as a white solid. ¹H NMR (400 MHz, CDCl₃) δ 6.34 (d, J=12.3 Hz, 1H), 5.58-5.38 (m, 2H), 4.60 (d, J=7.1 Hz, 1H), 4.42-4.21 (m, 1H), 3.00 (d, J=13.9 Hz, 1H), 2.66-2.51 (m, 2H), 2.41-2.26 (m, 2H), 1.97 (d, J=13.0 Hz, 1H), 1.81 (d, J=9.3 Hz, 1H), 1.64-1.39 (m, 16H).

Step 3: Synthesis of Compound 8C

To a solution of compound 8B (200 mg, 616.50 umol) in MeOH (10 mL) was added Pd/C (20 mg, 10% purity) under N₂. The suspension was degassed under vacuum and purged with H₂ 3 times. The mixture was stirred at 25° C. for 48 hrs under H₂ (50 psi). The reaction mixture was filtered and concentrated under reduced pressure to give a residue. Compound 8C (180 mg, yield: 89.44%) was obtained as a yellow oil, which was used directly for the next step without further purification. ¹H NMR (400 MHz, CDCl₃) δ 6.69 (br s, 1H), 4.51 (d, J=5.5 Hz, 1H), 4.22-4.03 (m, 1H), 3.85 (d, J=5.5 Hz, 1H), 2.90-2.69 (m, 1H), 1.90-1.21 (m, 25H).

Step 4: Synthesis of Compound 8D

To a solution of compound 8C (150 mg, 459.52 umol) in DCM (12 mL) was added TFA (6.16 g, 54.03 mmol, 4.00 mL). After addition, the reaction mixture was stirred at 25° C. for 3 hrs. The reaction mixture was concentrated. Compound 8D (135 mg, yield: 97.84%, TFA) was obtained as yellow oil, which was used directly for the next step without further purification. MS (ESI) m/z (M+H)⁺ 187.2.

Step 5: Synthesis of Compound 8E

A mixture of 2-phenylbenzoic acid (100 mg, 504.49 umol), compound 8D (151 mg, 504.49 umol, TFA), and HBTU (286 mg, 756.74 umol) in DMF (6 mL) was added DIEA (195 mg, 1.51 mmol, 264 uL) and stirred at 25° C. for 16 hrs. The reaction mixture was diluted with 30 mL water, and then extracted with EtOAc (10 mL×3). The combined organic phase was washed with 30 mL 0.5N HCl, and 30 mL saturated NaHCO₃, dried over Na₂SO₄, concentrated to give a residue. The residue was purified by preparatory-HPLC (HCl condition). Compound 8E (60 mg, yield: 32.13%) was obtained as a white solid. ¹H NMR (400 MHz, CDCl₃) δ 7.65 (d, J=7.7 Hz, 1H), 7.54-7.47 (m, 1H), 7.45-7.34 (m, 7H), 6.95 (br s, 1H), 5.82 (d, J=8.4 Hz, 1H), 4.02 (br s, 2H), 3.68-2.70 (m, 2H), 1.64-1.12 (m, 10H), 0.90 (br s, 1H). MS (ESI) m/z (M+H)⁺ 367.0.

Step 6: Synthesis of Compound 8

To a solution of Compound 8E (50 mg, 136.44 umol) in DCM (10 mL) and DMSO (500 uL) was added DMP (289 mg, 682.20 umol). The mixture was stirred at 25° C. for 16 hrs. The reaction mixture was quenched by addition sat. NaHCO₃ (10 mL) and Na₂S₂O₃ (10 mL) at 25° C., and then the mixture was stirred until the solution was clear, and extracted with DCM (10 mL×2). The combined organic layers were washed with H₂O (30 mL) and brine (30 mL), Step 1: Synthesis of Compound 8A PTSA (132 mg, 768.25 umol) was added to a solution of the compound 4G (1.2 g, 3.84 mmol) in 2,2-dimethoxypropane (17 g, 163.23 mmol, 20.00 mL) at 80° C. for 16 hrs dried over Na$_2$SO$_4$, filtered and concentrated under reduced pressure to give a residue. The residue was triturated in DCM (1 mL) and PE (10 mL), and then filtered. Compound 8 (20 mg, yield: 39.82%) was obtained as a white solid. $^1$H NMR (400 MHz, DMSO-d$_6$) δ 8.22 (br s, 1H), 7.51-7.46 (m, 2H), 7.43-7.40 (m, 3H), 7.38-7.27 (m, 5H), 3.88 (br s, 1H), 3.29-3.19 (m, 1H), 3.17-2.94 (m, 1H), 1.55 (br s, 1H), 1.49-1.35 (m, 3H), 1.24 (d, J=10.4 Hz, 3H), 1.16-0.97 (m, 3H). MS (ESI) m/z (M+H)$^+$ 365.2.

Example 8

Benzyl ((S)-1-(((S)-2,3-dioxoazacycloundecan-4-yl)amino)-3-methyl-1-oxobutan-2-yl)carbamate (9)

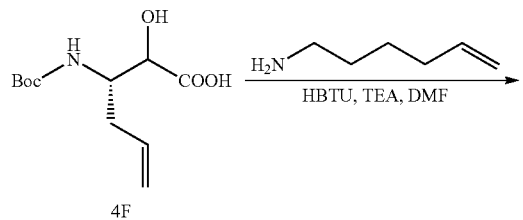

Step 1: Synthesis of Compound 9A

Compound 9A was prepared from compound 4F and hex-5-en-1-amine following the procedure of compound 4G. Compound 9A (1.1 g, yield 39.94%) was obtained as a colorless oil. $^1$H NMR (400 MHz, CDCl$_3$) δ 7.00-6.58 (m, 2H), 5.84-5.68 (m, 2H), 5.29 (s, 1H), 5.17-4.88 (m, 4H), 4.31-4.03 (m, 2H), 3.36-3.15 (m, 2H), 2.55-2.32 (m, 1H), 2.12-1.92 (m, 2H), 1.85 (br s, 1H), 1.59-1.47 (m, 2H), 1.46-1.37 (m, 9H), 1.36-1.18 (m, 2H). MS (ESI) m/z (M+H)$^+$ 327.9.

Step 2: Synthesis of Compound 9B

Compound 9B was prepared from compound 9A following the procedure of compound 8A. Compound 9B (550 mg, yield 44.53%) was obtained as a yellow oil. MS (ESI) m/z (M+H)$^+$ 367.1.

Step 3: Synthesis of Compound 9C

Compound 9C was prepared from compound 9B following the procedure of compound 8B. Compound 9C (200 mg, yield 7.05%) was obtained as a yellow oil. MS (ESI) m/z (M+H)$^+$ 339.0.

Step 4: Synthesis of Compound 9D

Compound 9D was prepared from compound 9C following the procedure of compound 8C. Compound 9D (250 mg, yield 99.41%) was obtained as a yellow oil. MS (ESI) m/z (M+H)$^+$ 341.1.

Step 5: Synthesis of Compound 9E

Compound 9E was prepared from compound 9D following the procedure of compound 8D. Compound 9E (146 mg, yield 99.28%) was obtained as a brown oil. MS (ESI) m/z (M+CH$_3$CN)$^+$ 241.2.

Step 6: Synthesis of Compound 9F

A mixture of compound 9E (130 mg, 413.62 umol, TFA), (2,5-dioxopyrrolidin-1-yl) (2S)-2-(benzyloxycarbonylamino)-3-methyl-butanoate (144.08 mg, 413.62 umol) in DMF (6 mL) was added DIEA (267.28 mg, 2.07 mmol, 361 uL) and stirred at 25° C. for 16 hrs. The reaction mixture was diluted with 30 mL water and then extracted with EtOAc (10 mL×3). The combined organic phase was washed with 30 mL 0.5N HCl, and 30 mL sat. NaHCO₃, dried over Na₂SO₄, concentrated to give a residue. The residue was purified by preparatory-HPLC (HCl condition). Compound 9F (35 mg, yield: 19.32%) was obtained as a white solid. $^1$H NMR (400 MHz, CDCl$_3$) δ 7.45-7.31 (m, 5H), 6.94-6.78 (m, 1H), 6.71 (br s, 1H), 5.37 (br s, 1H), 5.12 (s, 2H), 4.75 (br s, 1H), 4.18 (br s, 1H), 4.09-3.93 (m, 2H), 3.50-3.26 (m, 2H), 2.20-2.09 (m, 1H), 1.97 (br s, 1H), 1.80-1.60 (m, 2H), 1.52-1.22 (m, 9H), 0.96 (dd, J=6.7, 18.6 Hz, 6H). MS (ESI) m/z (M+H)$^+$ 434.2.

Step 7: Synthesis of Compound 9

Compound 9 was prepared from compound 9F following the procedure of compound 8. Compound 9 (12 mg, yield 58.47%) was obtained as a white solid. $^1$H NMR (400 MHz, DMSO-d$_6$) δ 8.88 (br s, 1H), 8.12 (d, J=6.6 Hz, 1H), 7.38-7.23 (m, 6H), 5.01 (s, 2H), 4.08-3.93 (m, 1H), 3.85 (d, J=17.0 Hz, 1H), 3.45 (br s, 1H), 2.96 (br s, 1H), 1.95 (dd, J=6.1, 13.1 Hz, 1H), 1.79 (br s, 1H), 1.60 (br s, 2H), 1.52-1.17 (m, 9H), 0.92-0.80 (m, 6H). MS (ESI) m/z (M+H)$^+$ 432.3.

Example 9

Synthesis of Key Intermediates

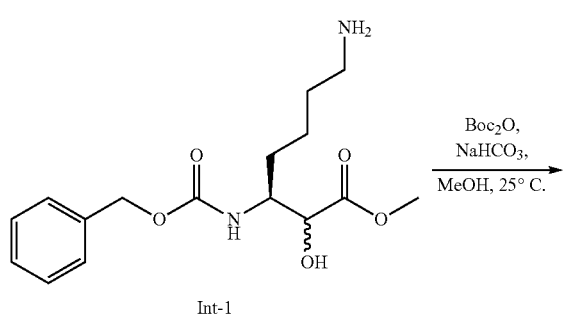

Int-1

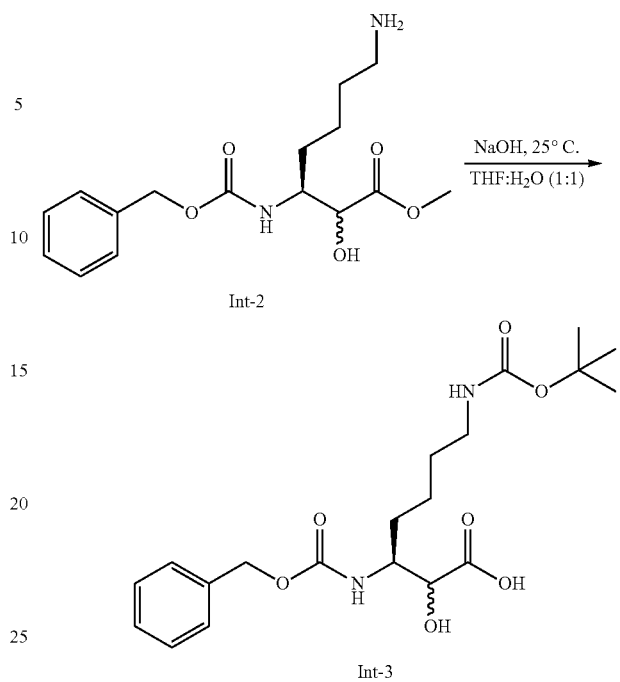

Int-2

Int-3

To compound Int-2 (500 mg, 1.18 umol) in THF:H₂O (1:1; 8 mL) was added NaOH (94 mg, 2.36 umol). The resultant solution was stirred at 25° C. for 1.5 hours after which time LC-MS indicated the disappearance of Int-2 and the formation of Int-3 as the major product. The reaction solution cooled to 0° C. and the pH adjusted to 4 with 2M HCl. The reaction solution was diluted with 80:20 CH₂Cl₂:MeOH (400 mL), H₂O (100 mL), saturated NaCl (100 mL), dry (MgSO4), filtered and concentrated to afford Int-3 (406 mg, 84%) as a cream foamy oil. LC-MS: m/e 411 (M+H).

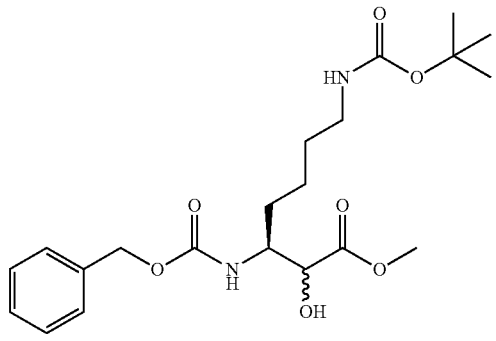

Int-2

To compound Int-1 (500 mg, 1.54 umol) in MeOH (8 mL) was added Boc₂O (392 mg, 1.85 umol) and NaHCO₃ (146.4 mg, 3.08 umol). The resultant mixture was stirred at 25° C. for 8 hours after which time LC-MS indicated the disappearance of Int-1 and the formation of Int-2 as the major product. The reaction mixture was concentrated under vacuum, diluted with EtOAc (200 mL), H₂O (100 mL), saturated NaCl (100 mL), dry (MgSO4), filter and concentrate to afford a colorless viscous oil. Purification over silica gel (50:50 Hexane:EtOAc) afforded Int-2 (555 mg, 85%). LC-MS: m/e 424 (M+H).

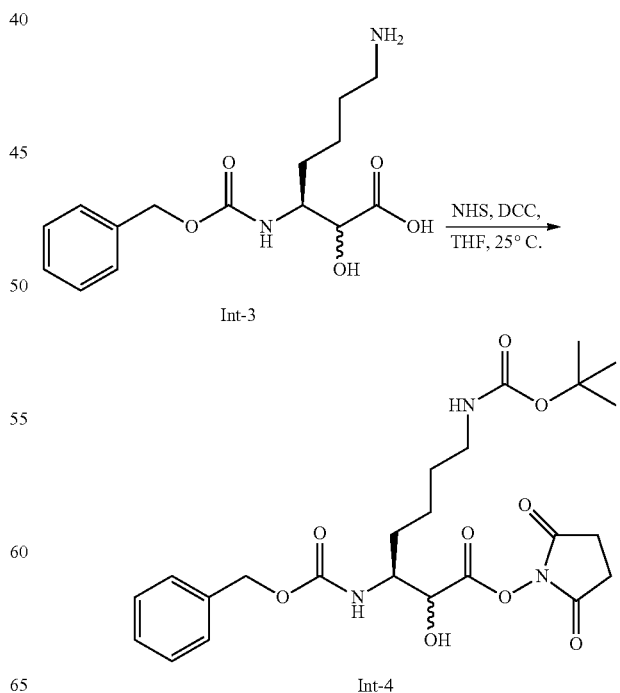

Int-3

Int-4

Both compound Int-3 (10 mg, 0.024 umol) and NHS (3 mg, 0.026 umol) were taken up in THF (1 mL) and cooled to 0° C. A THF (1 mL) solution of DCC (6 mg, 0.031 umol) was added dropwise. The solution was stirred at 0° C. for 0.5 hours before warming to 25° C. with stirring for an additional 2 hours. LC-MS indicated the disappearance of Int-3 and the formation of Int-4. The reaction solution was concentrated to afford Int-4 as a white waxy solid. The crude ester Int-4 was used directly in the next step without any further purification. LC-MS: m/e 508 (M+H).

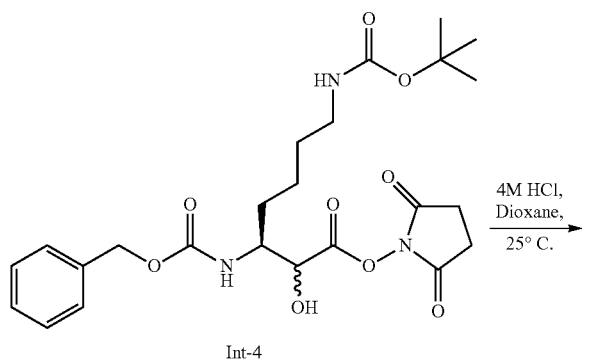

Int-4

Compound Int-4 (12 mg, 0.024 umol) was taken up in a 4M HCl/dioxane (1 mL) solution at 25° C. and stirring continued for 1 hour. LC-MS indicated the disappearance of Int-4 and the formation of Int-5. The reaction solution was concentrated to afford 5 as light yellow oil. The crude amine Int-5 was used directly in the next step without any further purification. LC-MS: m/e 408 (M+H).

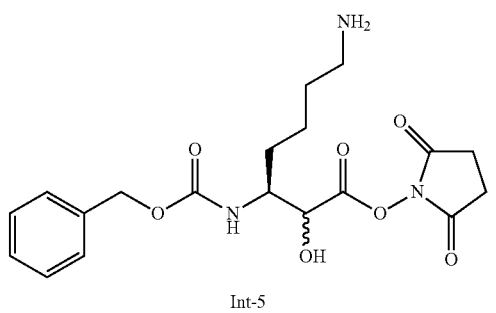

Int-5

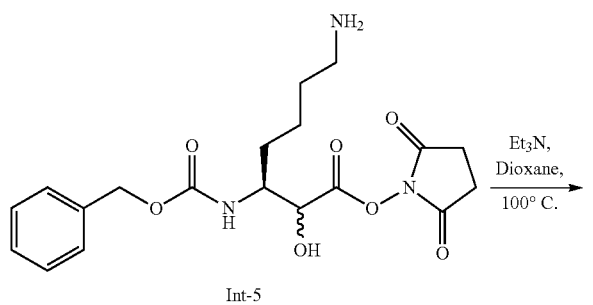

Int-5

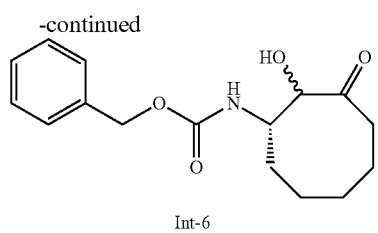

Int-6

Compound Int-5 (10 mg, 0.024 umol) was taken up in dioxane (1 mL) at 25° C. Addition of Et$_3$N (12 mg, 0.12 umol, 17 ul) was followed by stirring at 100° C. for 1 hour. LC-MS indicated the disappearance of Int-5 and the formation of Int-6. The reaction solution was concentrated to afford crude Int-6 as a brown solid. LC-MS: m/e 293 (M+H).

Example 10

Biological Assay Protocols

Biochemical inhibition of Calpains 1, 2, and 9.

Calpains 1, 2, and 9 activity and inhibition thereof are assessed by means of a continuous fluorescence assay. The SensoLyte 520 Calpain substrate (Anaspec Inc) is optimized for detecting calpain activity. This substrate contains a novel internally quenched 5-FAM/QXLTM 520 FRET pair. Calpains 1, 2 and 9 cleave the FRET substrate into two separate fragments resulting in an increase of 5-FAM fluorescence that is proportional to calpain activity.

Assays are typically setup in black 384-well plates using automated liquid handling as follows. Calpain assay base buffer typically contains 50 mM Tris, pH 7.5, 100 mM NaCl and 1 mM DTT. Inhibitors are serially diluted in DMSO and used to setup 2× mixtures with calpains in the aforementioned buffer. After incubation at ambient temperature (25 C), the reaction is initiated by adding a 2× mix of the fluorescent peptide substrate and CaCl$_2$ (required for in-situ calpain activation) in the same buffer. Reaction progress curve data are typically collected for 10 min using excitation/emission wavelengths of 490 nm/520 nm on SpectraMax i3x or the FLIPR-Tetra plate readers (Molecular Devices Inc). Reaction rates were calculated from progress curve slopes typically over 1-5 min. Dose response curves (rate vs. log inhibitor concentration) were typically fit to a 4-parameter logistic function to extract IC$_{50}$ values.

Inhibition of Cellular Calpain Activity

Calpain activity in SH-SYSY cells and inhibition thereof are assessed by means of the Calpain-Glo™ platform (Promega, Inc) which is a homogeneous, luminescence assay that uses the cell-permeable and pro-luminescent calpain substrate Suc-LLVY-amino-luciferin. Upon calpain cleavage followed by cell lysis and quenching the luminescence signal developed is proportional to intra-cellular calpain activity.

Assays are typically setup by seeding SH-SYSY cells in white 384-well plates at 40 k/per well in RPMI-1640 containing 1% serum followed by 37 C overnight incubation. Next morning, cells are pre-incubated for 1 hr with serially diluted compounds followed by addition of 20 uM each of Suc-LLVY-aminoluciferin substrate and A23187 (ionophore used to induce Ca flux and calpain activity) diluted in Calpain-Glo buffer. After a 4 hr incubation at 37 C (calpain reaction), cells are lysed at 37 C for 1 hr using 0.9% Triton X-100 containing PBS with 100 uM MDL-28170 (excess calpain inhibitor to quench calpain activity). After centrifugation at 300 rpm, the Calpain-Glo™ luciferase detection reagent in Calpain-Glo™ buffer is added followed by 10 min incubation prior to reading luminescence counts using an EnVision plate reader (Perkin Elmer Inc). Dose response curves (luminescence vs. log inhibitor concentration) were typically fit to a 4-parameter logistic function to extract $IC_{50}$ values.

Calpain Inhibition
Column A: Human Calpain 1/NS1 IC50 (nM)_MEAN
Column B: Human Calpain 2/NS1 IC50 (nM)_MEAN
Column C: Human Calpain 9/NS1 IC50 (nM)_MEAN
A: <3 uM;
B: 3-10 uM;
C: >10 uM;

| No. | Compound | Column A | Column B | Column C |
|---|---|---|---|---|
| 1 | | B | B | C |
| 2 | | C | B | C |
| 3 | | C | C | C |
| 4 | | A | A | A |
| 5 | | C | C | C |
| 6 | | C | C | C |

| No. | Compound | Column A | Column B | Column C |
|---|---|---|---|---|
| 7 | | C | C | C |
| 8 | | B | A | A |
| 9 | | A | A | A |

Example 11

Animal Models & Studies

Bleomycin-Induced Pulmonary Fibrosis in Mice or Rats

The method for inducing pulmonary fibrosis in mice is described in Current Protocols in Pharmacology: 5.46.1, entitled "Mouse Models of Bleomycin-induced Pulmonary Fibrosis". In order to induce pulmonary fibrosis, 6-8 week old C57Bl/6 mice or Wistar rats are instilled once oropharyngeally with ~1.5 U/kg of bleomycin sulfate (Calbiochem, Billerica, Mass.). Briefly, for oropharyngeal administration of bleomycin, mice or rats are anesthetized with isofluorane and then suspended on its back at a ~60 degree angle on an inclined surface with a rubber band running under the upper incisors. The airway is opened while securing the tongue with one arm of padded forceps and bleomycin is administered into the back of the oral cavity with a syringe. The study is terminated on day 14-28 for oropharyngeally administered bleomycin in mice and rats.

Alternatively, for systemic bleomycin administration by osmotic pumps in mice, the pumps are loaded with bleomycin and implanted subcutaneously under isofluorane anesthesia as described in Lee, Am J Physiol Lung Cell Mol Physiol, 2014. Briefly, mice are systemically administered ~50 U/kg bleomycin (Blenoxane; Teva Pharma, North Wales, Pa.) via osmotic pumps for 7 days. On day 10, the osmotic pumps are removed, and the study is continued until day 35.

All animals are euthanized at the termination of the studies by cervical dislocation for gross necropsy, and blood collected by cardiac puncture. The lungs from each animal are dissected from the animal and weighed. The BAL cells and fluid are collected by lavaging the lung twice with 0.5 ml Hanks Balanced Salt Solution (HBSS; VWR, Radnor, Pa.). After collection of BAL cells and fluid, lungs are dissected and removed from each animal. Whole lungs are inflated with 10% NBF and then fixed in 10% NBF for histology. Severity of fibrosis in the lungs is evaluated using a modified Ashcroft score (Hubner, Biotechniques, 2008).

Carbon Tetrachloride-Induced Liver Fibrosis in Mice or Rats

Carbon tetrachloride-induced liver fibrosis is a widely used and accepted model for evaluating novel antifibrotic therapies. The methods for inducing liver fibrosis by carbon tetrachloride administration is described in Lee, J Clin Invest, 1995 and Tsukamoto, Semin Liver Dis, 1990. Briefly, male C57BL/6 mice are challenged with 1 mg/kg carbon tetrachloride (Sigma Aldrich, diluted 1:7 in corn or olive oil) administered by intraperitoneal injection twice weekly for a period of 4 weeks. Mice are euthanized on day 28. In an alternative implementation, Wistar rats are administered carbon tetrachloride by intraperitoneal injection three times per week for 8-12 weeks. Rats are euthanized at the termination of the experiment, 8-12 after study initiation.

Blood is collected by cardiac puncture and processed into serum for evaluation of liver enzymes (including ALT, AST, ALP, etc) at several timepoints throughout the study and at termination of the study. The liver tissues from all animals are collected and fixed by immersion in 10% neutral buffered formalin, processed, paraffin embedded, sectioned, mounted, and stained with Masson's Trichrome (Tri) or Picrosirius Red (PSR) using standard histological methods for evaluation of fibrosis severity.

Mouse Unilateral Ureteral Obstruction Kidney Fibrosis Model

Female C57BL/6 mice (Harlan, 4-6 weeks of age) will be given free access to food and water and allowed to acclimate for at least 7 days prior to test initiation. After acclimation, mice are anesthetized and undergo unilateral ureteral obstruction (UUO) surgery or sham to left kidney. Briefly, a longitudinal, upper left incision is performed to expose the left kidney. The renal artery is located and 6/0 silk thread is passed between the artery and the ureter. The thread is looped around the ureter and knotted 3 times insuring full ligation of ureter. The kidney is returned to abdomen, the abdominal muscle is sutured and the skin is stapled closed. All animals are euthanized 4, 8, 14, 21, or 28 days after UUO surgery. Following sacrifice blood is collected via cardiac puncture, the kidneys are harvested and one half of the kidney is frozen at −80° C. and the other half is fixed in 10% neutral buffered formalin for histopathological assessment of kidney fibrosis.

Bleomycin Dermal Fibrosis Model

Bleomycin (Calbiochem, Billerica Mass.) is dissolved in phosphate buffered saline (PBS) at 10 ug/ml, and sterilized by filtration. Bleomycin or PBS control (100 ul) is injected subcutaneously into two locations on the shaved back of C57/BL6 or S129 mice (Charles River/Harlan Labs, 20-25 g) once daily for 28 days while under isoflourane anesthesia (5% in 100% 02). After 28 days, mice are euthanized and 6 mm-full thickness punch biopsies are obtained from each injection site. Dermal fibrosis is assessed by standard histopathology and hydroxyproline biochemical assays.

Example 12

Targeting Calpains

Targeting Calpains as a Novel Strategy Towards Inhibition of EpMT

Calpains are calcium dependent non-lysosomal cysteine proteases that selectively cleavage their target substrates, often leaving behind a functional domain and can be a form of post-translational modification. There are currently 14 known genes encoding for the large calpain subunit in humans: CAPN1 (NCBI Gene ID 823), CAPN2 (NCBI Gene ID 824), CAPN3 (NCBI Gene ID 825), CAPN5 (NCBI Gene ID 726), CAPN6 (NCBI Gene ID 827), CAPN7 (NCBI Gene ID 23473), CAPN8 (NCBI Gene ID 388743), CAPN9 (NCBI Gene ID 10753), CAPN10 (NCBI Gene ID 11132), CAPN11 (NCBI Gene ID 11131), CAPN12 (NCBI Gene ID 147968), CAPN13 (NCBI Gene ID 92251), CAPN14 (NCBI Gene ID 440854), CAPN15 (NCBI Gene ID 6650) and 2 known genes for the small regulatory subunits CAPN4/CAPNS1 (NCBI Gene ID 826) and CAPNS2 (NCBI Gene ID 84290) (Goll 2003; Schad 2002). The majority of research has focused on the ubiquitously expressed CAPN1 (aka mu-calpain) and CAPN2 (aka m-calpain), which require micro or millimolar levels of calcium for their activation, respectively. These isoforms, along with CAPN9, have been shown to form a heterodimer with the small regulatory subunit (CAPNS1 aka CAPN4) (Ravulapalli 2009). Calpains have been implicated in numerous cellular processes, including cytoskeletal rearrangement (Dourdin 2001), migration (Leloup 2006), signaling (Janossy 2004), and differentiation (Santos 2012).

For assessment of in vitro EMT, NMuMG cells (ATCC) were grown to confluence in 10% serum (Fetal Bovine Serum) growth media (Dubecco's Modified Eagles Medium supplemented with 10 ug/mL insulin) and then were followed by 24 h starvation in 0.5% serum media+/−drug inhibitors. Cells were then treated with recombinant human TGFb1 (R&D Systems 5 ng/mL)+/−drug inhibitors in 0.5% serum media. For time points greater than 24 h, the aforementioned media was refreshed every 24 hours. Cell lysates were analyzed for aSMA protein expression by western blot.

Miettinen et al. (1994). "TGF-beta induced transdifferentiation of mammary epithelial cells to mesenchymal cells: involvement of type I receptors." J Cell Biol 127 (6 Pt 2):2021-36

Lamouille et al. (2014). "Molecular mechanisms of epithelial-mesenchymal transition." Nat Rev Mol Cell Biol 15(3):178-96

For assessment of in vitro FMT, Normal Human Lung Fibroblasts (NHLF) cells (Lonza) were grown in Fibroblast Growth Media-2 (Lonza CC-3131/with CC-4126 bullet kit) and then were followed by 24 h starvation in serum/growth factor free Fibroblast Basal Media-2 (Lonza CC-3131)+/−drug inhibitors. Cells were then treated with TGFb1 (5 ng/mL) Fibroblast Basal Media+/−drug inhibitors. Cell lysates were analyzed for aSMA protein expression by western blot.

Pegorier et al. (2010). "Bone Morphogenetic Protein (BMP)-4 and BMP-7 regulate differentially Transforming Growth Factor (TGF)-B1 in normal human lung fibroblasts (NHLF)" Respir Res 11:85

Example 13

Human Treatment

The efficacy of treatment with a compound of a preferred embodiment compared with placebo in patients with idiopathic pulmonary fibrosis (IPF) and the safety of treatment with a compound of a preferred embodiment compared with placebo in patients with IPF is assessed. The primary outcome variable is the absolute change in percent predicted forced vital capacity (FVC) from baseline to Week 52. Other possible end-points would include, but are not limited to: mortality, progression free survival, change in rate of FVC decline, change in Sp02, and change in biomarkers (HRCT image analysis; molecular and cellular markers of disease activity). Secondary outcome measures include: composite outcomes of important IPF-related events; progression-free survival; the rate of death from any cause; the rate of death from IPF; categorical assessment of absolute change in percent predicted FVC from baseline to Week 52; change in Shortness-of-Breath from baseline to Week 52; change in percent predicted hemoglobin (Hb)-corrected carbon monoxide diffusing capacity (DLco) of the lungs from baseline to Week 52; change in oxygen saturation during the 6 minute walk test (6MWT) from baseline to Week 52; change in high-resolution computed tomography (HRCT) assessment from baseline to Week 52; change in distance walked in the 6MWT from baseline to Week 52. Patients eligible for this study include, but are not limited to: those patients that satisfy the following inclusion criteria: diagnosis of IPF; 40 to 80 years of age; FVC≥50% predicted value; DLco≥35% predicted value; either FVC or DLco≤90% predicted value; no improvement in past year; a ratio of the forced expiratory volume in 1 second ($FEV_1$) to the FVC of 0.80 or more; able to walk 150 meters in 6 minutes and maintain saturation ≥83% while on no more than 6 L/min supplemental oxygen. Patients are excluded from this study if they satisfy any of the following criteria: unable to undergo pulmonary function testing; evidence of significant obstructive lung disease or airway hyper-responsiveness; in the clinical opinion of the investigator, the patient is expected to need and be eligible for a lung transplant within 52 weeks of randomization; active infection; liver disease; cancer or other medical condition likely to result in death within 2 years; diabetes; pregnancy or lactation; substance abuse; personal or family history of long QT syndrome; other IPF treatment; unable to take study medication; withdrawal from other IPF trials. Patients are orally dosed with either placebo or an amount of a compound of a preferred embodiment (1 mg/day-1000 mg/day). The primary outcome variable will be the absolute change in percent predicted FVC from Baseline to Week 52. Patients will receive blinded study treatment from the time of randomization until the last patient randomized has been treated for 52 weeks. Physical and clinical laboratory assessments will be performed at defined intervals during the treatment duration, for example at weeks 2, 4, 8, 13, 26, 39, and 52. Pulmonary function, exercise tolerance, and shortness-of-breath will be assessed at defined intervals during the treatment duration, for example at weeks 13, 26, 39, and 52. A Data Monitoring Committee (DMC) will periodically review safety and efficacy data to ensure patient safety.

Example Trial in SSc

The efficacy of treatment with a compound of a preferred embodiment compared with placebo in patients with systemic sclerosis (SSc) and the safety of treatment with a compound of a preferred embodiment compared with placebo in patients with SSc is assessed. The primary outcome variable is the absolute change in Modified Rodnan Skin Score (mRSS) from baseline to Week 48. Other possible end-points would include, but are not limited to: mortality, percentage of patients with treatment-emergent adverse events (AEs) and serious adverse events (SAEs), composite measurement of disease progression, and change in biomarkers (molecular and cellular markers of disease activity, such as C-reactive protein). Secondary outcome measures include, but are not limited to: Scleroderma Health Assessment Questionnaire (SHAQ) score; the Health Assessment Questionnaire Disability Index (HAQ-DI); Functional Assessment of Chronic Illness Therapy-Fatigue (FACIT) score; severity of pruritus as measured by a standardized scale, such as the 5-D Itch Scale; St. George's Respiratory Questionnaire (SGRQ) score; Tender Joint Count 28 (TCJ28); lung function parameters; standard vital signs (including blood pressure, heart rate, and temperature); electrocardiogram measurements (ECGs); laboratory tests (clinical chemistry, hematology, and urinalysis); pharmacokinetics (PK) measurements. Included in these measurements and in addition, clinical and biomarker samples, such as skin biopsies and blood (or serum and/or plasma), will also be collected prior to initiation of treatment. Additionally, patients eligible for this study include, but are not limited to, those patients that satisfy the following criteria: Patients at least 18 years of age; diagnosis of SSc according to the American College of Rheumatology (ACR) and European League Against Rheumatism (EULAR) Criteria, meeting criteria for active disease and with a total disease duration of less than or equal to 60 months; 10 mRSS 35. Patients are excluded from this study if they satisfy any of the following criteria: major surgery within 8 weeks prior to screening; scleroderma limited to area distal to the elbows or knees; rheumatic autoimmune disease other than SSc; use of any investigational, biologic, or immunosuppressive therapies, including intra-articular or parenteral corticosteroids within 4 weeks of screening. Patients are orally dosed with either placebo or an amount of a compound of a preferred embodiment (1 mg/day-1000 mg/day). The primary outcome variable will be the absolute change in mRSS from Baseline to Week 48. Patients will receive blinded study treatment from the time of randomization until the last patient randomized has been treated for 48 weeks. Physical and clinical laboratory assessments will be performed at defined intervals during the treatment duration, such as Weeks 2, 4, 8, 12, 24, 36, and 48. Clinical and biomarker samples will also be collected at Week 48. A Data Monitoring Committee (DMC) will periodically review safety and efficacy data to ensure patient safety.

In some embodiments, patients may be treated with a calpain inhibitor in combination with additional therapies such as anti-inflammatories including glucocorticoids, analgesics (e.g. ibuprofen), aspirin, and agents that modulate a Th2-immune response, immunosuppressants including methotrexate, mycophenolate, cyclophosphamide, cyclosporine, thalidomide, pomalidomide, leflunomide, hydroxychloroquine, azathioprine, soluble bovine cartilage, vasodilators including endothelin receptor antagonists, prostacyclin analogues, nifedipine, and sildenafil, IL-6 receptor antagonists, selective and non-selective tyrosine kinase inhibitors, Wnt-pathway modulators, PPAR activators, caspase-3 inhibitors, LPA receptor antagonists, B cell depleting agents, CCR2 antagonists, pirfenidone, cannabinoid receptor agonists, ROCK inhibitors, miRNA-targeting agents, toll-like receptor antagonists, CTGF-targeting agents, NADPH oxidase inhibitors, tryptase inhibitors, TGF⎵ inhibitors, relaxin receptor agonists, and autologous adipose derived regenerative cells.

While some embodiments have been illustrated and described, a person with ordinary skill in the art, after reading the foregoing specification, can effect changes, substitutions of equivalents and other types of alterations to the compounds of the present technology or salts, pharmaceutical compositions, derivatives, prodrugs, metabolites, tautomers or racemic mixtures thereof as set forth herein. Each aspect and embodiment described above can also have included or incorporated therewith such variations or aspects as disclosed in regard to any or all of the other aspects and embodiments.

The present technology is also not to be limited in terms of the particular aspects described herein, which are intended as single illustrations of individual aspects of the present technology. Many modifications and variations of this present technology can be made without departing from its spirit and scope, as will be apparent to those skilled in the art. Functionally equivalent methods within the scope of the present technology, in addition to those enumerated herein, will be apparent to those skilled in the art from the foregoing descriptions. Such modifications and variations are intended to fall within the scope of the appended claims. It is to be understood that this present technology is not limited to particular methods, reagents, compounds, compositions, labeled compounds or biological systems, which can, of course, vary. It is also to be understood that the terminology used herein is for the purpose of describing particular aspects only, and is not intended to be limiting. Thus, it is intended that the specification be considered as exemplary only with the breadth, scope and spirit of the present technology indicated only by the appended claims, definitions therein and any equivalents thereof.

The embodiments, illustratively described herein may suitably be practiced in the absence of any element or elements, limitation or limitations, not specifically disclosed herein. Thus, for example, the terms "comprising," "including," "containing," etc. shall be read expansively and without limitation. Additionally, the terms and expressions employed herein have been used as terms of description and not of limitation, and there is no intention in the use of such terms and expressions of excluding any equivalents of the features shown and described or portions thereof, but it is recognized that various modifications are possible within the scope of the claimed technology. Additionally, the phrase "consisting essentially of" will be understood to include those elements specifically recited and those additional elements that do not materially affect the basic and novel characteristics of the claimed technology. The phrase "consisting of" excludes any element not specified.

In addition, where features or aspects of the disclosure are described in terms of Markush groups, those skilled in the art will recognize that the disclosure is also thereby described in terms of any individual member or subgroup of members of the Markush group. Each of the narrower species and subgeneric groupings falling within the generic disclosure also form part of the present technology. This includes the generic description of the present technology with a proviso or negative limitation removing any subject matter from the genus, regardless of whether or not the excised material is specifically recited herein.

All publications, patent applications, issued patents, and other documents (for example, journals, articles and/or textbooks) referred to in this specification are herein incorporated by reference as if each individual publication, patent application, issued patent, or other document was specifically and individually indicated to be incorporated by reference in its entirety. Definitions that are contained in text incorporated by reference are excluded to the extent that they contradict definitions in this disclosure.

Other embodiments are set forth in the following claims, along with the full scope of equivalents to which such claims are entitled.

While the invention has been particularly shown and described with reference to a preferred embodiment and various alternate embodiments, it will be understood by persons skilled in the relevant art that various changes in form and details can be made therein without departing from the spirit and scope of the invention.

All references, issued patents and patent applications cited within the body of the instant specification are hereby incorporated by reference in their entirety, for all purposes.

REFERENCES CITED

1. U.S. Pat. No. 5,145,684
2. Goll et al. (2003). "The calpain system." *Physiol Rev* 83(3):731-801.
3. Schad et al. (2002). "A novel human small subunit of calpains." *Biochem J* 362 (Pt 2):383-8.
4. Ravulapalli et al. (2009). "Distinguishing between calpain heterodimerization and homodimerization." *FEBS J* 276 (4):973-82.
5. Dourdin et al. (2001). "Reduced cell migration and disruption of the actin cytoskeleton in calpain-deficient embryonic fibroblasts." *J Biol Chem* 276(51):48382-8.
6. Leloup et al. (2006). "Involvement of calpains in growth factor-mediated migration." *Int J Biochem Cell Biol* 38(12):2049-63.
7. Janossy et al. (2004). "Calpain as a multi-site regulator of cell cycle." Biochem Pharmacol 67(8):1513-21.
8. Santos et al. (2012). "Distinct regulatory functions of calpain 1 and 2 during neural stem cell self-renewal and differentiation." PLoS One 7(3):e33468.
9. Miettinen et al. (1994). "TGF-beta induced transdifferentiation of mammary epithelial cells to mesenchymal cells: involvement of type I receptors." J Cell Biol 127 (6 Pt 2):2021-36.
10. Lamouille et al. (2014). "Molecular mechanisms of epithelial-mesenchymal transition." Nat Rev Mol Cell Biol 15(3):178-96.
11. Pegorier et al. (2010). "Bone Morphogenetic Protein (BMP)-4 and BMP-7 regulate differentially Transforming Growth Factor (TGF)-B1 in normal human lung fibroblasts (NHLF)" Respir Res 11:85.

We claim:
1. A compound having the structure of Formula I:

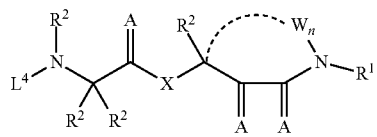

Formula I where:
n is from 1-12;
each A is independently selected from the group consisting of: O and S;
X is NH or $NR^2$;
each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;
each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;
each W is independently selected from the group consisting of: $CH_2$, $C(R^2)_2$, $CHR^2$, O, NH, $NR^2$, C(=O), C(=S), S, S(=O), $S(=O)_2$, —C—, —CH—, a $C_3$-$C_{12}$ spirocyclic group of

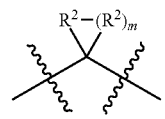

where m is 1-19, sulfonyl, substituted sulfonyl, sulfinyl, and substituted sulfinyl, wherein any two adjacent W atoms may form $CR^2$=$CR^2$ or C≡C;
$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO— ethylene glycol, —CO-polyethylene glycol, substituted sulfonyl, substituted sulfinyl, thioacyl, aminoacyl, phthalimido, and formyl;
and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

2. The compound of claim 1, wherein $L^4$ is —$SO_2$—Ar.

3. The compound of claim 1, wherein $L^4$ is CO—O— substituted alkyl.

4. The compound of claim 1, wherein $L^4$ is —CO—O—$(CH_3)_3$ or —CO—O—$CH_2$Ar.

5. The compound of claim 1, wherein $L^4$ is CO-alkyl or —CO— substituted alkyl.

6. The compound of claim 1, wherein $L^4$ is —CO—$CH_3$ or —CO—Ar.

7. The compound of claim 1, wherein one $R^2$ on the

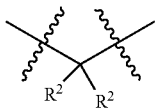

carbon atom is a substituted $C_1$-$C_8$ alkyl.

8. The compound of claim 1, wherein one $R^2$ on the

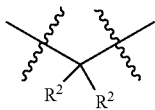

carbon atom is —CH—$(CH_3)_2$ or —$CH_2$—CH—$(CH_3)_2$.

9. The compound of claim 1, wherein one $R^2$ on the carbon atom is a $C_3$-$C_9$ heteroaryl or a substituted $C_3$-$C_9$ heteroaryl.

10. The compound of claim 1, wherein one $R^2$ on the

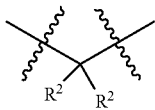

carbon atom is a $C_3$-$C_9$ heteroaryl or a naturally or non-naturally occurring amino acid side chain.

11. The compound of claim 1 having the structure of Formula II:

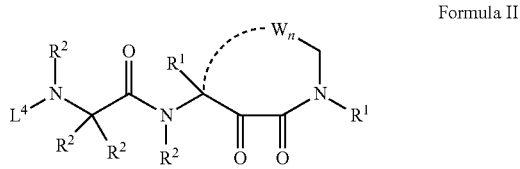

Formula II where:
n is from 1-11;
each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

each W is independently selected from the group consisting of: $CH_2$, $C(R^2)_2$, $CHR^2$, O, NH, $NR^2$, C(=O), C(=S), S, S(=O), S(=O)_2, —C—, —CH—, a $C_3$-$C_{12}$ spirocyclic group of

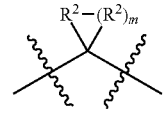

where m is 1-19, sulfonyl, substituted sulfonyl, sulfinyl, and substituted sulfinyl, wherein any two adjacent W atoms may form $CR^2$=$CR^2$ or C≡C;

$L^4$ is selected from the group consisting of: $R^2$, acyl, acylamino, aminocarbonylamino, aminothiocarbonyl, aminoacyl carbonyloxy, aminosulfonyl, amidino, carboxy ester, —CO— ethylene glycol, —CO-polyethylene glycol, substituted sulfonyl, substituted sulfinyl, thioacyl, aminoacyl, phthalimido, and formyl;

and wherein any two or more W groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

12. The compound of claim 11, wherein $L^4$ is selected from the group consisting of acyl, carboxy ester, —CO-ethylene glycol, —CO-polyethylene glycol, substituted sulfonyl, and formyl.

13. The compound of claim 11, wherein $L^4$ is —CO—O—$CH_2$-Ph or —$SO_2$—Ar.

14. The compound of claim 1 having the structure of Formula IV:

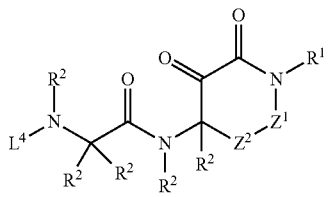

Formula IV where:
$Z^1$ and $Z^2$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

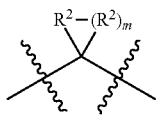

where m is 1-19, sulfonyl, substituted sulfonyl, sulfinyl, and substituted sulfinyl;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO— ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

15. The compound of claim 1 having the structure of Formula V:

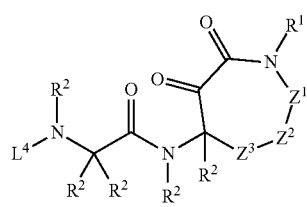

Formula V where:
$Z^1$, $Z^2$, and $Z^3$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

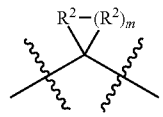

where m is 1-19, sulfonyl, substituted sulfonyl, sulfinyl, and substituted sulfinyl;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO— ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

16. The compound of claim 1 having the structure of Formula VIII:

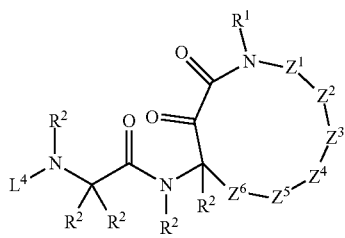

Formula VIII where:
$Z^1$, $Z^2$, $Z^3$, $Z^4$, $Z^5$, and $Z^6$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

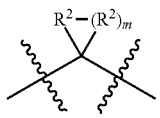

where m is 1-19, sulfonyl, substituted sulfonyl, sulfinyl, and substituted sulfinyl;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO— ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

17. The compound of claim 1 having the structure of Formula IX:

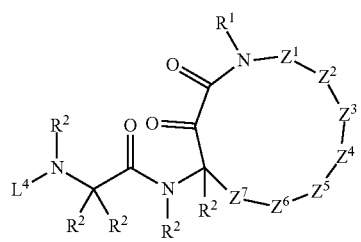

Formula IX where:
$Z^1$, $Z^2$, $Z^3$, $Z^4$, $Z^5$, $Z^6$, and $Z^7$ are each independently selected from the group consisting of: $CH_2$, $C(R^2)_2$, $CHR^2$, O, NH, $NR^2$, $C(=O)$, $C(=S)$, S, $S(=O)$, $S(=O)_2$, —C—, —CH—, a $C_3$-$C_{12}$ spirocyclic group of

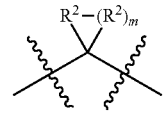

where m is 1-19, sulfonyl, substituted sulfonyl, sulfinyl, and substituted sulfinyl;

each $R^1$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, $C_1$-$C_8$ alkoxy, substituted $C_1$-$C_8$ alkoxy, amino, substituted amino, alkylthio, substituted alkylthio, OH, $OR^2$, $NH_2$, $NHR^2$, $SR^2$, substituted sulfonyl, and substituted sulfinyl;

each $R^2$ is independently selected from the group consisting of: hydrogen, $C_1$-$C_8$ alkyl, substituted $C_1$-$C_8$ alkyl, $C_1$-$C_8$ alkenyl, substituted $C_1$-$C_8$ alkenyl, $C_1$-$C_8$ alkynyl, substituted $C_1$-$C_8$ alkynyl, $C_3$-$C_7$ aryl, substituted $C_3$-$C_7$ aryl, cyano, OH, $C_1$-$C_8$ alkoxy, substituted $C_1$-$C_8$ alkoxy, amino, substituted amino, $C_3$-$C_{10}$ cycloalkyl, substituted $C_3$-$C_{10}$ cycloalkyl, $C_3$-$C_9$ heterocycloalkyl, substituted $C_3$-$C_9$ heterocycloalkyl, $C_3$-$C_9$ heteroaryl, substituted $C_3$-$C_9$ heteroaryl, and any naturally or non-naturally occurring amino acid side chain, wherein any $R^2$ substituent may be covalently bonded to or share another $R^2$ substituent to form a $C_3$-$C_{12}$ cyclic, heterocyclic, aryl, heteroaryl, spirocyclic, or bicyclic ring system;

$L^4$ is selected from the group consisting of: $R^2$, acyl, aminoacyl, aminocarbonyl, aminothiocarbonyl, aminoacyl carbonyloxy, aminosulfonyl, amidino, carboxy ester, —CO— ethylene glycol, —CO-polyethylene glycol, substituted sulfonyl, substituted sulfinyl, thioacyl, phthalimido, and formyl;

and wherein any two or more Z groups can be bonded together to form a $C_3$-$C_{12}$ cycloalkyl ring structure, a $C_3$-$C_{12}$ fused cycloalkyl ring structure, a $C_3$-$C_{12}$ aryl ring structure, a $C_3$-$C_{12}$ fused aryl ring structure, a $C_3$-$C_{12}$ heteroaryl ring structure, a $C_3$-$C_{12}$ fused heteroaryl ring structure, a $C_3$-$C_{12}$ heterocyclic ring structure, and a $C_3$-$C_{12}$ fused heterocyclic ring structure;

or a tautomer and/or a pharmaceutically acceptable salt thereof.

18. The compound of claim 1, having the structure selected from the group consisting of:

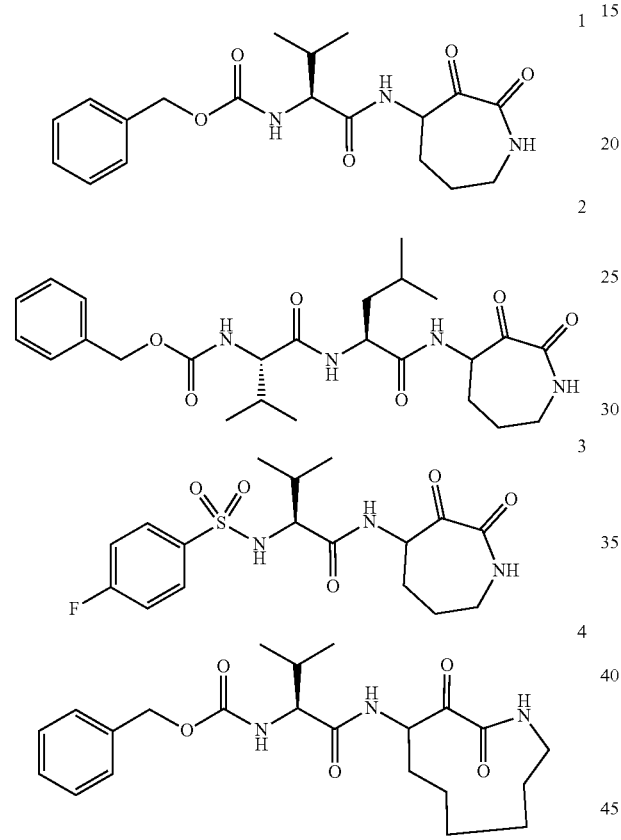

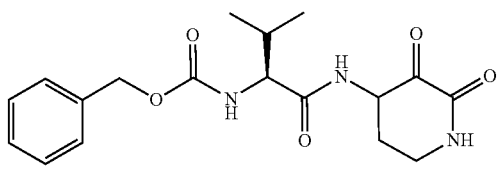

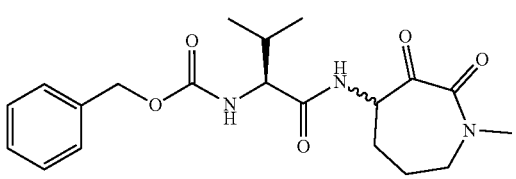

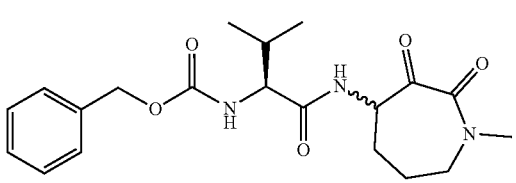

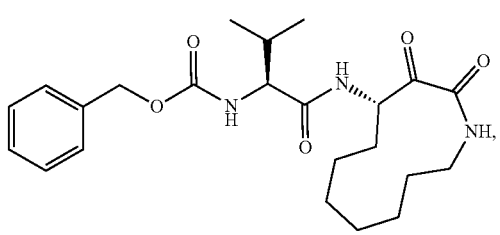

and pharmaceutically acceptable salts thereof.

19. A pharmaceutical composition comprising a compound of claim 1 and a pharmaceutically acceptable excipient.

* * * * *